(12) United States Patent
Bajjalieh et al.

(10) Patent No.: US 7,989,622 B2
(45) Date of Patent: Aug. 2, 2011

(54) PHOSPHATIDYLINOSITOL 3-KINASE INHIBITORS AND METHODS OF THEIR USE

(75) Inventors: William Bajjalieh, San Francisco, CA (US); Lynne Canne Bannen, Pacifica, CA (US); S. David Brown, San Carlos, CA (US); Patrick Kearney, San Francisco, CA (US); Morrison B. Mac, San Francisco, CA (US); Charles K. Marlowe, Emerald Hills, CA (US); John M. Nuss, Danville, CA (US); Zerom Tesfai, Castro Valley, CA (US); Yong Wang, Foster City, CA (US); Wei Xu, Danville, CA (US)

(73) Assignee: Exelixis, Inc., South San Francisco, CA (US)

( * ) Notice: Subject to any disclaimer, the term of this patent is extended or adjusted under 35 U.S.C. 154(b) by 368 days.

(21) Appl. No.: 11/988,862

(22) PCT Filed: Oct. 9, 2006

(86) PCT No.: PCT/US2006/039574
§ 371 (c)(1),
(2), (4) Date: Jan. 15, 2008

(87) PCT Pub. No.: WO2007/044729
PCT Pub. Date: Apr. 19, 2007

(65) Prior Publication Data
US 2010/0087440 A1    Apr. 8, 2010

Related U.S. Application Data

(60) Provisional application No. 60/724,570, filed on Oct. 7, 2005, provisional application No. 60/812,690, filed on Jun. 8, 2006.

(51) Int. Cl.
| | | |
|---|---|---|
| A61K 31/4985 | (2006.01) | |
| A61K 31/498 | (2006.01) | |
| C07D 241/36 | (2006.01) | |
| C07D 403/14 | (2006.01) | |
| C07D 471/04 | (2006.01) | |
| A61P 35/02 | (2006.01) | |
| A61P 35/00 | (2006.01) | |

(52) U.S. Cl. ......... 544/356; 514/249; 544/238; 544/350
(58) Field of Classification Search ................ None
See application file for complete search history.

(56) References Cited

U.S. PATENT DOCUMENTS
2006/0004010 A1    1/2006   Habashita et al.

FOREIGN PATENT DOCUMENTS

| | | |
|---|---|---|
| CS | 0156880 B1 | 11/1973 |
| EP | 1243583 A1 | 9/2002 |
| EP | 1661889 A1 | 5/2006 |
| JP | 2005-126549 A | 5/2005 |
| WO | WO-95-26957 A1 | 10/1995 |
| WO | WO-2004-000828 A1 | 12/2003 |
| WO | WO-2004-007472 A | 1/2004 |
| WO | WO-2005-014533 A2 | 2/2005 |
| WO | WO-2005-021513 A | 3/2005 |
| WO | WO-2005-023771 A1 | 3/2005 |
| WO | WO 2007/023186 * | 1/2007 |
| WO | WO-2007-023186 A | 3/2007 |

OTHER PUBLICATIONS

Budesinsky Z, et al, "Sulfanilamidoquinoxalines," Collection of Czechoslovak Chemical Communications, 1972, pp. 887-895, vol. 37, Institute of Organic and Biochemistry, Prague, CZ.
Loriga M, et al, "Quinoxaline Chemistry. Part 4," Il Farmaco, 1995, pp. 289-301, vol. 50, Societa Chimica Italiana, Pavia, IT.
Litvinenko S.V., et al, "Synthesis, Structure, and Chemical Properties of Some N-(3-Chloro-2-quinoxalyl)arylsulfonamides," Chemistry of Heterocyclic Compounds, 1994, pp. 340-344, vol. 30(3), Plenum Publishing Corporation, New York, US.
Dandegaonker and Mesta, "Quinoxaline Sulfonamides," Journal of Medicinal Chemistry, 1965, pp. 884-886, vol. 8(6), American Chemical Society, US.
Published Catalog Compounds, Database Registry, Chemical Abstracts Service, STN North America, Columbus, Ohio, www.cas.org/stn.html, Jan. 22, 2009 pp. 1-109.
CAS Registry Nos. 840497-84-9, 714932-70-4, and 573932-22-6, Database Registry, publication date Jan. 18, 2005, Chemical Abstracts Service, STN North America, Columbus, Ohio, www.cas.org/stn.html.
CAS Registry Nos. 325765-56-8 and 325765-07-9, Database Registry, date entered STN is Mar. 5, 2001 Chemical Abstracts Service, STN North America, Columbus, Ohio, www.cas.org/stn.html.
CAS Registry Nos. 560996-02-3 and 560995-76-8; Database Registry, date entered STN is Aug. 5, 2003 Chemical Abstracts Service, STN North America, Columbus, Ohio, www.cas.org/stn.html. CAS Registry Nos. 565199-13-5, Database Registry, date entered STN is Aug. 12, 2003 Chemical Abstracts Service, STN North America, Columbus, Ohio, www.cas.org/stn.html.
CAS Registry Nos. 568570-58-1, Database Registry, date entered STN is Aug. 18, 2003. Chemical Abstracts Service, STN North America, Columbus, Ohio, www.cas.org/stn.html.

* cited by examiner

Primary Examiner — Timothy Thomas
Assistant Examiner — Dennis Heyer
(74) Attorney, Agent, or Firm — Honigman Miller Schwartz & Cohn; Heidi M. Berven; Jonathan P. O'Brien

(57) ABSTRACT

The present invention comprises small molecule inhibitors of phosphatidylinositol 3-kinase (PI3K), which is associated with a number of malignancies such as ovarian cancer, cervical cancer, breast cancer, colon cancer, rectal cancer, and glioblastomas, among others. Accordingly, the compounds of the present invention are useful for treating, preventing, and/or inhibiting these diseases.

7 Claims, No Drawings

PHOSPHATIDYLINOSITOL 3-KINASE INHIBITORS AND METHODS OF THEIR USE

CROSS REFERENCE TO RELATED APPLICATIONS

The Applicants claim priority under 35 U.S.C. 119(e) to copending Provisional Applications No. 60/724,570 filed on Oct. 7, 2005 and No. 60/812,690 filed on Jun. 8, 2006, the disclosures of which are incorporated herein by reference in their entireties.

FIELD OF THE INVENTION

This invention relates to the field of protein kinases and inhibitors thereof. In particular, the invention relates to inhibitors of phosphatidylinositol 3-kinase (PI3K) signaling pathways, and methods of their use.

BACKGROUND OF THE INVENTION

The connection between abnormal protein phosphorylation and the cause or consequence of diseases has been known for over 20 years. Accordingly, protein kinases have become a very important group of drug targets. See Cohen, Nature, 1:309-315 (2002). Various protein kinase inhibitors have been used clinically in the treatment of a wide variety of diseases, such as cancer and chronic inflammatory diseases, including diabetes and stroke. See Cohen, Eur. J. Biochem., 268:5001-5010 (2001).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. Pharmaceutical Research, 17(11):1345-1353 (2000). Viral infections and the conditions related thereto have also been associated with the regulation of protein kinases. Park et al. Cell 101 (7), 777-787 (2000).

Phosphatidylinositol 3-kinase (PI3K or PIK3CA) is composed of an 85 kDa regulatory subunit and a 110 kDa catalytic subunit. The protein encoded by this gene represents the catalytic subunit, which uses ATP to phosphorylate PtdIns, PtdIns4P and PtdIns(4,5)P2. PTEN, a tumor suppressor which inhibits cell growth through multiple mechanisms, can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

PI3Kα has been implicated in the control of cytoskeletal reorganization, apoptosis, vesicular trafficking, proliferation and differentiation processes. Increased copy number and expression of PIK3CA is associated with a number of malignancies such as ovarian cancer (Campbell et al., Cancer Res 2004, 64, 7678-7681; Levine et al., Clin Cancer Res 2005, 11, 2875-2878; Wang et al., Hum Mutat 2005, 25, 322; Lee et al., Gynecol Oncol 2005, 97, 26-34), cervical cancer, breast cancer (Bachman, et al. Cancer Biol Ther 2004, 3, 772-775; Levine, et al., supra; Li et al., Breast Cancer Res Treat 2006, 96, 91-95; Saal et al., Cancer Res 2005, 65, 2554-2559; Samuels and Velculescu, Cell Cycle 2004, 3, 1221-1224), colorectal cancer (Samuels, et al. Science 2004, 304, 554; Velho et al. Eur J Cancer 2005, 41, 1649-1654), endometrial cancer (Oda et al. Cancer Res. 2005, 65, 10669-10673), gastric carcinomas (Byun et al., Int J Cancer 2003, 104, 318-327; Li et al., supra; Velho et al., supra; Lee et al., Oncogene 2005, 24, 1477-1480), hepatocellular carcinoma (Lee et al., id.), small and non-small cell lung cancer (Tang et al., Lung Cancer 2006, 51, 181-191; Massion et al., Am J Respir Crit Care Med 2004, 170, 1088-1094), thyroid carcinoma (Wu et al., J Clin Endocrinol Metab 2005, 90, 4688-4693), acute myelogenous leukemia (AML) (Sujobert et al., Blood 1997, 106, 1063-1066), chronic myelogenous leukemia (CML) (Hickey and Cotter J Biol Chem 2006, 281, 2441-2450), and glioblastomas (Hartmann et al. Acta Neuropathol (Berl) 2005, 109, 639-642; Samuels et al., supra).

In view of the important role of PI3Kα in biological processes and disease states, inhibitors and/or modulators of this protein kinase are desirable.

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

The invention comprises compounds of Formula I and Ia that inhibit PI3K and pharmaceutical compositions thereof. The invention is also directed to methods of inhibiting PI3K in a cell, and methods for treating a disease, disorder, or syndrome.

A first aspect of the invention provides a compound of Formula I:

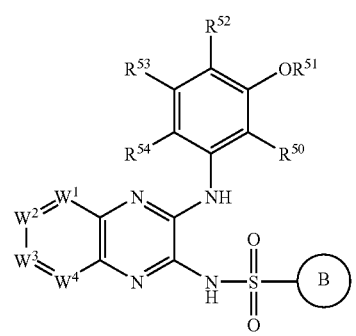

I or a pharmaceutically acceptable salt or solvate thereof, where $W^1$, $W^2$, $W^3$, and $W^4$ are —C($R^1$)=; or one or two of $W^1$, $W^2$, $W^3$, and $W^4$ are independently —N= and the remaining are —C($R^1$)=; and where each $R^1$ is independently hydrogen, alkyl, haloalkyl, nitro, alkoxy, haloalkoxy, halo, hydroxy, cyano, amino, alkylamino, or dialkylamino;

$R^{51}$ is hydrogen or alkyl;

$R^{52}$ is hydrogen or halo;

$R^{50}$, $R^{53}$, and $R^{54}$ are independently hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$N$R^{55}R^{55a}$, or alkylcarbonylamino and where $R^{55}$ and $R^{55b}$ are independently hydrogen, alkyl, or alkenyl and $R^{55a}$ is hydrogen, alkyl, alkenyl, hydroxy, or alkoxy; or $R^{53}$ and $R^{54}$ together with the carbons to which they are attached form a 5- or 6-membered heteroaryl or 5- or 6-membered heterocycloalkyl;

B is phenyl substituted with $R^{3a}$ and optionally further substituted with one, two, or three $R^3$; or B is heteroaryl optionally substituted with one, two, or three $R^3$;

$R^{3a}$ is cyano; hydroxyamino; carboxy; alkoxycarbonyl; alkylamino; dialkylamino; alkylcarbonyl; haloalkoxy; alkylsulfonyl; aminoalkyloxy; alkylaminoalkyloxy; dialkylaminoalkyloxy; or a) —N($R^7$)C(O)—$C_1$-$C_6$-alkylene-N($R^{7a}$)($R^{7b}$) where $R^7$ is hydrogen, alkyl, or alkenyl and $R^{7a}$ and $R^{7b}$ are independently hydrogen, alkyl, alkenyl, hydroxyalkyl, haloalkyl, alkoxy, alkoxyalkyl, aminoalkyl, alkylaminoalkyl, dialkylaminoalkyl, cycloalkyl, cycloalkylalkyl, heterocycloalkyl, heterocycloalkylalkyl, heteroaryl, heteroarylalkyl, aryl, arylalkyl, or arylalkyloxy and where the aryl, cycloalkyl, heterocycloalkyl and heteroaryl rings in $R^{7a}$ and $R^{7b}$ (either alone or as part of arylalkyl, cycloalkylalkyl, heterocycloalkylalkyl and heteroarylalkyl) are independently optionally substituted with 1, 2, or 3 groups independently selected from alkyl, amino, alkylamino, dialkylamino, hydroxy, halo, alkoxy, alkylthio, and oxo);

b) —C(O)N$R^8R^{8a}$ where $R^8$ is hydrogen, hydroxy, alkoxy, alkyl, alkenyl, haloalkyl, or haloalkoxy and $R^{8a}$ is hydrogen, alkyl, alkenyl, hydroxyalkyl, cyanoalkyl, alkoxyalkyl, alkylthioalkyl, heterocycloalkyl, heterocycloalkylalkyl, cycloalkyl, cycloalkylalkyl, heteroaryl, heteroarylalkyl, aryl, or arylalkyl and where the aryl, cycloalkyl, heteroaryl, and heterocycloalkyl rings in $R^{8a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, halo, haloalkyl, haloalkoxy, hydroxy, hydroxyalkyl, oxo, amino, alkylamino, dialkylamino, alkylcarbonyl, aminoalkyl, alkylaminoalkyl, dialkylaminoalkyl, alkoxycarbonyl, and —C(O)H;

c) —N$R^9$C(O)$R^{9a}$ where $R^9$ is hydrogen, hydroxy, alkoxy, alkyl, alkenyl, haloalkyl, or haloalkoxy and $R^{9a}$ is hydrogen, $C_{2-6}$-alkyl, alkenyl, hydroxyalkyl, alkoxyalkyl, cycloalkyl, cycloalkylalkyl, heterocycloalkyl, heterocycloalkylalkyl, heteroaryl, heteroarylalkyl, aryl, or arylalkyl; where the aryl, cycloalkyl, heteroaryl, and heterocycloalkyl rings in $R^{9a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, hydroxy, hydroxyalkyl, halo, haloalkyl, haloalkoxy, oxo, amino, alkylamino, dialkylamino, alkylcarbonyl, alkoxycarbonyl, —C(O)H, aryl (optionally substituted with one or two halo), arylalkyl, heteroaryl, heteroarylalkyl, heterocycloalkyl, heterocycloalkylalkyl, cycloalkyl, cycloalkylalkyl, and cycloalkylcarbonyl;

d) —C(O)N($R^{10}$)—$C_1$-$C_6$-alkylene-N($R^{10a}$)$R^{10b}$ where $R^{10a}$ is hydrogen, hydroxy, alkoxy, alkyl, alkenyl, haloalkyl, aminoalkyl, alkylaminoalkyl, dialkylaminoalkyl, or hydroxyalkyl and $R^{10}$ and $R^{10b}$ are independently hydrogen, alkyl, alkenyl, haloalkyl, aminoalkyl, alkylaminoalkyl, dialkylaminoalkyl, or hydroxyalkyl;

e) —N$R^{11}$C(O)N$R^{11a}R^{11b}$ where $R^{11a}$ is hydrogen, alkyl, alkenyl, hydroxy, or alkoxy and $R^{11}$ and $R^{11b}$ are independently hydrogen, alkyl, alkenyl, aminoalkyl, alkylaminoalkyl, or dialkylaminoalkyl;

f) —C(O)$R^{12}$ where $R^{12}$ is heterocycloalkyl optionally substituted with 1, 2, or 3 groups selected from alkyl, oxo, amino, alkylamino, and heterocycloalkylalkyl;

g) —N$R^{13}$C(O)O$R^{13a}$ where $R^{13}$ is hydrogen, alkyl, or alkenyl and $R^{13a}$ is aminoalkyl, alkylaminoalkyl, dialkylaminoalkyl, aryl, or arylalkyl;

h) —C(O)N($R^{14}$)N($R^{14a}$)($R^{14b}$) where $R^{14}$, $R^{14a}$, and $R^{14b}$ are independently hydrogen, alkyl, or alkenyl;

i) —S(O)$_2$N($R^{15}$)—$C_1$-$C_6$-alkylene-N($R^{15a}$)$R^{15b}$ where $R^{15}$, $R^{15a}$, and $R^{15b}$ are independently hydrogen, alkyl, or alkenyl;

j) —C(O)N($R^{16}$)—$C_1$-$C_6$-alkylene-C(O)O$R^{16a}$ where $R^{16}$ is hydrogen, alkyl, or alkenyl and $R^{16a}$ is alkyl or alkenyl;

k) heteroaryl optionally substituted with one or two aminoalkyl, alkylaminoalkyl, or dialkylaminoalkyl;

l) —N($R^{17}$)—C(=N($R^{17b}$)($R^{17a}$))(N$R^{17c}R^{17d}$) where $R^{17}$, $R^{17a}$, $R^{17b}$, $R^{17c}$, and $R^{17d}$ are independently hydrogen, alkyl, or alkenyl;

m) —N($R^{18}$)C(O)—$C_1$-$C_6$-alkylene-N($R^{18b}$)C(O)$R^{18a}$ where $R^{18a}$ is hydrogen, alkyl, alkenyl, or alkoxy and $R^{18}$ and $R^{18b}$ are independently hydrogen, alkyl, or alkenyl;

n) —C(O)N($R^{19}$)—$C_1$-$C_6$-alkylene-C(O)$R^{19a}$ where $R^{19}$ is hydrogen, alkyl, or alkenyl and $R^{19a}$ is amino, alkylamino, dialkylamino, or heterocycloalkyl;

o) —N($R^{20}$)C(O)—$C_1$-$C_6$-alkylene-C(O)$R^{20a}$ where $R^{20}$ is hydrogen, alkyl, or alkenyl and $R^{20a}$ is cycloalkyl or heterocycloalkyl;

p) —N$R^{21}$S(O)$_2$R—$C_1$-$C_6$-alkylene-N($R^{21b}$)$R^{21a}$ where $R^{21}$ is hydrogen, alkyl, or alkenyl and $R^{21a}$ and $R^{21b}$ are independently hydrogen, alkyl, or alkenyl;

q) —N($R^{22}$)C(O)—$C_1$-$C_6$-alkylene-N($R^{22b}$)—N($R^{22c}$)($R^{22a}$) where $R^{22}$, $R^{22a}$ and $R^{22b}$ are independently hydrogen, alkyl, or alkenyl;

r) —$C_0$-$C_6$-alkylene-N($R^{23}$)—$C_1$-$C_6$-alkylene-N($R^{23b}$)$R^{23a}$ where $R^{23}$, $R^{23a}$ and $R^{23b}$ are independently hydrogen, alkyl, or alkenyl; or s) —N$R^{24}$C(O)—$C_1$-$C_6$-alkylene-O$R^{24a}$ where $R^{24}$ is hydrogen, alkyl, or alkenyl and $R^{24a}$ is alkoxyalkyl or aryl optionally substituted with one or two halo or alkyl; and where each of the alkylene in $R^{3a}$ is independently optionally further substituted with 1, 2, 3, 4, or 5 groups selected from halo, hydroxy, amino, alkylamino, and dialkylamino; and each $R^3$ (when $R^3$ is present) is independently alkyl; alkenyl; alkynyl; halo; hydroxy; oxo; alkoxy; cyano; hydroxyamino; carboxy; alkoxycarbonyl; amino; alkylamino; dialkylamino; alkylcarbonyl; haloalkoxy; alkylsulfonyl; aminoalkyloxy; alkylaminoalkyloxy; dialkylaminoalkyloxy; or a) —N($R^7$)C(O)—$C_1$-$C_6$-alkylene-N($R^{7a}$)($R^{7b}$) where $R^7$ is hydrogen, alkyl, or alkenyl and $R^{7a}$ and $R^{7b}$ are independently hydrogen, alkyl, alkenyl, hydroxyalkyl, haloalkyl, alkoxy, alkoxyalkyl, aminoalkyl, alkylaminoalkyl, dialkylaminoalkyl, cycloalkyl, cycloalkylalkyl, heterocycloalkyl, heterocycloalkylalkyl, heteroaryl, heteroarylalkyl, aryl, arylalkyl, or arylalkyloxy and where the aryl, cycloalkyl, heterocycloalkyl and heteroaryl rings in $R^{7a}$ and $R^{7b}$ (either alone or as part of arylalkyl, cycloalkylalkyl, heterocycloalkylalkyl and heteroarylalkyl) are independently optionally substituted with 1, 2, or 3 groups independently selected from alkyl, amino, alkylamino, dialkylamino, hydroxy, halo, alkoxy, alkylthio, and oxo);

b) —C(O)NR$^8$R$^{8a}$ where R$^8$ is hydrogen, hydroxy, alkoxy, alkyl, alkenyl, haloalkyl, or haloalkoxy and R$^{8a}$ is hydrogen, alkyl, alkenyl, hydroxyalkyl, cyanoalkyl, alkoxyalkyl, alkylthioalkyl, heterocycloalkyl, heterocycloalkylalkyl, cycloalkyl, cycloalkylalkyl, heteroaryl, heteroarylalkyl, aryl, or arylalkyl and where the aryl, cycloalkyl, heteroaryl, and heterocycloalkyl rings in R$^{8e}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, halo, haloalkyl, haloalkoxy, hydroxy, hydroxyalkyl, oxo, amino, alkylamino, dialkylamino, alkylcarbonyl, aminoalkyl, alkylaminoalkyl, dialkylaminoalkyl, alkoxycarbonyl, and —C(O)H;

c) —NR$^9$C(O)R$^{9a}$ where R$^9$ is hydrogen, hydroxy, alkoxy, alkyl, alkenyl, haloalkyl, or haloalkoxy and R$^{9a}$ is hydrogen, C$_{2-6}$-alkyl, alkenyl, hydroxyalkyl, alkoxyalkyl, cycloalkyl, cycloalkylalkyl, heterocycloalkyl, heterocycloalkylalkyl, heteroaryl, heteroarylalkyl, aryl, or arylalkyl; where the aryl, cycloalkyl, heteroaryl, and heterocycloalkyl rings in R$^{9a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, hydroxy, hydroxyalkyl, halo, haloalkyl, haloalkoxy, oxo, amino, alkylamino, dialkylamino, alkylcarbonyl, alkoxycarbonyl, —C(O)H, aryl (optionally substituted with one or two halo), arylalkyl, heteroaryl, heteroarylalkyl, heterocycloalkyl, heterocycloalkylalkyl, cycloalkyl, cycloalkylalkyl, and cycloalkylcarbonyl;

d) —C(O)N(R$^{10}$)—C$_1$-C$_6$-alkylene-N(R$^{10a}$)R$^{10b}$ where R$^{10a}$ is hydrogen, hydroxy, alkoxy, alkyl, alkenyl, haloalkyl, or hydroxyalkyl and R$^{10}$ and R$^{10b}$ are independently hydrogen, alkyl, alkenyl, haloalkyl, or hydroxyalkyl;

e) —NR$^{11}$C(O)NR$^{11a}$R$^{11b}$ where R$^{11a}$ is hydrogen, alkyl, alkenyl, hydroxy, or alkoxy and R$^{11}$ and R$^{11b}$ are independently hydrogen, alkyl, alkenyl, aminoalkyl, alkylaminooalkyl, dialkylaminoalkyl;

f) —C(O)R$^{12}$ where R$^{12}$ is heterocycloalkyl optionally substituted with 1, 2, or 3 groups selected from alkyl, oxo, amino, alkylamino, and heterocycloalkylalkyl;

g) —NR$^{13}$C(O)OR$^{13a}$ where R$^{13}$ is hydrogen, alkyl, or alkenyl and R$^{13a}$ is aminoalkyl, alkylaminoalkyl, dialkylaminoalkyl, aryl, or arylalkyl);

h) —C(O)N(R$^{14}$)N(R$^{14a}$)(R$^{14b}$) where R$^{14}$, R$^{14a}$, and R$^{14b}$ are independently hydrogen, alkyl, or alkenyl;

i) —S(O)$_2$N(R$^{15}$)—C$_1$-C$_6$-alkylene-N(R$^{15a}$)R$^{15b}$ where R$^{15}$, R$^{15a}$, and R$^{15b}$ are independently hydrogen, alkyl, or alkenyl;

j) —C(O)N(R$^{16}$)—C$_1$-C$_6$-alkylene-C(O)OR$^{16a}$ where R$^{16}$ is hydrogen, alkyl, or alkenyl and R$^{16a}$ is alkyl or alkenyl;

k) heteroaryl optionally substituted with one or two aminoalkyl, alkylaminoalkyl, or dialkylaminoalkyl;

l) —N(R$^{17}$)—C(═N(R$^{17b}$)(R$^{17a}$))(NR$^{17c}$R$^{17d}$) where R$^{17}$, R$^{17a}$, R$^{17b}$, R$^{17c}$, and R$^{17d}$ are independently hydrogen, alkyl, or alkenyl;

m) —N(R$^{18}$)C(O)—C$_1$-C$_6$-alkylene-N(R$^{18b}$)C(O)R$^{18a}$ where R$^{18a}$ is hydrogen, alkyl, alkenyl, or alkoxy and R$^{18}$ and R$^{18b}$ are independently hydrogen, alkyl, or alkenyl;

n) —C(O)N(R$^{19}$)—C$_1$-C$_6$-alkylene-C(O)R$^{19a}$ where R$^{19}$ is hydrogen, alkyl, or alkenyl and R$^{19a}$ is amino, alkylamino, dialkylamino, or heterocycloalkyl;

o) —N(R$^{20}$)C(O)—C$_1$-C$_6$-alkylene-C(O)R$^{20a}$ where R$^{20}$ is hydrogen, alkyl, or alkenyl and R$^{20a}$ is cycloalkyl or heterocycloalkyl;

p) —NR$^{21}$S(O)$_2$R—C$_1$-C$_6$-alkylene-N(R$^{21b}$)R$^{21a}$ where R$^{21}$ is hydrogen, alkyl, or alkenyl and R$^{21a}$ and R$^{21b}$ are independently hydrogen, alkyl, or alkenyl;

q) —N(R$^{22}$)C(O)—C$_1$-C$_6$-alkylene-N(R$^{22}$—N(R$^{22}$) (R$^{22a}$), where R$^{22}$, R$^{22a}$ and R$^{22b}$ are independently hydrogen, alkyl, or alkenyl;

r) —C$_0$-C$_6$-alkylene-N(R$^{23}$)—C$_1$-C$_6$-alkylene-N(R$^{23b}$) R$^{23a}$ where R$^{23}$, R$^{23a}$ and R$^{23b}$ are independently hydrogen, alkyl, or alkenyl; or s) —NR$^{24}$C(O)—C$_1$-C$_6$-alkylene-OR$^{24a}$ where R$^{24}$ is hydrogen, alkyl, or alkenyl and R$^{24a}$ is alkoxyalkyl or aryl optionally substituted with one or two halo or alkyl;

wherein each of the alkylene in R$^3$ is independently optionally further substituted with 1, 2, 3, 4, or 5 groups selected from halo, hydroxy, amino, alkylamino, and dialkylamino; and provided that when R$^{50}$ and R$^{52}$ are hydrogen, R$^{51}$ is hydrogen or methyl, R$^{53}$ is hydrogen or methoxy, and R$^{54}$ is hydrogen or methoxy, then B is not 2,3-dihydro-1,4-benzodioxinyl, thien-2-yl, or thien-2-yl substituted with one R$^3$ where R$^3$ is halo.

A second aspect of the invention provides a compound of Formula II:

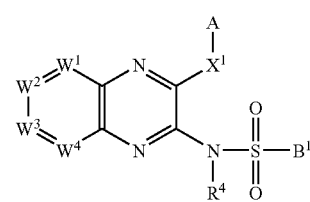

or a pharmaceutically acceptable salt or solvate thereof, wherein $W^1$, $W^2$, $W^3$, and $W^4$ are —C(R$^{1a}$)═; or one or two of $W^1$, $W^2$, $W^3$, and $W^4$ are independently —N═ and the remaining are —C(R$^{1a}$)═;

$X^1$ is —N(R$^{5a}$)—;

A is aryl, —S(O)$_2$-aryl, heteroaryl, cycloalkyl, heterocycloalkyl, halo, haloalkyl, haloalkoxy, alkyl, alkoxy, or -alkyl-N(R$^7$)R$^{7a}$, where each of the aryl, heteroaryl, cycloalkyl, heterocycloalkyl, alkyl and alkoxy groups, each either alone or as part of another group within A, are independently optionally substituted with one, two, three, or four R$^{2a}$; or B$^1$ is aryl, arylalkyl, alkyl, heteroaryl, or heteroarylalkyl, wherein each of the aryl, heteroaryl and alkyl groups are independently optionally substituted with one, two, three, or four R$^{3d}$;

each R$^{1a}$ is independently selected from hydrogen, alkoxy, alkyl, nitro, halo, cyano, and —C$_0$-C$_6$-alkyl-N(R$^7$)R$^{7a}$, wherein each of the alkyl and alkoxy groups is optionally substituted with 1, 2, 3, 4, or 5 groups selected from alkyl, alkoxy, halo, haloalkyl, haloalkoxy, nitro, cyano, hydroxy, —N($R^8$)$R^{8a}$, and —C(O)O$R^6$;

each $R^{2a}$ (when $R^{2a}$ is present) is independently selected from alkyl, alkenyl, -alkenyl-C(O)O$R^6$, —O$R^6$, —N($R^7$)C(O) $R^6$, —N($R^7$)C(O)—$C_0$-$C_6$ alkyl-N($R^{7b}$)$R^{7a}$, —OC(O)—$C_0$-$C_6$ alkyl-N($R^7$)$R^{7a}$, —N($R^7$)C(O)—$C_1$-$C_6$ alkylC(O)O$R^6$, $C_0$-$C_6$-alkyl-C(O)$R^6$, oxo, dioxo, —S(O)$_2$—N($R^7$)$R^{7a}$, —C(O)O$R^6$, —CH($R^6$)$_2$—C(O)O$R^6$, —S(O)$_2$$R^6$, cycloalkyl, heterocycloalkyl, heteroaryl, —C(O)N($R^7$)-alkyl-O$R^6$, —$C_0$-$C_6$ alkyl-C(O)N($R^7$)—$C_0$-$C_6$-alkyl-C(O)O$R^6$, —$C_0$-$C_6$-alkyl-C(O)N($R^7$)$R^{7a}$, aryl, arylalkyl, —S—($C_1$-$C_6$ alkyl), halo, oxo, nitro, —SCN, cyano, and —$C_0$-$C_6$ alkyl-N($R^7$)$R^{7a}$, wherein each of the alkyl (including, for example the alkyl within alkoxy), aryl, cycloalkyl, heterocycloalkyl, and heteroaryl groups, either alone or as part of another group within $R^2$, is independently optionally substituted with 1, 2, 3, 4, or 5 groups selected from alkyl, halo, haloalkyl, haloalkoxy, oxo, nitro, cyano, hydroxy, —N($R^8$)$R^{8a}$, alkoxy, and —C(O)O$R^9$;

each $R^{3d}$ (when $R^{3d}$ is present) is independently oxo, nitro, halo, cyano, alkyl, alkenyl, alkynyl, alkoxy, $C_3$-$C_6$-cycloalkyl, —$C_0$-$C_6$-alkyl-heterocycloalkyl, —$C_0$-$C_6$ alkyl-N($R^7$)C(O)—$C_0$-$C_6$-alkyl-N($R^{7b}$)$R^{7a}$, —$C_0$-$C_6$ alkyl-N($R^7$)C(O)—$C_0$-$C_6$-alkyl-N($R^7$)C(O)$R^{7a}$, —$C_0$-$C_6$ alkyl-C(O)—$C_0$-$C_6$-alkyl-N($R^7$)$R^{7a}$, —$C_0$-$C_6$-alkyl-C(O)N($R^7$)—$C_0$-$C_6$-alkyl-N($R^{7b}$)$R^{7a}$, —$C_0$-$C_6$-alkyl-C(O)N($R^7$)—$C_1$-$C_6$ alkylC(O)O$R^{7a}$, —$C_0$-$C_6$ alkyl-N($R^7$)C(O)—$C_0$-$C_6$-alkyl-($R^{7a}$), —$C_0$-$C_6$ alkyl-N($R^7$)—$C_0$-$C_6$-alkyl-N($R^{7b}$)$R^{7a}$, —$C_0$-$C_6$ alkyl-N($R^7$)C(O)—$C_0$-$C_6$-alkyl-N($R^{7b}$)—N($R^{7c}$)$R^{7a}$,—$C_0$-$C_6$ alkyl-N($R^7$)C(O)O—$C_0$-$C_6$-alkyl-aryl, —$C_0$-$C_6$ alkyl-C(O)N($R^7$)—$C_0$-$C_6$-alkyl-N($R^{7b}$)$R^{7a}$, —$C_0$-$C_6$ alkyl-N($R^7$)—$C_0$-$C_6$ alkyl-C(=N($R^{7b}$)($R^{7a}$))(N$R^{7c}$$R^{7d}$), —$C_0$-$C_6$-alkyl-aryl, —$C_0$-$C_6$-alkyl-heteroaryl, —$C_0$-$C_6$ alkyl-heterocycloalkyl, —O—$C_0$-$C_6$ alkyl-N($R^7$)$R^{7a}$, —$C_0$-$C_6$ alkyl-O$R_6$, —$C_0$-$C_6$ alkyl-C(O)O$R_6$, $C_0$-$C_6$-alkyl-N($R^7$)$R^{7a}$, —$C_0$-$C_6$ alkyl-C(O)N$R_7$$R^{7a}$, —$C_0$-$C_6$ alkyl-C(O)$R^7$, —S$R_7$, —S(O)$_2$$R_7$, —S(O)$_3$$R^7$, —S(O)$R^7$, —SO$_2$N($R^7$)$R^{7a}$, —SO$_2$N($R^7$)—$C_0$-$C_6$ alkyl-N($R^{7b}$)$R^{7a}$, —$C_0$-$C_6$-alkyl-N($R^7$)-aryl, —$C_0$-$C_6$-alkyl-N($R^7$)-heteroaryl, —$C_0$-$C_6$-alkyl-N($R^7$)-heterocycloalkyl, —$C_0$-$C_6$-alkyl-C(O)N($R^7$)—$C_0$-$C_6$-alkyl-cycloalkyl, $C_0$-$C_6$-alkyl-C(O)N($R^7$)—$C_0$-$C_6$-alkyl-aryl, $C_0$-$C_6$ alkyl-C(O)N($R^7$)—$C_0$-$C_6$ alkyl-heteroaryl, $C_0$-$C_6$ alkyl-C(O)N($R^7$)—$C_0$-$C_6$-alkyl-heterocycloalkyl, —$C_0$-$C_6$-alkyl-N($R^7$)C(O)—$C_0$-$C_6$-alkyl-cycloalkyl, —$C_0$-$C_6$-alkyl-N($R^7$)C(O)—$C_0$-$C_6$-alkyl-aryl, $C_0$-$C_6$-alkyl-N($R^7$)C(O)—$C_0$-$C_6$-alkyl-heteroaryl, —$C_0$-$C_6$-alkyl-N($R^7$)C(O)—$C_0$-$C_6$-alkyl-heterocycloalkyl, $C_0$-$C_6$-alkyl-N($R^7$)C(O)—$C_0$-$C_6$-alkyl-heterocycloalkyl-aryl, —N($R^7$)C(O)O$R^6$, or —NHC(O)H, wherein each of the alkyl, alkenyl, cycloalkyl, aryl, (including, for example the alkyl within alkoxy), heterocycloalkyl, and heteroaryl groups, either alone or as part of another group within $R^{3d}$, is independently optionally substituted with 1, 2, 3, 4, or 5 groups selected from alkyl, alkenyl, —$C_0$-$C_6$-alkyl-O$R^9$, cycloalkyl, halo, haloalkyl, haloalkoxy, —C(O)$R^9$, nitro, cyano, oxo, —$C_0$-$C_6$-alkyl-N($R^8$)$R^{8a}$, cycloalkyl, cycloalkylalkyl, heterocycloalkyl, heterocycloalkylalkyl, aryl, arylalkyl, heteroaryl, heteroarylalkyl, —C(O)O$R^9$, alkylthio, and hydroxyalkyl;

$R^4$ is hydrogen, aryl, —$C_0$-$C_6$-alkyl-N($R^7$)$R^{7a}$, alkoxy, or $C_1$-$C_6$ alkyl, wherein each of the alkyl and aryl groups, either alone or as part of another group in $R^4$, is independently optionally substituted with 1, 2, 3, 4, or 5 groups selected from alkyl, halo, haloalkyl, haloalkoxy, nitro, cyano, hydroxy, —N($R^8$)$R^{8a}$, alkoxy, and —C(O)O$R^6$; or $R^4$ and $X^1$ together with the atoms to which they are attached form a heterocycloalkyl or heteroaryl group, wherein $R^{5a}$ is absent when X is —N($R^{5a}$)—, wherein each of the heterocycloalkyl or heteroaryl is optionally substituted with 1, 2, 3, 4, or 5 groups selected from alkyl, halo, haloalkyl, haloalkoxy, nitro, cyano, hydroxy, —N($R^7$)$R^{7a}$, alkoxy, and —C(O)O$R^6$;

$R^{5a}$ is hydrogen, —$C_1$-$C_6$ alkyl-N($R^7$)$R^{7a}$, alkoxy, alkyl, or aryl, wherein each of the alkyl and aryl is optionally substituted with 1, 2, 3, 4, or 5 groups selected from alkyl, halo, haloalkyl, haloalkoxy, nitro, cyano, hydroxy, —N($R^8$)$R^{8a}$, $C_1$-$C_6$ alkoxy, or —C(O)O$R^6$; or $R^{5a}$ and $R^4$ together with the atoms to which they are attached form a heterocycloalkyl or heteroaryl group, wherein the heterocycloalkyl and heteroaryl is optionally substituted with 1, 2, 3, 4, or 5 groups selected from alkyl, halo, haloalkyl, haloalkoxy, nitro, cyano, hydroxy, —N($R^7$)$R^{7a}$, $C_1$-$C_6$ alkoxy, and —C(O)O$R^6$;

$R^6$ and $R^9$ are independently hydrogen, hydroxy, alkyl, aryl, arylalkyl, cycloalkyl, cycloalkylalkyl, heterocycloalkyl, heterocycloalkylalkyl, heteroaryl, heteroarylalkyl, or aryl, each alkyl, aryl, cycloalkyl, heterocycloalkyl, and heteroaryl, either alone or as part of another group within $R^6$ and $R^9$, is independently optionally substituted with 1, 2, 3, 4, or 5 groups independently selected from amino, hydroxy, alkoxy, alkyl, and halo; and $R^7$, $R^{7a}$, $R^{7b}$, $R^{7c}$, $R^{7d}$, $R^8$, and $R^{8a}$ are independently hydrogen, alkyl, alkenyl, hydroxy, alkyloxy, alkenyloxy, —O—$C_0$-$C_6$ alkyl-aryl, —$C_0$-$C_6$ alkyl-C(O)O$R^6$, —$C_0$-$C_6$ alkyl-C(O)$R^6$, aryl, arylalkyl, heteroaryl, heteroarylalkyl, cycloalkyl, cycloalkylalkyl, heterocycloalkyl, or heterocycloalkylalkyl, wherein each of the alkyl, aryl, heteroaryl, and heterocycloalkyl, either alone or part of another group within $R^7$, $R^{7a}$, $R^{7b}$, $R^{7c}$, $R^{7d}$, $R^8$, and $R^{8a}$ is independently optionally substituted with 1, 2, 3, 4, or 5 groups selected from amino, alkylamino, dialkylamino, aminoalkyl, alkylaminoalkyl, dialkylaminoalkyl, —S—$C_1$-$C_6$ alkyl, cyano, nitro, hydroxy, $C_1$-$C_6$ alkoxy, $C_1$-$C_6$ alkyl, halo, aryl, heterocycloalkylalkyl, and heteroaryl optionally substituted with one or two $C_1$-$C_6$ alkyl.

In a third aspect, the invention is directed to a pharmaceutical composition which comprises a compound of Formula I or a pharmaceutically acceptable salt thereof and a pharmaceutically acceptable carrier, excipient, or diluent.

In a fourth aspect, the invention comprises a method of inhibiting PI3K in a cell, comprising contacting a cell with a compound of Formula I or II or a pharmaceutically acceptable salt or solvate thereof, or with a pharmaceutical composition comprising a therapeutically effective amount of a compound of Formula I and a pharmaceutically acceptable carrier, excipient, or diluent.

In a fifth aspect, the Invention provides a method for treating a disease, disorder, or syndrome which method comprises administering to a patient a pharmaceutical composition comprising a therapeutically effective amount of a compound of Formula I or II or a pharmaceutically acceptable salt or solvate thereof, or a pharmaceutical composition comprising a therapeutically effective amount of a compound of Formula I, Ia, or II and a pharmaceutically acceptable carrier, excipient, or diluent.

A sixth aspect of the invention is directed to a process of preparing a compound of Formula I, comprising:

(a) reacting an intermediate of:

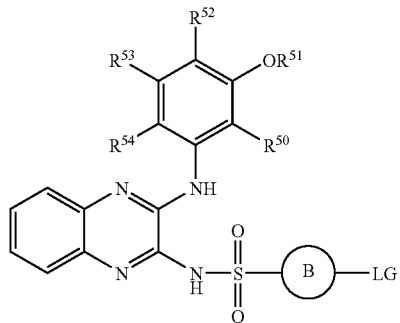

where LG is a leaving group such as chloro, and all other groups, are as defined in the Summary of the Invention, with an intermediate of formula NHR$^a$R$^b$ or HO—C$_1$-C$_6$-alkylene-NHR$^a$R$^b$ where R$^a$ and R$^b$ are independently hydrogen or alkyl to yield, respectively,

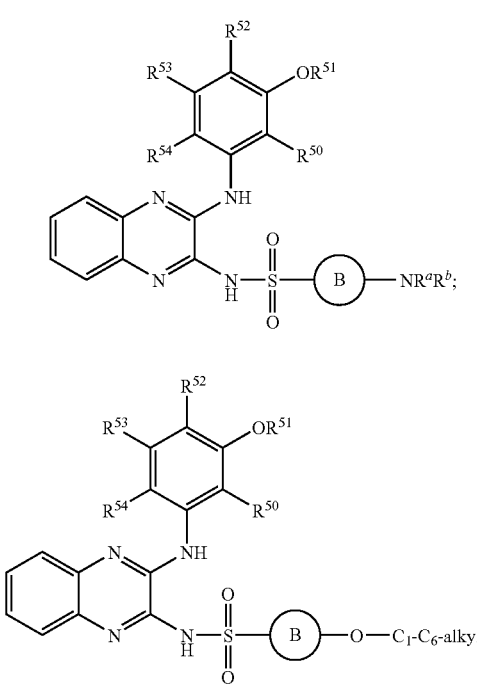

and
or
(b) reacting an intermediate of formula 8

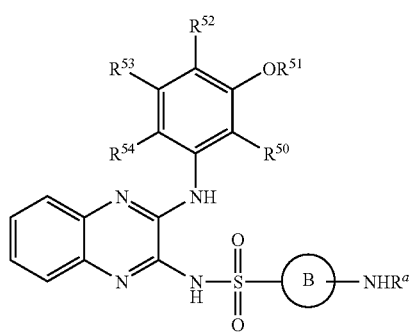

where R$^a$ is R$^7$, R$^9$, R$^{11}$, R$^{13}$, R$^{17}$, R$^{18}$, R$^{20}$, R$^{21}$, R$^{22}$, or R$^{24}$, each as defined in the Summary of the Invention for a Compound of Formula I and all other groups are as defined in the Summary of the Invention;

with an intermediate of formula 9(a), 9(b), 9(c), 9(d), 9(e), 9(f), or 9(g):

9(a) HOC(O)—C$_1$-C$_6$-alkylene-N(R$^{7a}$)(R$^{7b}$) where R$^a$ is R$^{7a}$ or a N-protecting group, such as Boc or Fmoc;

9(b) HOC(O)R$^{9a}$;

9(c) HOC(O)NR$^{11a}$R$^{11b}$;

9(d) HOC(O)OR$^{13a}$;

9(e) HOC(O)—C$_1$-C$_6$-alkylene-N(R$^{18b}$)C(O)R$^{18a}$;

9(f) HOC(O)—C$_1$-C$_6$-alkylene-C(O)R$^{20a}$;

9(g) LG-S(O)$_2$R—C$_1$-C$_6$-alkylene-N(R$^{21b}$)R$^a$ where R$^a$ is R$^{21a}$ or a N-protecting group, such as Boc or Fmoc;

to yield

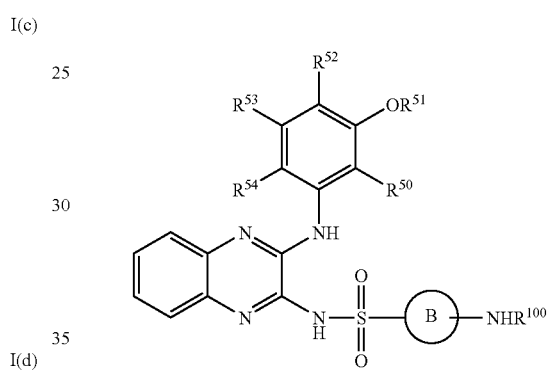

where R$^{100}$ is —C(O)R$^{9a}$, —C(O)NR$^{11a}$R$^{11b}$, —C(O)OR$^{13a}$, —C(O)—C$_1$-C$_6$-alkylene-N(R$^{18b}$)C(O)R$^{18a}$, —C(O)—C$_1$-C$_6$-alkylene-C(O)R$^{20a}$, or —S(O)$_2$R—C$_1$-C$_6$-alkylene-N(R$^{21b}$)R$^a$; or (c) reacting an intermediate of formula 11

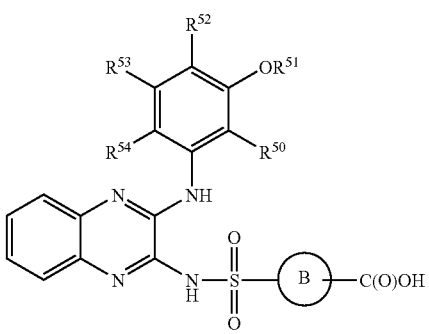

with one of the following intermediates NHR$^8$R$^{8a}$, NH(R$^{10}$)—C$_1$-C$_6$-alkylene-N(R$^{10a}$)R$^{10b}$, a cyclic amine, NH(R$^{14}$)N(R$^{14a}$)(R$^{14b}$), NH(R$^{16}$)—C$_1$-C$_6$-alkylene-C(O)OR$^{16a}$, and NH(R$^{19}$)—C$_1$-C$_6$-alkylene-C(O)R$^{19a}$ to yield a Compound of Formula I; or (d) reacting an intermediate of formula 12:

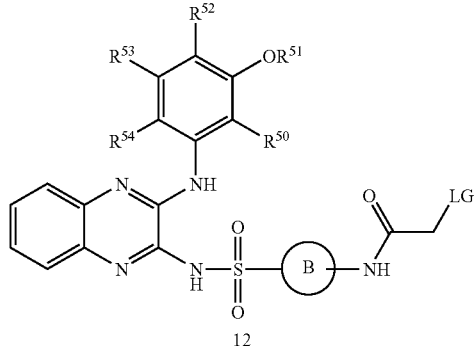

with an intermediate of formula $NH(R^{7b})R^{7a}$ to yield a Compound of Formula I(f):

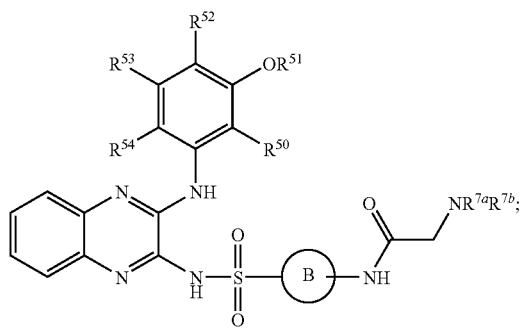

or (e) reacting an intermediate of formula 13 where LG is a leaving group, such as chloro, and all other groups are as defined in the Summary of the Invention:

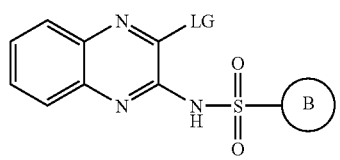

with an intermediate of formula:

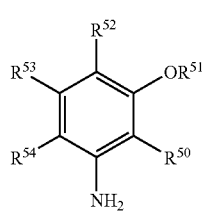

to yield a Compound of Formula I(h):

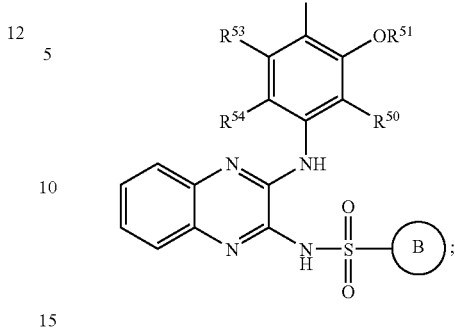

and (f) optionally further resolving individual isomers.

DETAILED DESCRIPTION OF THE INVENTION

Abbreviations and Definitions

The following abbreviations and terms have the indicated meanings throughout:

| Abbreviation | Meaning |
| --- | --- |
| br | broad |
| ° C. | degrees Celsius |
| CBZ | CarboBenZoxy = benzyloxycarbonyl |
| d | doublet |
| dd | doublet of doublet |
| dt | doublet of triplet |
| EI | Electron Impact ionization |
| Et | Ethyl |
| g | gram(s) |
| GC | gas chromatography |
| h or hr | hour(s) |
| HPLC | high pressure liquid chromatography |
| L | liter(s) |
| M | molar or molarity |
| m | Multiplet |
| mg | milligram(s) |
| MHz | megahertz (frequency) |
| Min | minute(s) |
| mL | milliliter(s) |
| mM | Millimolar |
| mmol | millimole(s) |
| mol | mole(s) |
| MS | mass spectral analysis |
| N | normal or normality |
| nM | Nanomolar |
| NMR | nuclear magnetic resonance spectroscopy |
| q | Quartet |
| RT | Room temperature |
| s | Singlet |
| s- | Secondary |
| t- | Tertiary |
| t or tr | Triplet |
| TFA | trifluoroacetic acid |
| THF | Tetrahydrofuran |
| μL | microliter(s) |
| μM | Micromole(s) or micromolar |

The symbol "—" means a single bond, "═" means a double bond, "≡" means a triple bond, and "-----" means a single bond and optionally a double bond. When chemical structures are depicted or described, unless explicitly stated otherwise, all carbons are assumed to have hydrogen substitution to conform to a valence of four.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more active agents (e.g., surgery, radiation, and chemotherapy, etc.), "administration" and its variants are each understood to include concurrent and sequential introduction of the compound or prodrug thereof and other agents.

"Alkenyl" or "lower alkenyl" means a straight or branched hydrocarbon radical having from 2 to 6 carbon atoms and at least one double bond and includes ethenyl, propenyl, 1-but-3-enyl, 1-pent-3-enyl, 1-hex-5-enyl and the like.

"Alkenylcarbonyl" means a C(O)R group where R is alkenyl, as defined herein.

"Alkenyloxy" or "lower alkenyloxy" means an —OR group where R is alkenyl, as defined herein. Representative examples include methoxy, ethoxy, 1-methoxyprop-1-en-3-yl, propoxy, isopropoxy, cyclopropyloxy, cyclohexyloxy and the like.

"Alkoxy" or "lower alkoxy" means an —OR group where R is alkyl, as defined herein. Representative examples include methoxy, ethoxy, 1-methoxyprop-1-en-3-yl, propoxy, isopropoxy, cyclopropyloxy, cyclohexyloxy and the like.

"Alkoxyalkyl" means an alkyl group, as defined herein, substituted with one, two, or three alkoxy groups, as defined herein.

"Alkoxycarbonyl" means a —C(O)OR group where R is alkyl as defined herein.

"Alkoxycarbonylalkyl" means an alkyl group, as defined herein, substituted with one, two, or three alkoxycarbonyl groups, as defined herein.

"Alkyl" or "lower alkyl" means a linear or branched hydrocarbon group having one to six carbon atoms. Examples of lower alkyl groups include methyl, ethyl, propyl, isopropyl, butyl, s-butyl, t-butyl, isobutyl, pentyl, hexyl and the like. A "$C_0$" alkyl (as in "$C_0$-$C_6$-alkyl") is a covalent bond. "$C_6$ alkyl" refers to, for example, n-hexyl, iso-hexyl, and the like.

"Alkylamino" means a —NHR radical where R is alkyl as defined herein, or an N-oxide derivative thereof, e.g., methylamino, ethylamino, n-, iso-propylamino, n-, iso-, tert-butylamino, or methylamino-N-oxide, and the like.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a C(O)R group where R is alkyl, as defined herein.

"Alkylcarbonylamino" means a —NRC(O)R' group where R is hydrogen or alkyl, as defined herein, and R' is alkyl, as defined herein.

"Alkylene" refers to straight or branched divalent hydrocarbon, containing no unsaturation and having from two to eight carbon atoms. Examples of alkylene include ethdiyl (—$CH_2CH_2$—), prop-1,3-diyl (—$CH_2CH_2CH_2$—), 2,2-dimethylprop-1,3-diyl (—$CH_2C(CH_3)_2CH_2$—), and the like.

"Alkylsulfonyl" means a —$S(O)_2R$ group where R is alkyl, as defined herein.

"Alkylthio" means a —SR group where R is alkyl, as defined herein. Examples of alkylthio include methylthio and ethylthio, and the like.

"Alkylthioalkyl" means an alkyl group substituted with one or two alkylthio groups, as defined herein, e.g. 2-(methylthio)-ethyl and 2-(ethylthio)-ethyl.

"Alkynyl" or "lower alkynyl" means a straight or branched hydrocarbon radical having from 2 to 6 carbon atoms and at least one triple bond and includes ethynyl, propynyl, butynyl, pentyn-2-yl and the like.

"Amino" means a —$NH_2$.

"Aminoalkyl" means an alkyl group substituted with at least one, specifically one, two, or three, amino groups.

"Aminoalkyloxy" means an —OR group where R is aminoalkyl, as defined herein.

"Aryl" means a monovalent six- to fourteen-membered, mono- or bi-carbocyclic ring, wherein the monocyclic ring is aromatic and at least one of the rings in the bicyclic ring is aromatic. Representative examples include phenyl, naphthyl, and indanyl, and the like.

"Arylalkyl" means an alkyl group, as defined herein, substituted with one or two aryl groups, as defined herein. Examples include benzyl, phenethyl, phenylvinyl, phenylallyl and the like.

"Aryloxy" means a —OR group where R is aryl as defined herein.

"Arylalkyloxy" means a —OR group where R is arylalkyl as defined herein.

"Arylsulfonyl" means a —$SO_2R$ group where R is aryl as defined herein.

"Carboxyalkyl" means an alkyl group, as defined herein, substituted with one, two, or three —C(O)OH groups.

"Carboxy ester" means a —C(O)OR group where R is lower alkyl, lower alkenyl, lower alkynyl, cycloalkyl, aryl or arylalkyl, each of which is defined herein. Representative examples include methoxycarbonyl, ethoxycarbonyl, and benzyloxycarbonyl, and the like.

"Cyanoalkyl" means an alkyl, alkenyl, or alkynyl radical, as defined herein, substituted with at least one, specifically one, two, or three, cyano groups.

"Cycloalkyl" means a monocyclic or polycyclic hydrocarbon radical having three to thirteen carbon atoms. The cycloalkyl can be saturated or partially unsaturated, but cannot contain an aromatic ring. Cycloalkyl includes fused, bridged, and spiro ring systems. Examples of such radicals include cyclopropyl, cyclobutyl, cyclopentyl and cyclohexyl.

"Cycloalkylalkyl" means alkyl group substituted with one or two cycloalkyl group(s), as defined herein. Representative examples include cyclopropylmethyl and 2-cyclobutyl-ethyl, and the like.

"Cycloalkylcarbonyl" means a —C(O)R group where R is cycloalkyl as defined herein.

"Dialkylamino" means a —NRR' radical where R and R' are independently alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or dialkylamino group(s), as defined herein.

"Dialkylaminoalkyloxy" means an —OR group where R is dialkylaminoalkyl, as defined herein.

"Fused ring system" and "fused ring" refer to a polycyclic ring system that contains bridged or fused rings; that is, where two rings have more than one shared atom in their ring structures. In this application, fused-polyciclics and fused ring systems are not necessarily all aromatic ring systems. Typically, but not necessarily, fused-polycyclics share a vicinal set of atoms, for example naphthalene or 1,2,3,4-tetrahydronaphthalene. A spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Haloalkoxy" means an —OR' group where R' is haloalkyl as defined herein, e.g., trifluoromethoxy or 2,2,2-trifluoroethoxy, and the like.

"Haloalkoxyalkyl" means an alkyl group, as defined herein, substituted with one, two, or three haloalkoxy, as defined herein.

"Halogen" or "halo" means fluoro, chloro, bromo and iodo.

"Haloalkenyl means an alkenyl group, as defined herein, substituted with one or more halogens, specifically one to five halo atoms.

"Haloalkyl" means an alkyl group, as defined herein, substituted with one or more halogens, specifically one to five halo atoms. Representative examples includes 2,2-difluoroethyl, trifluoromethyl, and 2-chloro-1-fluoroethyl, and the like.

"Heteroaryl" means a monocyclic, fused bicyclic, or fused tricyclic, monovalent radical of 5 to 14 ring atoms containing one or more, specifically one, two, three, or four ring heteroatoms independently selected from —O—, —S(O)$_n$— (n is 0, 1, or 2), —N—, —N(R$^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^x$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. In particular, when the point of valency is located on the nitrogen, R$^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Heteroarylalkyl" means an alkyl group substituted with one or two heteroaryl group(s) as defined herein.

"Heterocycloalkyl" means a saturated or partially unsaturated monovalent monocyclic group of 3 to 8 ring atoms or a saturated or partially unsaturated monovalent fused bicyclic group of 5 to 12 ring atoms in which one or more, specifically one, two, three, or four ring heteroatoms independently selected from —O—, —S(O)$_n$— (n is 0, 1, or 2), —N=, —N(R$^y$)— (where R$^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. In particular, when the point of valency is located on a nitrogen atom, R$^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof and N-oxide or a protected derivative thereof.

"Heterocycloalkylalkyl" means an alkyl group, as defined herein, substituted with one or two heterocycloalkyl group(s), as defined herein.

"Hydroxyalkyl" means an alkyl radical, as defined herein, substituted with at least one, specifically one, two, or three, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, specifically 2-hydroxyethyl, 2,3-dihydroxypropyl, or 1-(hydroxymethyl)-2-hydroxyethyl, and the like.

"Hydroxyamino" means a —NH(OH) group.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylC$_{1-8}$ alkyl," both the "C$_{1-8}$alkyl" portion and the "aryl" portion of the molecule may or may not be substituted. A list of exemplary optional substitutions is presented below in the definition of "substituted."

"Optionally substituted alkyl" means an alkyl radical, as defined herein, optionally substituted with one or more group(s), specifically one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, optionally substituted alkenyl, optionally substituted alkynyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, alkyl, optionally substituted alkenyl, optionally substituted alkynyl, hydroxy, alkoxy, alkenyloxy, or cyanoalkyl).

"Optionally substituted alkenyl" means an alkenyl radical, as defined herein, optionally substituted with one or more group(s), specifically one, two, or three groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, optionally substituted alkyl, optionally substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, optionally substituted alkyl, alkenyl, optionally substituted alkynyl, hydroxy, alkoxy, or alkenyloxy).

"Optionally substituted aryl" means an aryl group, as defined herein, which is optionally substituted with one, two, three, four, of five groups selected from halo, haloalkyl, haloalkoxy, hydroxy, lower alkyl, lower alkenyl, lower alkynyl, alkoxy, carboxy, carboxy ester, amino, alkylamino, dialkylamino, optionally substituted cycloalkyl, optionally substituted heterocycloalkyl, optionally substituted heteroaryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted heteroaryl" means a heteroaryl group, as defined herein, optionally substituted with one, two, three, four, or five groups selected from halo, haloalkyl, haloalkoxy, lower alkyl, lower alkenyl, lower alkynyl, alkoxy, hydroxy, oxo (valency rules permitting), carboxy, carboxy ester, amino, alkylamino, dialkylamino, optionally substituted cycloalkyl, optionally substituted heterocycloalkyl, heteroaryl, optionally substituted aryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted heterocycloalkyl" means a heterocycloalkyl, as defined herein, optionally substituted with one, two, three, four, or five groups selected from halo, haloalkyl, haloalkoxy, hydroxy, oxo, lower alkyl, lower alkenyl, lower alkynyl, alkoxy, optionally substituted cycloalkyl, heterocycloalkyl, optionally substituted aryl, optionally substituted heteroaryl, alkylaminoalkyl, dialkylaminoalkyl, carboxy, carboxy ester, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), amino, alkylamino, dialkylamino, and —NHS(O)$_2$R' (where R' is alkyl, aryl, or heteroaryl).

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings C and C'), but not a bridgehead atom, can be a shared atom between the saturated bridged ring system and a spirocyclyl (ring D) attached thereto. A spirocyclyl can be carbocyclic or heteroalicyclic.

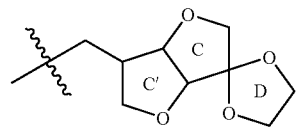

"Patient" for the purposes of the present invention includes humans and other animals, particularly mammals, and other organisms. Thus the methods are applicable to both human therapy and veterinary applications. In a specific embodiment the patient is a mammal, and in a more specific embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma], vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Specific salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the active ingredient of the above formulae, for example, by hydrolysis in blood. Common examples of a prodrug include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons).

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

EMBODIMENTS OF THE INVENTION

One embodiment (A) of the invention is directed to a compound of Formula I where $W^1$, $W^2$, $W^3$, and $W^4$ are —C($R^1$)=; or one or two of $W^1$, $W^2$, $W^3$, and $W^4$ are independently —N= and the remaining are —C($R^1$)=; where each $R^1$ is independently hydrogen, alkyl, haloalkyl, nitro, alkoxy, haloalkoxy, halo, hydroxy, cyano, amino, alkylamino, or dialkylamino; and all other groups are as defined in the Summary of the Invention. Specifically, $W^1$, $W^2$, $W^3$, and $W^4$ are —C($R^1$)= and each $R^1$ is independently hydrogen or alkyl; or one of $W^1$ and $W^4$ is —N= and the other is —C(H)=. More specifically, $W^1$, $W^2$, $W^3$, and $W^4$ are —C($R^1$)= where each $R^1$ is independently hydrogen or alkyl. Even more specifically, $R^1$ is hydrogen.

Another embodiment (B) of the invention is a Compound of Formula I where $R^{50}$ is hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$NR$^{55}$R$^{55a}$, or alkylcarbonylamino; where $R^{55}$ and $R^{55b}$ are independently hydrogen, alkyl, or alkenyl and $R^{55a}$ is hydrogen, alkyl, alkenyl, hydroxy, or alkoxy; and all other groups are as defined in the Summary of the Invention. Specifically, $R^{50}$ is hydrogen.

Another embodiment (C) of the invention is a Compound of Formula I where $R^{51}$ is hydrogen or alkyl; and all other groups are as defined in the Summary of the Invention. Specifically, $R^{51}$ is alkyl, More specifically, $R^{51}$ is methyl.

Another embodiment (D) of the invention is a Compound of Formula I where $R^{52}$ is hydrogen or halo; and all other groups are as defined in the Summary of the Invention. Specifically $R^{52}$ is hydrogen or fluoro. More specifically, $R^{52}$ is hydrogen.

Another embodiment (E) of the invention is a Compound of Formula I where $R^{53}$ is hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$NR$^{55}$R$^{55a}$, or alkylcarbonylamino; where $R^{55}$ and $R^{55b}$ are independently hydrogen, alkyl, or alkenyl and $R^{55a}$ is hydrogen, alkyl, alkenyl, hydroxy, or alkoxy; and all other groups are as defined in the Summary of the Invention. Specifically, $R^{53}$ is hydrogen, alkoxy, nitro, amino, or —N($R^{55}$)C(O)—$C_1$-$C_6$-alkylene-N($R^{55a}$)$R^{55b}$. More specifically, $R^{53}$ is hydrogen, methoxy, nitro, amino, or —NHC(O)CH$_2$N(CH$_3$)$_2$. Even more specifically, $R^{53}$ is hydrogen or methoxy.

Another embodiment (F) of the invention is a Compound of Formula I where $R^{54}$ is hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$NR$^{55}$R$^{55a}$, or alkylcarbonylamino; where $R^{55}$ and $R^{55b}$ are independently hydrogen, alkyl, or alkenyl and $R^{55a}$ is hydrogen, alkyl, alkenyl, hydroxy, or alkoxy; and all other groups are as defined in the Summary of the Invention. Specifically, $R^{54}$ is hydrogen, alkyl, alkoxy, or halo. More specifically, $R^{54}$ is hydrogen, methyl, methoxy, bromo, or chloro. Even more specifically, $R^{54}$ is hydrogen, methoxy, or chloro.

Another embodiment (G) of the invention is directed to a compound of Formula I where $R^{50}$, $R^{52}$, and $R^{53}$ are hydrogen and $R^{54}$ is halo or alkoxy; $R^{50}$, $R^{52}$, and $R^{54}$ are hydrogen and $R^{53}$ is alkoxy; or $R^{50}$ and $R^{52}$ are hydrogen and $R^{53}$ and $R^{54}$ together with the carbons to which they are attached form a 6-membered heteroaryl; and all other groups are as defined in the Summary of the Invention. More specifically, $R^{50}$, $R^{52}$, and $R^{53}$ are hydrogen and $R^{54}$ is chloro or methoxy; $R^{50}$, $R^{52}$, and $R^{54}$ are hydrogen and $R^{53}$ is methoxy; or $R^{50}$ and $R^{52}$ are hydrogen and $R^{53}$ and $R^{54}$ together with the carbons to which they are attached form pyridinyl. Even more specifically, $R^{50}$, $R^{52}$, and $R^{53}$ are hydrogen and $R^{54}$ is chloro or methoxy; or $R^{50}$, $R^{52}$, and $R^{54}$ are hydrogen and $R^{53}$ is methoxy.

In a more specific embodiment (G1) of embodiment G is a compound of Formula I where $R^{51}$ is methyl.

Another embodiment (H) of the invention is a compound of Formula I where B is phenyl substituted with $R^{3a}$ and optionally further substituted with one, two, or three $R^3$; and all other groups are as defined in the Summary of the Invention. Specifically, B is phenyl substituted with $R^{3a}$. More specifically the Compound is of Formula I(a):

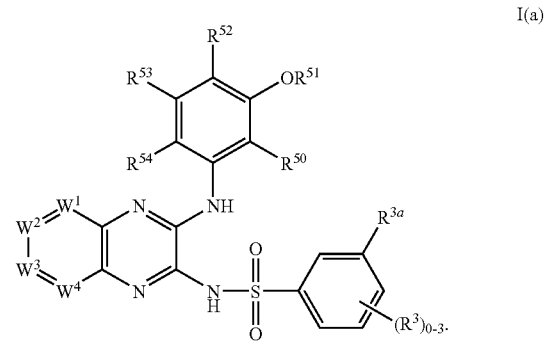

Even more specifically, B is phenyl substituted with $R^{3a}$ as depicted in Ia and is not further substituted with $R^3$.

Another embodiment of the Invention (J) is directed to a compound of Formula I where B is heteroaryl optionally substituted with one, two, or three $R^3$. Specifically, B is thien-3-yl, pyridinyl, pyrimidinyl, pyridazinyl, pyrazinyl, oxazolyl, isoxazolyl, pyrrolyl, imidazolyl, pyrazolyl, or thiazolyl, each of which is optionally substituted with one or two $R^3$. More specifically, B is thien-3-yl, pyridin-2-yl, pyridin-3-yl, pyridin-4-yl, oxazol-2-yl, oxazol-4-yl, oxazol-5-yl, isoxazol-3-yl, isoxazol-4-yl, isoxazol-5-yl, imidazol-2-yl, pyrrol-2-yl, pyrrol-3-yl, imidazol-4-yl, imidazol-5-yl, pyrazol-3-yl, pyrazol-4-yl, or pyrazol-5-yl, each of which is optionally substituted with one or two $R^3$. Even more specifically, B is thien-3-yl, pyridin-3-yl, pyridin-4-yl, isoxazol-4-yl, or pyrazol-4-yl, each of which is optionally substituted with one or two $R^3$. Yet even more specifically, B is pyridin-3-yl, 2-hydroxypyridin-5-yl, isoxazol-4-yl, or pyrazol-4-yl, each of which is optionally substituted with one or two $R^3$.

Another embodiment (K) provides a compound of Formula I or Ia where $R^{3a}$ is cyano; hydroxyamino; carboxy; alkylsulfonyl, aminoalkyloxy; alkylaminoalkyloxy; dialkylaminoalkyloxy; —N($R^7$)C(O)—$C_1$-$C_6$-alkylene-N($R^{7a}$)($R^{7b}$); —C(O)N$R^8R^{8a}$; —N$R^9$C(O)$R^{9a}$; —C(O)N($R^{10}$)—$C_1$-$C_6$-alkylene-N($R^{10a}$)$R^{11b}$; —N$R^{11}$C(O)N$R^{11a}R^{11b}$ where $R^{11a}$; —C(O)$R^{12}$; —N$R^{13}$C(O)O$R^{13a}$; —C(O)N($R^{14}$)N($R^{14a}$)($R^{14b}$); —S(O)$_2$N($R^{15}$)—$C_1$-$C_6$-alkylene-N($R^{15a}$)$R^{15b}$; —C(O)N($R^{16}$)—$C_1$-$C_6$-alkylene-C(O)O$R^{16a}$; heteroaryl optionally substituted with one or two aminoalkyl, alkylaminoalkyl, or dialkylaminoalkyl; —N($R^{17}$)—C(=N($R^{17b}$)($R^{17a}$))(N$R^{17c}R^{17d}$); —N($R^{18}$)C(O)—$C_1$-$C_6$-alkylene-N($R^{8b}$)C(O)$R^{18a}$; —C(O)N($R^{19}$)—$C_1$-$C_6$-alkylene-C(O)$R^{19a}$; —N($R^{22}$)C(O)—$C_1$-$C_6$-alkylene-N($R^{22b}$)—N($R^{22c}$)($R^{22a}$); —$C_0$-$C_6$-alkylene-N($R^{23}$)—$C_1$-$C_6$-alkylene-N($R^{23b}$)$R^{23a}$; or —N$R^{24}$C(O)—$C_1$-$C_6$-alkylene-O$R^{24a}$; where each of the alkylene in $R^{3a}$ is independently optionally further substituted with 1, 2, 3, 4, or groups selected from halo, hydroxy, amino, alkylamino, and dialkylamino; and all other groups are as defined in the Summary of the Invention.

Specifically, $R^{3a}$ is —NHC(O)CH$_2$NH(CH$_3$), —NHC(O)CH$_2$NH(CH$_2$CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, —NHC(O)CH(CH$_3$)NH(CH$_3$), —NHC(O)CH$_2$NH$_2$, —NHC(O)H, —NHC(O)CH$_2$ (azetidin-1-yl), —NHC(O)(pyrrolidin-2-yl), —NHC(O)CH(NH$_2$)CH$_2$OH, —NHC(O)(azetidin-4-yl), —NHC(O)C(CH$_3$)$_2$NH(CH$_3$), —NH$_2$, —NHC(O)CH$_2$NH(CH$_2$CH$_3$), —NHC(O)CH$_2$CH$_2$NH$_2$, —NHOH, —NHC(O)(piperidin-3-yl), —NHC(O)CH$_2$ (4-methyl-1,4-diazepan-1-yl), —NHC(O)CH(NH$_2$)(CH$_2$CH$_3$), —NHC(O)CH$_2$NH(CH$_2$CH(OH)(CH$_3$)), —NHC(O)CH$_2$NHCH$_2$CH$_2$F, —NHC(O)CH$_2$NH(OCH$_2$CH(CH$_3$)$_2$), —NHC(O)(1-aminocycloprop-1-yl), —NHC(O)CH$_2$NH(CH$_2$cyclopropyl), —NHC(O)CH$_2$ (3-(dimethylamino)-azetidin-1-yl), —NHC(O)(piperidin-2-yl), —NHC(O)(morpholin-4-yl), —NHC(O)CH$_2$ (pyrrolidin-1-yl), —NHC(O)CH(NH$_2$)CH$_2$CH$_2$CH$_2$CH$_2$N(CH$_3$)$_2$, —NHC(O)CH$_2$N(CH$_3$)(CH$_2$CH$_3$), —NHC(O)CH$_2$ (imidazol-5-yl), —NHC(O)(1-aminocyclopent-1-yl), —NHC(O)CH$_2$NH(CH$_2$CH(CH$_3$)$_2$), —NHC(O)CH$_2$N(CH$_3$)(CH$_2$CH$_3$), —NHC(O)(N-(imidazol-4-ylmethyl)-azetidin-3-yl), —NHC(O)(N-ethyl-azetidin-3-yl), —NHCH$_2$N(CH$_3$)CH$_2$CH$_2$N(CH$_3$)$_2$, —NHC(O)CH$_2$N(CH$_3$)(N-methyl-pyrrolidin-3-yl), —NHC(O)CH$_2$N(CH$_3$)(CH$_2$CH$_2$N(CH$_3$)$_2$), —NHC(O)CH$_2$ (3-hydroxy-pyrrolidin-1-yl), —NHC(O)(1-amino-cyclobut-1-yl), —NHC(O)CH$_2$NH(CH$_2$)$_3$CH$_3$, —NHC(O)CH$_2$ (3-piperidin-1-ylazetidin-1yl), —NHC(O)NH$_2$, —NHC(O)(1-hydroxycyclopropyl), —NHC(O)CH$_2$NHN(CH$_3$)$_2$, —NHC(O)NH(CH$_2$)$_2$N(CH$_3$)$_2$, —NHC(O)CH$_2$OH, —NHC(O)(pyridazin-4-yl), —NHC(O)(N-methyl-piperidin-4-yl), —NHC(O)CH$_2$NHCH(CH$_3$)$_3$, —NHC(O)CH$_2$(3-dimethylamino-pyrrolidin-1-yl), —NHC(O)CH$_2$NH(CH$_2$)$_2$N(CH$_3$)$_2$, —NHC(O)(1-cyclopropylmethyl-azetidin-3-yl), —NHC(O)CH$_2$NH(CH$_3$)$_3$, —NHC(O)(imidazol-2-yl), —NHC(O)(imidazol-4-yl), —NHC(O)(1,2-oxazol-5-yl), —NHC(O)CH$_2$NHCH$_2$CF$_3$, —NHC(O)CH$_2$CH$_2$(piperidin-1-yl), —NHC(O)(3-oxo-cyclopent-1-yl), —NHC(O)(2-hydroxy-pyridin-6-yl), —NHC(O)CH$_2$NH(3-fluoro-4-hydroxyphenyl), —NHC(O)(CH$_2$)$_3$N(CH$_3$)$_2$, —NHC(O)(1-(furan-2-ylmethyl)-azetidin-3-yl), —NHC(O)(pyrimidin-5-yl), —NHC(O)(pyrrol-2-yl), —NHC(O)CH$_2$N(CH$_3$)CH(CH$_3$)$_2$, —NHC(O)CH$_2$N(CH$_3$)$_2$, —NHC(O)CH$_2$ (3-methyl-1,2-oxazol-5-yl), —NHC(O)CH$_2$NHCH$_2$ (3-hydroxyphenyl), —NHC(O)(N-methyl-pyrrol-2-yl), —NHC(O)(2-amino-tetrahydropyran-2-yl), —NHC(O)CH$_2$ (4-methylamino-piperidin-1-yl), —NHC(O)(piperidin-1-yl), —NH—C(O)(N-methyl-pyrrolidin-2-yl), —NHC(O)(thien-3-yl), —NHC(O)(N-(cyclopropylcarbonyl)azetidin-3-yl), —NHC(O)CH$_2$ (4-methylpiperazin-1-yl), —NHC(O)(N-benzylazetidine-3-yl), —NHC(O)(2-chloro-pyridin-3-yl), —NHC(O)CH$_2$ (pyridin-4-yl), —NHC(O)CH$_2$N(CH$_3$)(CH$_2$CH=CH$_2$), —NHC(O)CH$_2$NH(benzyl), —NHC(O)CH$_2$OCH$_3$, —NHC(O) [1-(C(O)CH$_2$CH$_3$)-azetidin-3-yl], —NHC(O)(pyridin-3-yl), —NHC(O)CH$_2$NHCH$_2$CH$_2$OCH$_3$, —NHC(O)(1-[C(O)CH$_3$]piperidin-4-yl), —NHC(O)CH$_2$ (2-methyl-pyrrolidin-1-yl), —NHC(O)(furan-3-yl), —NHC(O)CH$_2$N(CH$_3$)$_2$, —NHC(O)(2-chloro-pyridin-5-yl), —NHC(O)(2-chlorophenyl), —NHC(O)CH$_2$ (pyridin-2-yl), —NHC(O)CH$_2$ (3-dimethylamino-azetidin-1-yl), —NHC(O)CH$_2$ (pyridin-3-yl), —NHC(O)CH$_2$ (2-chlorophenyl), —NHC(O)CH$_2$N(CH$_3$)CH$_2$CH$_2$CH$_2$N(CH$_3$)$_2$, —NHC(O)CH$_2$N(CH$_2$CH$_3$)CH$_2$CH$_2$OH, —NHC(O)CH$_2$ (2-benzyl-pyrrolidin-1-yl), —NHC(O)(furan-2-yl), —NHC(O)(2-chloro-pyridin-4-yl), —NHC(O)CH$_2$NHC(O)CH$_3$, —NHC(O)CH$_2$CH$_2$CH$_3$, —NHC(O)(4-chlorophenyl), —NHC(O)(4-methyl-phenyl), —NHC(O)CH$_2$NHC(O)O(CH$_3$)$_3$, —NHC(O)(benzo[d][1,3]dioxol-5-yl), —NHC(O)CH$_2$NHOCH$_2$ (2-methoxyphenyl), —NHC(O)(pyridin-4-yl), —NHC(O)CH$_2$[4-(3,4-dichlorophenyl)-piperazin-1-yl], —NHC(O)CH$_2$ (pyridin-3-yl), —NHC(O)(tetrahydrofuran-3-yl), —NHC(O)CH$_2$NHCH$_2$ (2-methylphenyl), —NHC(O)CH(CH$_3$)CH$_2$CH$_3$, —NHC(O)CH$_2$ (3-fluorophenyl), —NHC(O)CH$_2$C(CH$_3$)$_2$-phenyl, —NHC(O)(2-methyl-cycloprop-1-yl), —NHC(O)(2-methyl-4-methoxyphenyl), —NHC(O)(2-methylpyridin-3-yl), —NHC(O)(4-methoxyphenyl), —NHC(O)CH$_2$(4-ethylpiperazin-1-yl), —NHC(O)(thien-2-yl), —NHC(O)(3-fluoro-2-methylphenyl), —NHC(O)(2-bromo-thien-3-yl), —NHC(O)(4-fluorophenyl), —NHC(O)CH$_2$(3-methylpiperidin-1-yl), —NHC(O)CH(CH$_3$)$_2$, —NHC(O)(CH$_2$)$_3$CH$_3$, —NHC(O)CH$_2$OCH$_2$CH$_3$, —NHC(O)CH$_2$NH(2-fluorophenyl), —NHC(O)(3-dimethylaminophenyl), —NHC(O)CH$_2$(4-methylpiperidin-1-yl), —NHC(O)CH$_2$NH(2-n-propylphenyl), —NHC(O)phenyl, —NHC(O)(pyrazin2-yl), —NHC(O)(3-fluoro-4-methoxyphenyl), —NHC(O)C(CH$_3$)$_2$CH$_2$CH$_3$, —NHC(O)CH$_2$O(4-fluorophenyl), —NHC(O)(1-methylcarbonyl-azetidin-3-yl), —NHC(O)CH$_2$NH(4-methylphenyl), —NHC(O)CH$_2$NH(phenyl), —NHC(O)CH$_2$ (4-allyl-piperazin-1-yl), —NHC(O)(2-methylphenyl), —NHC(O)CH$_2$CH$_2$OCH$_3$, —NHC(O)(3-methyl-furan-2-yl), —NHC(O)C(CH$_3$)$_3$, —NHC(O)CH$_2$NHObenzyl, —NHC(O)CH$_2$NH(3-chlorophenyl), —NH—C(O)cyclobutyl, —NHC(O)CH$_2$(3-methoxyphenyl), —NHC(O)(1-methylcycloprop-1-yl), —NHC(O)(3-fluorophenyl), —NHC(O)(4-dimethylaminophenyl), —NHC(O)(3,4-dichlorophenyl), —NHC(O)CH$_2$NHCH$_2$ (2-methylthiophenyl), —NHC(O)CH$_2$ (2-fluorophenyl), —NHC(O)CH$_2$N(CH$_2$CH$_3$)CH(CH$_3$)$_2$, —NHC(O)(thiazol-4-yl), —NHC(O)CH$_2$N(CH$_3$)benzyl, —NHC(O)CH$_2$NHCH$_2$ (thien-2-yl), —NHC(O)CH$_2$NHCH$_2$ (pyridin-2-yl), —NHC(O)(3-methoxyphenyl), —NHC(O)CH$_2$NHCH$_2$ (3-chloro-4-methylphenyl), —NHC(O)CH(CH$_3$)CH$_2$CH$_2$CH$_3$, —NHC(O)CH$_2$ (4-chlorophenyl), —NHC(O)(3-fluoro-4-methylphenyl), —NHC(O)CH$_2$O(2-methylphenyl), —NHC(O)CH$_2$ (cyclohexyl), —NHC(O)(2-phenyl-cycloprop-1-yl), —NHC(O)(3-chlorophenyl), —NHC(O)CH$_2$ (2-methoxyphenyl), —NHC(O)CH$_2$CH$_2$ (3-methoxyphenyl), —NHC(O)CH$_2$NH(2-fluoro-4-methylphenyl), —NHC(O)CH$_2$NHCH$_2$ (3-fluoro-phenyl), —NHC(O)CH$_2$ (4-methoxy-phenyl), —NHC(O)benzyl, —NHC(O)(2,4-dichlorophenyl), —NH—C(O)(3-oxo-cyclohex-1-yl), —NHC(O)CH$_2$NH(3-fluorophenyl), —NHC(O)CH$_2$ (3-chlorophenyl), —NHC(O)CH₂NHCH₂CH(CH₃)phenyl, —NHC(O)CH₂NHCH₂ (2,4-dimethylphenyl), —NHC(O)CH₂ (2-methyl-piperidin-1-yl), —NHC(O)CH₂NH(2-methoxyphenyl), —NHC(O)CH₂ (1,2,3,4-tetrahydroisoquinolin-2-yl), —NHC(O)CH₂CH₂CH=CH₂, —NHC(O)CH₂NH(2-methylphenyl), —NHC(O)CH₂ (4-oxo-piperidin-1-yl), —NHC(O)(2-fluorophenyl), —NHC(O)CH₂NHCH(CH₃) phenyl, —NHC(O)(2-fluoro-6-methoxyphenyl), —NHC(O)CH₂NH(2-isopropylphenyl), —NH—C(O)CH₂CH₂ (2-methoxyphenyl), —NHC(O)CH₂CH₂CH(CH₃)₂, —NHC(O)CH₂ (2-phenyl-morpholin-4-yl), —NHC(O)CH₂CH₂(4-methoxyphenyl), —NHC(O)CH₂N(allyl)cyclopentyl, —NHC(O)CH₂N(CH₃)CH₂CH₂OCH₃, —NHC(O)CH₂CH₂C(O)cyclopropyl, —NHC(O)CH₂NH(3-tert-butylphenyl), —NHC(O)CH₂N(n-propyl)(cyclopropylmethyl), —NHC(O)CH₂ (2-oxo-cyclopentyl), —NHC(O)CH₂NH(4-chlorophenyl), —NHC(O)CH₂(4-piperidin-1-ylpiperidin-1-yl), —NHC(O)CH₂(4-cyclopentylpiperazin-1-yl), —NHC(O)CH₂(2-methylphenyl), —NHC(O)CH₂NHCH₂(3-fluoro-6-methylphenyl), —NHC(O)CH₂C(CH₃)₃, —NHC(O)CH₂NH(2-chlorophenyl), —NHC(O)(3-fluoro-6-methylphenyl), —NHC(O)(4-fluoro-3-methylphenyl), —NHC(O)(2,3-dichlorophenyl), —NH—C(O)CH₂Ophenyl, —NHC(O)CH₂NH(2,3-dimethylphenyl), —NHC(O)(2-fluoro-5-methylphenyl), —NHC(O)CH₂NHOCH₂ (4-methylphenyl), —NH—C(O)CH₂(4-isopropylpiperazin-1-yl), —NHC(O)CH₂(4-fluorophenyl), —NHC(O)CH₂CH(CH₃)₂, —NHC(O)(2-methoxy-4-methylphenyl), —NH—C(O)CH₂ (4-n-propylpiperidin-1-yl), —NHC(O)CH₂O(3-methylphenyl), —NH—C(O)(tetrahydrofuran-2-yl), —NHC(O)CH₂(3-hydroxymethylpiperidin-1-yl), —NHC(O)(1-tert-butoxycarbonylpiperidin-2-yl), —NH—C(O)CH₂N(CH₃)CH₂(pyridin-3-yl), —NHC(O)CH₂N(CH₂CH₃)phenyl, —NHC(O)CH₂OCH₂CH₂OCH₃, —NHC(O)CH₂CH₂ (cyclopentyl), —NHC(O)(2,5-dichlorophenyl), —NHC(O)CH₂(4-methylcarbonylpiperazin-1-yl), —NHC(O)(5-fluoro-2-methoxyphenyl), —NHC(O)CH₂N(CH₂CH₃)cyclohexyl, —NHC(O)(5-methyl-1,2-oxazol-3-yl), —NHC(O)(3-methylpyridin-3-yl), —NHC(O)(2-methoxypyridin-3-yl), —NHC(O)(3,5-dichlorophenyl), —NHC(O)CH₂(thiazolidin3-yl), —NHC(O)CH₂ (4-[C(O)H]-piperazin-1-yl), —NHC(O)CH₂ (2-pyridin-4-ylpiperidin-1-yl), —NHC(O)(2-methoxyphenyl), —NHC(O)CH₂N(CH₃)CH₂CH(CH₃)₂, —NHC(O)CH₂(4-[C(O)H]-homopiperazin-1-yl), —NHC(O)CH₂(1-phenylcycloprop-1-yl), —NHC(O)CH₂(2,6-dimethylmorpholin-4-yl), NHC(O)CH₂ (2-phenylpyrrolidin-1-yl), —NHC(O)CH₂(morpholin-4-yl), —C(O)NHCH(CH₃)CH₂N(CH₃)₂, —C(O)NHCH₂CH₂N(CH₃)₂, —C(O)NH(pyrrolidin-3-yl), —C(O)NHCH₂CH₂ (pyrrolidin-1-yl), —C(O)NHCH₂CH₂NH₂, —C(O)N(CH₃)CH₂CH₂N(CH₃)₂, —C(O)NHCH₂(piperidin-2-yl), —C(O)NH(1-methylazetidin-3-yl), —C(O)NHCH₂CH₂(piperidin-1-yl), —C(O)NHCH₂CH₂N(CH₂CH₃)₂, —C(O)NH(1-methylpiperidin-3-yl), —C(O)NH(piperidin-3-yl), —C(O)NHCH₂(1-methylpiperidin-3-yl), —C(O)NHCH₂CH₂N(CH₂CH₂OH)₂, —C(O)NH(1-ethylpiperidin-3-yl), —C(O)NH₂, —C(O)(3-aminopyrrolidin-1-yl), —C(O)(3-methylaminopyrrolidine-1-yl), —C(O)OH, —C(O)NHCH₂CH₂ (morpholin-4-yl), —C(O)NHCH₂ (1-ethylpyrrolidin-2-yl), —C(O)(4-amino-3-oxo-pyrazolidin-1-yl), —C(O)NHCH₃, —C(O)(3-aminocyclobut-1-yl), —C(O)NHCH₂ (pyridin-3-yl), —C(O)NHCH₂CH₂OH, —C(O)NH(3-oxo-pyrazolidin-4-yl), —NHCH₂ (imidazol-4-yl), —C(O)(3-dimethylaminopyrrolidin-1-yl), —C(O)NHCH₂ (pyridin-4-yl), —C(O)N(CH₃)(1-methyl-pyrrolidin-3-yl), —C(O)(3-diethylaminopyrrolidin-1-yl), —C(O)NH(pyrrol-1-yl), —C(O)NHCH₂CH₂CH₂ (pyrrolidin-1-yl), —C(O)N(CH₃)CH₂CH₂CN, —C(O)NHCH₂CH₂OCH₃, —C(O)N(CH₂CH₃)CH₂CH₂CN, —C(O)(3-aminopiperidin-1-yl), —C(O)NHCH₂CH₂CH₂N(CH₃)₂, —C(O)NH(morpholin-4-yl), —C(O)NHN(CH₃)₂, —C(O)NHCH₂CH₂CH₂(imidazol-1-yl), —C(O)NHCH₂CH₂CH₂N(CH₂CH₃)₂, —C(O)NHCH₂CH₂CN, —C(O)NHCH₂CH₂C(O)OCH₃, —C(O)NHCH₂CH₂SCH₃, —C(O)NHCH₂CH₂SCH₂CH₃, —C(O)N(CH₂CH₃)CH₂CH₂N(CH₃)₂, —C(O)NHCH₂CH₂CH₂ (2-oxo-pyrrolidin-1-yl), —C(O)NHCH₂CH₂ (pyridin-4-yl), —C(O)NHCH₂CH₂CH₂OCH₂CH₃, —C(O)NHCH₂CH₂CH₂ (morpholin-4-yl), —C(O)NHCH₂CH₂CH₂OCH₃, —C(O)N(CH₃)CH₂CH₂CH₂N(CH₃)₂, —C(O)NHCH₂CH₂CH₂OCH₂CH₃, —C(O)NHCH₂CH₂C(O)OCH₂CH₃, —C(O)NHCH₂CH₂CH₂OCH(CH₃)₂, —C(O)NHC(CH₃)₂CH₂(piperidin-1-yl), —C(O)N(CH₃)CH₂CH₂CH₃, —C(O)NH(piperidin-1-yl), —C(O)NHCH(CH₃)CH₂OCH₃, —C(O)NHC(CH₃)₂CH₂ (morpholin-4-yl), —C(O)(2-dimethylaminomethylpiperidin-1-yl), —C(O)NH(CH₂)₃O(CH₂)₃CH₃, —C(O)NHCH(CH₃)(CH₂)₃N(CH₂CH₃)₂, —C(O)NHC(CH₃)₂C(O)(piperidin-1-yl), —C(O)(4-methylpiperazin-1-yl), —C(O)(2-piperidin-1-yl-methyl-piperidin-1-yl), cyano, —NHCH₃, —CH(CH₃)NHCH₂CH₂N(CH₃)₂, —C(O)CH₃, —S(O)₂NHCH₂CH₂N(CH₃)₂, —S(O)₂NH(CH₂)₃N(CH₃)₂, 5-(N,N-dimethylaminomethyl)-1,3,4-oxadiazol-2-yl, —NHCH₂CH₂N(CH₃)₂, —N(CH₃)₂, —OCH₂CH₂N(CH₃)₂, —NHC[N(CH₃)₂][=N(CH₃)₂], —OCHF₂, —S(O)₂CH₃, —OCF₃, or —NHC(O)CH₂(4-dimethylaminopiperidin-1-yl).

In a more specific embodiment (L), the compound of Formula I or Ia is that where $R^{3a}$ is hydroxyamino, —N(R⁷)C(O)—C₁-C₆-alkylene-N(R⁷ᵃ)(R⁷ᵇ), —C(O)NR⁸R⁸ᵃ, —NR⁹C(O)R⁹ᵃ, —C(O)N(R¹⁰)—C₁-C₆-alkylene-N(R¹⁰ᵃ)R¹⁰ᵇ, NR¹¹C(O)NR¹¹ᵃR¹¹ᵇ, —N(R²²)C(O)—C₁-C₆-alkylene-N(R²²ᵇ)—N(R²²ᶜ)(R²²ᵃ), NR¹³C(O)OR¹³ᵃ, —N(R¹⁸)C(O)—C₁-C₆-alkylene-N(R¹⁸ᵇ)C(O)R¹⁸ᵃ, —NR²⁴C(O)—C₁-C₆-alkylene-OR²⁴ᵃ, or —N(R²⁰)C(O)—C₁-C₆-alkylene-C(O)R²⁰ᵃ; where each of the alkylene in $R^{3a}$ is independently optionally further substituted with 1, 2, 3, 4, or 5 groups selected from halo, hydroxy, and amino; and all other groups are as defined in the Summary of the Invention. Specifically, $R^{3a}$ is —NHC(O)CH₂NH(CH₃), —NHC(O)CH(CH₃)NH₂, —NHC(O)C(CH₃)₂NH₂, —NHC(O)CH₂N(CH₃)₂, —NHC(O)CH₂N(CH₃)CH₂CH₂N(CH₃)₂, —NHC(O)CH(NH₂)CH₂CH₃, —NHC(O)CH₂N(CH₃)CH₂CH₂N(CH₃)₂, —NHC(O)CH(CH₃)NH(CH₃), —NHC(O)H, —NHC(O)CH₂ (azetidin-1-yl), —NHC(O)(pyrrolidin-2-yl), —NHC(O)CH(NH₂)CH₂OH, —NHC(O)(azetidin-4-yl), —NHC(O)C(CH₃)₂NH(CH₃), —NH₂, —NHC(O)CH₂NH(CH₂CH₂CH₃), —NHC(O)CH₂CH₂NH₂, —NHOH, or —NHC(O)(piperidin-3-yl).

In a more specific embodiment (M) the compound is of Formula I or Ia and $R^{3a}$—N(R⁷)C(O)—C₁-C₆-alkylene-N(R⁷ᵃ)(R⁷ᵇ); and R⁷ is hydrogen or alkyl and R⁷ᵃ and R⁷ᵇ are independently hydrogen, alkyl, aminoalkyl, alkylaminoalkyl, or dialkylaminoalkyl; and all other groups are as defined in the Summary of the Invention. More specifically, $R^{3a}$ is —NHC(O)CH₂NH(CH₃), —NHC(O)CH(CH₃)NH₂, —NHC(O)C(CH₃)₂NH₂, —NHC(O)CH₂N(CH₃)₂, —NHC(O)CH₂N(CH₃)CH₂CH₂N(CH₃)₂, —NHC(O)CH(NH₂)CH₂CH₃, —NHC(O)CH₂N(CH₃)CH₂CH₂N(CH₃)₂, or —NHC(O)CH(CH₃)NH(CH₃).

Embodiment (N) provides a compound of Formula I where each R³ is independently halo; cyano; alkyl; alkenyl; alkoxy; hydroxyamino; carboxy; alkylsulfonyl, aminoalkyloxy; alkylaminoalkyloxy; dialkylaminoalkyloxy; —N(R⁷)C (O)—C$_1$-C$_6$-alkylene-N(R$^{7a}$)(R$^{7b}$); —C(O)NR$^8$R$^{8a}$; —NR$^9$C(O)R$^{9a}$; —C(O)N(R$^{10}$)—C$_1$-C$_6$-alkylene-N(R$^{10a}$)R$^{10b}$; —NR$^{11}$C(O)NR$^{11a}$R$^{11b}$ where R$^{11a}$; —C(O)R$^{12}$; —NR$^{13}$C(O)OR$^{13a}$; —C(O)N(R$^{14}$)N(R$^{14a}$)(R$^{14b}$); —S(O)$_2$N(R$^{15}$)—C$_1$-C$_6$-alkylene-N(R$^{15a}$)R$^{15b}$; —C(O)N(R$^{16}$)—C$_1$-C$_6$-alkylene-C(O)OR$^{16a}$; heteroaryl optionally substituted with one or two aminoalkyl, alkylaminoalkyl, or dialkylaminoalkyl; —N(R$^{17}$)—C(═N(R$^{17b}$)(R$^{17a}$))(NR$^{17c}$R$^{17d}$); —N(R$^{18}$)C(O)—C$_1$-C$_6$-alkylene-N(R$^{18b}$)C(O)R$^{18a}$; —C(O)N(R$^9$)—C$_1$-C$_6$-alkylene-C(O)R$^{19a}$; —N(R$^{22}$)C(O)—C$_1$-C$_6$-alkylene-N(R$^{22b}$)—N(R$^{22c}$)(R$^{22a}$); —C$_0$-C$_6$-alkylene-N(R$^{23}$)—C$_1$-C$_6$-alkylene-N(R$^{23b}$)R$^{23a}$; or —NR$^{24}$C(O)—C$_1$-C$_6$-alkylene-OR$^{24a}$; where each of the alkylene in R$^3$ is independently optionally further substituted with 1, 2, 3, 4, or 5 groups selected from halo, hydroxy, amino, alkylamino, and dialkylamino; and all other groups are as defined in the Summary of the Invention.

Specifically, each R$^3$ is independently methyl, bromo, chloro, fluoro, —NHC(O)CH$_2$NH(CH$_3$), —NHC(O)CH$_2$NH(CH$_2$CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, —NHC(O)CH(CH$_3$)NH(CH$_3$), —NHC(O)CH$_2$NH$_2$, —NHC(O)H, —NHC(O)CH$_2$(azetidin-1-yl), —NHC(O)(pyrrolidin-2-yl), —NHC(O)CH(NH$_2$)CH$_2$OH, —NHC(O)(azetidin-4-yl), —NHC(O)C(CH$_3$)$_2$NH(CH$_3$), —NH$_2$, —NHC(O)CH$_2$NH(CH$_2$CH$_3$), —NHC(O)CH$_2$CH$_2$NH$_2$, —NHOH, —NHC(O)(piperidin-3-yl), —NHC(O)CH$_2$(4-methyl-1,4-diazepan-1-yl), —NHC(O)CH(NH$_2$)(CH$_2$CH$_3$), —NHC(O)CH$_2$NH(CH$_2$C$_2$CH(OH)(CH$_3$)), —NHC(O)CH$_2$NHCH$_2$CH$_2$F, —NHC(O)CH$_2$NH(OCH$_2$CH(CH$_3$)$_2$), —NHC(O)(1-aminocycloprop-1-yl), —NHC(O)CH$_2$NH(CH$_2$cyclopropyl), —NHC(O)CH$_2$(3-(dimethylamino)-azetidin-1-yl), —NHC(O)(piperidin-2-yl), —NHC(O)(morpholin-4-yl), —NHC(O)CH$_2$(pyrrolidin-1-yl), —NHC(O)CH(NH$_2$)CH$_2$CH$_2$CH$_2$CH$_2$N(CH$_3$)$_2$, —NHC(O)CH$_2$N(CH$_3$)(CH$_2$CH$_3$), —NHC(O)CH$_2$(imidazol-5-yl), —NHC(O)(1-aminocyclopent-1-yl), —NHC(O)CH$_2$NH(CH$_2$CH(CH$_3$)$_2$), —NHC(O)CH$_2$N(CH$_3$)(CH$_2$CH$_3$), —NHC(O)(N-(imidazol-4-ylmethyl)-azetidin-3-yl), —NHC(O)(N-ethyl-azetidin-3-yl), —NHCH$_2$N(CH$_3$)CH$_2$CH$_2$N(CH$_3$)$_2$, —NH—C(O)CH$_2$N(CH$_3$)(N-methyl-pyrrolidin-3-yl), —NHC(O)CH$_2$N(CH$_3$)(CH$_2$CH$_2$N(CH$_3$)$_2$), —NHC(O)CH$_2$(3-hydroxy-pyrrolidin-1-yl), —NHC(O)(1-amino-cyclobut-1-yl), —NHC(O)CH$_2$NH(CH$_2$)$_3$CH$_3$, —NHC(O)CH$_2$(3-piperidin-1-ylazetidin-1yl), —NHC(O)NH$_{12}$, —NHC(O)(1-hydroxycyclopropyl), —NHC(O)CH$_2$NHN(CH$_3$)$_2$, —NHC(O)N(CH$_2$)$_2$N(CH$_3$)$_2$, —NHC(O)CH$_2$OH, —NHC(O)(pyridazin-4-yl), —NHC(O)(N-methyl-piperidin-4-yl), —NHC(O)CH$_2$NHCH(CH$_3$)$_3$, —NH—C(O)CH$_2$(3-dimethylamino-pyrrolidin-1yl), —NHC(O)CH$_2$NH—(CH$_2$)$_2$N(CH$_3$)$_2$, —NHC(O)(1-cyclopropylmethyl-azetidin-3-yl), —NHC(O)CH$_2$NH(CH$_3$)$_3$, —NHC(O)(imidazol-2-yl), —NHC(O)(imidazol-4-yl), —NHC(O)(1,2-oxazol-5-yl), —NHC(O)CH$_2$NHCH$_2$CF$_3$, —NHC(O)CH$_2$CH$_2$(piperidin-1-yl), —NHC(O)(3-oxo-cyclopent-1-yl), —NHC(O)(2-hydroxy-pyridin-6-yl), —NHC(O)CH$_2$NH(3-fluoro-4-hydroxyphenyl), —NHC(O)(CH$_2$)$_3$N(CH$_3$)$_2$, —NH—C(O)(1-(furan-2-ylmethyl)-azetidin-3-yl), —NHC(O)(pyrimidin-5-yl), —NHC(O)(pyrrol-2-yl), —NHC(O)CH$_2$N(CH$_3$)CH(CH$_3$)$_2$, —NHC(O)CH$_2$N(CH$_2$CH$_3$)$_2$, —NHC(O)CH$_2$(3-methyl-1,2-oxazol-5-yl), —NHC(O)CH$_2$NHCH$_2$(3-hydroxyphenyl), —NHC(O)(N-methyl-pyrrol-2-yl), —NHC(O)(2-amino-tetrahydropyran-2-yl), —NHC(O)CH$_2$(4-methylamino-piperidin-1-yl), —NHC(O)(piperidin-1-yl), —NHC(O)(N-methyl-pyrrolidin-2-yl), —NHC(O)(thien-3-yl), —NHC(O)(N-(cyclopropylcarbonyl)azetidin-3-yl), —NHC(O)CH$_2$(4-methylpiperazin-1-yl), —NHC(O)(N-benzylazetidine-3-yl), —NHC(O)(2-chloro-pyridin-3-yl), —NHC(O)CH$_2$(pyridin-4-yl), —NHC(O)CH$_2$N(CH$_3$)(CH$_2$CH═CH$_2$), —NHC(O)CH$_2$NI-(benzyl), —NHC(O)CH$_2$OCH$_3$, —NHC(O)[1-(C(O)CH$_2$CH$_3$)-azetidin-3-yl], —NHC(O)(pyridin-3-yl), —NHC(O)CH$_2$NHCH$_2$CH$_2$OCH$_3$, —NHC(O)(1-[C(O)CH$_3$]piperidin-4-yl), —NHC(O)CH$_2$(2-methyl-pyrrolidin-1-yl), —NHC(O)(furan-3-yl), —NHC(O)CH$_2$N(CH$_3$)$_2$, —NHC(O)(2-chloro-pyridin-5-yl), —NHC(O)(2-chlorophenyl), —NHC(O)CH$_2$(pyridin-2-yl), —NHC(O)CH$_2$(3-dimethylamino-azetidin-1-yl), —NHC(O)CH$_2$(pyridin-3-yl), —NHC(O)CH$_2$(2-chlorophenyl), —NHC(O)CH$_2$N(CH$_3$)CH$_2$CH$_2$CH$_2$N(CH$_3$)$_2$, —NHC(O)CH$_2$N(CH$_2$CH$_3$)CH$_2$CH$_2$OH, —NHC(O)CH$_2$(2-benzyl-pyrrolidin-1-yl), —NH—C(O)(furan-2-yl, —NHC(O)(2-chloro-pyridin-4-yl), —NHC(O)CH$_2$NHC(O)CH$_3$, —NHC(O)CH$_2$CH$_2$CH$_3$, —NHC(O)(4-chlorophenyl), —NHC(O)(4-methyl-phenyl), —NHC(O)CH$_2$NHC(O)O(CH$_3$)$_3$, —NHC(O)(benzo[d][1,3]dioxol-5-yl), —NHC(O)CH$_2$NHOCH$_2$(2-methoxyphenyl), —NHC(O)(pyridin-4-yl), —NHC(O)CH$_2$[4-(3,4-dichlorophenyl)-piperazin-1-yl], —NHC(O)CH$_2$CH$_2$(pyridin-3-yl), —NHC(O)(tetrahydrofuran-3-yl), —NHC(O)CH$_2$NHCH$_2$(2-methylphenyl), —NHC(O)CH(CH$_3$)CH$_2$CH$_3$, —NHC(O)CH$_2$(3-fluorophenyl), —NHC(O)CH$_2$C(CH$_3$)$_2$-phenyl, —NHC(O)(2-methyl-cycloprop-1-yl), —NHC(O)(2-methyl-4-methoxyphenyl), —NHC(O)(2-methylpyridin-3-yl), —NHC(O)(4-methoxyphenyl), —NHC(O)CH$_2$(4-ethylpiperazin-1-yl), —NHC(O)(thien-2-yl), —NHC(O)(3-fluoro-2-methylphenyl), —NHC(O)(2-bromo-thien-3-yl), —NHC(O)(4-fluorophenyl), —NHC(O)CH$_2$(3-methylpiperidin-1-yl), —NHC(O)CH(CH$_3$)$_2$, —NHC(O)(CH$_2$)$_3$CH$_3$, —NHC(O)CH$_2$OCH$_2$CH$_3$, —NHC(O)CH$_2$NH(2-fluorophenyl), —NHC(O)(3-dimethylaminophenyl), —NHC(O)CH$_2$(4-methylpiperidin-1-yl), —NHC(O)CH$_2$NH(2-n-propylphenyl), —NHC(O)phenyl, —NHC(O)(pyrazin2-yl), —NHC(O)(3-fluoro-4-methoxyphenyl), —NHC(O)C(CH$_3$)$_2$CH$_2$CH$_3$, —NHC(O)CH$_2$O(4-fluorophenyl), —NHC(O)(1-methylcarbonyl-azetidin-3-yl), —NHC(O)CH$_2$NH-(4-methylphenyl), —NHC(O)CH$_2$NH(phenyl), —NHC(O)CH$_2$(4-allyl-piperazin-1-yl), —NHC(O)(2-methylphenyl), —NHC(O)CH$_2$CH$_2$OCH$_3$, —NHC(O)(3-methyl-furan-2-yl), —NHC(O)C(CH$_3$)$_3$, —NHC(O)CH$_2$NHObenzyl, —NHC(O)CH$_2$NH(3-chlorophenyl), —NHC(O)cyclobutyl, —NHC(O)CH$_2$(3-methoxyphenyl), —NHC(O)(1-methylcycloprop-1-yl), —NHC(O)(3-fluorophenyl), —NH—C(O)(4-dimethylaminophenyl), —NHC(O)(3,4-dichlorophenyl), —NHC(O)CH$_2$NHCH$_2$(2-methylthiophenyl), —NHC(O)CH$_2$(2-fluorophenyl), —NHC(O)CH$_2$N(CH$_2$CH$_3$)CH(CH$_3$)$_2$, —NHC(O)(thiazol-4-yl), —NHC(O)CH$_2$N(CH$_3$)benzyl, —NHC(O)CH$_2$NHCH$_2$(thien-2-yl), —NHC(O)CH$_2$NHCH$_2$(pyridin-2-yl), —NHC(O)(3-methoxyphenyl), —NHC(O)CH$_2$NHCH$_2$(3-chloro-4-methylphenyl), —NHC(O)CH(CH$_3$)CH$_2$CH$_2$CH$_3$, —NHC(O)CH$_2$(4-chlorophenyl), —NHC(O)(3-fluoro-4-methylphenyl), —NHC(O)CH$_2$O(2-methylphenyl), —NHC(O)CH$_2$(cyclohexyl), —NHC(O)(2-phenyl-cycloprop-1-yl), —NHC(O)(3-chlorophenyl), —NHC(O)CH$_2$(2-methoxyphenyl), —NHC(O)CH$_2$CH$_2$(3-methoxyphenyl), —NHC(O)CH$_2$NH(2-fluoro-4-methyl-phenyl), —NHC(O)CH$_2$NHCH$_2$(3-fluorophenyl), —NHC(O)CH$_2$(4-methoxy-phenyl), —NHC(O)benzyl, —NH—C(O)(2,4-dichlorophenyl), —NHC(O)(3-oxo-cyclohex-1-yl), —NHC(O)CH$_2$NH(3-fluorophenyl), —NHC(O)CH$_2$(3-chlorophenyl), —NHC(O)CH$_2$NHCH$_2$CH(CH$_3$)phenyl, —NHC(O)CH$_2$NHCH$_2$(2,4- dimethylphenyl), —NHC(O)CH$_2$(2-methyl-piperidin-1-yl), —NHC(O)CH$_2$NH(2-methoxyphenyl), —NHC(O)CH$_2$(1,2,3,4-tetrahydroisoquinolin-2-yl), —NHC(O)CH$_2$CH$_2$CH=CH$_2$, —NHC(O)CH$_2$NH(2-methylphenyl), —NHC(O)CH$_2$(4-oxo-piperidin-1-yl), —NHC(O)(2-fluorophenyl), —NHC(O)CH$_2$NH—CH(CH$_3$)phenyl, —NHC(O)(2-fluoro-6-methoxyphenyl), —NHC(O)CH$_2$NH(2-isopropylphenyl), —NHC(O)CH$_2$CH$_2$(2-methoxyphenyl), —NHC(O)CH$_2$CH$_2$CH(CH$_3$)$_2$, —NHC(O)CH$_2$(2-phenyl-morpholin-4-yl), —NHC(O)CH$_2$CH$_2$(4-methoxyphenyl), —NHC(O)CH$_2$N(allyl)cyclopentyl, —NHC(O)CH$_2$N(CH$_3$)CH$_2$CH$_2$OCH$_3$, —NHC(O)CH$_2$CH$_2$C(O)cyclopropyl, —NHC(O)CH$_2$NH(3-tert-butylphenyl), —NHC(O)CH$_2$N(n-propyl)(cyclopropylmethyl), —NHC(O)CH$_2$(2-oxo-cyclopentyl), —NHC(O)CH$_2$NH(4-chlorophenyl), —NHC(O)CH$_2$(4-piperidin-1-ylpiperidin-1-yl), —NHC(O)CH$_2$(4-cyclopentylpiperazin-1-yl), —NHC(O)CH$_2$(2-methylphenyl), —NH—C(O)CH$_2$NHCH$_2$(3-fluoro-6-methylphenyl), —NHC(O)CH$_2$C(CH$_3$)$_3$, —NHC(O)CH$_2$NH(2-chlorophenyl), —NHC(O)(3-fluoro-6-methylphenyl), —NHC(O)(4-fluoro-3-methylphenyl), —NHC(O)(2,3-dichlorophenyl), —NHC(O)CH$_2$Ophenyl, —NHC(O)CH$_2$NH(2,3-dimethylphenyl), —NHC(O)(2-fluoro-5-methylphenyl), —NHC(O)CH$_2$NHOCH$_2$(4-methylphenyl), —NHC(O)CH$_2$(4-isopropylpiperazin-1-yl), —NHC(O)CH$_2$(4-fluorophenyl), —NHC(O)CH$_2$CH(CH$_3$)$_2$, —NHC(O)(2-methoxy-4-methylphenyl), —NHC(O)CH$_2$(4-n-propylpiperidin-1-yl), —NH—C(O)CH$_2$O(3-methylphenyl), —NHC(O)(tetrahydrofuran-2-yl), —NHC(O)CH$_2$(3-hydroxymethylpiperidin-1-yl), —NHC(O)(1-tert-butoxycarbonylpiperidin-2-yl), —NHC(O)CH$_2$N(CH$_3$)CH$_2$(pyridin-3-yl), —NHC(O)CH$_2$N(CH$_2$CH$_3$)phenyl, —NHC(O)CH$_2$OCH$_2$CH$_2$OCH$_3$, —NHC(O)CH$_2$CH$_2$(cyclopentyl), —NHC(O)(2,5-dichlorophenyl), —NHC(O)CH$_2$(4-methylcarbonylpiperazin-1-yl), —NHC(O)(5-fluoro-2-methoxyphenyl), —NHC(O)CH$_2$N(CH$_2$CH$_3$)cyclohexyl, —NHC(O)(5-methyl-1,2-oxazol-3-yl), —NH—C(O)(3-methylpyridin-3-yl), —NHC(O)(2-methoxypyridin-3-yl), —NHC(O)(3,5-dichlorophenyl), —NHC(O)CH$_2$(thiazolidin3-yl), —NHC(O)CH$_2$(4-[C(O)H]-piperazin-1-yl), —NHC(O)CH$_2$(2-pyridin-4-ylpiperidin-1-yl), —NH—C(O)(2-methoxyphenyl), —NHC(O)CH$_2$N(CH$_3$)CH$_2$CH(CH$_3$)$_2$, —NHC(O)CH$_2$(4-[C(O)H]-homopiperazin-1-yl), —NHC(O)(1-phenylcycloprop-1-yl), —NHC(O)CH$_2$(2,6-dimethylmorpholin-4-yl), NHC(O)CH$_2$(2-phenylpyrrolidin-1-yl), —NHC(O)CH$_2$(morpholin-4-yl), —C(O)NHCH(CH$_3$)CH$_2$N(CH$_3$)$_2$, —C(O)NHCH$_2$CH$_2$N(CH$_3$)$_2$, —C(O)NH(pyrrolidin-3-yl), —C(O)NHCH$_2$CH$_2$(pyrrolidin-1-yl), —C(O)NHCH$_2$CH$_2$NH$_2$, —C(O)N(CH$_3$)CH$_2$CH$_2$N(CH$_3$)$_2$, —C(O)NHCH$_2$(piperidin-2-yl), —C(O)NH(1-methylazetidin-3-yl), —C(O)NHCH$_2$CH$_2$(piperidin-1-yl), —C(O)NHCH$_2$CH$_2$N(CH$_2$CH$_3$)$_2$, —C(O)NH(1-methylpiperidin-3-yl), —C(O)NH-(piperidin-3-yl), —C(O)NHCH$_2$(1-methylpiperidin-3-yl), —C(O)NHCH$_2$CH$_2$N(CH$_2$CH$_2$OH)$_2$, —C(O)NH(1-ethylpiperidin-3-yl), —C(O)NH$_2$, —C(O)(3-aminopyrrolidin-1-yl), —C(O)(3-methylaminopyrrolidine-1-yl), —C(O)OH, —C(O)NHCH$_2$(morpholin-4-yl), —C(O)NHCH$_2$(1-ethylpyrrolidin-2-yl), —C(O)(4-amino-3-oxo-pyrazolidin-1-yl), —C(O)NHCH$_3$, —C(O)(3-aminocyclobut-1-yl), —C(O)NHCH$_2$(pyridin-3-yl), —C(O)NHCH$_2$CH$_2$OH, —C(O)NH(3-oxo-pyrazolidin-4-yl), —NHCH$_2$CH$_2$(imidazol-4-yl), —C(O)(3-dimethylaminopyrrolidin-1-yl), —C(O)NHCH$_2$(pyridin-4-yl), —C(O)NH(CH$_3$)(1-methyl-pyrrolidin-3-yl), —C(O)(3-diethylaminopyrrolidin-1-yl), —C(O)NH(pyrrol-1-yl), —C(O)NHCH$_2$CH$_2$CH$_2$(pyrrolidin-1-yl), —C(O)N(CH$_3$)CH$_2$CH$_2$CN, —C(O)NHCH$_2$CH$_2$OCH$_3$, —C(O)N(CH$_2$CH$_3$)CH$_2$CH$_2$CN, —C(O)(3-aminopiperidin-1-yl), —C(O)NHCH$_2$CH$_2$CH$_2$N(CH$_3$)$_2$, —C(O)NH(morpholin-4-yl), —C(O)NHN(CH$_3$)$_2$, —C(O)NHCH$_2$CH$_2$CH$_2$(imidazol-1-yl), —C(O)NHCH$_2$CH$_2$CH$_2$N(CH$_2$CH$_3$)$_2$, —C(O)NHCH$_2$CH$_2$CN, —C(O)NHCH$_2$CH$_2$C(O)OCH$_3$, —C(O)NHCH$_2$CH$_2$SCH$_3$, —C(O)NHCH$_2$CH$_2$SCH$_2$CH$_3$, —C(O)N(CH$_2$CH$_3$)CH$_2$CH$_2$N(CH$_3$)$_2$, —C(O)NHCH$_2$CH$_2$(2-oxo-pyrrolidin-1-yl), —C(O)NHCH$_2$CH$_2$(pyridin-4-yl), —C(O)NHCH$_2$CH$_2$CH$_2$OCH$_2$CH$_3$, —C(O)NHCH$_2$CH$_2$CH$_2$(morpholin-4-yl), —C(O)NHCH$_2$CH$_2$OCH$_3$, —C(O)N(CH$_3$)CH$_2$CH$_2$CH$_2$N(CH$_3$)$_2$, —C(O)NHCH$_2$CH$_2$CH$_2$OCH$_2$CH$_3$, —C(O)NHCH$_2$C(O)OCH$_2$CH$_3$, —C(O)NHCH$_2$CH$_2$OCH(CH$_3$)$_2$, —C(O)NHC(CH$_3$)$_2$CH$_2$(piperidin-1-yl), —C(O)N(CH$_3$)CH$_2$CH$_2$CH$_3$, —C(O)NH(piperidin-1-yl), —C(O)NHCH(CH$_3$)CH$_2$OCH$_3$, —C(O)NHC(CH$_3$)$_2$CH$_2$(morpholin-4-yl), —C(O)(2-dimethylaminomethylpiperidin-1-yl), —C(O)NH(CH$_2$)$_3$O(CH$_2$)$_3$CH$_3$, —C(O)NHCH(CH$_3$)(CH$_2$)$_3$N(CH$_2$CH$_3$)$_2$, —C(O)NHC(CH$_3$)$_2$C(O)(piperidin-1-yl), —C(O)(4-methylpiperazin-1-yl), —C(O)(2-piperidin-1-ylmethyl-piperidin-1-yl), cyano, —NHCH$_3$, —CH(CH$_3$)NHCH$_2$CH$_2$N(CH$_3$)$_2$, —C(O)CH$_3$, —S(O)$_2$NHCH$_2$CH$_2$N(CH$_3$)$_2$, —S(O)$_2$NH(CH$_2$)$_3$N(CH$_3$)$_2$, 5-(N,N-dimethylaminomethyl)-1,3,4-oxadiazol-2-yl, —NHCH$_2$CH$_2$N(CH$_3$)$_2$, —N(CH$_3$)$_2$, —OCH$_2$CH$_2$N(CH$_3$)$_2$, —NHC[N(CH$_3$)$_2$][═N(CH$_3$)$_2$], —OCHF$_2$, —CF$_3$, —S(O)$_2$CH$_3$, —OCF$_3$, —NHC(O)CH$_2$(4-dimethylaminopiperidin-1-yl), or methoxy.

In a more specific embodiment (P), the Compound of Formula I is that where each $R^3$ is independently halo, alkyl, hydroxyamino, —N($R^7$)C(O)—$C_1$-$C_6$-alkylene-N($R^{7a}$)($R^{7b}$), —C(O)N$R^8R^{8a}$, —N$R^9$C(O)$R^{9a}$, —C(O)N($R^{10}$)—$C_1$-$C_6$-alkylene-N($R^{10a}$)$R^{10b}$—N$R^{11}$C(O)N$R^{11a}R^{11b}$, —N($R^{22}$)C(O)—$C_1$-$C_6$-alkylene-N($R^{22b}$)—N($R^{22c}$)($R^{22a}$), —N$R^{13}$C(O)O$R^{13a}$, —N($R^{18}$)C(O)—$C_1$-$C_6$-alkylene-N($R^{18b}$)C(O)$R^{18a}$, —N$R^{24}$C(O)—$C_1$-$C_6$-alkylene-O$R^{24a}$, or —N($R^{20}$)C(O)—$C_1$-$C_6$-alkylene-C(O)$R^{20a}$; where each of the alkylene in $R^3$ is independently optionally further substituted with 1, 2, 3, 4, or 5 groups selected from halo, hydroxy, and amino; and all other groups are as defined in the Summary of the Invention. Specifically, each $R^3$ is independently methyl, chloro, —NHC(O)CH$_2$NH(CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, —NHC(O)CH(CH$_3$)NH(CH$_3$), —NHC(O)H, —NHC(O)CH$_2$(azetidin-1-yl), —NHC(O)(pyrrolidin-2-yl), —NHC(O)CH(NH$_2$)CH$_2$OH, —NHC(O)(azetidin-4-yl), —NHC(O)C(CH$_3$)$_2$NH(CH$_3$), —NH$_2$, —NHC(O)CH$_2$NH(CH$_2$CH$_2$CH$_3$), —NHC(O)CH$_2$CH$_2$NH$_2$, —NHOH, or —NHC(O)(piperidin-3-yl).

In a more specific embodiment (Q), the Compound of Formula I is that where $R^3$ is alkyl or —N($R^7$)C(O)—$C_1$-$C_6$-alkylene-N($R^{7a}$)($R^{7b}$); and $R^7$ is hydrogen or alkyl and $R^{7a}$ and $R^{7b}$ are independently hydrogen, alkyl, aminoalkyl, alkylaminoalkyl, or dialkylaminoalkyl; and all other groups are as defined in the Summary of the Invention. More specifically, each $R^3$ is independently methyl, —NHC(O)CH$_2$NH(CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, or —NHC(O)CH(CH$_3$)NH(CH$_3$).

In another specific embodiment (R), the Compound of Formula I is that where B is phenyl, $R^3$ is not present or $R^3$ is halo, alkyl, or alkoxy; $R^{3a}$ is —C(O)N$R^8R^{8a}$, —N$R^9$C(O)$R^{9a}$, —N($R^7$)C(O)—$C_1$-$C_6$-alkylene-N($R^{7a}$)($R^{7b}$), or —C(O)N($R^{10}$)—$C_1$-$C_6$-alkylene-N($R^{10a}$)$R^{10b}$ where each of the alkylene in $R^{3a}$ is independently optionally further substituted with 1, 2, 3, 4, or 5 groups selected from halo, hydroxy, and amino; and all other groups are as defined in the Summary of the Invention.

In a more specific embodiment ($R^1$) of embodiment R, the compound is that where $R^{50}$, $R^{52}$, and $R^{53}$ are hydrogen and $R^{54}$ is halo or alkoxy; $R^{50}$, $R^{52}$, and $R^{54}$ are hydrogen and $R^{53}$ is alkoxy; or $R^{50}$ and $R^{52}$ are hydrogen and $R^{53}$ and $R^{54}$ together with the carbons to which they are attached form a 6-membered heteroaryl; and all other groups are as defined in the Summary of the Invention. Specifically, $R^{50}$, $R^{52}$, and $R^{53}$ are hydrogen and $R^{54}$ is halo or alkoxy; or $R^{50}$, $R^{52}$, and $R^{54}$ are hydrogen and $R^{53}$ is alkoxy.

In a more specific embodiment of ($R^2$) of embodiment R, the compound is that where $R^{51}$ is methyl.

In a more specific embodiment (S), the compound of Formula Ia:

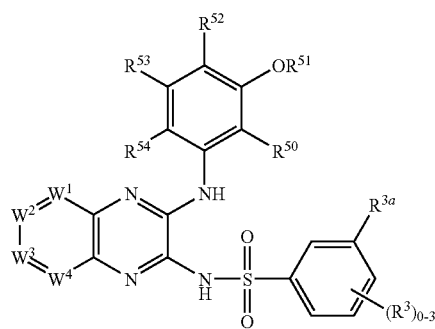

I(a)

is that where $R^3$ is not present or $R^3$ is alkyl and $R^{3a}$ is —N($R^7$)C(O)—$C_1$-$C_6$-alkylene-N($R^{7a}$)($R^{7b}$), —C(O)N$R^8R^{8a}$, —N$R^9$C(O)$R^{9a}$, or —C(O)N($R^{10}$)—$C_1$-$C_6$-alkylene-N($R^{10a}$)$R^{10b}$; where each of the alkylene in $R^{3a}$ is independently optionally further substituted with 1, 2, 3, 4, or 5 groups selected from halo, hydroxy, and amino; and all other groups are as defined in the Summary of the Invention. Specifically, $R^3$ is not present or is methyl. More specifically, $R^3$ is not present.

In a more specific embodiment (S1) of embodiment S is that where $R^7$ is hydrogen or alkyl and $R^{7a}$, and $R^{7b}$ are independently hydrogen, alkyl, hydroxyalkyl, aminoalkyl, alkylaminoalkyl, or dialkylaminoalkyl; $R^8$ is hydrogen or alkyl and $R^{8a}$ is heterocycloalkyl or heterocycloalkylalkyl; $R^9$ is hydrogen or alkyl and $R^{9a}$ is hydrogen, heterocycloalkyl, or heterocycloalkylalkyl; and $R^{10}$, $R^{10a}$, and $R^{10b}$ are independently hydrogen, alkyl, hydroxyalkyl, aminoalkyl, alkylaminoalkyl, or dialkylaminoalkyl.

In a more specific embodiment (S2) of embodiment S is that where $R^{50}$, $R^{52}$, and $R^{53}$ are hydrogen and $R^{54}$ is halo or alkoxy; or $R^{50}$, $R^{52}$, and $R^{54}$ are hydrogen and $R^{53}$ is alkoxy; or $R^{50}$ and $R^{52}$ are hydrogen and $R^{53}$ and $R^{54}$ together with the carbons to which they are attached form a 6-membered heteroaryl. Specifically, $R^{50}$, $R^{52}$, and $R^{53}$ are hydrogen and $R^{54}$ is halo or alkoxy; or $R^{50}$, $R^{52}$, and $R^{54}$ are hydrogen and $R^{53}$ is alkoxy.

In a more specific of (S3) of embodiment S, the compound is that where $R^{51}$ is methyl.

In another specific embodiment (T), the Compound of Formula I is that where B is heteroaryl, one $R^3$ is halo, alkyl, or alkoxy and a second $R^3$ is —C(O)N$R^8R^{8a}$, —N$R^9$C(O)$R^{9a}$, —N($R^7$)C(O)—$C_1$-$C_6$-alkylene-N($R^{7a}$)($R^{7b}$), or —C(O)N($R^{10}$)—$C_1$-$C_6$-alkylene-N($R^{10a}$)$R^{10b}$ where each of the alkylene in $R^3$ is independently optionally further substituted with 1, 2, 3, 4, or 5 groups selected from halo, hydroxy, and amino; and all other groups are as defined in the Summary of the Invention.

In another specific (T1) of embodiment T, the compound is that where $R^7$ is hydrogen or alkyl and $R^{7a}$, and $R^{7b}$ are independently hydrogen, alkyl, hydroxyalkyl, aminoalkyl, alkylaminoalkyl, or dialkylaminoalkyl; $R^8$ is hydrogen or alkyl and $R^{8a}$ is heterocycloalkyl or heterocycloalkylalkyl; $R^9$ is hydrogen or alkyl and $R^{9a}$ is hydrogen, heterocycloalkyl, or heterocycloalkylalkyl; $R^{10}$, $R^{10a}$, and $R^{10b}$ are independently hydrogen, alkyl, hydroxyalkyl, aminoalkyl, alkylaminoalkyl, or dialkylaminoalkyl.

In another specific embodiment U, the compound of Formula I is that where B is

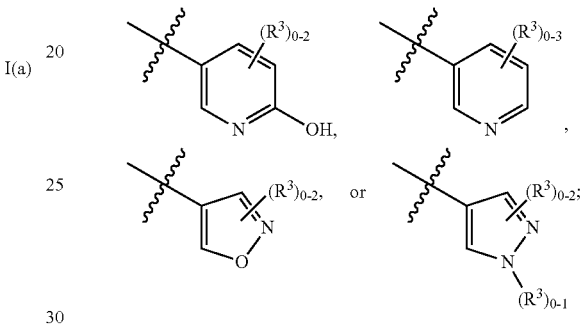

each $R^3$ (when $R^3$ is present) is independently halo, alkyl, alkoxy, aminoalkyloxy, alkylaminoalkyloxy, dialkylaminoalkyloxy, alkylamino, dialkylamino, —C(O)N$R^8R^{8a}$, —N$R^9$C(O)$R^{9a}$, —N($R^7$)C(O)—$C_1$-$C_6$-alkylene-N($R^{7a}$)($R^{7b}$), or —C(O)N($R^{10}$)—$C_1$-$C_6$-alkylene-N($R^{10a}$)$R^{10b}$; and all other groups are as defined in the Summary of the Invention.

In a more specific embodiment (U1) of embodiment U, the compound of Formula I is that where $R^{50}$, $R^{52}$, and $R^{53}$ are hydrogen and $R^{54}$ is halo or alkoxy; $R^{50}$, $R^{52}$, and $R^{54}$ are hydrogen and $R^{53}$ is alkoxy; or $R^{50}$ and $R^{52}$ are hydrogen and $R^{53}$ and $R^{54}$ together with the carbons to which they are attached form a 6-membered heteroaryl; and all other groups are as defined in the Summary of the Invention. Specifically, $R^{50}$, $R^{52}$, and $R^{53}$ are hydrogen and $R^{54}$ is halo or alkoxy; or $R^{50}$, $R^{52}$, and $R^{54}$ are hydrogen and $R^{53}$ is alkoxy.

In a more specific embodiment (U2) of embodiment U1, the compound of Formula I is that where $R^{51}$ is methyl.

In another specific embodiment (U3) of embodiment U, the Compound of Formula I is that where $R^7$ is hydrogen or alkyl and $R^{7a}$, and $R^{7b}$ are independently hydrogen, alkyl, hydroxyalkyl, aminoalkyl, alkylaminoalkyl, or dialkylaminoalkyl; $R^8$ is hydrogen or alkyl and $R^{8a}$ is heterocycloalkyl or heterocycloalkylalkyl; $R^9$ is hydrogen or alkyl and $R^{9a}$ is hydrogen, heterocycloalkyl, or heterocycloalkylalkyl; $R^{10}$, $R^{10a}$, and $R^{10b}$ are independently hydrogen, alkyl, hydroxyalkyl, aminoalkyl, alkylaminoalkyl, or dialkylaminoalkyl In another embodiment of the Invention (V) the Compound of Formula I is that
where $W^1$, $W^2$, $W^3$, and $W^4$ are —C(H)=; or $W^2$ and $W^3$ are —C(H)= and one of $W^1$ and $W^4$ is —N= and the other is —C(H)=;
$R^{50}$ is hydrogen;
$R^{51}$ is hydrogen or alkyl;
$R^{52}$ is hydrogen;
$R^{53}$ is hydrogen, alkoxy, nitro, amino, or —N($R^{55}$)C(O)—

$C_1$-$C_6$-alkylene-N($R^{55a}$)$R^{55b}$; and $R^{54}$ is hydrogen, alkyl, alkoxy, or halo; or $R^{53}$ and $R^{54}$ together with the carbons to which they are attached form a 6-membered heteroaryl;

B is phenyl substituted with $R^{3a}$ and optionally further substituted with one $R^3$; or B is heteroaryl optionally substituted with one or two $R^3$;

$R^{3a}$ is cyano; hydroxyamino; carboxy; alkylsulfonyl, aminoalkyloxy; alkylaminoalkyloxy; dialkylaminoalkyloxy; —N($R^7$)C(O)—$C_1$-$C_6$-alkylene-N($R^{7a}$)($R^{7b}$); —C(O)N$R^8R^{8a}$; —N$R^9$C(O)$R^{9a}$; —C(O)N($R^{10}$)—$C_1$-$C_6$-alkylene-N($R^{10a}$)$R^{10b}$; —N$R^{11}$C(O)N$R^{11a}R^{11b}$ where $R^{11a}$; —C(O)$R^{12}$; —N$R^{13}$C(O)O$R^{13a}$; —C(O)N($R^{14}$)N($R^{14a}$)($R^{14b}$); —S(O)$_2$N($R^{15}$)—$C_1$-$C_6$-alkylene-N($R^{15a}$)$R^{15b}$; —C(O)N($R^{16}$)—$C_1$-$C_6$-alkylene-C(O)O$R^{16a}$; heteroaryl optionally substituted with one or two aminoalkyl, alkylaminoalkyl, or dialkylaminoalkyl; —N($R^{17}$)—C(=N($R^{17b}$)($R^{17a}$))(N$R^{17c}R^{17d}$); —N($R^{18}$)C(O)—$C_1$-$C_6$-alkylene-N($R^{18b}$)C(O)$R^{18a}$; —C(O)N($R^{19}$)—$C_1$-$C_6$-alkylene-C(O)$R^{19a}$; —N($R^{22}$)C(O)—$C_1$-$C_6$-alkylene-N($R^{22b}$)—N($R^{22c}$)($R^{22a}$); —$C_0$-$C_6$-alkylene-N($R^{23}$)—$C_1$-$C_6$-alkylene-N($R^{23b}$)$R^{23a}$; or —N$R^{24}$C(O)—$C_1$-$C_6$-alkylene-O$R^{24a}$; where each of the alkylene in $R^{3a}$ is independently optionally further substituted with 1, 2, 3, 4, or 5 groups selected from halo, hydroxy, and amino;

each $R^3$ (when $R^3$ is present) is independently halo; cyano; alkyl; alkenyl; alkoxy; hydroxyamino; carboxy; alkylsulfonyl, aminoalkyloxy; alkylaminoalkyloxy; dialkylaminoalkyloxy; —N($R^7$)C(O)—$C_1$-$C_6$-alkylene-N($R^{7a}$)($R^{7b}$); —C(O)N$R^8R^{8a}$; —N$R^9$C(O)$R^{9a}$; —C(O)N($R^{10}$)—$C_1$-$C_6$-alkylene-N($R^{10a}$)$R^{10b}$; N$R^{11}$C(O)N$R^{11a}R^{11b}$ where $R^{11a}$; —C(O)$R^{12}$; —N$R^{13}$C(O)O$R^{13a}$; —C(O)N($R^{14}$)N($R^{14a}$)($R^{14b}$); —S(O)$_2$N($R^{15}$)—$C_1$-$C_6$-alkylene-N($R^{15a}$)$R^{15b}$; —C(O)N($R^{16}$)—$C_1$-$C_6$-alkylene-C(O)O$R^{16a}$; heteroaryl optionally substituted with one or two aminoalkyl, alkylaminoalkyl, or dialkylaminoalkyl; —N($R^{17}$)—C(=N($R^{17b}$)($R^{17a}$))(N$R^{17c}R^{17d}$); —N($R^{18}$)C(O)—$C_1$-$C_6$-alkylene-N($R^{18b}$)C(O)$R^{18a}$; —C(O)N($R^{19}$)—$C_1$-$C_6$-alkylene-C(O)$R^{19a}$; —N($R^{22}$)C(O)—$C_1$-$C_6$-alkylene-N($R^{22b}$)—N($R^{22c}$)($R^{22a}$); —$C_0$-$C_6$-alkylene-N($R^{23}$)—$C_1$-$C_6$-alkylene-N($R^{23b}$)$R^{23a}$; or —N$R^{24}$C(O)—$C_1$-$C_6$-alkylene-O$R^{24a}$; where each of the alkylene in $R^3$ is independently optionally further substituted with 1, 2, 3, 4, or 5 groups selected from halo, hydroxy, and amino;

provided that when $R^{50}$ and $R^{52}$ are hydrogen, $R^{51}$ is hydrogen or methyl, $R^{53}$ is hydrogen or methoxy, and $R^{54}$ is hydrogen or methoxy, then B is not 2,3-dihydro-1,4-benzodioxinyl, thien-2-yl, or thien-2-yl substituted with one $R^3$ where $R^3$ is halo.

Another embodiment (W) of the invention is a Compound of Formula I where $R^{50}$, $R^{53}$, and $R^{54}$ are independently hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$N$R^{55}R^{55a}$, or alkylcarbonylamino and where $R^{55}$ and $R^{55b}$ are independently hydrogen, alkyl, or alkenyl and $R^{55a}$ is hydrogen, alkyl, alkenyl, hydroxy, or alkoxy; or $R^{53}$ and $R^{54}$ together with the carbons to which they are attached form a 5- or 6-membered heteroaryl or 5- or 6-membered heterocycloalkyl.

Another embodiment (X) of the invention is a Compound of Formula I where $R^{53}$ and $R^{54}$ together with the carbons to which they are attached form a 5- or 6-membered heteroaryl or 5- or 6-membered heterocycloalkyl.

Another specific embodiment of the invention is a pharmaceutical composition comprising a compound of Formula I, Formula Ia, or a compound according the above Embodiments A-X and a pharmaceutically acceptable carrier, excipient, or diluent.

Another specific embodiment of the invention is a method of inhibiting PI3K in a cell, comprising contacting a cell in which inhibition of PI3K is desired with a compound of Formula I, Ia, or II or a compound according to Embodiments A-X. Specifically, the Compound is of Formula I or Ia.

Another specific embodiment of the invention is a method of treating a disease, disorder, or syndrome mediated by PI3K which method comprises administering to a patient a pharmaceutical composition comprising a therapeutically effective amount of a compound of Formula I, Ia, or II or a compound according to embodiments A-X. Specifically, the Compound is of Formula I or Ia. More specifically, the Compound is of Formula Ia.

More specifically, the disease is cancer. Even more specifically, the cancer is breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), or thyroid carcinoma. Even more specifically, the cancer is ovarian cancer, cervical cancer, breast cancer, colon cancer, rectal cancer, or glioblastoma.

Another aspect of the Invention is directed to employing the compounds of the invention in a method of screening for candidate agents that bind to, for example PI3K. In that method, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, PI3K may be done in a number of ways. In one example, the candidate agent (the compound of the invention) is labeled, for example, with a fluorescent or radioactive moiety and binding determined directly. For example, this may be done by attaching all or a portion of the PI3K protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, PI3K protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to PI3K.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocycloalkyl structures and/or aromatic or heteroaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to IGF1R, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to PI3K protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to PI3K and thus is capable of binding to, and potentially modulating, the activity of the PI3K. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to PI3K with a higher affinity. Thus, if the candidate agent is labeled, the presence of the label on the support, coupled with a lack of competitor binding, may indicate the candidate agent is capable of binding to PI3K.

It may be of value to identify the binding site of PI3K. This can be done in a variety of ways. In one embodiment, once PI3K is identified as binding to the candidate agent, the PI3K is fragmented or modified and the assays repeated to identify the necessary components for binding.

Modulation is tested by screening for candidate agents capable of modulating the activity of PI3K comprising the steps of combining a candidate agent with PI3K, as above, and determining an alteration in the biological activity of the PI3K. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native PI3K, but cannot bind to modified PI3K.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

One of ordinary skill in the art would understand that certain crystallized, protein-ligand complexes, in particular PI3K-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

Another aspect of the invention is directed to suitable x-ray quality crystals, and one of ordinary skill in the art would appreciate that they can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

Representative Compounds

Representative compounds of Formula I and/or II are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Names in Table 1 were generated using ACD/Labs naming software 8.00 release, product version 8.08 with the exception of Compound 374 which was named using ChemDraw v. 9.0.1.

TABLE 1

| Cpd. No. | Structure | Name |
| --- | --- | --- |
| 1 | 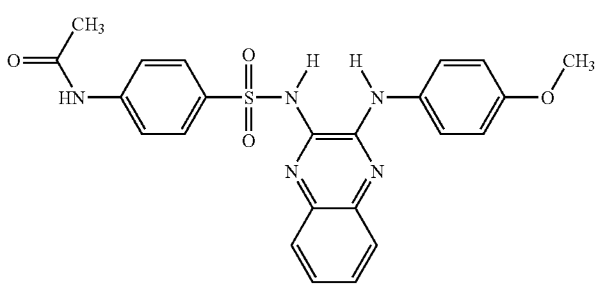 | N-(4-{[(3-{[4-(methoxy)phenyl]amino}quinoxalin-2-yl) amino] sulfonyl}phenyl) acetamide |
| 2 | 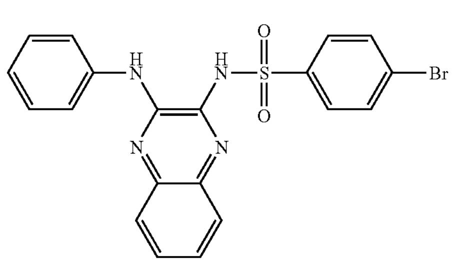 | 4-bromo-N-{3-(phenylamino)quinoxalin-2-yl} benzene sulfonamide |

TABLE 1-continued

| Cpd. No. | Structure | Name |
| --- | --- | --- |
| 3 | 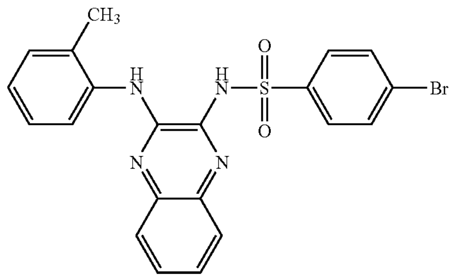 | 4-bromo-N-{3-[(2-methylphenyl)amino]quinoxalin-2-yl}benzene sulfonamide |
| 4 | 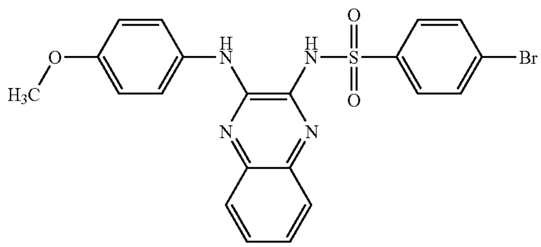 | 4-bromo-N-(3-{[4-(methoxy)phenyl]amino}quinoxalin-2-yl)benzene sulfonamide |
| 5 | 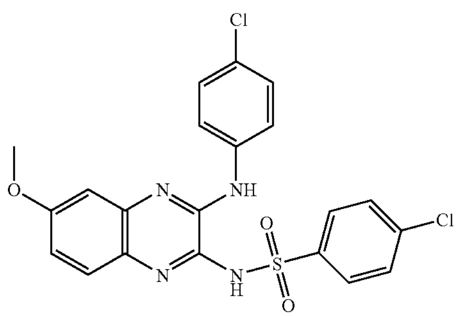 | 4-chloro-N-{3-[(4-chlorophenyl)amino]-6-(methoxy)quinoxalin-2-yl}benzenesulfonamide |
| 6 | 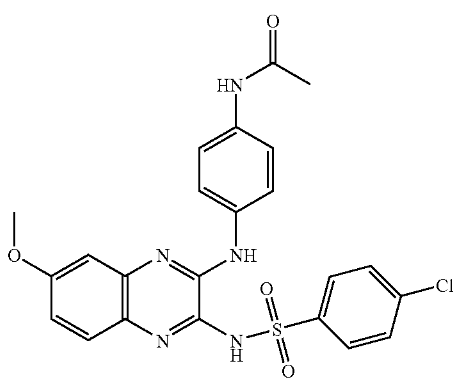 | N-(4-{[3-{[(4-chlorophenyl)sulfonyl]amino}-7-(methoxy)quinoxalin-2-yl]amino}phenyl)acetamide |
| 7 | 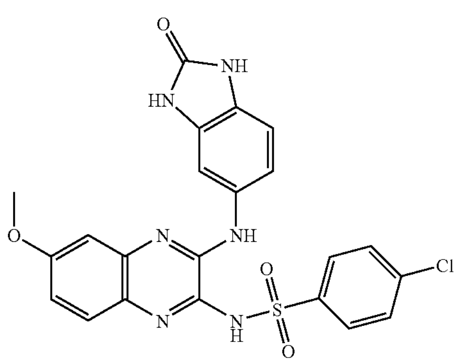 | 4-chloro-N-{6-(methoxy)-3-[(2-oxo-2,3-dihydro-1H-benzimidazol-5-yl)amino]quinoxalin-2-yl}benzenesulfonamide |

TABLE 1-continued

| Cpd. No. | Structure | Name |
|---|---|---|
| 8 | 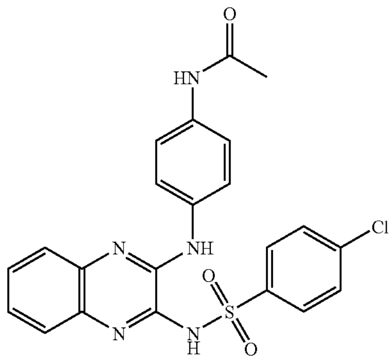 | N-{4-[(3-{[(4-chlorophenyl)sulfonyl]amino}quinoxalin-2-yl)amino]phenyl}acetamide |
| 9 | 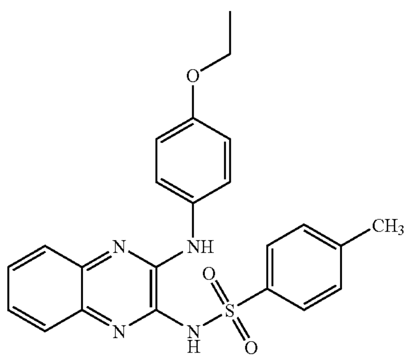 | N-(3-{[4-(ethyloxy)phenyl]amino}quinoxalin-2-yl)-4-methylbenzene sulfonamide |
| 10 | 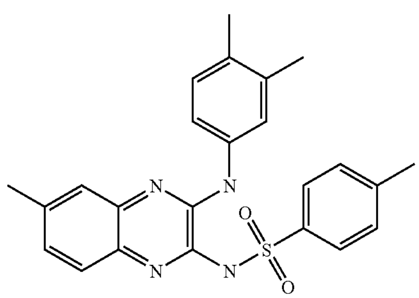 | N-{3-[(3,4-dimethylphenyl)amino]-6-methylquinoxalin-2-yl}-4-methylbenzene sulfonamide |
| 11 | 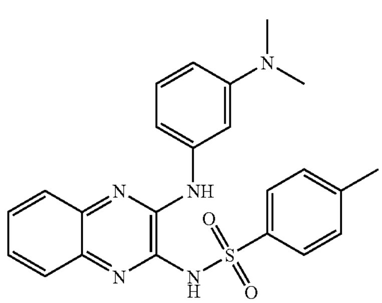 | N-(3-{[3-(dimethylamino)phenyl]amino}quinoxalin-2-yl)-4-methylbenzene sulfonamide |

TABLE 1-continued

| Cpd. No. | Structure | Name |
|---|---|---|
| 12 | 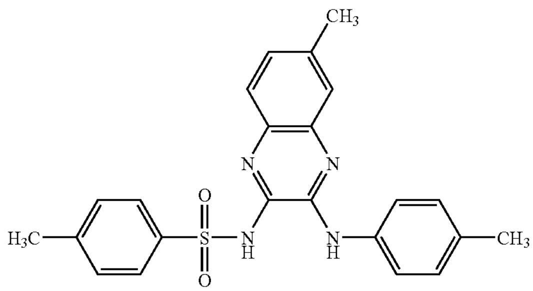 | 4-methyl-N-{6-methyl-3-[(4-methylphenyl)amino]quinoxalin-2-yl}benzene sulfonamide |
| 13 | 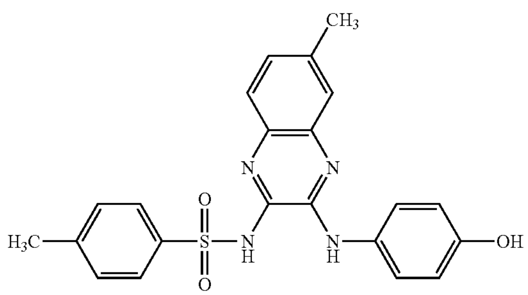 | N-{3-[(4-hydroxyphenyl)amino]-6-methylquinoxalin-2-yl}-4-methylbenzene sulfonamide |
| 14 | 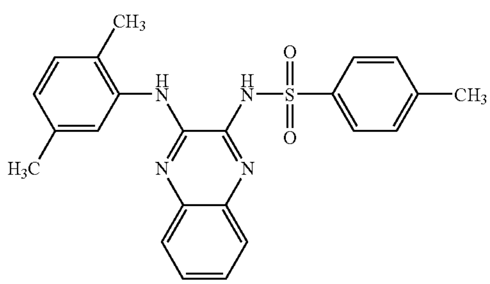 | N-{3-[(2,5-dimethylphenyl)amino]quinoxalin-2-yl}-4-methylbenzenesulfonamide |
| 15 | 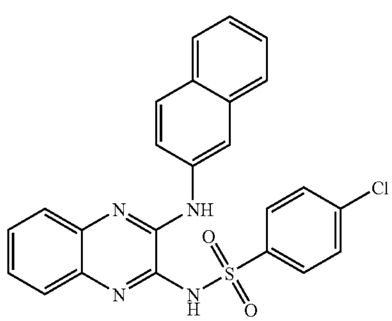 | 4-chloro-N-[3-(naphthalen-2-ylamino)quinoxalin-2-yl]benzenesulfonamide |
| 16 | 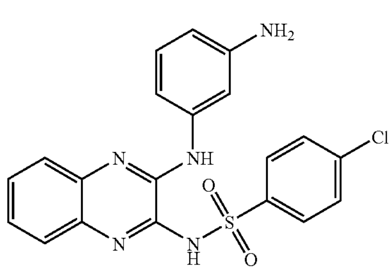 | N-{3-[(3-aminophenyl)amino]quinoxalin-2-yl}-4-chlorobenzenesulfonamide |

TABLE 1-continued

| Cpd. No. | Structure | Name |
|---|---|---|
| 17 | 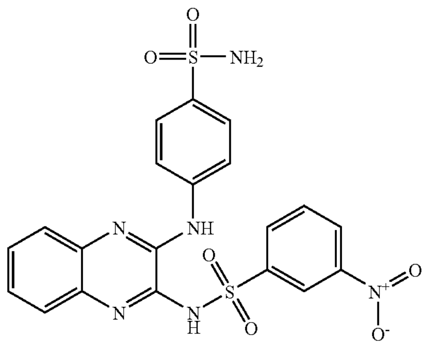 | N-(3-{[4-(aminosulfonyl)phenyl]amino}quinoxalin-2-yl)-3-nitrobenzenesulfonamide |
| 18 | 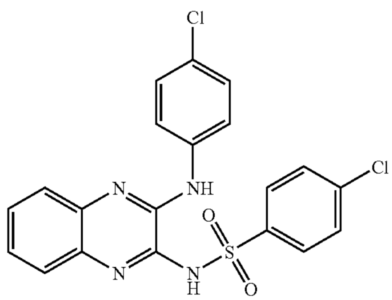 | 4-chloro-N-{3-[(4-chlorophenyl)amino]quinoxalin-2-yl}benzenesulfonamide |
| 19 | 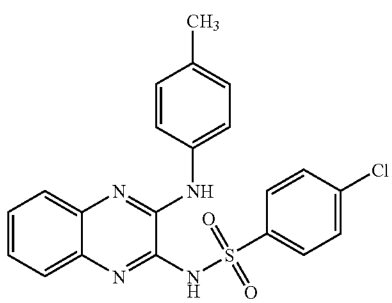 | 4-chloro-N-{3-[(4-methylphenyl)amino]quinoxalin-2-yl}benzenesulfonamide |
| 20 | 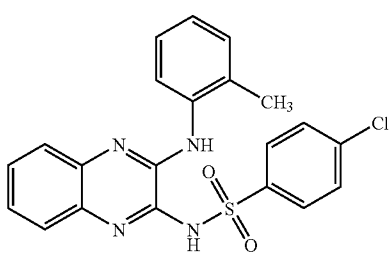 | 4-chloro-N-{3-[(2-methylphenyl)amino]quinoxalin-2-yl}benzenesulfonamide |
| 21 | 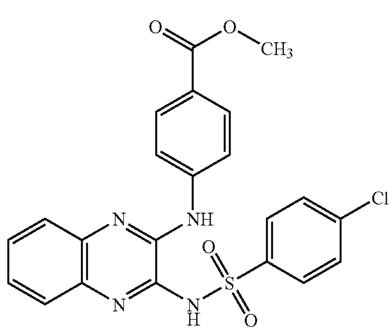 | methyl 4-[(3-{[(4-chlorophenyl)sulfonyl]amino}quinoxalin-2-yl)amino]benzoate |

TABLE 1-continued
| Cpd. No. | Structure | Name |
|---|---|---|
| 22 | 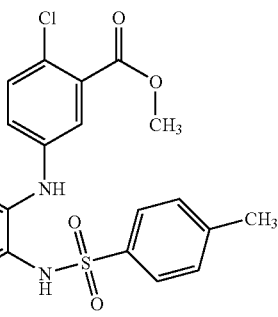 | methyl 2-chloro-5-[(3-{[(4-methylphenyl)sulfonyl]amino}quinoxalin-2-yl)amino]benzoate |
| 23 | 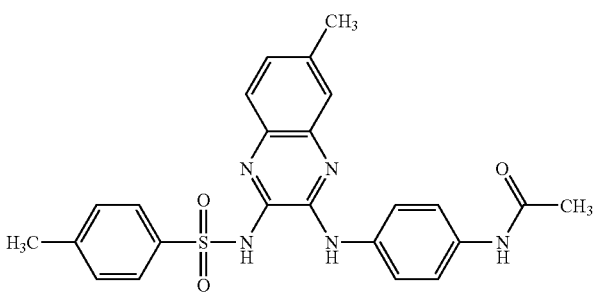 | N-{4-[(7-methyl-3-{[(4-methylphenyl)sulfonyl]amino}quinoxalin-2-yl)amino]phenyl}acetamide |
| 24 | 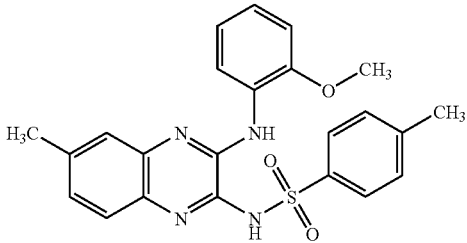 | 4-methyl-N-(6-methyl-3-{[2-(methoxy)phenyl]amino}quinoxalin-2-yl)benzenesulfonamide |
| 25 | 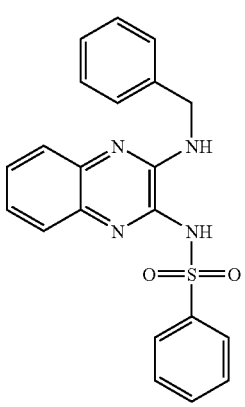 | N-{3-[(phenylmethyl)amino]quinoxalin-2-yl}benzenesulfonamide |

TABLE 1-continued
| Cpd. No. | Structure | Name |
|---|---|---|
| 26 | 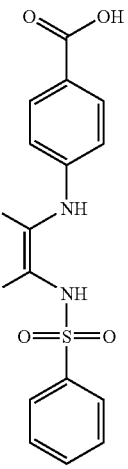 | 4-({3-[(phenylsulfonyl)amino]quinoxalin-2-yl}amino)benzoic acid |
| 27 | 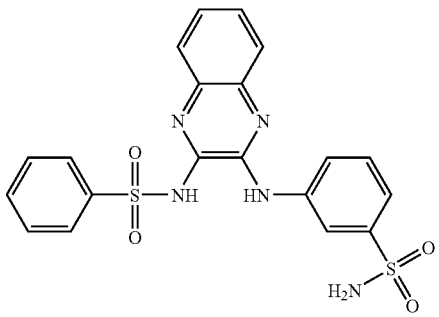 | 3-({3-[(phenylsulfonyl)amino]quinoxalin-2-yl}amino)benzenesulfonamide |
| 28 | 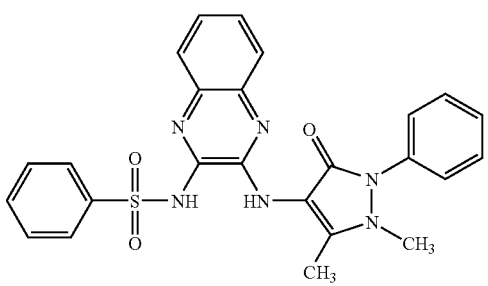 | N-{3-[(1,5-dimethyl-3-oxo-2-phenyl-2,3-dihydro-1H-pyrazol-4-yl)amino]quinoxalin-2-yl}benzenesulfonamide |
| 29 | 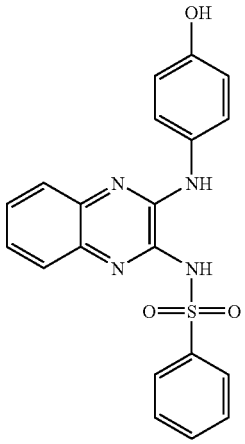 | N-{3-[(4-hydroxyphenyl)amino]quinoxalin-2-yl}benzenesulfonamide |

TABLE 1-continued
| Cpd. No. | Structure | Name |
|---|---|---|
| 30 | 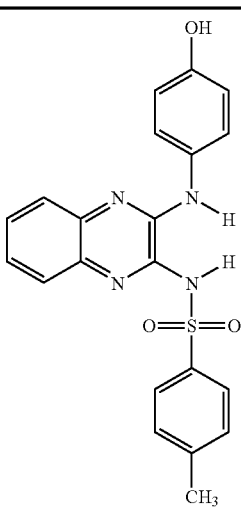 | N-{3-[(4-hydroxyphenyl)amino]quinoxalin-2-yl}-4-methylbenzenesulfonamide |
| 31 | 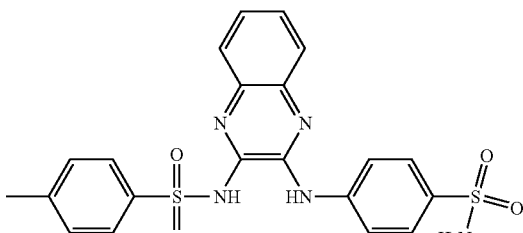 | N-(3-{[4-(aminosulfonyl)phenyl]amino}quinoxalin-2-yl)-4-methylbenzenesulfonamide |
| 32 | 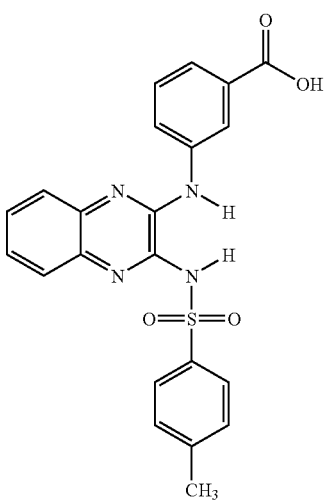 | 3-[(3-{[(4-methylphenyl)sulfonyl]amino}quinoxalin-2-yl)amino]benzoic acid |

TABLE 1-continued

| Cpd. No. | Structure | Name |
|---|---|---|
| 33 | 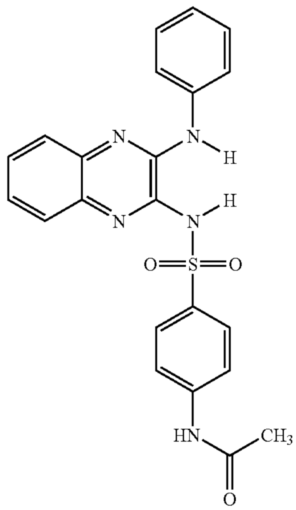 | N-[4-({[3-(phenylamino)quinoxalin-2-yl]amino}sulfonyl)phenyl]acetamide |
| 34 | 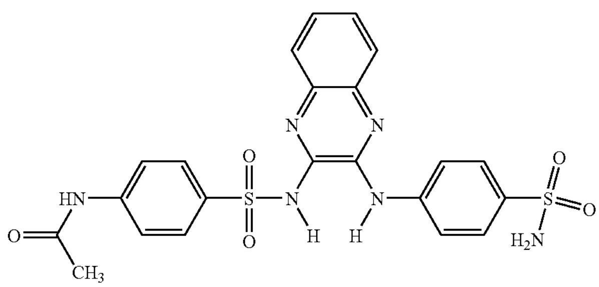 | N-(4-{[(3-{[4-(aminosulfonyl)phenyl]amino}quinoxalin-2-yl)amino]sulfonyl}phenyl)acetamide |
| 35 | 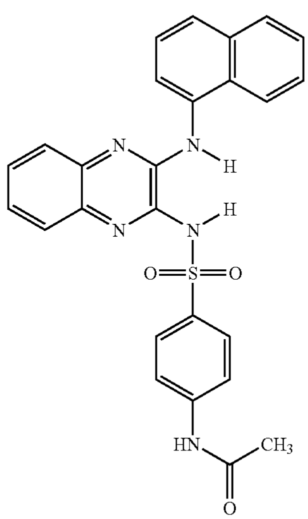 | N-[4-({[3-(naphthalen-1-ylamino)quinoxalin-2-yl]amino}sulfonyl)phenyl]acetamide |
| 36 | 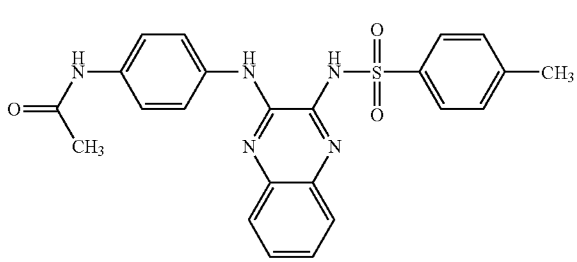 | N-{4-[(3-{[(4-methylphenyl)sulfonyl]amino}quinoxalin-2-yl)amino]phenyl}acetamide |

TABLE 1-continued

| Cpd. No. | Structure | Name |
|---|---|---|
| 37 | 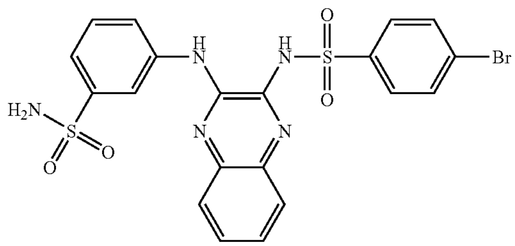 | N-(3-{[3-(aminosulfonyl)phenyl]amino}quinoxalin-2-yl)-4-bromobenzenesulfonamide |
| 38 | 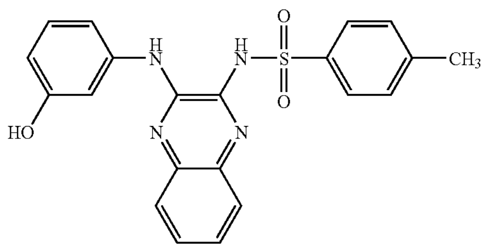 | N-{3-[(3-hydroxyphenyl)amino]quinoxalin-2-yl}-4-methylbenzenesulfonamide |
| 39 | 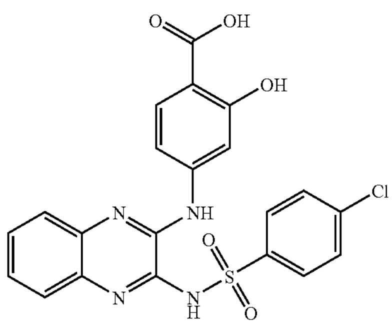 | 4-[(3-{[(4-chlorophenyl)sulfonyl]amino}quinoxalin-2-yl)amino]-2-hydroxybenzoic acid |
| 40 | 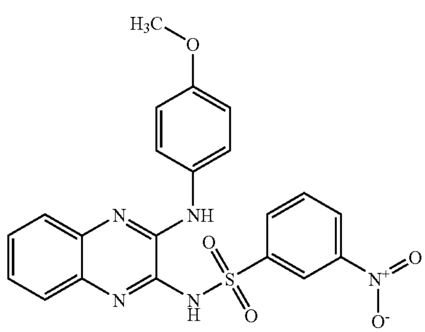 | N-(3-{[4-(methoxy)phenyl]amino}quinoxalin-2-yl)-3-nitrobenzenesulfonamide |
| 41 | 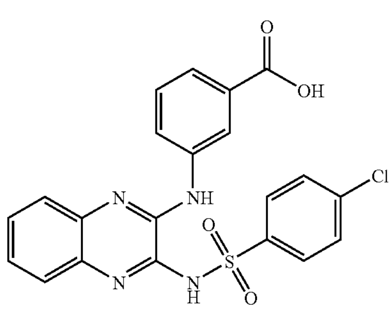 | 3-[(3-{[(4-chlorophenyl)sulfonyl]amino}quinoxalin-2-yl)amino]benzoic acid |

TABLE 1-continued
| Cpd. No. | Structure | Name |
|---|---|---|
| 42 | 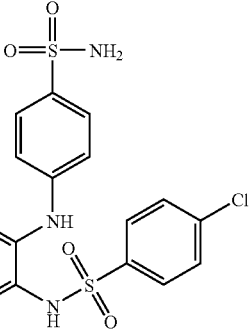 | N-(3-{[4-(aminosulfonyl)phenyl]amino}quinoxalin-2-yl)-4-chlorobenzenesulfonamide |
| 43 | 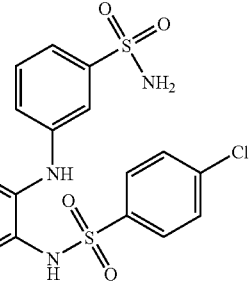 | N-(3-{[3-(aminosulfonyl)phenyl]amino}quinoxalin-2-yl)-4-chlorobenzenesulfonamide |
| 44 | 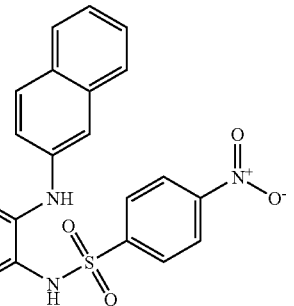 | N-[3-(naphthalen-2-ylamino)quinoxalin-2-yl]-4-nitrobenzenesulfonamide |
| 45 | 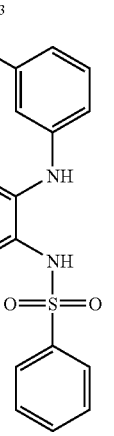 | N-(3-{[3-(methoxy)phenyl]amino}quinoxalin-2-yl)benzenesulfonamide |

TABLE 1-continued

| Cpd. No. | Structure | Name |
|---|---|---|
| 46 | 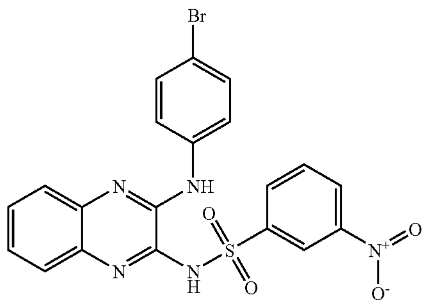 | N-{3-[(4-bromophenyl)amino]quinoxalin-2-yl}-3-nitrobenzenesulfonamide |
| 47 | 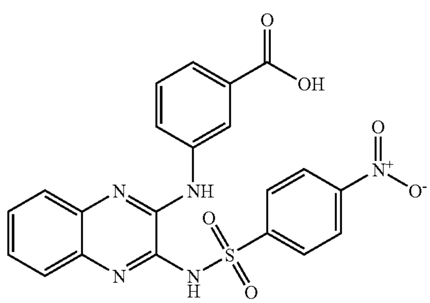 | 3-[(3-{[(4-nitrophenyl)sulfonyl]amino}quinoxalin-2-yl)amino]benzoic acid |
| 48 | 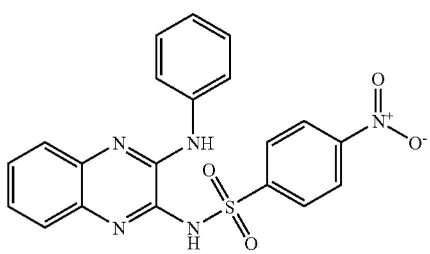 | 4-nitro-N-[3-(phenylamino)quinoxalin-2-yl]benzenesulfonamide |
| 49 | 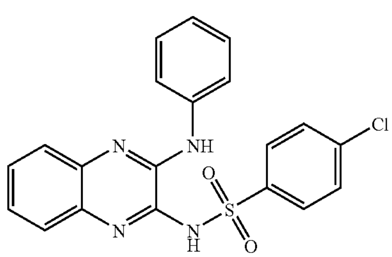 | 4-chloro-N-[3-(phenylamino)quinoxalin-2-yl]benzenesulfonamide |
| 50 | 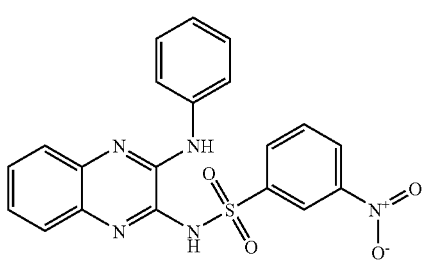 | 3-nitro-N-[3-(phenylamino)quinoxalin-2-yl]benzenesulfonamide |

TABLE 1-continued

| Cpd. No. | Structure | Name |
|---|---|---|
| 51 | 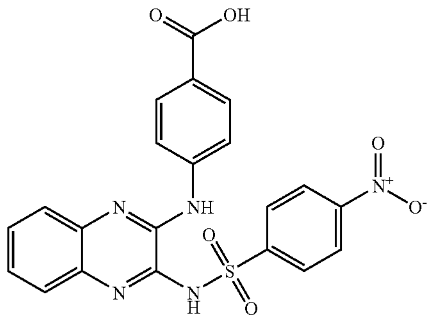 | 4-[(3-{[(4-nitrophenyl)sulfonyl]amino}quinoxalin-2-yl)amino]benzoic acid |
| 52 | 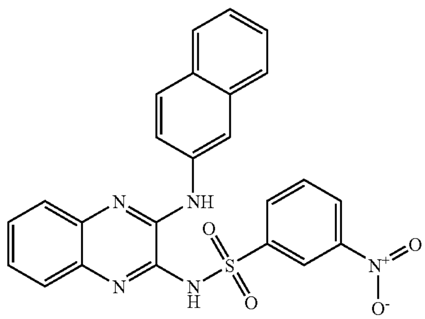 | N-[3-(naphthalen-2-ylamino)quinoxalin-2-yl]-3-nitrobenzenesulfonamide |
| 53 | 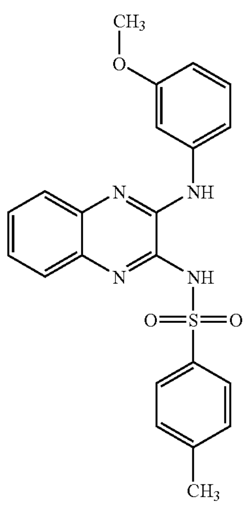 | 4-methyl-N-(3-{[3-(methoxy)phenyl]amino}quinoxalin-2-yl)benzenesulfonamide |
| 54 | 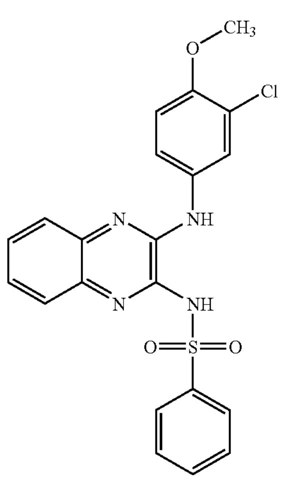 | N-(3-{[3-chloro-4-(methoxy)phenyl]amino}quinoxalin-2-yl)benzenesulfonamide |

TABLE 1-continued

| Cpd. No. | Structure | Name |
|---|---|---|
| 55 | 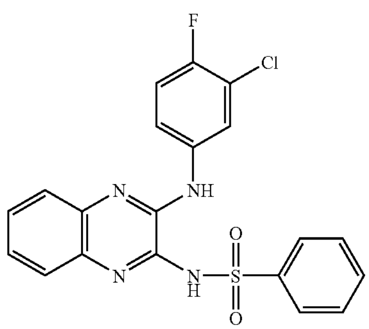 | N-{3-[(3-chloro-4-fluorophenyl)amino]quinoxalin-2-yl}benzenesulfonamide |
| 56 | 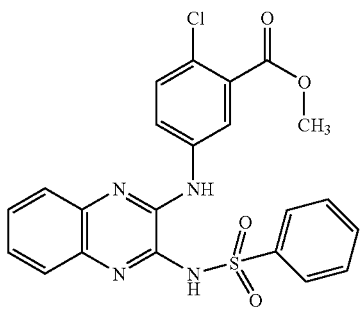 | methyl 2-chloro-5-({3-[(phenylsulfonyl)amino]quinoxalin-2-yl}amino)benzoate |
| 57 | 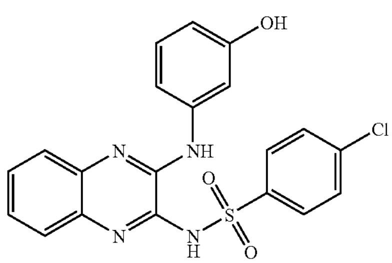 | 4-chloro-N-{3-[(3-hydroxyphenyl)amino]quinoxalin-2-yl}benzenesulfonamide |
| 58 | 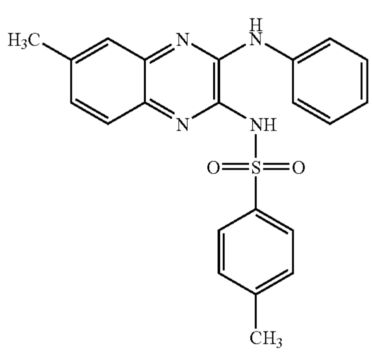 | 4-methyl-N-[6-methyl-3-(phenylamino)quinoxalin-2-yl]benzenesulfonamide |

TABLE 1-continued

| Cpd. No. | Structure | Name |
|---|---|---|
| 59 | 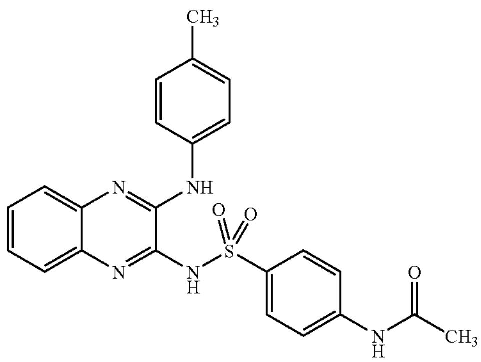 | N-{4-[({3-[(4-methylphenyl)amino]quinoxalin-2-yl}amino)sulfonyl]phenyl}acetamide |
| 60 | 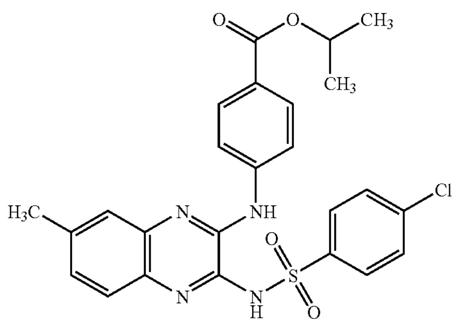 | 1-methylethyl 4-[(3-{[(4-chlorophenyl)sulfonyl]amino}-7-methylquinoxalin-2-yl)amino]benzoate |
| 61 | 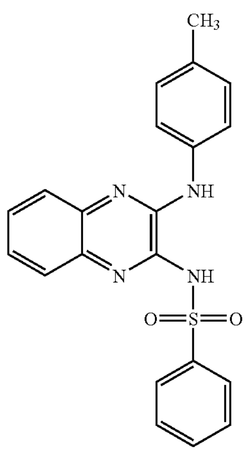 | N-{3-[(4-methylphenyl)amino]quinoxalin-2-yl}benzenesulfonamide |
| 62 | 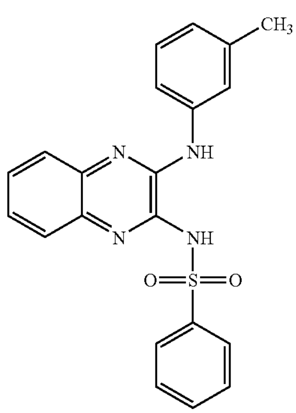 | N-{3-[(3-methylphenyl)amino]quinoxalin-2-yl}benzenesulfonamide |

TABLE 1-continued

| Cpd. No. | Structure | Name |
|---|---|---|
| 63 | 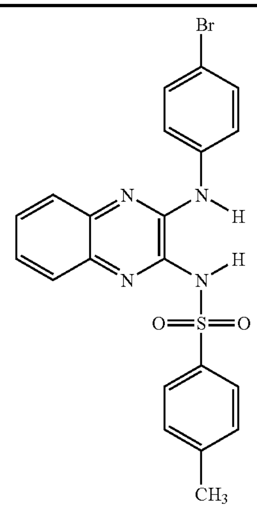 | N-{3-[(4-bromophenyl)amino]quinoxalin-2-yl}-4-methylbenzenesulfonamide |
| 64 | 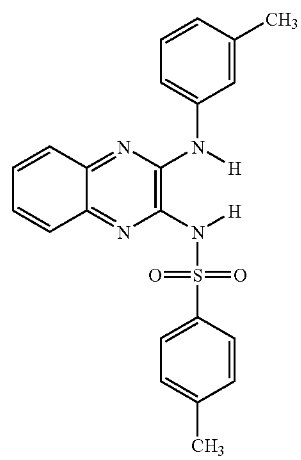 | 4-methyl-N-{3-[(3-methylphenyl)amino]quinoxalin-2-yl}benzenesulfonamide |
| 65 | 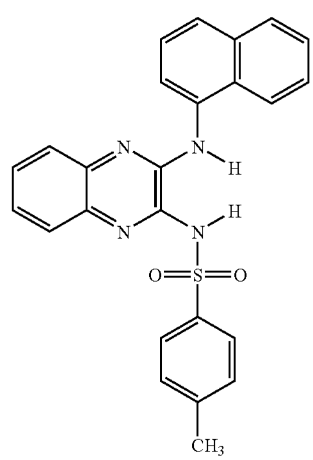 | 4-methyl-N-[3-(naphthalen-1-ylamino)quinoxalin-2-yl]benzenesulfonamide |

TABLE 1-continued

| Cpd. No. | Structure | Name |
|---|---|---|
| 66 | 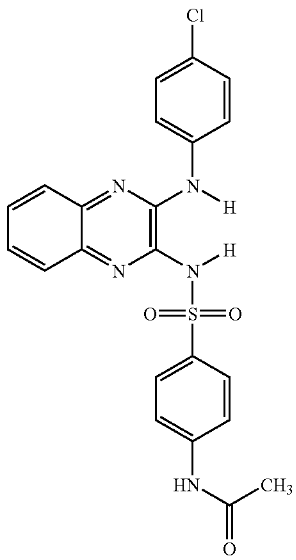 | N-{4-[({3-[(4-chlorophenyl)amino]quinoxalin-2-yl}amino)sulfonyl]phenyl}acetamide |
| 67 | 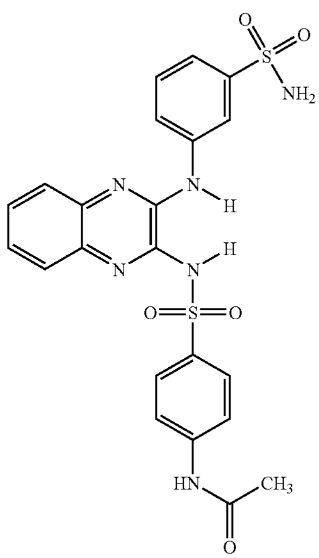 | N-(4-{[(3{[3-(aminosulfonyl)phenyl]amino}quinoxalin-2-yl)amino]sulfonyl}phenyl)acetamide |
| 68 | 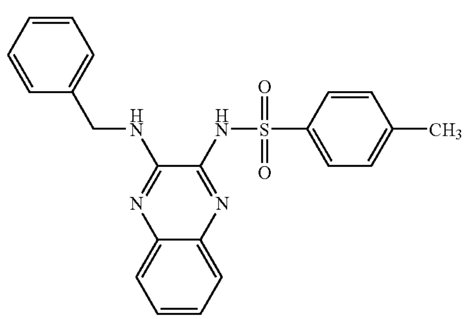 | 4-methyl-N-{3-[(phenylmethyl)amino]quinoxalin-2-yl}benzenesulfonamide |

TABLE 1-continued

| Cpd. No. | Structure | Name |
|---|---|---|
| 69 | 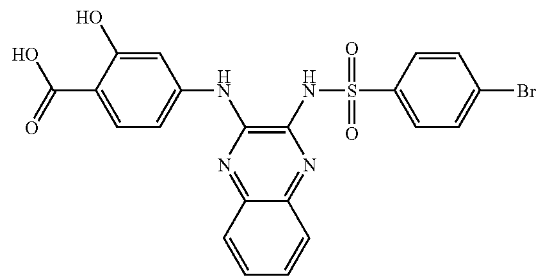 | 4-[(3-{[(4-bromophenyl)sulfonyl]amino}quinoxalin-2-yl)amino]-2-hydroxybenzoic acid |
| 70 | 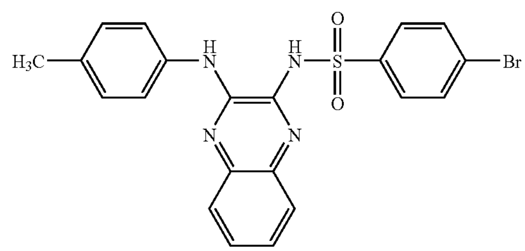 | 4-bromo-N-{3-[(4-methylphenyl)amino]quinoxalin-2-yl}benzenesulfonamide |
| 71 | 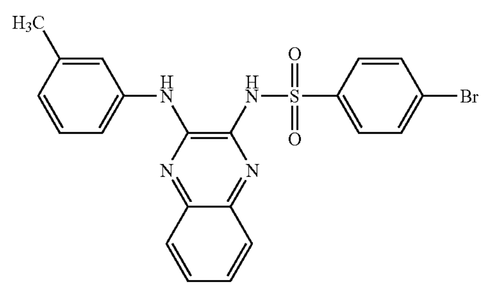 | 4-bromo-N-{3-[(3-methylphenyl)amino]quinoxalin-2-yl}benzenesulfonamide |
| 72 | 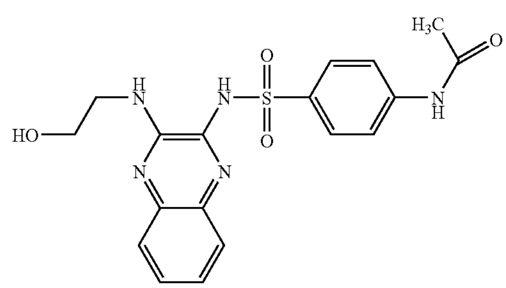 | N-{4-[({3-[(2-hydroxyethyl)amino]quinoxalin-2-yl}amino)sulfonyl]phenyl}acetamide |
| 73 | 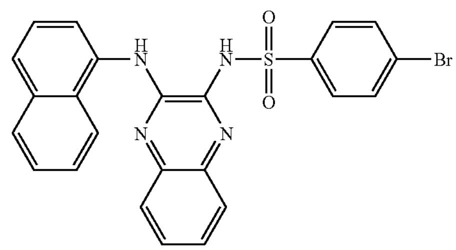 | 4-bromo-N-[3-(naphthalen-1-ylamino)quinoxalin-2-yl]benzenesulfonamide |

TABLE 1-continued

| Cpd. No. | Structure | Name |
|---|---|---|
| 74 | 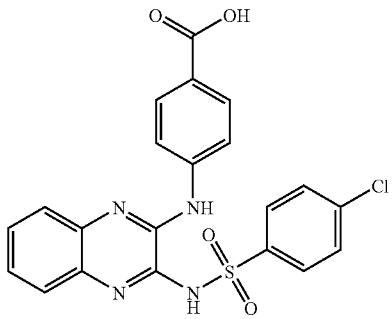 | 4-[(3-{[(4-chlorophenyl)sulfonyl]amino}quinoxalin-2-yl)amino]benzoic acid |
| 75 | 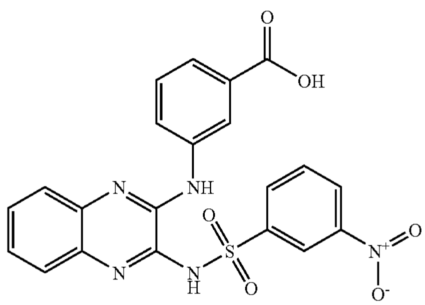 | 3-[(3-{[(3-nitrophenyl)sulfonyl]amino}quinoxalin-2-yl)amino]benzoic acid |
| 76 | 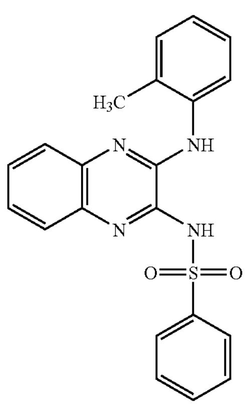 | N-{3-[(2-methylphenyl)amino]quinoxalin-2-yl}benzenesulfonamide |
| 77 | 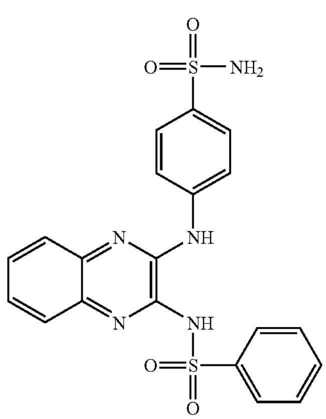 | 4-({3-[(phenylsulfonyl)amino]quinoxalin-2-yl}amino)benzenesulfonamide |

TABLE 1-continued
| Cpd. No. | Structure | Name |
|---|---|---|
| 78 | 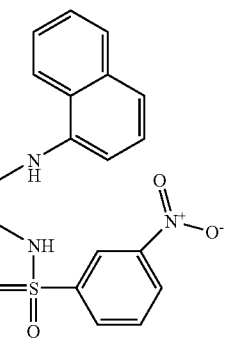 | N-[3-(naphthalen-1-ylamino)quinoxalin-2-yl]-3-nitrobenzenesulfonamide |
| 79 | 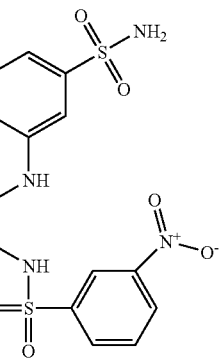 | N-(3-{[3-(aminosulfonyl)phenyl]amino}quinoxalin-2-yl)-3-nitrobenzenesulfonamide |
| 80 | 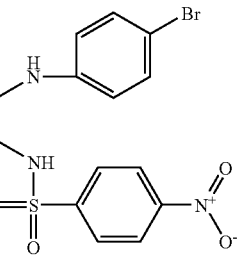 | N-{3-[(4-bromophenyl)amino]quinoxalin-2-yl}-4-nitrobenzenesulfonamide |
| 81 | 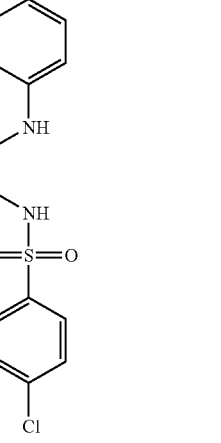 | 4-chloro-N-[3-(naphthalen-1-ylamino)quinoxalin-2-yl]benzenesulfonamide |

TABLE 1-continued

| Cpd. No. | Structure | Name |
| --- | --- | --- |
| 82 | 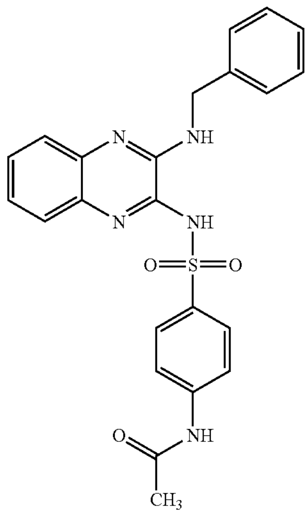 | N-{4-[({3-[(phenylmethyl)amino]quinoxalin-2-yl}amino)sulfonyl]phenyl}acetamide |
| 83 | 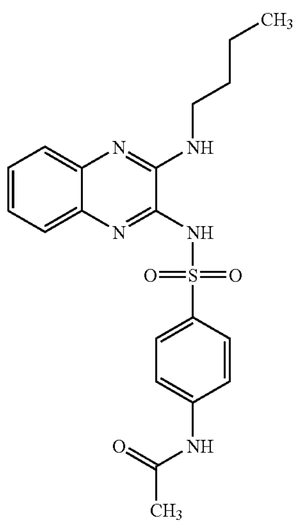 | N-[4-({[3-(butylamino)quinoxalin-2-yl]amino}sulfonyl)phenyl]acetamide |
| 84 | 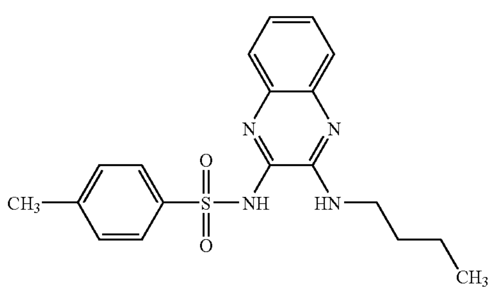 | N-[3-(butylamino)quinoxalin-2-yl]-4-methylbenzenesulfonamide |
| 85 | 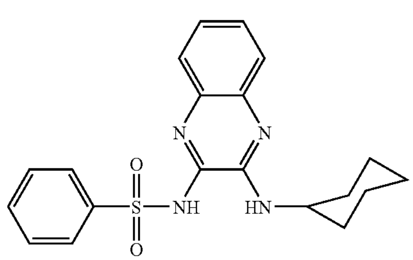 | N-[3-(cyclohexylamino)quinoxalin-2-yl]benzenesulfonamide |

TABLE 1-continued

| Cpd. No. | Structure | Name |
|---|---|---|
| 86 | 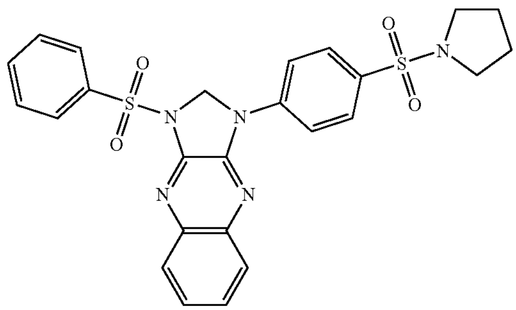 | 1-(phenylsulfonyl)-3-[4-(pyrrolidin-1-ylsulfonyl)phenyl]-2,3-dihydro-1H-imidazo[4,5-b]quinoxaline |
| 87 | 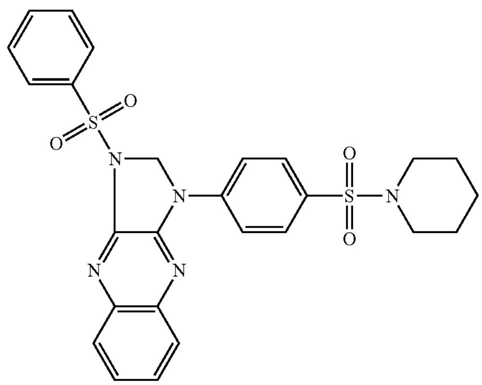 | 1-(phenylsulfonyl)-3-[4-(piperidin-1-ylsulfonyl)phenyl]-2,3-dihydro-1H-imidazo[4,5-b]quinoxaline |
| 88 | 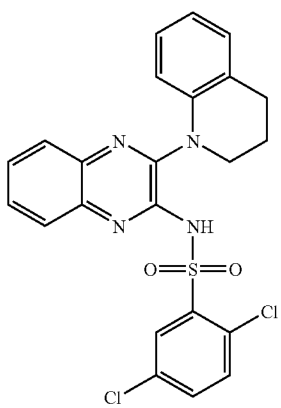 | 2,5-dichloro-N-[3-(3,4-dihydroquinolin-1(2H)-yl)quinoxalin-2-yl]benzenesulfonamide |
| 89 | 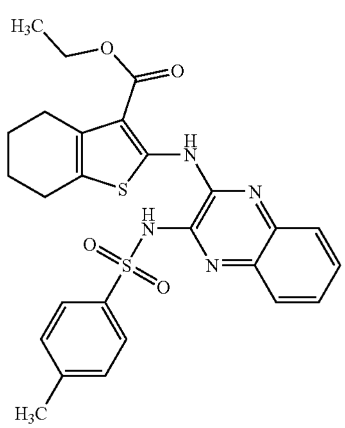 | ethyl 2-[(3-{[(4-methylphenyl)sulfonyl]amino}quinoxalin-2-yl)amino]-4,5,6,7-tetrahydro-1-benzothiophene-3-carboxylate |

TABLE 1-continued

| Cpd. No. | Structure | Name |
|---|---|---|
| 90 | 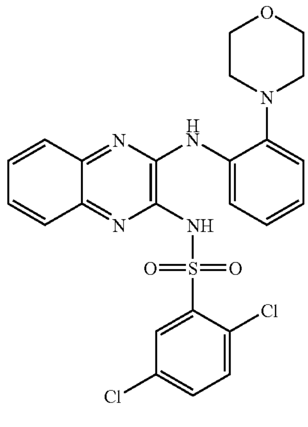 | 2,5-dichloro-N-{3-[(2-morpholin-4-ylphenyl)amino]quinoxalin-2-yl}benzenesulfonamide |
| 91 | 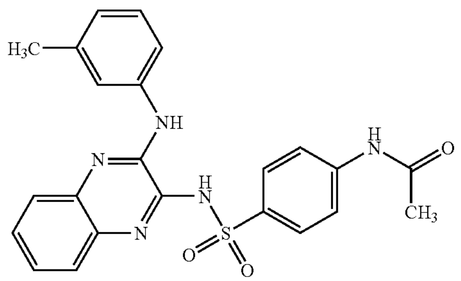 | N-{4-[({3-[(3-methylphenyl)amino]quinoxalin-2-yl}amino)sulfonyl]phenyl}acetamide |
| 92 | 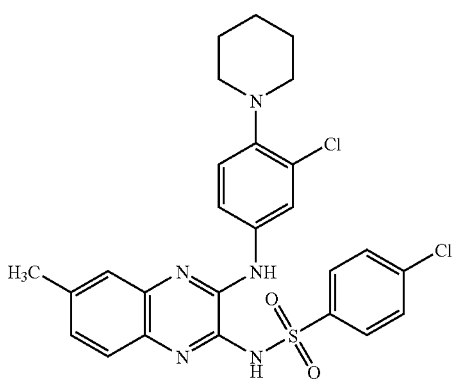 | 4-chloro-N-{3-[(3-chloro-4-piperidin-1-ylphenyl)amino]-6-methylquinoxalin-2-yl}benzenesulfonamide |
| 93 | 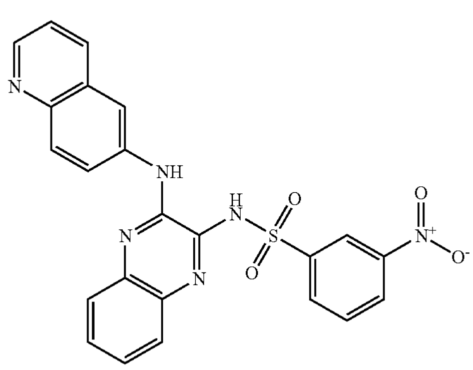 | 3-nitro-N-[3-(quinolin-6-ylamino)quinoxalin-2-yl]benzenesulfonamide |

TABLE 1-continued

| Cpd. No. | Structure | Name |
|---|---|---|
| 94 | 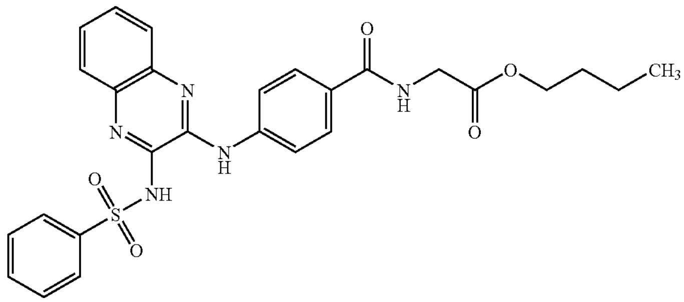 | butyl N-{[4-({3-[(phenylsulfonyl)amino]quinoxalin-2-yl}amino)phenyl]carbonyl}glycinate |
| 95 | 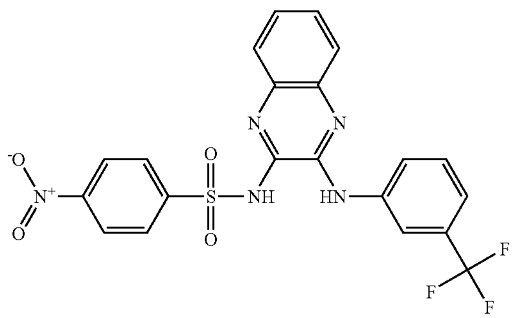 | 4-nitro-N-(3-{[3-(trifluoromethyl)phenyl]amino}quinoxalin-2-yl)benzenesulfonamide |
| 96 | 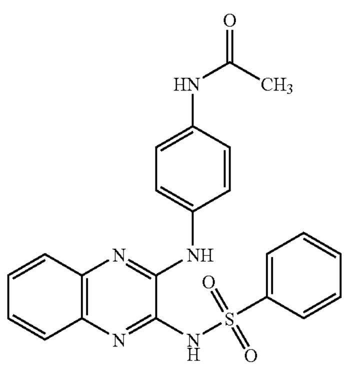 | N-[4-({3-[(phenylsulfonyl)amino]quinoxalin-2-yl}amino)phenyl]acetamide |
| 97 | 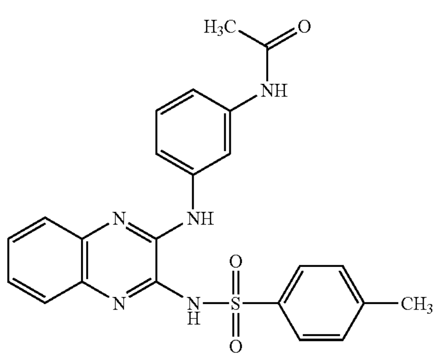 | N-{3-[(3-{[(4-methylphenyl)sulfonyl]amino}quinoxalin-2-yl)amino]phenyl]acetamide |

TABLE 1-continued

| Cpd. No. | Structure | Name |
|---|---|---|
| 98 | 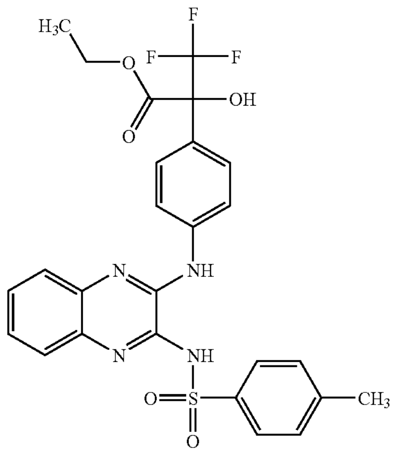 | ethyl 3,3,3-trifluoro-2-hydroxy-2-{4-[(3-{[(4-methylphenyl)sulfonyl]amino}quinoxalin-2-yl)amino]phenyl}propanoate |
| 99 | 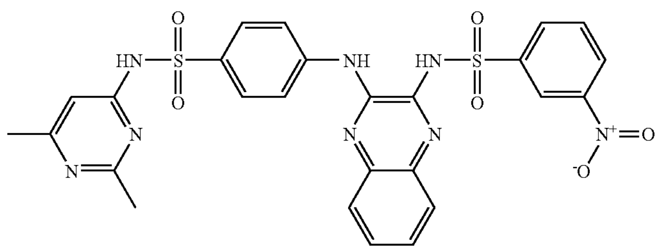 | N-{3-[(4-{[(2,6-dimethylpyrimidin-4-yl)amino]sulfonyl}phenyl)amino]quinoxalin-2-yl}-3-nitrobenzenesulfonamide |
| 100 | 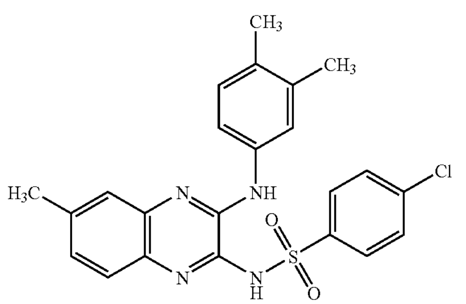 | 4-chloro-N-{3-[(3,4-dimethylphenyl)amino]-6-methylquinoxalin-2-yl}benzenesulfonamide |
| 101 | 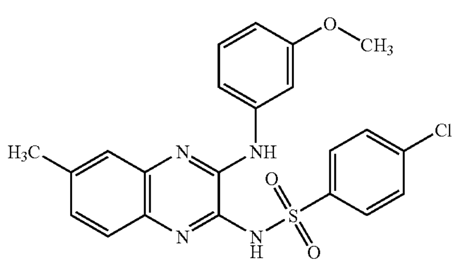 | 4-chloro-N-(6-methyl-3-{[3-(methoxy)phenyl]amino}quinoxalin-2-yl)benzenesulfonamide |
| 102 | 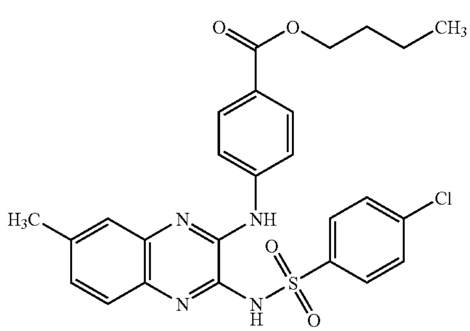 | butyl 4-[(3-{[(4-chlorophenyl)sulfonyl]amino}-7-methylquinoxalin-2-yl)amino]benzoate |

TABLE 1-continued

| Cpd. No. | Structure | Name |
|---|---|---|
| 103 | 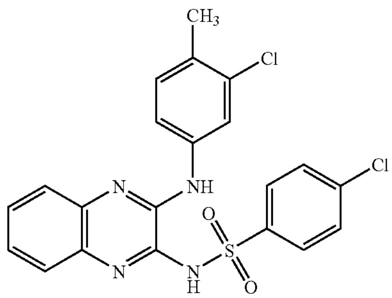 | 4-chloro-N-{3-[(3-chloro-4-methylphenyl)amino]quinoxalin-2-yl}benzenesulfonamide |
| 104 | 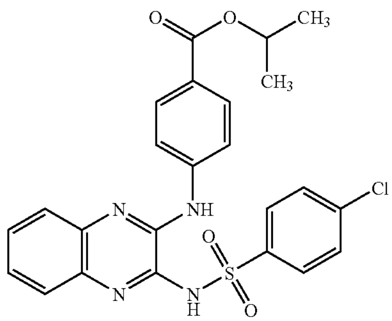 | 1-methylethyl 4-[(3-{[(4-chlorophenyl)sulfonyl]amino}quinoxalin-2-yl)amino]benzoate |
| 105 | 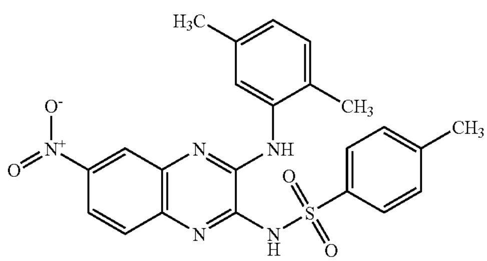 | N-{3-[(2,5-dimethylphenyl)amino]-6-nitroquinoxalin-2-yl}-4-methylbenzenesulfonamide |
| 106 | 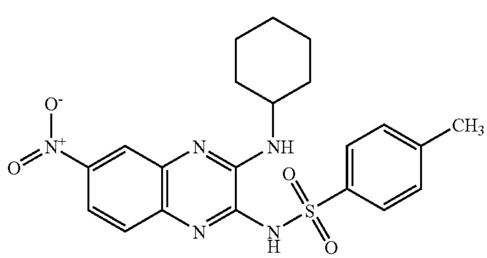 | N-[3-(cyclohexylamino)-6-nitroquinoxalin-2-yl]-4-methylbenzenesulfonamide |
| 107 | 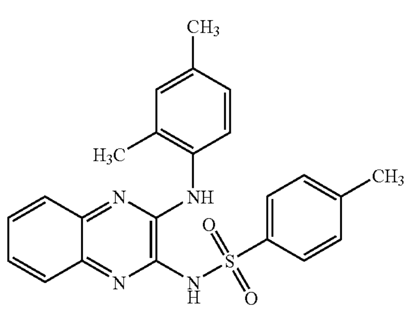 | N-{3-[(2,4-dimethylphenyl)amino]quinoxalin-2-yl}-4-methylbenzenesulfonamide |

TABLE 1-continued

| Cpd. No. | Structure | Name |
|---|---|---|
| 108 | 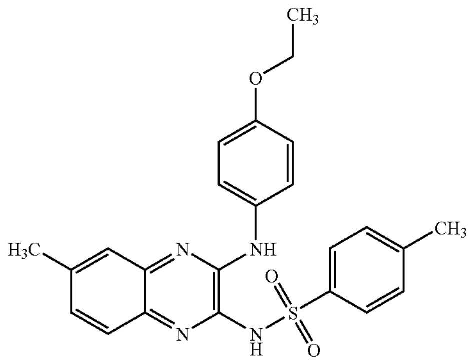 | N-(3-{[4-(ethyloxy)phenyl]amino}-6-methylquinoxalin-2-yl)-4-methylbenzenesulfonamide |
| 109 | 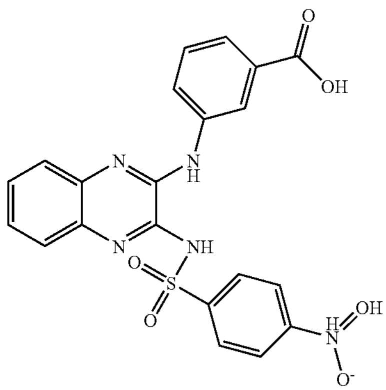 | 3-({3-[({4-[hydroxy(oxido)amino]phenyl}sulfonyl)amino]quinoxalin-2-yl}amino)benzoic acid |
| 110 | 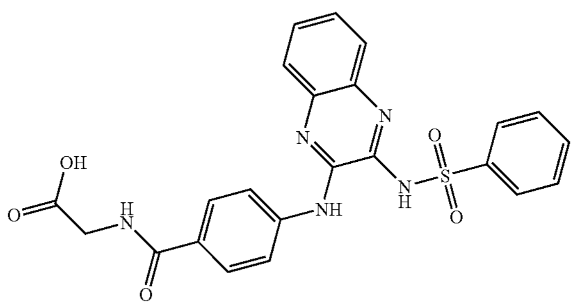 | N-{[4-({3-[(phenylsulfonyl)amino]quinoxalin-2-yl}amino)phenyl]carbonyl}glycine |
| 111 | 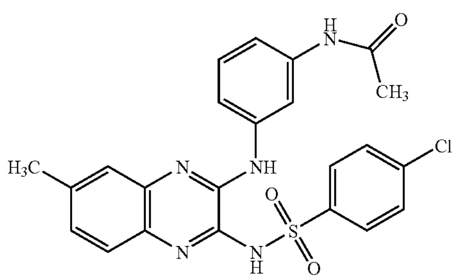 | N-{3-[(3-{[(4-chlorophenyl)sulfonyl]amino}-7-methylquinoxalin-2-yl)amino]phenyl}acetamide |
| 112 | 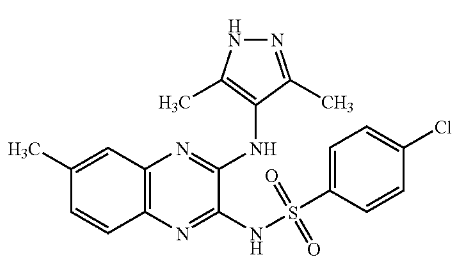 | 4-chloro-N-{3-[(3,5-dimethyl-1H-pyrazol-4-yl)amino]-6-methylquinoxalin-2-yl}benzenesulfonamide |

TABLE 1-continued

| Cpd. No. | Structure | Name |
|---|---|---|
| 113 | 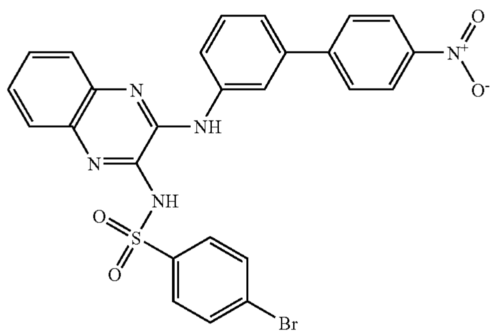 | 4-bromo-N-{3-[(4'-nitrobiphenyl-3-yl)amino]quinoxalin-2-yl}benzenesulfonamide |
| 114 | 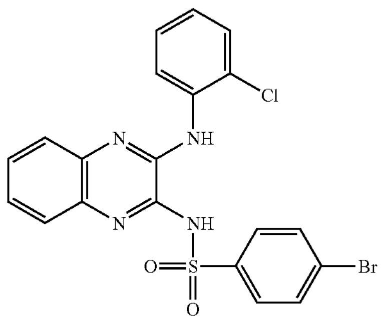 | 4-bromo-N-{3-[(2-chlorophenyl)amino]quinoxalin-2-yl}benzenesulfonamide |
| 115 | 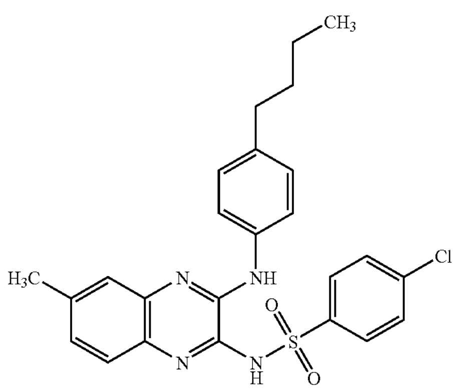 | N-{3-[(4-butylphenyl)amino]-6-methylquinoxalin-2-yl}-4-chlorobenzenesulfonamide |
| 116 | 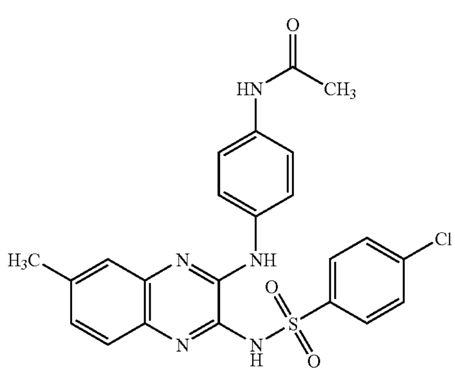 | N-{4-[(3-{[(4-chlorophenyl)sulfonyl]amino}-7-methylquinoxalin-2-yl)amino]phenyl}acetamide |

TABLE 1-continued

| Cpd. No. | Structure | Name |
|---|---|---|
| 117 | 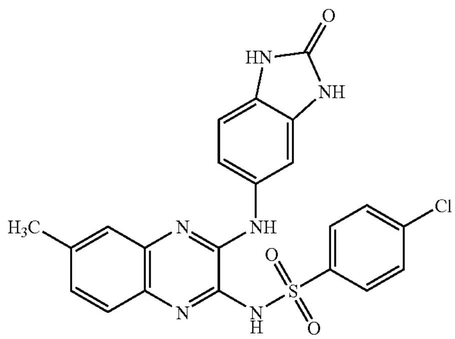 | 4-chloro-N-{6-methyl-3-[(2-oxo-2,3-dihydro-1H-benzimidazol-5-yl)amino]quinoxalin-2-yl}benzenesulfonamide |
| 118 | 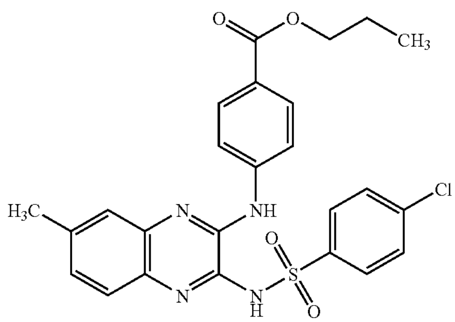 | propyl 4-[(3-{[(4-chlorophenyl)sulfonyl]amino}-7-methylquinoxalin-2-yl)amino]benzoate |
| 119 | 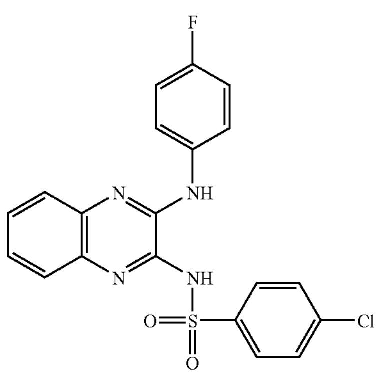 | 4-chloro-N-{3-[(4-fluorophenyl)amino]quinoxalin-2-yl}benzenesulfonamide |
| 120 | 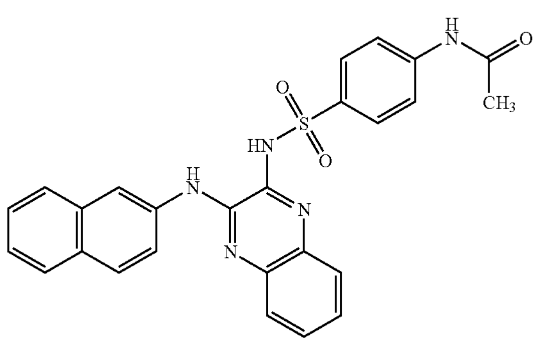 | N-[4-({[3-(naphthalen-2-ylamino)quinoxalin-2-yl]amino}sulfonyl)phenyl]acetamide |

TABLE 1-continued

| Cpd. No. | Structure | Name |
|---|---|---|
| 121 | 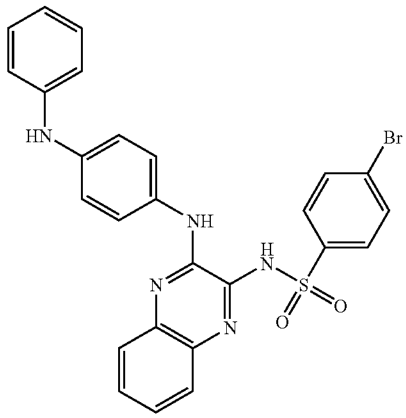 | 4-bromo-N-(3-{[4-(phenylamino)phenyl]amino}quinoxalin-2-yl)benzenesulfonamide |
| 122 | 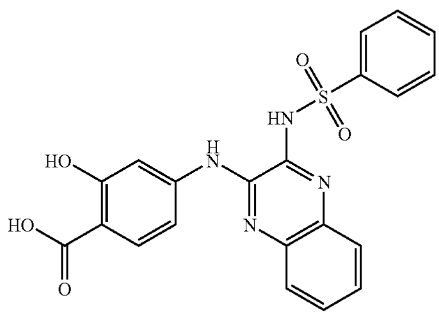 | 2-hydroxy-4-({3-[(phenylsulfonyl)amino]quinoxalin-2-yl}amino)benzoic acid |
| 123 | 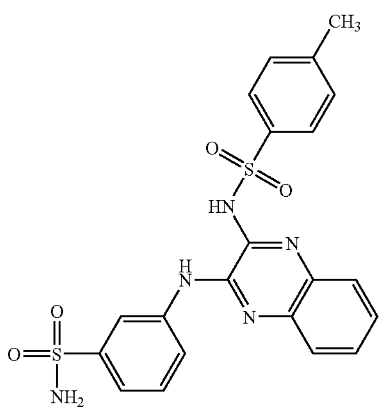 | N-(3-{[3-(aminosulfonyl)phenyl]amino}quinoxalin-2-yl)-4-methylbenzenesulfonamide |
| 124 | 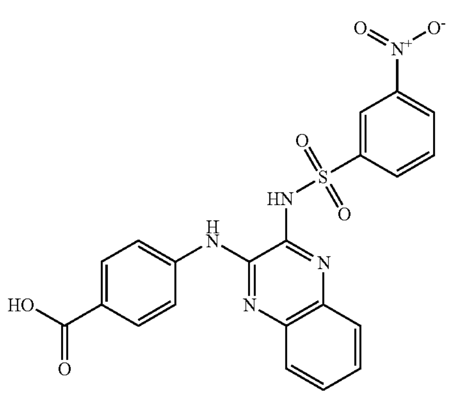 | 4-[(3-{[(3-nitrophenyl)sulfonyl]amino}quinoxalin-2-yl)amino]benzoic acid |

TABLE 1-continued

| Cpd. No. | Structure | Name |
|---|---|---|
| 125 | 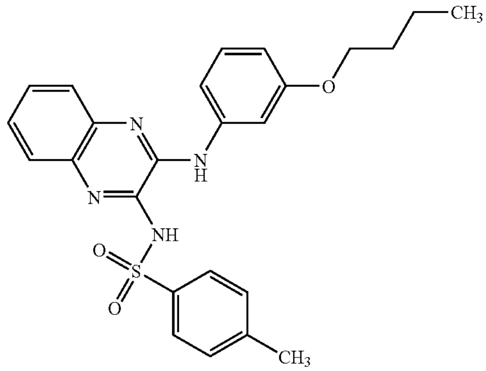 | N-(3-{[3-(butyloxy)phenyl]amino}quinoxalin-2-yl)-4-methylbenzenesulfonamide |
| 126 | 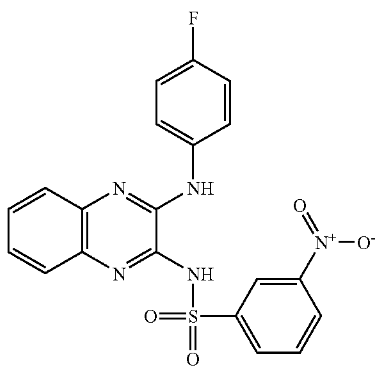 | N-{3-[(4-fluorophenyl)amino]quinoxalin-2-yl}-3-nitrobenzenesulfonamide |
| 127 | 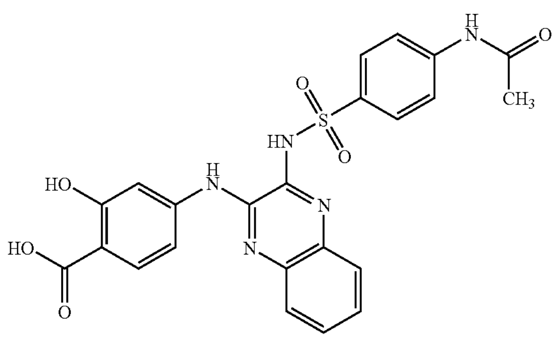 | 4-{[3-({[4-(acetylamino)phenyl]sulfonyl}amino)quinoxalin-2-yl]amino}-2-hydroxybenzoic acid |
| 128 | 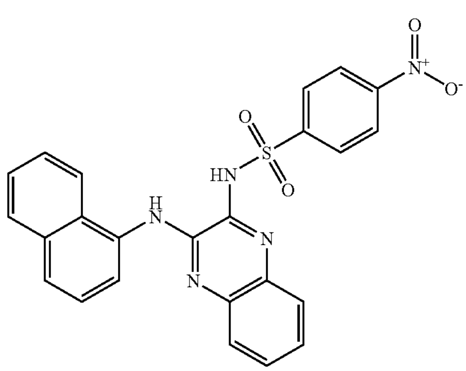 | N-[3-(naphthalen-1-ylamino)quinoxalin-2-yl]-4-nitrobenzenesulfonamide |

TABLE 1-continued

| Cpd. No. | Structure | Name |
|---|---|---|
| 129 | 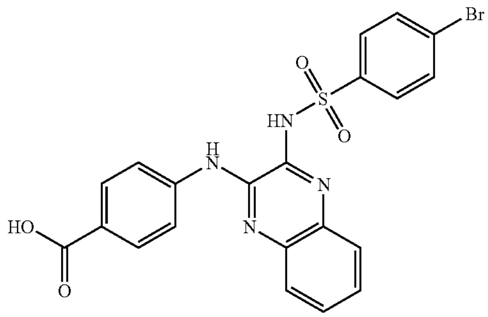 | 4-[(3-{[(4-bromophenyl)sulfonyl]amino}quinoxalin-2-yl)amino]benzoic acid |
| 130 | 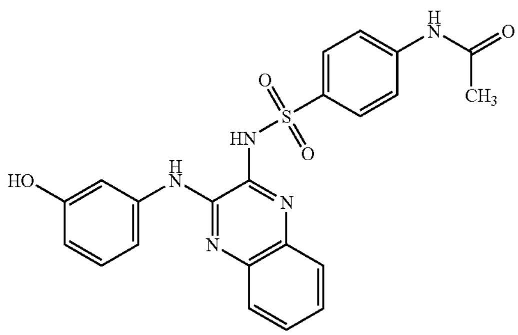 | N-{4-[({3-[(3-hydroxyphenyl)amino]quinoxalin-2-yl}amino)sulfonyl]phenyl}acetamide |
| 131 | 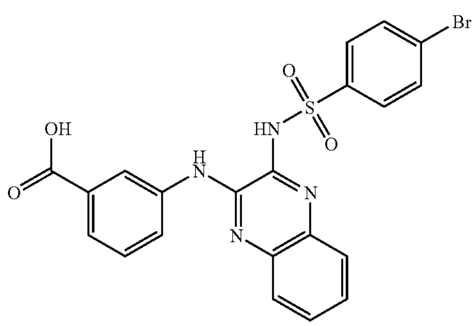 | 3-[(3-{[(4-bromophenyl)sulfonyl]amino}quinoxalin-2-yl)amino]benzoic acid |
| 132 | 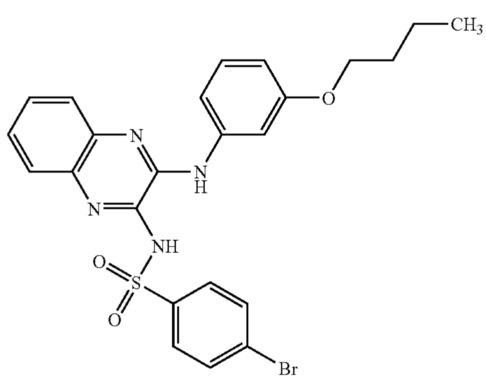 | 4-bromo-N-(3-{[3-(butyloxy)phenyl]amino}quinoxalin-2-yl)benzenesulfonamide |

TABLE 1-continued
| Cpd. No. | Structure | Name |
|---|---|---|
| 133 | 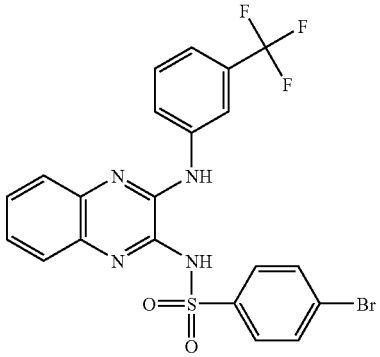 | 4-bromo-N-(3-{[3-(trifluoromethyl)phenyl]amino}quinoxalin-2-yl)benzenesulfonamide |
| 134 | 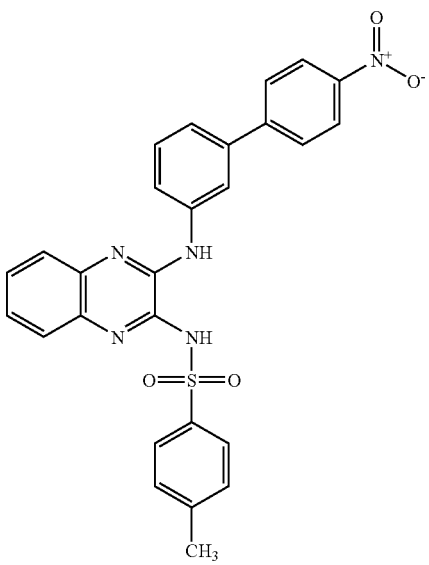 | 4-methyl-N-{3-[(4'-nitrobiphenyl-3-yl)amino]quinoxalin-2-yl}benzenesulfonamide |
| 135 | 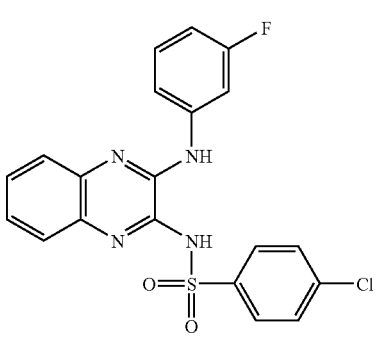 | 4-chloro-N-{3-[(3-fluorophenyl)amino]quinoxalin-2-yl}benzenesulfonamide |

TABLE 1-continued
| Cpd. No. | Structure | Name |
|---|---|---|
| 136 | 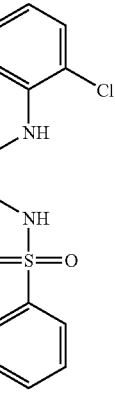 | N-{3-[(2-chlorophenyl)amino]quinoxalin-2-yl}benzenesulfonamide |
| 137 | 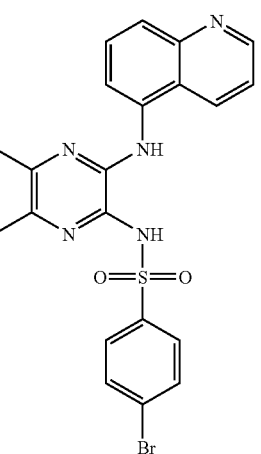 | 4-bromo-N-[3-(quinolin-5-ylamino)quinoxalin-2-yl]benzenesulfonamide |
| 138 | 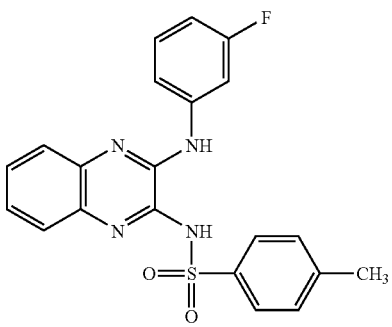 | N-{3-[(3-fluorophenyl)amino]quinoxalin-2-yl}-4-methylbenzenesulfonamide |
| 139 | 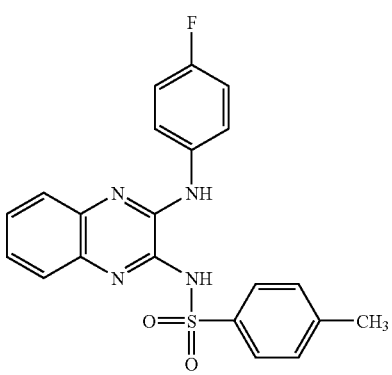 | N-{3-[(4-fluorophenyl)amino]quinoxalin-2-yl}-4-methylbenzenesulfonamide |

TABLE 1-continued

| Cpd. No. | Structure | Name |
|---|---|---|
| 140 | 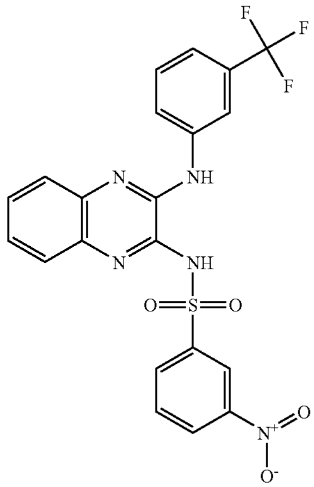 | 3-nitro-N-(3-{[3-(trifluoromethyl)phenyl]amino}quinoxalin-2-yl)benzenesulfonamide |
| 141 | 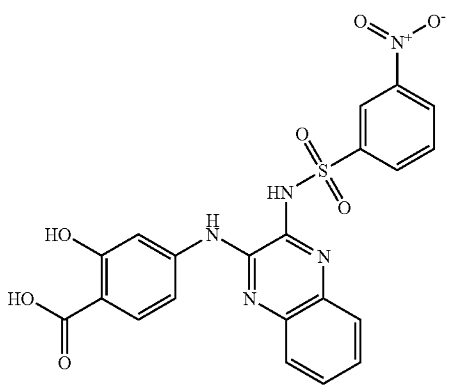 | 2-hydroxy-4-[(3-{[(3-nitrophenyl)sulfonyl]amino}quinoxalin-2-yl)amino]benzoic acid |
| 142 | 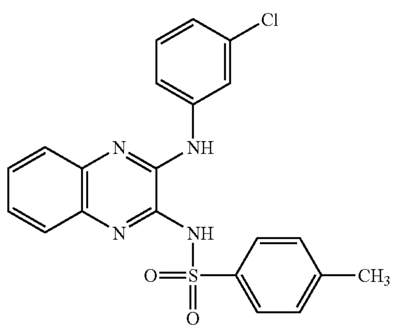 | N-{3-[(3-chlorophenyl)amino]quinoxalin-2-yl}-4-methylbenzenesulfonamide |
| 143 | 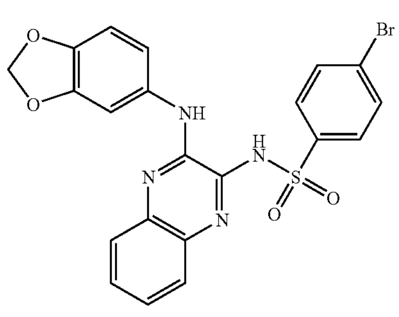 | N-[3-(1,3-benzodioxol-5-ylamino)quinoxalin-2-yl]-4-bromobenzenesulfonamide |

TABLE 1-continued

| Cpd. No. | Structure | Name |
|---|---|---|
| 144 | 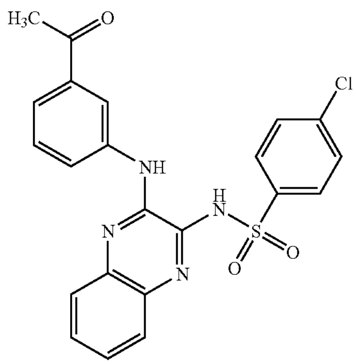 | N-{3-[(3-acetylphenyl)amino]quinoxalin-2-yl}-4-chlorobenzenesulfonamide |
| 145 | 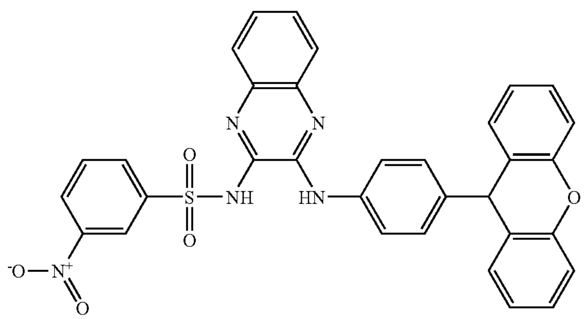 | 3-nitro-N-(3-{[4-(9H-xanthen-9-yl)phenyl]amino}quinoxalin-2-yl)benzenesulfonamide |
| 146 | 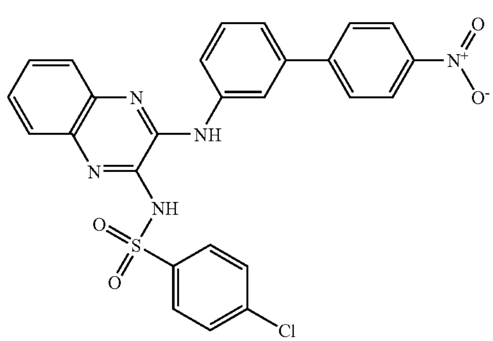 | 4-chloro-N-{3-[(4'-nitrobiphenyl-3-yl)amino]quinoxalin-2-yl}benzenesulfonamide |
| 147 | 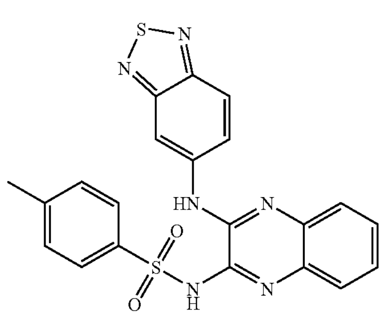 | N-[3-(2,1,3-benzothiadiazol-5-ylamino)quinoxalin-2-yl]-4-tolylsulfonamide |

TABLE 1-continued

| Cpd. No. | Structure | Name |
|---|---|---|
| 148 | 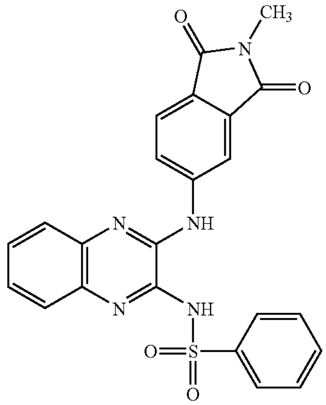 | N-{3-[(2-methyl-1,3-dioxo-2,3-dihydro-1H-isoindol-5-yl)amino]quinoxalin-2-yl}benzenesulfonamide |
| 149 | 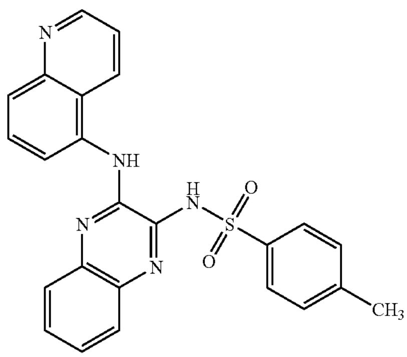 | 4-methyl-N-[3-(quinolin-5-ylamino)quinoxalin-2-yl]benzenesulfonamide |
| 150 | 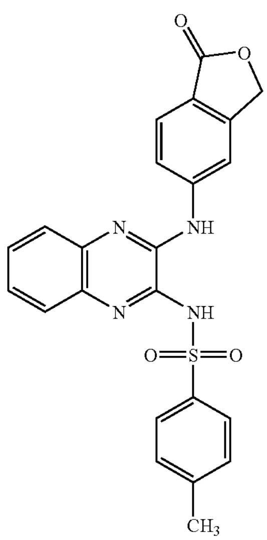 | 4-methyl-N-{3-[(1-oxo-1,3-dihydro-2-benzofuran-5-yl)amino]quinoxalin-2-yl}benzenesulfonamide |
| 151 | 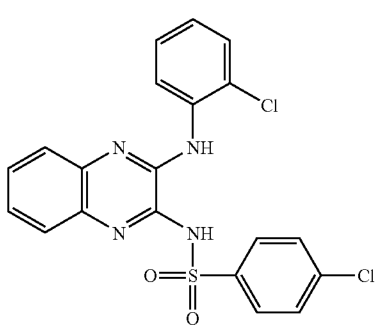 | 4-chloro-N-{3-[(2-chlorophenyl)amino]quinoxalin-2-yl}benzenesulfonamide |

TABLE 1-continued

| Cpd. No. | Structure | Name |
|---|---|---|
| 152 | 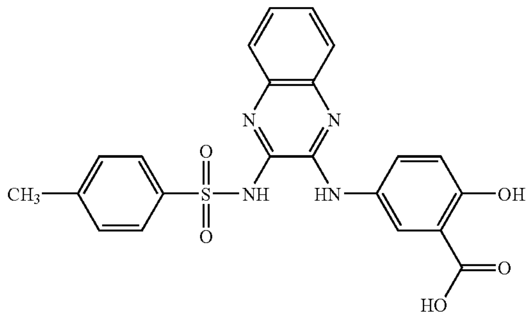 | 2-hydroxy-5-[(3-{[(4-methylphenyl)sulfonyl]amino}quinoxalin-2-yl)amino]benzoic acid |
| 153 | 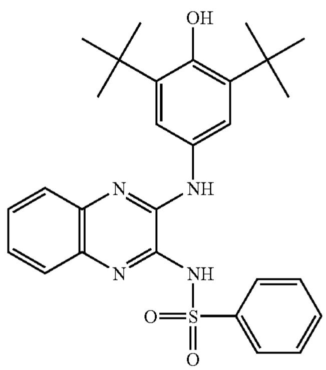 | N-(3-{[3,5-bis(1,1-dimethylethyl)-4-hydroxyphenyl]amino}quinoxalin-2-yl)benzenesulfonamide |
| 154 | 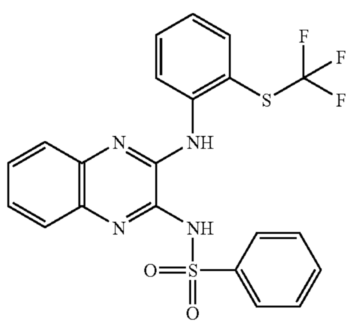 | N-[3-({2-[(trifluoromethyl)thio]phenyl}amino)quinoxalin-2-yl]benzenesulfonamide |
| 155 | 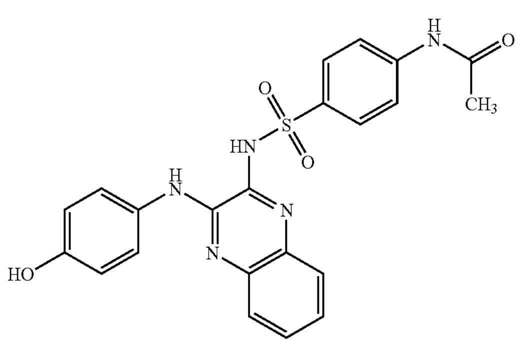 | N-{4-[({3-[(4-hydroxyphenyl)amino]quinoxalin-2-yl}amino)sulfonyl]phenyl}acetamide |

TABLE 1-continued

| Cpd. No. | Structure | Name |
|---|---|---|
| 156 | 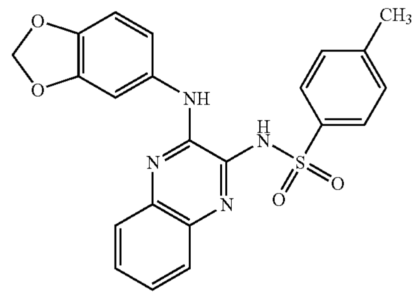 | N-[3-(1,3-benzodioxol-5-ylamino)quinoxalin-2-yl]-4-methylbenzenesulfonamide |
| 157 | 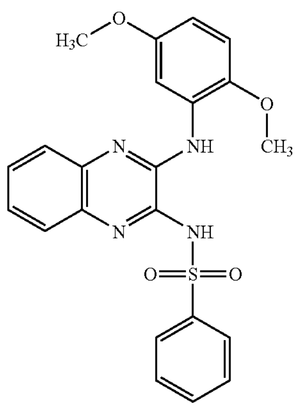 | N-(3-{[2,5-bis(methoxy)phenyl]amino}quinoxalin-2-yl)benzenesulfonamide |
| 158 | 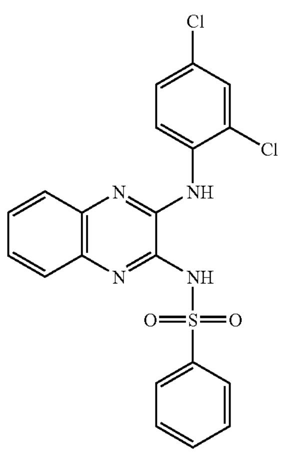 | N-{3-[(2,4-dichlorophenyl)amino]quinoxalin-2-yl}benzenesulfonamide |
| 159 | 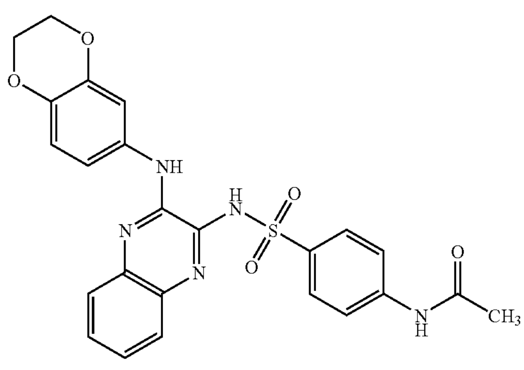 | N-[4-({[3-(2,3-dihydro-1,4-benzodioxin-6-ylamino)quinoxalin-2-yl]amino}sulfonyl)phenyl]acetamide |

TABLE 1-continued
| Cpd. No. | Structure | Name |
|---|---|---|
| 160 | 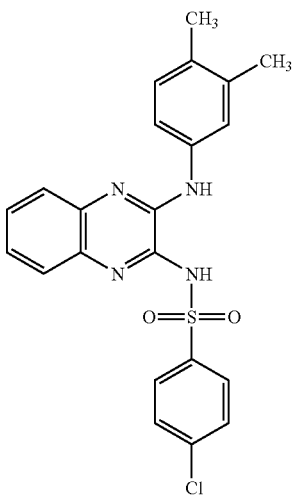 | 4-chloro-N-{3-[(3,4-dimethylphenyl)amino]quinoxalin-2-yl}benzenesulfonamide |
| 161 | 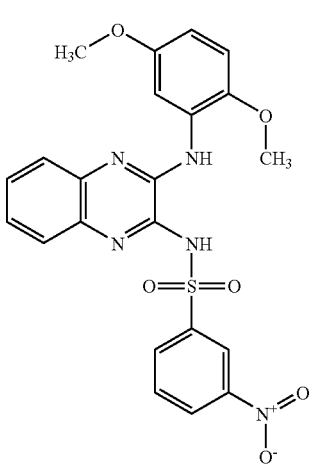 | N-(3-{[2,5-bis(methoxy)phenyl]amino}quinoxalin-2-yl)-3-nitrobenzenesulfonamide |
| 162 | 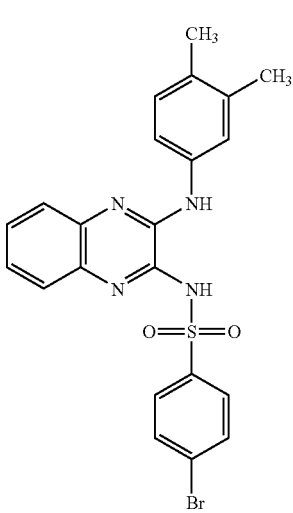 | 4-bromo-N-{3-[(3,4-dimethylphenyl)amino]quinoxalin-2-yl}benzenesulfonamide |

TABLE 1-continued

| Cpd. No. | Structure | Name |
|---|---|---|
| 163 | 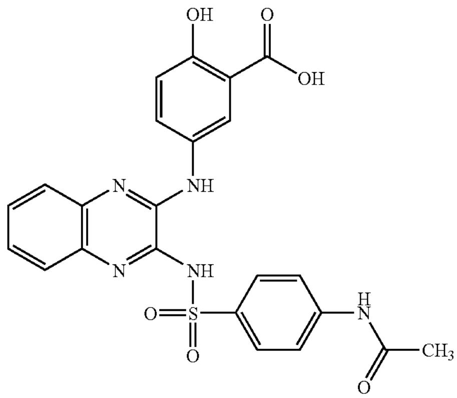 | 5-{[3-({[4-(acetylamino)phenyl]sulfonyl}amino)quinoxalin-2-yl]amino}-2-hydroxybenzoic acid |
| 164 | 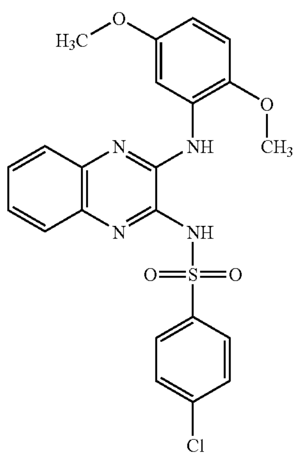 | N-(3-{[2,5-bis(methoxy)phenyl]amino}quinoxalin-2-yl)-4-chlorobenzenesulfonamide |
| 165 | 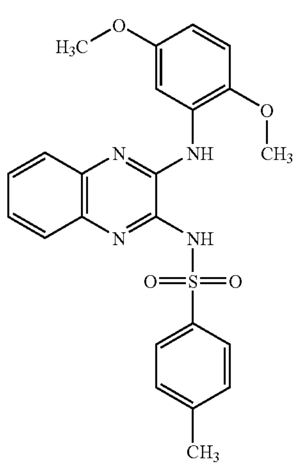 | N-(3-{[2,5-bis(methoxy)phenyl]amino}quinoxalin-2-yl)-4-methylbenzenesulfonamide |

TABLE 1-continued

| Cpd. No. | Structure | Name |
|---|---|---|
| 166 | 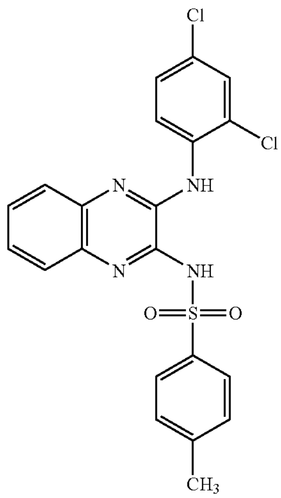 | N-{3-[(2,4-dichlorophenyl)amino]quinoxalin-2-yl}-4-methylbenzenesulfonamide |
| 167 | 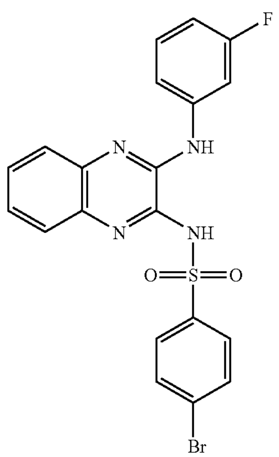 | 4-bromo-N-{3-[(3-fluorophenyl)amino]quinoxalin-2-yl}benzenesulfonamide |
| 168 | 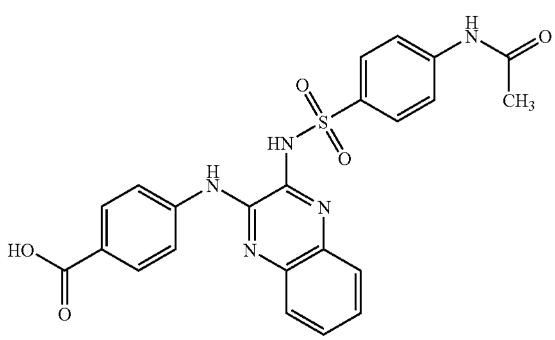 | 4-{[3-({[4-(acetylamino)phenyl]sulfonyl}amino)quinoxalin-2-yl]amino}benzoic acid |
| 169 | 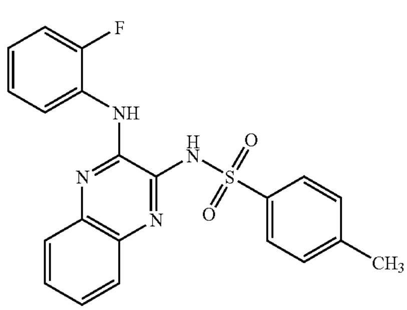 | N-{3-[(2-fluorophenyl)amino]quinoxalin-2-yl}-4-methylbenzenesulfonamide |

TABLE 1-continued

| Cpd. No. | Structure | Name |
|---|---|---|
| 170 | 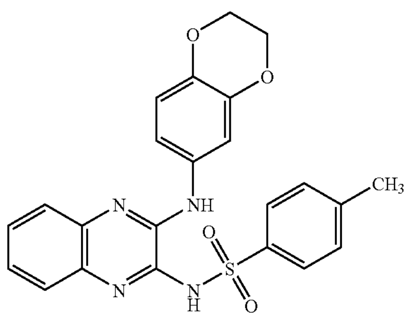 | N-[3-(2,3-dihydro-1,4-benzodioxin-6-ylamino)quinoxalin-2-yl]-4-methylbenzenesulfonamide |
| 171 | 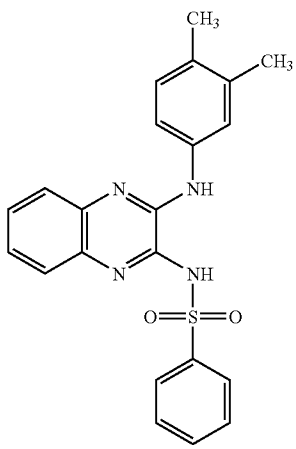 | N-{3-[(3,4-dimethylphenyl)amino]quinoxalin-2-yl}benzenesulfonamide |
| 172 | 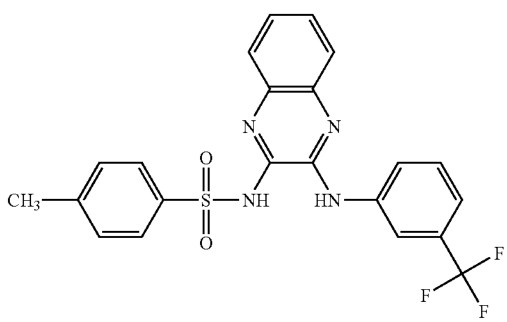 | 4-methyl-N-(3-{[3-(trifluoromethyl)phenyl]amino}quinoxalin-2-yl)benzenesulfonamide |
| 173 | 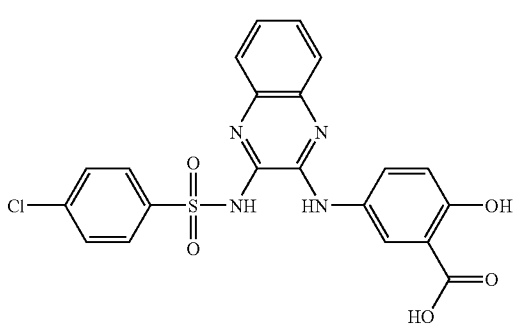 | 5-[(3-{[(4-chlorophenyl)sulfonyl]amino}quinoxalin-2-yl)amino]-2-hydroxybenzoic acid |

TABLE 1-continued

| Cpd. No. | Structure | Name |
|---|---|---|
| 174 | 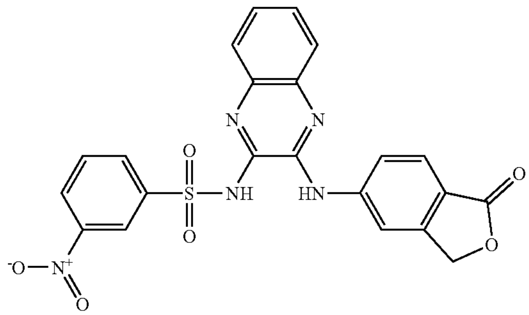 | 3-nitro-N-{3-[(1-oxo-1,3-dihydro-2-benzofuran-5-yl)amino]quinoxalin-2-yl}benzenesulfonamide |
| 175 | 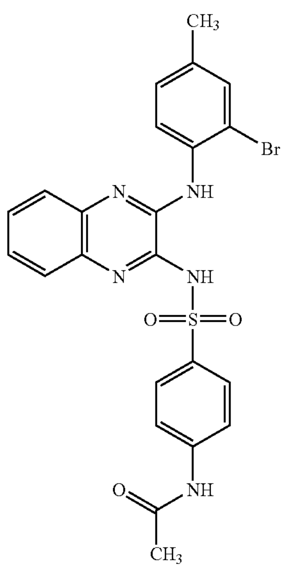 | N-{4-[({3-[(2-bromo-4-methylphenyl)amino]quinoxalin-2-yl}amino)sulfonyl]phenyl}acetamide |
| 176 | 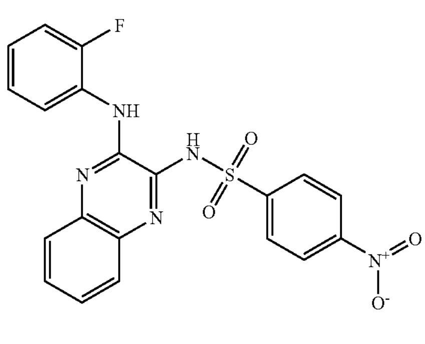 | N-{3-[(2-fluorophenyl)amino]quinoxalin-2-yl}-4-nitrobenzenesulfonamide |

TABLE 1-continued
| Cpd. No. | Structure | Name |
|---|---|---|
| 177 | 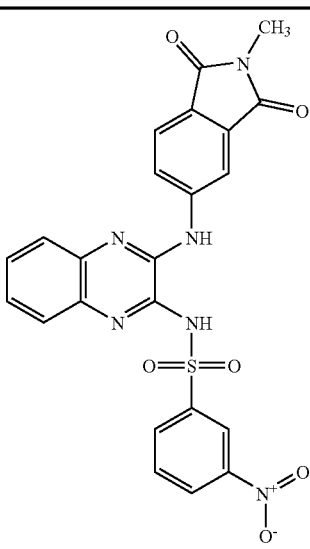 | N-{3-[(2-methyl-1,3-dioxo-2,3-dihydro-1H-isoindol-5-yl)amino]quinoxalin-2-yl}-3-nitrobenzenesulfonamide |
| 178 | 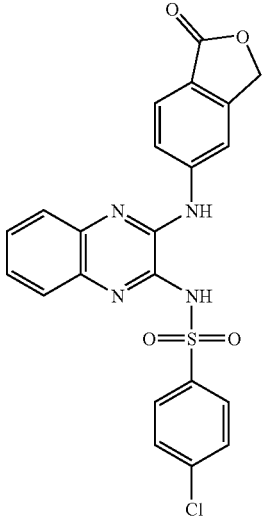 | 4-chloro-N-{3-[(1-oxo-1,3-dihydro-2-benzofuran-5-yl)amino]quinoxalin-2-yl}benzenesulfonamide |
| 179 | 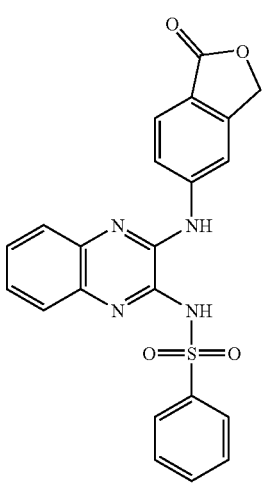 | N-{3-[(1-oxo-1,3-dihydro-2-benzofuran-5-yl)amino]quinoxalin-2-yl}benzenesulfonamide |

TABLE 1-continued

| Cpd. No. | Structure | Name |
|---|---|---|
| 180 | 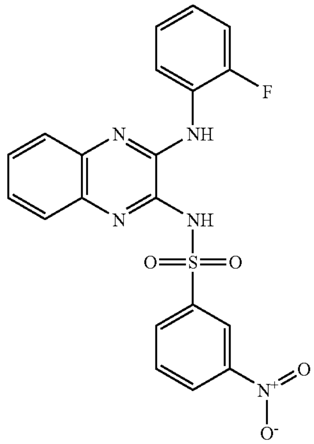 | N-{3-[(2-fluorophenyl)amino]quinoxalin-2-yl}-3-nitrobenzenesulfonamide |
| 181 | 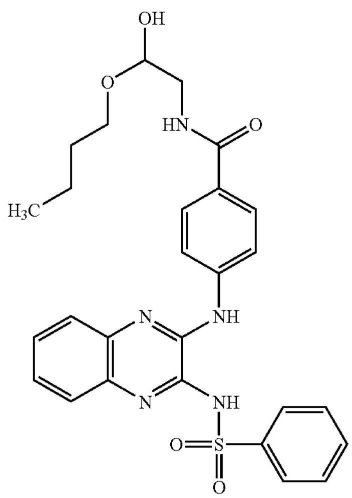 | N-[2-(butyloxy)-2-hydroxyethyl]-4-({3-[(phenylsulfonyl)amino]quinoxalin-2-yl}amino)benzamide |
| 182 | 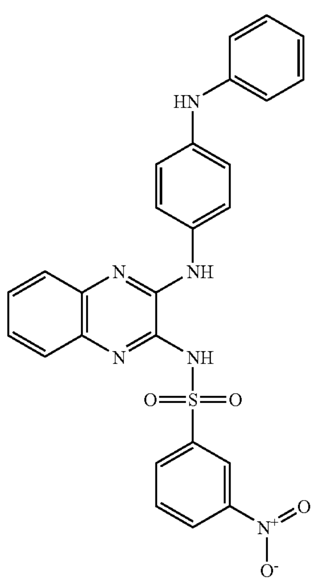 | 3-nitro-N-(3-{[4-(phenylamino)phenyl]amino}quinoxalin-2-yl)benzenesulfonamide |

TABLE 1-continued

| Cpd. No. | Structure | Name |
| --- | --- | --- |
| 183 | 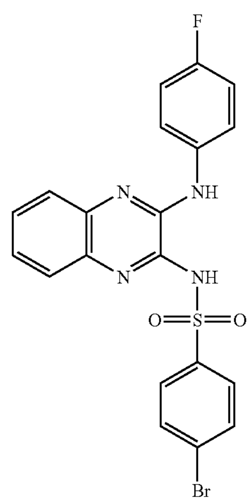 | 4-bromo-N-{3-[(4-fluorophenyl)amino]quinoxalin-2-yl}benzenesulfonamide |
| 184 | 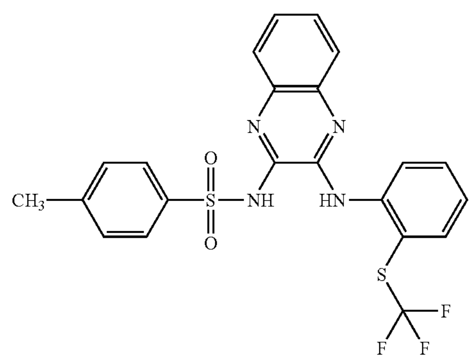 | 4-methyl-N-[3-({2-[(trifluoromethyl)thio]phenyl}amino)quinoxalin-2-yl]benzenesulfonamide |
| 185 | 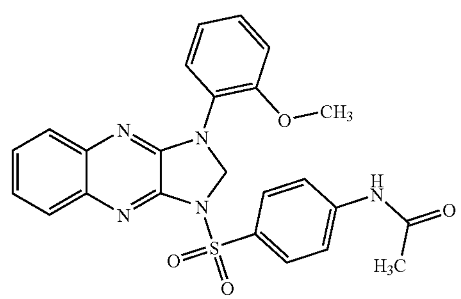 | N-[4-({3-[2-(methoxy)phenyl]-2,3-dihydro-1H-imidazo[4,5-b]quinoxalin-1-yl}sulfonyl)phenyl]acetamide |
| 186 | 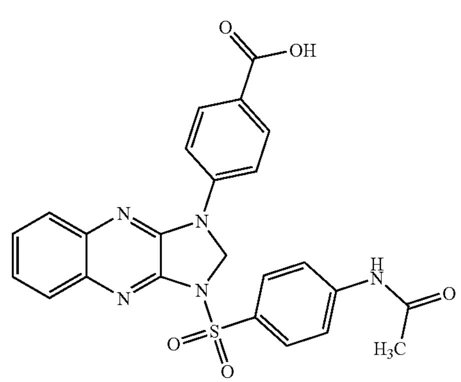 | 4-(3-{[4-(acetylamino)phenyl]sulfonyl}-2,3-dihydro-1H-imidazo[4,5-b]quinoxalin-1-yl)benzoic acid |

TABLE 1-continued

| Cpd. No. | Structure | Name |
| --- | --- | --- |
| 187 | 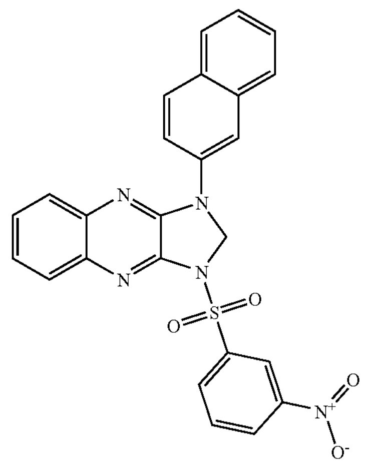 | 1-naphthalen-2-yl-3-[(3-nitrophenyl)sulfonyl]-2,3-dihydro-1H-imidazo[4,5-b]quinoxaline |
| 188 | 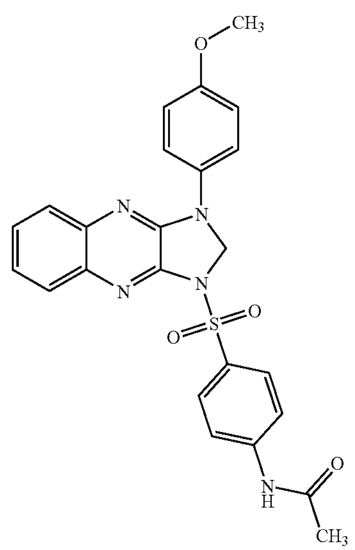 | N-[4-({3-[4-(methoxy)phenyl]-2,3-dihydro-1H-imidazo[4,5-b]quinoxalin-1-yl}sulfonyl)phenyl]acetamide |
| 189 | 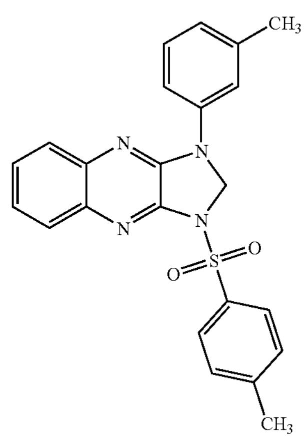 | 1-(3-methylphenyl)-3-[(4-methylphenyl)sulfonyl]-2,3-dihydro-1H-imidazo[4,5-b]quinoxaline |

TABLE 1-continued

| Cpd. No. | Structure | Name |
|---|---|---|
| 190 | 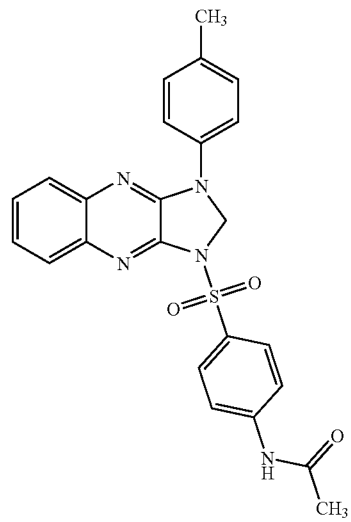 | N-(4-{[3-(4-methylphenyl)-2,3-dihydro-1H-imidazo[4,5-b]quinoxalin-1-yl]sulfonyl}phenyl)acetamide |
| 191 | 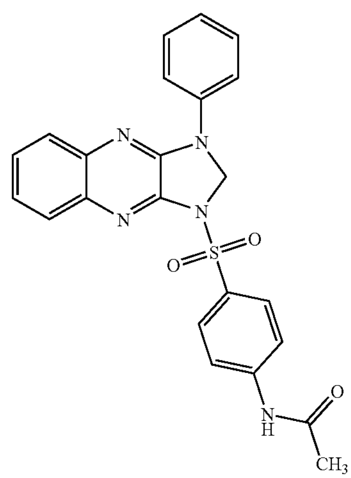 | N-{4-[(3-phenyl-2,3-dihydro-1H-imidazo[4,5-b]quinoxalin-1-yl)sulfonyl]phenyl}acetamide |
| 192 | 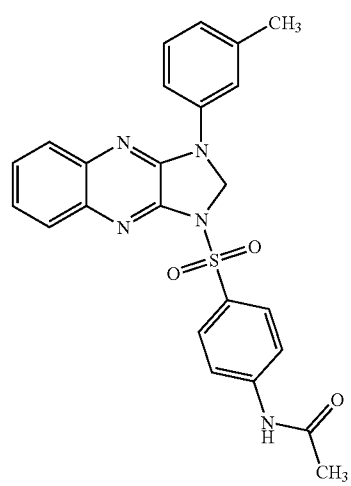 | N-(4-{[3-(3-methylphenyl)-2,3-dihydro-1H-imidazo[4,5-b]quinoxalin-1-yl]sulfonyl}phenyl)acetamide |

TABLE 1-continued

| Cpd. No. | Structure | Name |
|---|---|---|
| 193 | 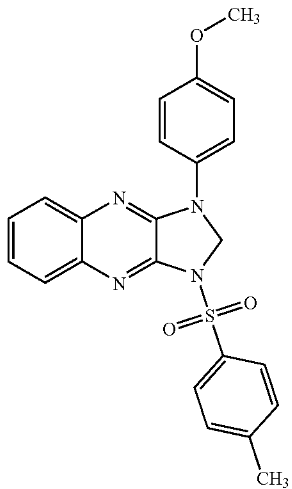 | 1-[4-(methoxy)phenyl]-3-[(4-methylphenyl)sulfonyl]-2,3-dihydro-1H-imidazo[4,5-b]quinoxaline |
| 194 | 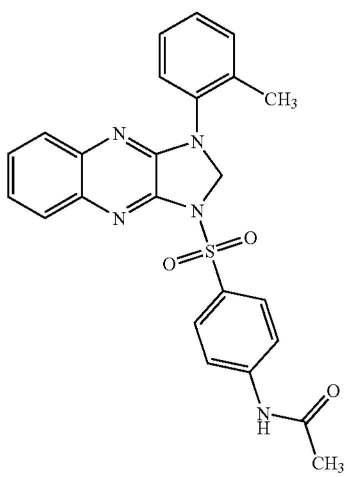 | N-(4-{[3-(2-methylphenyl)-2,3-dihydro-1H-imidazo[4,5-b]quinoxalin-1-yl]sulfonyl}phenyl)acetamide |
| 195 | 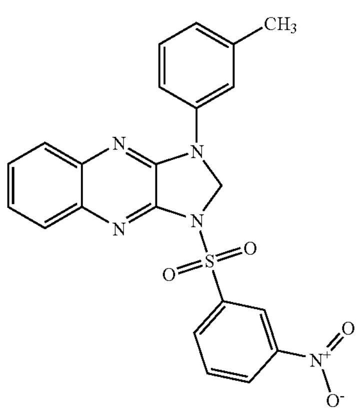 | 1-(3-methylphenyl)-3-[(3-nitrophenyl)sulfonyl]-2,3-dihydro-1H-imidazo[4,5-b]quinoxaline |

TABLE 1-continued

| Cpd. No. | Structure | Name |
|---|---|---|
| 196 | 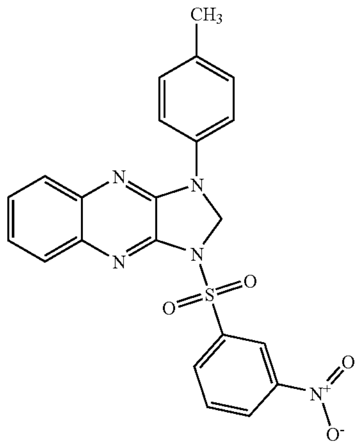 | 1-(4-methylphenyl)-3-[(3-nitrophenyl)sulfonyl]-2,3-dihydro-1H-imidazo[4,5-b]quinoxaline |
| 197 | 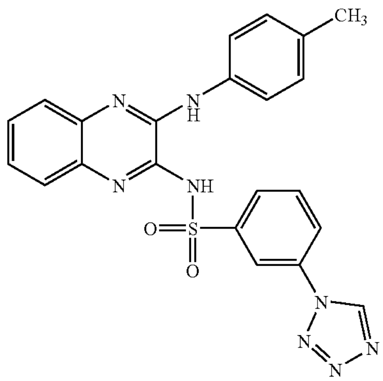 | N-{3-[(4-methylphenyl)amino]quinoxalin-2-yl}-3-(1H-tetrazol-1-yl)benzenesulfonamide |
| 198 | 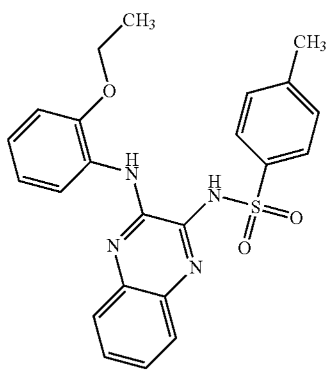 | N-(3-{[2-(ethyloxy)phenyl]amino}quinoxalin-2-yl)-4-methylbenzenesulfonamide |
| 199 | 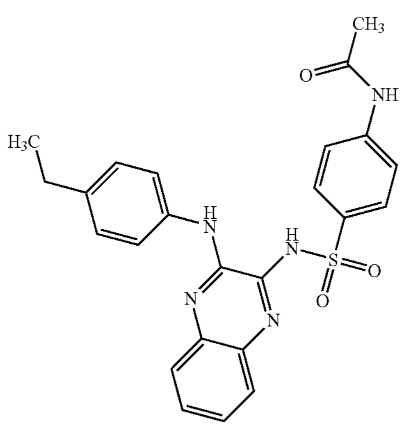 | N-{4-[({3-[(4-ethylphenyl)amino]quinoxalin-2-yl}amino)sulfonyl]phenyl}acetamide |

TABLE 1-continued

| Cpd. No. | Structure | Name |
|---|---|---|
| 200 | 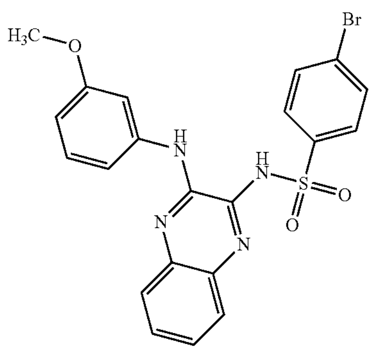 | 4-bromo-N-(3-{[3-(methoxy)phenyl]amino}quinoxalin-2-yl)benzenesulfonamide |
| 201 | 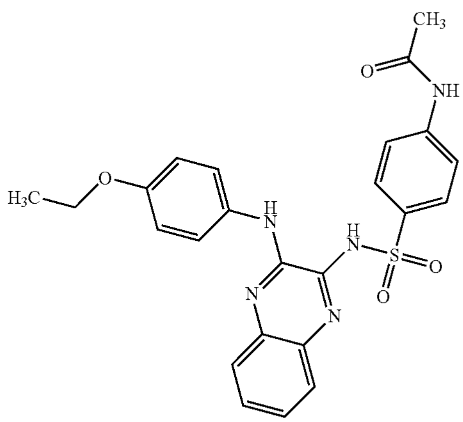 | N-(4-{[(3-{[4-(ethyloxy)phenyl]amino}quinoxalin-2-yl)amino]sulfonyl}phenyl)acetamide |
| 202 | 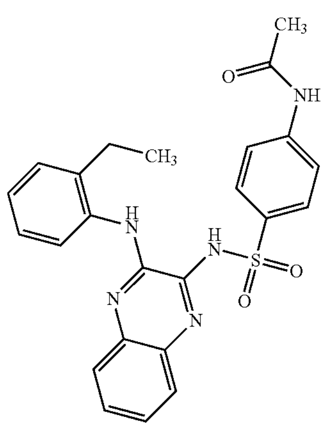 | N-{4-[({3-[(2-ethylphenyl)amino]quinoxalin-2-yl}amino)sulfonyl]phenyl}acetamide |
| 203 | 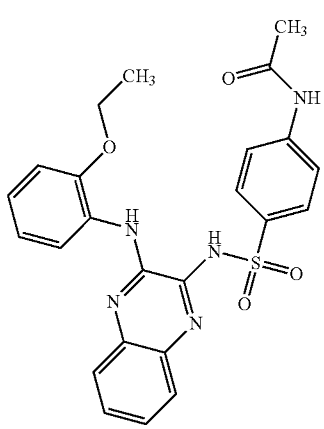 | N-(4-{[(3-{[2-(ethyloxy)phenyl]amino}quinoxalin-2-yl)amino]sulfonyl}phenyl)acetamide |

TABLE 1-continued

| Cpd. No. | Structure | Name |
|---|---|---|
| 204 | 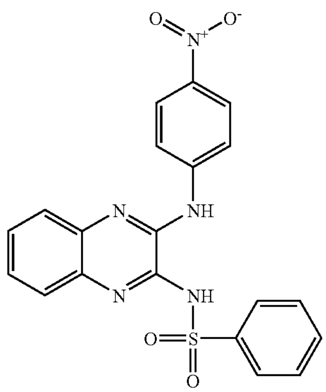 | N-{3-[(4-nitrophenyl)amino]quinoxalin-2-yl}benzenesulfonamide |
| 205 | 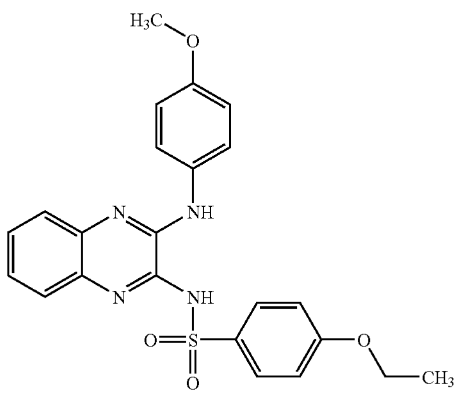 | 4-(ethyloxy)-N-(3-{[4-(methoxy)phenyl]amino}quinoxalin-2-yl)benzenesulfonamide |
| 206 | 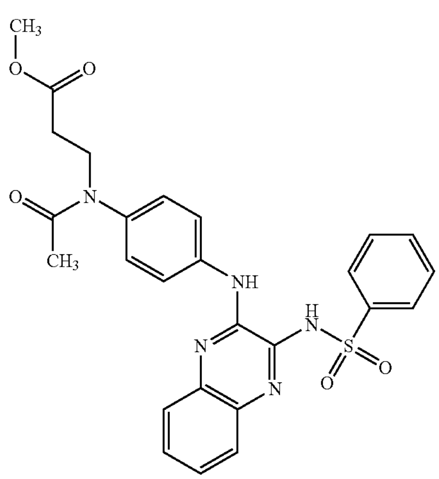 | methyl N-acetyl-N-[4-({3-[(phenylsulfonyl)amino]quinoxalin-2-yl}amino)phenyl]-beta-alaninate |

| Cpd. No. | Structure | Name |
|---|---|---|
| 207 | 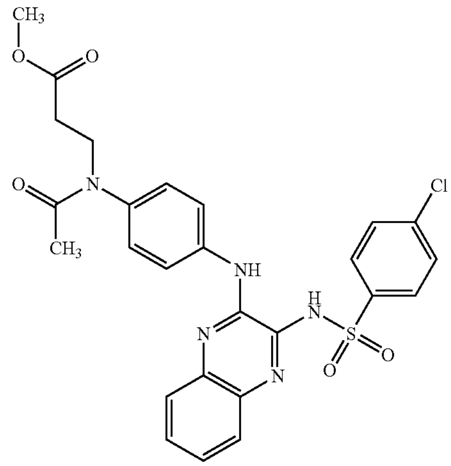 | methyl N-acetyl-N-{4-[(3-{[(4-chlorophenyl)sulfonyl]amino}quinoxalin-2-yl)amino]phenyl}-beta-alaninate |
| 208 | 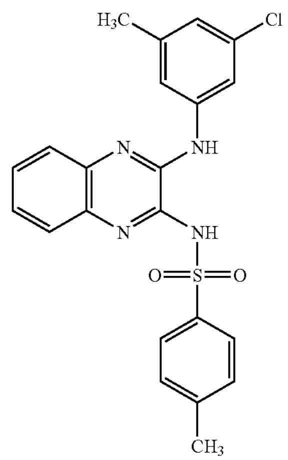 | N-{3-[(3-chloro-5-methylphenyl)amino]quinoxalin-2-yl}-4-methylbenzenesulfonamide |
| 209 | 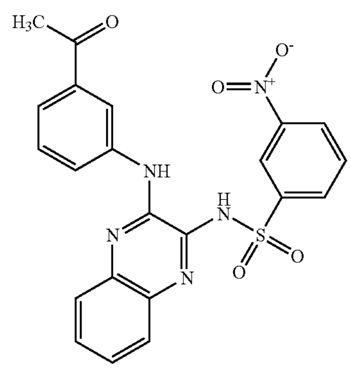 | N-{3-[(3-acetylphenyl)amino]quinoxalin-2-yl}-3-nitrobenzenesulfonamide |

TABLE 1-continued

| Cpd. No. | Structure | Name |
|---|---|---|
| 210 | 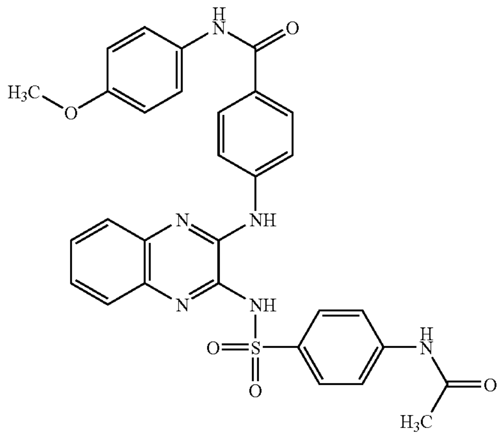 | 4-{[3-({[4-(acetylamino)phenyl]sulfonyl}amino)quinoxalin-2-yl]amino}-N-[4-(methoxy)phenyl]benzamide |
| 211 | 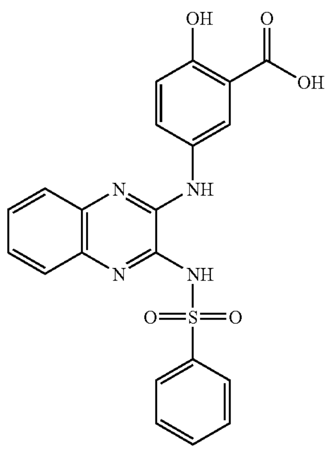 | 2-hydroxy-5-({3-[(phenylsulfonyl)amino]quinoxalin-2-yl}amino)benzoic acid |
| 212 | 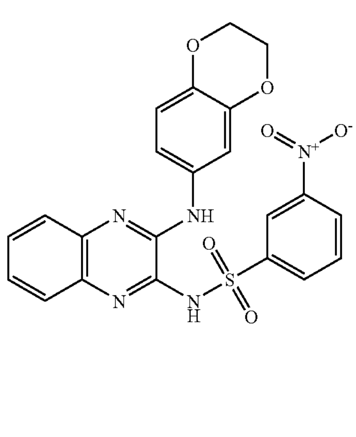 | N-[3-(2,3-dihydro-1,4-benzodioxin-6-ylamino)quinoxalin-2-yl]-3-nitrobenzenesulfonamide |

TABLE 1-continued
| Cpd. No. | Structure | Name |
|---|---|---|
| 213 | 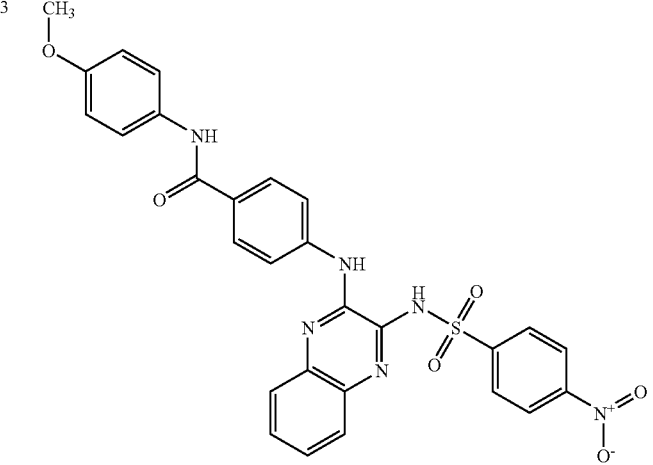 | N-[4-(methoxy)phenyl]-4-[(3-{[(4-nitrophenyl)sulfonyl]amino}-quinoxalin-2-yl)amino]benzamide |
| 214 | 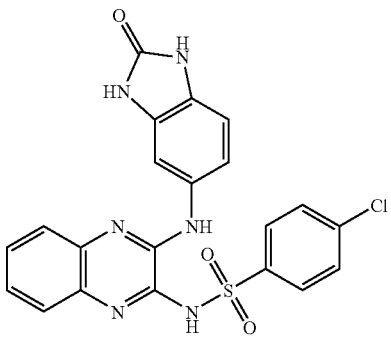 | 4-chloro-N-{3-[(2-oxo-2,3-dihydro-1H-benzimidazol-5-yl)amino]quinoxalin-2-yl}benzenesulfonamide |
| 215 | 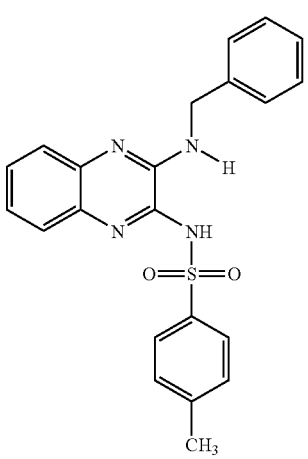 | 4-methyl-N-{3-[methyl(phenylmethyl)amino]quinoxalin-2-yl}benzenesulfonamide |

TABLE 1-continued

| Cpd. No. | Structure | Name |
|---|---|---|
| 216 | 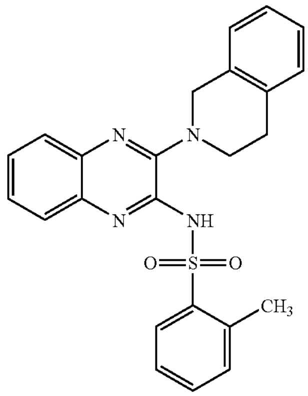 | N-[3-(3,4-dihydroisoquinolin-2(1H)-yl)quinoxalin-2-yl]-2-methylbenzenesulfonamide |
| 217 | 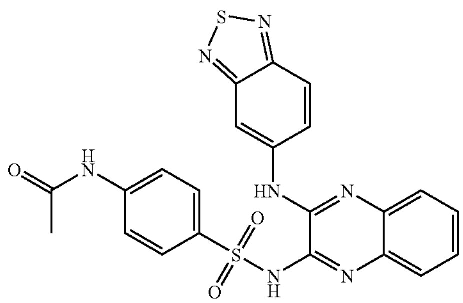 | N-[4-({[3-(2,1,3-benzothiadiazol-5-ylamino)quinoxalin-2-yl]amino}sulfonyl)phenyl]acetamide |
| 218 | 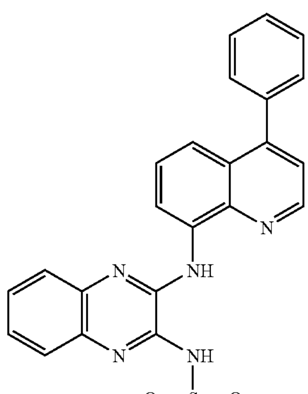 | 4-bromo-N-{3-[(4-phenylquinolin-8-yl)amino]quinoxalin-2-yl}benzenesulfonamide |
| 219 | 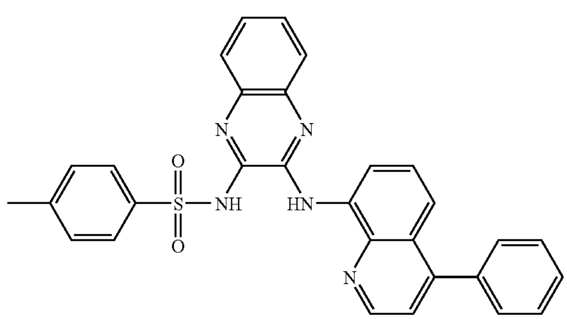 | 4-methyl-N-{3-[(4-phenylquinolin-8-yl)amino]quinoxalin-2-yl}benzenesulfonamide |

TABLE 1-continued

| Cpd. No. | Structure | Name |
|---|---|---|
| 220 | 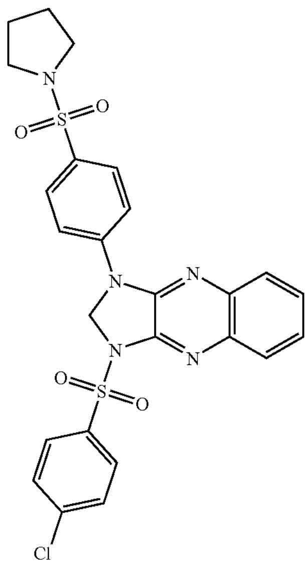 | 1-[(4-chlorophenyl)sulfonyl]-3-[4-(pyrrolidin-1-ylsulfonyl)phenyl]-2,3-dihydro-1H-imidazo[4,5-b]quinoxaline |
| 221 | 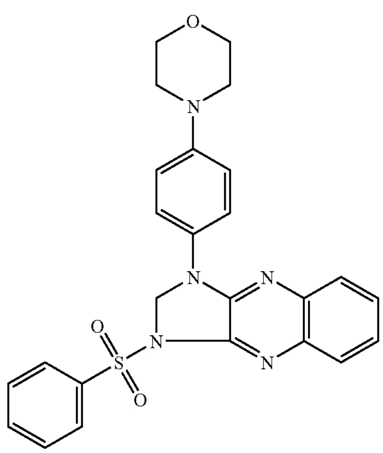 | 1-(4-morpholin-4-ylphenyl)-3-(phenylsulfonyl)-2,3-dihydro-1H-imidazo[4,5-b]quinoxaline |
| 222 | 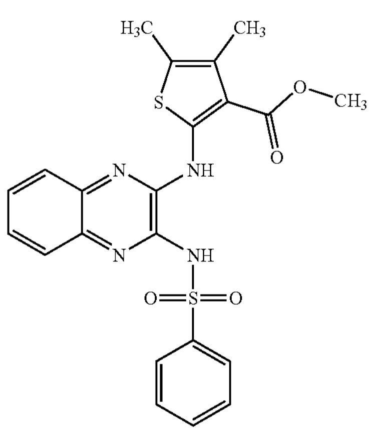 | methyl 4,5-dimethyl-2-({3-[(phenylsulfonyl)amino]quinoxalin-2-yl}amino)thiophene-3-carboxylate |

TABLE 1-continued

| Cpd. No. | Structure | Name |
|---|---|---|
| 223 | 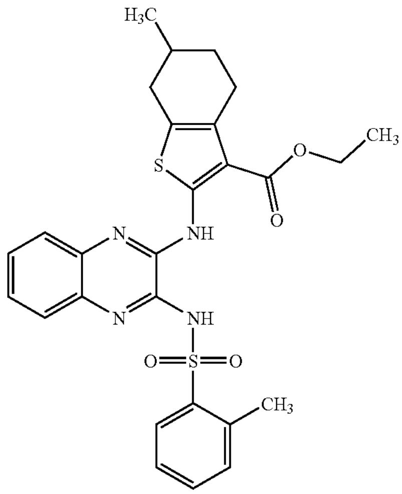 | ethyl 6-methyl-2-[(3-{[(2-methylphenyl)sulfonyl]amino}quinoxalin-2-yl)amino]-4,5,6,7-tetrahydro-1-benzothiophene-3-carboxylate |
| 224 | 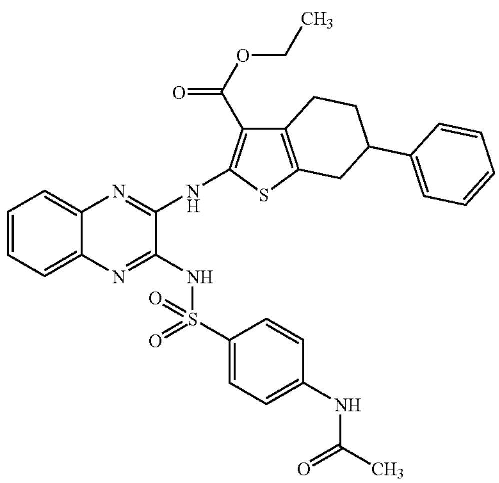 | ethyl 2-{[3-({[4-(acetylamino)phenyl]sulfonyl}amino)quinoxalin-2-yl]amino}-6-phenyl-4,5,6,7-tetrahydro-1-benzothiophene-3-carboxylate |
| 225 | 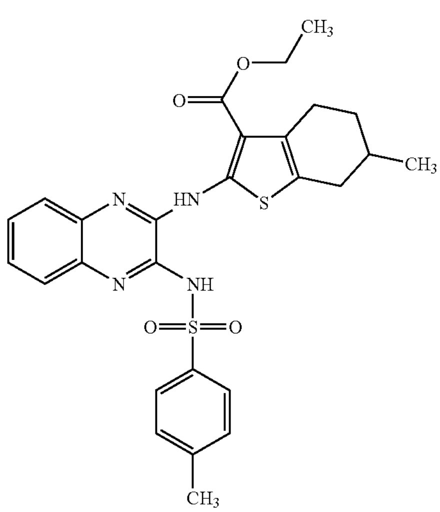 | ethyl 6-methyl-2-[(3-{[(4-methylphenyl)sulfonyl]amino}quinoxalin-2-yl)amino]-4,5,6,7-tetrahydro-1-benzothiophene-3-carboxylate |

TABLE 1-continued

| Cpd. No. | Structure | Name |
|---|---|---|
| 226 | 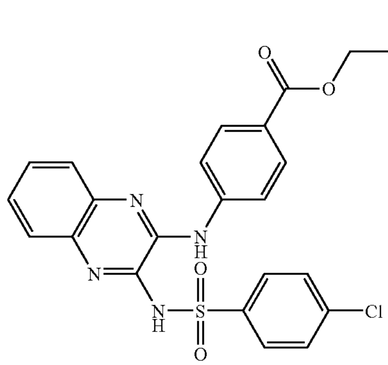 | propyl 4-[(3-{[(4-chlorophenyl)sulfonyl]amino}quinoxalin-2-yl)amino]benzoate |
| 227 | 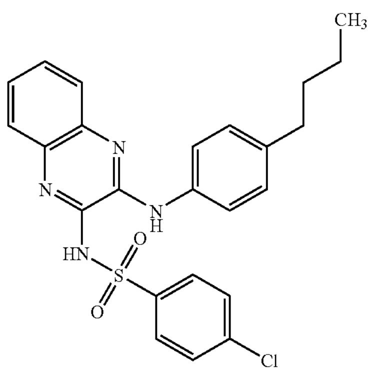 | N-{3-[(4-butylphenyl)amino]quinoxalin-2-yl}-4-chlorobenzenesulfonamide |
| 228 | 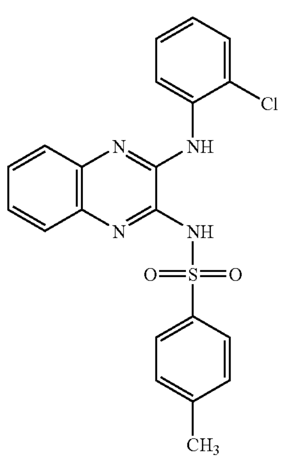 | N-{3-[(2-chlorophenyl)amino]quinoxalin-2-yl}-4-methylbenzenesulfonamide |

TABLE 1-continued

| Cpd. No. | Structure | Name |
|---|---|---|
| 229 | 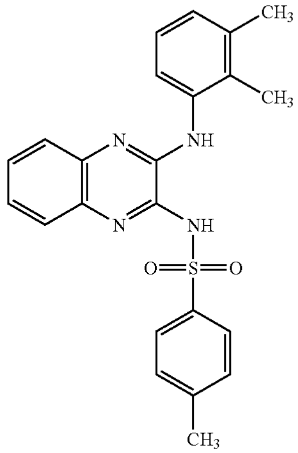 | N-{3-[(2,3-dimethylphenyl)amino]quinoxalin-2-yl}-4-methylbenzenesulfonamide |
| 230 | 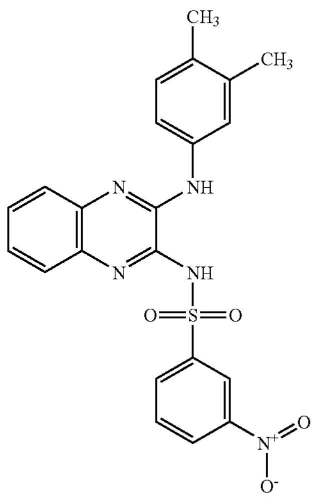 | N-{3-[(3,4-dimethylphenyl)amino]quinoxalin-2-yl}-3-nitrobenzenesulfonamide |
| 231 | 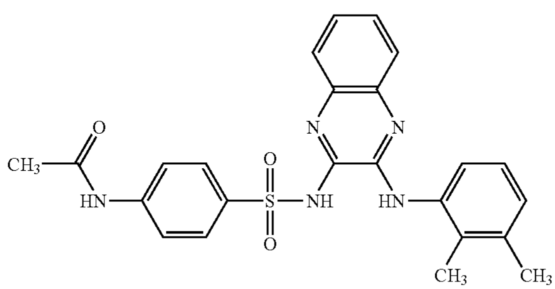 | N-{4-[({3-[(2,3-dimethylphenyl)amino]quinoxalin-2-yl}amino)sulfonyl]phenyl}acetamide |
| 232 | 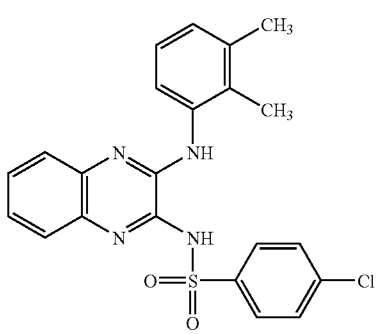 | 4-chloro-N-{3-[(2,3-dimethylphenyl)amino]quinoxalin-2-yl}benzenesulfonamide |

TABLE 1-continued

| Cpd. No. | Structure | Name |
|---|---|---|
| 233 | 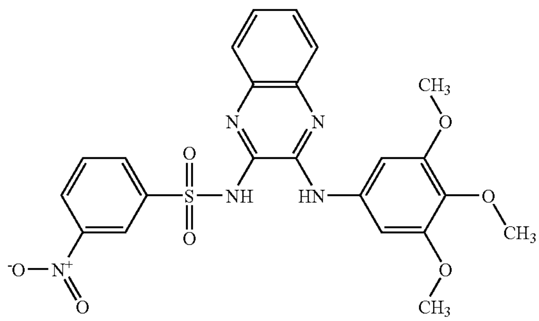 | 3-nitro-N-(3-{[3,4,5-tris(methoxy)phenyl]amino}quinoxalin-2-yl)benzenesulfonamide |
| 234 | 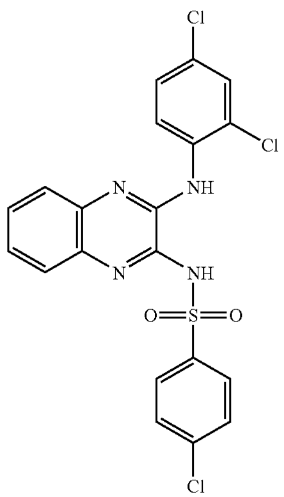 | 4-chloro-N-{3-[(2,4-dichlorophenyl)amino]quinoxalin-2-yl}benzenesulfonamide |
| 235 | 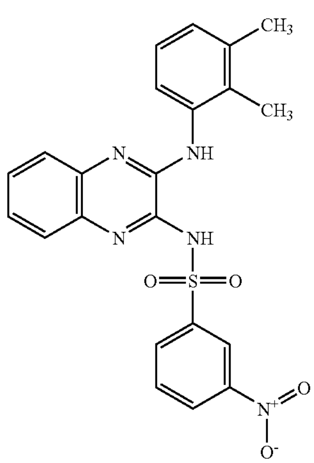 | N-{3-[(2,3-dimethylphenyl)amino]quinoxalin-2-yl}-3-nitrobenzenesulfonamide |
| 236 | 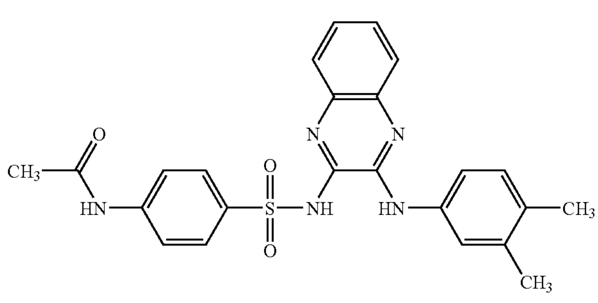 | N-{4-[({3-[(3,4-dimethylphenyl)amino]quinoxalin-2-yl}amino)sulfonyl]phenyl}acetamide |

| Cpd. No. | Structure | Name |
|---|---|---|
| 237 | 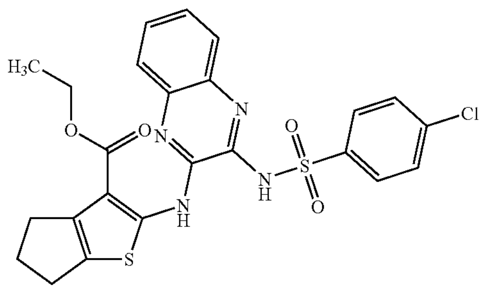 | ethyl 2-[(3-{[(4-chlorophenyl)sulfonyl]amino}quinoxalin-2-yl)amino]-5,6-dihydro-4H-cyclopenta[b]thiophene-3-carboxylate |
| 238 | 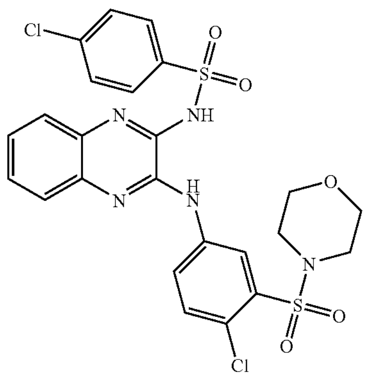 | 4-chloro-N-(3-{[4-chloro-3-(morpholin-4-ylsulfonyl)phenyl]amino}quinoxalin-2-yl)benzenesulfonamide |
| 239 | 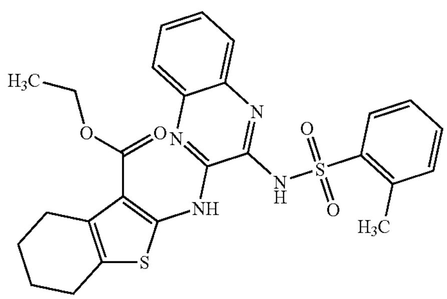 | ethyl 2-[(3-{[(2-methylphenyl)sulfonyl]amino}quinoxalin-2-yl)amino]-4,5,6,7-tetrahydro-1-benzothiophene-3-carboxylate |
| 240 | 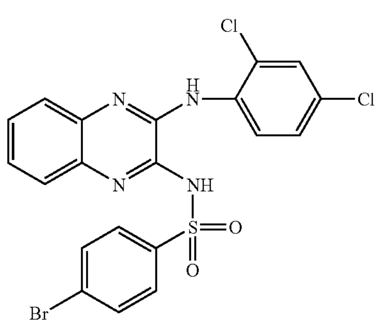 | 4-bromo-N-{3-[(2,4-dichlorophenyl)amino]quinoxalin-2-yl}benzenesulfonamide |
| 241 | 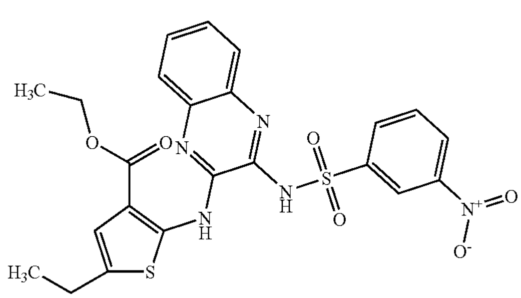 | ethyl 5-ethyl-2-[(3-{[(3-nitrophenyl)sulfonyl]amino}quinoxalin-2-yl)amino]thiophene-3-carboxylate |

TABLE 1-continued

| Cpd. No. | Structure | Name |
|---|---|---|
| 242 | 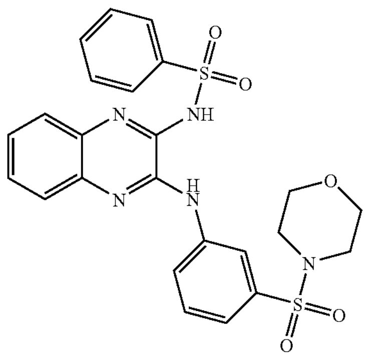 | N-(3-{[3-morpholin-4-ylsulfonyl)phenyl]amino}quinoxalin-2-yl)benzenesulfonamide |
| 243 | 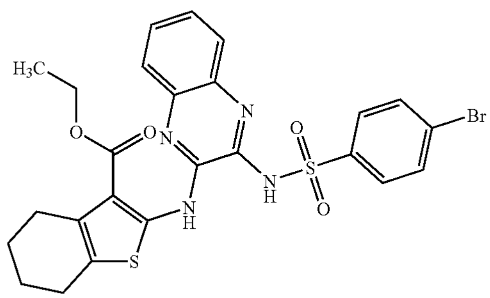 | ethyl 2-[(3-{[(4-bromophenyl)sulfonyl]amino}quinoxalin-2-yl)amino]-4,5,6,7-tetrahydro-1-benzothiophene-3-carboxylate |
| 244 | 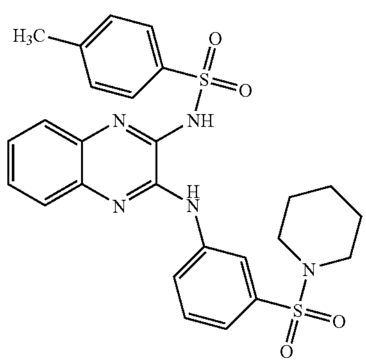 | 4-methyl-N-(3-{[3-(piperidin-1-ylsulfonyl)phenyl]amino}quinoxalin-2-yl)benzenesulfonamide |
| 245 | 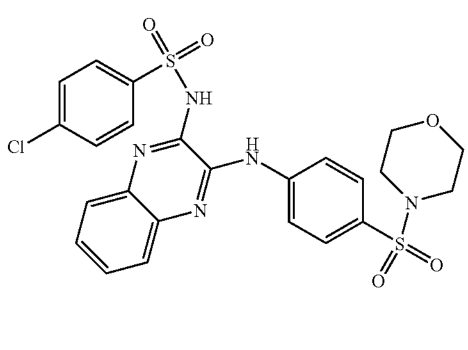 | 4-chloro-N-(3-{[4-(morpholin-4-ylsulfonyl)phenyl]amino}quinoxalin-2-yl)benzenesulfonamide |

TABLE 1-continued

| Cpd. No. | Structure | Name |
|---|---|---|
| 246 | | 4-chloro-N-(3-{[3-(morpholin-4-ylsulfonyl)phenyl]amino}quinoxalin-2-yl)benzenesulfonamide |
| 247 | 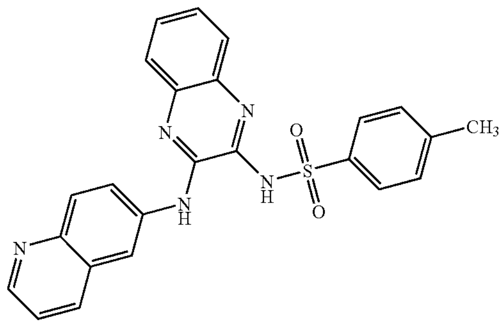 | 4-methyl-N-[3-(quinolin-6-ylamino)quinoxalin-2-yl]benzenesulfonamide |
| 248 | 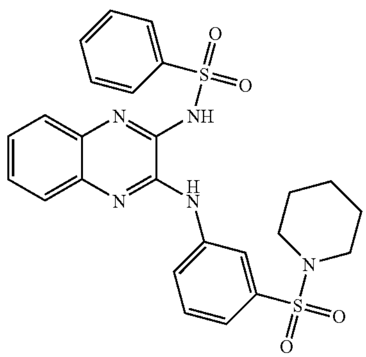 | N-(3-{[3-(piperidin-1-ylsulfonyl)phenyl]amino}quinoxalin-2-yl)benzenesulfonamide |
| 249 | 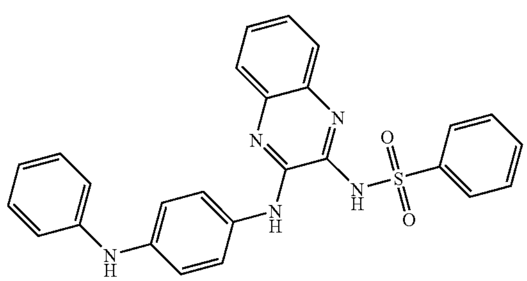 | N-(3-{[4-(phenylamino)phenyl]amino}quinoxalin-2-yl)benzenesulfonamide |
| 250 | 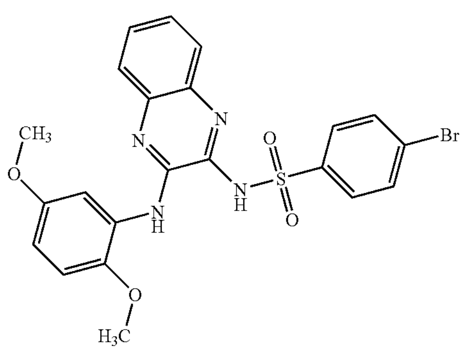 | N-(3-{[2,5-bis(methoxy)phenyl]amino}quinoxalin-2-yl)-4-bromobenzenesulfonamide |

TABLE 1-continued

| Cpd. No. | Structure | Name |
|---|---|---|
| 251 | 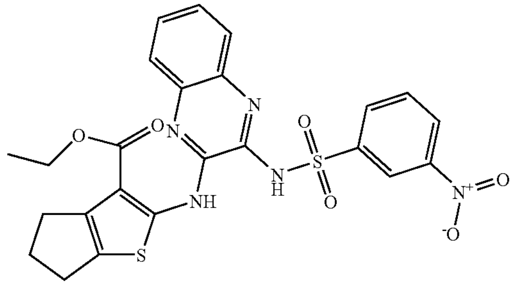 | ethyl 2-[(3-{[(3-nitrophenyl)sulfonyl]amino}quinoxalin-2-yl)amino]-5,6-dihydro-4H-cyclopenta[b]thiophene-3-carboxylate |
| 252 | 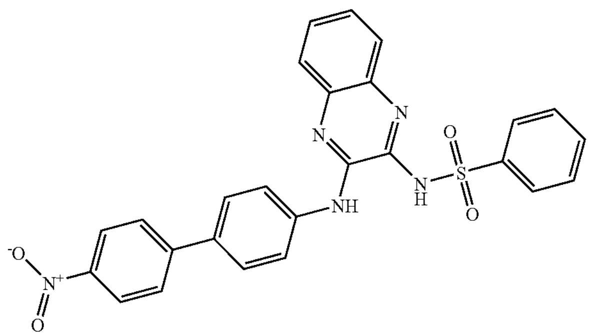 | N-{3-[(4'-nitrobiphenyl-4-yl)amino]quinoxalin-2-yl}benzenesulfonamide |
| 253 | 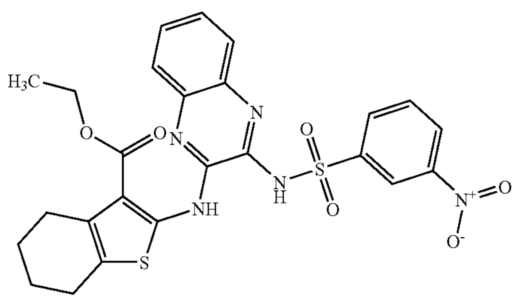 | ethyl 2-[(3-{[(3-nitrophenyl)sulfonyl]amino}quinoxalin-2-yl)amino]-4,5,6,7-tetrahydro-1-benzothiophene-3-carboxylate |
| 254 | 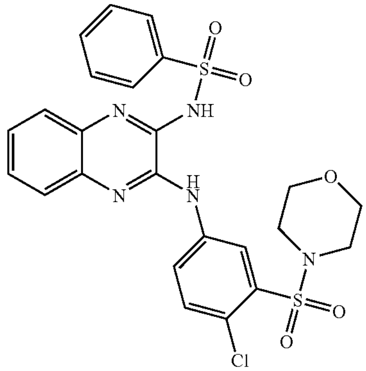 | N-(3-{[4-chloro-3-(morpholin-4-ylsulfonyl)phenyl]amino}quinoxalin-2-yl)benzenesulfonamide |
| 255 | 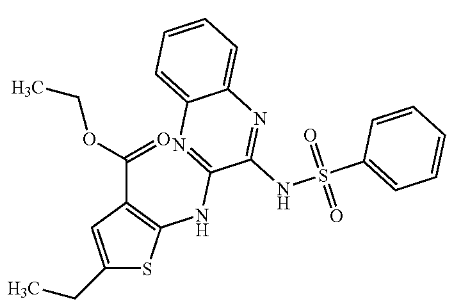 | ethyl 5-ethyl-2-({3-[(phenylsulfonyl)amino]quinoxalin-2-yl}amino)thiophene-3-carboxylate |

TABLE 1-continued

| Cpd. No. | Structure | Name |
|---|---|---|
| 256 | 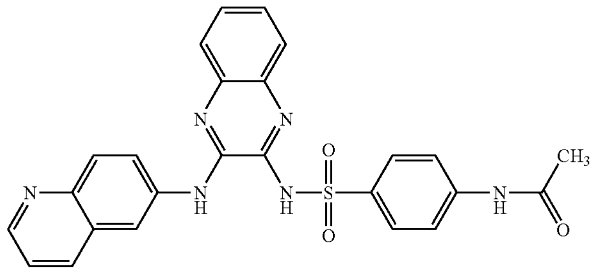 | N-[4-({[3-(quinolin-6-ylamino)quinoxalin-2-yl]amino}sulfonyl)phenyl]acetamide |
| 257 | 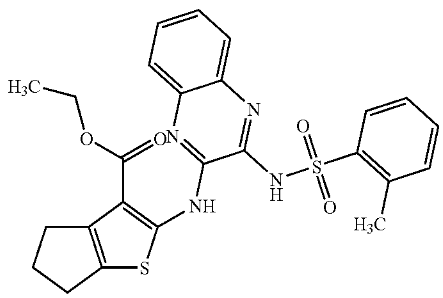 | ethyl 2-[(3-{[(2-methylphenyl)sulfonyl]amino}quinoxalin-2-yl)amino]-5,6-dihydro-4H-cyclopenta[b]thiophene-3-carboxylate |
| 258 | 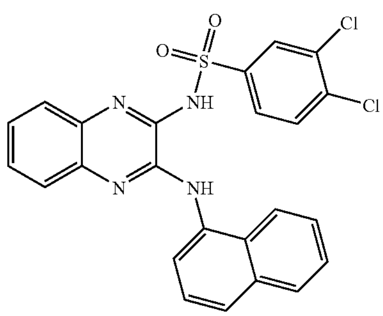 | 3,4-dichloro-N-[3-(naphthalen-1-ylamino)quinoxalin-2-yl]benzenesulfonamide |
| 259 | 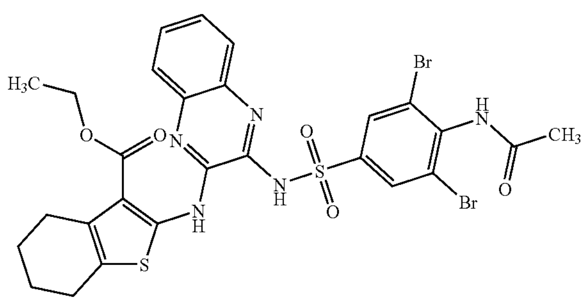 | ethyl 2-{[3-({[4-(acetylamino)-3,5-dibromophenyl]sulfonyl}amino)quinoxalin-2-yl]amino}-4,5,6,7-tetrahydro-1-benzothiophene-3-carboxylate |
| 260 | 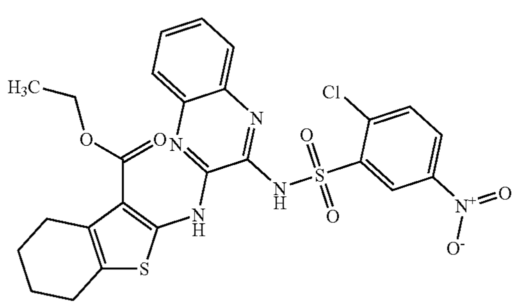 | ethyl 2-[(3-{[(2-chloro-5-nitrophenyl)sulfonyl]amino}quinoxalin-2-yl)amino]-4,5,6,7-tetrahydro-1-benzothiophene-3-carboxylate |

| Cpd. No. | Structure | Name |
|---|---|---|
| 261 | 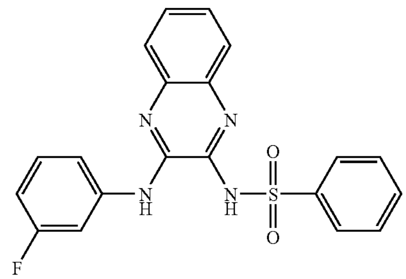 | N-{3-[(3-fluorophenyl)amino]quinoxalin-2-yl}benzenesulfonamide |
| 262 | 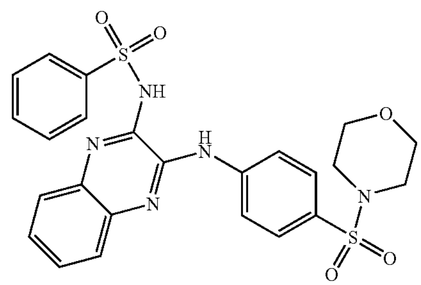 | N-(3-{[4-(morpholin-4-ylsulfonyl)phenyl]amino}quinoxalin-2-yl)benzenesulfonamide |
| 263 | 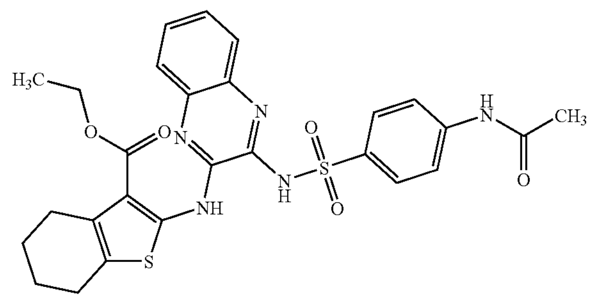 | ethyl 2-{[3-({[4-(acetylamino)phenyl]sulfonyl}amino)quinoxalin-2-yl]amino}-4,5,6,7-tetrahydro-1-benzothiophene-3-carboxylate |
| 264 | 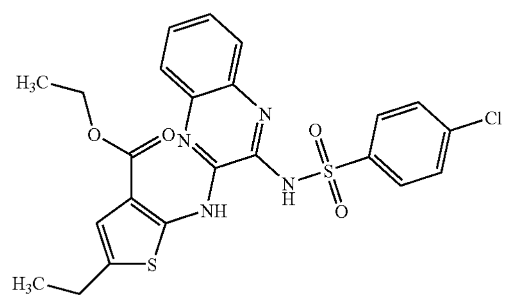 | ethyl 2-[(3-{[(4-chlorophenyl)sulfonyl]amino}quinoxalin-2-yl)amino]-5-ethylthiophene-3-carboxylate |
| 265 | 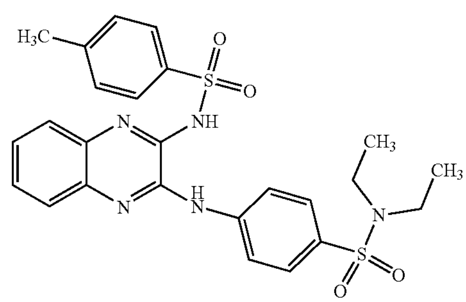 | N,N-diethyl-4-[(3-{[(4-methylphenyl)sulfonyl]amino}quinoxalin-2-yl)amino]benzenesulfonamide |

TABLE 1-continued

| Cpd. No. | Structure | Name |
|---|---|---|
| 266 | 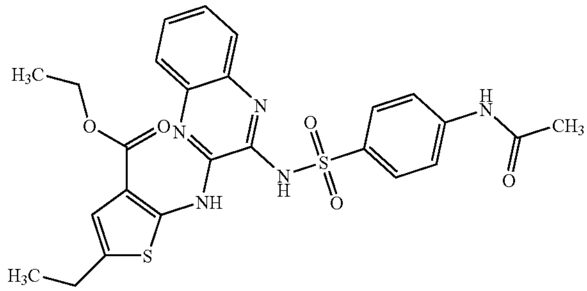 | ethyl 2-{[3-({[4-(acetylamino)phenyl]sulfonyl}amino)quinoxalin-2-yl]amino}-5-ethylthiophene-3-carboxylate |
| 267 | 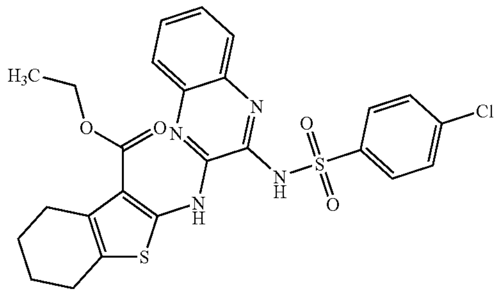 | ethyl 2-[(3-{[(4-chlorophenyl)sulfonyl]amino}quinoxalin-2-yl)amino]-4,5,6,7-tetrahydro-1-benzothiophene-3-carboxylate |
| 268 | 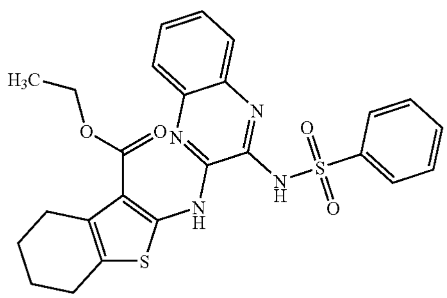 | ethyl 2-({3-[(phenylsulfonyl)amino]quinoxalin-2-yl}amino)-4,5,6,7-tetrahydro-1-benzothiophene-3-carboxylate |
| 269 | 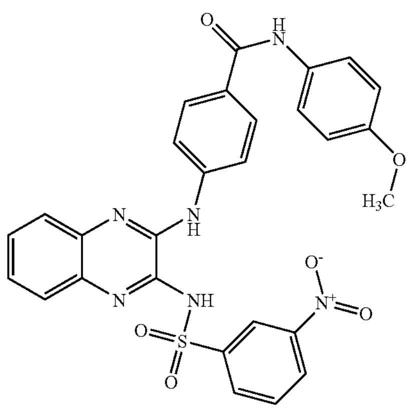 | N-[4-(methoxy)phenyl]-4-[(3-{[(3-nitrophenyl)sulfonyl]amino}quinoxalin-2-yl)amino]benzamide |
| 270 | 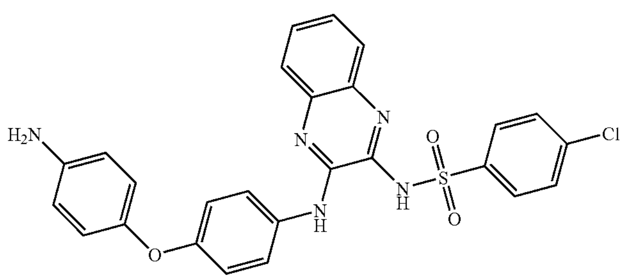 | N-[3-({4-[(4-aminophenyl)oxy]phenyl}amino)quinoxalin-2-yl]-4-chlorobenzenesulfonamide |

TABLE 1-continued

| Cpd. No. | Structure | Name |
|---|---|---|
| 271 | 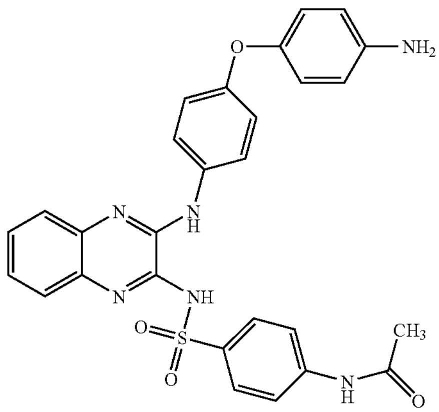 | N-[4-({[3-({4-[(4-aminophenyl)oxy]phenyl}amino)quinoxalin-2-yl]amino}sulfonyl)phenyl]acetamide |
| 272 | 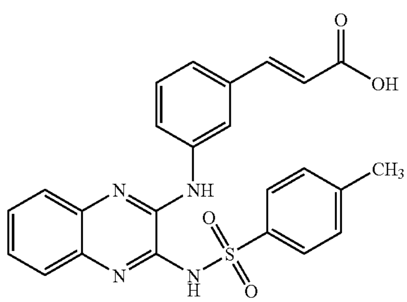 | (2E)-3-{3-[(3-{[(4-methylphenyl)sulfonyl]amino}quinoxalin-2-yl)amino]phenyl}prop-2-enoic acid |
| 273 | 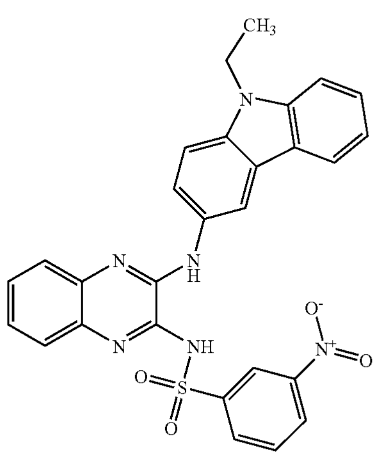 | N-{3-[(9-ethyl-9H-carbazol-3-yl)amino]quinoxalin-2-yl}-3-nitrobenzenesulfonamide |

TABLE 1-continued

| Cpd. No. | Structure | Name |
|---|---|---|
| 274 | 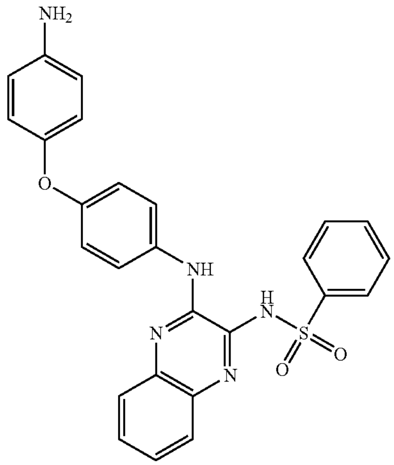 | N-[3-({4-[(4-aminophenyl)oxy]phenyl}amino)quinoxalin-2-yl]benzenesulfonamide |
| 275 | 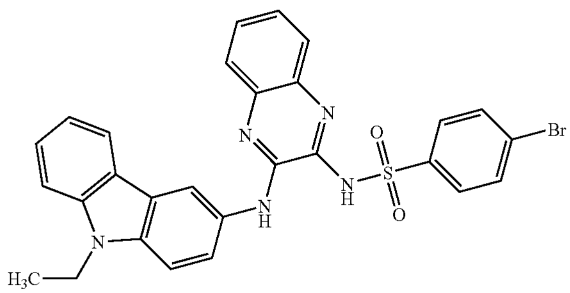 | 4-bromo-N-{3-[(9-ethyl-9H-carbazol-3-yl)amino]quinoxalin-2-yl}benzenesulfonamide |
| 276 | 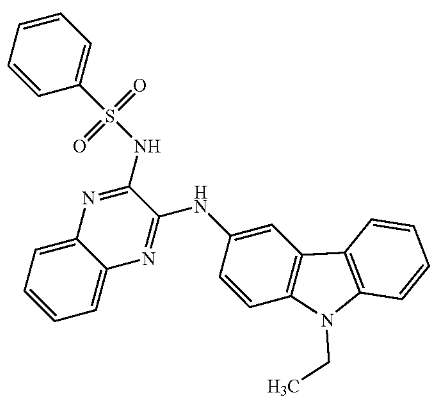 | N-{3-[(9-ethyl-9H-carbazol-3-yl)amino]quinoxalin-2-yl}benzenesulfonamide |
| 277 | 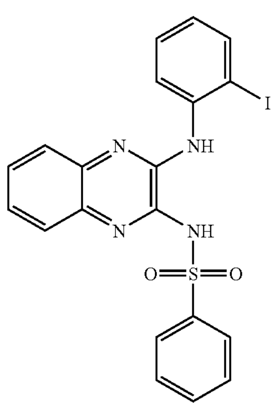 | N-{3-[(2-iodophenyl)amino]quinoxalin-2-yl}benzenesulfonamide |

TABLE 1-continued
| Cpd. No. | Structure | Name |
|---|---|---|
| 278 | 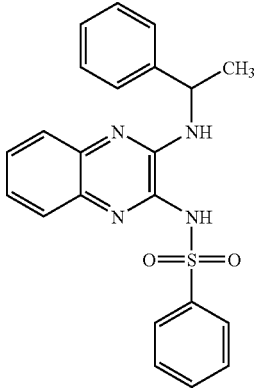 | N-{3-[(1-phenylethyl)amino]quinoxalin-2-yl}benzenesulfonamide |
| 279 | 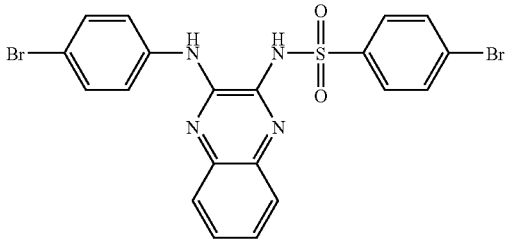 | 4-bromo-N-{3-[(4-bromophenyl)amino]quinoxalin-2-yl}benzenesulfonamide |
| 280 | 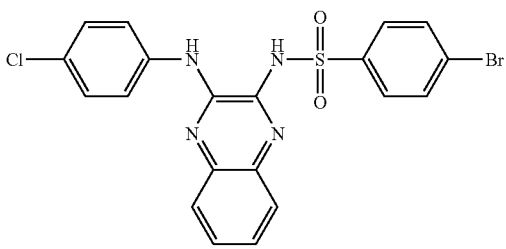 | 4-bromo-N-{3-[(4-chlorophenyl)amino]quinoxalin-2-yl}benzenesulfonamide |
| 281 | 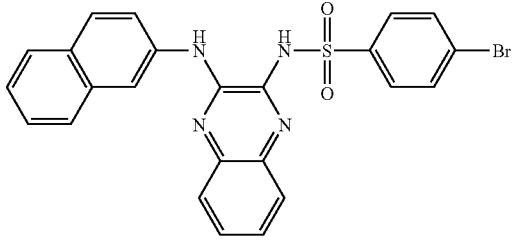 | 4-bromo-N-[3-(naphthalen-2-ylamino)quinoxalin-2-yl]benzenesulfonamide |
| 282 | 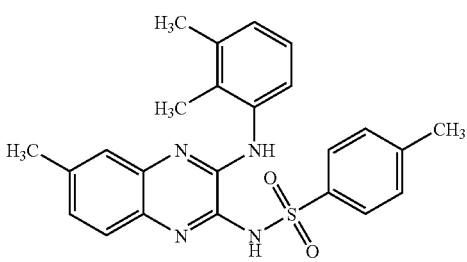 | N-{3-[(2,3-dimethylphenyl)amino]-6-methylquinoxalin-2-yl}-4-methylbenzenesulfonamide |

TABLE 1-continued

| Cpd. No. | Structure | Name |
|---|---|---|
| 283 | 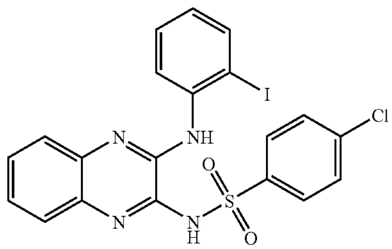 | 4-chloro-N-{3-[(2-iodophenyl)amino]quinoxalin-2-yl}benzenesulfonamide |
| 284 | 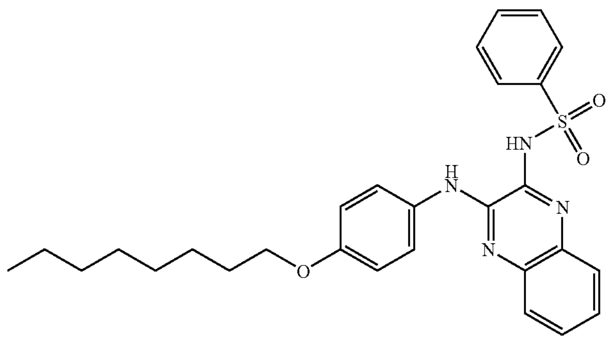 | N-(3-{[4-(octyloxy)phenyl]amino}quinoxalin-2-yl)benzenesulfonamide |
| 285 | 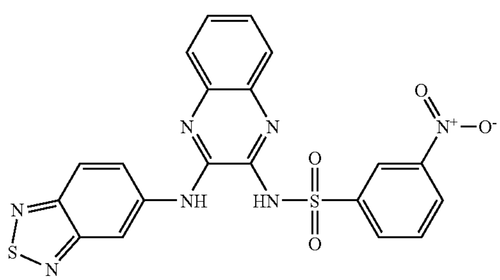 | N-[3-(2,1,3-benzothiadiazol-5-ylamino)quinoxalin-2-yl]-3-nitrobenzenesulfonamide |
| 286 | 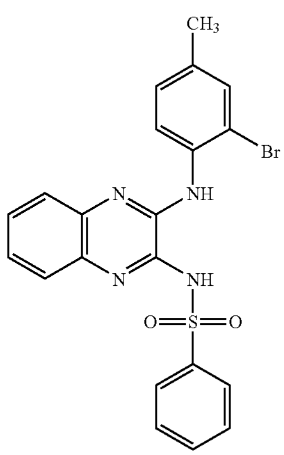 | N-{3-[(2-bromo-4-methylphenyl)amino]quinoxalin-2-yl}benzenesulfonamide |

TABLE 1-continued

| Cpd. No. | Structure | Name |
|---|---|---|
| 287 | 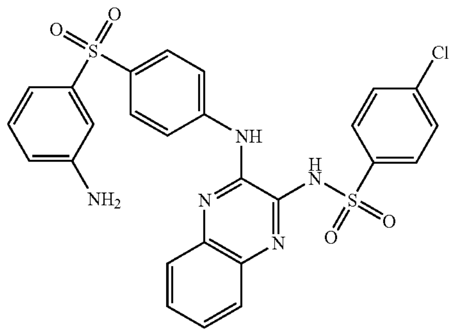 | N-[3-({4-[(3-aminophenyl)sulfonyl]phenyl}amino)quinoxalin-2-yl]-4-chlorobenzenesulfonamide |
| 288 | 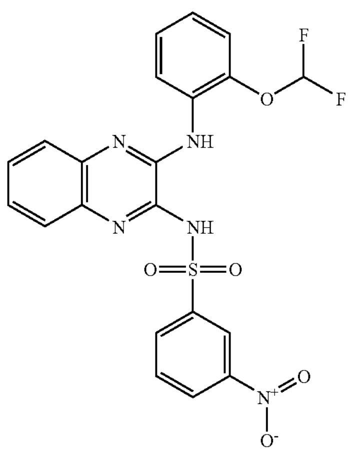 | N-[3-({2-[(difluoromethyl)oxy]phenyl}amino)quinoxalin-2-yl]-3-nitrobenzenesulfonamide |
| 289 | 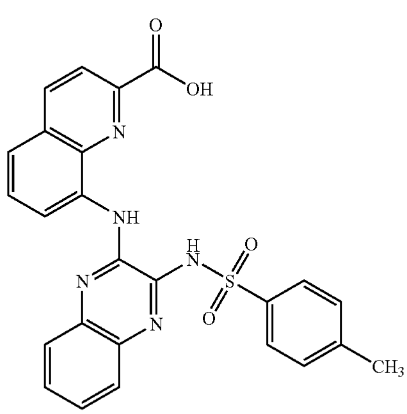 | 8-[(3-{[(4-methylphenyl)sulfonyl]amino}quinoxalin-2-yl)amino]quinoline-2-carboxylic acid |

TABLE 1-continued

| Cpd. No. | Structure | Name |
|---|---|---|
| 290 | 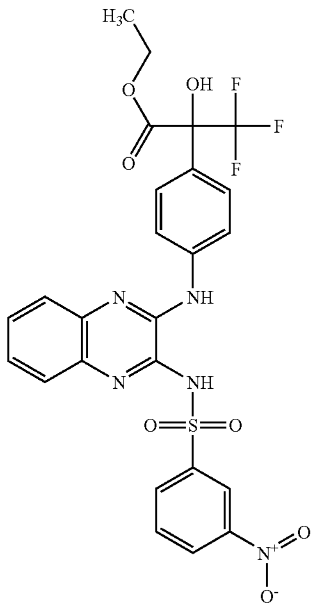 | ethyl 3,3,3-trifluoro-2-hydroxy-2-{4-[(3-{[(3-nitrophenyl)sulfonyl]amino}quinoxalin-2-yl)amino]phenyl}propanoate |
| 291 | 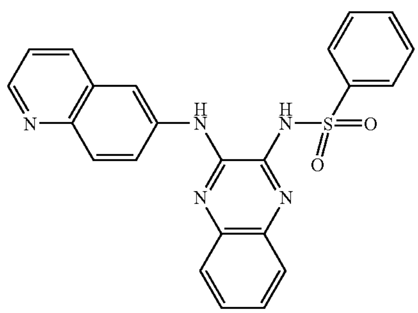 | N-[3-(quinolin-6-ylamino)quinoxalin-2-yl]benzenesulfonamide |
| 292 | 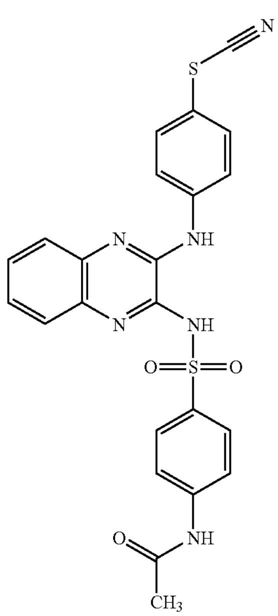 | 4-{[3-({[4-(acetylamino)phenyl]sulfonyl}amino)quinoxalin-2-yl]amino}phenyl thiocyanate |

TABLE 1-continued

| Cpd. No. | Structure | Name |
| --- | --- | --- |
| 293 | 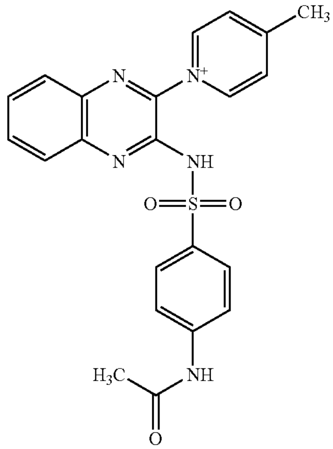 | 1-[3-({[4-(acetylamino)phenyl]sulfonyl}amino)quinoxalin-2-yl]-4-methylpyridinium |
| 294 | 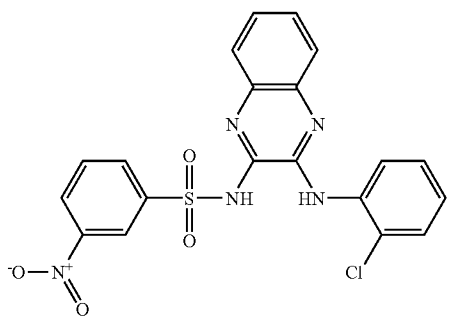 | N-{3-[(2-chlorophenyl)amino]quinoxalin-2-yl}-3-nitrobenzenesulfonamide |
| 295 | 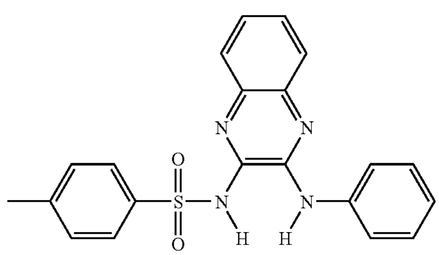 | 4-methyl-N-[3-(phenylamino)quinoxalin-2-yl]benzenesulfonamide |
| 296 | 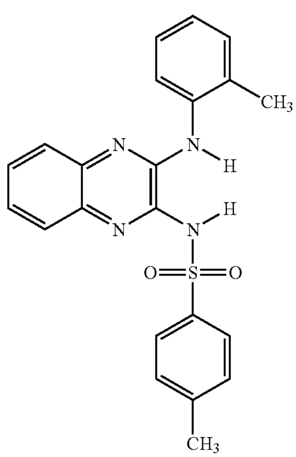 | 4-methyl-N-{3-[(2-methylphenyl)amino]quinoxalin-2-yl}benzenesulfonamide |

TABLE 1-continued

| Cpd. No. | Structure | Name |
|---|---|---|
| 297 | 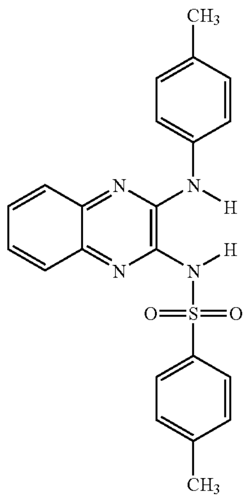 | 4-methyl-N-{3-[(4-methylphenyl)amino]quinoxalin-2-yl}benzenesulfonamide |
| 298 | 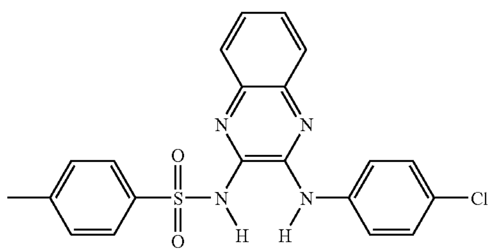 | N-{3-[(4-chlorophenyl)amino]quinoxalin-2-yl}-4-methylbenzenesulfonamide |
| 299 | 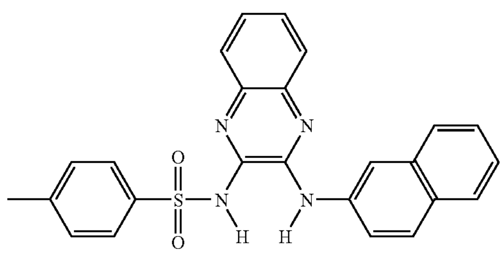 | 4-methyl-N-[3-(naphthalen-2-ylamino)quinoxalin-2-yl]benzenesulfonamide |
| 300 | 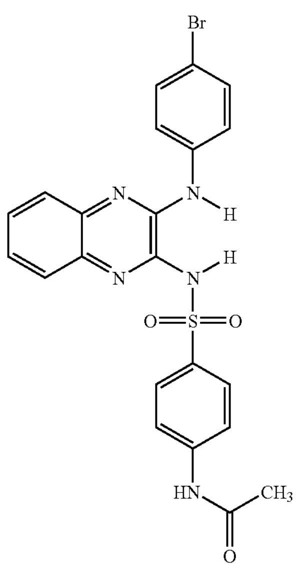 | N-{4-[({3-[(4-bromophenyl)amino]quinoxalin-2-yl}amino)sulfonyl]phenyl}acetamide |

TABLE 1-continued

| Cpd. No. | Structure | Name |
|---|---|---|
| 301 | 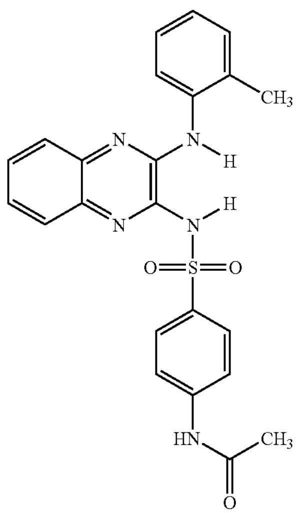 | N-{4-[({3-[(2-methylphenyl)amino]quinoxalin-2-yl}amino)sulfonyl]phenyl}acetamide |
| 302 | 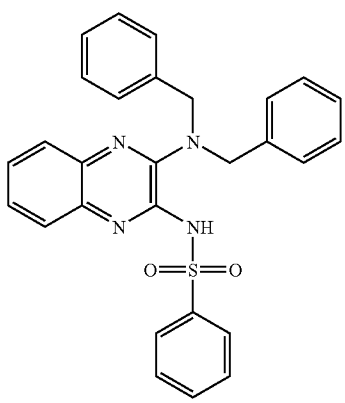 | N-{3-[bis(phenylmethyl)amino]quinoxalin-2-yl}benzenesulfonamide |
| 303 | 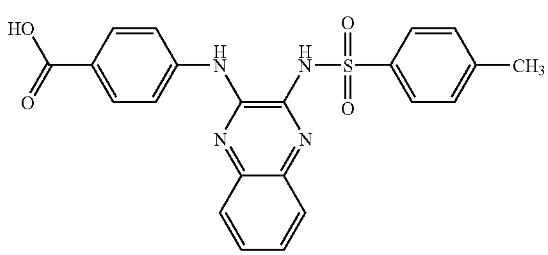 | 4-[(3-{[(4-methylphenyl)sulfonyl]amino}quinoxalin-2-yl)amino]benzoic acid |
| 304 | 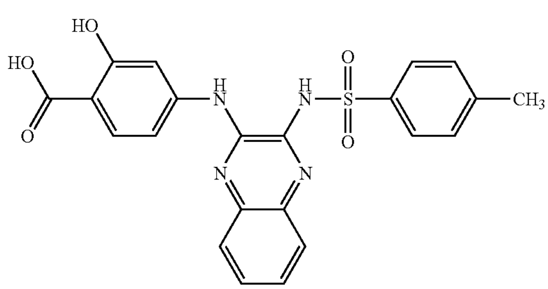 | 2-hydroxy-4-[(3-{[(4-methylphenyl)sulfonyl]amino}quinoxalin-2-yl)amino]benzoic acid |

TABLE 1-continued

| Cpd. No. | Structure | Name |
|---|---|---|
| 305 | 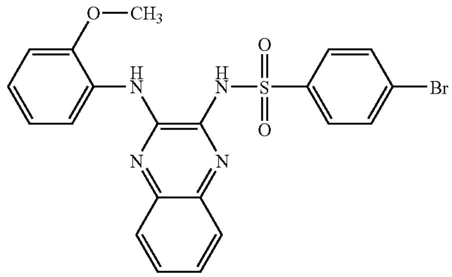 | 4-bromo-N-(3-{[2-(methoxy)phenyl]amino}quinoxalin-2-yl)benzenesulfonamide |
| 306 | 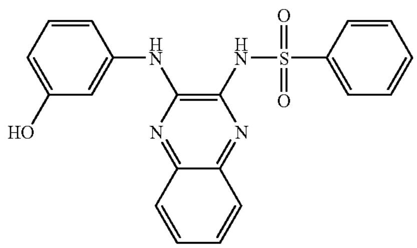 | N-{3-[(3-hydroxyphenyl)amino]quinoxalin-2-yl}benzenesulfonamide |
| 307 | 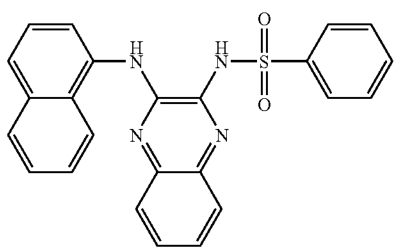 | N-[3-(naphthalen-1-ylamino)quinoxalin-2-yl]benzenesulfonamide |
| 308 | 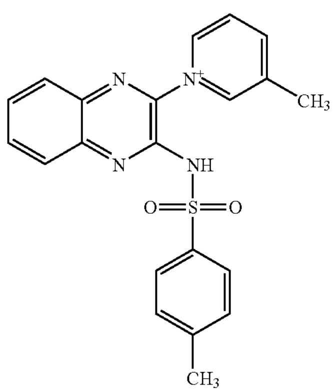 | 3-methyl-1-(3-{[(4-methylphenyl)sulfonyl]amino}quinoxalin-2-yl)pyridinium |
| 309 | 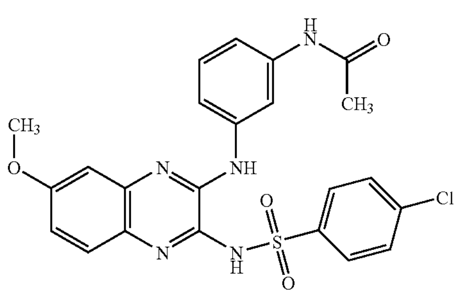 | N-(3-{[3-{[(4-chlorophenyl)sulfonyl]amino}-7-(methoxy)quinoxalin-7-yl]amino}phenyl)acetamide |

| Cpd. No. | Structure | Name |
|---|---|---|
| 310 | 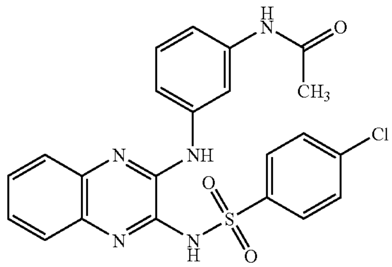 | N-{3-[(3-{[(4-chlorophenyl)sulfonyl]amino}quinoxalin-2-yl)amino]phenyl}acetamide |
| 311 | 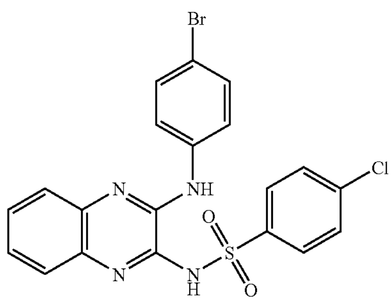 | N-{3-[(4-bromophenyl)amino]quinoxalin-2-yl}-4-chlorobenzenesulfonamide |
| 312 | 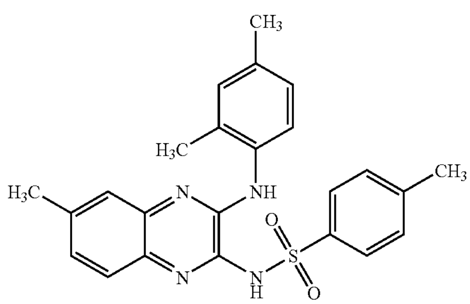 | N-{3-[(2,4-dimethylphenyl)amino]-6-methylquinoxalin-2-yl}-4-methylbenzenesulfonamide |
| 313 | 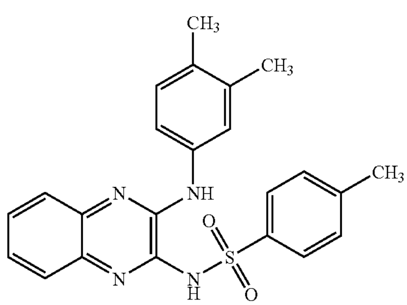 | N-{3-[(3,4-dimethylphenyl)amino]quinoxalin-2-yl}-4-methylbenzenesulfonamide |
| 314 | 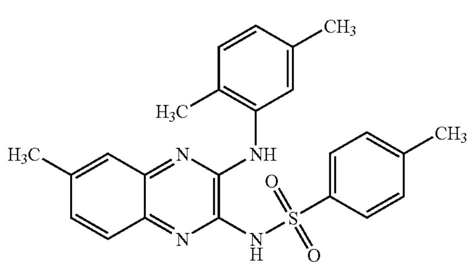 | N-{3-[(2,5-dimethylphenyl)amino]-6-methylquinoxalin-2-yl}-4-methylbenzenesulfonamide |

TABLE 1-continued
| Cpd. No. | Structure | Name |
|---|---|---|
| 315 | 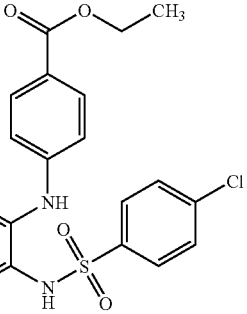 | ethyl 4-[(3-{[(4-chlorophenyl)sulfonyl]amino}quinoxalin-2-yl)amino]benzoate |
| 316 | 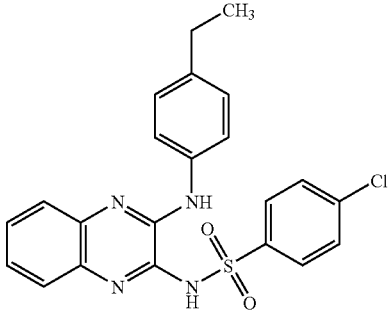 | 4-chloro-N-{3-[(4-ethylphenyl)amino]quinoxalin-2-yl}benzenesulfonamide |
| 317 | 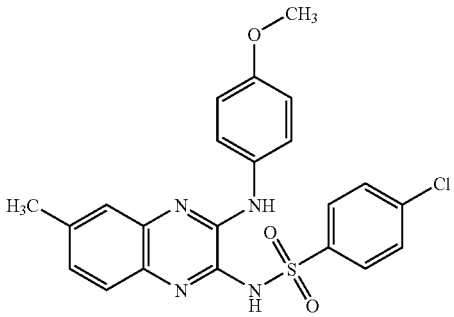 | 4-chloro-N-(6-methyl-3-{[4-(methoxy)phenyl]amino}quinoxalin-2-yl)benzenesulfonamide |
| 318 | 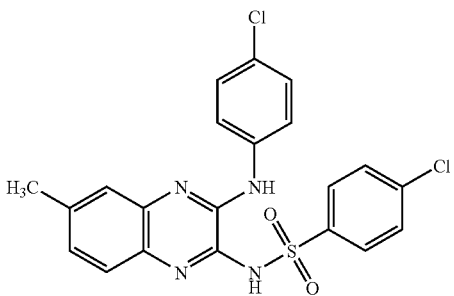 | 4-chlorro-N-{3-[(4-chlorophenyl)amino]-6-methylquinoxalin-2-yl}benzenesulfonamide |

TABLE 1-continued

| Cpd. No. | Structure | Name |
|---|---|---|
| 319 | 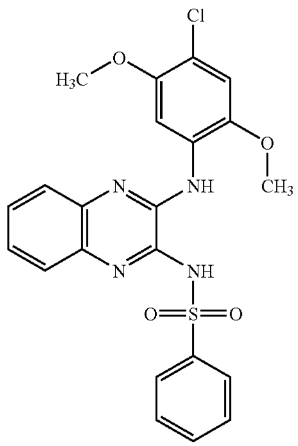 | N-(3-{[4-chloro-2,5-bis(methoxy)phenyl]amino}quinoxalin-2-yl)benzenesulfonamide |
| 320 | 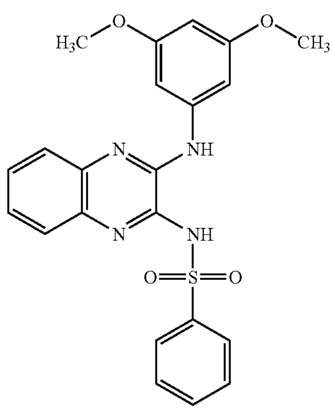 | N-(3-{[3,5-bis(methoxy)phenyl]amino}quinoxalin-2-yl)benzenesulfonamide |
| 321 | 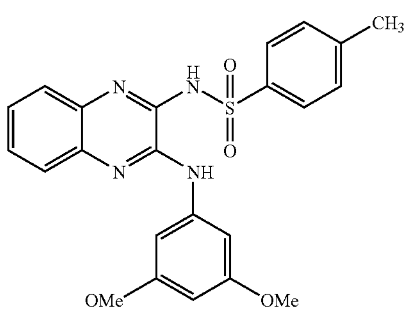 | N-(3-{[3,5-bis(methoxy)phenyl]amino}quinoxalin-2-yl)-4-methylbenzenesulfonamide |
| 322 | 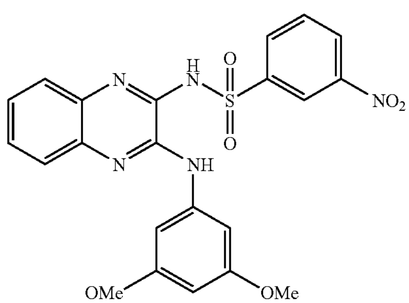 | N-(3-{[3,5-bis(methoxy)phenyl]amino}quinoxalin-2-yl)-3-nitrobenzenesulfonamide |

TABLE 1-continued

| Cpd. No. | Structure | Name |
|---|---|---|
| 323 | 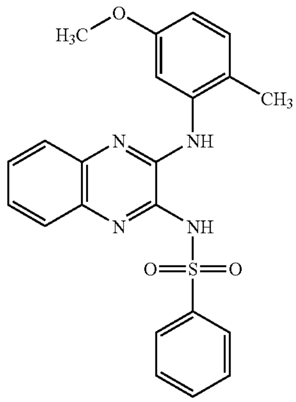 | N-(3-{[2-methyl-5-(methoxy)phenyl]amino}quinoxalin-2-yl)benzenesulfonamide |
| 324 | 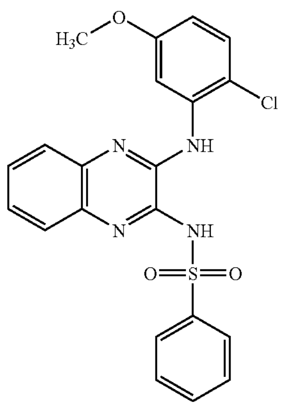 | N-[3-(2-Chloro-5-methoxy-phenylamino)-quinoxalin-2-yl]-benzenesulfonamide |
| 325 | 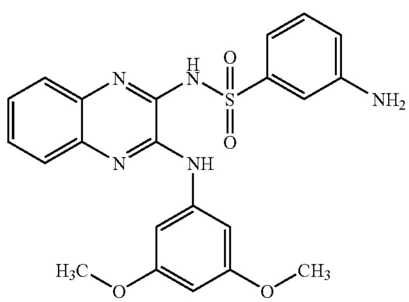 | 3-amino-N-(3-{[3,5-bis(methoxy)phenyl]amino}quinoxalin-2-yl)benzenesulfonamide |
| 326 | 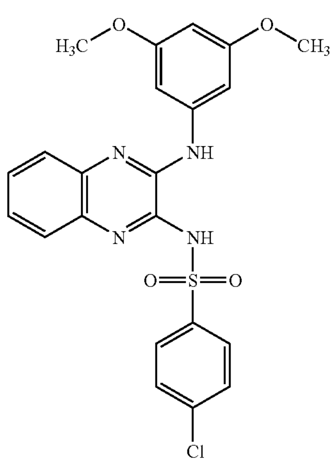 | N-(3-{[3,5-bis(methoxy)phenyl]amino}quinoxalin-2-yl)-4-chlorobenzenesulfonamide |

TABLE 1-continued

| Cpd. No. | Structure | Name |
|---|---|---|
| 327 | 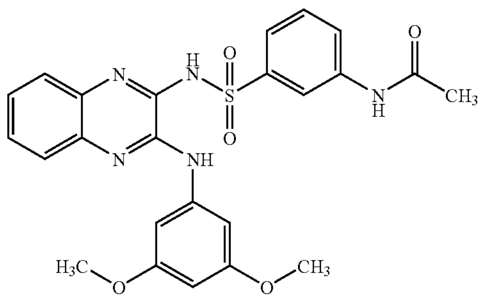 | N-(3-{[(3-{[3,5-bis(methoxy)phenyl]amino}quinoxalin-2-yl)amino]sulfonyl}phenyl)acetamide |
| 328 | 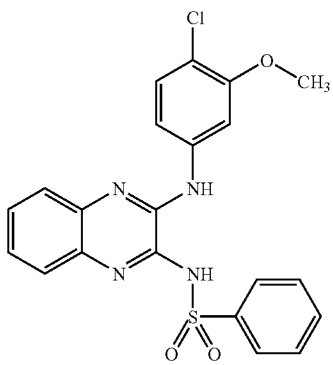 | N-(3-{[4-chloro-3-(methoxy)phenyl]amino}quinoxalin-2-yl)benzenesulfonamide |
| 329 | 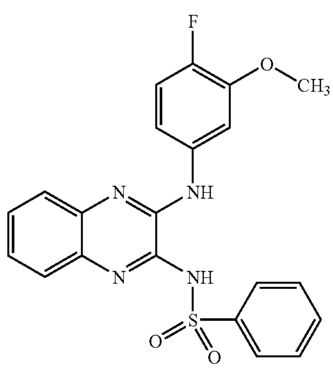 | N-(3-{[4-fluoro-3-(methoxy)phenyl]amino}quinoxalin-2-yl)benzenesulfonamide |
| 330 | 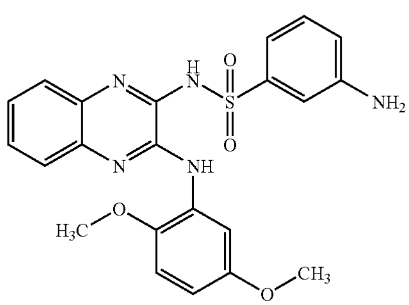 | 3-amino-N-(3-{[2,5-bis(methoxy)phenyl]amino}quinoxalin-2-yl)benzenesulfonamide |

| Cpd. No. | Structure | Name |
| --- | --- | --- |
| 331 | 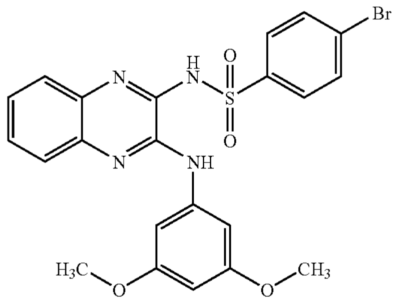 | N-(3-{[3,5-bis(methoxy)phenyl]amino}quinoxalin-2-yl)-4-bromobenzenesulfonamide |
| 332 | 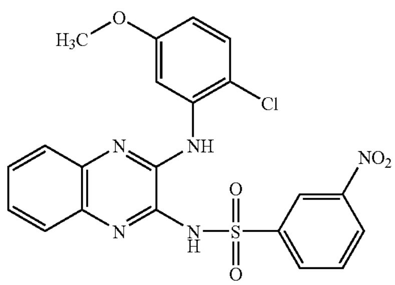 | N-(3-{[2-chloro-5-(methoxy)phenyl]amino}quinoxalin-2-yl)-3-nitrobenzenesulfonamide |
| 333 | 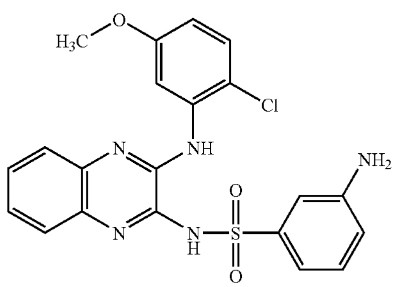 | 3-amino-N-(3-{[2-chloro-5-(methoxy)phenyl]amino}quinoxalin-2-yl)benzenesulfonamide |
| 334 | 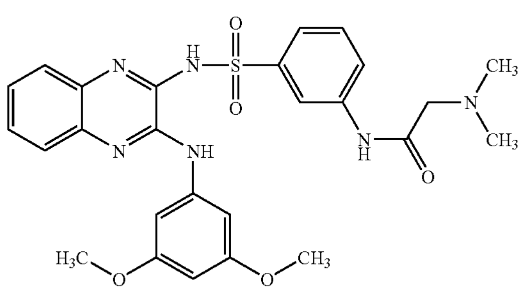 | N-(3-{[(3-{[3,5-bis(methoxy)phenyl]amino}quinoxalin-2-yl)amino]sulfonyl}phenyl)-N-2-,N-2-dimethylglycinamide |
| 335 | 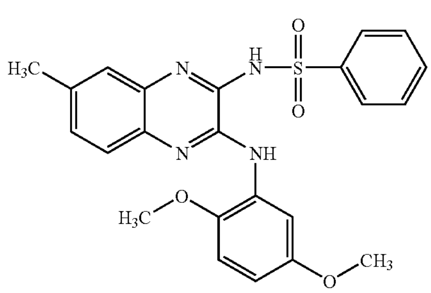 | N-(3-{[2,5-bis(methoxy)phenyl]amino}-7-methylquinoxalin-2-yl)benzenesulfonamide |

TABLE 1-continued

| Cpd. No. | Structure | Name |
|---|---|---|
| 336 | 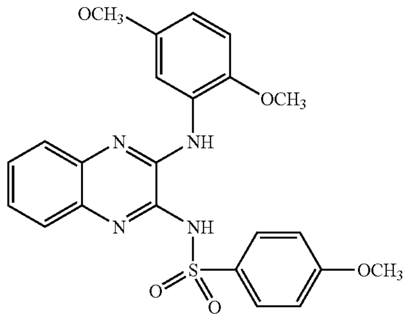 | N-(3-{[2,5-bis(methoxy)phenyl]amino}quinoxalin-2-yl)-4-(methoxy)benzenesulfonamide |
| 337 | 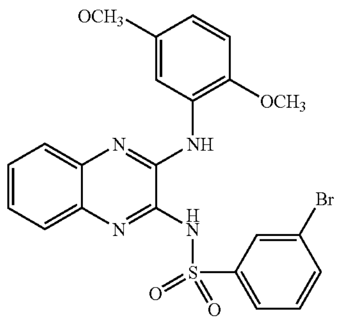 | N-(3-{[2,5-bis(methoxy)phenyl]amino}quinoxalin-2-yl)-3-bromobenzenesulfonamide |
| 338 | 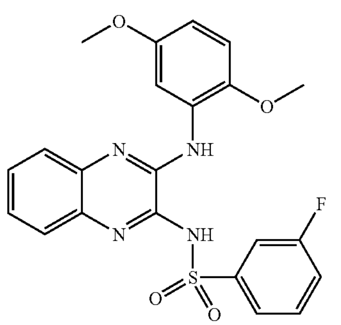 | N-(3-{[2,5-bis(methoxy)phenyl]amino}quinoxalin-2-yl)-3-fluorobenzenesulfonamide |
| 339 | 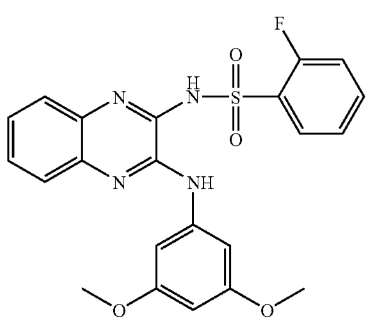 | N-(3-{[3,5-bis(methoxy)phenyl]amino}quinoxalin-2-yl)-2-fluorobenzenesulfonamide |
| 340 | 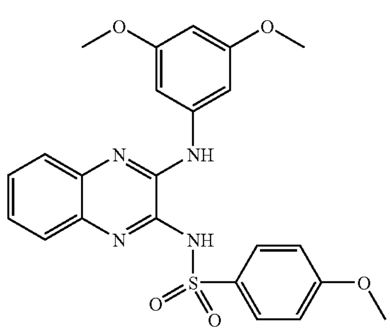 | N-(3-{[3,5-bis(methoxy)phenyl]amino}quinoxalin-2-yl)-4-(methoxy)benzenesulfonamide |

TABLE 1-continued

| Cpd. No. | Structure | Name |
|---|---|---|
| 341 | 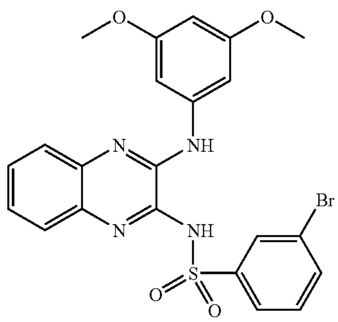 | N-(3-{[3,5-bis(methoxy)phenyl]amino}quinoxalin-2-yl)-3-bromobenzenesulfonamide |
| 342 | 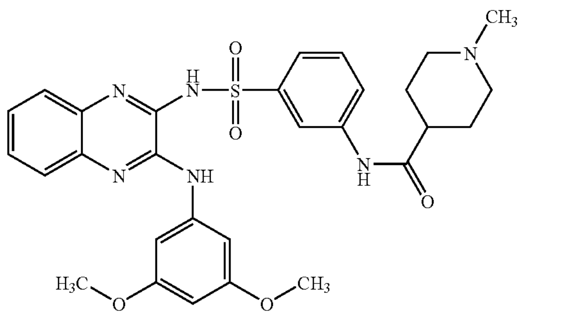 | N-(3-{[(3-{[3,5-bis(methoxy)phenyl]amino}quinoxalin-2-yl)amino]sulfonyl}phenyl)-1-methylpiperidine-4-carboxamide |
| 343 | 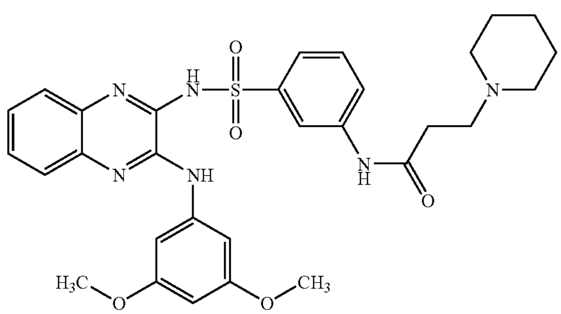 | N-(3-{[(3-{[3,5-bis(methoxy)phenyl]amino}quinoxalin-2-yl)amino]sulfonyl}phenyl)-3-piperidin-1-ylpropanamide |
| 344 | 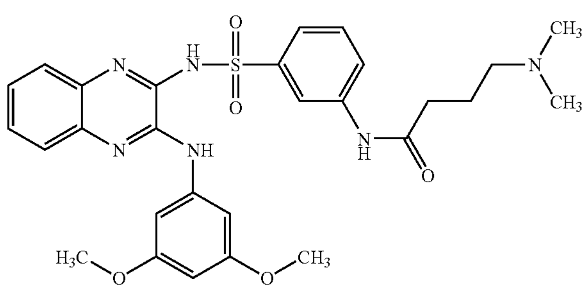 | N-(3-{[(3-{[3,5-bis(methoxy)phenyl]amino}quinoxalin-2-yl)amino]sulfonyl}phenyl)-4-(dimethylamino)butanamide |
| 345 | 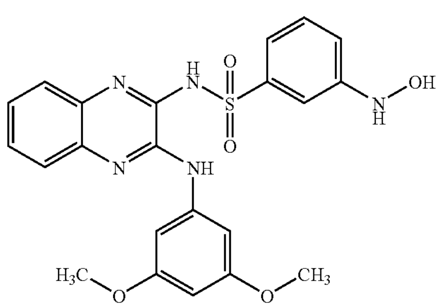 | N-(3-{[3,5-bis(methoxy)phenyl]amino}quinoxalin-2-yl)-3-(hydroxyamino)benzenesulfonamide |

TABLE 1-continued

| Cpd. No. | Structure | Name |
|---|---|---|
| 346 | 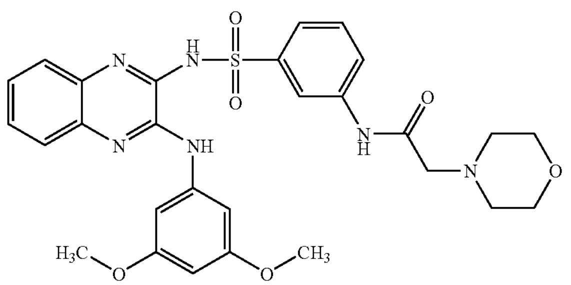 | N-(3-{[(3-{[3,5-bis(methoxy)phenyl]amino}quinoxalin-2-yl)amino]sulfonyl}phenyl)-2-morpholin-4-ylacetamide |
| 347 | 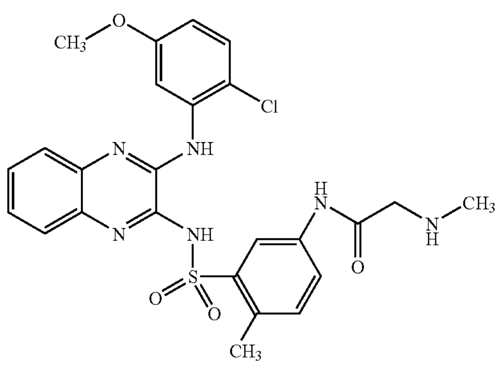 | N-(3-{[(3-{[2-chloro-5-(methoxy)phenyl]amino}quinoxalin-2-yl)amino]sulfonyl}-4-methylphenyl)-N-2-methylglycinamide |
| 348 | Abs | N-(3-{[(3-{[2-chloro-5-(methoxy)phenyl]amino}quinoxalin-2-yl)amino]sulfonyl}-4-methylphenyl)-L-alaninamide |
| 349 | 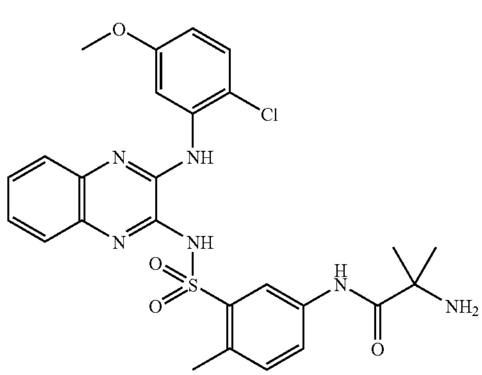 | N-(3-{[(3-{[2-chloro-5-(methoxy)phenyl]amino}quinoxalin-2-yl)amino]sulfonyl}-4-methylphenyl)-2-methylalaninamide |

TABLE 1-continued

| Cpd. No. | Structure | Name |
|---|---|---|
| 350 | 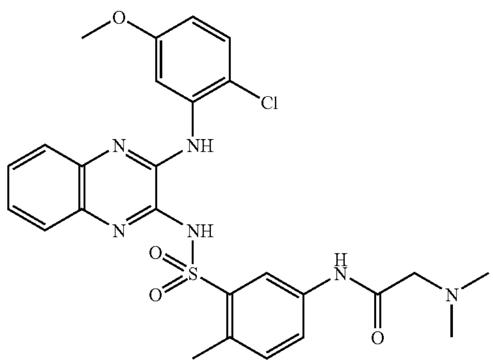 | N-(3-{[(3-{[2-chloro-5-(methoxy)phenyl]amino}quinoxalin-2-yl)amino)sulfonyl}-4-methylphenyl)-N-2-,N-2-dimethylglycinamide |
| 351 | Abs | N-(3-{[(3-{[3,5-bis(methoxy)phenyl]amino}quinoxalin-2-yl)amino]sulfonyl}phenyl)-D-alaninamide |
| 352 | 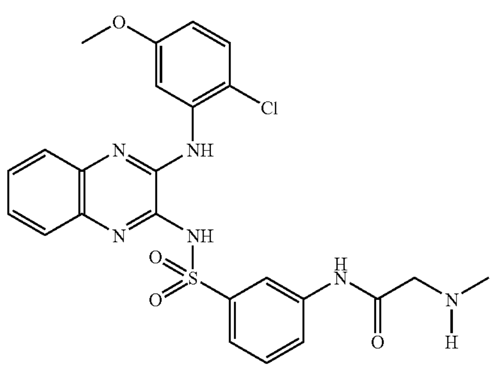 | N-(3-{[(3-{[2-chloro-5-(methoxy)phenyl]amino}quinoxalin-2-yl)amino]sulfonyl}phenyl)-N-2-methylglycinamide |
| 353 | ABS | N-(3-{[(3-{[2-chloro-5-(methoxy)phenyl]amino}quinoxalin-2-yl)amino]sulfonyl}-4-methylphenyl)-D-alaninamide |

TABLE 1-continued

| Cpd. No. | Structure | Name |
|---|---|---|
| 354 | 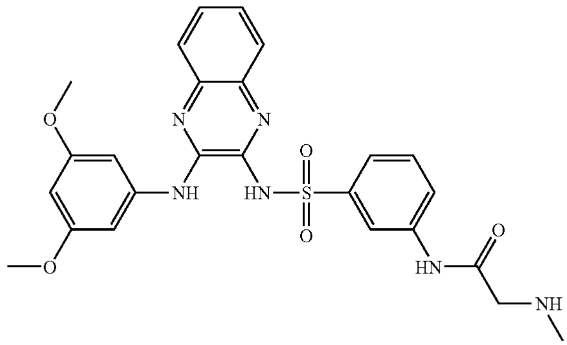 | N-(3-{[(3-{[3,5-bis(methoxy)phenyl]amino}quinoxalin-2-yl)amino]sulfonyl}phenyl)-N-2-methylglycinamide |
| 355 | Abs | N-(3-{[(3-{[2-chloro-5-(methoxy)phenyl]amino}quinoxalin-2-yl)amino]sulfonyl}phenyl)-L-alaninamide |
| 356 | Abs | N-(3-{[(3-{[2-chloro-5-(methoxy)phenyl]amino}quinoxalin-2-yl)amino]sulfonyl}phenyl)-D-alaninamide |
| 357 | 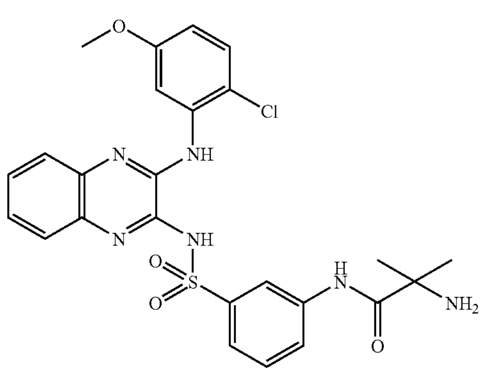 | N-(3-{[(3-{[2-chloro-5-(methoxy)phenyl]amino}quinoxalin-2-yl)amino]sulfonyl}phenyl)-2-methylalaninamide |

TABLE 1-continued

| Cpd. No. | Structure | Name |
|---|---|---|
| 358 | 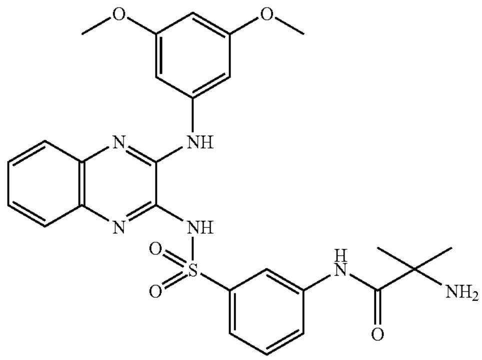 | N-(3-{[(3-{[3,5-bis(methoxy)phenyl]amino}quinoxalin-2-yl)amino]sulfonyl}phenyl)-2-methylalaninamide |
| 359 | 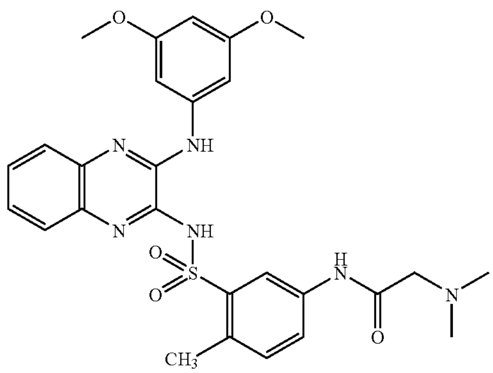 | N-(3-{[(3-{[3,5-bis(methoxy)phenyl]amino}quinoxalin-2-yl)amino]sulfonyl}-4-methylphenyl)-N-2-,N-2-dimethylglycinamide |
| 360 | 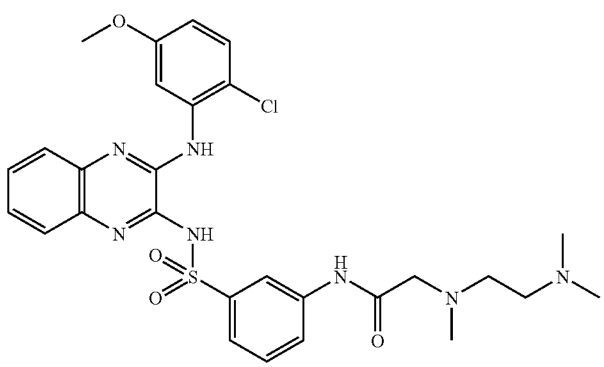 | N-(3-{[(3-{[2-chloro-5-(methoxy)phenyl]amino}quinoxalin-2-yl)amino]sulfonyl}phenyl)-N-2-[2-(dimethylamino)ethyl]-N-2-methylglycinamide |
| 361 | 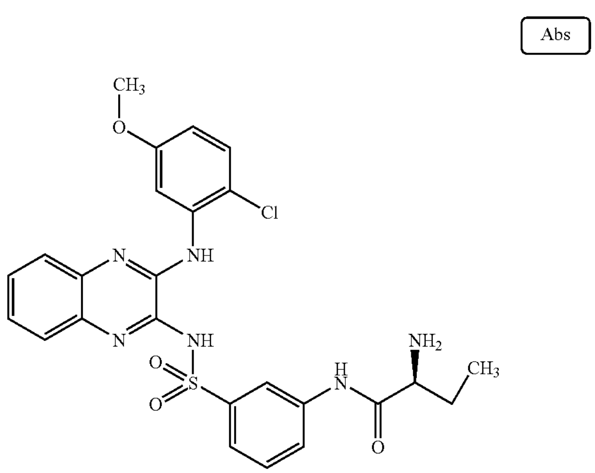 | (2S)-2-amino-N-(3-{[(3-{[2-chloro-5-(methoxy)phenyl]amino}quinoxalin-2-yl)amino]sulfonyl}phenyl)butanamide |

TABLE 1-continued

| Cpd. No. | Structure | Name |
|---|---|---|
| 362 | 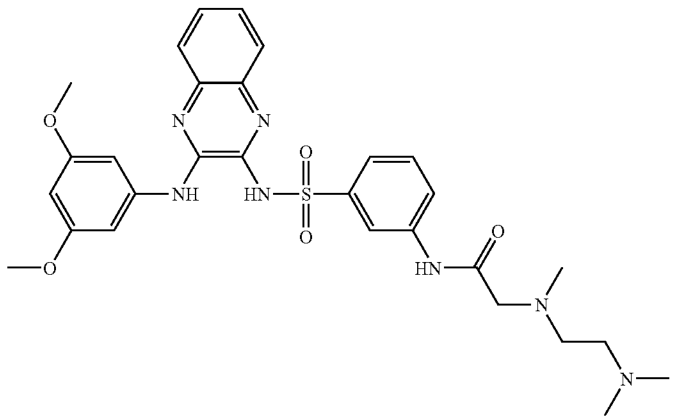 | N-(3-{[(3-{[3,5-bis(methoxy)phenyl]amino}quinoxalin-2-yl)amino]sulfonyl}phenyl)-N-2-[2-(dimethylamino)ethyl]-N-2-methylglycinamide |
| 363 | 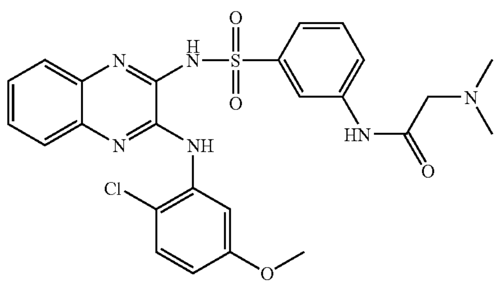 | N-(3-{[(3-{[2-chloro-5-(methoxy)phenyl]amino}quinoxalin-2-yl)amino]sulfonyl}phenyl)-N-2-,N-2-dimethylglycinamide |
| 364 | Abs | N-(3-{[(3-{[3,5-bis(methoxy)phenyl]amino}quinoxalin-2-yl)amino]sulfonyl}phenyl)-N-2-methyl-L-alaninamide |
| 365 | 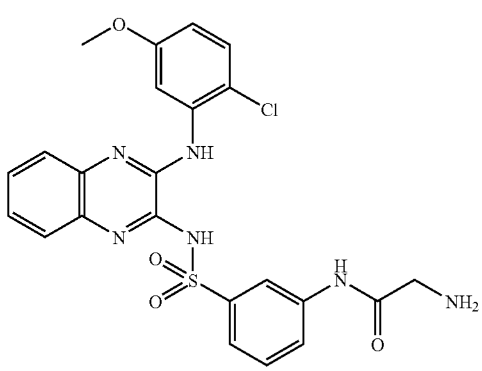 | N-(3-{[(3-{[2-chloro-5-(methoxy)phenyl]amino}quinoxalin-2-yl)amino]sulfonyl}phenyl)glycinamide |

TABLE 1-continued

| Cpd. No. | Structure | Name |
|---|---|---|
| 366 | 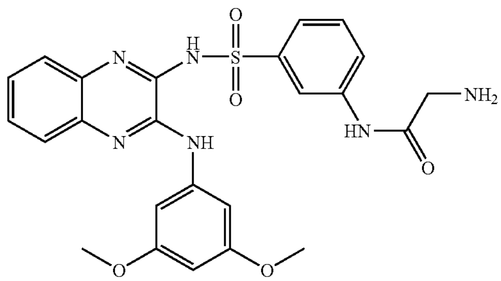 | N-(3-{[(3-{[3,5-bis(methoxy)phenyl]amino}quinoxalin-2-yl)amino]sulfonyl}phenyl)glycinamide |
| 367 | 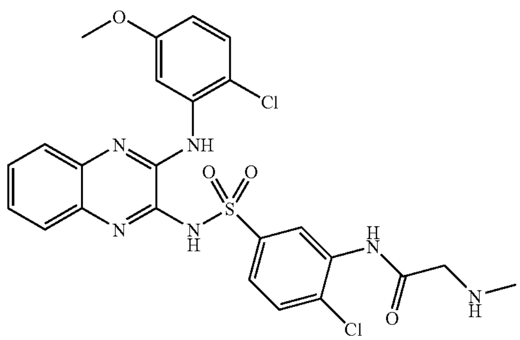 | N-(2-chloro-5-{[(3-{[2-chloro-5-(methoxy)phenyl]amino}quinoxalin-2-yl)amino]sulfonyl}phenyl)-N-2-methylglycinamide |
| 368 | 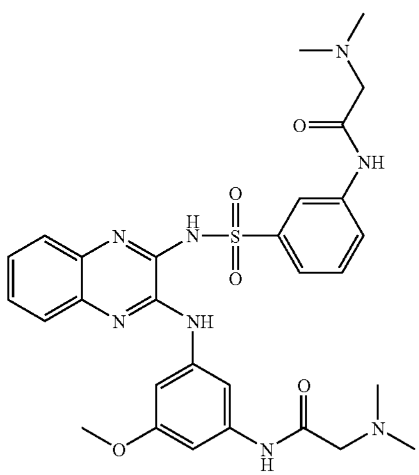 | 2-(dimethylamino)-N-(3-(N-(3-(3-(2-(dimethylamino)acetamido)-5-methoxyphenylamino)quinoxalin-2-yl)sulfamoyl)phenyl)acetamide |
| 369 | 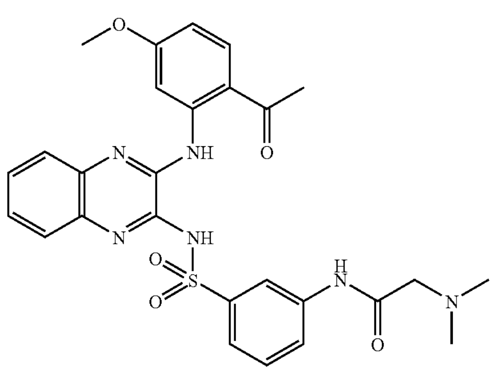 | N-(3-{[(3-{[2-acetyl-5-(methoxy)phenyl]amino}quinoxalin-2-yl)amino]sulfonyl}phenyl)-N-2-,N-2-dimethylglycinamide |

TABLE 1-continued

| Cpd. No. | Structure | Name |
|---|---|---|
| 370 | 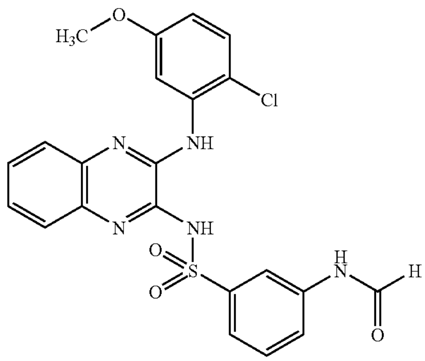 | N-(3-{[2-chloro-5-(methoxy)phenyl]amino}quinoxalin-2-yl)-3-(formylamino)benzenesulfonamide |
| 371 | 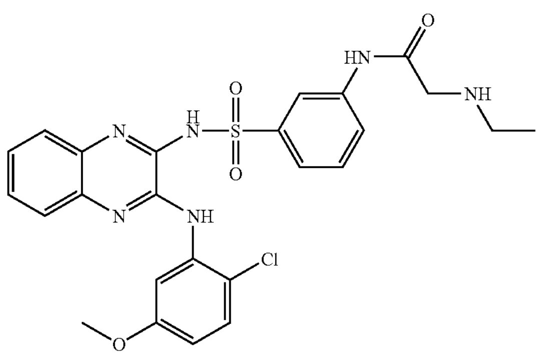 | N-(3-{[(3-{[2-chloro-5-(methoxy)phenyl]amino}quinoxalin-2-yl)amino]sulfonyl}phenyl)-N-2-ethylglycinamide |
| 372 | 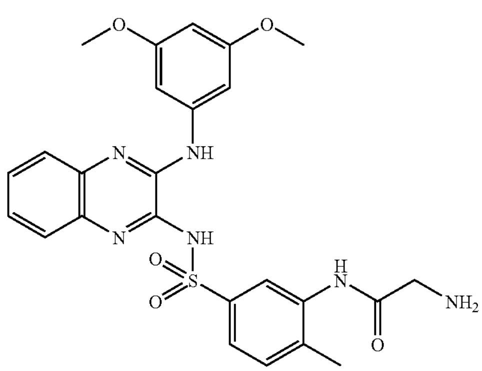 | N-(5-{[(3-{[3,5-bis(methoxy)phenyl]amino}quinoxalin-2-yl)amino]sulfonyl}-2-methylphenyl)glycinamide |
| 373 | 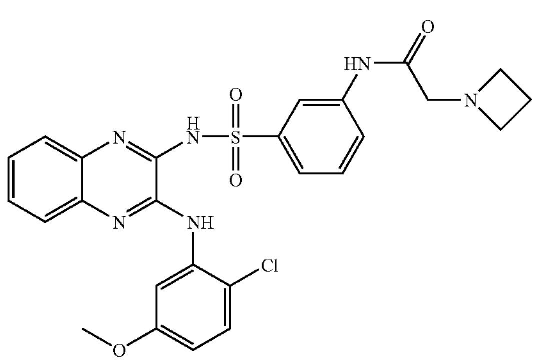 | 2-azetidin-1-yl-N-(3-{[(3-{[2-chloro-5-(methoxy)phenyl]amino}quinoxalin-2-yl)amino]sulfonyl}phenyl)acetamide |

TABLE 1-continued
| Cpd. No. | Structure | Name |
|---|---|---|
| 374 | 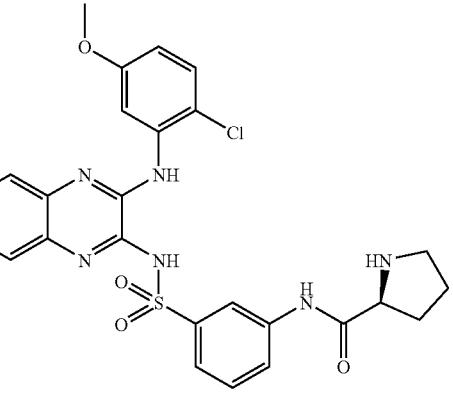 | N-(3-{[(3-{[2-chloro-5-(methoxy)phenyl]amino}quinoxalin-2-yl)amino]sulfonyl}phenyl)-L-prolinamide |
| 375 | 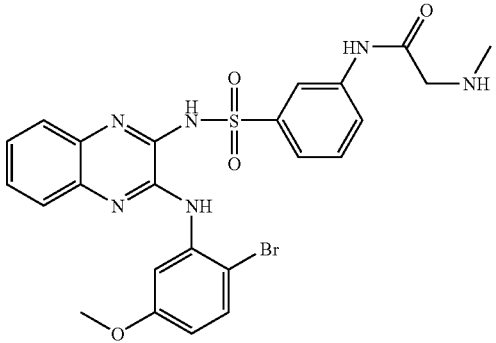 | N-(3-{[(3-{[2-bromo-5-(methoxy)phenyl]amino}quinoxalin-2-yl)amino]sulfonyl}phenyl)-N-2-methylglycinamide |
| 376 | 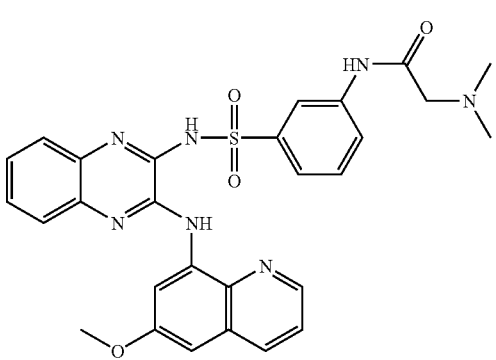 | N-2-,N-2-dimethyl-N-(3-{[(3-{[6-(methoxy)quinolin-8-yl]amino}quinoxalin-2-yl)amino]sulfonyl}phenyl)glycinamide |

| Cpd. No. | Structure | Name |
|---|---|---|
| 377 | 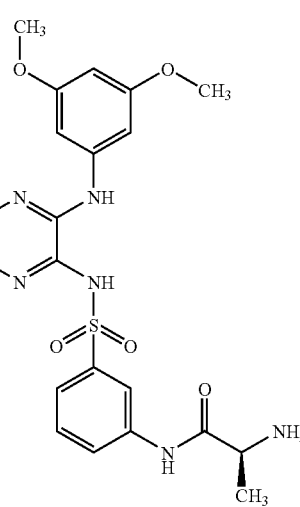 | N-(3-{[(3-{[3,5-bis(methoxy)phenyl]amino}quinoxalin-2-yl)amino]sulfonyl}phenyl)-L-alaninamide |
| 378 | 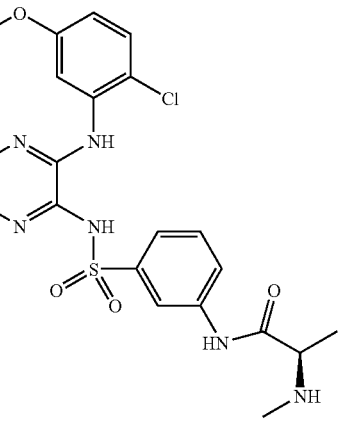 | N-(3-{[(3-{[2-chloro-5-(methoxy)phenyl]amino}quinoxalin-2-yl)amino]sulfonyl}phenyl)-N-2-methyl-D-alaninamide |
| 379 | 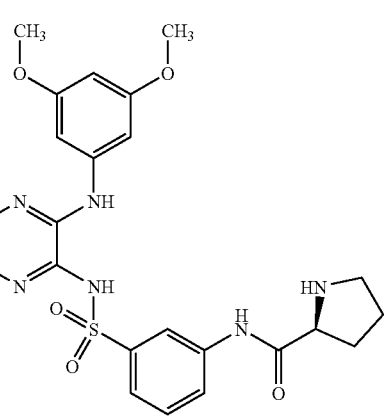 | N-(3-{[(3-{[3,5-bis(methoxy)phenyl]amino}quinoxalin-2-yl)amino]sulfonyl}phenyl)-L-prolinamide |

TABLE 1-continued
| Cpd. No. | Structure | Name |
|---|---|---|
| 380 | 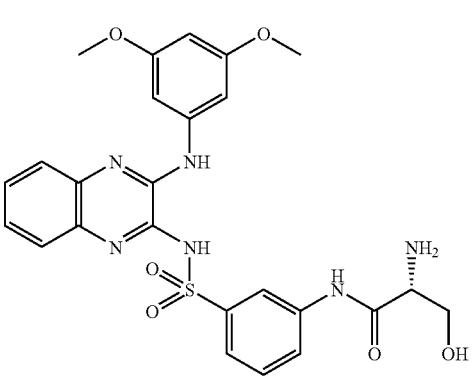 | N-(3-{[(3-{[3,5-bis(methoxy)phenyl]amino}quinoxalin-2-yl)amino]sulfonyl}phenyl)-D-serinamide |
| 381 | 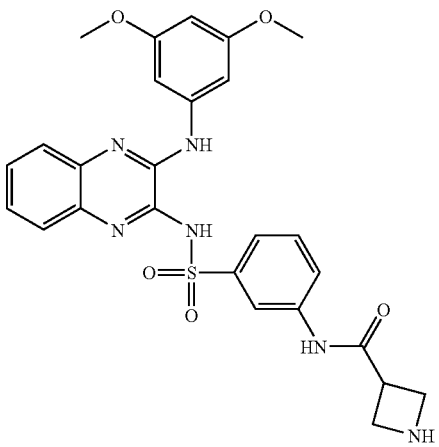 | N-(3-{[(3-{[3,5-bis(methoxy)phenyl]amino}quinoxalin-2-yl)amino]sulfonyl}phenyl)azetidine-3-carboxamide |
| 382 | 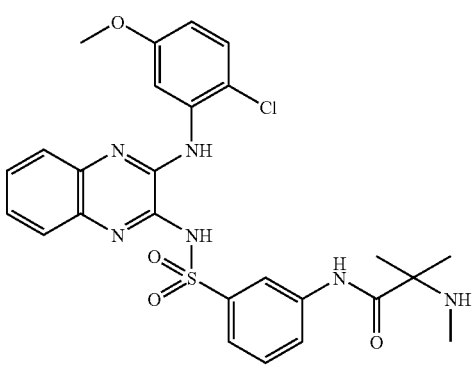 | N-(3-{[(3-{[2-chloro-5-(methoxy)phenyl]amino}quinoxalin-2-yl)amino]sulfonyl}phenyl)-N-2-,2-dimethylalaninamide |

US 7,989,622 B2

TABLE 1-continued

| Cpd. No. | Structure | Name |
|---|---|---|
| 383 | 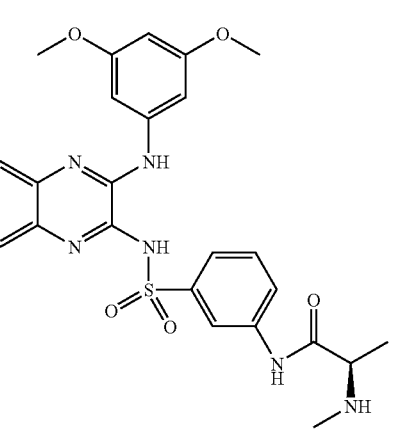 | N-(3-{[(3-{[3,5-bis(methoxy)phenyl]amino}quinoxalin-2-yl)amino]sulfonyl}phenyl)-N-2-methyl-D-alaninamide |
| 384 | 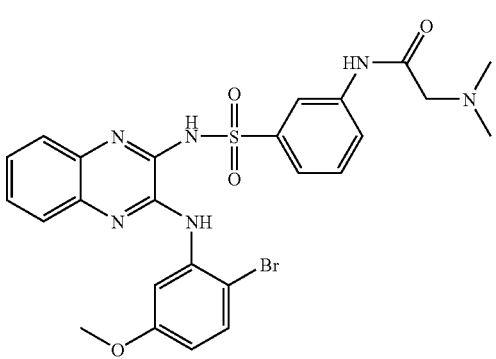 | N-(3-{[(3-{[2-bromo-5-(methoxy)phenyl]amino}quinoxalin-2-yl)amino]sulfonyl}phenyl)-N-2-,N-2-dimethylglycinamide |
| 385 | 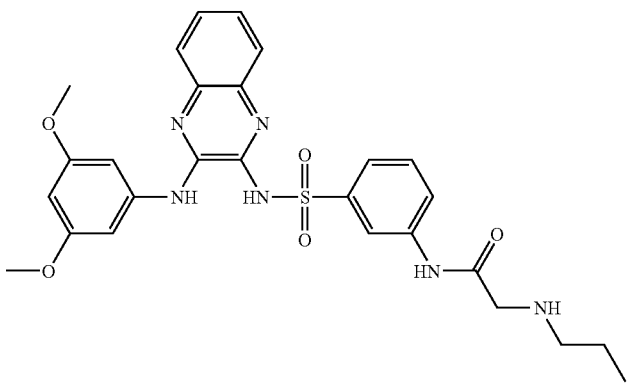 | N-(3-{[(3-{[3,5-bis(methoxy)phenyl]amino}quinoxalin-2-yl)amino]sulfonyl}phenyl)-N-2-propylglycinamide |
| 386 | 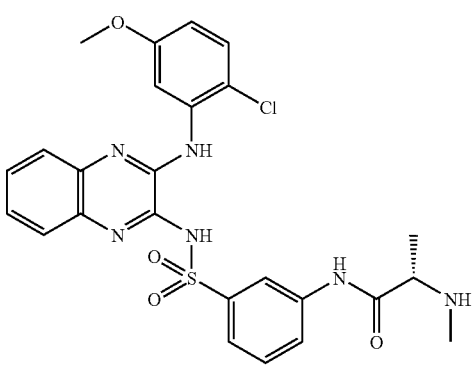 | N-(3-{[(3-{[2-chloro-5-(methoxy)phenyl]amino}quinoxalin-2-yl)amino]sulfonyl}phenyl)-N-2-methyl-L-alaninamide |

TABLE 1-continued

| Cpd. No. | Structure | Name |
|---|---|---|
| 387 | 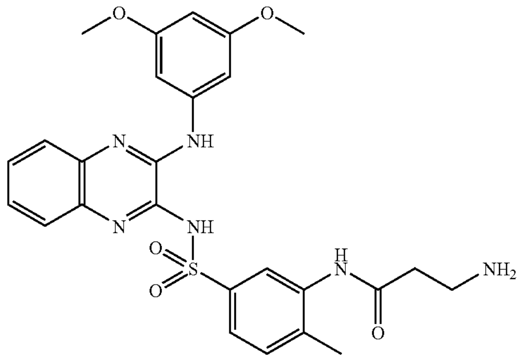 | N-(5-{[(3-{[3,5-bis(methoxy)phenyl]amino}quinoxalin-2-yl)amino]-sulfonyl}-2-methylphenyl)-beta-alaninamide |
| 388 | 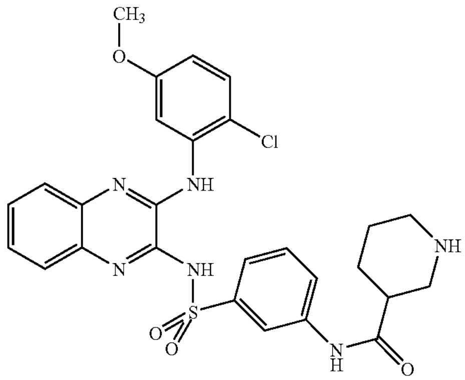 | N-(3-{[(3-{[2-chloro-5-(methoxy)phenyl]amino}quinoxalin-2-yl)amino]sulfonyl}phenyl)piperidine-3-carboxamide |
| 389 | 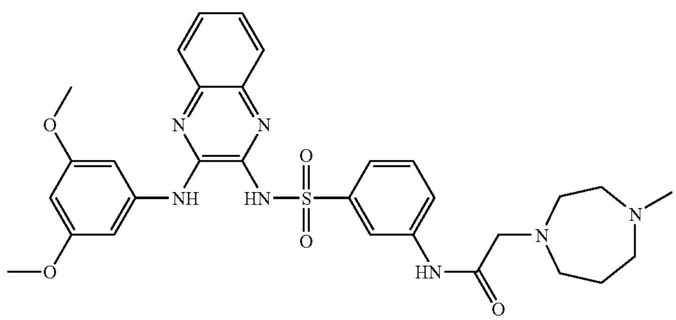 | N-(3-{[(3-{[3,5-bis(methoxy)phenyl]amino}quinoxalin-2-yl)amino]sulfonyl}phenyl)-2-(4-methyl-1,4-diazepan-1-yl)acetamide |
| 390 | 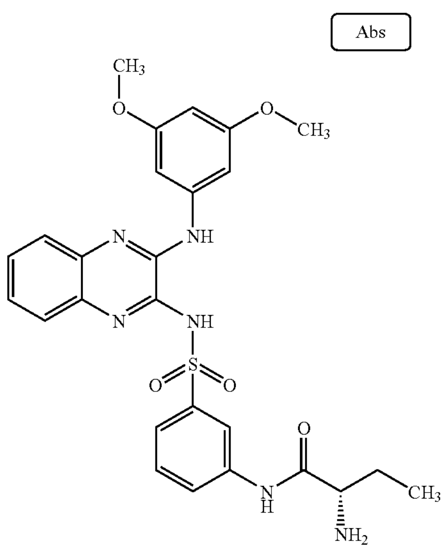 | (2S)-2-amino-N-(3-{[(3-{[3,5-bis(methoxy)phenyl]amino}quinoxalin-2-yl)amino]sulfonyl}phenyl)butanamide |

TABLE 1-continued

| Cpd. No. | Structure | Name |
|---|---|---|
| 391 | 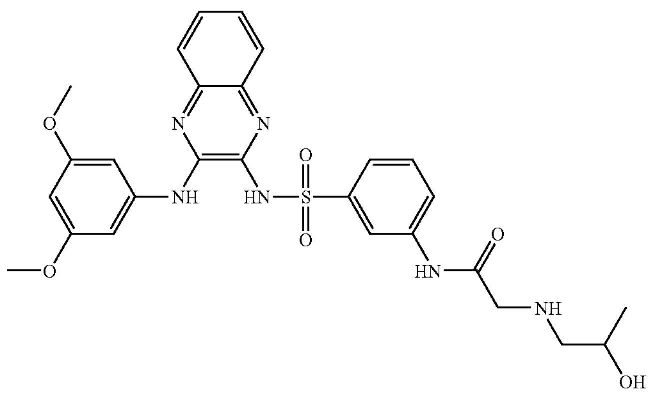 | N-(3-{[(3-{[3,5-bis(methoxy)phenyl]amino}quinoxalin-2-yl)amino]sulfonyl}phenyl)-N-2-(2-hydroxypropyl)glycinamide |
| 392 | 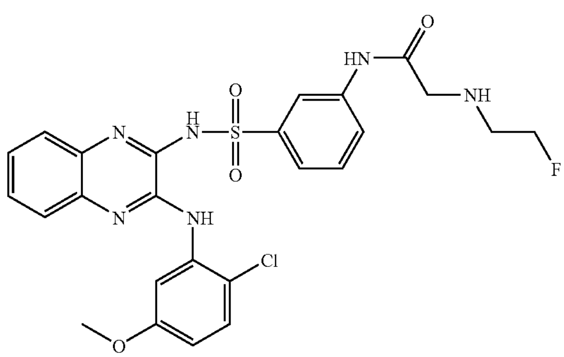 | N-(3-{[(3-{[2-chloro-5-(methoxy)phenyl]amino}quinoxalin-2-yl)amino]sulfonyl}phenyl)-N-2-(2-fluoroethyl)glycinamide |
| 393 | 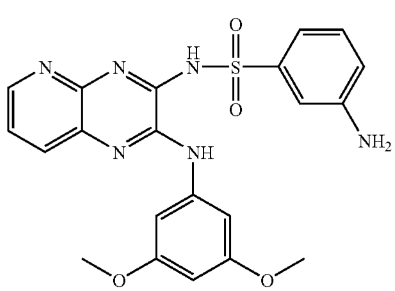 | 3-amino-N-(2-{[3,5-bis(methoxy)phenyl]amino}pyrido[2,3-b]pyrazin-3-yl)benzenesulfonamide |
| 394 | 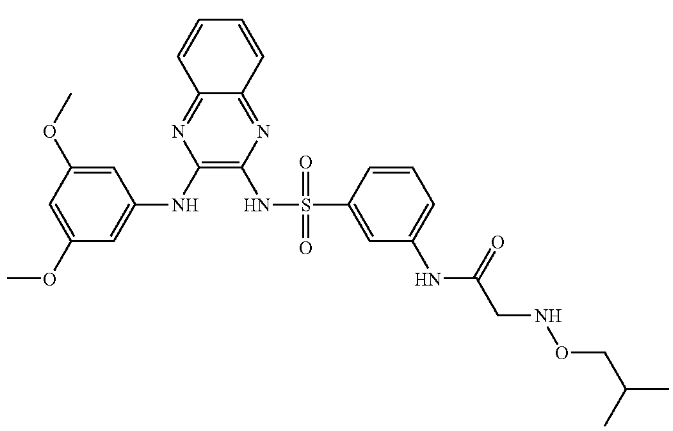 | N-(3-{[(3-{[3,5-bis(methoxy)phenyl]amino}quinoxalin-2-yl)amino]sulfonyl}phenyl)-N-2-[(2-methylpropyl)oxy]glycinamide |

TABLE 1-continued

| Cpd. No. | Structure | Name |
|---|---|---|
| 395 | 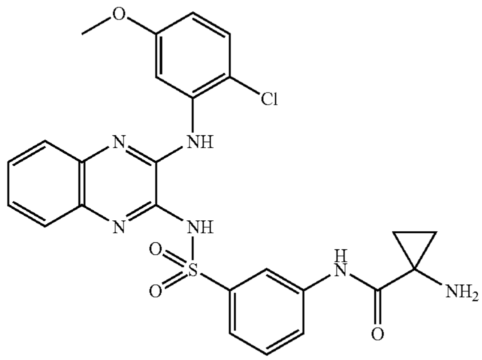 | 1-amino-N-(3-{[(3-{[2-chloro-5-(methoxy)phenyl]amino}quinoxalin-2-yl)amino]sulfonyl}phenyl)cyclopropanecarboxamide |
| 396 | 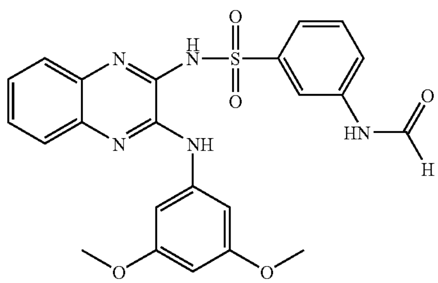 | N-(3-{[3,5-bis(methoxy)phenyl]amino}quinoxalin-2-yl)-3-(formylamino)benzenesulfonamide |
| 397 | 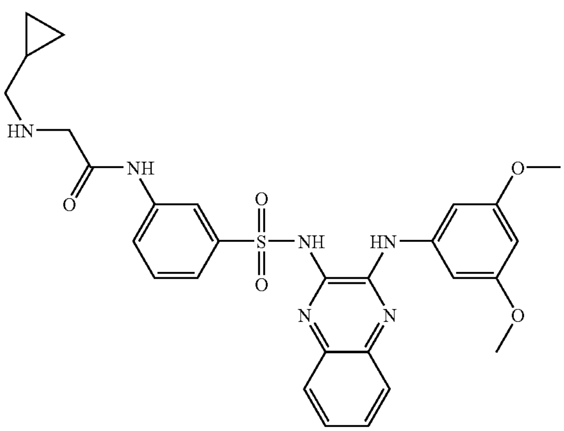 | N-(3-{[(3-{[3,5-bis(methoxy)phenyl]amino}quinoxalin-2-yl)amino]sulfonyl}phenyl)-N-2-(cyclopropylmethyl)glycinamide |
| 398 | Abs | N-(3-{[(3-{[3,5-bis(methoxy)phenyl]amino}quinoxalin-2-yl)amino]sulfonyl}phenyl)-D-proplinamide |

TABLE 1-continued

| Cpd. No. | Structure | Name |
|---|---|---|
| 399 | 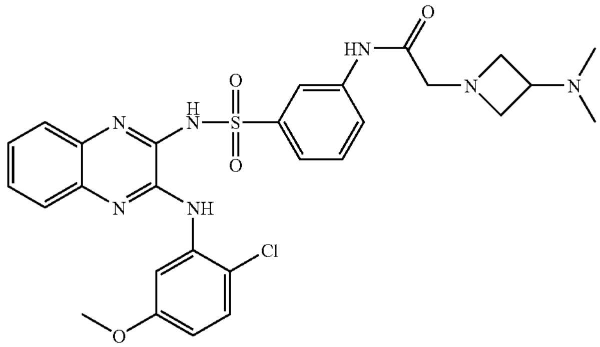 | N-(3-{[(3-{[2-chloro-5-(methoxy)phenyl]amino}quinoxalin-2-yl)amino]sulfonyl}phenyl)-2-[3-(dimethylamino)azetidin-1-yl]acetamide |
| 400 | Abs | N-(3-{[(3-{[2-chloro-5-(methoxy)phenyl]amino}quinoxalin-2-yl)amino]sulfonyl}phenyl)-D-prolinamide |
| 401 | 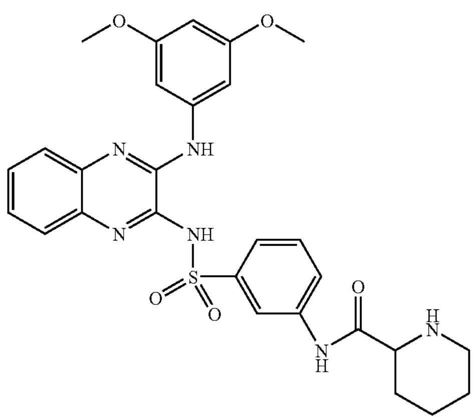 | N-(3-{[(3-{[3,5-bis(methoxy)phenyl]amino}quinoxalin-2-yl)amino]sulfonyl}phenyl)piperidine-2-carboxamide |
| 402 | 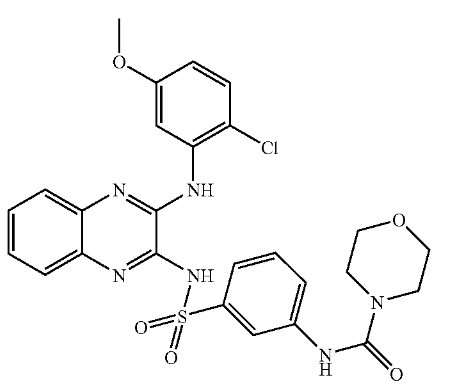 | N-(3-{[(3-{[2-chloro-5-(methoxy)phenyl]amino}quinoxalin-2-yl)amino]sulfonyl}phenyl)morpholine-4-carboxamide |

TABLE 1-continued

| Cpd. No. | Structure | Name |
| --- | --- | --- |
| 403 | 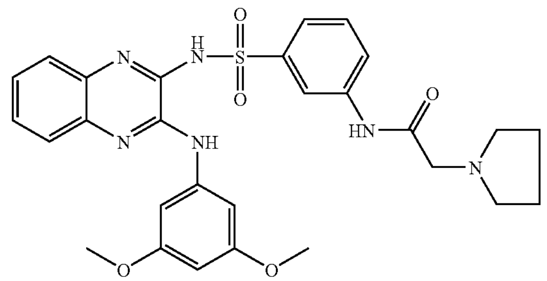 | N-(3-{[(3-{[3,5-bis(methoxy)phenyl]amino}quinoxalin-2-yl)amino]sulfonyl}phenyl)-2-pyrrolidin-1-ylacetamide |
| 404 | 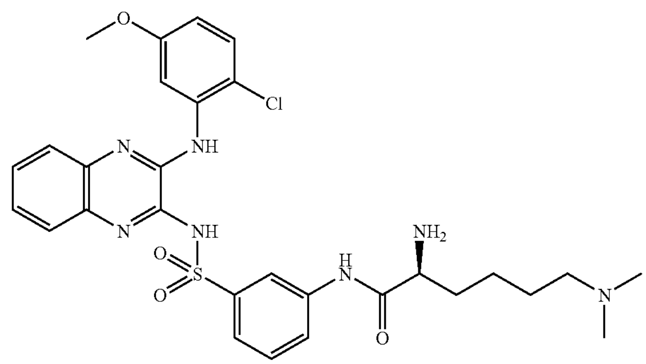 | N-(3-{[(3-{[2-chloro-5-(methoxy)phenyl]amino}quinoxalin-2-yl)amino]sulfonyl}phenyl)-N-6,N-6-dimethyl-L-lysinamide |
| 405 | 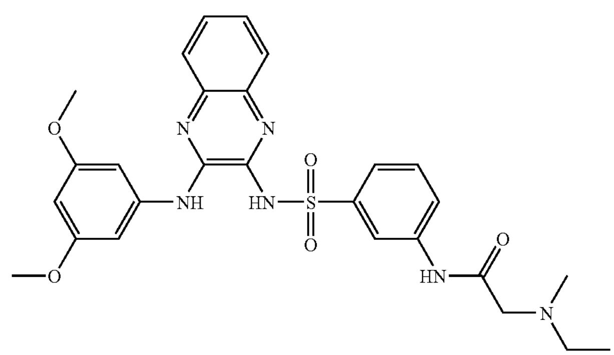 | N-(3-{[(3-{[3,5-bis(methoxy)phenyl]amino}quinoxalin-2-yl)amino]sulfonyl}phenyl)-N-2-ethyl-N-2-methylglycinamide |
| 406 | 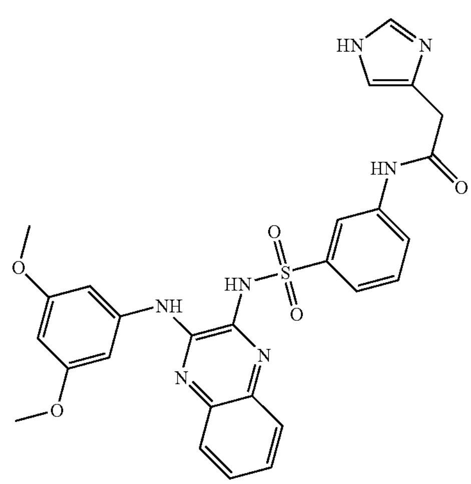 | N-(3-{[(3-{[3,5-bis(methoxy)phenyl]amino}quinoxalin-2-yl)amino]sulfonyl}phenyl)-2-(1H-imidazol-4-yl)acetamide |

TABLE 1-continued

| Cpd. No. | Structure | Name |
|---|---|---|
| 407 | 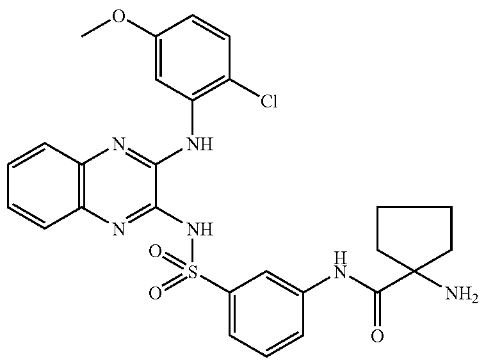 | 1-amino-N-(3-{[(3-{[2-chloro-5-(methoxy)phenyl]amino}quinoxalin-2-yl)amino]sulfonyl}phenyl)cyclopentanecarboxamide |
| 408 | 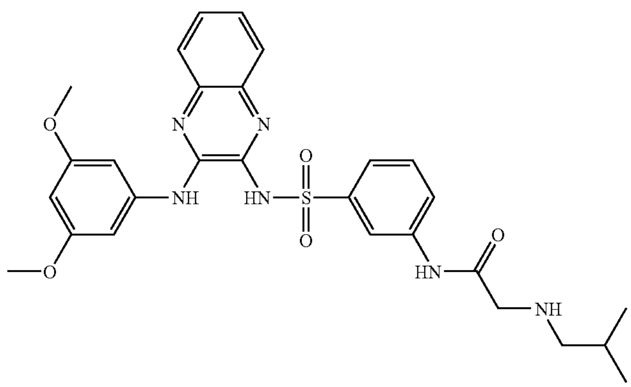 | N-(3-{[(3-{[3,5-bis(methoxy)phenyl]amino}quinoxalin-2-yl)amino]sulfonyl}phenyl)-N-2-(2-methylpropyl)glycinamide |
| 409 | 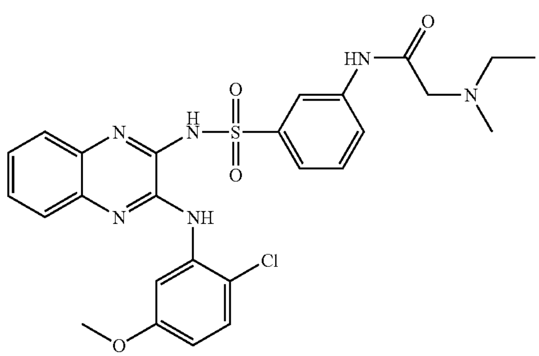 | N-(3-{[(3-{[2-chloro-5-(methoxy)phenyl]amino}quinoxalin-2-yl)amino]sulfonyl}phenyl)-N-2-ethyl-N-2-methylglycinamide |
| 410 | 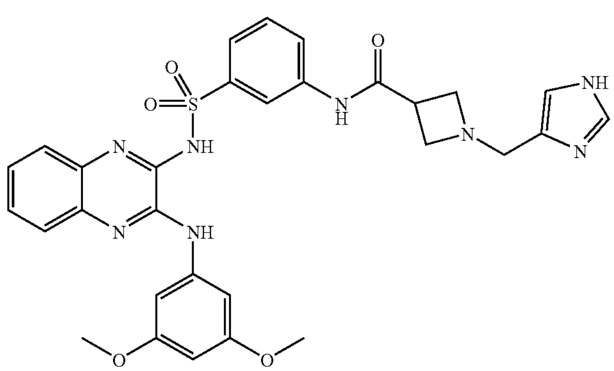 | N-(3-{[(3-{[3,5-bis(methoxy)phenyl]amino}quinoxalin-2-yl)amino]sulfonyl}phenyl)-1-(1H-imidazol-4-ylmethyl)azetidine-3-carboxamide |

TABLE 1-continued

| Cpd. No. | Structure | Name |
|---|---|---|
| 411 | 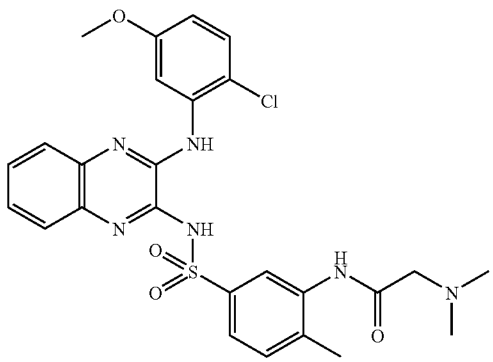 | N-(5-{[(3-{[2-chloro-5-(methoxy)phenyl]amino}quinoxalin-2-yl)amino]sulfonyl}-2-methylphenyl)-N-2-,N-2-dimethylglycinamide |
| 412 | 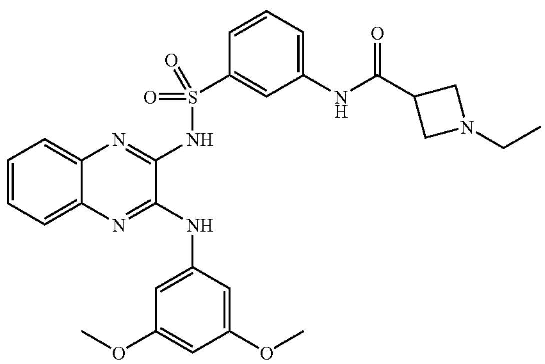 | N-(3-{[(3-{[3,5-bis(methoxy)phenyl]amino}quinoxalin-2-yl)amino]sulfonyl}phenyl)-1-ethylazetidine-3-carboxamide |
| 413 | 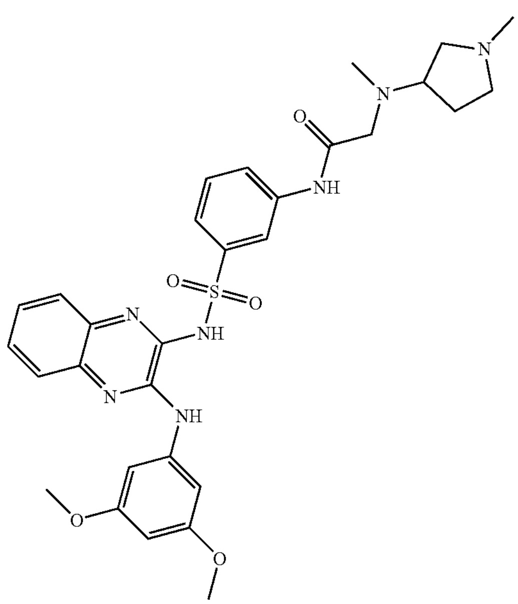 | N-(3-{[(3-{[3,5-bis(methoxy)phenyl]amino}quinoxalin-2-yl)amino]sulfonyl}phenyl)-N-2-methyl-N-2-(1-methylpyrrolidin-3-yl)glycinamide |

| Cpd. No. | Structure | Name |
|---|---|---|
| 414 | 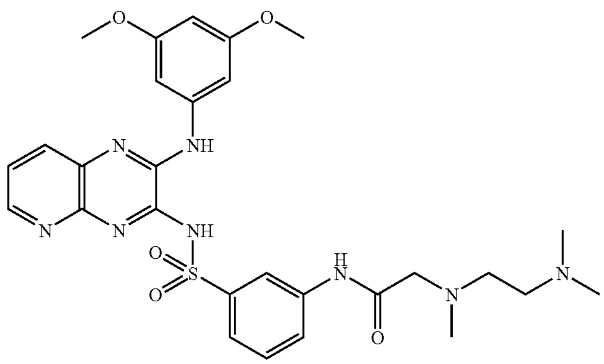 | N-(3-{[(2-{[3,5-bis(methoxy)phenyl]amino}pyrido[2,3-b]pyrazin-3-yl)amino]sulfonyl}phenyl)-N-2-[2-(dimethylamino)ethyl]-N-2-methylglycinamide |
| 415 | Abs | N-(3-{[(3-{[3,5-bis(methoxy)phenyl]amino}quinoxalin-2-yl)amino]sulfonyl}phenyl)-2-[(3S)-3-hydroxypyrrolidin-1-yl]acetamide |
| 416 | 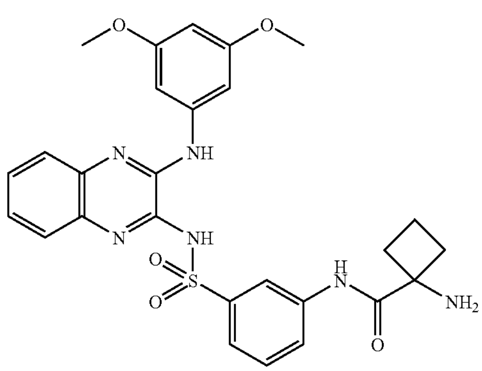 | 1-amino-N-(3-{[(3-{[3,5-bis(methoxy)phenyl]amino}quinoxalin-2-yl)amino]sulfonyl}phenyl)cyclobutanecarboxamide |

TABLE 1-continued

| Cpd. No. | Structure | Name |
|---|---|---|
| 417 | 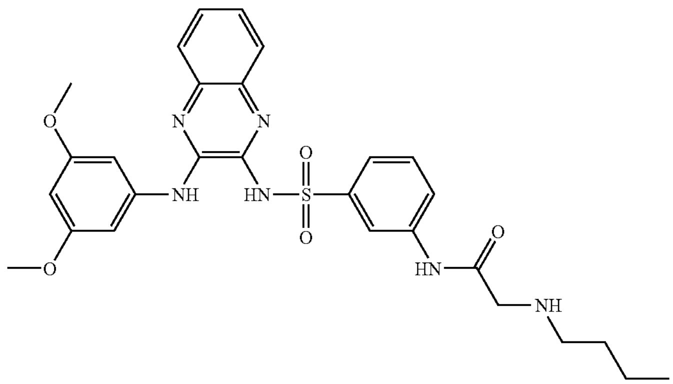 | N-(3-{[(3-{[3,5-bis(methoxy)phenyl]amino}quinoxalin-2-yl)amino]sulfonyl}phenyl)-N-2-butylglycinamide |
| 418 | 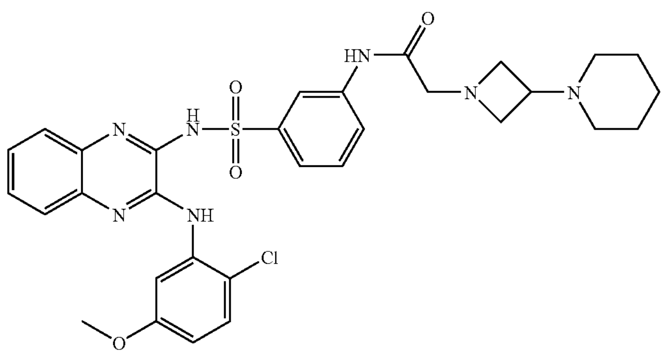 | N-(3-{[(3-{[2-chloro-5-(methoxy)phenyl]amino}quinoxalin-2-yl)amino]sulfonyl}phenyl)-2-(3-piperidin-1-ylazetidin-1-yl)acetamide |
| 419 | 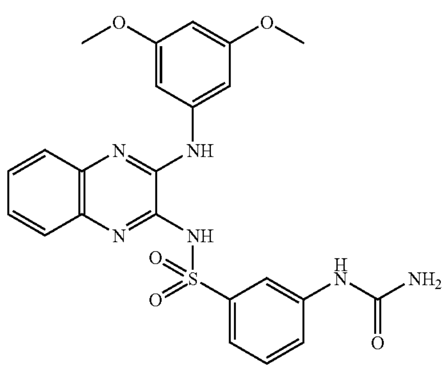 | 3-[(aminocarbonyl)amino]-N-(3-{[3,5-bis(methoxy)phenyl]amino}quinoxalin-2-yl)benzenesulfonamide |
| 420 | 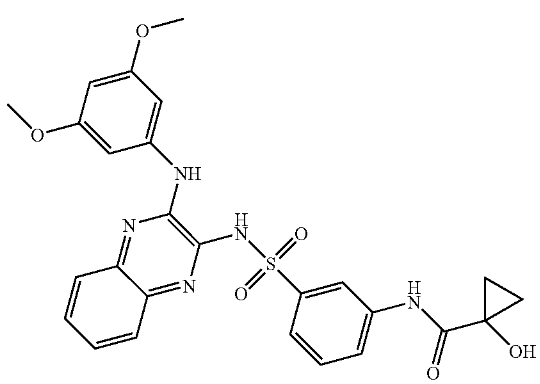 | N-(3-{[(3-{[3,5-bis(methoxy)phenyl]amino}quinoxalin-2-yl)amino]sulfonyl}phenyl)-1-hydroxycyclopropanecarboxamide |

| Cpd. No. | Structure | Name |
|---|---|---|
| 421 | 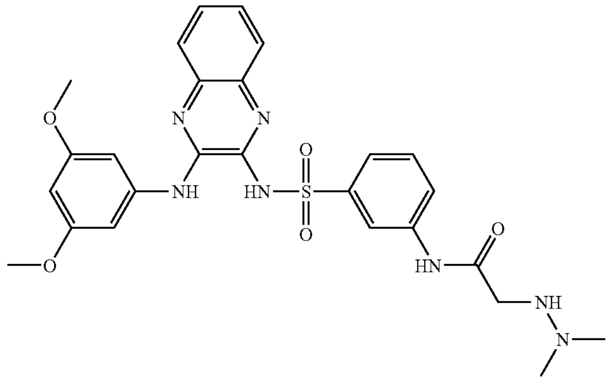 | N-(3-{[(3-{[3,5-bis(methoxy)phenyl]amino}quinoxalin-2-yl)amino]sulfonyl}phenyl)-2-(2,2-dimethylhydrazino)acetamide |
| 422 | 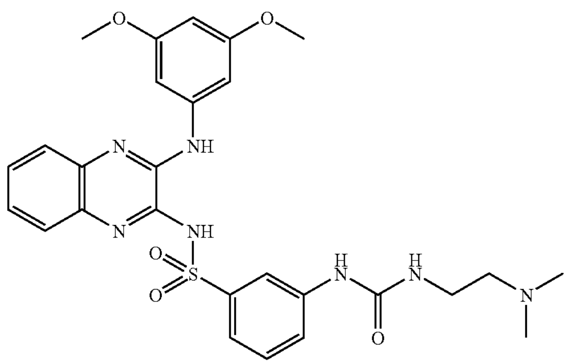 | N-(3-{[3,5-bis(methoxy)phenyl]amino}quinoxalin-2-yl)-3-[({[2-(dimethylamino)ethyl]amino}carbonyl)amino]benzenesulfonamide |
| 423 | 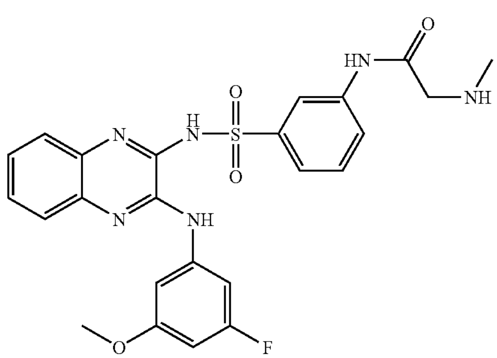 | N-(3-{[(3-{[3-fluoro-5-(methoxy)phenyl]amino}quinoxalin-2-yl)amino]sulfonyl}phenyl)-N-2-methylglycinamide |
| 424 | 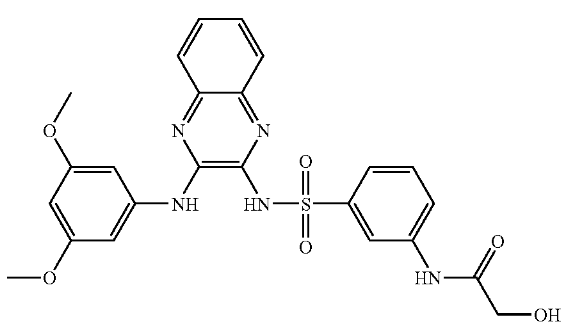 | N-(3-{[(3-{[3,5-bis(methoxy)phenyl]amino}quinoxalin-2-yl)amino]sulfonyl}phenyl)-2-hydroxyacetamide |

| Cpd. No. | Structure | Name |
|---|---|---|
| 425 | 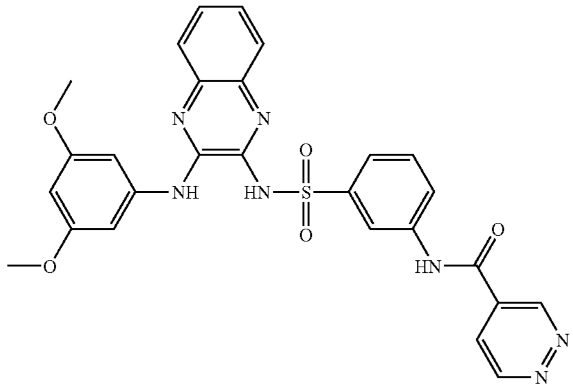 | N-(3-{[(3-{[3,5-bis(methoxy)phenyl]amino}quinoxalin-2-yl)amino]sulfonyl}phenyl)pyridazine-4-carboxamide |
| 426 | 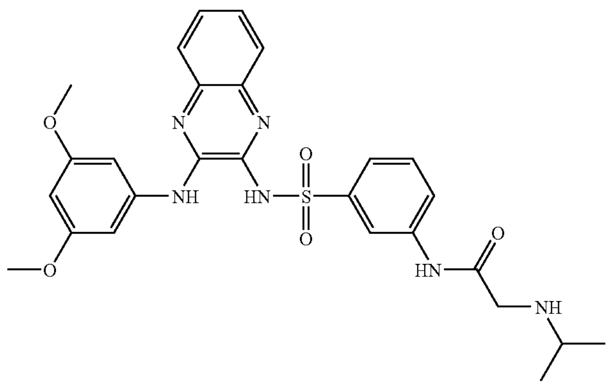 | N-(3-{[(3-{[3,5-bis(methoxy)phenyl]amino}quinoxalin-2-yl)amino]sulfonyl}phenyl)-N-2-(1-methylethyl)glycinamide |
| 427 | 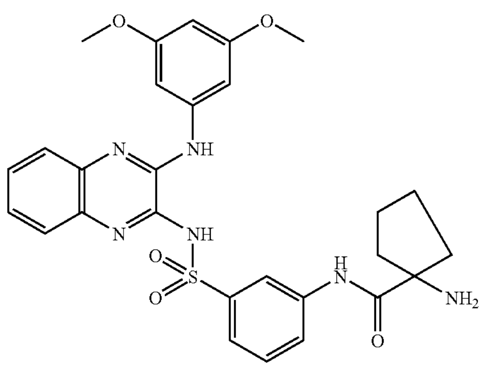 | 1-amino-N-(3-{[(3-{[3,5-bis(methoxy)phenyl]amino}quinoxalin-2-yl)amino]sulfonyl}phenyl)cyclopentanecarboxamide |
| 428 | 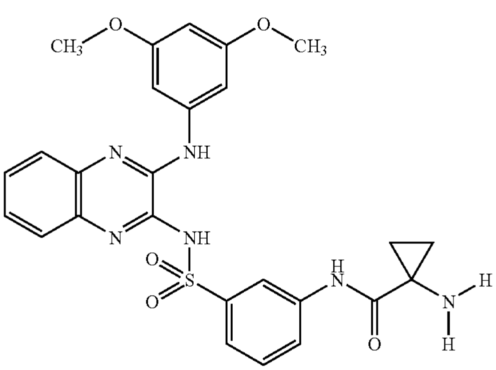 | 1-amino-N-(3-{[(3-{[3,5-bis(methoxy)phenyl]amino}quinoxalin-2-yl)amino]sulfonyl}phenyl)cyclopropanecarboxamide |

TABLE 1-continued

| Cpd. No. | Structure | Name |
|---|---|---|
| 429 | 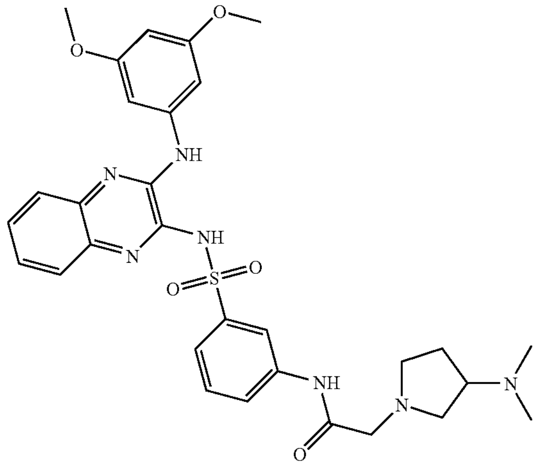 | N-(3-{[(3-{[3,5-bis(methoxy)phenyl]amino}quinoxalin-2-yl)amino]sulfonyl}phenyl)-2-[3-(dimethylamino)pyrrolidin-1-yl]acetamide |
| 430 | 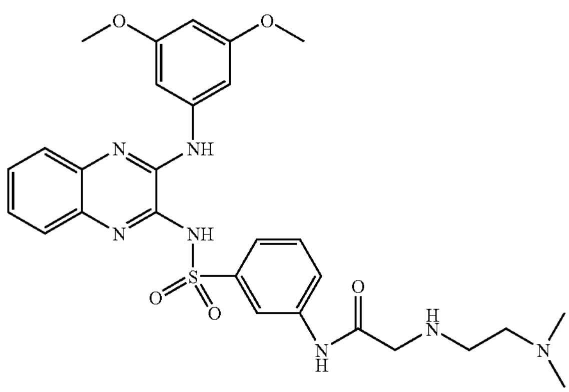 | N-(3-{[(3-{[3,5-bis(methoxy)phenyl]amino}quinoxalin-2-yl)amino]sulfonyl}phenyl)-N-2-[2-(dimethylamino)ethyl]glycinamide |
| 431 | 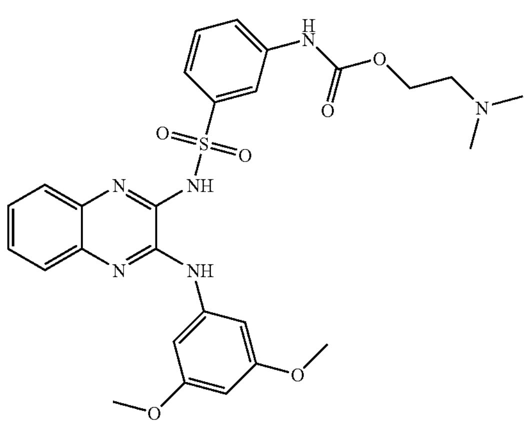 | 2-(dimethylamino)ethyl(3-{[(3-{[3,5-bis(methoxy)phenyl]amino}quinoxalin-2-yl)amino]sulfonyl}phenyl)carbamate |

TABLE 1-continued

| Cpd. No. | Structure | Name |
|---|---|---|
| 432 | 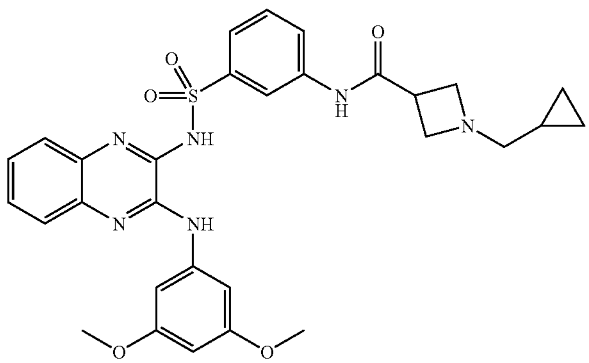 | N-(3-{[(3-{[3,5-bis(methoxy)phenyl]amino}quinoxalin-2-yl)amino]sulfonyl}phenyl)-1-(cyclopropylmethyl)azetidine-3-carboxamide |
| 433 | 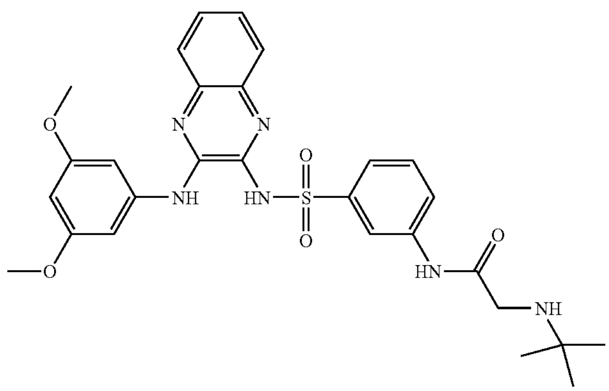 | N-(3-{[(3-{[3,5-bis(methoxy)phenyl]amino}quinoxalin-2-yl)amino]sulfonyl}phenyl)-N-2-(1,1-dimethylethyl)glycinamide |
| 434 | 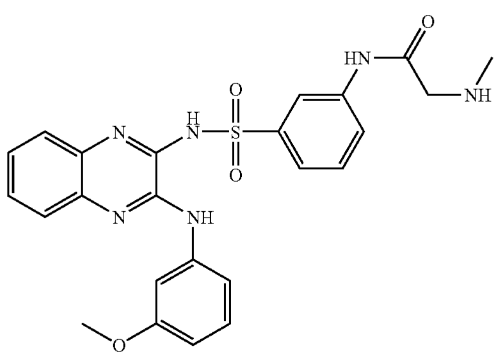 | N-2-methyl-N-(3-{[(3-{[3-(methoxy)phenyl]amino}quinoxalin-2-yl)amino]sulfonyl}phenyl)glycinamide |
| 435 | 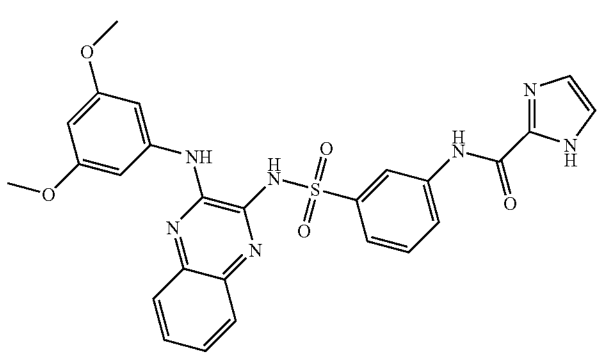 | N-(3-{[(3-{[3,5-bis(methoxy)phenyl]amino}quinoxalin-2-yl)amino]sulfonyl}phenyl)-1H-imidazole-2-carboxamide |

| Cpd. No. | Structure | Name |
|---|---|---|
| 436 | 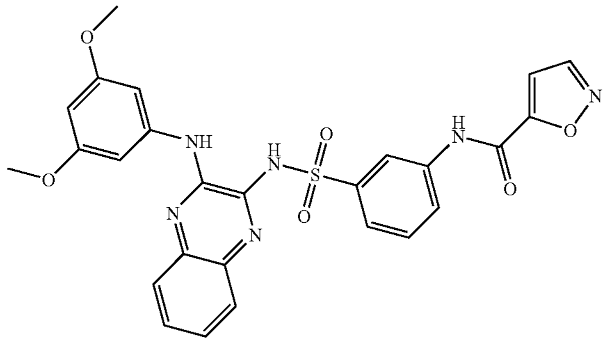 | N-(3-{[(3-{[3,5-bis(methoxy)phenyl]amino}quinoxalin-2-yl)amino]sulfonyl}phenyl(isoxazole-5-carboxamide |
| 437 | 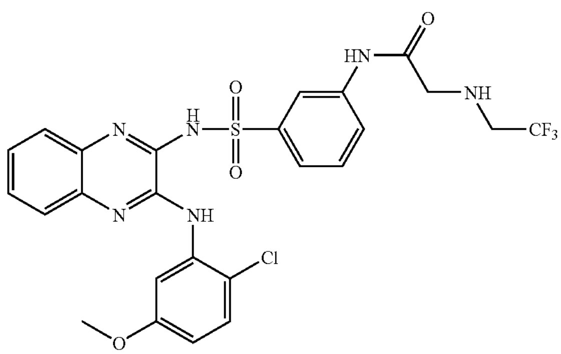 | N-(3-{[(3-{[2-chloro-5-(methoxy)phenyl]amino}quinoxalin-2-yl)amino]sulfonyl}phenyl)-N-2-(2,2,2-trifluoroethyl)glycinamide |
| 438 | 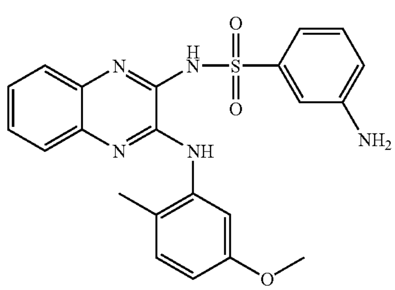 | 3-amino-N-(3-{[2-methyl-5-(methoxy)phenyl]amino}quinoxalin-2-yl)benzenesulfonamide |
| 439 | 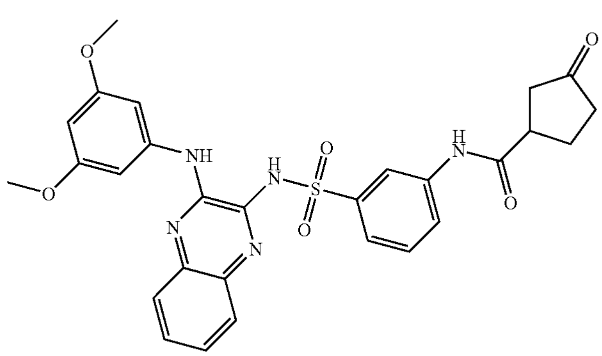 | N-(3-{[(3-{[3,5-bis(methoxy)phenyl]amino}quinoxalin-2-yl)amino]sulfonyl}phenyl)-3-oxocyclopentanecarboxamide |

TABLE 1-continued

| Cpd. No. | Structure | Name |
|---|---|---|
| 440 | 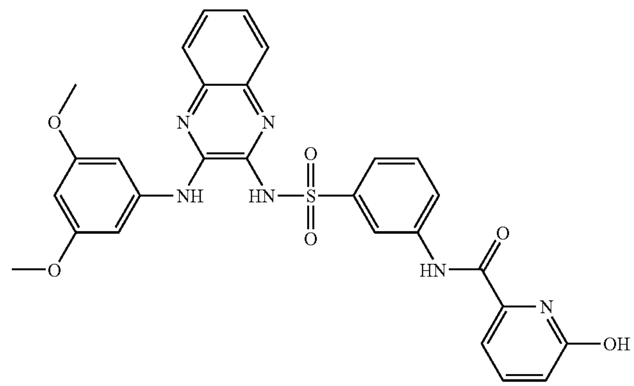 | N-(3-{[(3-{[3,5-bis(methoxy)phenyl]amino}quinoxalin-2-yl)amino]sulfonyl}phenyl)-6-hydroxypyridine-2-carboxamide |
| 441 | 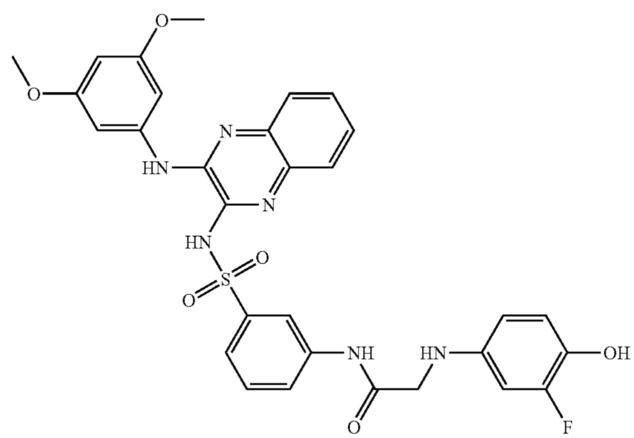 | N-(3-{[(3-{[3,5-bis(methoxy)phenyl]amino}quinoxalin-2-yl)amino]sulfonyl}phenyl)-N-2-(3-fluoro-4-hydroxyphenyl)glycinamide |
| 442 | 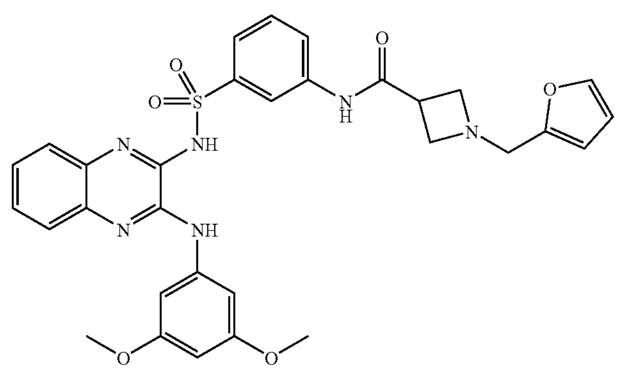 | N-(3-{[(3-{[3,5-bis(methoxy)phenyl]amino}quinoxalin-2-yl)amino]sulfonyl}phenyl)-1-(furan-2-ylmethyl)azetidine-3-carboxamide |
| 443 | 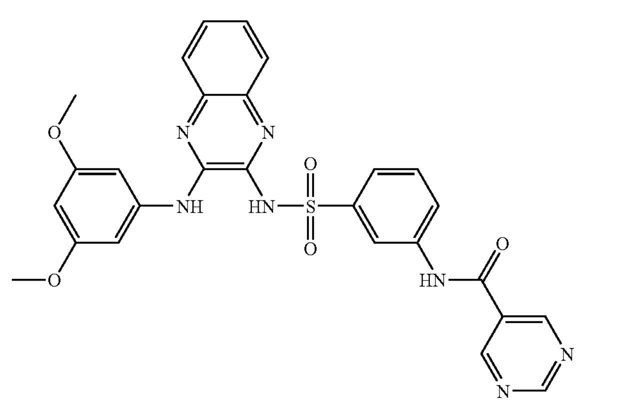 | N-(3-{[(3-{[3,5-bis(methoxy)phenyl]amino}quinoxalin-2-yl)amino]sulfonyl}phenyl)pyrimidine-5-carboxamide |

TABLE 1-continued

| Cpd. No. | Structure | Name |
|---|---|---|
| 444 | 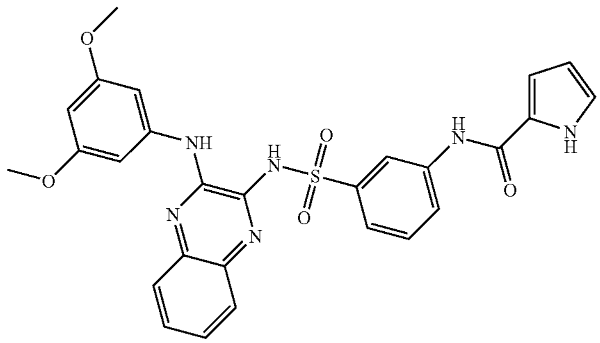 | N-(3-{[(3-{[3,5-bis(methoxy)phenyl]amino}quinoxalin-2-yl)amino]sulfonyl}phenyl)-1H-pyrrole-2-carboxamide |
| 445 | 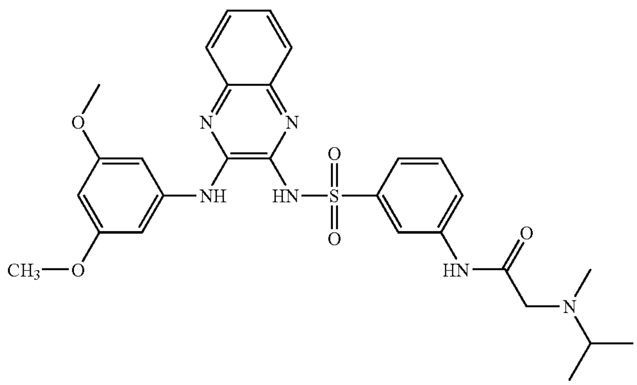 | N-(3-{[(3-{[3,5-bis(methoxy)phenyl]amino}quinoxalin-2-yl)amino]sulfonyl}phenyl)-N-2-methyl-N-2-(1-methylethyl)glycinamide |
| 446 | 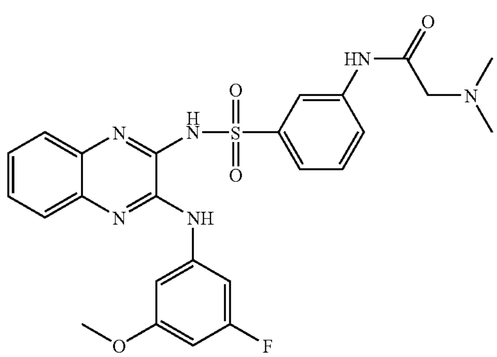 | N-(3-{[(3-{[3-fluoro-5-(methoxy)phenyl]amino}quinoxalin-2-yl)amino]sulfonyl}phenyl)-N-2-,N-2-dimethylglycinamide |
| 447 | 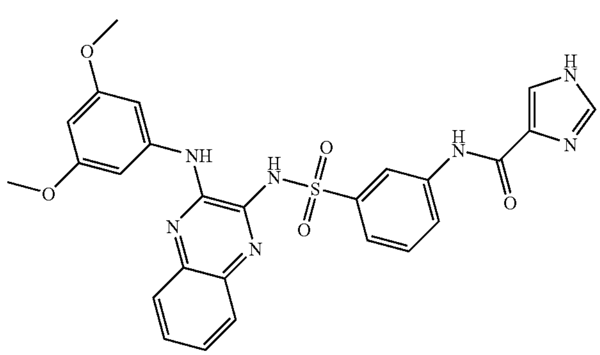 | N-(3-{[(3-{[3,5-bis(methoxy)phenyl]amino}quinoxalin-2-yl)amino]sulfonyl}phenyl)-1H-imidazole-4-carboxamide |

TABLE 1-continued

| Cpd. No. | Structure | Name |
|---|---|---|
| 448 | 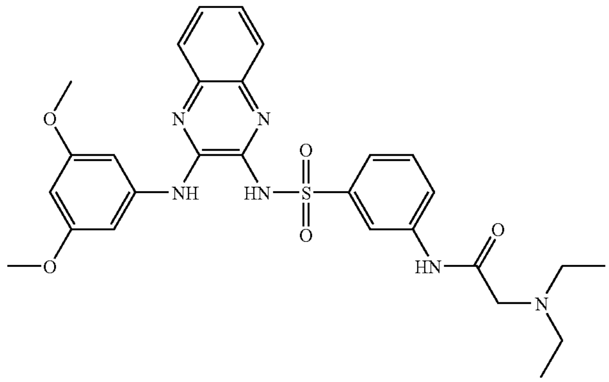 | N-(3-{[(3-{[3,5-bis(methoxy)phenyl]amino}quinoxalin-2-yl)amino]sulfonyl}phenyl)-N-2-,N-2-diethylglycinamide |
| 449 | 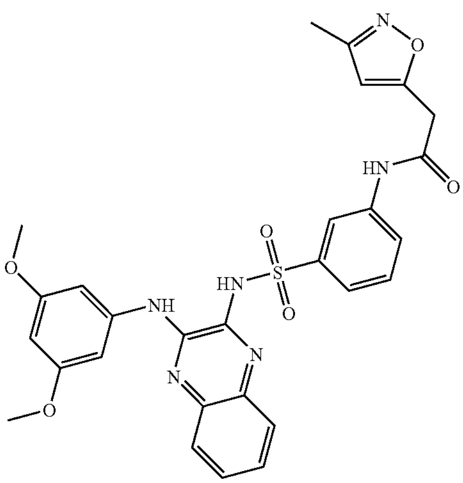 | N-(3-{[(3-{[3,5-bis(methoxy)phenyl]amino}quinoxalin-2-yl)amino]sulfonyl}phenyl)-2-(3-methylisoxazol-3-yl)acetamide |
| 450 | 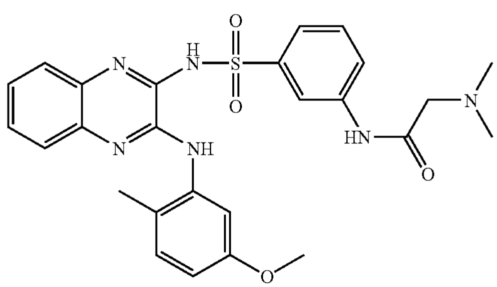 | N-2-,N-2-dimethyl-N-(3-{[(3-{[2-methyl-5-(methoxy)phenyl]amino}quinoxalin-2-yl)amino]sulfonyl}phenyl)glycinamide |
| 451 | 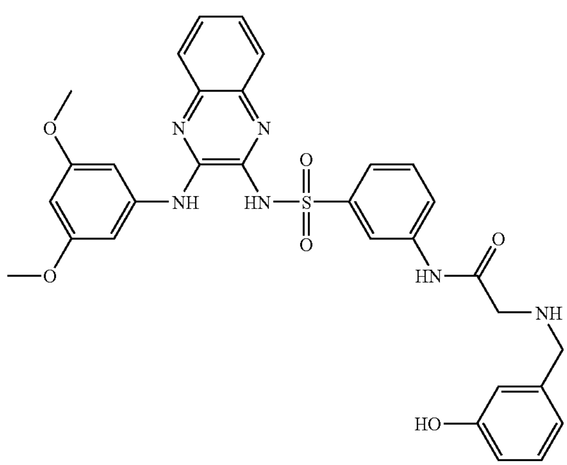 | N-(3-{[(3-{[3,5-bis(methoxy)phenyl]amino}quinoxalin-2-yl)amino]sulfonyl}phenyl)-N-2-[(3-hydroxyphenyl)methyl]glycinamide |

TABLE 1-continued

| Cpd. No. | Structure | Name |
|---|---|---|
| 452 | 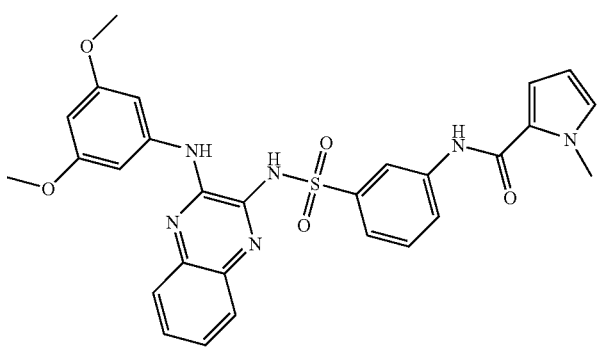 | N-(3-{[(3-{[3,5-bis(methoxy)phenyl]amino}quinoxalin-2-yl)amino]sulfonyl}phenyl)-1-methyl-1H-pyrrole-2-carboxamide |
| 453 | 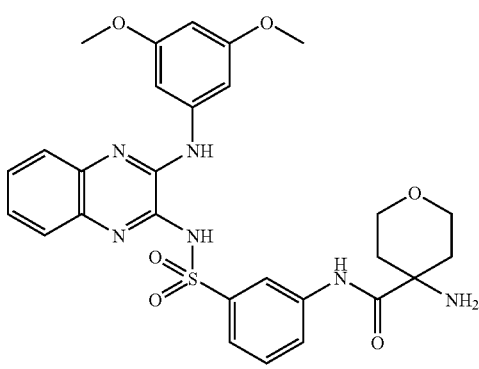 | 4-amino-N-(3-{[(3-{[3,5-bis(methoxy)phenyl]amino}quinoxalin-2-yl)amino]sulfonyl}phenyl)tetrahydro-2H-pyran-4-carboxamide |
| 454 | 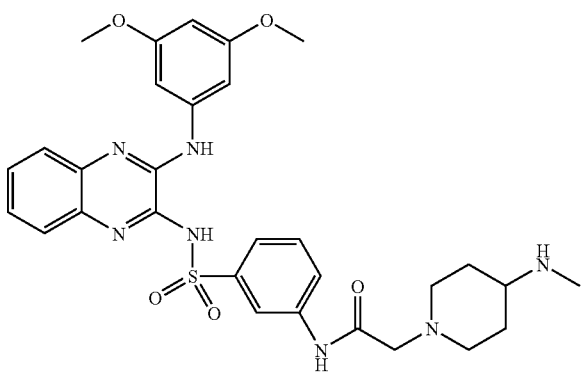 | N-(3-{[(3-{[3,5-bis(methoxy)phenyl]amino}quinoxalin-2-yl)amino]sulfonyl}phenyl)-2-[4-(methylamino)piperidin-1-yl]acetamide |
| 455 | 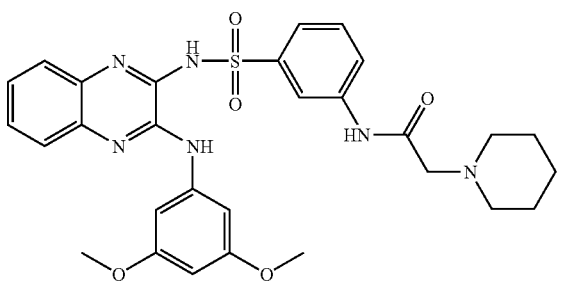 | N-(3-{[(3-{[3,5-bis(methoxy)phenyl]amino}quinoxalin-2-yl)amino]sulfonyl}phenyl)-2-piperidin-1-ylacetamide |

TABLE 1-continued

| Cpd. No. | Structure | Name |
|---|---|---|
| 456 | 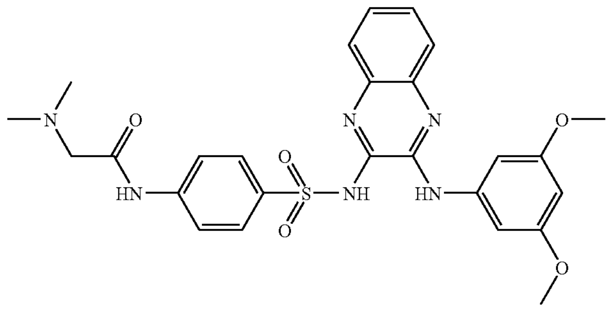 | N-(4-{[(3-{[3,5-bis(methoxy)phenyl]amino}quinoxalin-2-yl)amino]sulfonyl}phenyl)-N-2-,N-2-dimethylglycinamide |
| 457 | Abs | N-(3-{[(3-{[3,5-bis(methoxy)phenyl]amino}quinoxalin-2-yl)amino]sulfonyl}phenyl)-1-methyl-L-prolinamide |
| 458 | 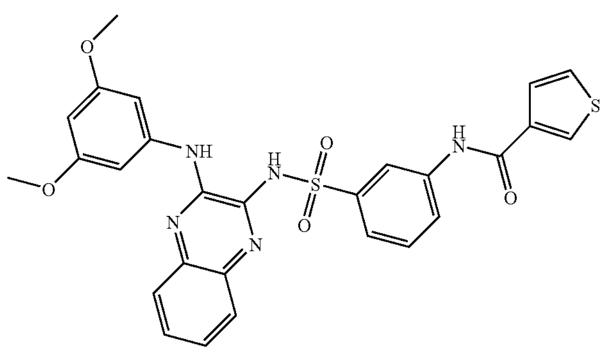 | N-(3-{[(3-{[3,5-bis(methoxy)phenyl]amino}quinoxalin-2-yl)amino]sulfonyl}thiophene-3-carboxamide |
| 459 | 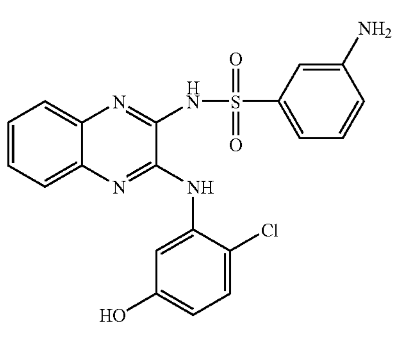 | 3-amino-N-{3-[(2-chloro-5-hydroxyphenyl)amino]quinoxalin-2-yl}benzenesulfonamide |

TABLE 1-continued

| Cpd. No. | Structure | Name |
|---|---|---|
| 460 | 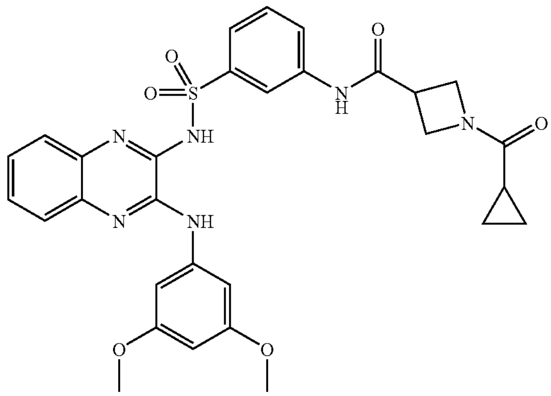 | N-(3-{[(3-{[3,5-bis(methoxy)phenyl]amino}quinoxalin-2-yl)amino]sulfonyl}phenyl)-1-(cyclopropylcarbonyl)azetidine-3-carboxamide |
| 461 | 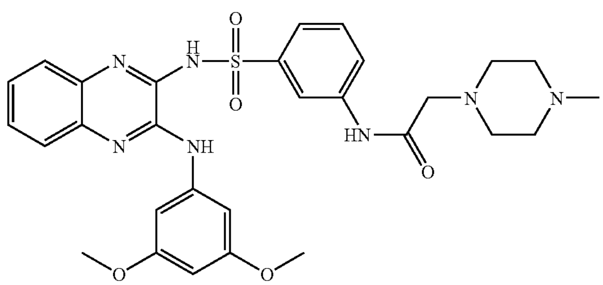 | N-(3-{[(3-{[3,5-bis(methoxy)phenyl]amino}quinoxalin-2-yl)amino]sulfonyl}phenyl)-2-(4-methylpiperazin-1-yl)acetamide |
| 462 | 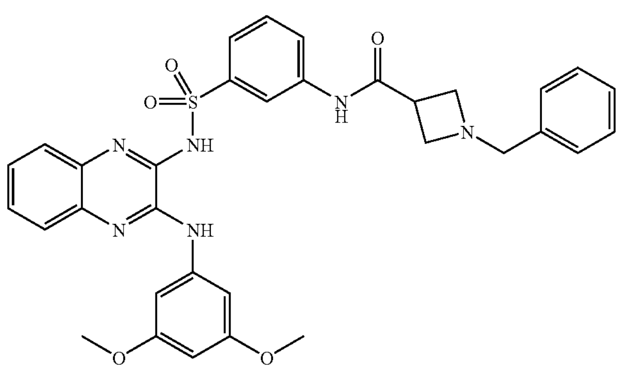 | N-(3-{[(3-{[3,5-bis(methoxy)phenyl]amino}quinoxalin-2-yl)amino]sulfonyl}phenyl)-1-(phenylmethyl)azetidine-3-carboxamide |
| 463 | 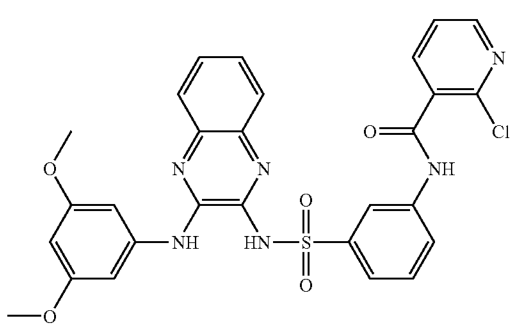 | N-(3-{[(3-{[3,5-bis(methoxy)phenyl]amino}quinoxalin-2-yl)amino]sulfonyl}phenyl)-2-chloropyridine-3-carboxamide |

TABLE 1-continued

| Cpd. No. | Structure | Name |
|---|---|---|
| 464 | 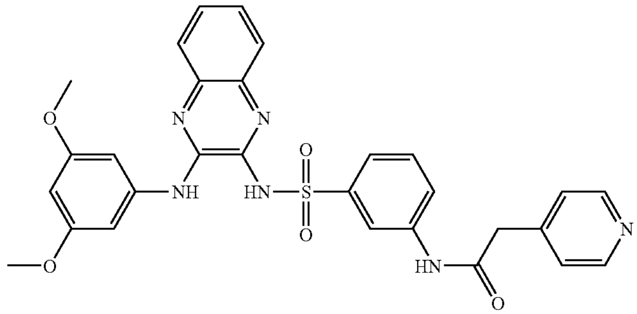 | N-(3-{[(3-{[3,5-bis(methoxy)phenyl]amino}quinoxalin-2-yl)amino]sulfonyl}phenyl)-2-pyridin-4-ylacetamide |
| 465 | 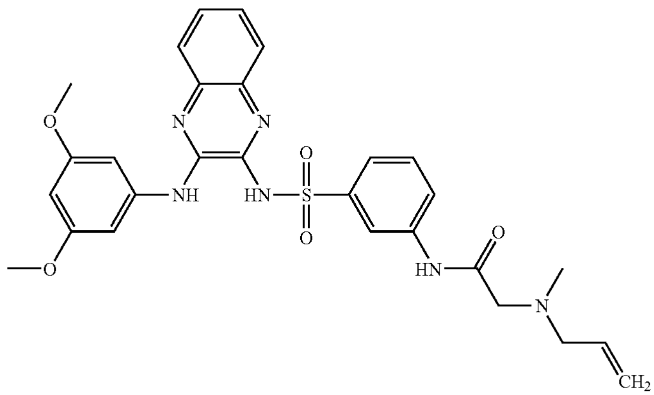 | N-(3-{[(3-{[3,5-bis(methoxy)phenyl]amino}quinoxalin-2-yl)amino]sulfonyl}phenyl)-N-2-methyl-N-2-prop-2-en-1-ylglycinamide |
| 466 | 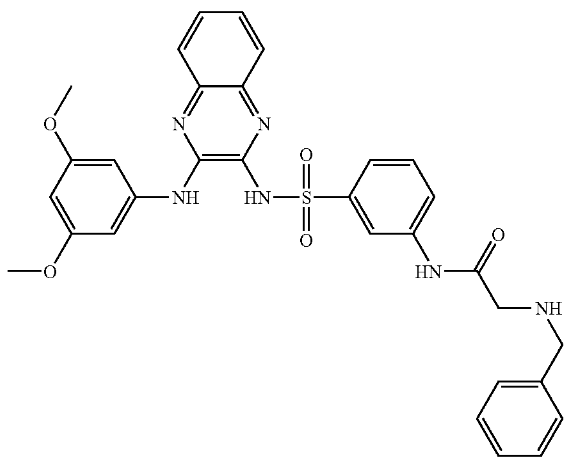 | N-(3-{[(3-{[3,5-bis(methoxy)phenyl]amino}quinoxalin-2-yl)amino]sulfonyl}phenyl)-N-2-(phenylmethyl)glycinamide |
| 467 | 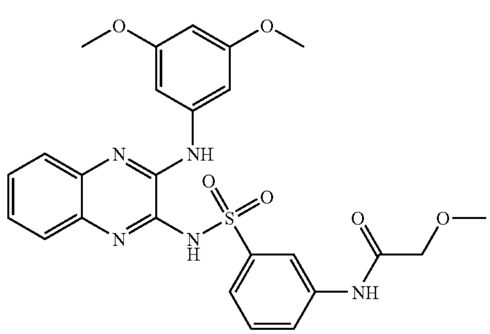 | N-(3-{[(3-{[3,5-bis(methoxy)phenyl]amino}quinoxalin-2-yl)amino]sulfonyl}phenyl)-2-(methoxy)acetamide |

TABLE 1-continued

| Cpd. No. | Structure | Name |
|---|---|---|
| 468 | 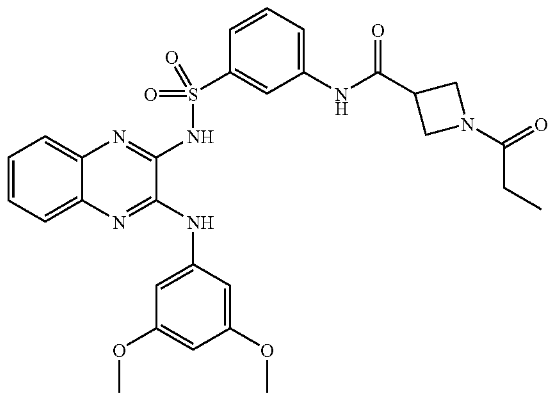 | N-(3-{[(3-{[3,5-bis(methoxy)phenyl]amino}quinoxalin-2-yl)amino]sulfonyl}phenyl)-1-propanoylazetidine-3-carboxamide |
| 469 | 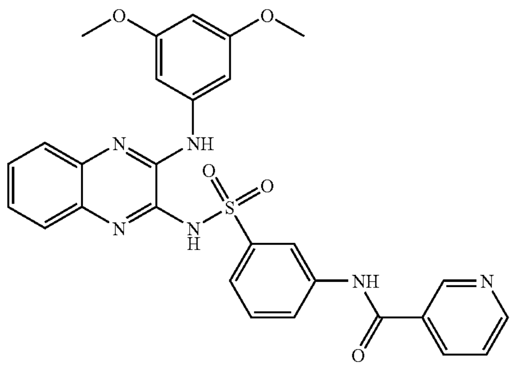 | N-(3-{[(3-{[3,5-bis(methoxy)phenyl]amino}quinoxalin-2-yl)amino]sulfonyl}phenyl)pyridine-3-carboxamide |
| 470 | 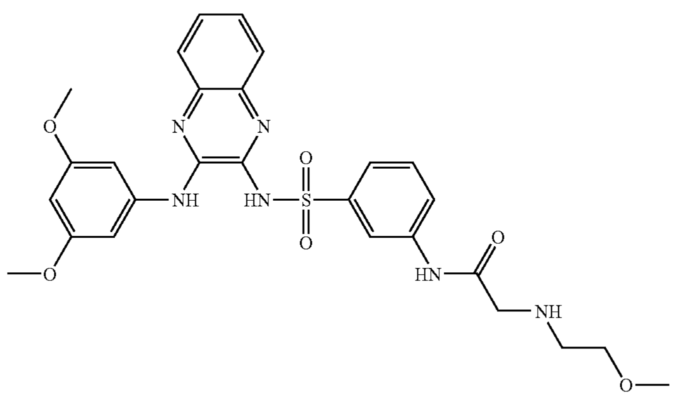 | N-(3-{[(3-{[3,5-bis(methoxy)phenyl]amino}quinoxalin-2-yl)amino]sulfonyl}phenyl)-N-2-[2-(methoxy)ethyl]glycinamide |
| 471 | 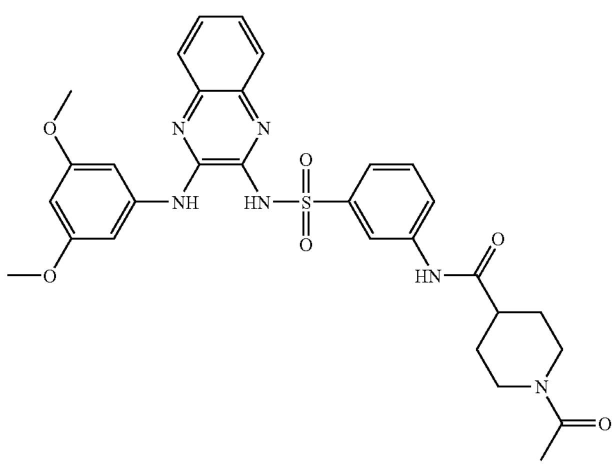 | 1-acetyl-N-(3-{[(3-{[3,5-bis(methoxy)phenyl]amino}quinoxalin-2-yl)amino]sulfonyl}phenyl)piperidine-4-carboxamide |

TABLE 1-continued

| Cpd. No. | Structure | Name |
|---|---|---|
| 472 | 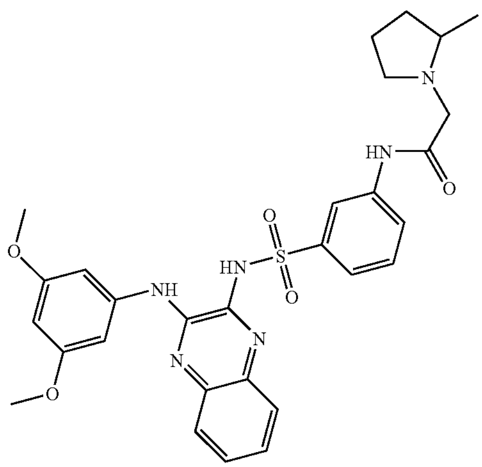 | N-(3-{[(3-{[3,5-bis(methoxy)phenyl]amino}quinoxalin-2-yl)amino]sulfonyl}phenyl)-2-(2-methylpyrrolidin-1-yl)acetamide |
| 473 | 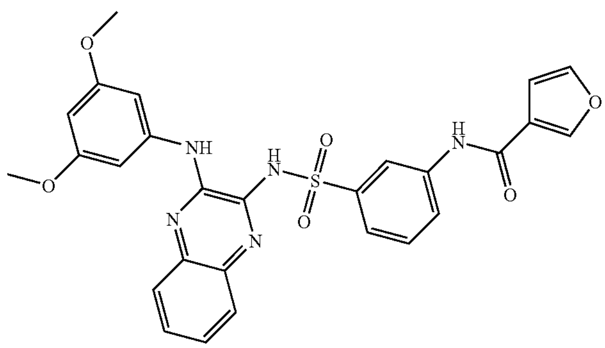 | N-(3-{[(3-{[3,5-bis(methoxy)phenyl]amino}quinoxalin-2-yl)amino]sulfonyl}phenyl)furan-3-carboxamide |
| 474 | 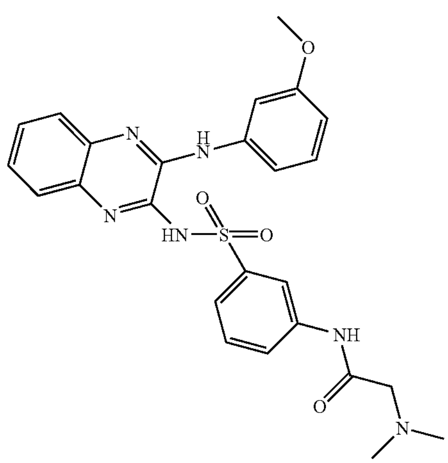 | N-2-,N-2-dimethyl-N-(3-{[(3-{[3-(methoxy)phenyl]amino}quinoxalin-2-yl)amino]sulfonyl}phenyl)glycinamide |
| 475 | 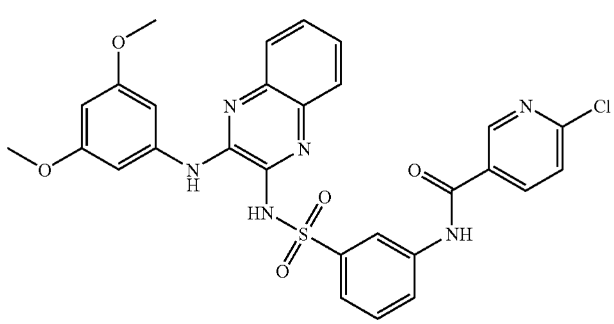 | N-(3-{[(3-{[3,5-bis(methoxy)phenyl]amino}quinoxalin-2-yl)amino]sulfonyl}phenyl)-6-chloropyridine-3-carboxamide |

TABLE 1-continued

| Cpd. No. | Structure | Name |
|---|---|---|
| 476 | 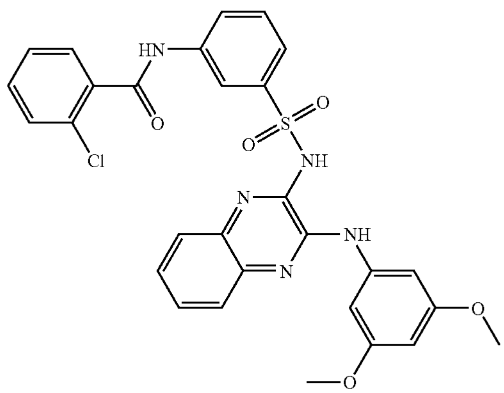 | N-(3-{[(3-{[3,5-bis(methoxy)phenyl]amino}quinoxalin-2-yl)amino]sulfonyl}phenyl)-2-chlorobenzamide |
| 477 | 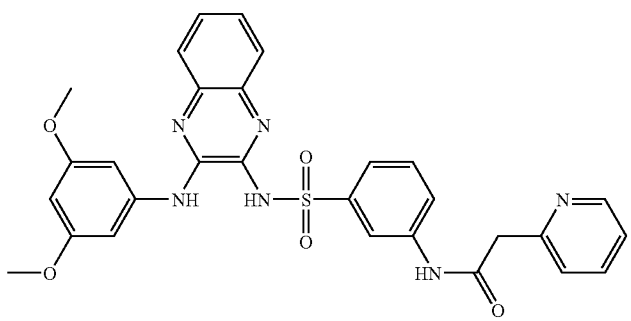 | N-(3-{[(3--{[3,5-bis(methoxy)phenyl]amino}quinoxalin-2-yl)amino]sulfonyl}phenyl)-2-pyridin-2-ylacetamide |
| 478 | 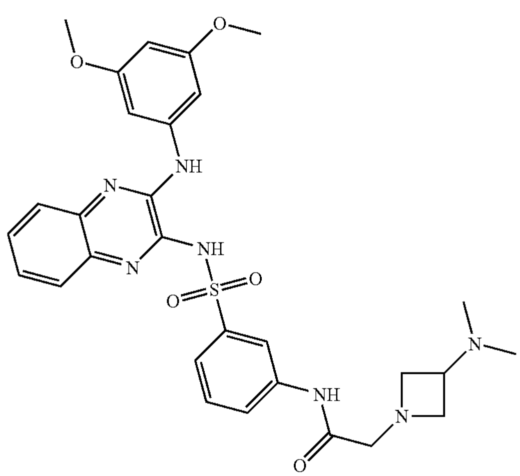 | N-(3-{[(3-{[3,5-bis(methoxy)phenyl]amino}quinoxalin-2-yl)amino]sulfonyl}phenyl)-2-[3-(dimethylamino)azetidin-1-yl]acetamide |
| 479 | 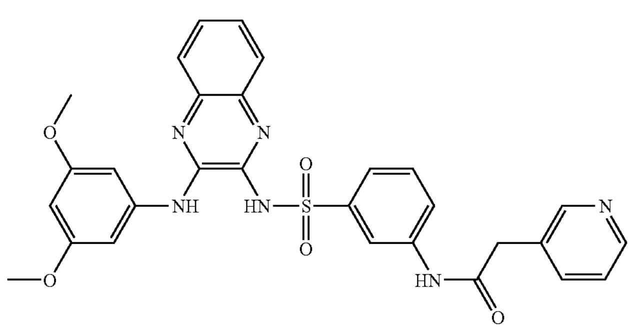 | N-(3-{[(3-{[3,5-bis(methoxy)phenyl]amino}quinoxalin-2-yl)amino]sulfonyl}phenyl)-2-pyridin-3-ylacetamide |

TABLE 1-continued

| Cpd. No. | Structure | Name |
|---|---|---|
| 480 | 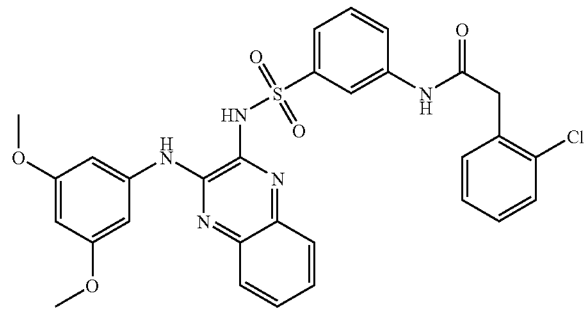 | N-(3-{[(3-{[3,5-bis(methoxy)phenyl]amino}quinoxalin-2-yl)amino]sulfonyl}phenyl)-2-(2-chlorophenyl)acetamide |
| 481 | 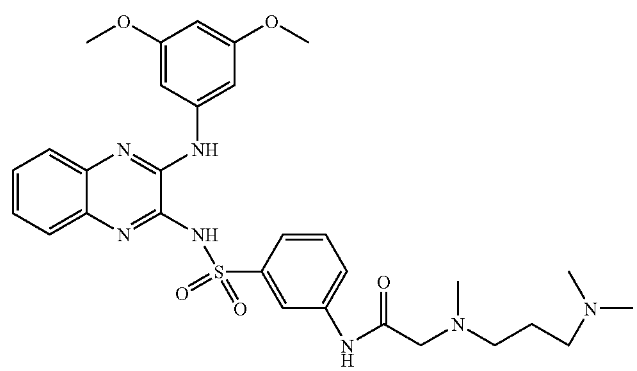 | N-(3-{[(3-{[3,5-bis(methoxy)phenyl]amino}quinoxalin-2-yl)amino]sulfonyl}phenyl)-N-2-[3-(dimethylamino)propyl]-N-2-methylglycinamide |
| 482 | 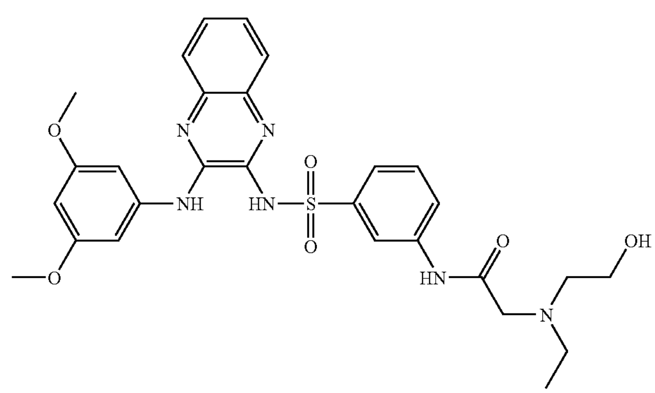 | N-(3-{[(3-{[3,5-bis(methoxy)phenyl]amino}quinoxalin-2-yl)amino]sulfonyl}phenyl)-N-2-ethyl-N-2-(2-hydroxyethyl)glycinamide |

TABLE 1-continued

| Cpd. No. | Structure | Name |
|---|---|---|
| 483 | 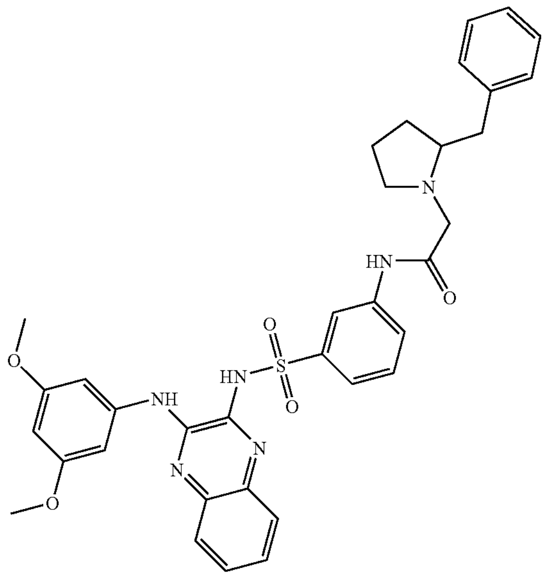 | N-(3-{[(3-{[3,5-bis(methoxy)phenyl]amino}quinoxalin-2-yl)amino]sulfonyl}phenyl)-2-[2-(phenylmethyl)pyrrolidin-1-yl]acetamide |
| 484 | 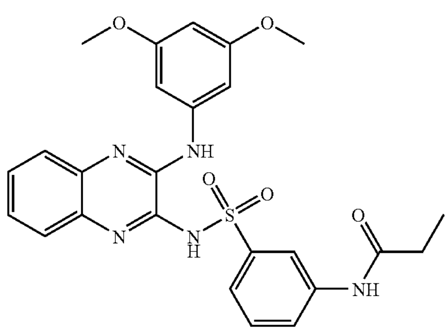 | N-(3-{[(3-{[3,5-bis(methoxy)phenyl]amino}quinoxalin-2-yl)amino]sulfonyl}phenyl)propanamide |
| 485 | 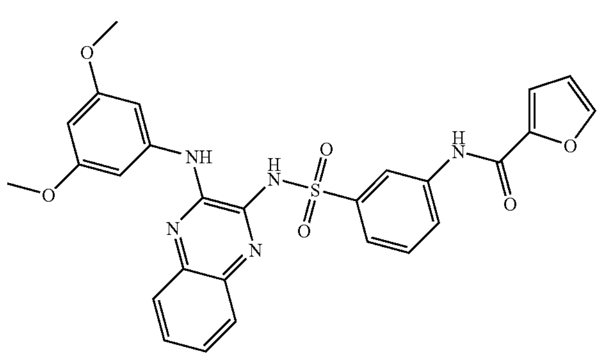 | N-(3-{[(3-{[3,5-bis(methoxy)phenyl]amino}quinoxalin-2-yl)amino]sulfonyl}phenyl)furan-2-carboxamide |

| Cpd. No. | Structure | Name |
|---|---|---|
| 486 | 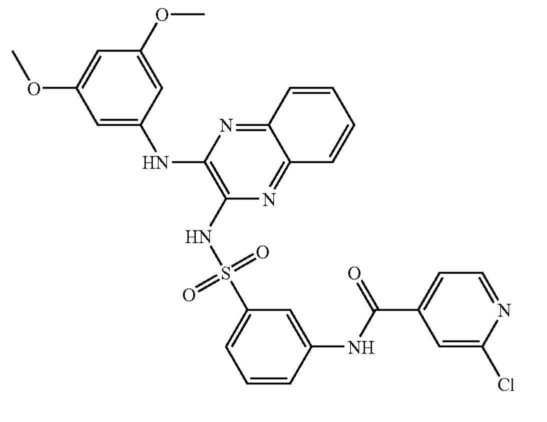 | N-(3-{[(3-{[3,5-bis(methoxy)phenyl]amino}quinoxalin-2-yl)amino]sulfonyl}phenyl)-2-chloropyridine-4-carboxamide |
| 487 | 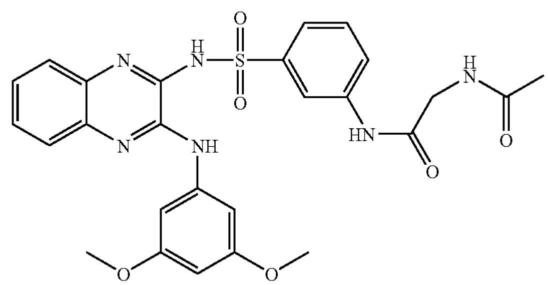 | N-2-acetyl-N-(3-{[(3-{[3,5-bis(methoxy)phenyl]amino}quinoxalin-2-yl)amino]sulfonyl}phenyl)glycinamide |
| 488 | 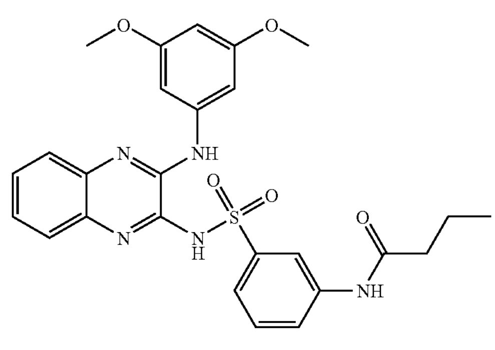 | N-(3-{[(3-{[3,5-bis(methoxy)phenyl]amino}quinoxalin-2-yl)amino]sulfonyl}phenyl)butanamide |
| 489 | 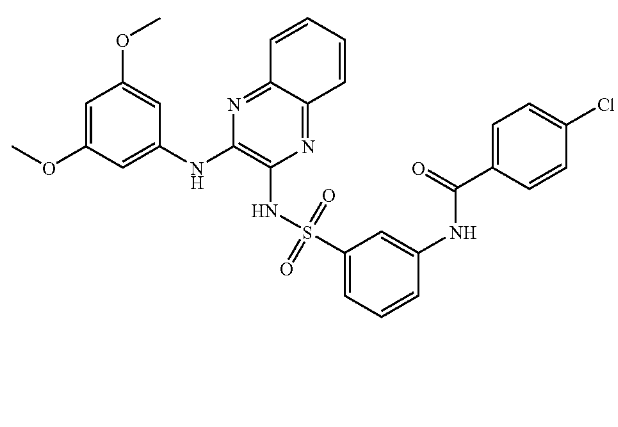 | N-(3-{[(3-{[3,5-bis(methoxy)phenyl]amino}quinoxalin-2-yl)amino]sulfonyl}phenyl)-4-chlorobenzamide |

TABLE 1-continued

| Cpd. No. | Structure | Name |
| --- | --- | --- |
| 490 | 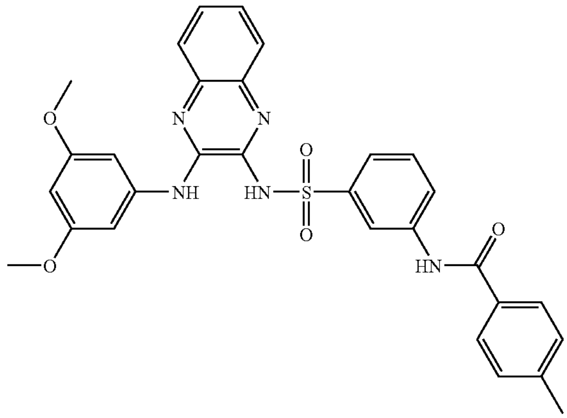 | N-(3-{[(3-{[3,5-bis(methoxy)phenyl]amino}quinoxalin-2-yl)amino]sulfonyl}phenyl)-4-methylbenzamide |
| 491 | 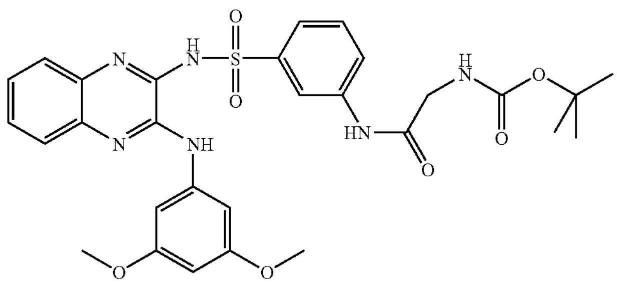 | 1,1-dimethylethyl {2-[(3-{[(3-{[3,5-bis(methoxy)phenyl]amino}quinoxalin-2-yl)amino]sulfonyl}phenyl)amino]-2-oxoethyl}carbamate |
| 492 | 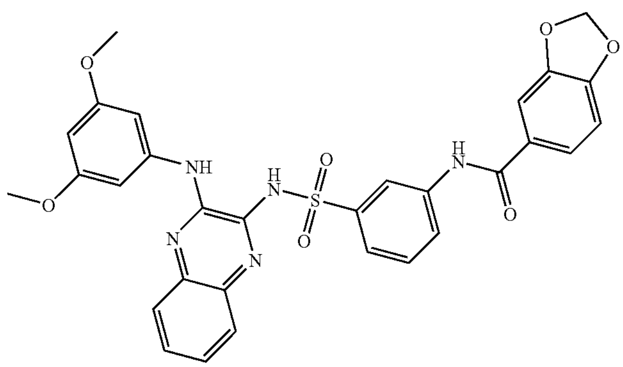 | N-(3-{[(3-{[3,5-bis(methoxy)phenyl]amino}quinoxalin-2-yl)amino]sulfonyl}phenyl)-1,3-benzodioxole-5-carboxamide |
| 493 | 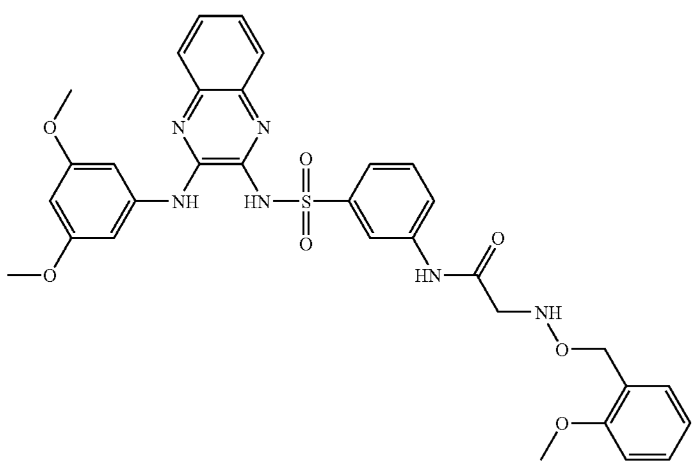 | N-(3-{[(3-{[3,5-bis(methoxy)phenyl]amino}quinoxalin-2-yl)amino]sulfonyl}phenyl)-N-2-({[2-(methoxy)phenyl]methyl}oxy)glycinamide |

TABLE 1-continued

| Cpd. No. | Structure | Name |
|---|---|---|
| 494 | 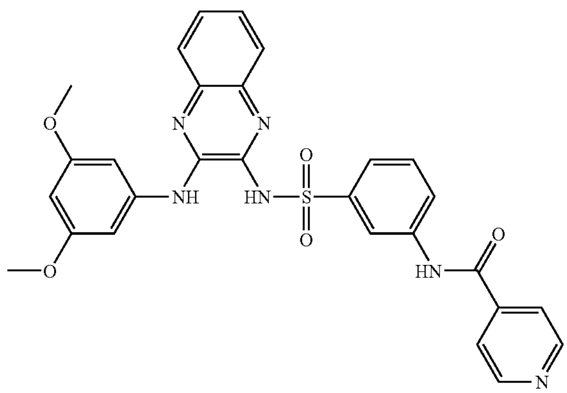 | N-(3-{[(3-{[3,5-bis(methoxy)phenyl]amino}quinoxalin-2-yl)amino]sulfonyl}phenyl)pyridine-4-carboxamide |
| 495 | 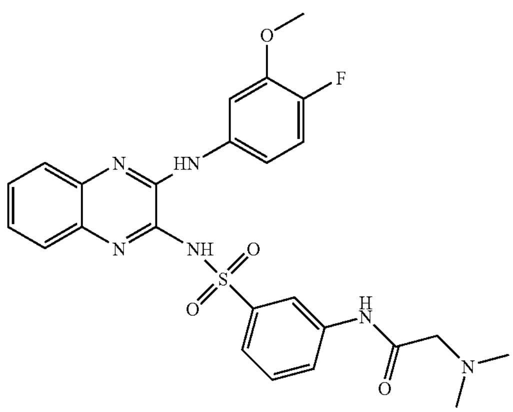 | N-(3-{[(3-{[4-fluoro-3-(methoxy)phenyl]amino}quinoxalin-2-yl)amino]sulfonyl}phenyl)-N-2-,N-2-dimethylglycinamide |
| 496 | 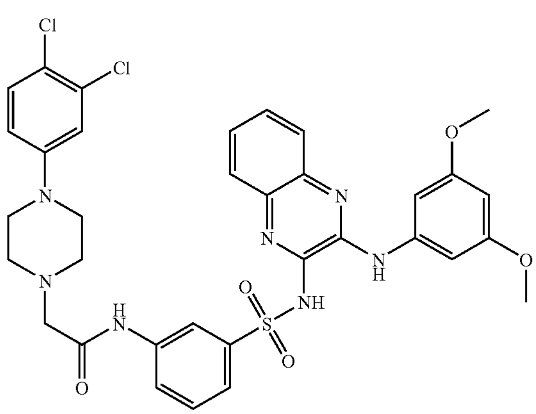 | N-(3-{[(3-{[3,5-bis(methoxy)phenyl]amino}quinoxalin-2-yl)amino]sulfonyl}phenyl)-2-[4-(3,4-dichlorophenyl)piperazin-1-yl]acetamide |

TABLE 1-continued

| Cpd. No. | Structure | Name |
|---|---|---|
| 497 | 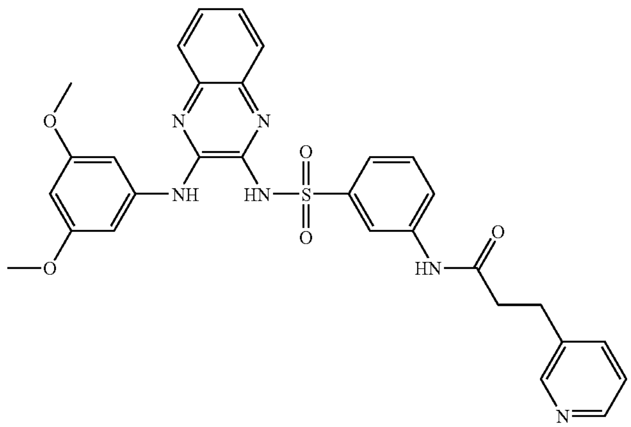 | N-(3-{[(3-{[3,5-bis(methoxy)phenyl]amino}quinoxalin-2-yl)amino]sulfonyl}phenyl)-3-pyridin-3-ylpropanamide |
| 498 | 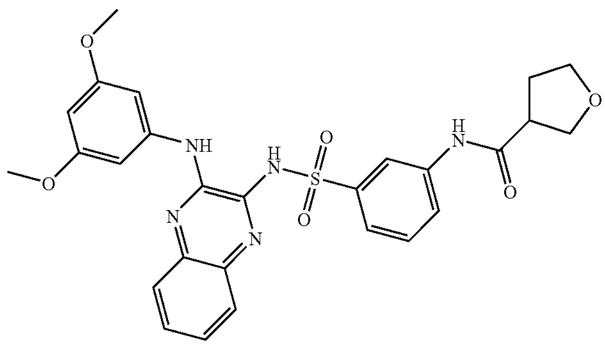 | N-(3-{[(3-{[3,5-bis(methoxy)phenyl]amino}quinoxalin-2-yl)amino]sulfonyl}phenyl)tetrahydrofuran-3-carboxamide |
| 499 | 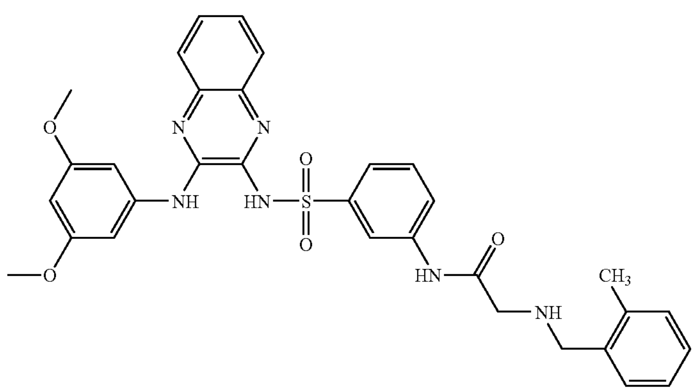 | N-(3-{[(3-{[3,5-bis(methoxy)phenyl]amino}quinoxalin-2-yl)amino]sulfonyl}phenyl)-N-2-[(2-methylphenyl)methyl]glycinamide |
| 500 | 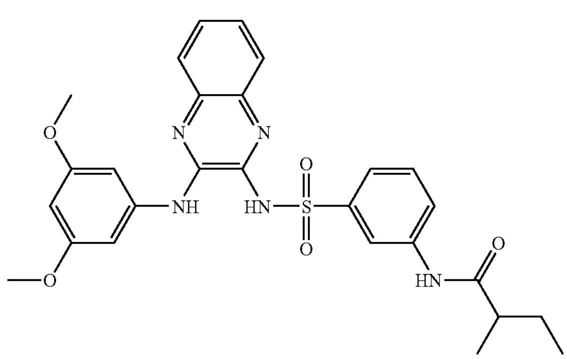 | N-(3-{[(3-{[3,5-bis(methoxy)phenyl]amino}quinoxalin-2-yl)amino]sulfonyl}phenyl)-2-methylbutanamide |

TABLE 1-continued

| Cpd. No. | Structure | Name |
|---|---|---|
| 501 | 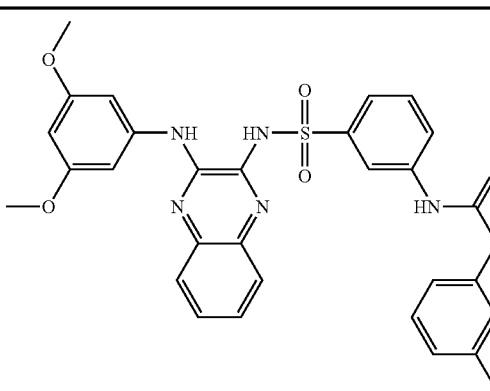 | N-(3-{[(3-{[3,5-bis(methoxy)phenyl]amino}quinoxalin-2-yl)amino]sulfonyl}phenyl)-2-(3-fluorophenyl)acetamide |
| 502 | 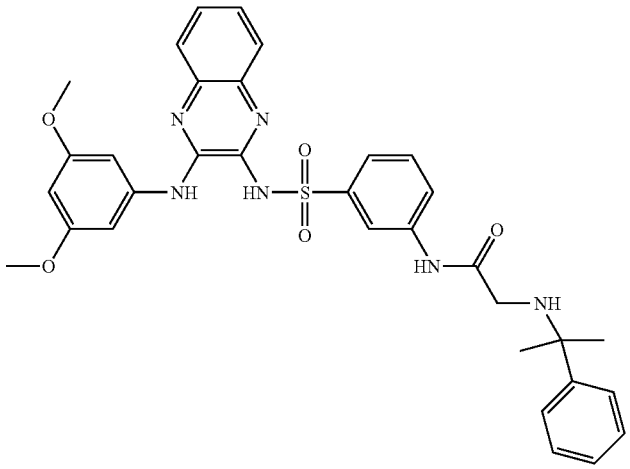 | N-(3-{[(3-{[3,5-bis(methoxy)phenyl]amino}quinoxalin-2-yl)amino]sulfonyl}phenyl)-N-2-(1-methyl-1-phenylethyl)glycinamide |
| 503 | 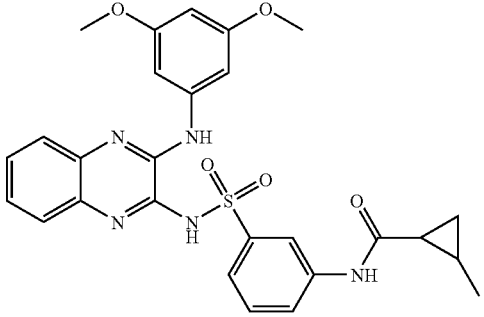 | N-(3-{[(3-{[3,5-bis(methoxy)phenyl]amino}quinoxalin-2-yl)amino]sulfonyl}phenyl)-2-methylcyclopropanecarboxamide |
| 504 | 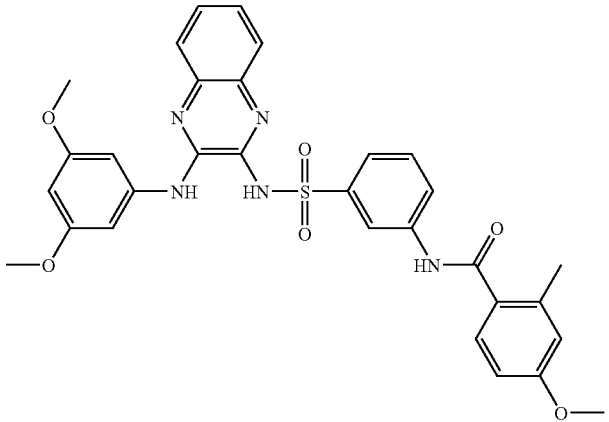 | N-(3-{[(3-{[3,5-bis(methoxy)phenyl]amino}quinoxalin-2-yl)amino]sulfonyl}phenyl)-2-methyl-4-(methoxy)benzamide |

TABLE 1-continued

| Cpd. No. | Structure | Name |
|---|---|---|
| 505 | 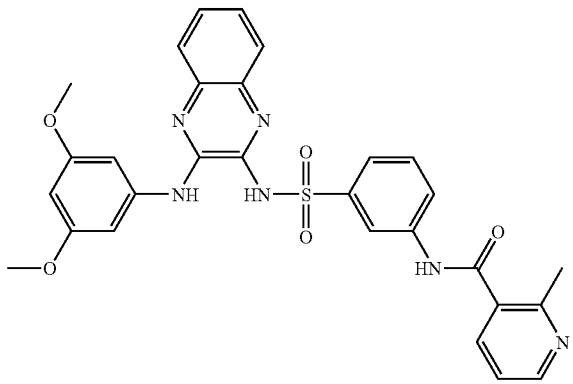 | N-(3-{[(3-{[3,5-bis(methoxy)phenyl]amino}quinoxalin-2-yl)amino]sulfonyl}phenyl)-2-methylpyridine-3-carboxamide |
| 506 | 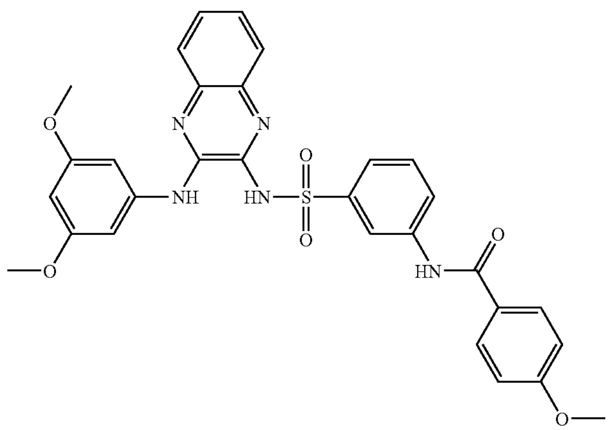 | N-(3-{[(3-{[3,5-bis(methoxy)phenyl]amino}quinoxalin-2-yl)amino]sulfonyl}phenyl)-4-(methoxy)benzamide |
| 507 | 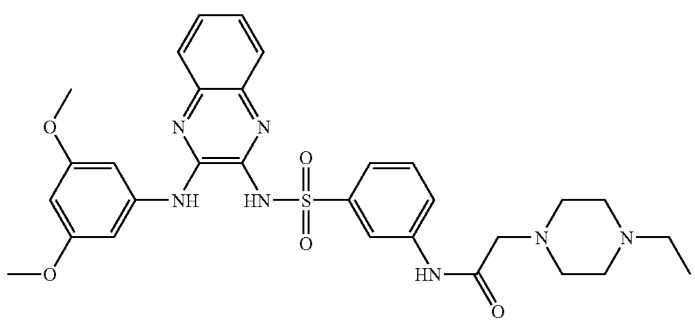 | N-(3-{[(3-{[3,5-bis(methoxy)phenyl]amino}quinoxalin-2-yl)amino]sulfonyl}phenyl)-2-(4-ethylpiperazin-1-yl)acetamide |
| 508 | 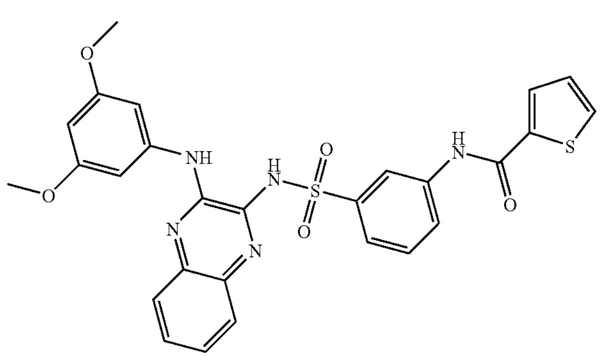 | N-(3-{[(3-{[3,5-bis(methoxy)phenyl]amino}quinoxalin-2-yl)amino]sulfonyl}phenyl)thiophene-2-carboxamide |

| Cpd. No. | Structure | Name |
|---|---|---|
| 509 | 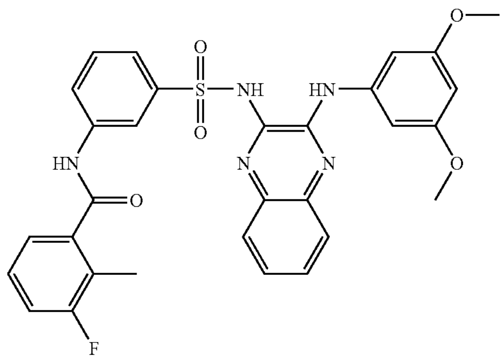 | N-(3-{[(3-{[3,5-bis(methoxy)phenyl]amino}quinoxalin-2-yl)amino]sulfonyl}phenyl)-3-fluoro-2-methylbenzamide |
| 510 | 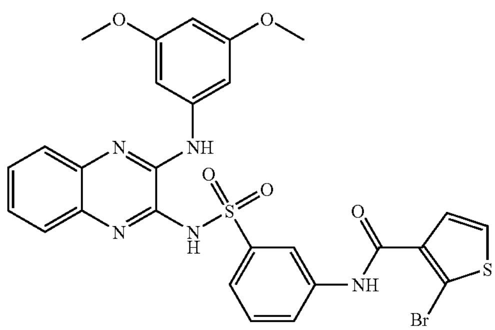 | N-(3-{[(3-{[3,5-bis(methoxy)phenyl]amino}quinoxalin-2-yl)amino]sulfonyl}phenyl)-2-bromothiophene-3-carboxamide |
| 511 | 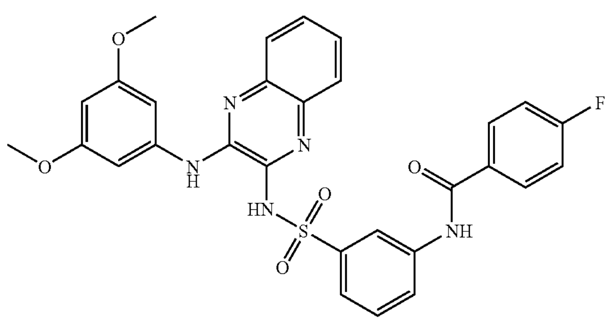 | N-(3-{[(3-{[3,5-bis(methoxy)phenyl]amino}quinoxalin-2-yl)amino]sulfonyl}phenyl)-4-fluorobenzamide |
| 512 | 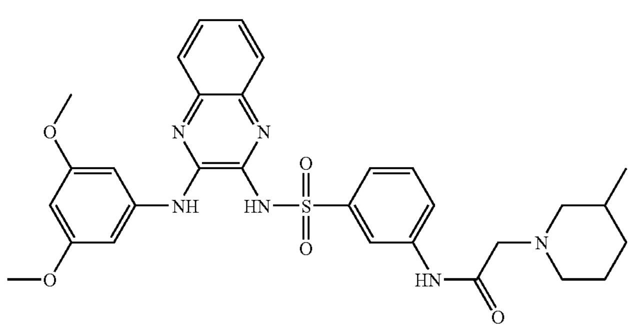 | N-(3-{[(3-{[3,5-bis(methoxy)phenyl]amino}quinoxalin-2-yl)amino]sulfonyl}phenyl)-2-(3-methylpiperidin-1-yl)acetamide |

TABLE 1-continued

| Cpd. No. | Structure | Name |
|---|---|---|
| 513 | 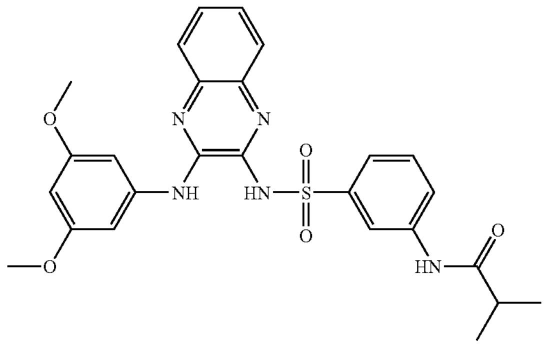 | N-(3-{[(3-{[3,5-bis(methoxy)phenyl]amino}quinoxalin-2-yl)amino]sulfonyl}phenyl)-2-methylpropanamide |
| 514 | 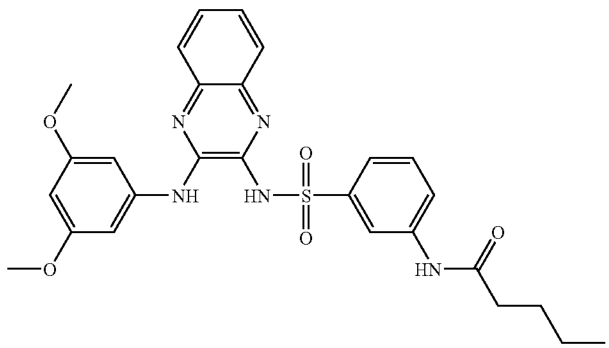 | N-(3-{[(3-{[3,5-bis(methoxy)phenyl]amino}quinoxalin-2-yl)amino]sulfonyl}phenyl)pentanamide |
| 515 | 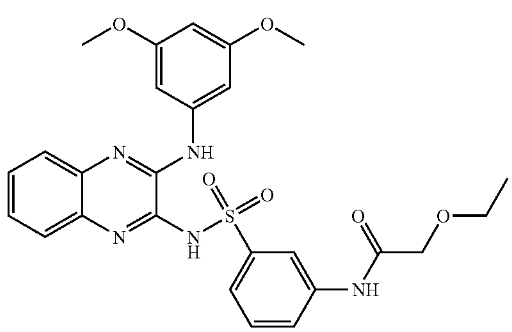 | N-(3-{[(3-{[3,5-bis(methoxy)phenyl]amino}quinoxalin-2-yl)amino]sulfonyl}phenyl)-2-(ethyloxy)acetamide |
| 516 | 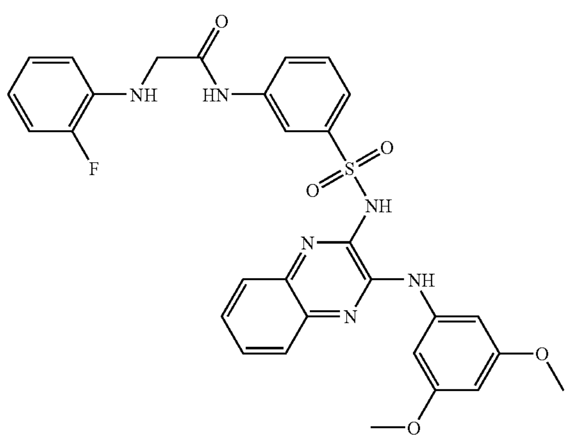 | N-(3-{[(3-{[3,5-bis(methoxy)phenyl]amino}quinoxalin-2-yl)amino]sulfonyl}phenyl)-N-2-(2-fluorophenyl)glycinamide |

TABLE 1-continued

| Cpd. No. | Structure | Name |
|---|---|---|
| 517 | 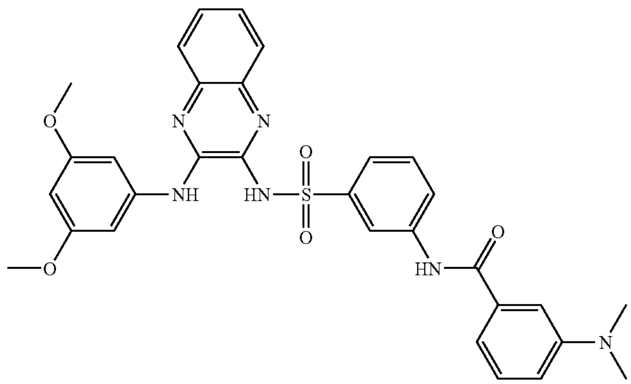 | N-(3-{[(3-{[3,5-bis(methoxy)phenyl]amino}quinoxalin-2-yl)amino]sulfonyl}phenyl)-3-(dimethylamino)benzamide |
| 518 | 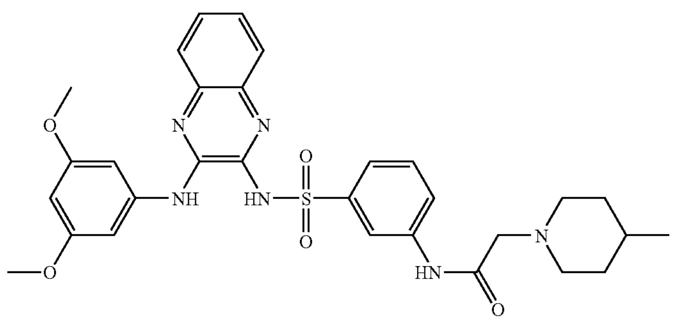 | N-(3-{[(3-{[3,5-bis(methoxy)phenyl]amino}quinoxalin-2-yl)amino]sulfonyl}phenyl)-2-(4-methylpiperidin-1-yl)acetamide |
| 519 | 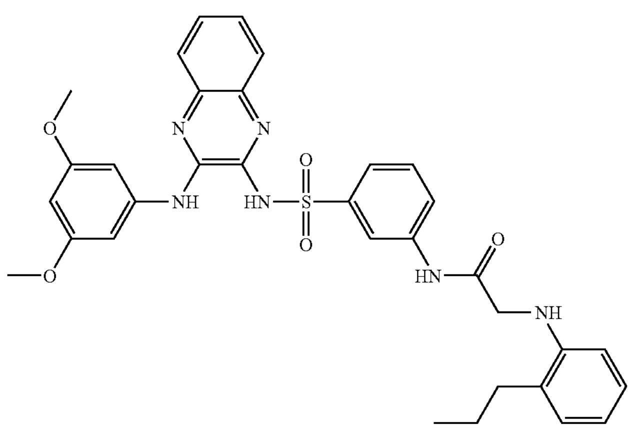 | N-(3-{[(3-{[3,5-bis(methoxy)phenyl]amino}quinoxalin-2-yl)amino]sulfonyl}phenyl)-N-2-(2-propylphenyl)glycinamide |
| 520 | 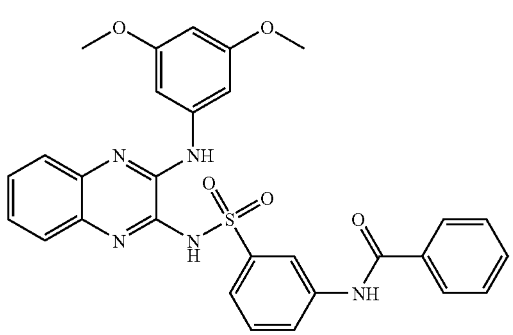 | N-(3-{[(3-{[3,5-bis(methoxy)phenyl]amino}quinoxalin-2-yl)amino]sulfonyl}phenyl)benzamide |

TABLE 1-continued

| Cpd. No. | Structure | Name |
| --- | --- | --- |
| 521 | 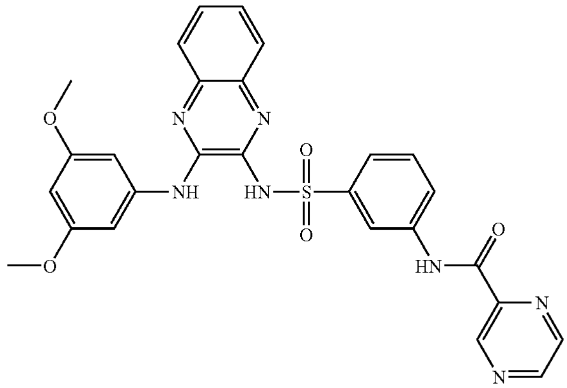 | N-(3-{[(3-{[3,5-bis(methoxy)phenyl]amino}quinoxalin-2-yl)amino]sulfonyl}phenyl)pyrazine-2-carboxamide |
| 522 | 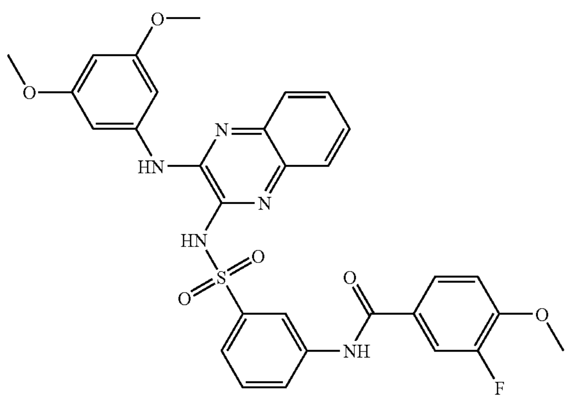 | N-(3-{[(3-{[3,5-bis(methoxy)phenyl]amino}quinoxalin-2-yl)amino]sulfonyl}phenyl)-3-fluoro-4-(methoxy)benzamide |
| 523 | 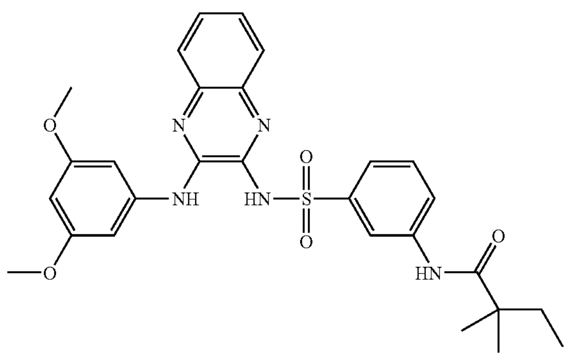 | N-(3-{[(3-{[3,5-bis(methoxy)phenyl]amino}quinoxalin-2-yl)amino]sulfonyl}phenyl)-2,2-dimethylbutanamide |
| 524 | 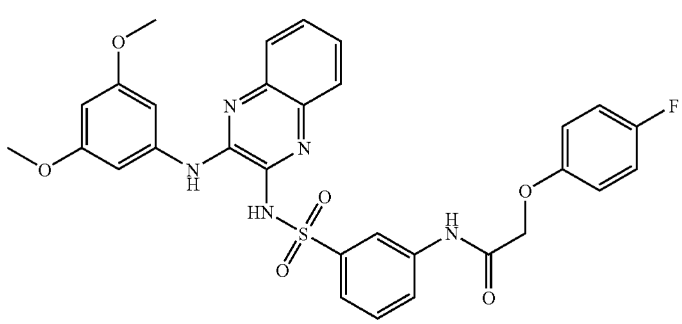 | N-(3-{[(3-{[3,5-bis(methoxy)phenyl]amino}quinoxalin-2-yl)amino]sulfonyl}phenyl)-2-[(4-fluorophenyl)oxy]acetamide |

TABLE 1-continued

| Cpd. No. | Structure | Name |
|---|---|---|
| 525 | 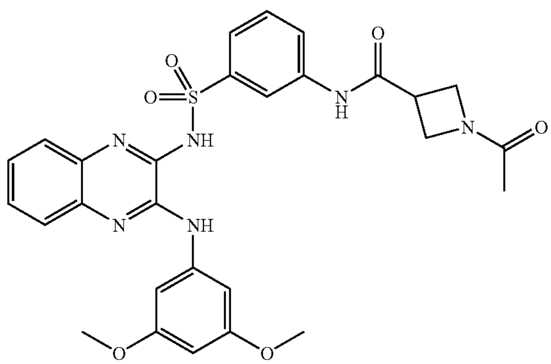 | 1-acetyl-N-(3-{[(3-{[3,5-bis(methoxy)phenyl]amino}quinoxalin-2-yl)amino]sulfonyl}phenyl)azetidine-3-carboxamide |
| 526 | 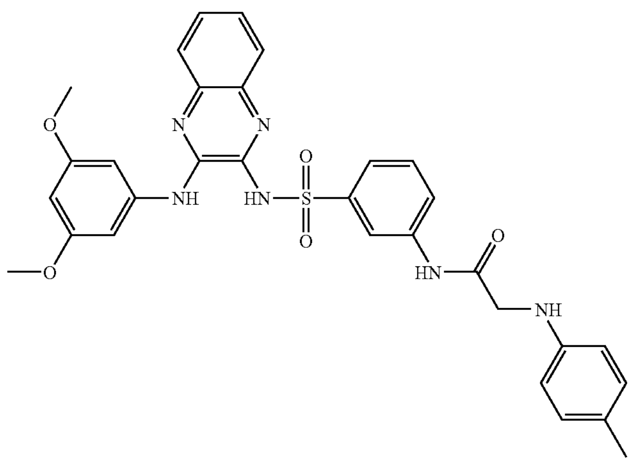 | N-(3-{[(3-{[3,5-bis(methoxy)phenyl]amino}quinoxalin-2-yl)amino]sulfonyl}phenyl)-N-2-(4-methylphenyl)glycinamide |
| 527 | 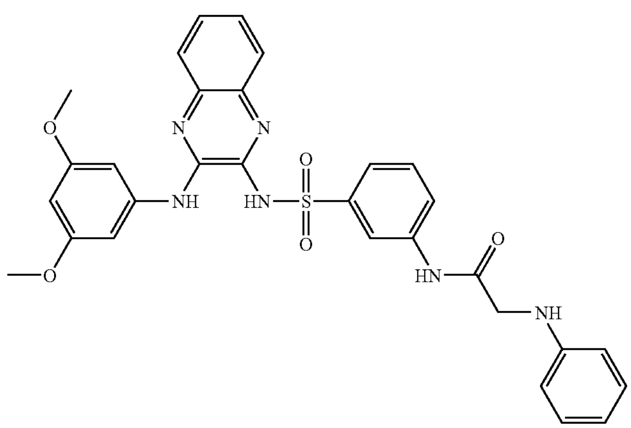 | N-(3-{[(3-{[3,5-bis(methoxy)phenyl]amino}quinoxalin-2-yl)amino]sulfonyl}phenyl)-N-2-phenylglycinamide |
| 528 | 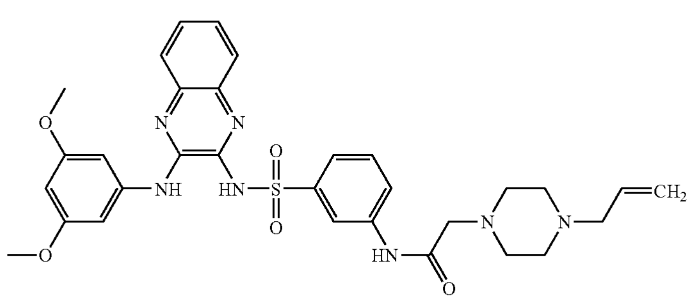 | N-(3-{[(3-{[3,5-bis(methoxy)phenyl]amino}quinoxalin-2-yl)amino]sulfonyl}phenyl)-2-(4-prop-2-en-1-ylpiperazin-1-yl)acetamide |

TABLE 1-continued

| Cpd. No. | Structure | Name |
|---|---|---|
| 529 | 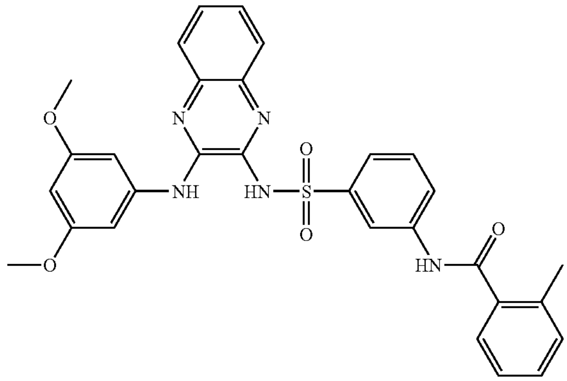 | N-(3-{[(3-{[3,5-bis(methoxy)phenyl]amino}quinoxalin-2-yl)amino]sulfonyl}phenyl)-2-methylbenzamide |
| 530 | 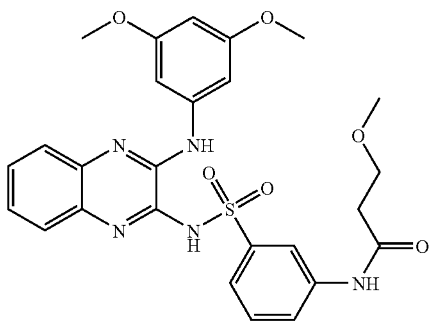 | N-(3-{[(3-{[3,5-bis(methoxy)phenyl]amino}quinoxalin-2-yl)amino]sulfonyl}phenyl)-3-(methoxy)propanamide |
| 531 | 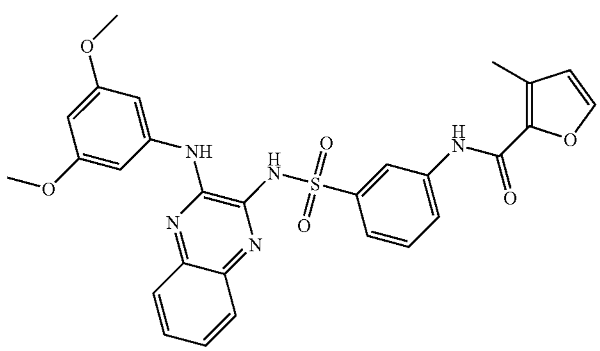 | N-(3-{[(3-{[3,5-bis(methoxy)phenyl]amino}quinoxalin-2-yl)amino]sulfonyl}phenyl)-3-methylfuran-2-carboxamide |
| 532 | 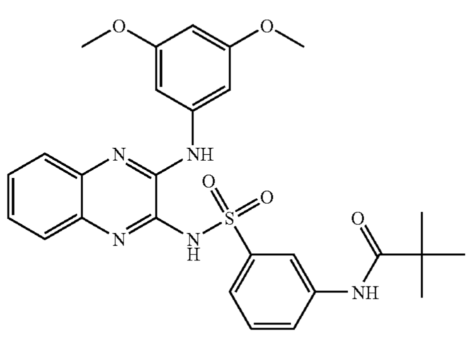 | N-(3-{[(3-{[3,5-bis(methoxy)phenyl]amino}quioxalin-2-yl)amino]sulfonyl}phenyl)-2,2-dimethylpropanamide |

TABLE 1-continued

| Cpd. No. | Structure | Name |
|---|---|---|
| 533 | 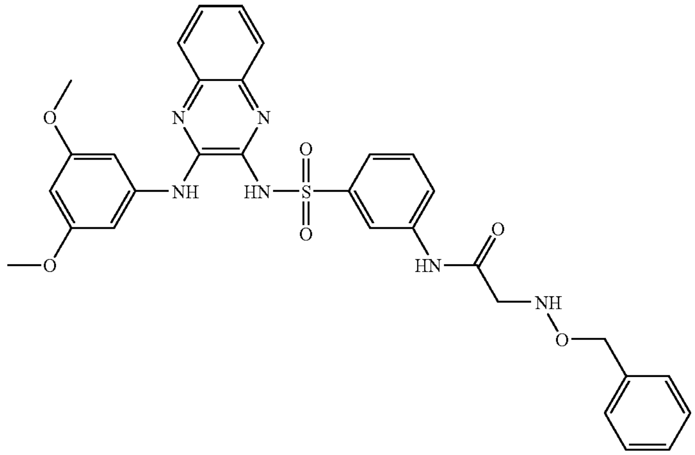 | N-(3-{[(3-{[3,5-bis(methoxy)phenyl]amino}quinoxalin-2-yl)amino]sulfonyl}phenyl)-N-2-[(phenylmethyl)oxy]glycinamide |
| 534 | 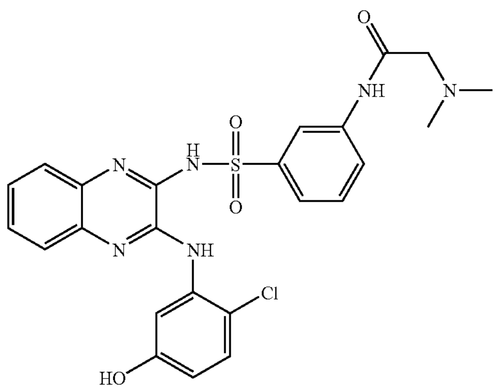 | N-{3-[({3-[(2-chloro-5-hydroxyphenyl)amino]quinoxalin-2-yl}amino)sulfonyl]phenyl}-N-2-,N-2-dimethylglycinamide |
| 535 | 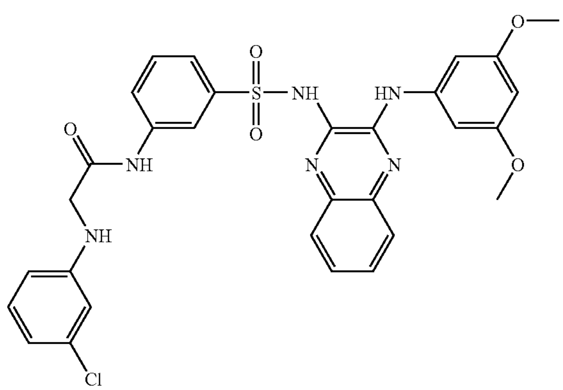 | N-(3-{[(3-{[3,5-bis(methoxy)phenyl]amino}quinoxalin-2-yl)amino]sulfonyl}phenyl)-N-2-(3-chlorophenyl)glycinamide |
| 536 | 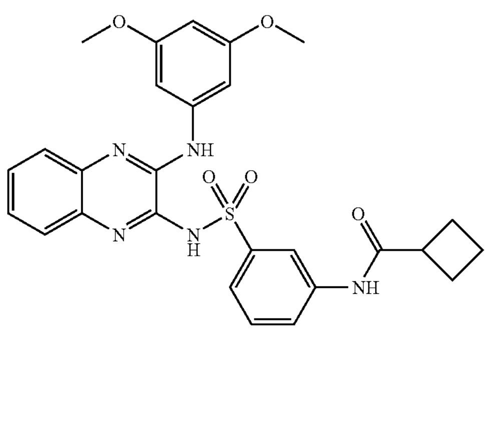 | N-(3-{[(3-{[3,5-bis(methoxy)phenyl]amino}quinoxalin-2-yl)amino]sulfonyl}phenyl)cyclobutanaecarboxamide |

TABLE 1-continued

| Cpd. No. | Structure | Name |
| --- | --- | --- |
| 537 | 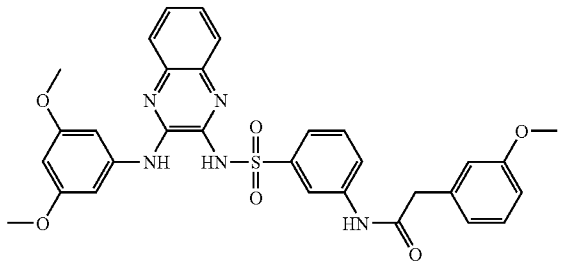 | N-(3-{[(3-{[3,5-bis(methoxy)phenyl]amino}quinoxalin-2-yl)amino]sulfonyl}phenyl)-2-[3-(methoxy)phenyl]acetamide |
| 538 | 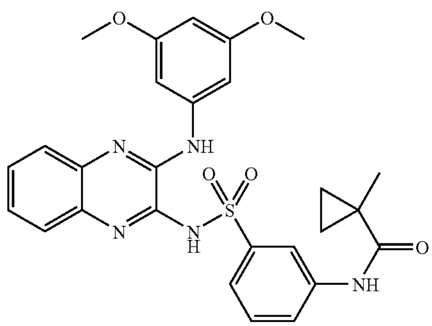 | N-(3-{[(3-{[3,5-bis(methoxy)phenyl]amino}quinoxalin-2-yl)amino]sulfonyl}phenyl)-1-methylcyclopropanecarboxamide |
| 539 | 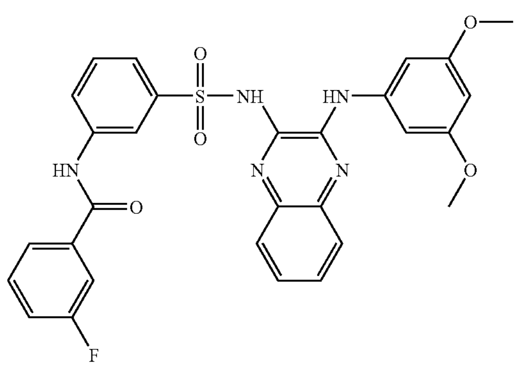 | N-(3-{[(3-{[3,5-bis(methoxy)phenyl]amino}quinoxalin-2-yl)amino]sulfonyl}phenyl)-3-fluorobenzamide |
| 540 | 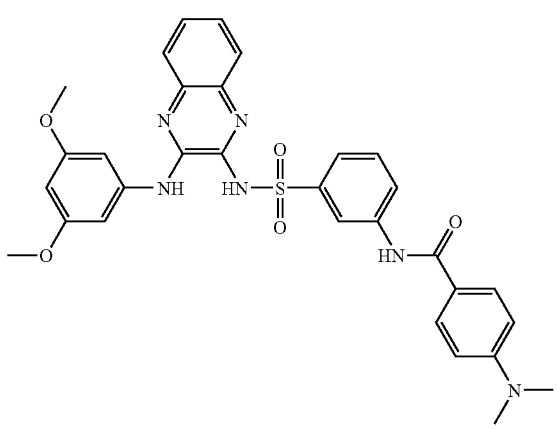 | N-(3-{[(3-{[3,5-bis(methoxy)phenyl]amino}quinoxalin-2-yl)amino]sulfonyl}phenyl)-4-(dimethylamino)benzamide |

TABLE 1-continued

| Cpd. No. | Structure | Name |
|---|---|---|
| 541 | 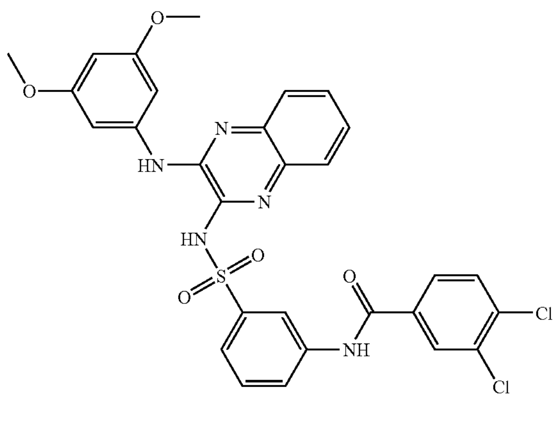 | N-(3-{[(3-{[3,5-bis(methoxy)phenyl]amino}quinoxalin-2-yl)amino]sulfonyl}phenyl)-3,4-dichlorobenzamide |
| 542 | 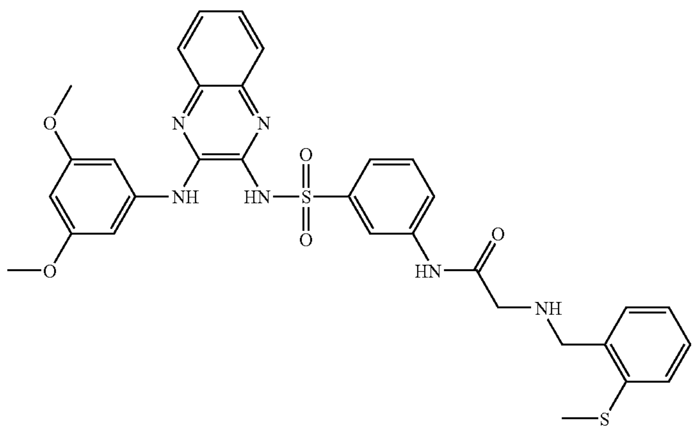 | N-(3-{[(3-{[3,5-bis(methoxy)phenyl]amino}quinoxalin-2-yl)amino]sulfonyl}phenyl)-N-2-{[2-(methylthio)phenyl]methyl}glycinamide |
| 543 | 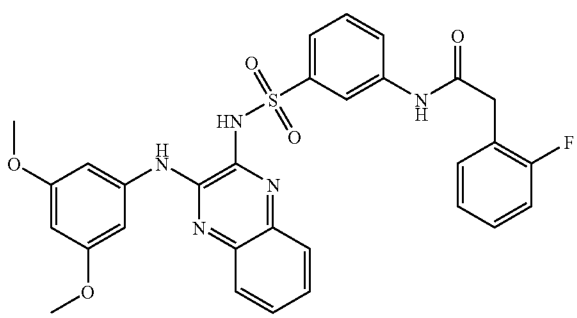 | N-(3-{[(3-{[3,5-bis(methoxy)phenyl]amino}quinoxalin-2-yl)amino]sulfonyl}phenyl)-2-(2-fluorophenyl)acetamide |
| 544 | 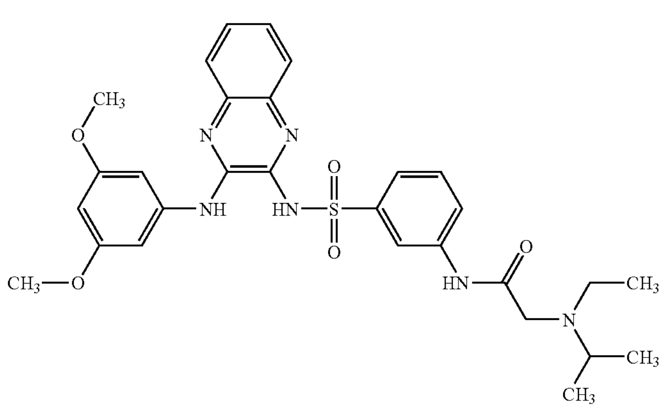 | N-(3-{[(3-{[3,5-bis(methoxy)phenyl]amino}quinoxalin-2-yl)amino]sulfonyl}phenyl)-N-2-ethyl-N-2-(1-methylethyl)glycinamide |

TABLE 1-continued

| Cpd. No. | Structure | Name |
|---|---|---|
| 545 | 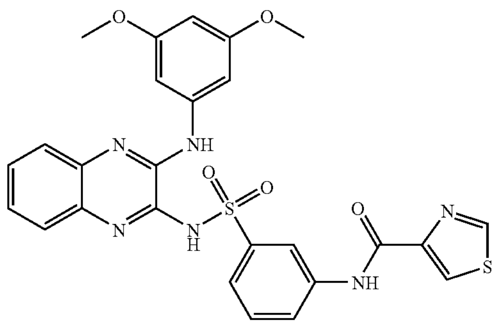 | N-(3-{[(3-{[3,5-bis(methoxy)phenyl]amino}quinoxalin-2-yl)amino]sulfonyl}phenyl)-1,3-thiazole-4-carboxamide |
| 546 | 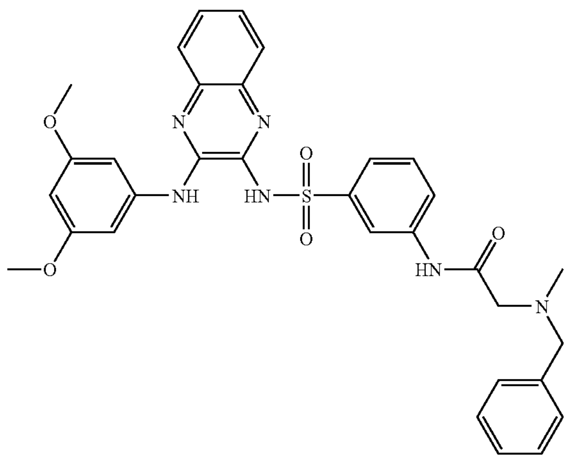 | N-(3-{[(3-{[3,5-bis(methoxy)phenyl]amino}quinoxalin-2-yl)amino]sulfonyl}phenyl)-N-2-methyl-N-2-(phenylmethyl)glycinamide |
| 547 | 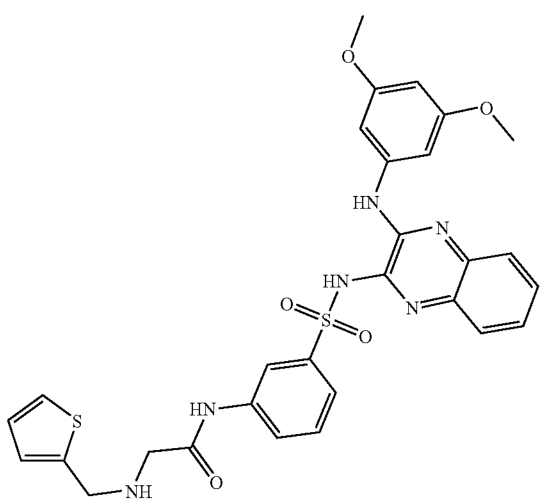 | N-(3-{[(3-{[3,5-bis(methoxy)phenyl]amino}quinoxalin-2-yl)amino]sulfonyl}phenyl)-N-2-(2-thienylmethyl)glycinamide |

TABLE 1-continued

| Cpd. No. | Structure | Name |
|---|---|---|
| 548 | 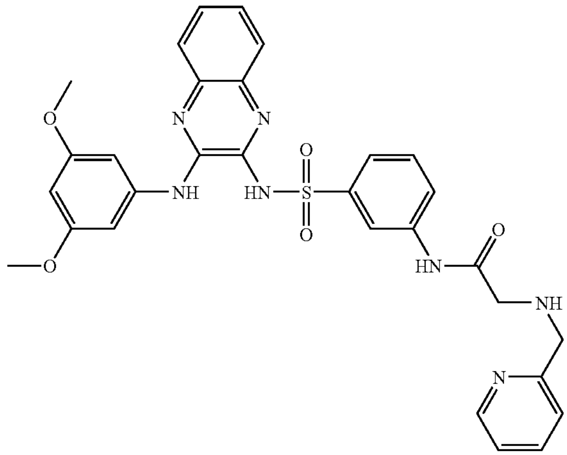 | N-(3-{[(3-{[3,5-bis(methoxy)phenyl]amino}quinoxalin-2-yl)amino]sulfonyl}phenyl)-N-2-(pyridin-2-ylmethyl)glycinamide |
| 549 | 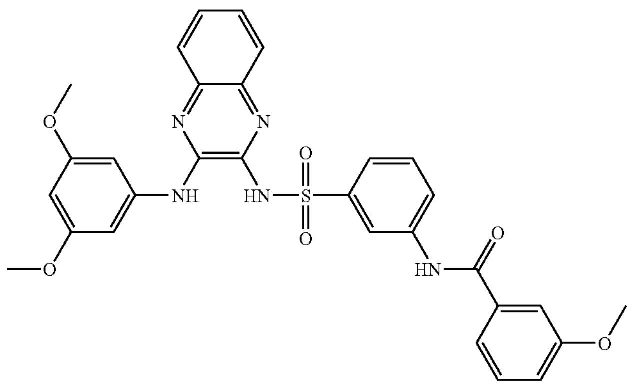 | N-(3-{[(3-{[3,5-bis(methoxy)phenyl]amino}quinoxalin-2-yl)amino]sulfonyl}phenyl)-3-(methoxy)benzamide |
| 550 | 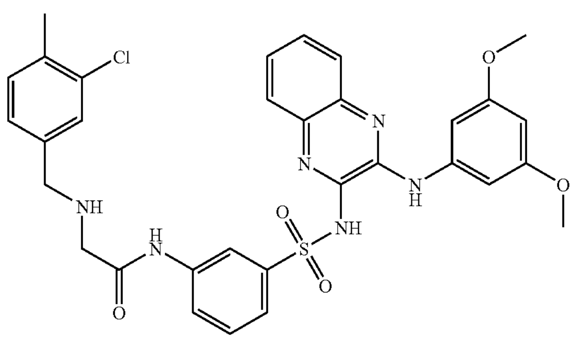 | N-(3-{[(3-{[3,5-bis(methoxy)phenyl]amino}quinoxalin-2-yl)amino]sulfonyl}phenyl)-N-2-[(3-chloro-4-methylphenyl)methyl]glycinamide |
| 551 | 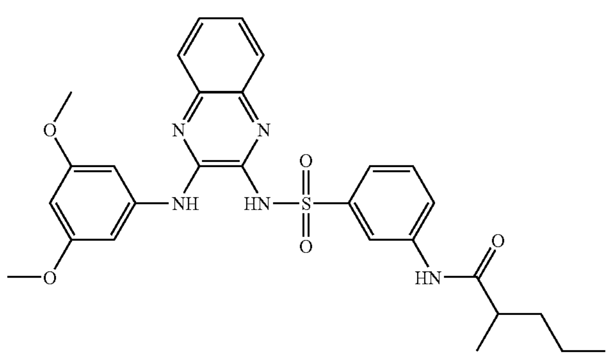 | N-(3-{[(3-{[3,5-bis(methoxy)phenyl]amino}quinoxalin-2-yl)amino]sulfonyl}phenyl)-2-methylpentanamide |

TABLE 1-continued

| Cpd. No. | Structure | Name |
|---|---|---|
| 552 | 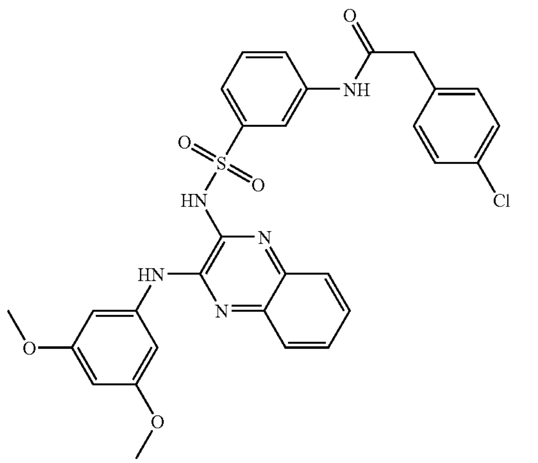 | N-(3-{[(3-{[3,5-bis(methoxy)phenyl]amino}quinoxalin-2-yl)amino]sulfonyl}phenyl)-2-(4-chlorophenyl)acetamide |
| 553 | 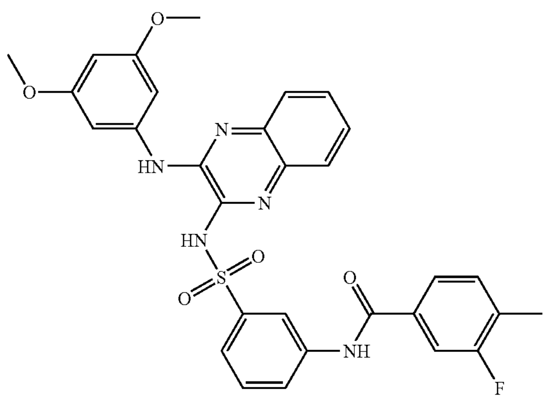 | N-(3-{[(3-{[3,5-bis(methoxy)phenyl]amino}quinoxalin-2-yl)amino]sulfonyl}phenyl)-3-fluoro-4-methylbenzamide |
| 554 | 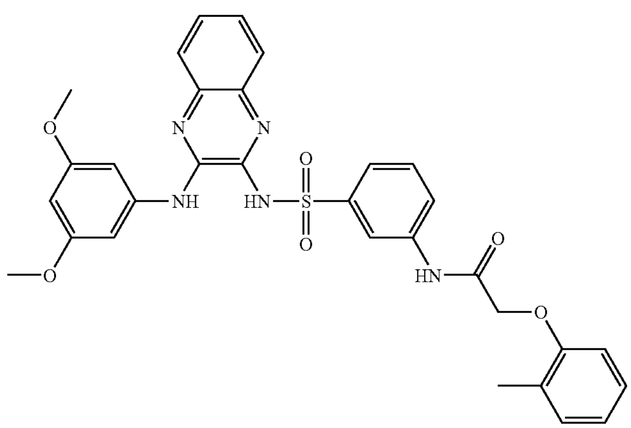 | N-(3-{[(3-{[3,5-bis(methoxy)phenyl]amino}quinoxalin-2-yl)amino]sulfonyl}phenyl)-2-[(2-methylphenyl)oxy]acetamide |
| 555 | 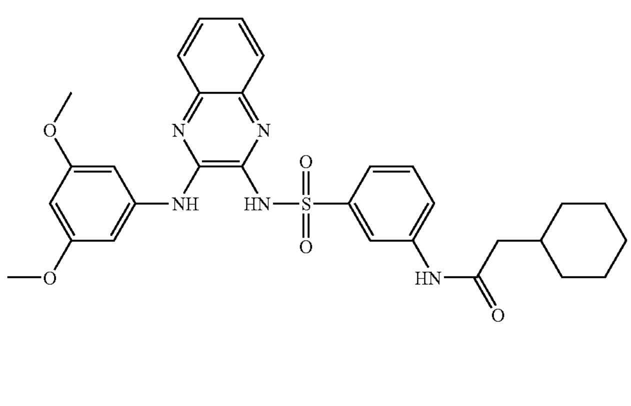 | N-(3-{[(3-{[3,5-bis(methoxy)phenyl]amino}quinoxalin-2-yl)amino]sulfonyl}phenyl)-2-cyclohexylacetamide |

TABLE 1-continued

| Cpd. No. | Structure | Name |
|---|---|---|
| 556 | 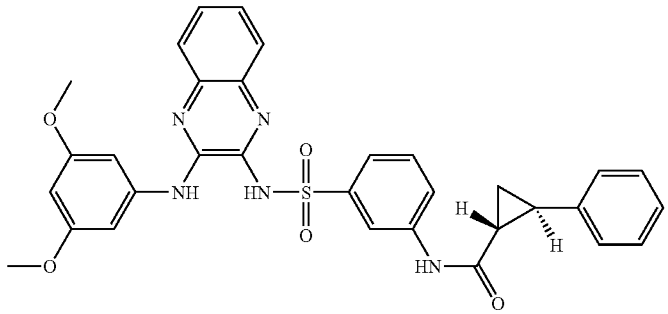 | (1R,2R)-N-(3-{[(3-{[3,5-bis(methoxy)phenyl]amino}quinoxalin-2-yl)amino]sulfonyl}phenyl)-2-phenylcyclopropanecarboxamide |
| 557 | 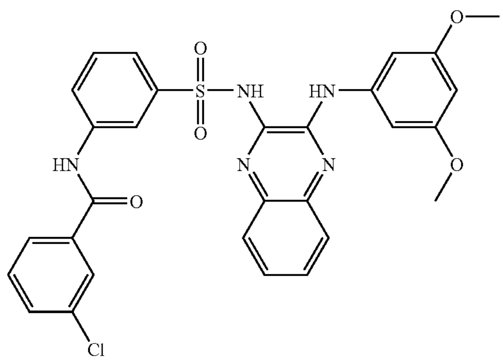 | N-(3-{[(3-{[3,5-bis(methoxy)phenyl]amino}quinoxalin-2-yl)amino]sulfonyl}phenyl)-3-chlorobenzamide |
| 558 | 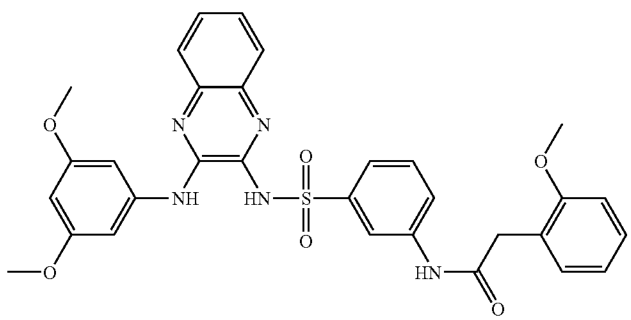 | N-(3-{[(3-{[3,5-bis(methoxy)phenyl]amino}quinoxalin-2-yl)amino]sulfonyl}phenyl)-2-[2-(methoxy)phenyl]acetamide |
| 559 | 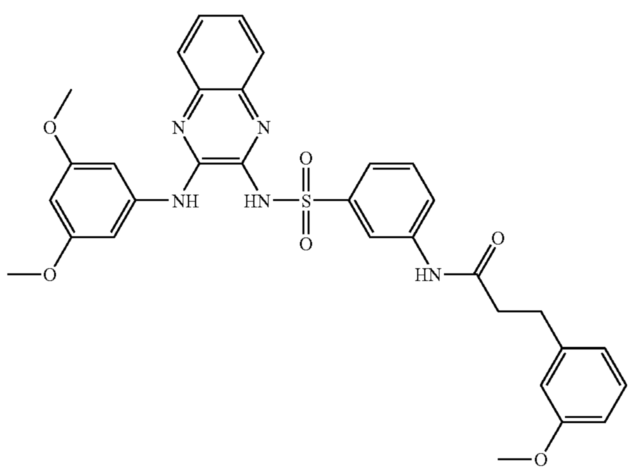 | N-(3-{[(3-{[3,5-bis(methoxy)phenyl]amino}quinoxalin-2-yl)amino]sulfonyl}phenyl)-3-[3-(methoxy)phenyl]propanamide |

TABLE 1-continued

| Cpd. No. | Structure | Name |
|---|---|---|
| 560 | 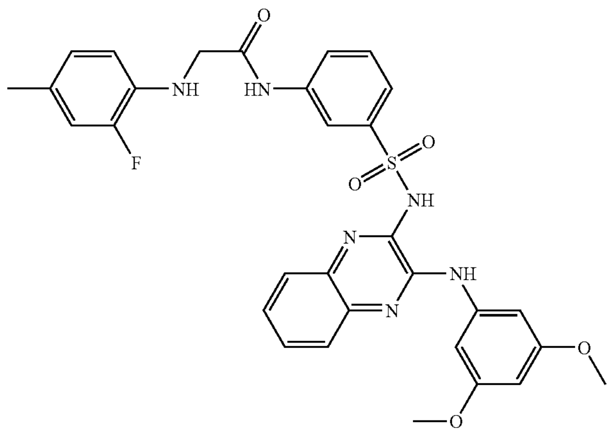 | N-(3-{[(3-{[3,5-bis(methoxy)phenyl]amino}quinoxalin-2-yl)amino]sulfonyl}phenyl)-N-2-(2-fluoro-4-methylphenyl)glycinamide |
| 561 | 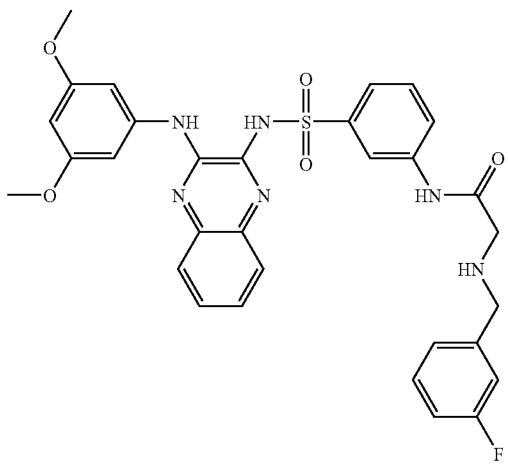 | N-(3-{[(3-{[3,5-bis(methoxy)phenyl]amino}quinoxalin-2-yl)amino]sulfonyl}phenyl)-N-2-[(3-fluorophenyl)methyl]glycinamide |
| 562 | 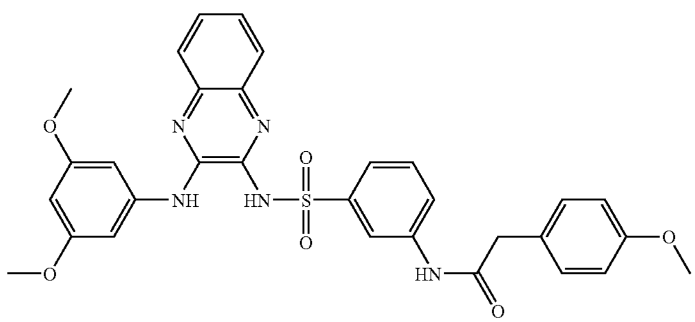 | N-(3-{[(3-{[3,5-bis(methoxy)phenyl]amino}quinoxalin-2-yl)amino]sulfonyl}phenyl)-2-[4-(methoxy)phenyl]acetamide |
| 563 | 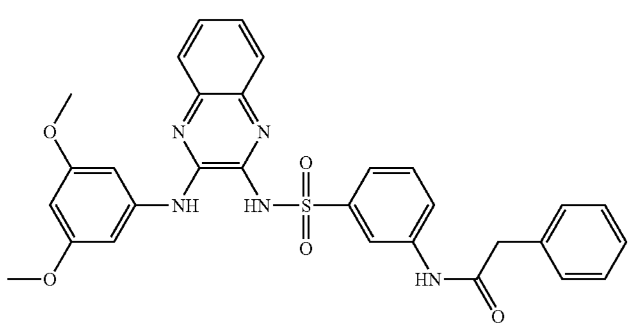 | N-(3-{[(3-{[3,5-bis(methoxy)phenyl]amino}quinoxalin-2-yl)amino]sulfonyl}phenyl)-2-phenylacetamide |

TABLE 1-continued

| Cpd. No. | Structure | Name |
|---|---|---|
| 564 | 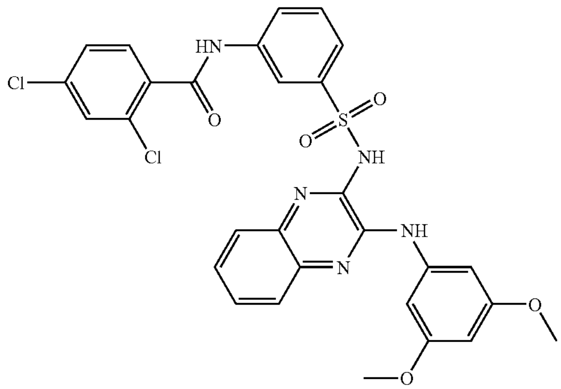 | N-(3-{[(3-{[3,5-bis(methoxy)phenyl]amino}quinoxalin-2-yl)amino]sulfonyl}phenyl)-2,4-dichlorobenzamide |
| 565 | 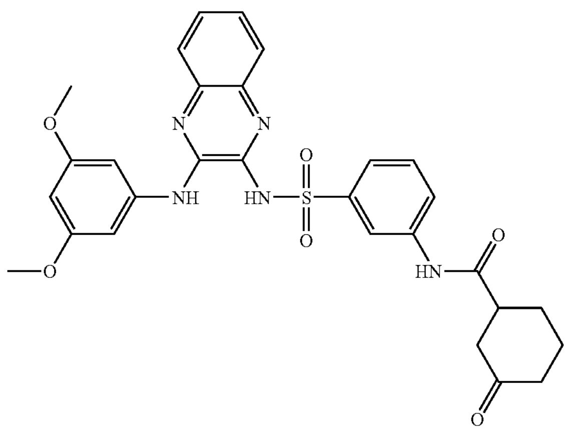 | N-(3-{[(3-{[3,5-bis(methoxy)phenyl]amino}quinoxalin-2-yl)amino]sulfonyl}phenyl)-3-oxocyclohexanecarboxamide |
| 566 | 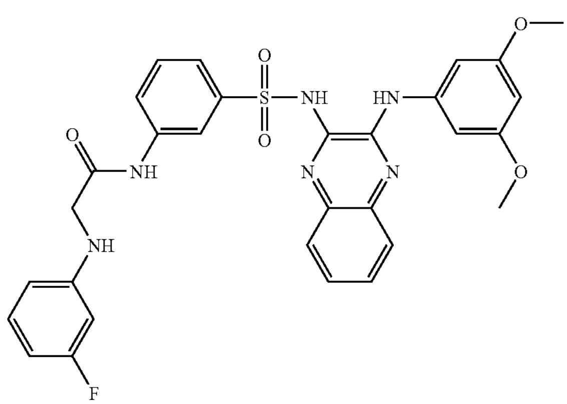 | N-(3-{[(3-{[3,5-bis(methoxy)phenyl]amino}quinoxalin-2-yl)amino]sulfonyl}phenyl)-N-2-(3-fluorophenyl)glycinamide |
| 567 | 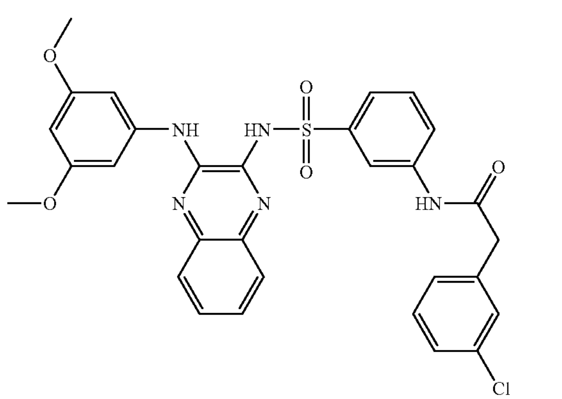 | N-(3-{[(3-{[3,5-bis(methoxy)phenyl]amino}quinoxalin-2-yl)amino]sulfonyl}phenyl)-2-(3-chlorophenyl)acetamide |

TABLE 1-continued

| Cpd. No. | Structure | Name |
|---|---|---|
| 568 | 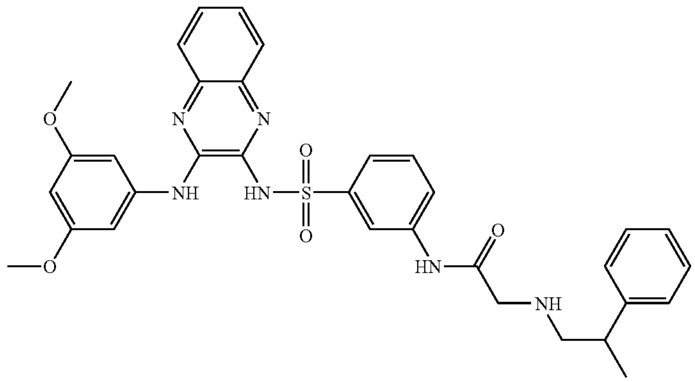 | N-(3-{[(3-{[3,5-bis(methoxy)phenyl]amino}quinoxalin-2-yl)amino]sulfonyl}phenyl)-N-2-(2-phenylpropyl)glycinamide |
| 569 | 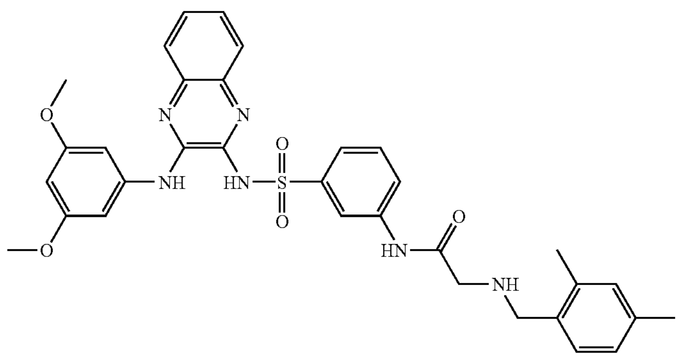 | N-(3-{[(3-{[3,5-bis(methoxy)phenyl]amino}quinoxalin-2-yl)amino]sulfonyl}phenyl)-N-2-[(2,4-dimethylphenyl)methyl]glycinamide |
| 570 | 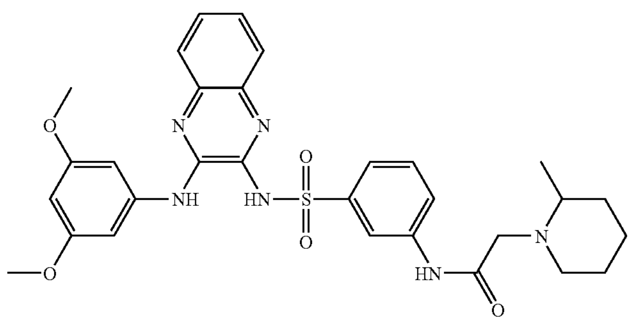 | N-(3-{[(3-{[3,5-bis(methoxy)phenyl]amino}quinoxalin-2-yl)amino]sulfonyl}phenyl)-2-(2-methylpiperidin-1-yl)acetamide |
| 571 | 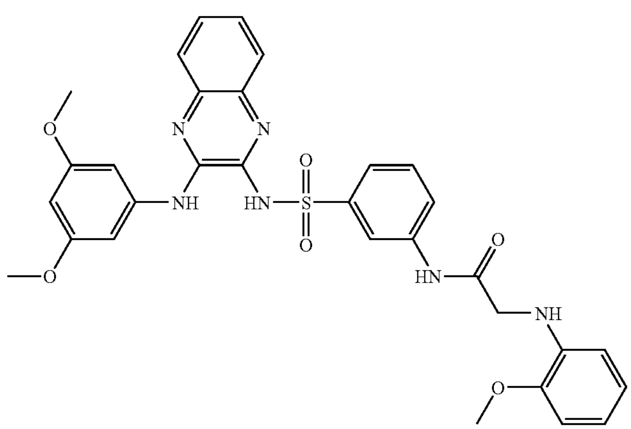 | N-(3-{[(3-{[3,5-bis(methoxy)phenyl]amino}quinoxalin-2-yl)amino]sulfonyl}phenyl)-N-2-[2-(methoxy)phenyl]glycinamide |

| Cpd. No. | Structure | Name |
| --- | --- | --- |
| 572 | 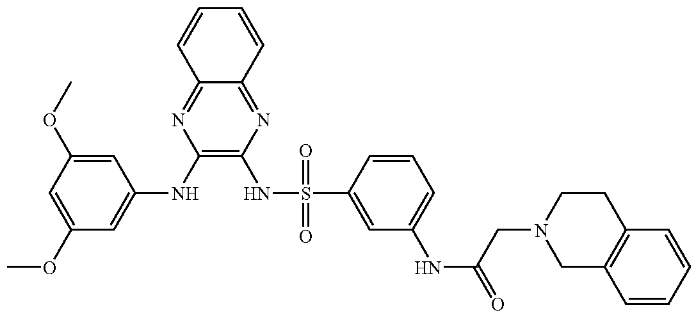 | N-(3-{[(3-{[3,5-bis(methoxy)phenyl]amino}quinoxalin-2-yl)amino]sulfonyl}phenyl)-2-(3,4-dihydroisoquinolin-2(1H)-yl)acetamide |
| 573 | 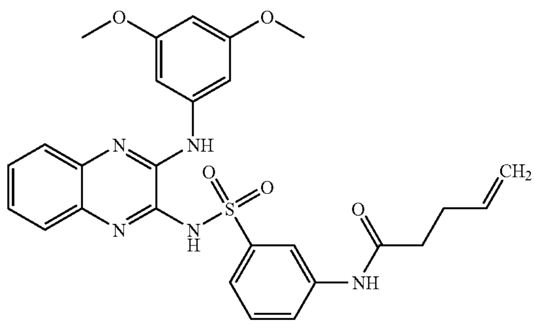 | N-(3-{[(3-{[3,5-bis(methoxy)phenyl]amino}quinoxalin-2-yl)amino]sulfonyl}phenyl)pent-4-enamide |
| 574 | 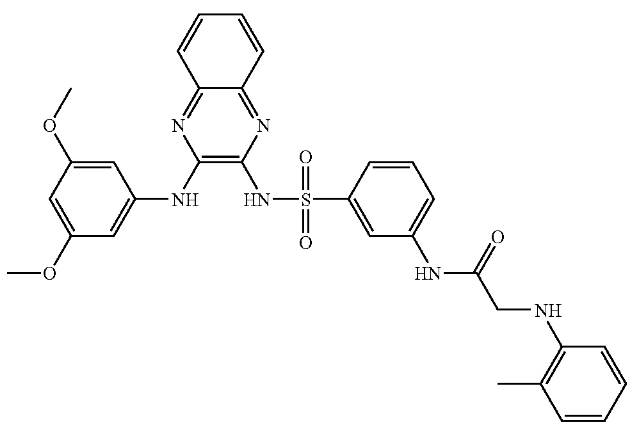 | N-(3-{[(3-{[3,5-bis(methoxy)phenyl]amino}quinoxalin-2-yl)amino]sulfonyl}phenyl)-N-2-(2-methylphenyl)glycinamide |
| 575 | 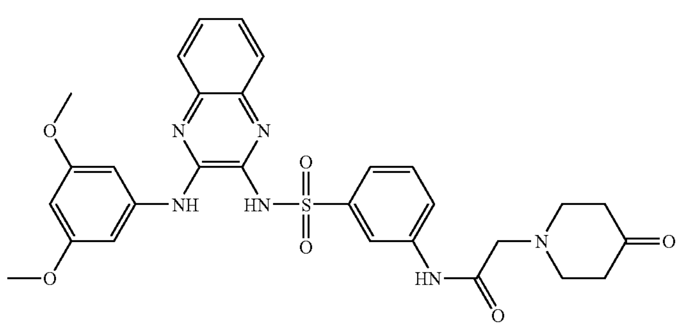 | N-(3-{[(3-{[3,5-bis(methoxy)phenyl]amino}quinoxalin-2-yl)amino]sulfonyl}phenyl)-2-(4-oxopiperidin-1-yl)acetamide |

TABLE 1-continued

| Cpd. No. | Structure | Name |
|---|---|---|
| 576 | 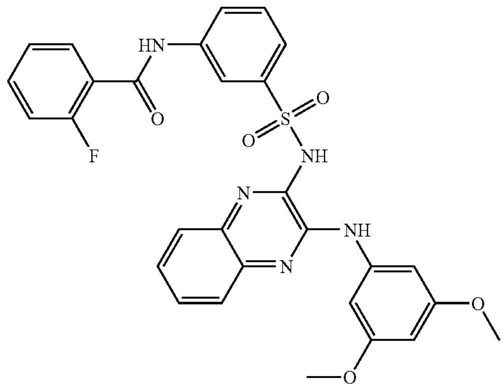 | N-(3-{[(3-{[3,5-bis(methoxy)phenyl]amino}quinoxalin-2-yl)amino]sulfonyl}phenyl)-2-fluorobenzamide |
| 577 | 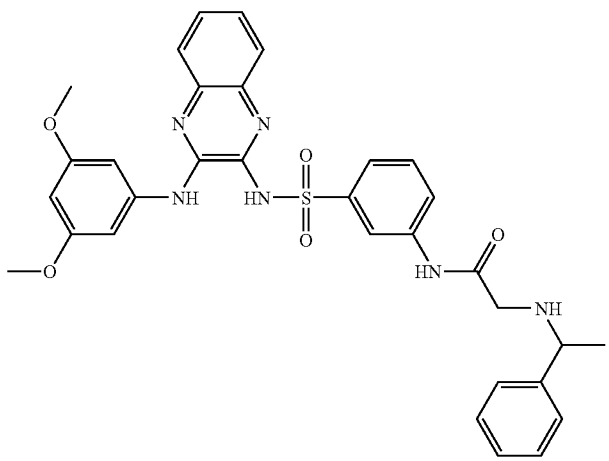 | N-(3-{[(3-{[3,5-bis(methoxy)phenyl]amino}quinoxalin-2-yl)amino]sulfonyl}phenyl)-N-2-(1-phenylethyl)glycinamide |
| 578 | 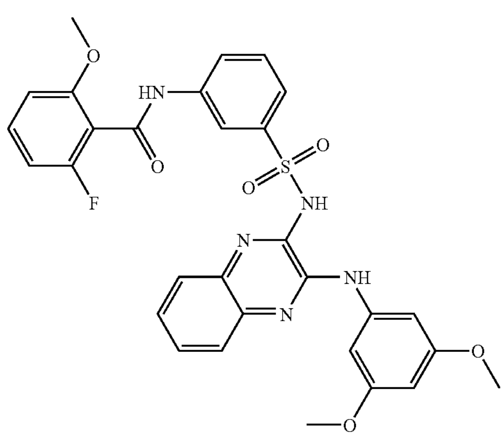 | N-(3-{[(3-{[3,5-bis(methoxy)phenyl]amino}quinoxalin-2-yl)amino]sulfonyl}phenyl)-2-fluoro-6-(methoxy)benzamide |

TABLE 1-continued

| Cpd. No. | Structure | Name |
|---|---|---|
| 579 | 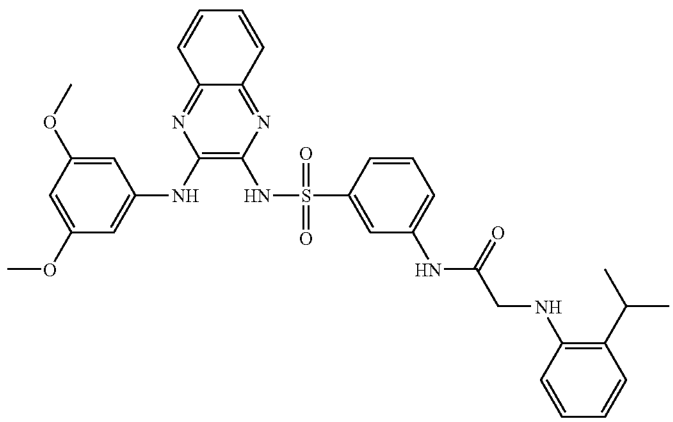 | N-(3-{[(3-{[3,5-bis(methoxy)phenyl]amino}quinoxalin-2-yl)amino]sulfonyl}phenyl)-N-2-[2-(1-methylethyl)phenyl]glycinamide |
| 580 | 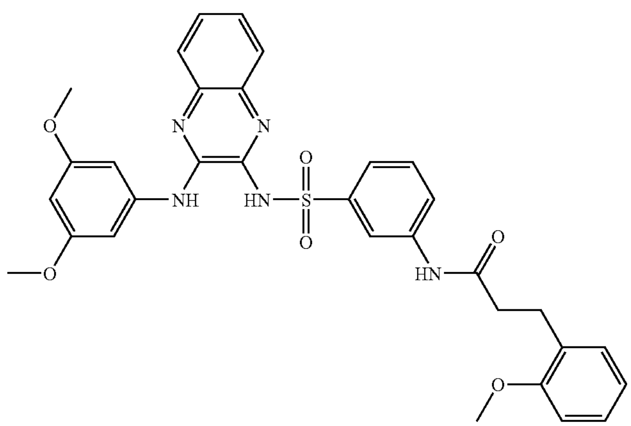 | N-(3-{[(3-{[3,5-bis(methoxy)phenyl]amino}quinoxalin-2-yl)amino]sulfonyl}phenyl)-3-[2-(methoxy)phenyl]propanamide |
| 581 | 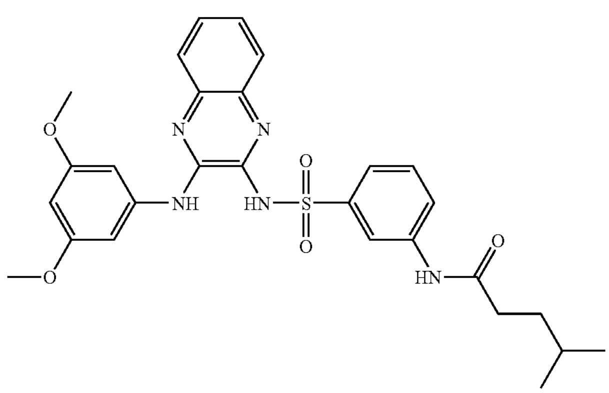 | N-(3-{[(3-{[3,5-bis(methoxy)phenyl]amino}quinoxalin-2-yl)amino]sulfonyl}phenyl)-4-methylpentanamide |
| 582 | 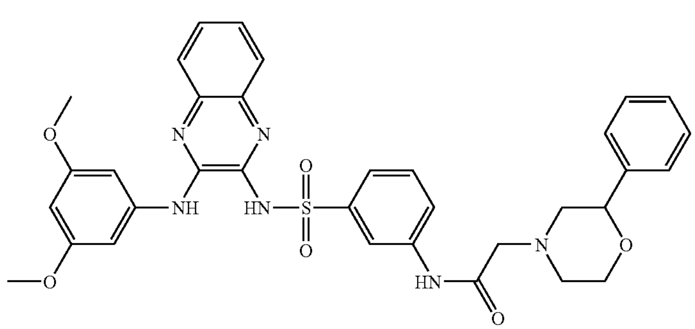 | N-(3-{[(3-{[3,5-bis(methoxy)phenyl]amino}quinoxalin-2-yl)amino]sulfonyl}phenyl)-2-(2-phenylmorpholin-4-yl)acetamide |

TABLE 1-continued

| Cpd. No. | Structure | Name |
|---|---|---|
| 583 | 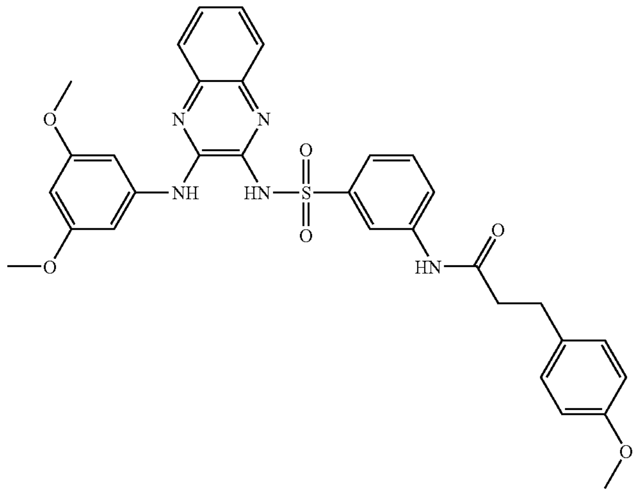 | N-(3-{[(3-{[3,5-bis(methoxy)phenyl]amino}quinoxalin-2-yl)amino]sulfonyl}phenyl)-3-[4-(methoxy)phenyl]propanamide |
| 584 | 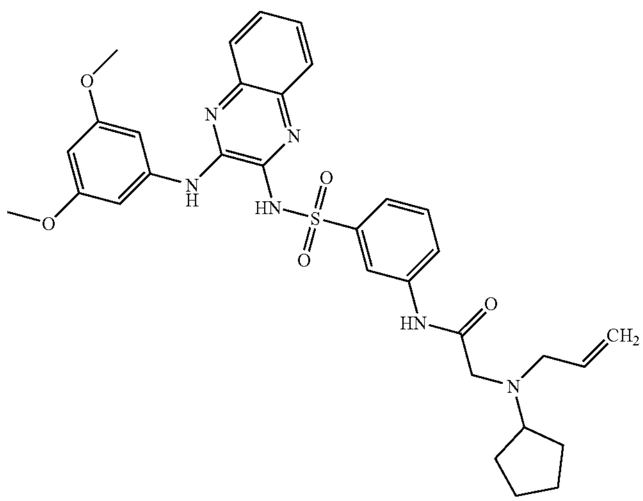 | N-(3-{[(3-{[3,5-bis(methoxy)phenyl]amino}quinoxalin-2-yl)amino]sulfonyl}phenyl)-N-2-cyclopentyl-N-2-prop-2-en-1-ylglycinamide |
| 585 | 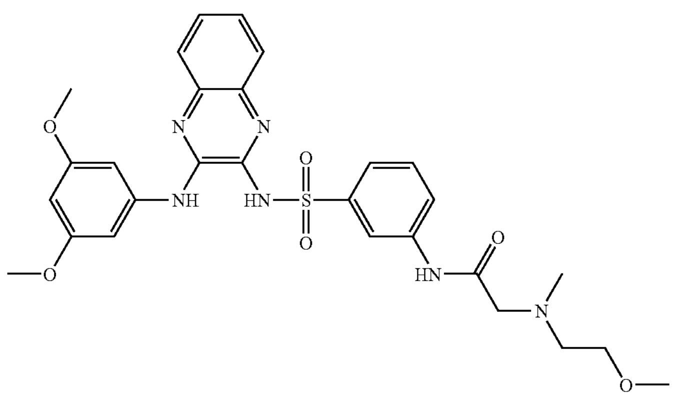 | N-(3-{[(3-{[3,5-bis(methoxy)phenyl]amino}quinoxalin-2-yl)amino]sulfonyl}phenyl)-N-2-methyl-N-2-[2-(methoxy)ethyl]glycinamide |

TABLE 1-continued

| Cpd. No. | Structure | Name |
|---|---|---|
| 586 | 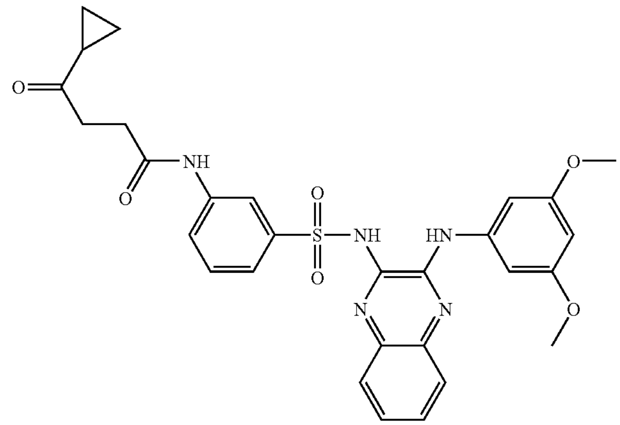 | N-(3-{[(3-{[3,5-bis(methoxy)phenyl]amino}quinoxalin-2-yl)amino]sulfonyl}phenyl)-4-cyclopropyl-4-oxobutanamide |
| 587 | 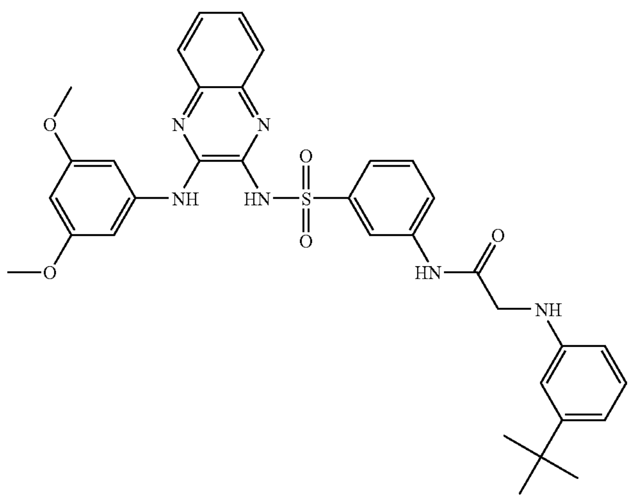 | N-(3-{[(3-{[3,5-bis(methoxy)phenyl]amino}quinoxalin-2-yl)amino]sulfonyl}phenyl)-N-2-[3-(1,1-dimethylethyl)phenyl]glycinamide |
| 588 | 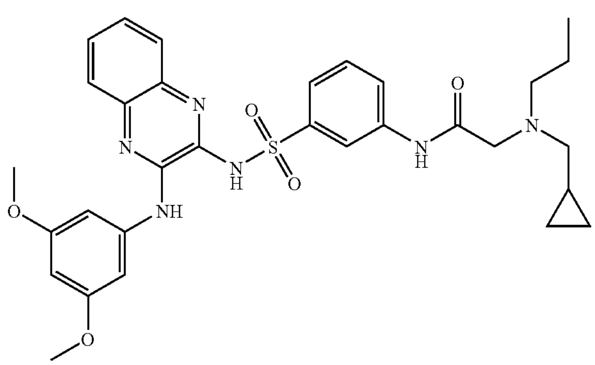 | N-(3-{[(3-{[3,5-bis(methoxy)phenyl]amino}quinoxalin-2-yl)amino]sulfonyl}phenyl)-N-2-(cyclopropylmethyl)-N-2-propylglycinamide |

TABLE 1-continued

| Cpd. No. | Structure | Name |
|---|---|---|
| 589 | 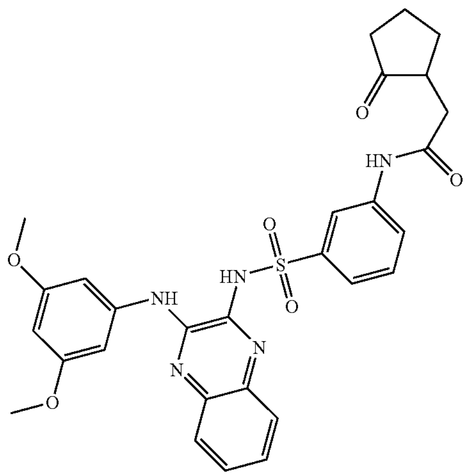 | N-(3-{[(3-{[3,5-bis(methoxy)phenyl]amino}quinoxalin-2-yl)amino]sulfonyl}phenyl)-2-(2-oxocyclopentyl)acetamide |
| 590 | 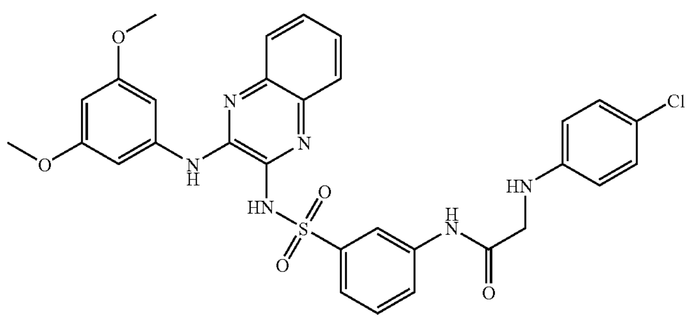 | N-(3-{[(3-{[3,5-bis(methoxy)phenyl]amino}quioxalin-2-yl)amino]sulfonyl}phenyl)-N-2-(4-chlorophenyl)glycinamide |
| 591 | 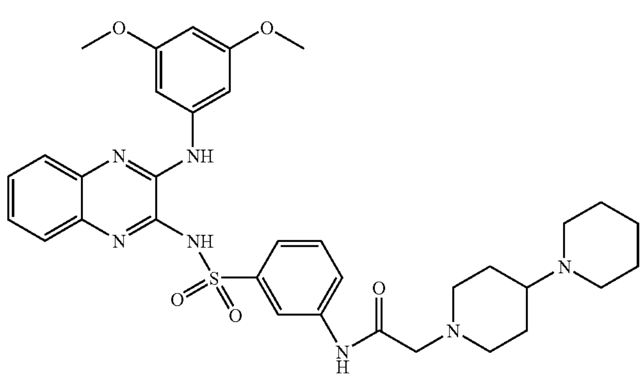 | 2-(1,4'-bipiperidin-1'-yl)-N-(3-{[(3-{[3,5-bis(methoxy)phenyl]amino}quinoxalin-2-yl)amino]sulfonyl}phenyl)acetamide |

TABLE 1-continued

| Cpd. No. | Structure | Name |
|---|---|---|
| 592 | 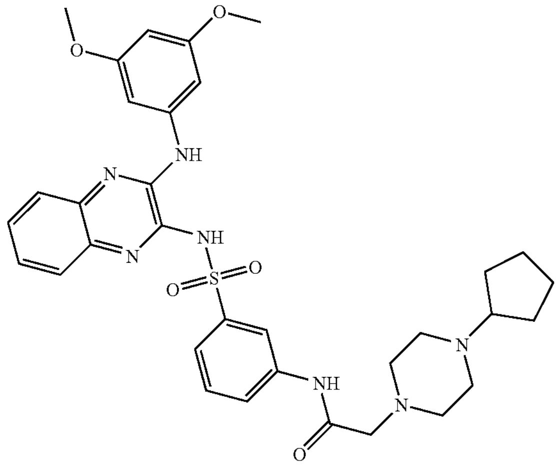 | N-(3-{[(3-{[3,5-bis(methoxy)phenyl]amino}quinoxalin-2-yl)amino]sulfonyl}phenyl)-2-(4-cyclopentylpiperazin-1-yl)acetamide |
| 593 | 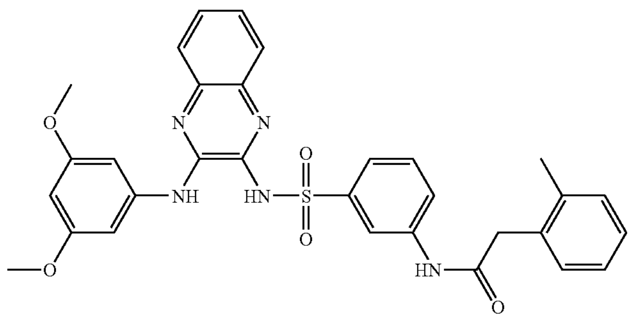 | N-(3-{[(3-{[3,5-bis(methoxy)phenyl]amino}quinoxalin-2-yl)amino]sulfonyl}phenyl)-2-(2-methylphenyl)acetamide |
| 594 | 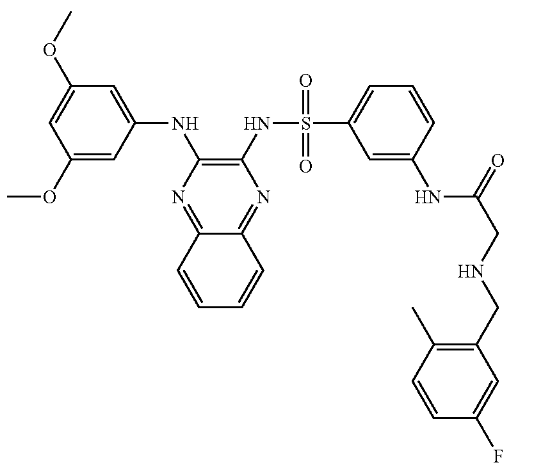 | N-(3-{[(3-{[3,5-bis(methoxy)phenyl]amino}quinoxalin-2-yl)amino]sulfonyl}phenyl)-N-2-[(5-fluoro-2-methylphenyl)methyl]glycinamide |
| 595 | 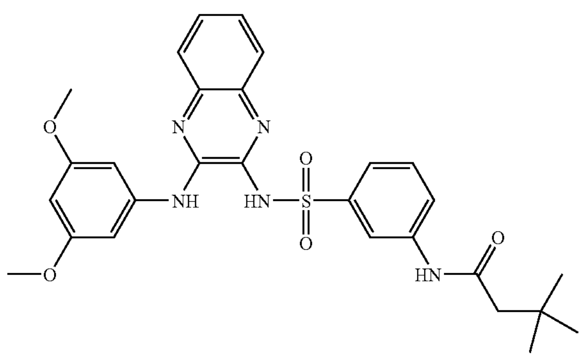 | N-(3-{[(3-{[3,5-bis(methoxy)phenyl]amino}quinoxalin-2-yl)amino]sulfonyl}phenyl)-3,3-dimethylbutanamide |

TABLE 1-continued

| Cpd. No. | Structure | Name |
|---|---|---|
| 596 | 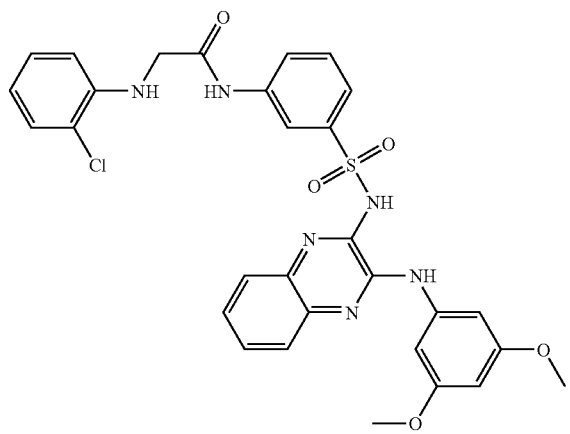 | N-(3-{[(3-{[3,5-bis(methoxy)phenyl]amino}quinoxalin-2-yl)amino]sulfonyl}phenyl)-N$^2$-(2-chlorophenyl)glycinamide |
| 597 | 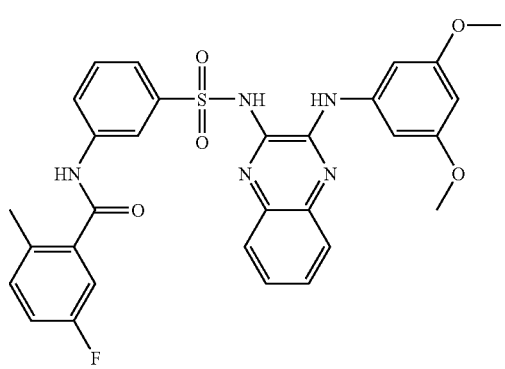 | N-(3-{[(3-{[3,5-bis(methoxy)phenyl]amino}quinoxalin-2-yl)amino]sulfonyl}phenyl)-5-fluoro-2-methylbenzamide |
| 598 | 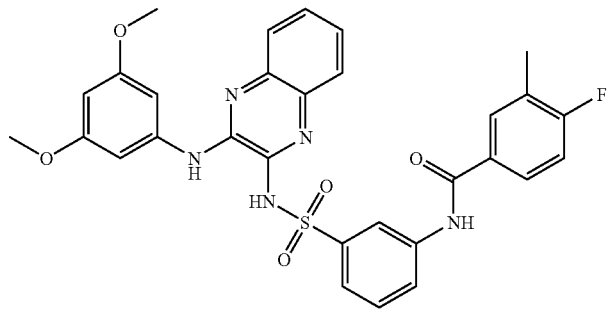 | N-(3-{[(3-{[3,5-bis(methoxy)phenyl]amino}quinoxalin-2-yl)amino]sulfonyl}phenyl)-4-fluoro-3-methylbenzamide |
| 599 | 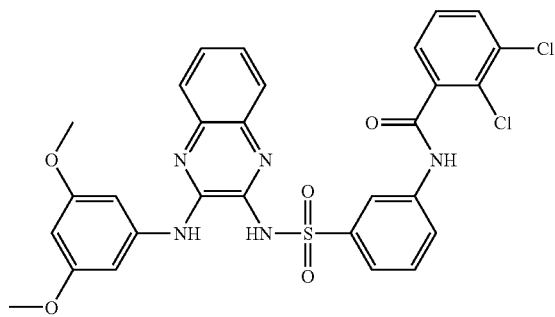 | N-(3-{[(3-{[3,5-bis(methoxy)phenyl]amino}quinoxalin-2-yl)amino]sulfonyl}phenyl)-2,3-dichlorobenzamide |

TABLE 1-continued

| Cpd. No. | Structure | Name |
|---|---|---|
| 600 | 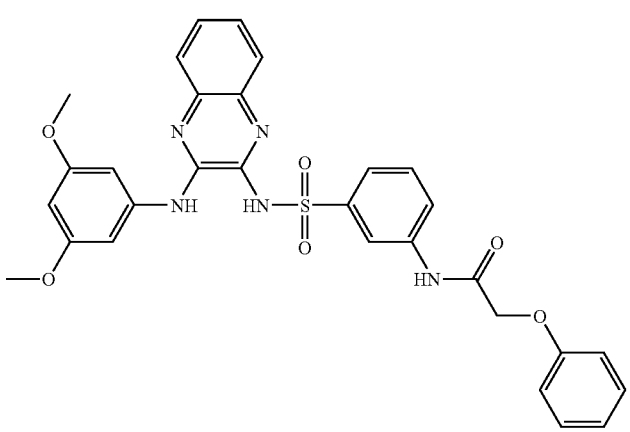 | N-(3-{[(3-{[3,5-bis(methoxy)phenyl]amino}quinoxalin-2-yl)amino]sulfonyl}phenyl)-2-(phenyloxy)acetamide |
| 601 | 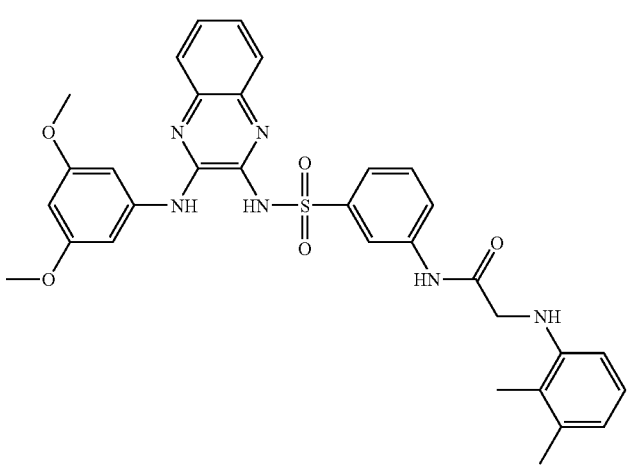 | N-(3-{[(3-{[3,5-bis(methoxy)phenyl]amino}quinoxalin-2-yl)amino]sulfonyl}phenyl)-N-2-(2,3-dimethylphenyl)glycinamide |
| 602 | 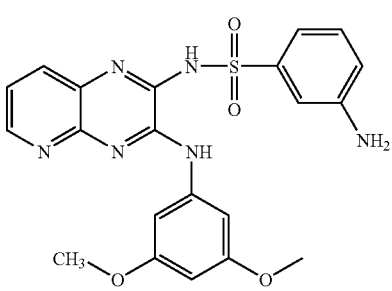 | 3-amino-N-(3-{[(3-{[3,5-bis(methoxy)phenyl]amino}pyrido[2,3-b]pyrazin-2-yl)benzenesulfonamide |
| 603 | 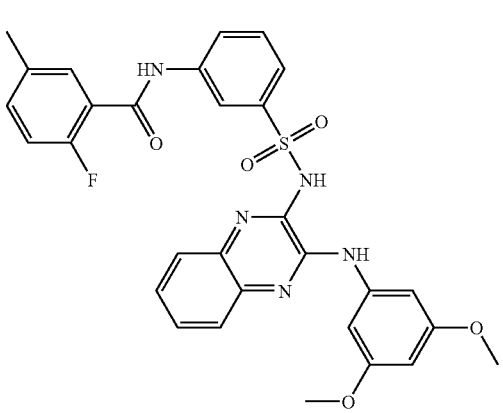 | N-(3-{[(3-{[3,5-bis(methoxy)phenyl]amino}quinoxalin-2-yl)amino]sulfonyl}phenyl)-2-fluoro-5-methylbenzamide |

TABLE 1-continued

| Cpd. No. | Structure | Name |
|---|---|---|
| 604 | 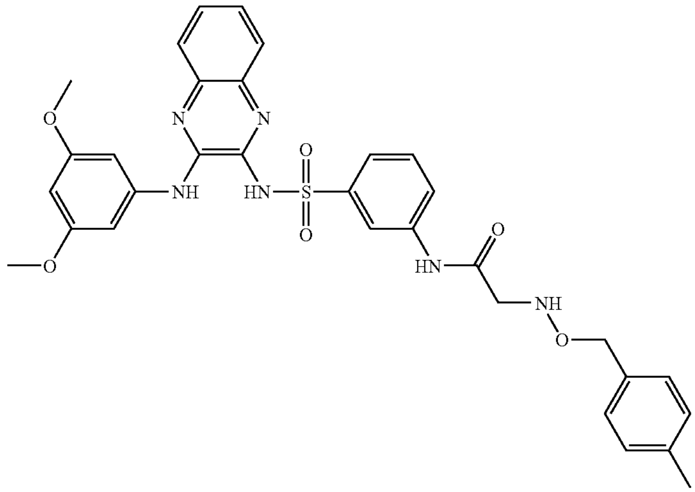 | N-(3-{[(3-{[3,5-bis(methoxy)phenyl]amino}quinoxalin-2-yl)amino]sulfonyl}phenyl)-N-2-{[(4-methylphenyl)methyl]oxy}glycinamide |
| 605 | 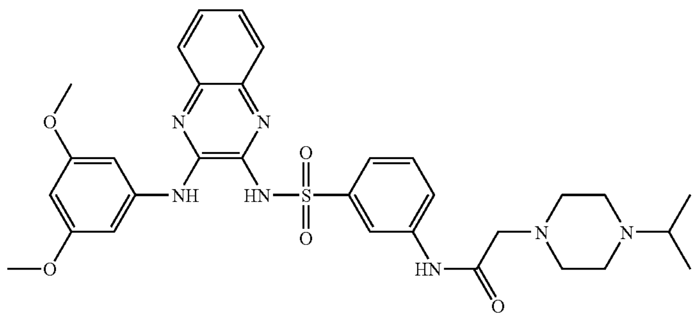 | N-(3-{[(3-{[3,5-bis(methoxy)phenyl]amino}quinoxalin-2-yl)amino]sulfonyl}phenyl)-2-[4-(1-methylethyl)piperazin-1-yl]acetamide |
| 606 | 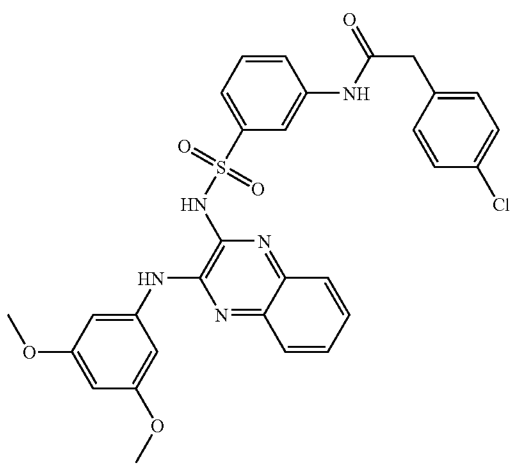 | N-(3-{[(3-{[3,5-bis(methoxy)phenyl]amino}quinoxalin-2-yl)amino]sulfonyl}phenyl)-2-(4-fluorophenyl)acetamide |
| 607 | 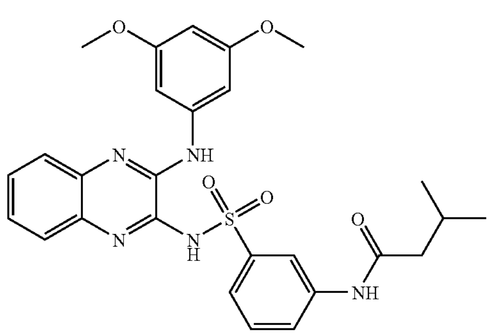 | N-(3-{[(3-{[3,5-bis(methoxy)phenyl]amino}quinoxalin-2-yl)amino]sulfonyl}phenyl)-3-methylbutanamide |

TABLE 1-continued

| Cpd. No. | Structure | Name |
|---|---|---|
| 608 | 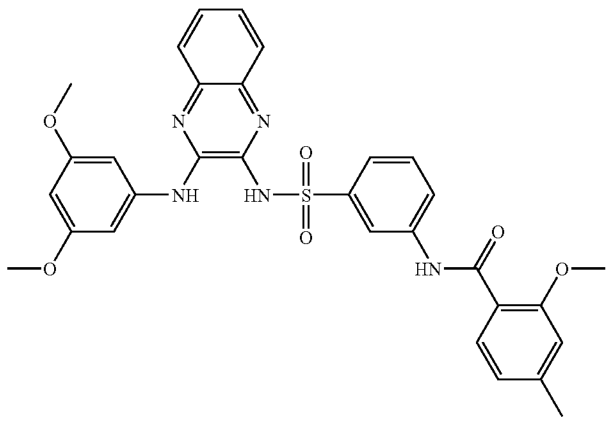 | N-(3-{[(3-{[3,5-bis(methoxy)phenyl]amino}quinoxalin-2-yl)amino]sulfonyl}phenyl)-4-methyl-2-(methoxy)benzamide |
| 609 | 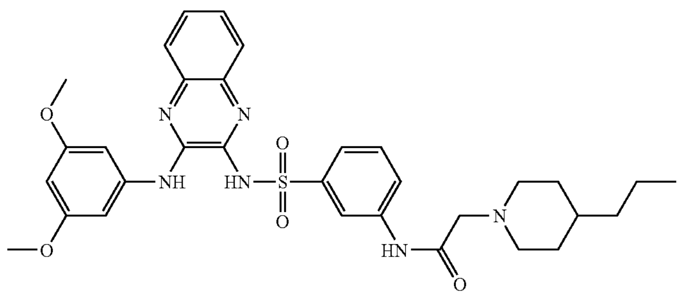 | N-(3-{[(3-{[3,5-bis(methoxy)phenyl]amino}quinoxalin-2-yl)amino]sulfonyl}phenyl)-2-(4-propylpiperidin-1-yl)acetamide |
| 610 | 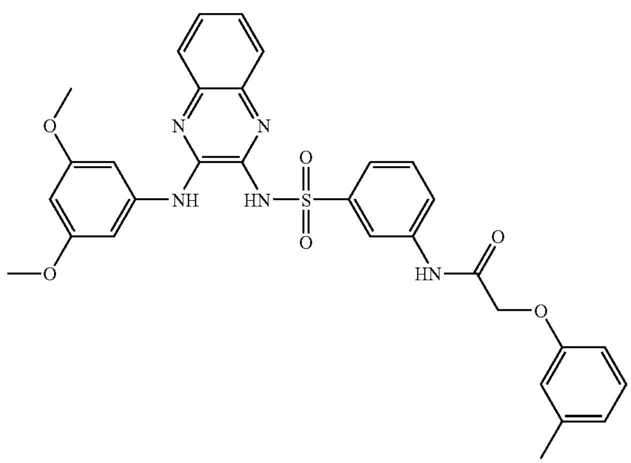 | N-(3-{[(3-{[3,5-bis(methoxy)phenyl]amino}quinoxalin-2-yl)amino]sulfonyl}phenyl)-2-[(3-methylphenyl)oxy]acetamide |
| 611 | 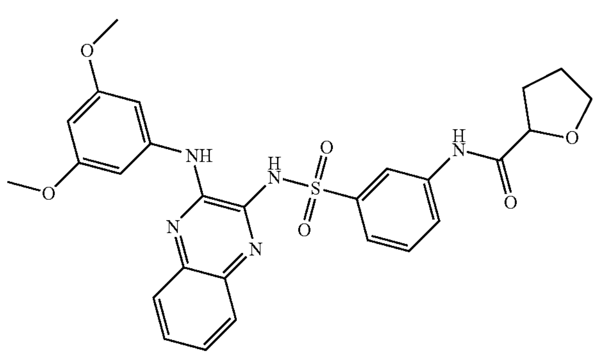 | N-(3-{[(3-{[3,5-bis(methoxy)phenyl]amino}quinoxalin-2-yl)amino]sulfonyl}phenyl)tetrahydrofuran-2-carboxamide |

TABLE 1-continued

| Cpd. No. | Structure | Name |
|---|---|---|
| 612 | 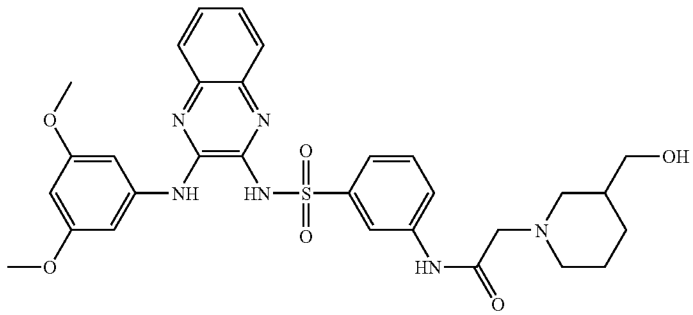 | N-(3-{[(3-{[3,5-bis(methoxy)phenyl]amino}quinoxalin-2-yl)amino]sulfonyl}phenyl)-2-[3-(hydroxymethyl)piperidin-1-yl]acetamide |
| 613 | 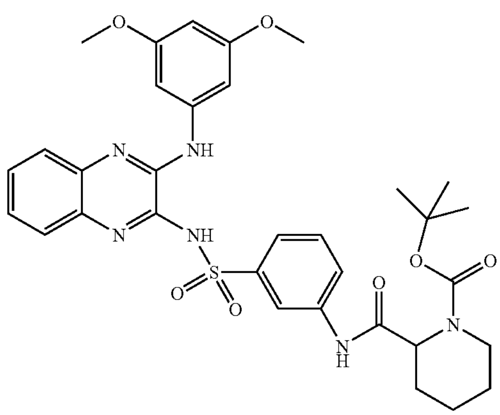 | 1,1-dimethylethyl2-{[(3-{[(3-{[3,5-bis(methoxy)phenyl]amino}quinoxalin-2-yl)amino]sulfonyl}phenyl)amino]carbonyl}-piperidine-1-carboxylate |
| 614 | 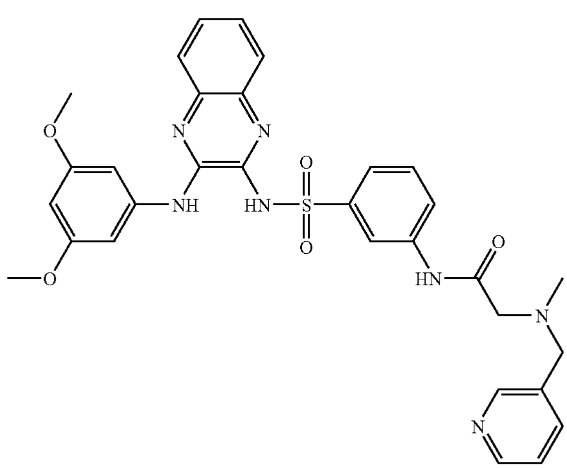 | N-(3-{[(3-{[3,5-bis(methoxy)phenyl]amino}quinoxalin-2-yl)amino]sulfonyl}phenyl)-N-2-methyl-N-2-(pyridin-3-ylmethyl)glycinamide |

| Cpd. No. | Structure | Name |
|---|---|---|
| 615 | 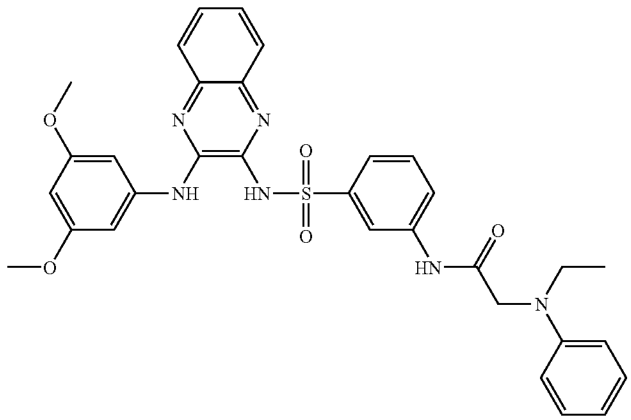 | N-(3-{[(3-{[3,5-bis(methoxy)phenyl]amino}quinoxalin-2-yl)amino]sulfonyl}phenyl)-N-2-ethyl-N-2-phenylglycinamide |
| 616 | 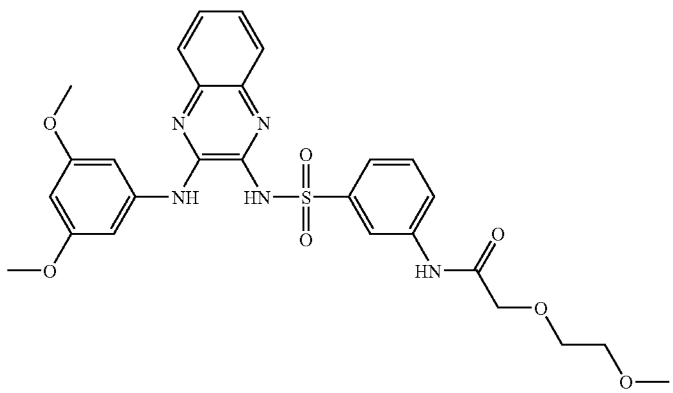 | N-(3-{[(3-{[3,5-bis(methoxy)phenyl]amino}quinoxalin-2-yl)amino]sulfonyl}phenyl)-2-{[2-(methoxy)ethyl]oxy}acetamide |
| 617 | 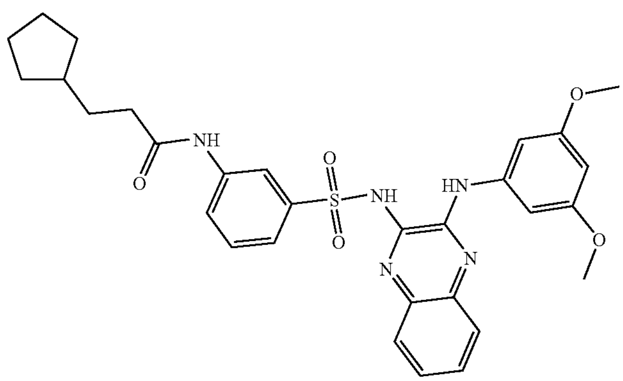 | N-(3-{[(3-{[3,5-bis(methoxy)phenyl]amino}quinoxalin-2-yl)amino]sulfonyl}phenyl)-3-cyclopentylpropanamide |
| 618 | 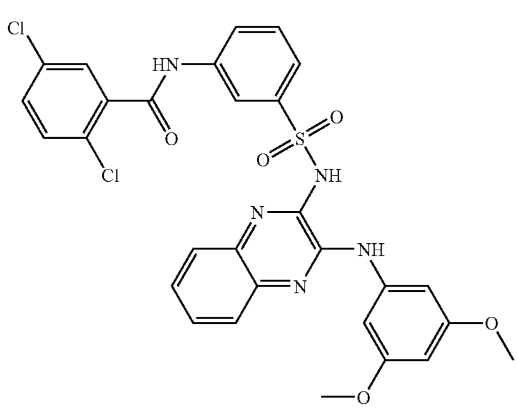 | N-(3-{[(3-{[3,5-bis(methoxy)phenyl]amino}quinoxalin-2-yl)amino]sulfonyl}phenyl)-2,5-dichlorobenzamide |

TABLE 1-continued

| Cpd. No. | Structure | Name |
|---|---|---|
| 619 | 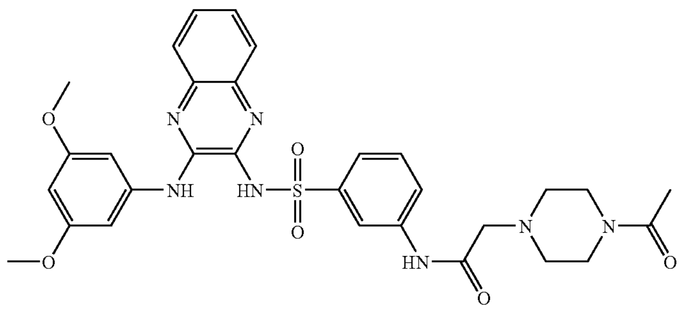 | 2-(4-acetylpiperazin-1-yl)-N-(3-{[(3-{[3,5-bis(methoxy)phenyl]amino}quinoxalin-2-yl)amino]sulfonyl}phenyl)acetamide |
| 620 | 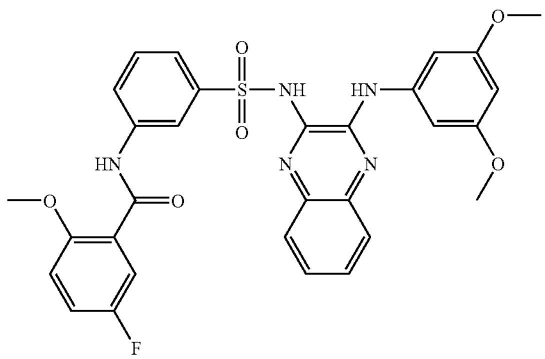 | N-(3-{[(3-{[3,5-bis(methoxy)phenyl]amino}quinoxalin-2-yl)amino]sulfonyl}phenyl)-5-fluoro-2-(methoxy)benzamide |
| 621 | 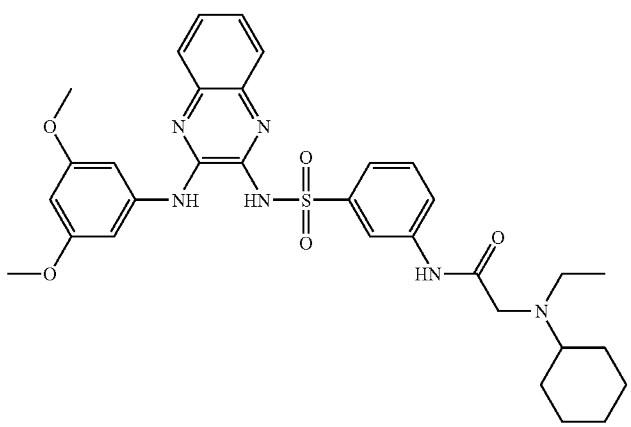 | N-(3-{[(3-{[3,5-bis(methoxy)phenyl]amino}quinoxalin-2-yl)amino]sulfonyl}phenyl)-N-2-cyclohexyl-N-2-ethylglycinamide |
| 622 | 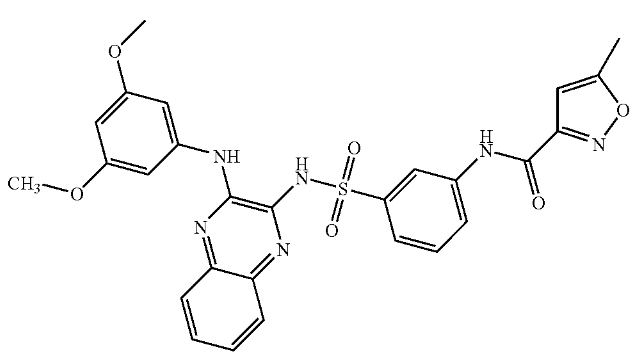 | N-(3-{[(3-{[3,5-bis(methoxy)phenyl]amino}quinoxalin-2-yl)amino]sulfonyl}phenyl)-5-methylisoxazole-3-carboxamide |

TABLE 1-continued

| Cpd. No. | Structure | Name |
|---|---|---|
| 623 | 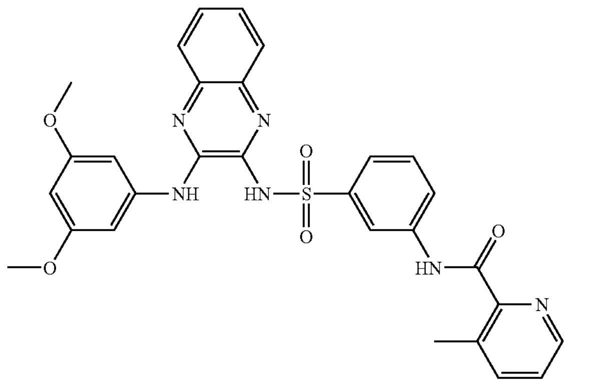 | N-(3-{[(3-{[3,5-bis(methoxy)phenyl]amino}quinoxalin-2-yl)amino]sulfonyl}phenyl)-3-methylpyridine-2-carboxamide |
| 624 | 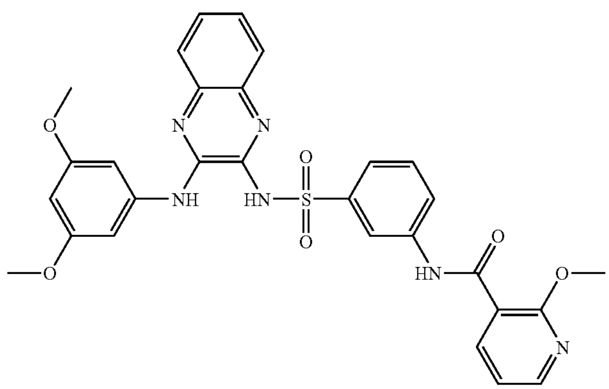 | N-(3-{[(3-{[3,5-bis(methoxy)phenyl]amino}quinoxalin-2-yl)amino]sulfonyl}phenyl)-2-(methoxy)pyridine-3-carboxamide |
| 625 | 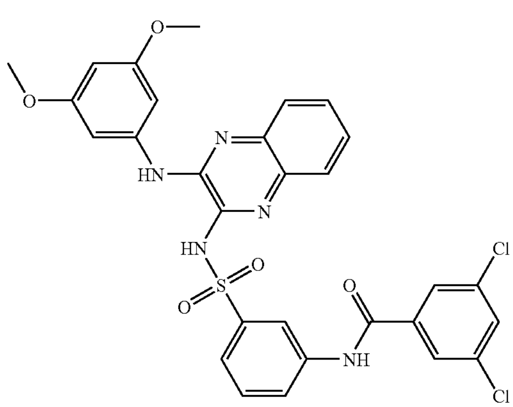 | N-(3-{[(3-{[3,5-bis(methoxy)phenyl]amino}quinoxalin-2-yl)amino]sulfonyl}phenyl)-3,5-dichlorobenzamide |

TABLE 1-continued

| Cpd. No. | Structure | Name |
|---|---|---|
| 626 | 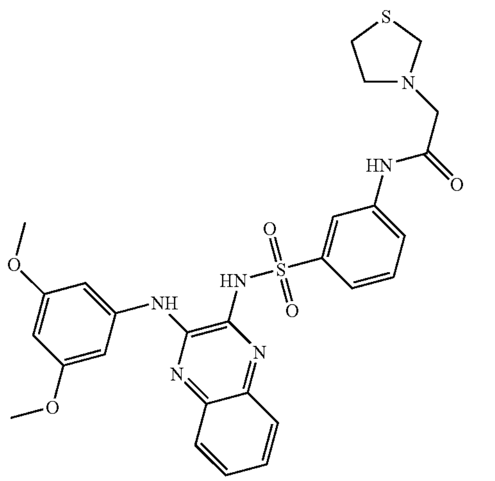 | N-(3-{[(3-{[3,5-bis(methoxy)phenyl]amino}quinoxalin-2-yl)amino]sulfonyl}phenyl)-2-(1,3-thiazolidin-3-yl)acetamide |
| 627 | 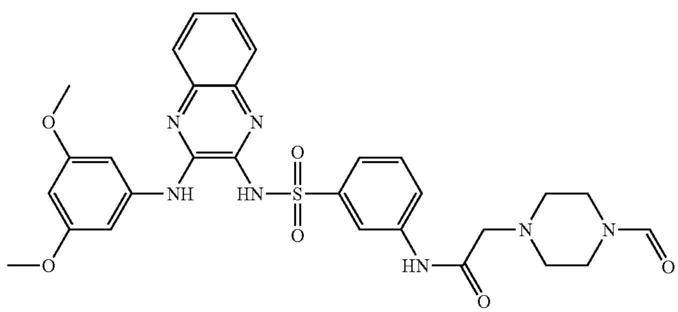 | N-(3-{[(3-{[3,5-bis(methoxy)phenyl]amino}quinoxalin-2-yl)amino]sulfonyl}phenyl)-2-(4-formylpiperazin-1-yl)acetamide |
| 628 | 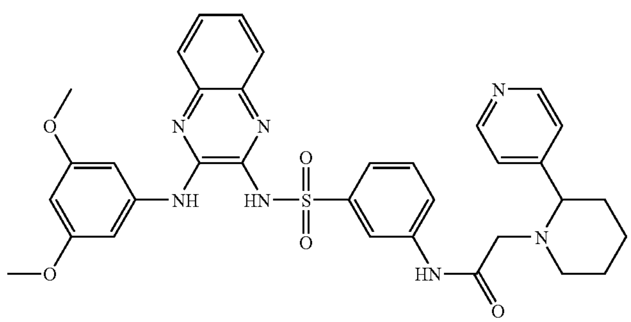 | N-(3-{[(3-{[3,5-bis(methoxy)phenyl]amino}quinoxalin-2-yl)amino]sulfonyl}phenyl)-2-(2-pyridin-4-ylpiperidin-1-yl)acetamide |
| 629 | 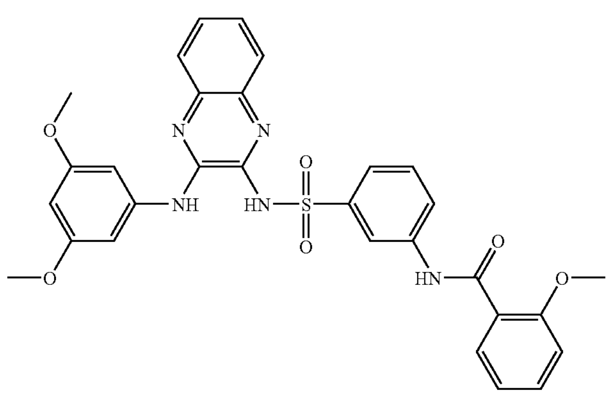 | N-(3-{[(3-{[3,5-bis(methoxy)phenyl]amino}quinoxalin-2-yl)amino]sulfonyl}phenyl)-2-(methoxy)benzamide |

TABLE 1-continued

| Cpd. No. | Structure | Name |
|---|---|---|
| 630 | 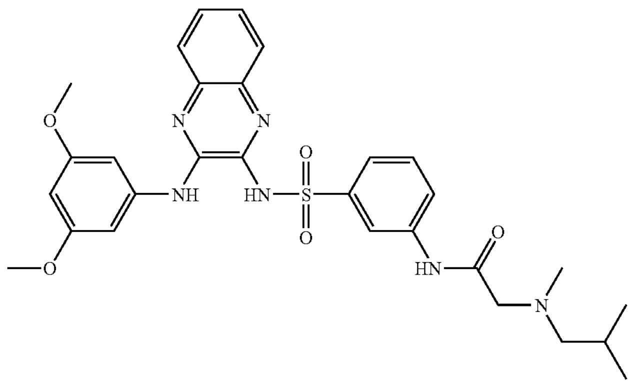 | N-(3-{[(3-{[3,5-bis(methoxy)phenyl]amino}quinoxalin-2-yl)amino]sulfonyl}phenyl)-N-2-methyl-N-2-(2-methylpropyl)glycinamide |
| 631 | 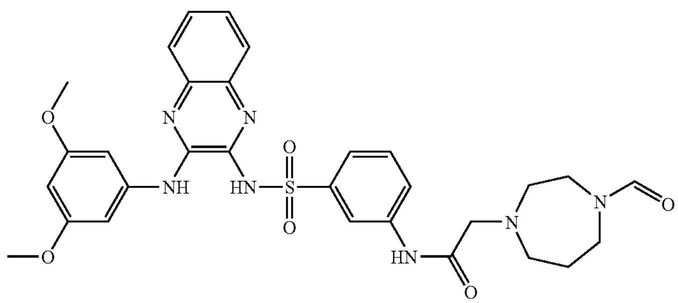 | N-(3-{[(3-{[3,5-bis(methoxy)phenyl]amino}quinoxalin-2-yl)amino]sulfonyl}phenyl)-2-(4-formyl-1,4-diazepan-1-yl)acetamide |
| 632 | 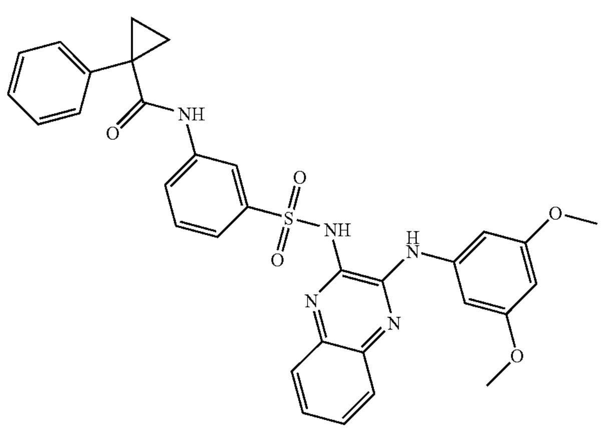 | N-(3-{[(3-{[3,5-bis(methoxy)phenyl]amino}quinoxalin-2-yl)amino]sulfonyl}phenyl)-1-phenylcyclopropanecarboxamide |
| 633 | 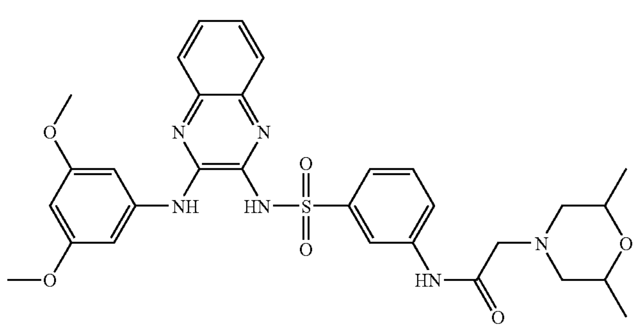 | N-(3-{[(3-{[3,5-bis(methoxy)phenyl]amino}quinoxalin-2-yl)amino]sulfonyl}phenyl)-2-(2,6-dimethylmorpholin-4-yl)acetamide |

| Cpd. No. | Structure | Name |
|---|---|---|
| 634 | 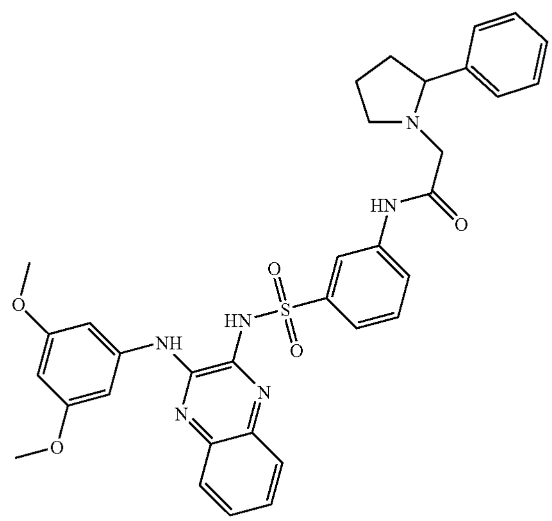 | N-(3-{[(3-{[3,5-bis(methoxy)phenyl]amino}quinoxalin-2-yl)amino]sulfonyl}phenyl)-2-(2-phenylpyrrolidin-1-yl)acetamide |
| 635 | 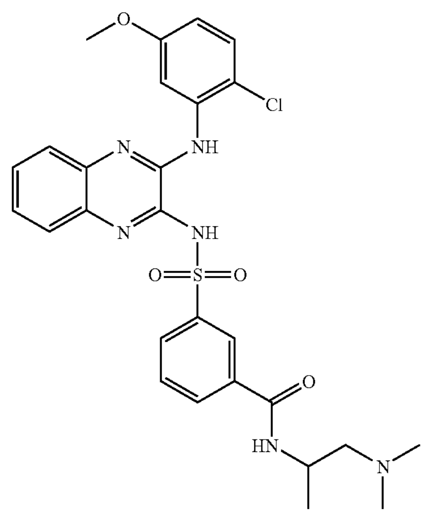 | 3-{[(3-{[2-chloro-5-(methoxy)phenyl]amino}quinoxalin-2-yl)amino]sulfonyl}-N-[2-(dimethylamino)-1-methylethyl]benzamide |
| 636 | 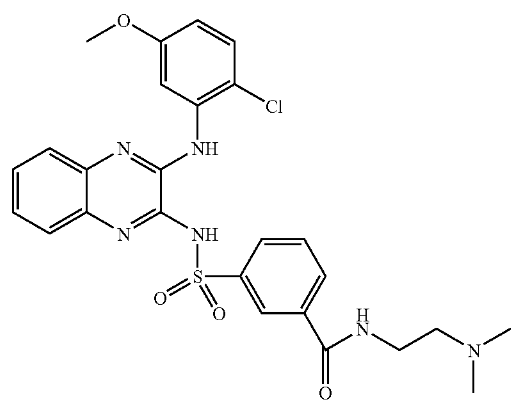 | 3-{[(3-{[2-chloro-5-(methoxy)phenyl]amino}quinoxalin-2-yl)amino]sulfonyl}-N-[2-(dimethylamino)ethyl]benzamide |

TABLE 1-continued

| Cpd. No. | Structure | Name |
|---|---|---|
| 637 | 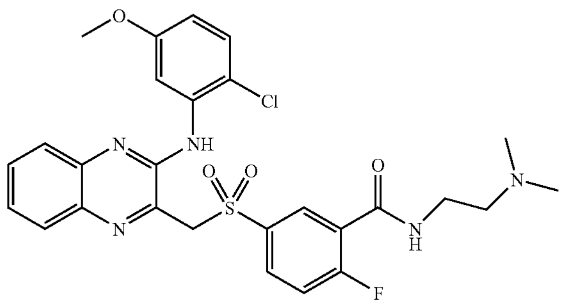 | 5-{[(3-{[2-chloro-5-(methoxy)phenyl]amino}quinoxalin-2-yl)amino]sulfonyl}-N-[2-(dimethylamino)ethyl]-2-fluorobenzamide |
| 638 | 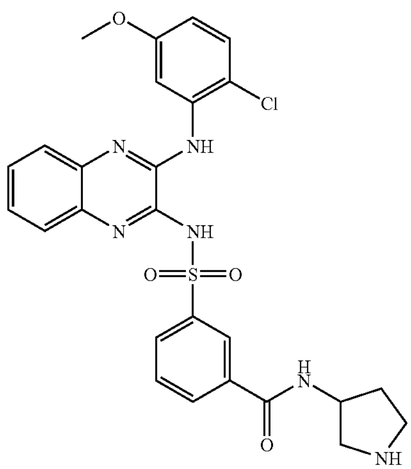 | 3-{[(3-{[2-chloro-5-(methoxy)phenyl]amino}quinoxalin-2-yl)amino]sulfonyl}-N-pyrrolidin-3-ylbenzamide |
| 639 | 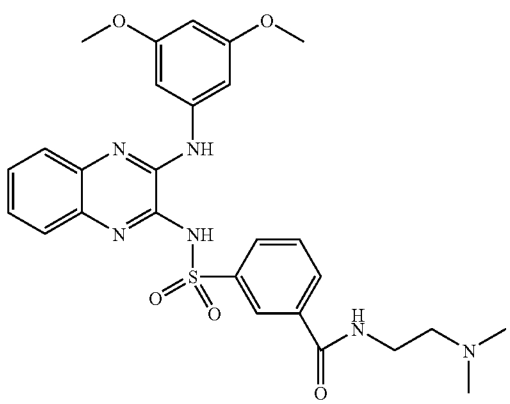 | 3-{[(3-{[3,5-bis(methoxy)phenyl]amino}quinoxalin-2-yl)amino]sulfonyl}-N-[2-(dimethylamino)ethyl]benzamide |
| 640 | 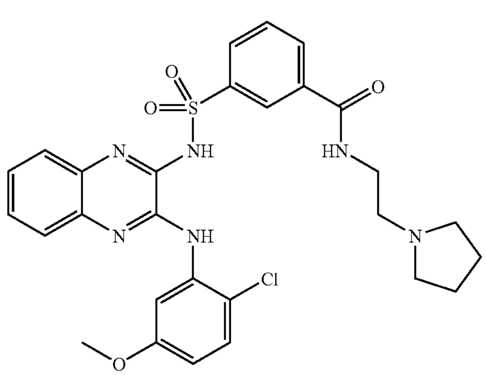 | 3-{[(3-{[2-chloro-5-(methoxy)phenyl]amino}quinoxalin-2-yl)amino]sulfonyl}-N-(2-pyrrolidin-1-ylethyl)benzamide |

TABLE 1-continued

| Cpd. No. | Structure | Name |
|---|---|---|
| 641 | 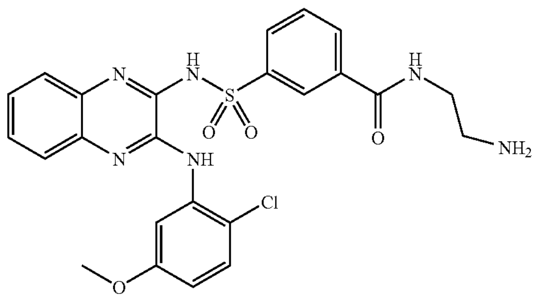 | N-(2-aminoethyl)-3-{[(3-{[2-chloro-5-(methoxy)phenyl]amino}quinoxalin-2-yl)amino]sulfonyl}benzamide |
| 642 | 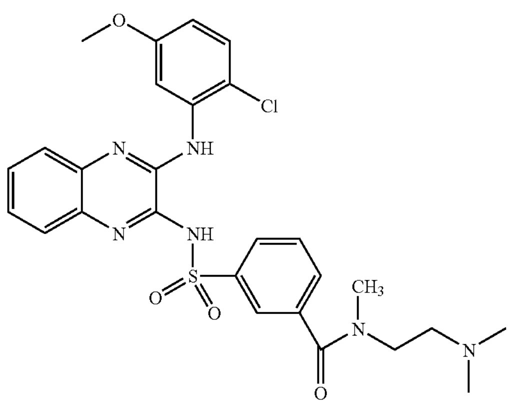 | 3-{[(3-{[2-chloro-5-(methoxy)phenyl]amino}quinoxalin-2-yl)amino]sulfonyl}-N-[2-(dimethylamino)ethyl]-N-methylbenzamide |
| 643 | 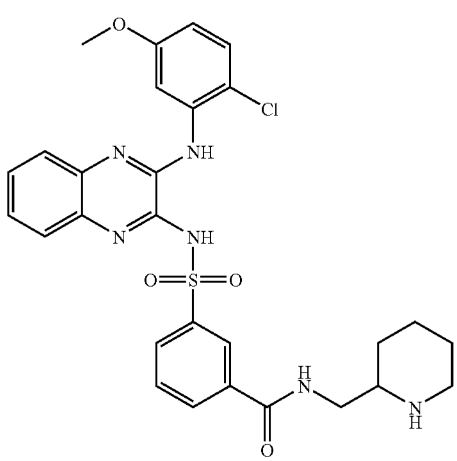 | 3-{[(3-{[2-chloro-5-(methoxy)phenyl]amino}quinoxalin-2-yl)amino]sulfonyl}-N-(piperidin-2-ylmethyl)benzamide |

| Cpd. No. | Structure | Name |
|---|---|---|
| 644 | 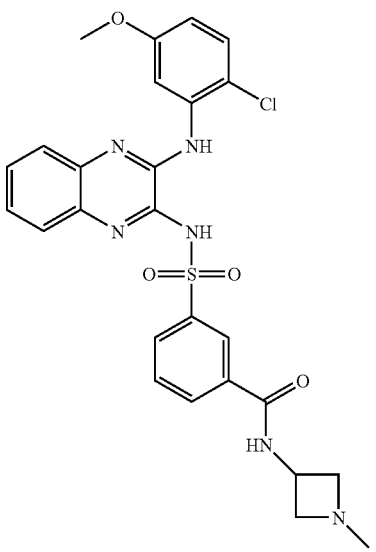 | 3-{[(3-{[2-chloro-5-(methoxy)phenyl]amino}quinoxalin-2-yl)amino]sulfonyl}-N-(1-methylazetidin-3-yl)benzamide |
| 645 | 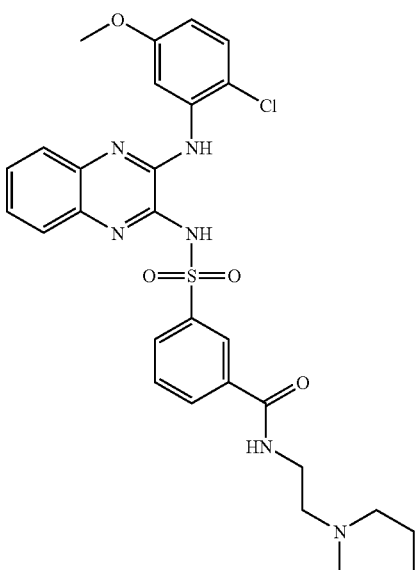 | 3-{[(3-{[2-chloro-5-(methoxy)phenyl]amino}quinoxalin-2-yl)amino]sulfonyl}-N-(2-piperidin-1-ylethyl)benzamide |

TABLE 1-continued

| Cpd. No. | Structure | Name |
|---|---|---|
| 646 | 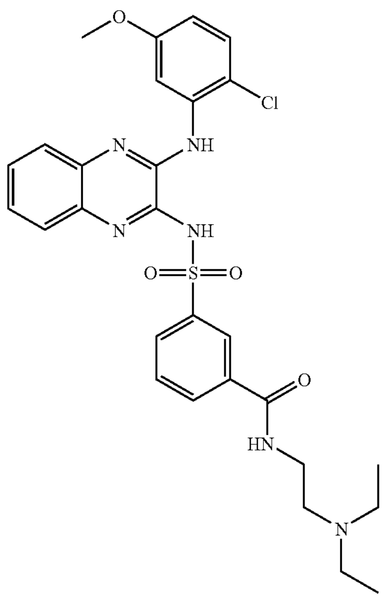 | 3-{[(3-{[2-chloro-5-(methoxy)phenyl]amino}quinoxalin-2-yl)amino]sulfonyl}-N-[2-(diethylamino)ethyl]benzamide |
| 647 | 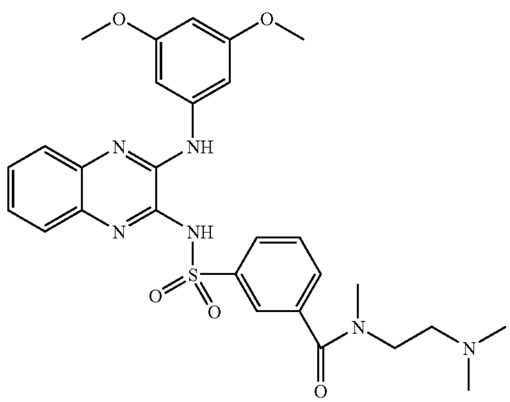 | 3-{[(3-{[3,5-bis(methoxy)phenyl]amino}quinoxalin-2-yl)amino]sulfonyl}-N-[2-(dimethylamino)ethyl]-N-methylbenzamide |
| 648 | 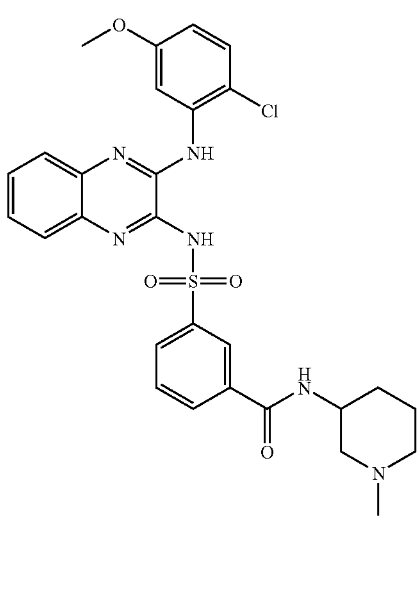 | 3-{[(3-{[2-chloro-5-(methoxy)phenyl]amino}quinoxalin-2-yl)amino]sulfonyl}-N-(1-methylpiperidin-3-yl)benzamide |

TABLE 1-continued
| Cpd. No. | Structure | Name |
|---|---|---|
| 649 | 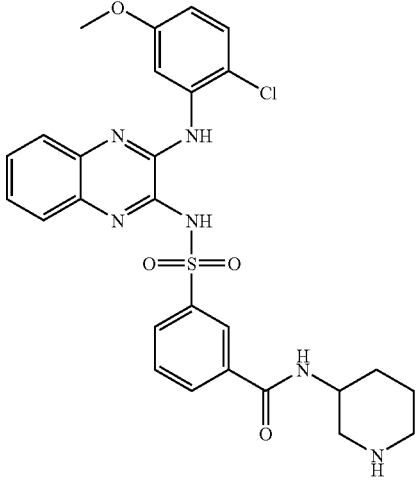 | 3-{[(3-{[2-chloro-5-(methoxy)phenyl]amino}quinoxalin-2-yl)amino]sulfonyl}-N-piperidin-3-ylbenzamide |
| 650 | 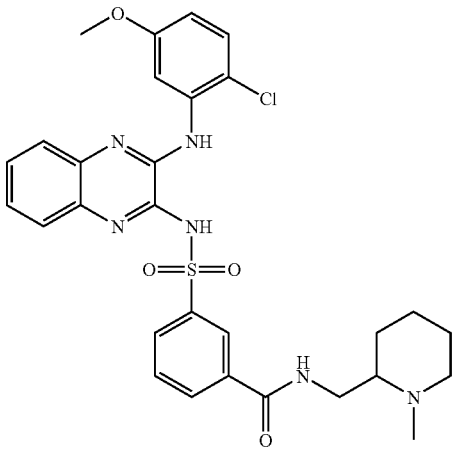 | 3-{[(3-{[2-chloro-5-(methoxy)phenyl]amino}quinoxalin-2-yl)amino]sulfonyl}-N-[(1-methylpiperidin-2-yl)methyl]benzamide |
| 651 | 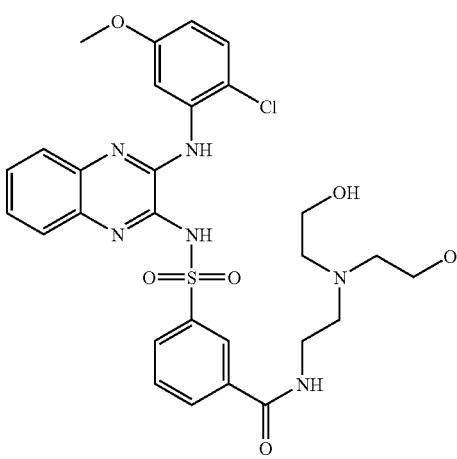 | N-{2-[bis(2-hydroxyethyl)amino]ethyl}-3-{[(3-{[2-chloro-5-(methoxy)phenyl]amino}quinoxalin-2-yl)amino]sulfonyl}benzamide |

TABLE 1-continued

| Cpd. No. | Structure | Name |
|---|---|---|
| 652 | 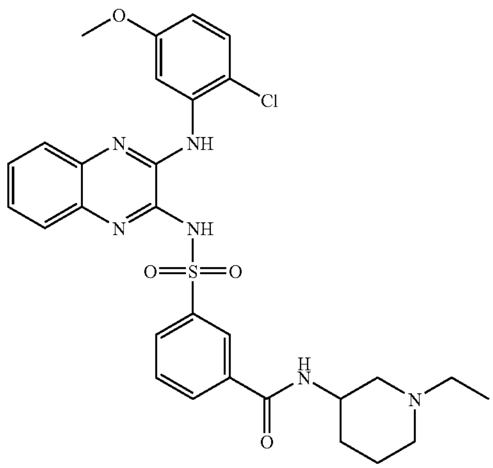 | 3-{[(3-{[2-chloro-5-(methoxy)phenyl]amino}quinoxalin-2-yl)amino]sulfonyl}-N-(1-ethylpiperidin-3-yl)benzamide |
| 653 | 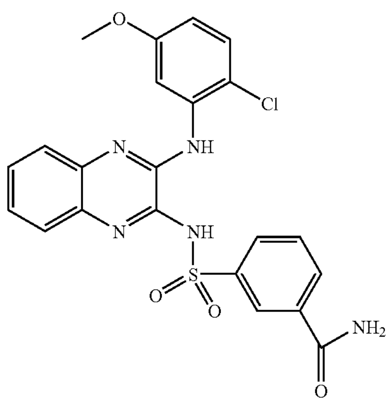 | 3-{[(3-{[2-chloro-5-(methoxy)phenyl]amino}quinoxalin-2-yl)amino]sulfonyl}benzamide |
| 654 | 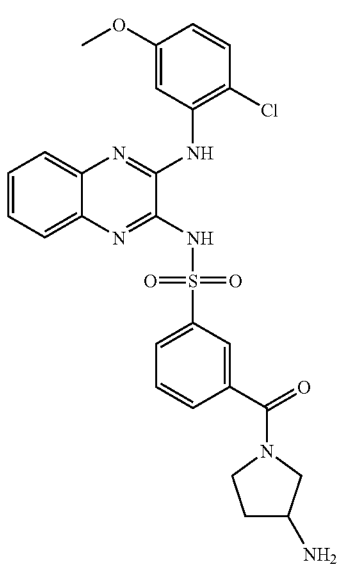 | 3-[(3-aminopyrrolidin-1-yl)carbonyl]-N-(3-{[2-chloro-5-(methoxy)phenyl]amino}quinoxalin-2-yl)benzenesulfonamide |

TABLE 1-continued

| Cpd. No. | Structure | Name |
|---|---|---|
| 655 | 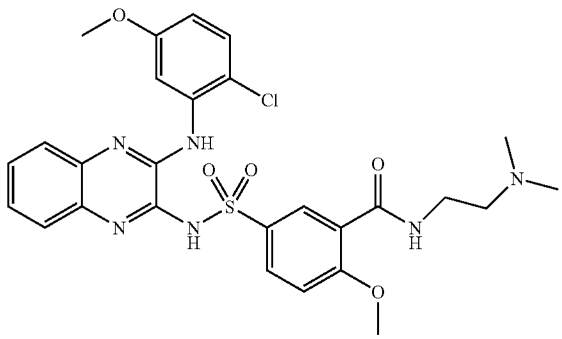 | 5-{[(3-{[2-chloro-5-(methoxy)phenyl]amino}quinoxalin-2-yl)amino]sulfonyl}-N-[2-(dimethylamino)ethyl]-2-(methoxy)benzamide |
| 656 | 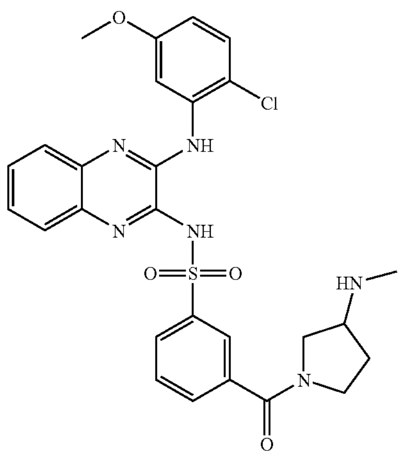 | N-(3-{[2-chloro-5-(methoxy)phenyl]amino}quinoxalin-2-yl)-3-{[3-(methylamino)pyrrolidin-1-yl]carbonyl}benzenesulfonamide |
| 657 | 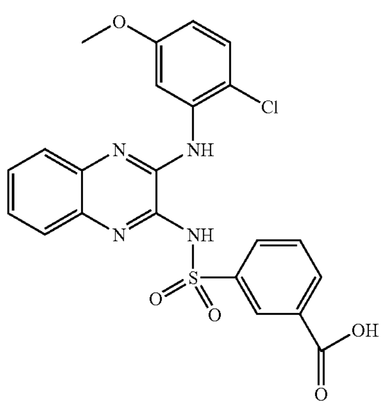 | 3-{[(3-{[(2-chloro-5-(methoxy)phenyl]amino}quinoxalin-2-yl)amino]sulfonyl}benzoicacid |
| 658 | 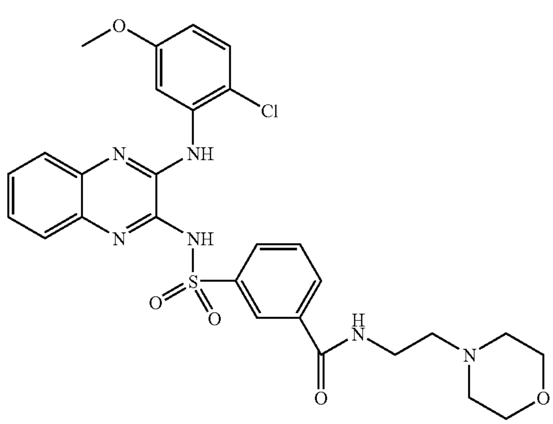 | 3-{[(3-{[2-chloro-5-(methoxy)phenyl]amino}quinoxalin-2-yl)amino]sulfonyl}-N-(2-morpholin-4-ylethyl)benzamide |

TABLE 1-continued

| Cpd. No. | Structure | Name |
|---|---|---|
| 659 | 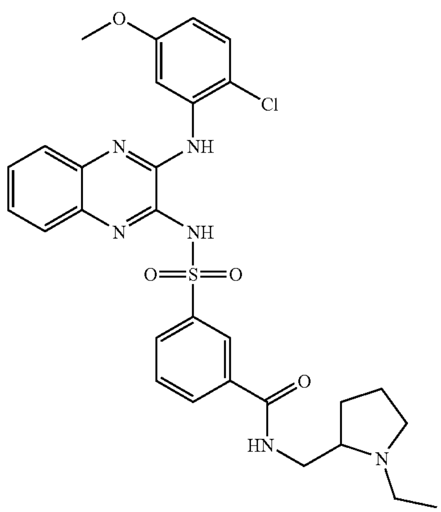 | 3-{[(3-{[2-chloro-5-(methoxy)phenyl]amino}quinoxalin-2-yl)amino]sulfonyl}-N-[(1-ethylpyrrolidin-2-yl)methyl]benzamide |
| 660 | 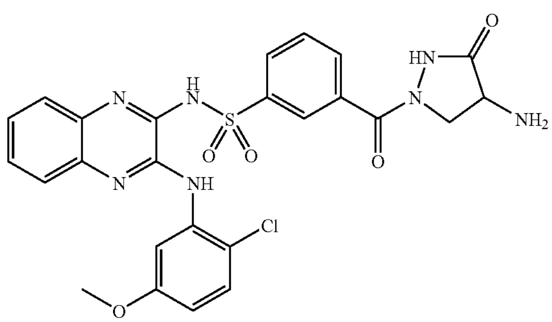 | 3-[(4-amino-3-oxopyrazolidin-1-yl)carbonyl]-N-(3-{[2-chloro-5-(methoxy)phenyl]amino}quinoxalin-2-yl)benzenesulfonamide |
| 661 | 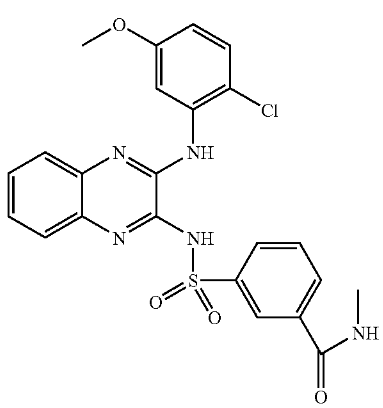 | 3-{[(3-{[2-chloro-5-(methoxy)phenyl]amino}quinoxalin-2-yl)amino]sulfonyl}-N-methylbenzamide |

TABLE 1-continued

| Cpd. No. | Structure | Name |
|---|---|---|
| 662 | 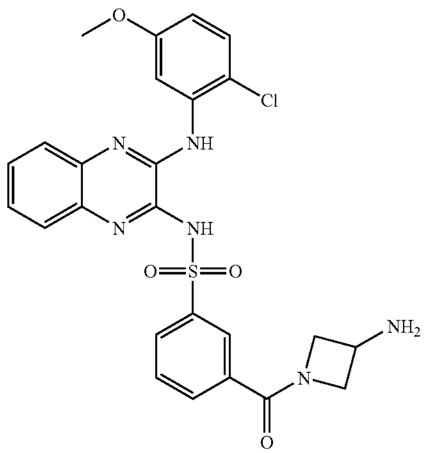 | 3-[(3-aminoazetidin-1-yl)carbonyl]-N-(3-{[2-chloro-5-(methoxy)phenyl]amino}quinoxalin-2-yl)benzenesulfonamide |
| 663 | 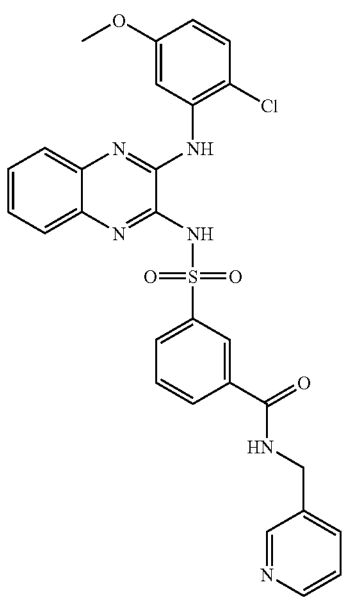 | 3-{[(3-{[2-chloro-5-(methoxy)phenyl]amino}quinoxalin-2-yl)amino]sulfonyl}-N-(pyridin-3-ylmethyl)benzamide |
| 664 | 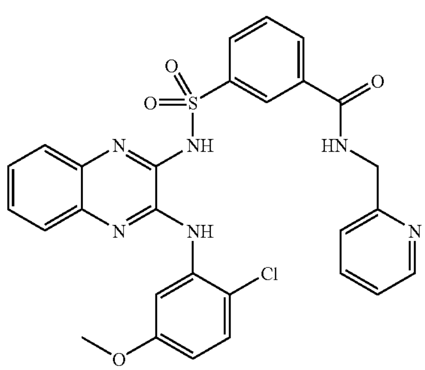 | 3-{[(3-{[2-chloro-5-(methoxy)phenyl]amino}quinoxalin-2-yl)amino]sulfonyl}-N-(pyridin-2-ylmethyl)benzamide |

TABLE 1-continued

| Cpd. No. | Structure | Name |
|---|---|---|
| 665 | 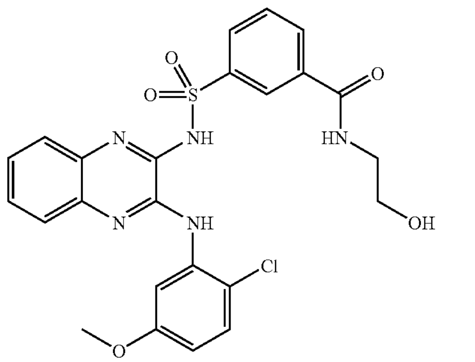 | 3-{[(3-{[2-chloro-5-(methoxy)phenyl]amino}quinoxalin-2-yl)amino]sulfonyl}-N-(2-hydroxyethyl)benzamide |
| 666 | 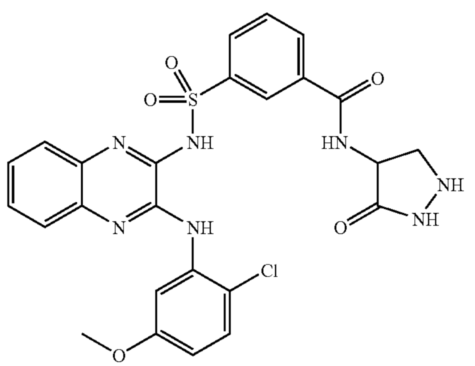 | 3-{[(3-{[2-chloro-5-(methoxy)phenyl]amino}quinoxalin-2-yl)amino]sulfonyl}-N-(3-oxopyrazolidin-4-yl)benzamide |
| 667 | 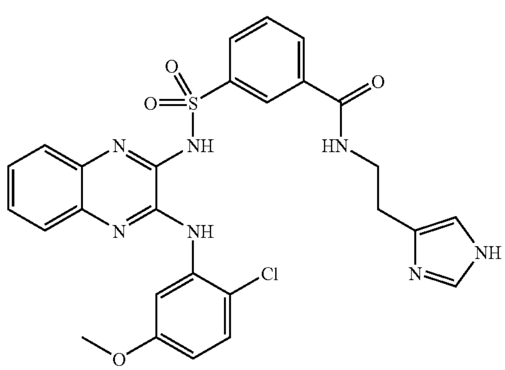 | 3-{[(3-{[2-chloro-5-(methoxy)phenyl]amino}quinoxalin-2-yl)amino]sulfonyl}-N-[2-(1H-imidazol-4-yl)ethyl]benzamide |
| 668 | 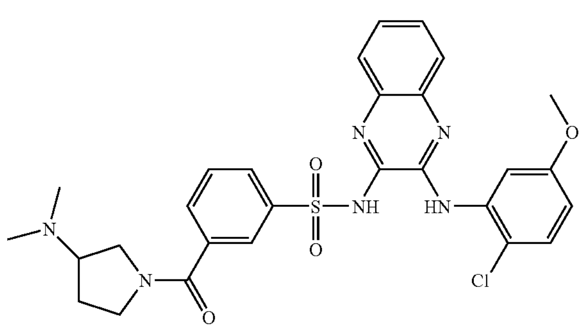 | N-(3-{[2-chloro-5-(methoxy)phenyl]amino}quinoxalin-2-yl)-3-{[3-(dimethylamino)pyrrolidin-1-yl]carbonyl}benzenesulfonamide |

TABLE 1-continued

| Cpd. No. | Structure | Name |
|---|---|---|
| 669 | 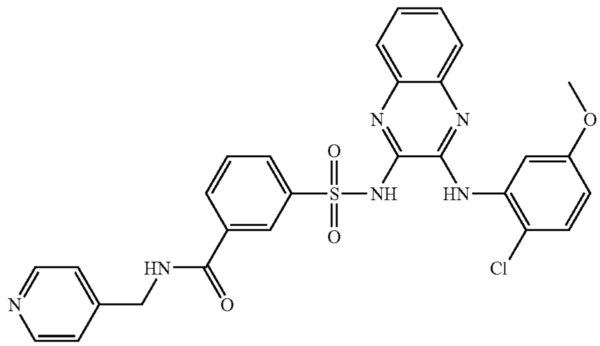 | 3-{[(3-{[2-chloro-5-(methoxy)phenyl]amino}quinoxalin-2-yl)amino]sulfonyl}-N-(pyridin-4-ylmethyl)benzamide |
| 670 | 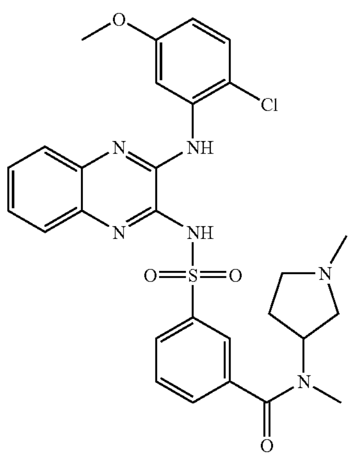 | 3-{[(3-{[2-chloro-5-(methoxy)phenyl]amino}quinoxalin-2-yl)amino]sulfonyl}-N-methyl-N-(1-methylpyrrolidin-3-yl)benzamide |
| 671 | 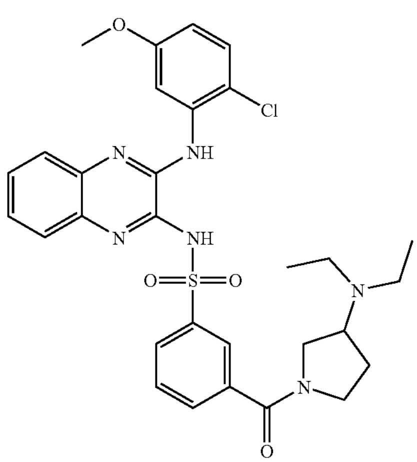 | N-(3-{[2-chloro-5-(methoxy)phenyl]amino}quinoxalin-2-yl)-3-{[3-(diethylamino)pyrrolidin-1-yl]carbonyl}benzenesulfonamide |

| Cpd. No. | Structure | Name |
|---|---|---|
| 672 | 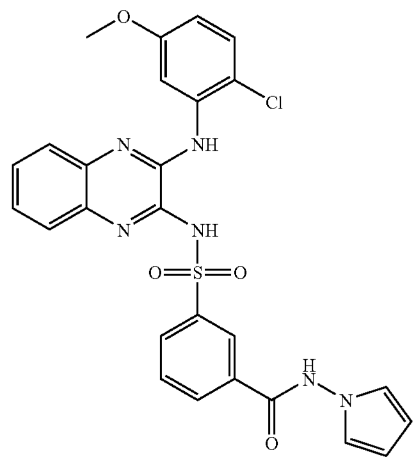 | 3-{[(3-{[2-chloro-5-(methoxy)phenyl]amino}quinoxalin-2-yl)amino]sulfonyl}-N-1H-pyrrol-1-ylbenzamide |
| 673 | 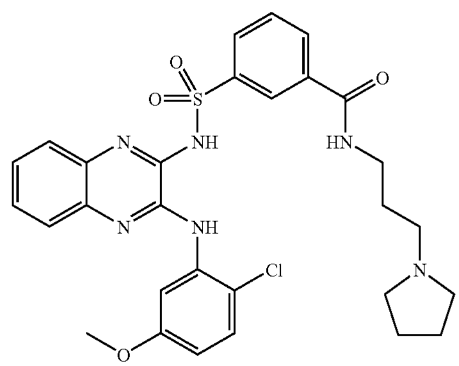 | 3-{[(3-{[2-chloro-5-(methoxy)phenyl]amino}quinoxalin-2-yl)amino]sulfonyl}-N-(3-pyrrolidin-1-ylpropyl)benzamide |
| 674 | 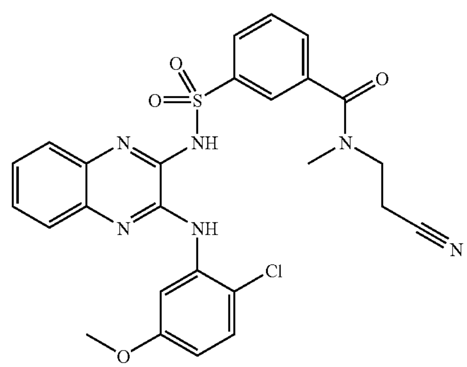 | 3-{[(3-{[2-chloro-5-(methoxy)phenyl]amino}quinoxalin-2-yl)amino]sulfonyl}-N-(2-cyanoethyl)-N-methylbenzamide |
| 675 | 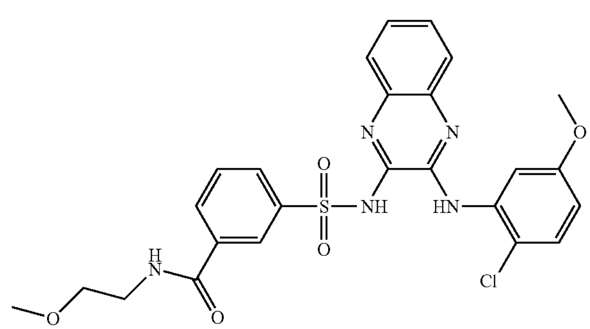 | 3-{[(3-{[2-chloro-5-(methoxy)phenyl]amino}quinoxalin-2-yl)amino]sulfonyl}-N-[2-(methoxy)ethyl]benzamide |

| Cpd. No. | Structure | Name |
|---|---|---|
| 676 | 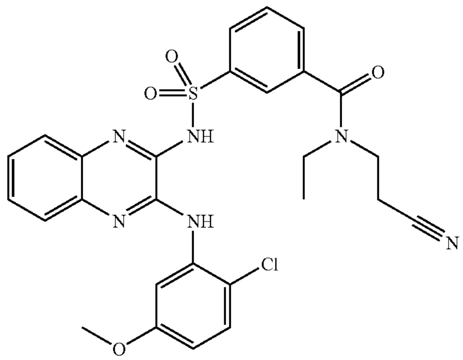 | 3-{[(3-{[2-chloro-5-(methoxy)phenyl]amino}quinoxalin-2-yl)amino]sulfonyl}-N-(2-cyanoethyl)-N-ethylbenzamide |
| 677 | 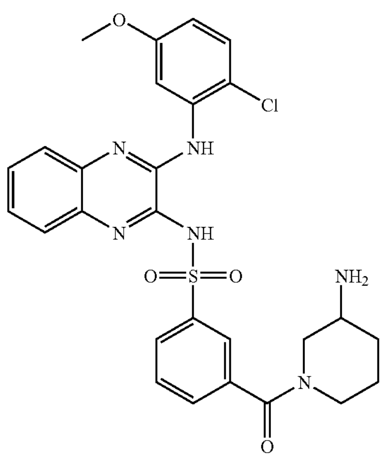 | 3-[(3-aminopiperidin-1-yl)carbonyl]-N-(3-{[2-chloro-5-(methoxy)phenyl]amino}quinoxalin-2-yl)benzenesulfonamide |
| 678 | 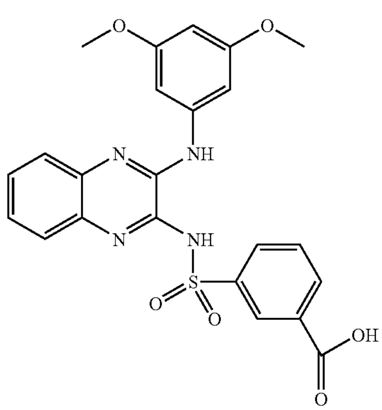 | 3-{[(3-{[3,5-bis(methoxy)phenyl]amino}quinoxalin-2-yl)amino]sulfonyl}benzoicacid |

TABLE 1-continued

| Cpd. No. | Structure | Name |
|---|---|---|
| 679 | 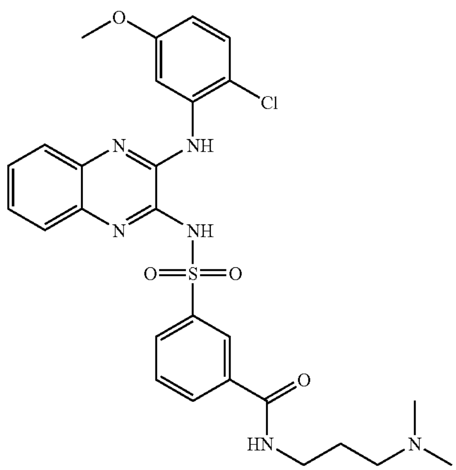 | 3-{[(3-{[2-chloro-5-(methoxy)phenyl]amino}quinoxalin-2-yl)amino]sulfonyl}-N-[3-(dimethylamino)propyl]benzamide |
| 680 | 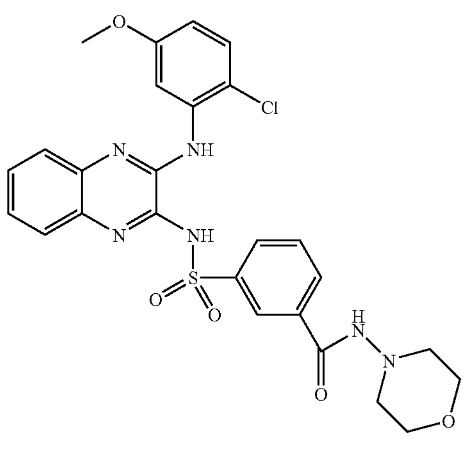 | 3-{[(3-{[2-chloro-5-(methoxy)phenyl]amino}quinoxalin-2-yl)amino]sulfonyl}-N-morpholin-4-ylbenzamide |
| 681 | 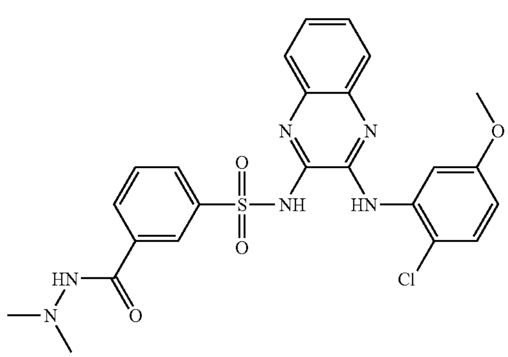 | N-(3-{[2-chloro-5-(methoxy)phenyl]amino}quinoxalin-2-yl)-3-[(2,2-dimethylhydrazino)carbonyl]benzenesulfonamide |

TABLE 1-continued

| Cpd. No. | Structure | Name |
|---|---|---|
| 682 | 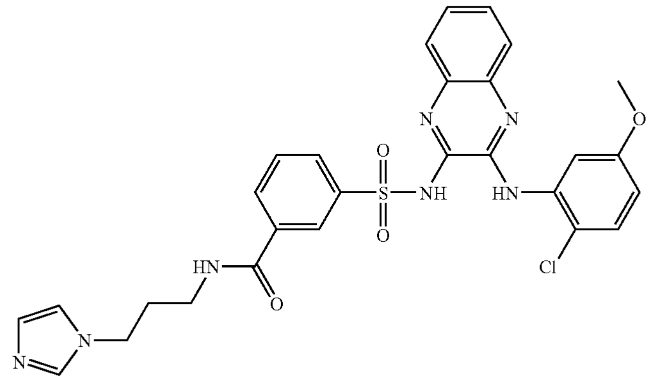 | 3-{[(3-{[2-chloro-5-(methoxy)phenyl]amino}quinoxalin-2-yl)amino]sulfonyl}-N-[3-(1H-imidazol-1-yl)propyl]benzamide |
| 683 | 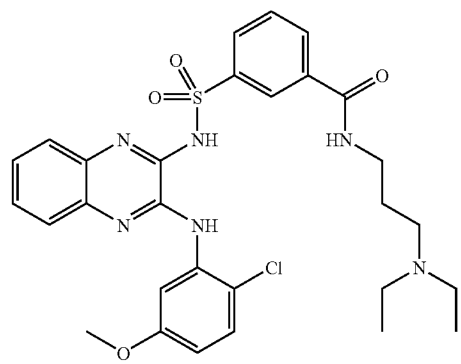 | 3-{[(3-{[2-chloro-5-(methoxy)phenyl]amino}quinoxalin-2-yl)amino]sulfonyl}-N-[3-(diethylamino)propyl]benzamide |
| 684 | 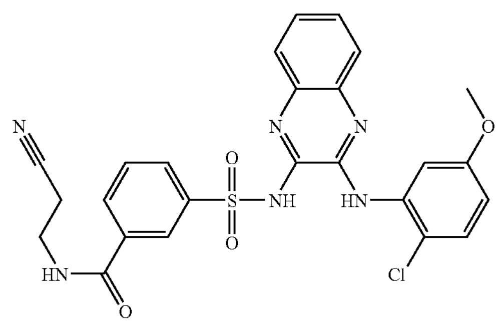 | 3-{[(3-{[2-chloro-5-(methoxy)phenyl]amino}quinoxalin-2-yl)amino]sulfonyl}-N-(2-cyanoethyl)benzamide |
| 685 | 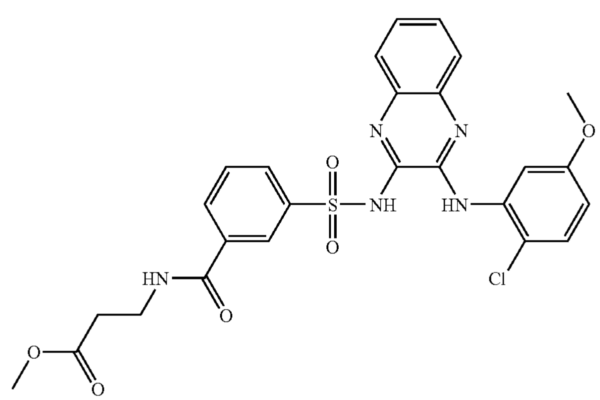 | methylN-[(3-{[(3-{[2-chloro-5-(methoxy)phenyl]amino}quinoxalin-2-yl)amino]sulfonyl}phenyl)carbinyl]-beta-alaninate |

TABLE 1-continued

| Cpd. No. | Structure | Name |
|---|---|---|
| 686 | 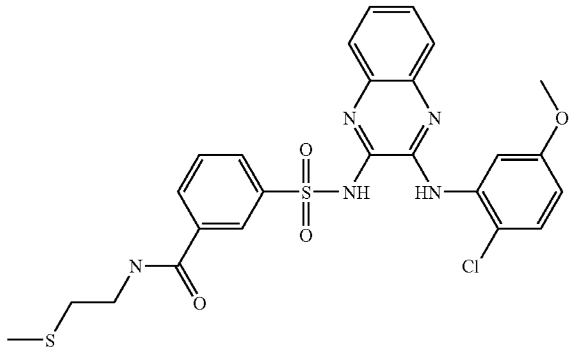 | 3-{[(3-{[2-chloro-5-(methoxy)phenyl]amino}quinoxalin-2-yl)amino]sulfonyl}-N-[2-(methylthio)ethyl]benzamide |
| 687 | 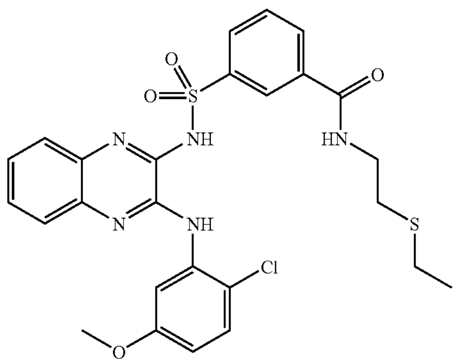 | 3-{[(3-{[2-chloro-5-(methoxy)phenyl]amino}quinoxalin-2-yl)amino]sulfonyl}-N-[2-(ethylthio)ethyl]benzamide |
| 688 | 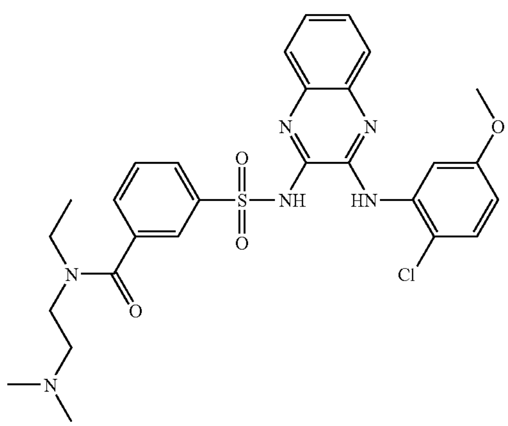 | 3-{[(3-{[2-chloro-5-(methoxy)phenyl]amino}quinoxalin-2-yl)amino]sulfonyl}-N-[2-(dimethylamino)ethyl]-N-ethylbenzamide |
| 689 | 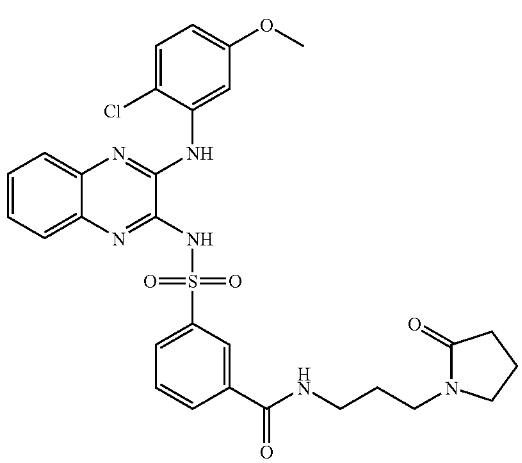 | 3-{[(3-{[2-chloro-5-(methoxy)phenyl]amino}quinoxalin-2-yl)amino]sulfonyl}-N-[3-(2-oxopyrrolidin-1-yl)propyl]benzamide |

TABLE 1-continued

| Cpd. No. | Structure | Name |
|---|---|---|
| 690 | 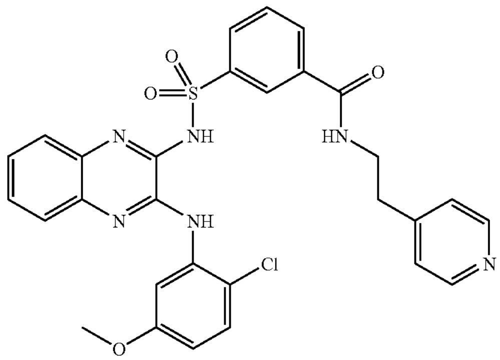 | 3-{[(3-{[2-chloro-5-(methoxy)phenyl]amino}quinoxalin-2-yl)amino]sulfonyl}-N-(2-pyridin-4-ylethyl)benzamide |
| 691 | 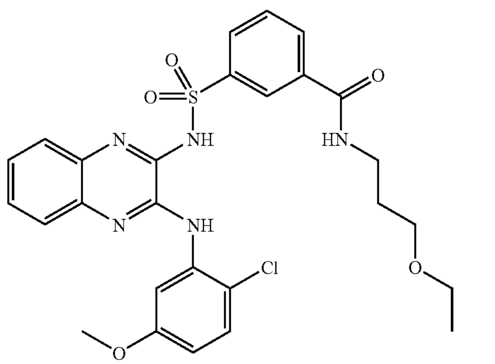 | 3-{[(3-{[2-chloro-5-(methoxy)phenyl]amino}quinoxalin-2-yl)amino]sulfonyl}-N-[3-(ethyloxy)propyl]benzamide |
| 692 | 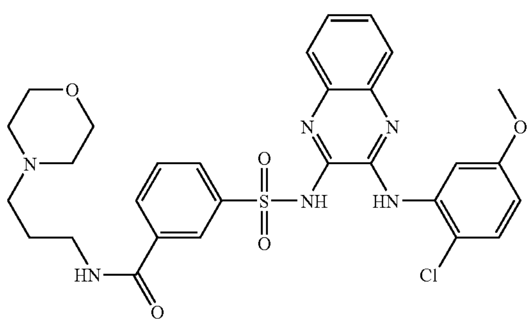 | 3-{[(3-{[2-chloro-5-(methoxy)phenyl]amino}quinoxalin-2-yl)amino]sulfonyl}-N-(3-morpholin-4-ylpropyl)benzamide |
| 693 | 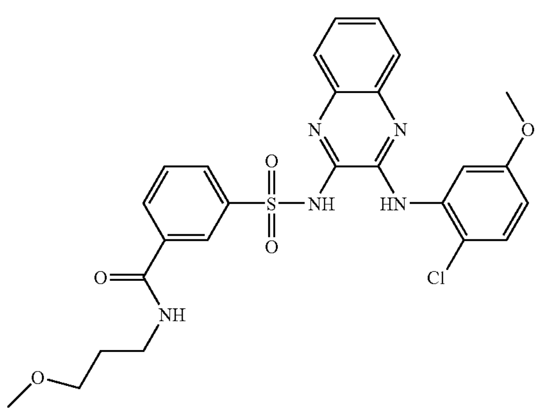 | 3-{[(3-{[2-chloro-5-(methoxy)phenyl]amino}quinoxalin-2-yl)amino]sulfonyl}-N-[3-(methoxy)propyl]benzamide |

| Cpd. No. | Structure | Name |
|---|---|---|
| 694 | 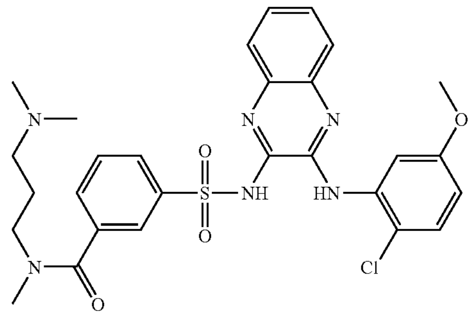 | 3-{[(3-{[2-chloro-5-(methoxy)phenyl]amino}quinoxalin-2-yl)amino]sulfonyl}-N-[3-(dimethylamino)propyl]-N-methylbenzamide |
| 695 | 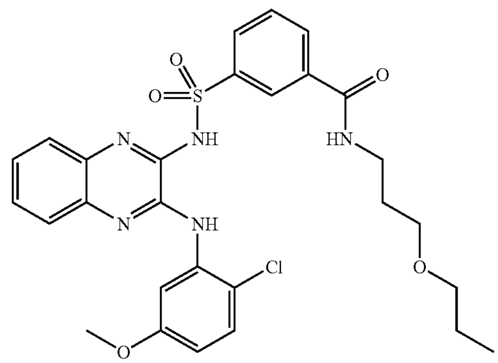 | 3-{[(3-{[2-chloro-5-(methoxy)phenyl]amino}quinoxalin-2-yl)amino]sulfonyl}-N-[3-(propyloxy)propyl]benzamide |
| 696 | 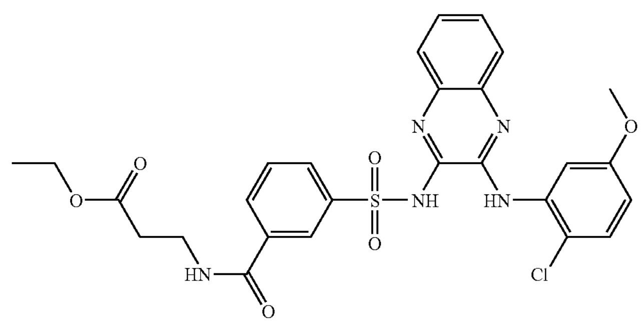 | ethylN-[(3-{[(3-{[2-chloro-5-(methoxy)phenyl]amino}quinoxalin-2-yl)amino]sulfonyl}phenyl)carbonyl]-beta-alaninate |
| 697 | 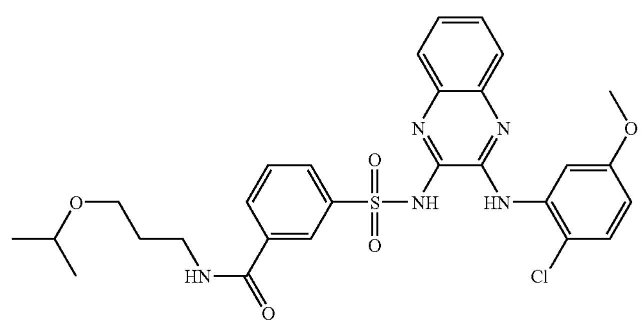 | 3-{[(3-{[2-chloro-5-(methoxy)phenyl]amino}quinoxalin-2-yl)amino]sulfonyl}-N-{3-[(1-methylethyl)oxy]propyl}benzamide |

| Cpd. No. | Structure | Name |
|---|---|---|
| 698 | 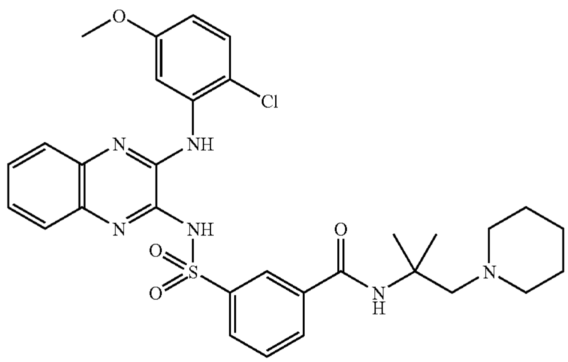 | 3-{[(3-{[2-chloro-5-(methoxy)phenyl]amino}quinoxalin-2-yl)amino]sulfonyl}-N-(1,1-dimethyl-2-piperidin-1-ylethyl)benzamide |
| 699 | 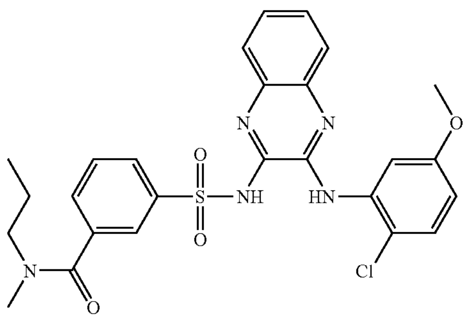 | 3-{[(3-{[2-chloro-5-(methoxy)phenyl]amino}quinoxalin-2-yl)amino]sulfonyl}-N-methyl-N-propylbenzamide |
| 700 | 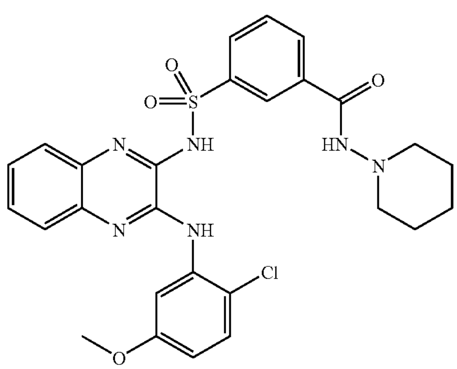 | 3-{[(3-{[2-chloro-5-(methoxy)phenyl]amino}quinoxalin-2-yl)amino]sulfonyl}-N-piperidin-1-ylbenzamide |
| 701 | 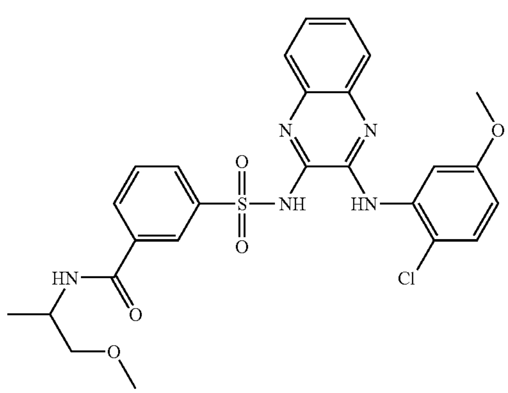 | 3-{[(3-{[2-chloro-5-(methoxy)phenyl]amino}quinoxalin-2-yl)amino]sulfonyl}-N-[1-methyl-2-(methoxy)ethyl]benzamide |

TABLE 1-continued

| Cpd. No. | Structure | Name |
|---|---|---|
| 702 | 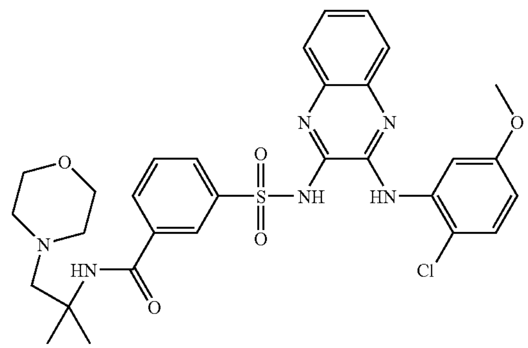 | 3-{[(3-{[2-chloro-5-(methoxy)phenyl]amino}quinoxalin-2-yl)amino]sulfonyl}-N-(1,1-dimethyl-2-morpholin-4-ylethyl)benzamide |
| 703 | 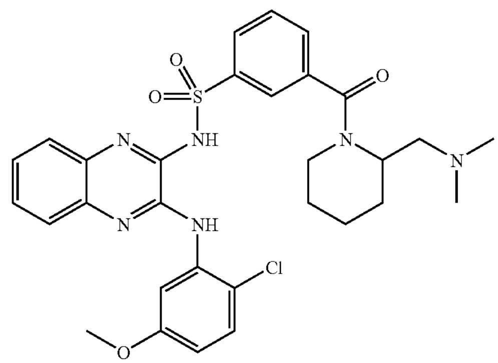 | N-(3-{[2-chloro-5-(methoxy)phenyl]amino}quinoxalin-2-yl)-3-({2-[(dimethylamino)methyl]piperidin-1-yl}carbonyl)benzenesulfonamide |
| 704 | 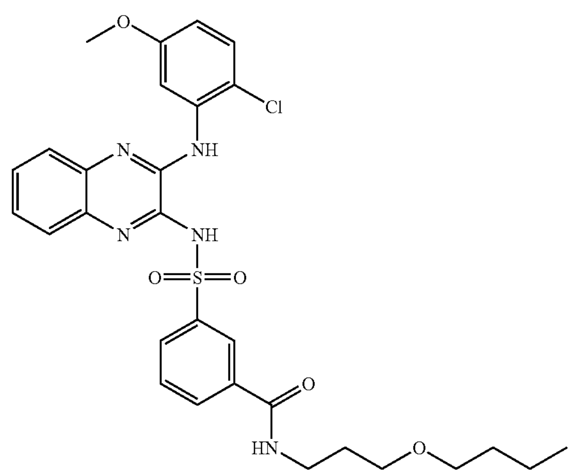 | N-[3-(butyloxy)propyl]-3-{[(3-{[2-chloro-5-(methoxy)phenyl]amino}quinoxalin-2-yl)amino]sulfonyl}benzamide |
| 705 | 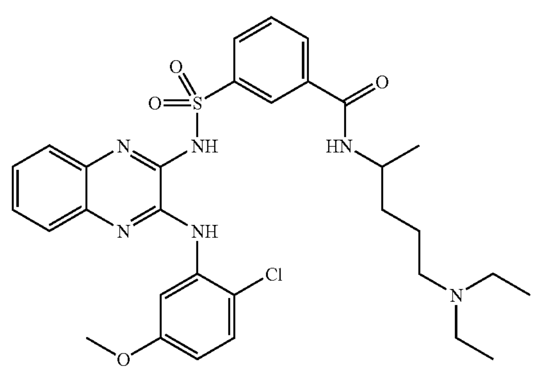 | 3-{[(3-{[2-chloro-5-(methoxy)phenyl]amino}quinoxalin-2-yl)amino]sulfonyl}-N-[4-(diethylamino)-1-methylbutyl]benzamide |

TABLE 1-continued

| Cpd. No. | Structure | Name |
|---|---|---|
| 706 | 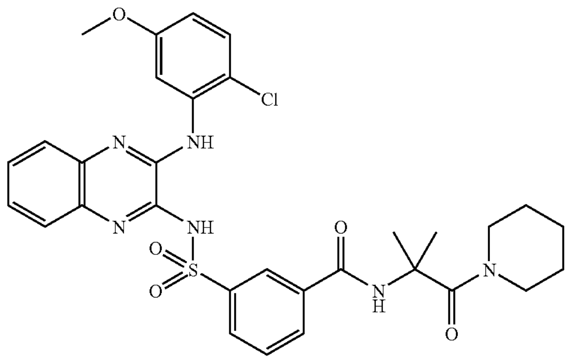 | 3-{[(3-{[2-chloro-5-(methoxy)phenyl]amino}quinoxalin-2-yl)amino]sulfonyl}-N-(1,1-dimethyl-2-oxo-2-piperidin-1-ylethyl)benzamide |
| 707 | 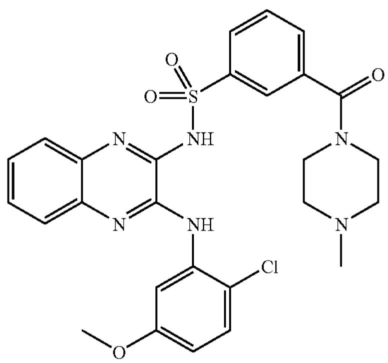 | N-(3-{[2-chloro-5-(methoxy)phenyl]amino}quinoxalin-2-yl)-3-[(4-methylpiperazin-1-yl)carbonyl]benzenesulfonamide |
| 708 | 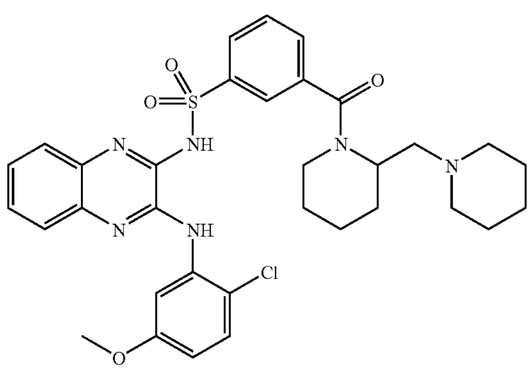 | N-(3-{[2-chloro-5-(methoxy)phenyl]amino}quinoxalin-2-yl)-3-{[2-(piperidin-1-ylmethyl)piperidin-1-yl]carbonyl}benzenesulfonamide |
| 709 | 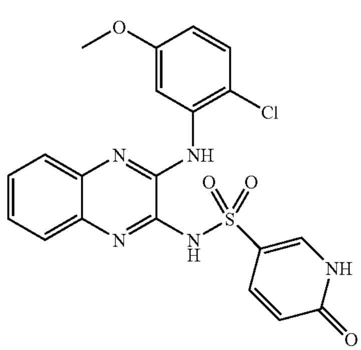 | N-(3-{[2-chloro-5-(methoxy)phenyl]amino}quinoxalin-2-yl)-6-oxo-1,6-dihydropyridine-3-sulfonamide |

TABLE 1-continued

| Cpd. No. | Structure | Name |
|---|---|---|
| 710 | 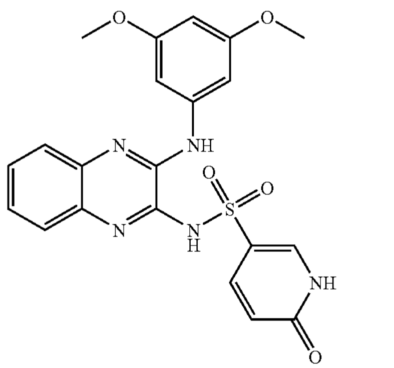 | N-(3-{[3,5-bis(methoxy)phenyl]amino}quinoxalin-2-yl)-6-oxo-1,6-dihydropyridine-3-sulfonamide |
| 711 | 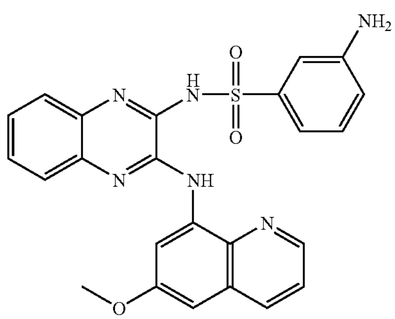 | 3-amino-N-(3-{[6-(methoxy)quinolin-8-yl]amino}quinoxalin-2-yl)benzenesulfonamide |
| 712 | 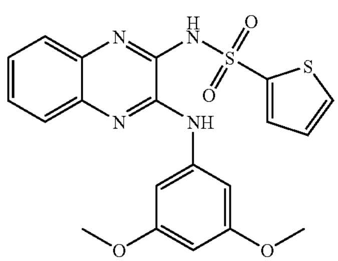 | N-(3-{[3,5-bis(methoxy)phenyl]amino}quinoxalin-2-yl)thiophene-2-sulfonamide |
| 713 | 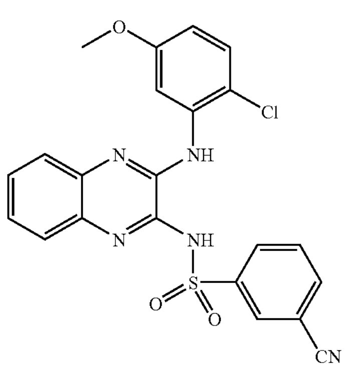 | N-(3-{[2-chloro-5-(methoxy)phenyl]amino}quinoxalin-2-yl)-3-cynaobenzenesulfonamide |

TABLE 1-continued

| Cpd. No. | Structure | Name |
|---|---|---|
| 714 | 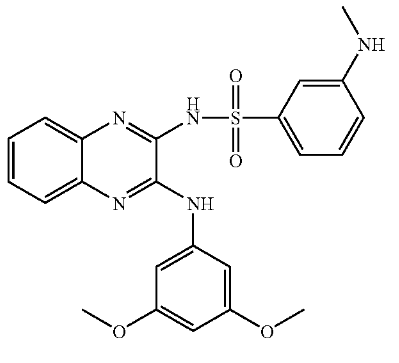 | N-(3-{[3,5-bis(methyoxy)phenyl]amino}quinoxalin-2-yl)-3-(methylamino)benzenesulfonamide |
| 715 | 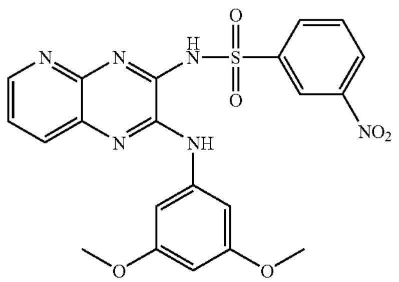 | N-(2-{[3,5-bis(methoxy)phenyl]amino}pyrido-[2,3-b]pyrazin-3-yl)-3-nitrobenzenesulfonamide |
| 716 | 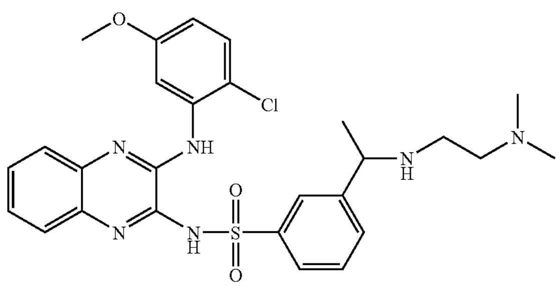 | N-(3-{[2-chloro-5-(methoxy)phenyl]amino}quinoxalin-2-yl)-3-(1-{[2-(dimethylamino)ethyl]amino}ethyl)benzenesulfonamide |
| 717 | 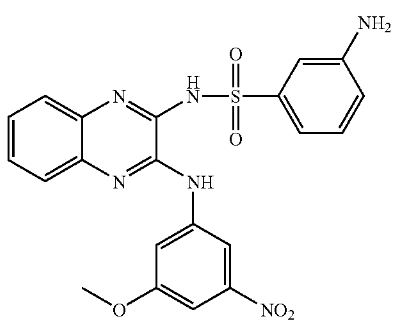 | 3-amino-N-(3-{[3-(methoxy)-5-nitrophenyl]amino}quinoxalin-2-yl)benzenesulfonamide |
| 718 | 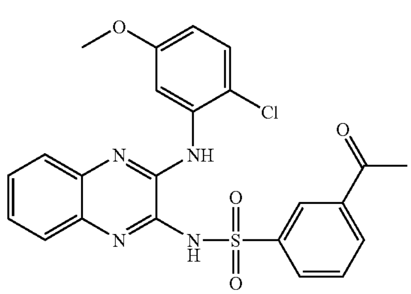 | 3-acetyl-N-(3-{[2-chloro-5-(methoxy)phenyl]amino}quinoxalin-2-yl)benzenesulfonamide |

TABLE 1-continued

| Cpd. No. | Structure | Name |
|---|---|---|
| 719 | 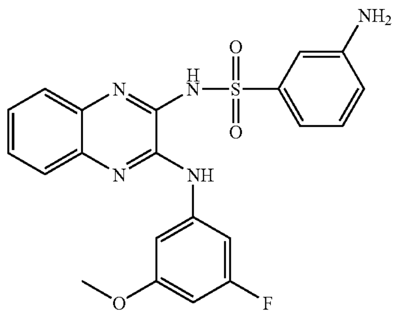 | 3-amino-N-(3-{[3-fluoro-5-(methoxy)phenyl]amino}quinoxalin-2-yl)benzenesulfonamide |
| 720 | 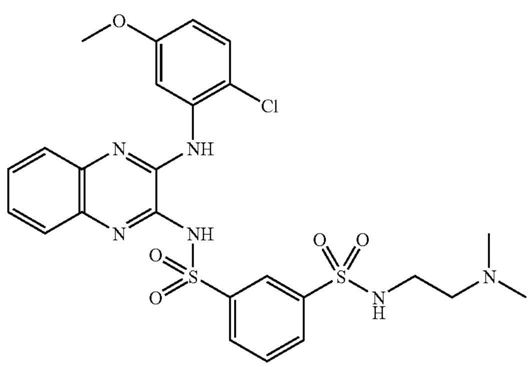 | N-(3-{[2-chloro-5-(methoxy)phenyl]amino}quinoxalin-2-yl)-N'-[2-(dimethylamino)ethyl]benzene-1,3-disulfonamide |
| 721 | 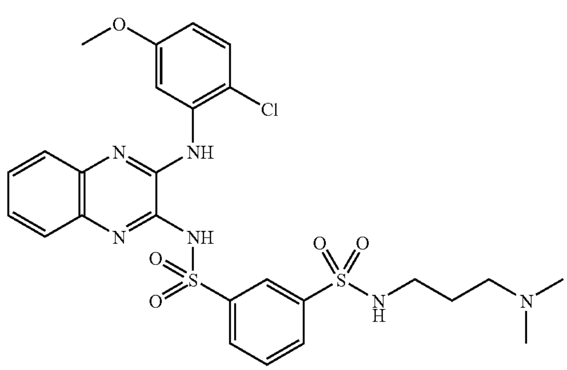 | N-(3-{[2-chloro-5-(methoxy)phenyl]amino}quinoxalin-2-yl)-N'-[3-(dimethylamino)propyl]benzene-1,3-disulfonamide |
| 722 | 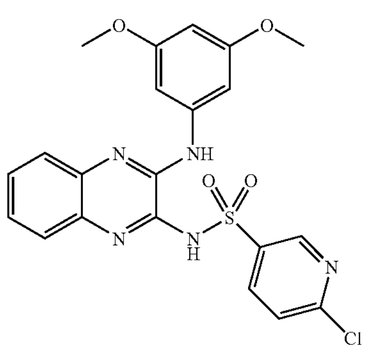 | N-(3-{[3,5-bis(methoxy)phenyl]amino}quinoxalin-2-yl)-6-chloropyridine-3-sulfonamide |

TABLE 1-continued

| Cpd. No. | Structure | Name |
|---|---|---|
| 723 | 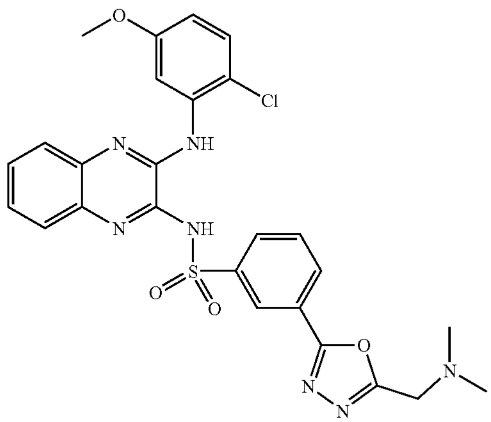 | N-(3-{[2-chloro-5-(methoxy)phenyl]amino}quinoxalin-2-yl)-3-{5-[(dimethylamino)methyl]-1,3,4-oxadiazol-2-yl}benzenesulfonamide |
| 724 | 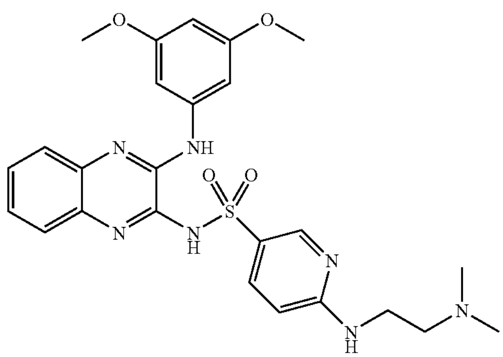 | N-(3-{[3,5-bis(methoxy)phenyl]amino}quinoxalin-2-yl)-6-{[2-(dimethylamino)ethyl]amino}pyridine-3-sulfonamide |
| 725 | 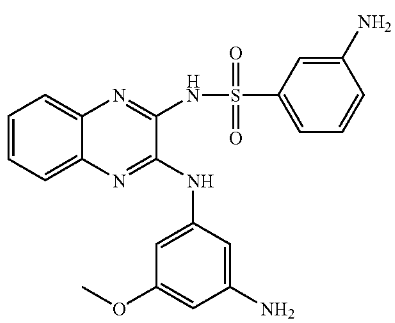 | 3-amino-N-(3-{[3-amino-5-(methoxy)phenyl]amino}quinoxalin-2-yl)benzenesulfonamide |
| 726 | 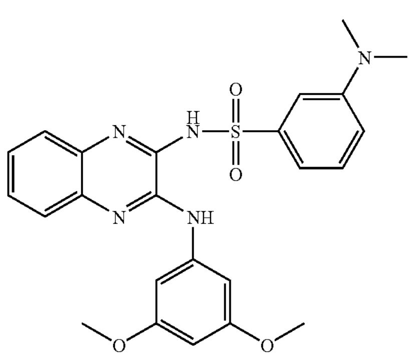 | N-(3-{[3,5-bis(methoxy)phenyl]amino}quinoxalin-2-yl)-3-(dimethylamino)benzenesulfonamide |

TABLE 1-continued

| Cpd. No. | Structure | Name |
|---|---|---|
| 727 | 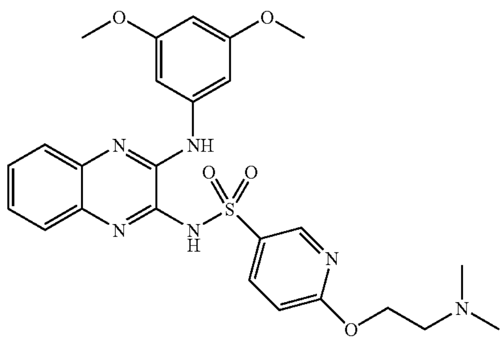 | N-(3-{[3,5-bis(methoxy)phenyl]amino}quinoxalin-2-yl)-6-{[2-(dimethylamino)ethyl]oxy}pyridin-3-sulfonamide |
| 728 | 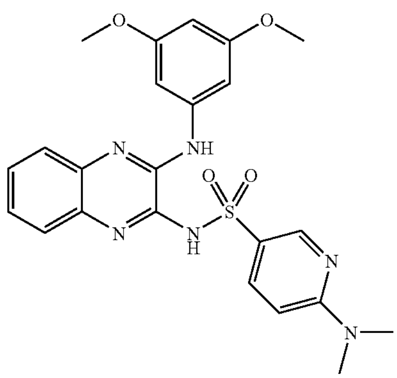 | N-(3-{[3,5-bis(methoxy)phenyl]amino}quinoxalin-2-yl)-6-(dimethylamino)pyridine-3-sulfonamide |
| 729 | 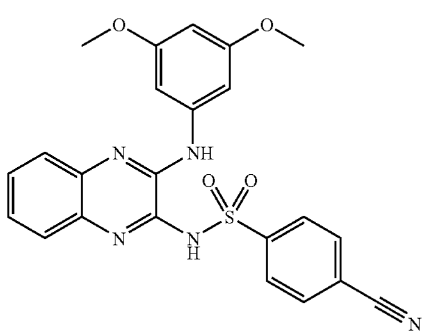 | N-(3-{[3,5-bis(methoxy)phenyl]amino}quinoxalin-2-yl)-4-cyanobenzenesulfonamide |
| 730 | 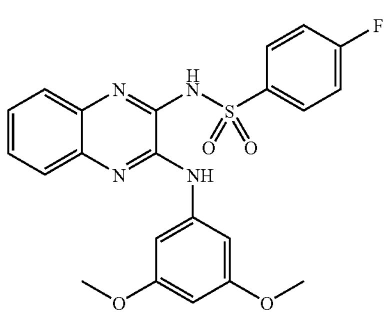 | N-(3-{[3,5-bis(methoxy)phenyl]amino}quinoxalin-2-yl)-4-fluorobenzenesulfonamide |

TABLE 1-continued

| Cpd. No. | Structure | Name |
|---|---|---|
| 731 | 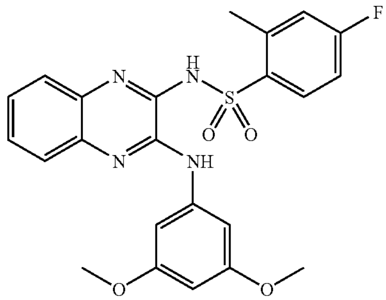 | N-(3-{[3,5-bis(methoxy)phenyl]amino}quinoxalin-2-yl)-4-fluoro-2-methylbenzenesulfonamide |
| 732 | 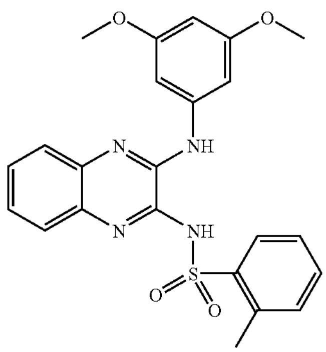 | N-(3-{[3,5-bis(methoxy)phenyl]amino}quinoxalin-2-yl)-2-methylbenzenesulfonamide |
| 733 | 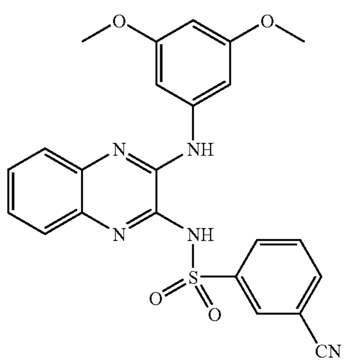 | N-(3-{[3,5-bis(methoxy)phenyl]amino}quinoxalin-2-yl)-3-cyanobenzenesulfonamide |
| 734 | 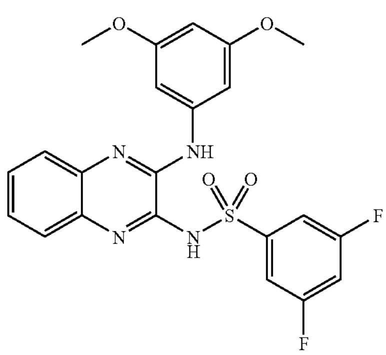 | N-(3-{[3,5-bis(methoxy)phenyl]amino}quinoxalin-2-yl)-3,5-difluorobenzenesulfonamide |

TABLE 1-continued

| Cpd. No. | Structure | Name |
|---|---|---|
| 735 | 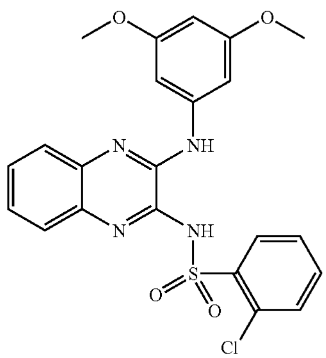 | N-(3-{[3,5-bis(methoxy)phenyl]amino}quinoxalin-2-yl)-2-chlorobenzenesulfonamide |
| 736 | 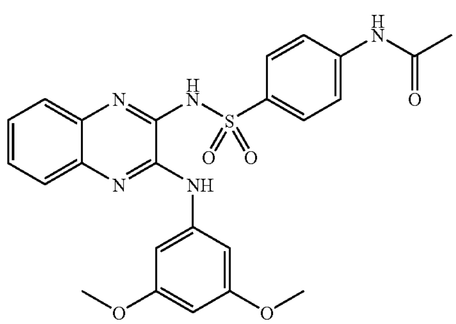 | N-(4-{[(3-{[3,5-bis(methoxy)phenyl]amino}quinoxalin-2-yl)amino]sulfonyl}phenyl)acetamide |
| 737 | 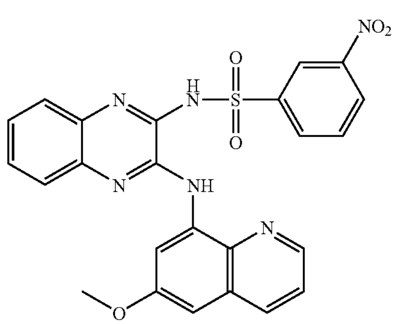 | N-(3-{[6-(methoxy)quinolin-8-yl]amino}quinoxalin-2-yl)-3-nitrobenzenesulfonamide |
| 738 | 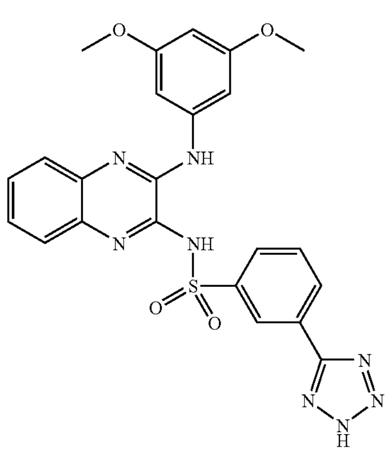 | N-(3-{[3,5-bis(methoxy)phenyl]amino}quinoxalin-2-yl)-3-(2H-tetrazol-5-yl)benzenesulfonamide |

TABLE 1-continued

| Cpd. No. | Structure | Name |
|---|---|---|
| 739 | 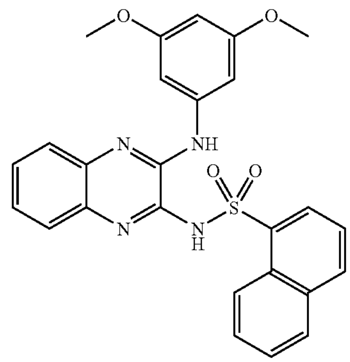 | N-(3-{[3,5-bis(methoxy)phenyl]amino}quinoxalin-2-yl)naphthalene-1-sulfonate |
| 740 | 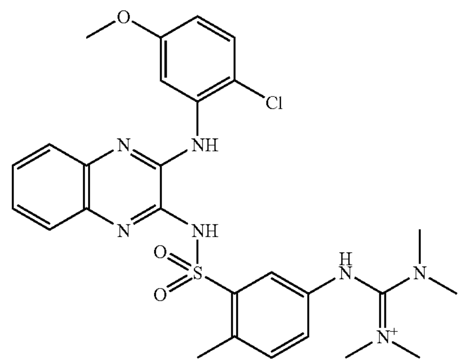 | N-{[(3-{[(3-{[2-chloro-5-(methoxy)phenyl]amino}quinoxalin-2-yl)amino]sulfonyl}-4-methylphenyl)amino](dimethylamino)methylidene}-N-methylmethanaminium |
| 741 | 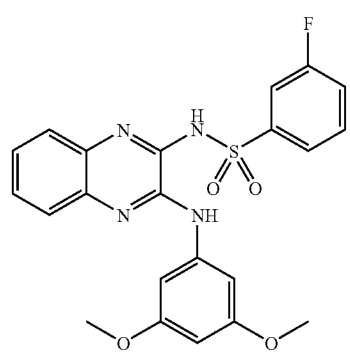 | N-(3-{[3,5-bis(methoxy)phenyl]amino}quinoxalin-2-yl)-3-fluorobenzenesulfonamide |
| 742 | 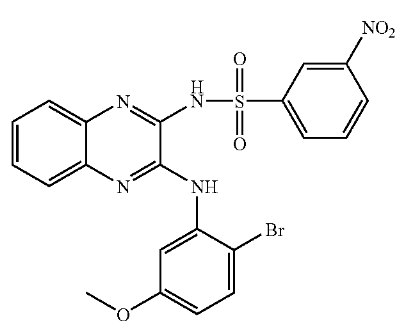 | N-(3-{[2-bromo-5-(methoxy)phenyl]amino}quinoxalin-2-yl)-3-nitrobenzenesulfonamide |

TABLE 1-continued

| Cpd. No. | Structure | Name |
|---|---|---|
| 743 | 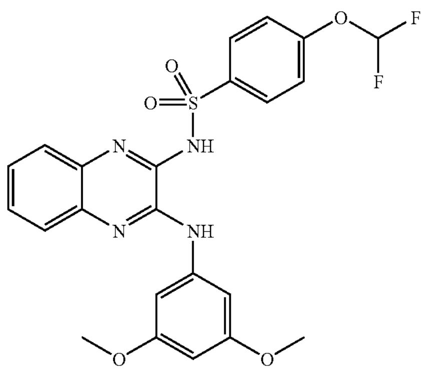 | N-(3-{[3,5-bis(methoxy)phenyl]amino}quinoxalin-2-yl)-4-[(difluoromethyl)oxy]benzenesulfonamide |
| 744 | 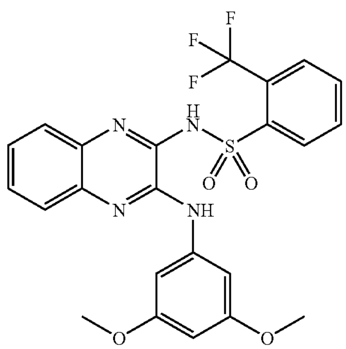 | N-(3-{[3,5-bis(methoxy)phenyl]amino}quinoxalin-2-yl)-2-(trifluoromethyl)benzenesulfonamide |
| 745 | 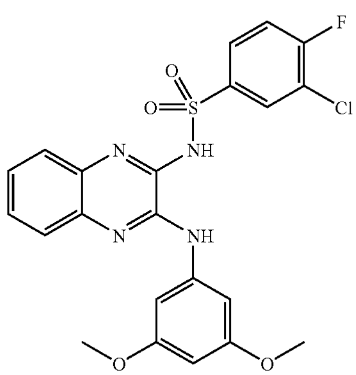 | N-(3-{[3,5-bis(methoxy)phenyl]amino}quinoxalin-2-yl)-3-chloro-4-fluorobenzenesulfonamide |
| 746 | 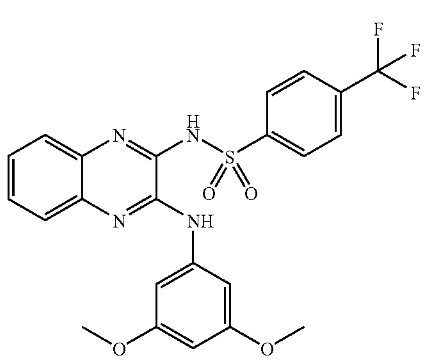 | N-(3-{[3,5-bis(methoxy)phenyl]amino}quinoxalin-2-yl)-4-(trifluoromethyl)benzenesulfonamide |

TABLE 1-continued

| Cpd. No. | Structure | Name |
|---|---|---|
| 747 | 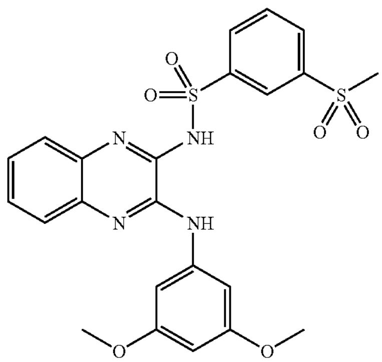 | N-(3-{[3,5-bis(methoxy)phenyl]amino}quinoxalin-2-yl)-3-(methylsulfonyl)benzenesulfonamide |
| 748 | 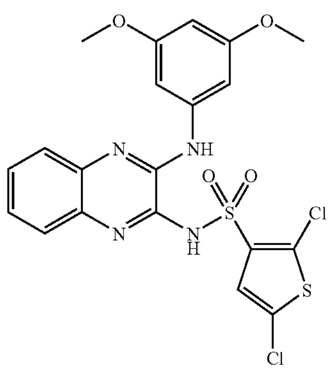 | N-(3-{[3,5-bis(methoxy)phenyl]amino}quinoxalin-2-yl)-2,5-dichlorothiophene-3-sulfonamide |
| 749 | 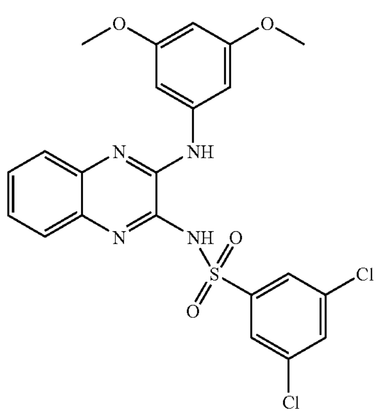 | N-(3-{[3,5-bis(methoxy)phenyl]amino}quinoxalin-2-yl)-3,5-dichlorobenzenesulfonamide |
| 750 | 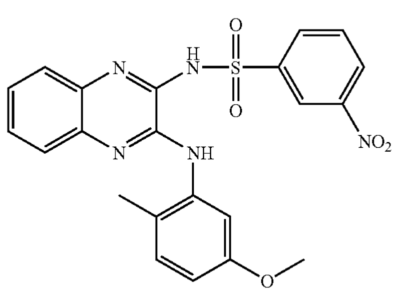 | N-(3-{[2-methyl-5-(methoxy)phenyl]amino}quinoxalin-2-yl)-3-nitrobenzenesulfonamide |

TABLE 1-continued

| Cpd. No. | Structure | Name |
|---|---|---|
| 751 | 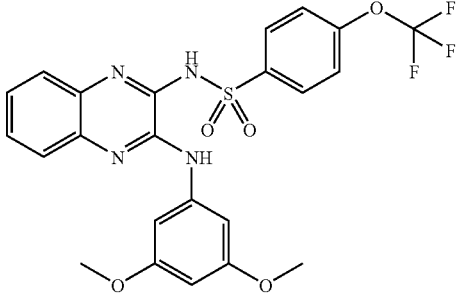 | N-(3-{[3,5-bis(methoxy)phenyl]amino}quinoxalin-2-yl)-4-[(trifluoromethyl)oxy]benzenesulfonamide |
| 752 | 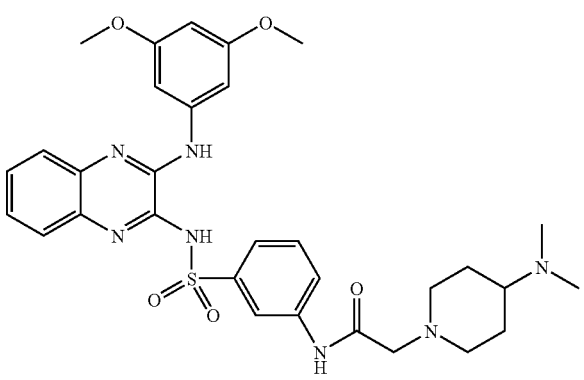 | N-(3-{[(3-{[3,5-bis(methoxy)phenyl]amino}quinoxalin-2-yl)amino]sulfonyl}phenyl)-2-[4-(dimethylamino)piperidin-1-yl]acetamide |
| 753 | 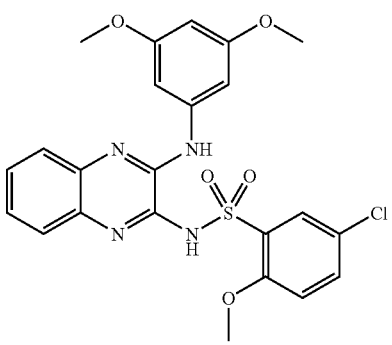 | N-(3-{[3,5-bis(methoxy)phenyl]amino}quinoxalin-2-yl)-5-chloro-2-(methoxy)benzenesulfonamide |
| 754 | 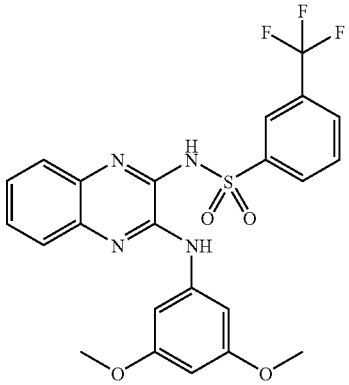 | N-(3-{[3,5-bis(methoxy)phenyl]amino}quinoxalin-2-yl)-3-(trifluoromethyl)benzenesulfonamide |

TABLE 1-continued

| Cpd. No. | Structure | Name |
|---|---|---|
| 755 | 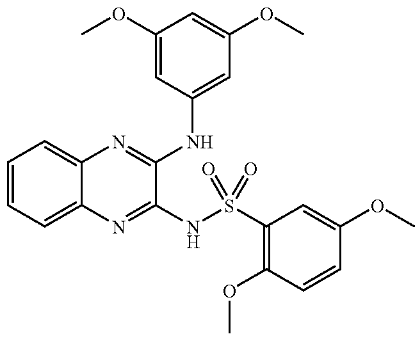 | N-(3-{[3,5-bis(methoxy)phenyl]amino}quinoxalin-2-yl)-2,5-bis(methoxy)benzenesulfonamide |
| 756 | 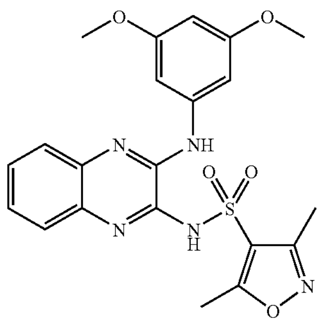 | N-(3-{[3,5-bis(methoxy)phenyl]amino}quinoxalin-2-yl)-3,5-dimethylisoxazole-4-sulfonamide |
| 757 | 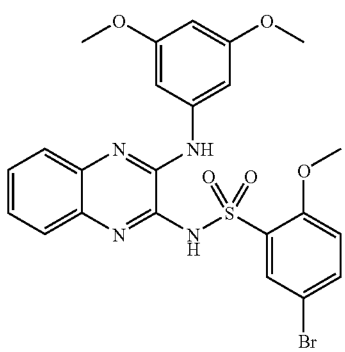 | N-(3-{[3,5-bis(methoxy)phenyl]amino}quinoxalin-2-yl)-5-bromo-2-(methoxy)benzenesulfonamide |
| 758 | 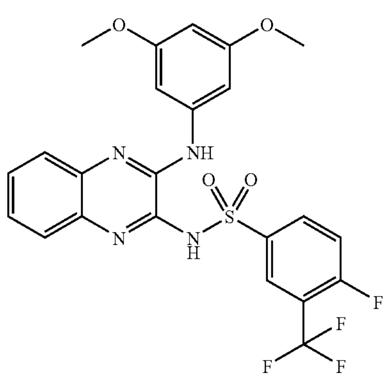 | N-(3-{[3,5-bis(methoxy)phenyl]amino}quinoxalin-2-yl)-4-fluoro-3-(trifluoromethyl)benzenesulfonamide |

TABLE 1-continued

| Cpd. No. | Structure | Name |
|---|---|---|
| 759 | 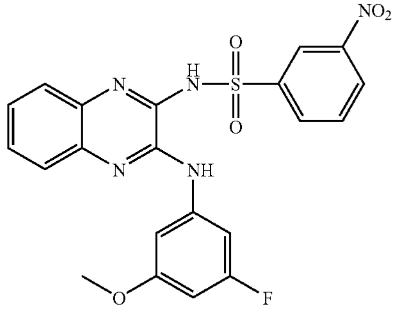 | N-(3-{[3-fluoro-5-(methoxy)phenyl]amino}quinoxalin-2-yl)-3-nitrobenzenesulfonamide |
| 760 | 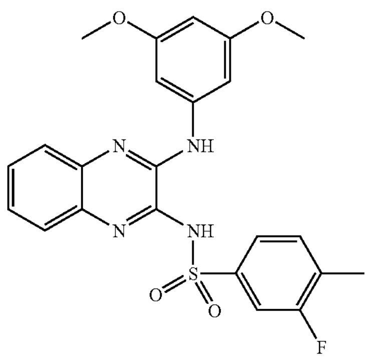 | N-(3-{[3,5-bis(methoxy)phenyl]amino}quinoxalin-2-yl)-3-fluoro-4-methylbenzenesulfonamide |
| 761 | 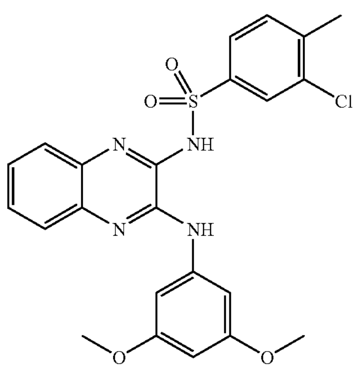 | N-(3-{[3,5-bis(methoxy)phenyl]amino}quinoxalin-2-yl)-3-chloro-4-methylbenzenesulfonamide |
| 762 | 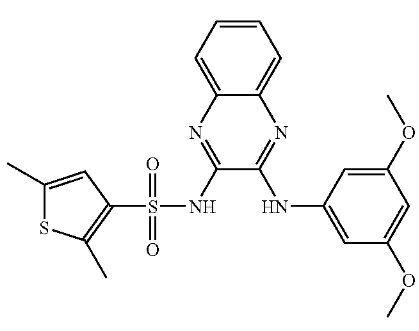 | N-(3-{[3,5-bis(methoxy)phenyl]amino}quinoxalin-2-yl)-2,5-dimethylthiophene-3-sulfonamide |

TABLE 1-continued
| Cpd. No. | Structure | Name |
|---|---|---|
| 763 | 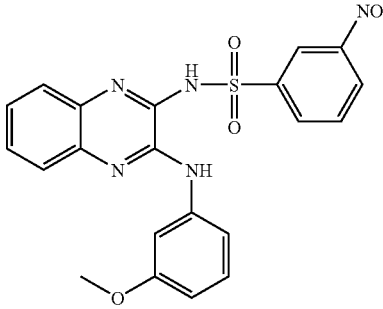 | N-(3-{[3-(methoxy)phenyl]amino}quinoxalin-2-yl)-3-nitrobenzenesulfonamide |
| 764 | 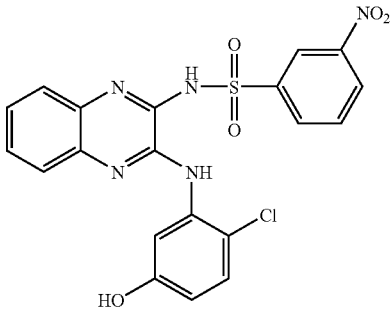 | N-{3-[(2-chloro-5-hydroxyphenyl)amino]quinoxalin-2-yl}-3-nitrobenzenesulfonamide |
| 765 | 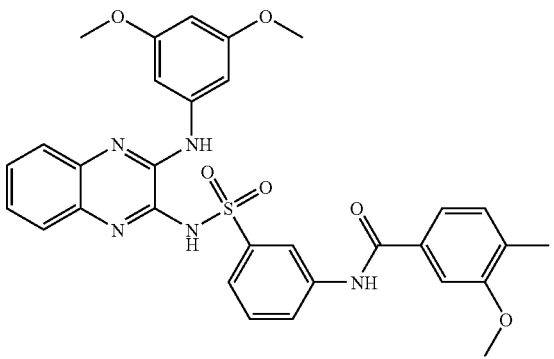 | N-(3-{[(3-{[3,5-bis(methoxy)phenyl]amino}quinoxalin-2-yl)amino]sulfonyl}phenyl)-4-methyl-3-(methoxy)benzamide |
| 766 | 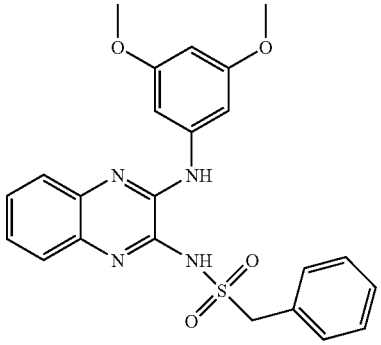 | N-(3-{[3,5-bis(methoxy)phenyl]amino}quinoxalin-2-yl)-1-phenylmethanesulfonamide |

TABLE 1-continued

| Cpd. No. | Structure | Name |
|---|---|---|
| 767 | 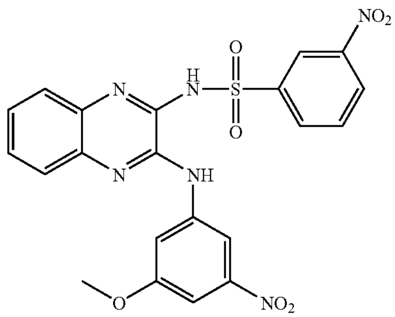 | N-(3-{[3-(methoxy)-5-nitrophenyl]amino}quinoxalin-2-yl)-3-nitrobenzenesulfonamide |
| 768 | 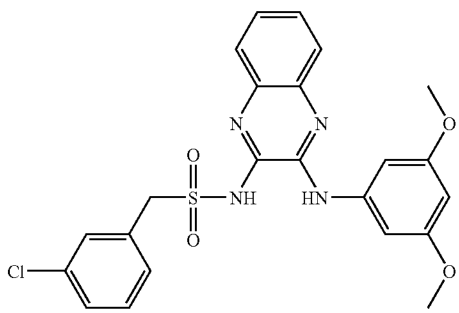 | N-(3-{[3,5-bis(methoxy)phenyl]amino}quinoxalin-2-yl)-1-(3-chlorophenyl)methanesulfonamide |
| 769 | 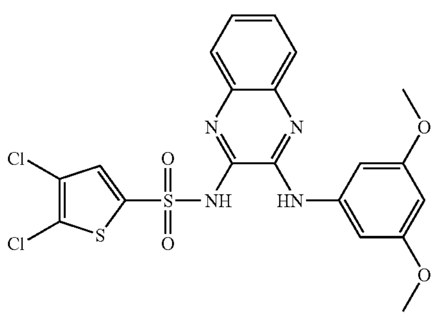 | N-(3-{[3,5-bis(methoxy)phenyl]amino}quinoxalin-2-yl)-4,5-dichlorothiophene-2-sulfonamide |
| 770 | 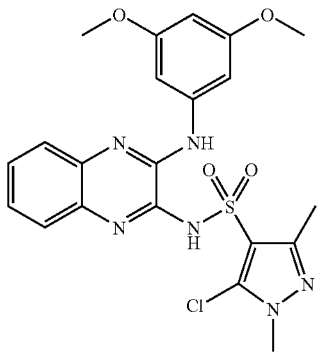 | N-(3-{[3,5-bis(methoxy)phenyl]amino}quinoxalin-2-yl)-5-chloro-1,3-dimethyl-1H-pyrazole-4-sulfonamide |

TABLE 1-continued

| Cpd. No. | Structure | Name |
|---|---|---|
| 771 | 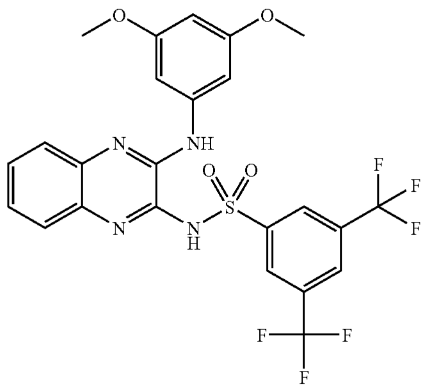 | N-(3-{[3,5-bis(methoxy)phenyl]amino}quinoxalin-2-yl)-3,5-bis(trifluoromethyl)benzenesulfonamide |

General Administration

In one aspect, the invention provides pharmaceutical compositions comprising an inhibitor of PI3K according to the invention and a pharmaceutically acceptable carrier, excipient, or diluent. In certain other specific embodiments, administration may specifically be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages.

The compositions will include a conventional pharmaceutical carrier or excipient and a compound of the invention as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt or solvate thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt or solvate thereof, and 99% to 1% by weight of a suitable pharmaceutical excipient. In one example, the composition will be between about 5% and about 75% by weight of a compound(s) of the invention, or a pharmaceutically acceptable salt or solvate thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt or solvate thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Representative pharmaceutical formulations containing a compound of Formula I are described below in the Pharmaceutical Composition Examples.

Utility

Certain compounds of this invention have been tested using the assay described in Biological Example 1 and have been determined to be PI3K inhibitors. As such compounds of Formula I are useful for treating diseases, particularly cancer in which PI3K activity contributes to the pathology and/or symptomotology of the disease. For example, cancer in which PI3K activity contributes to its pathology and/or symptomotology include breast cancer, colorectal cancer, endometrial cancer, gastric carcinoma, glioblastoma, hepatocellular carcinoma, small cell lung cancer, non-small cell lung cancer, melanoma, ovarian cancer, pancreatic cancer, prostate carcinoma, and thyroid carcinoma, and the like.

Suitable in vitro assays for measuring PI3K activity and the inhibition thereof by compounds are known. Typically, the assay will measure PI3K-induced ATP consumption. For further details of an in vitro assay for measuring PI3K activity see Biological Examples, Example 1 infra. Cellular activity can be determined using assays as described in Biological Examples 2, 3, and 4 infra. Suitable in vivo models of cancer are known to those of ordinary skill in the art. For further details of in vivo assays see Biological Examples 5-10, infra. Following the examples disclosed herein, as well as that disclosed in the art, a person of ordinary skill in the art can determine the inhibitory activity of a compound of this invention.

Preparations of the Intermediates and Compounds of the Invention

Compounds of this invention can be made by the synthetic procedures described below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., more specifically from about 0° C. to about 125° C. and most specifically at about room (or ambient) temperature, e.g., about 20° C. Unless otherwise stated (as in the case of an hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of pro-drugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all-purposes.

The compounds of the invention, or their pharmaceutically acceptable salts, may have asymmetric carbon atoms or quaternized nitrogen atoms in their structure. Compounds of Formula I that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention. Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention.

In particular, in this application B can be 2-hydroxy-pyridinyl, also described as its structure:

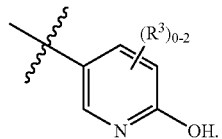

14

Both 2-hydroxy-pyridinyl and the above structure 14 include, and are equivalent to, pyridin-2(1H)-one and its structure 15:

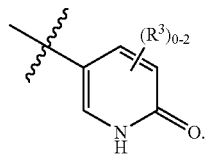

15

Regardless of which structure or which terminology is used, each tautomer is included within the scope of the Invention.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In Compounds of Formula I

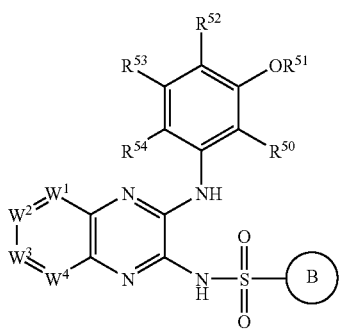

the hydrogen on the —NHS(O)$_2$— group is highly acidic. Thus, intermediates leading to Compounds of Formula I, as well as Compounds of Formula I themselves, can be recovered as uncharged or zwitterionic molecules, or cationic salts such a sodium or potassium, depending on the substitutions on the B ring and on reaction conditions. In the examples that follow, unless otherwise specified, the final form of the compound was assumed to be the uncharged molecule in the absence of analytical techniques that would have determined otherwise.

Compounds of Formula I can be prepared using methods known to one of ordinary skill in the art. Specifically, fusion of appropriate reagents at 180° C. in the presence of a base such as K$_2$CO$_3$ and metallic copper is known to provide intermediates of formula 1 (see S. H. Dandegaonker and C. K. Mesta, *J. Med. Chem.* 1965, 8, 884).

Alternatively, the intermediate of formula 3 can be prepared according to the scheme below where each LG$^1$ is a leaving group (specifically, halo, more specifically,

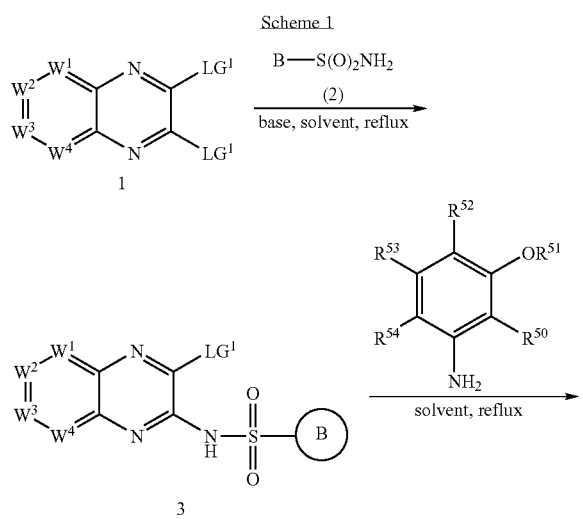

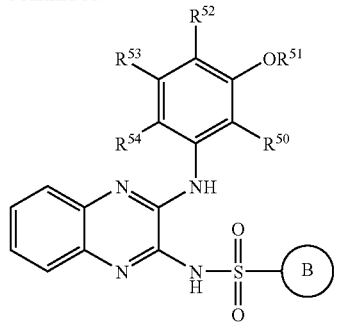

In scheme 1, an intermediate of formula 3 can be prepared by briefly heating commercially available 2,3-dichloroquinoxaline and an intermediate of formula 2 (which are commercially available or can be prepared by one of ordinary skill in the art), a base such as K$_2$CO$_3$, in a solvent, such as DMF or DMSO. Upon completion (about 2 hours), the reaction mixture is then poured into water and followed by 2 N HCl. The product is then extracted into a solvent such as ethyl acetate and washed with water and brine. The organic layers are combined and dried over a drying agent such as sodium sulfate, filtered, and concentrated under vacuum.

The intermediate of formula 3 is then treated with an intermediate of formula 4 in a solvent such as DMF or p-xylene at reflux temperature. Upon completion of the reaction (about 16 hours or less), the reaction is allowed to cool, extracted into DCM, washed with 2 N HCl and brine, dried over a drying agent such as sodium sulfate or magnesium sulfate, filtered, and concentrated to give a compound of Formula I.

Alternatively, other methods to prepare quinoxaline derivatives are known to one skilled in the art and include, but are not limited to S. V. Litvinenko, V. I. Savich, D. D. Bobrovnik, *Chem. Heterocycl. Compd.* (Engl. Transl), 1994, 30, 340 and W. C. Lumma, R. D. Hartman, *J. Med. Chem.* 1981, 24, 93.

The following compounds were prepared in a manner similar to that described above.

Example 1

N-(3-{[2,5-bis(methoxy)phenyl]amino}quinoxalin-2-yl)-3-nitrobenzenesulfonamide.

Example 2

N-(3-{[2,5-bis(methoxy)phenyl]amino}) quinoxalin-2-yl)-4-chlorobenzenesulfonamide.

Example 3

N-(3-chloroquinoxalin-2-yl)-3-nitrobenzenesulfonamide.

Example 4

4-chloro-N-(3-chloroquinoxalin-2-yl)benzenesulfonamide.

Example 5

4-chloro-N-(3-(2,5-dimethoxy-phenylamino)quinoxalin-2-yl)benzenesulfonamide $^1$H NMR (400 MHz, DMSO-d$_6$) δ 9.18 (s, 1H), 8.78 (s, 1H), 8.40-8.60 (m, 3H), 7.98 (t, 2H), 7.62 (d, 1H), 7.41 (m, 2H), 6.98 (d, 1H), 6.59 (d, 1H), 3.78 (s, 3H), 3.76 (s, 3H); MS (EI) m/z for $C_{22}H_{19}N_5O_6S$: 482.1 (MH$^+$).

Example 6

N-(3-(2,5-dimethoxyphenylamino)quinoxalin-2-yl)-3-nitrobenzenesulfonamide $^1$H NMR (400 MHz, CDCl$_3$) δ 12.68 (br s, 1H), 9.18 (s, 1H), 8.55 (s, 1H), 8.08 (d, 2H), 7.98 (d, 1H), 7.78 (d, 2H), 7.62 (dd, 1H), 7.40 (m, 2H), 7.00 (d, 1H), 6.60 (dd, 1H), 3.78 (s, 6H); MS (EI) m/z for $C_{22}H_{19}ClN_4O_4S$: 471.1 (MH$^+$).

Example 7

N-(3-(N-(3-(2-chloro-5-methoxyphenylamino)quinoxalin-2-yl)sulfamoyl)-4-methylphenyl)-2-(dimethylamino)acetamide $^1$H NMR (400 MHz, DMSO-d$_6$) δ 12.0 (br s, 1H), 10.6 (s, 1H), 10.0 (br s, 1H), 9.52 (s, 1H), 8.91 (d, 1H), 8.25 (d, 1H), 7.69 (dd, 1H), 7.47 (m, 1H), 7.39 (d, 1H), 7.16 (m, 3H), 6.01 (dd, 1H); MS (EI) m/z for $C_{26}H_{27}ClN_6O_4S$: 555 (MH$^+$).

Compounds of Formula I where B is phenyl substituted with $R^{3a}$ where $R^{3a}$ is alkylamino or dialkylamino or B is heteroaryl substituted with $R^3$ where $R^3$ is amino, alkylamino, or dialkylamino, and all other groups are as defined in the Summary of the Invention can be prepared according to Scheme 2.

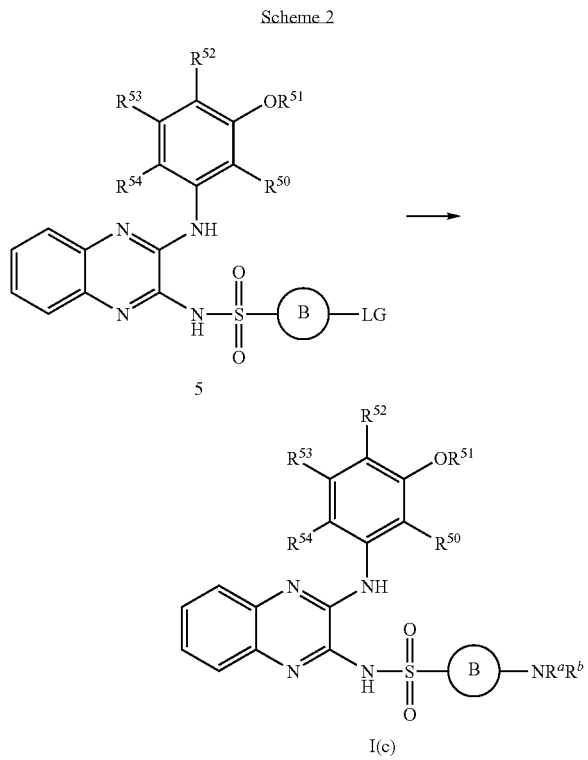

Scheme 2

LG is a leaving group such as chloro. 5 is reacted with NHR$^a$R$^b$ or HO—C$_1$-C$_6$-alkylene-NHR$^a$R$^b$ where R$^a$ and R$^b$ are independently hydrogen or alkyl. The reaction is carried out in the presence of a base, such as KHCO$_3$, in a solvent such as DMF.

Compounds of Formula I where B is phenyl substituted with $R^{3a}$ where $R^{3a}$ is aminoalkyloxy, alkylaminoalkyloxy, or dialkylaminoalkyloxy or B is heteroaryl substituted with $R^3$ where $R^3$ is aminoalkyloxy, alkylaminoalkyloxy, or dialkylaminoalkyloxy, and all other groups are as defined in the Summary of the Invention can be prepared according to Scheme 3.

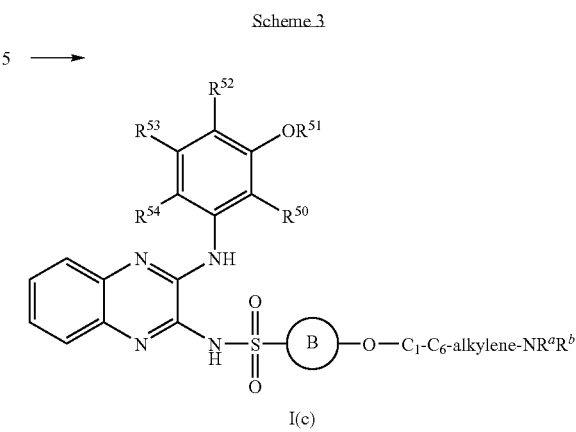

Scheme 3

The reaction is carried out in the presence of a base such as NaH in a solvent such as DMF.

Compounds of Formula I where B is phenyl substituted with $R^{3a}$ or B is heteroaryl substituted with $R^3$ where $R^{3a}$ and $R^3$ are i. —N(R$^7$)C(O)—C$_1$-C$_6$-alkylene-N(R$^{7a}$)(R$^{7b}$) where R$^7$, R$^{7a}$, and R$^{7b}$ are as defined in the Summary of the Invention;

ii. —NR$^9$C(O)R$^{9a}$ where R$^9$ is as defined in the Summary of the Invention;

iii. —NR$^{11}$C(O)NR$^{11a}$R$^{11b}$ where R$^{11}$, R$^{11a}$, and R$^{11b}$ are as defined in the Summary of the Invention;

iv. —NR$^{13}$C(O)OR$^{13a}$ where R$^{13}$ and R$^{13a}$ are as defined in the Summary of the Invention;

v. —N(R$^{18}$)C(O)—C$_1$-C$_6$-alkylene-N(R$^{18b}$)C(O)R$^{18a}$ where R$^{18}$, R$^{18a}$, and R$^{18b}$ are as defined in the Summary of the Invention;

vi. —N(R$^{20}$)C(O)—C$_1$-C$_6$-alkylene-C(O)R$^{20a}$ where R$^{20}$ and R$^{20a}$ as defined in the Summary of the Invention;

vii. —NR$^{21}$S(O)$_2$R—C$_1$-C$_6$-alkylene-N(R$^{21b}$)R$^{21a}$ where R$^{21}$, R$^{21a}$, and R$^{21b}$ are as defined in the Summary of the Invention;

viii. —N(R$^{22}$)C(O)—C$_0$-C$_6$-alkylene-N(R$^{22b}$)—N(R$^{22c}$)(R$^{22a}$), where R$^{22}$, R$^{22a}$ and R$^{22b}$ are as defined in the Summary of the Invention;

ix. —NR$^{24}$C(O)—C$_1$-C$_6$-alkylene-OR$^{24a}$ where R$^{24}$ and R$^{24a}$ are as defined in the Summary of the Invention;

and where the alkylene in $R^3$ and $R^{3a}$ are independently optionally substituted as described in the Summary of the Invention can be prepared according to Scheme 4 by reacting with an intermediate of formula 9(a), 9(b), 9(c), 9(d), 9(e), 9(f), or 9(g):

9(a) HOC(O)—C$_1$-C$_6$-alkylene-N(R$^{7a}$)(R$^{7b}$) where R$^a$ is R$^{7a}$ or a N-protecting group, such as Boc or Fmoc;

9(b) HOC(O)R$^{9a}$;

9(c) HOC(O)NR$^{11a}$R$^{11b}$;

9(d) HOC(O)OR$^{13a}$;

9(e) HOC(O)—C$_1$-C$_6$-alkylene-N(R$^{18b}$)C(O)R$^{18a}$;

9(f) HOC(O)—C$_1$-C$_6$-alkylene-C(O)R$^{20a}$;

9(g) LG-S(O)$_2$R—C$_1$-C$_6$-alkylene-N(R$^{21b}$)R$^a$ where R$^a$ is

R²¹ᵃ or a N-protecting group, such as Boc or Fmoc.

Scheme 4

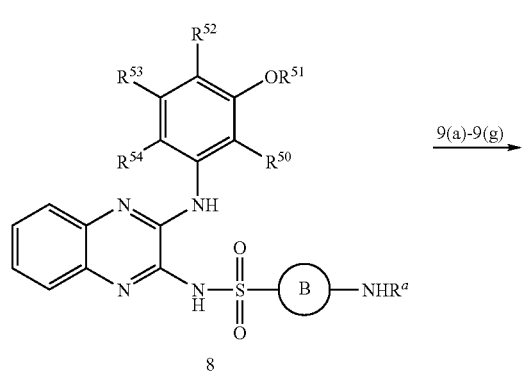

8

9(a)-9(g) →

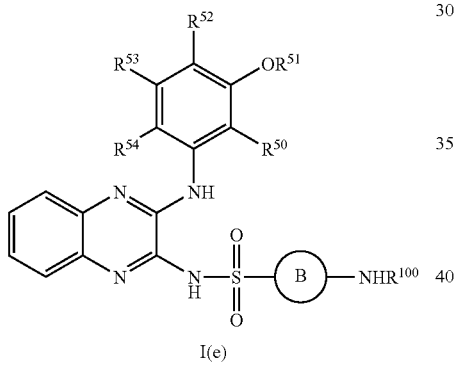

I(e)

$R^{100}$ in Scheme 4 is —C(O)R$^{9a}$, —C(O)NR$^{11a}$R$^{11b}$, —C(O)OR$^{13a}$, —C(O)—C$_1$-C$_6$-alkylene-N(R$^{18b}$)C(O)R$^{18a}$, —C(O)—C$_1$-C$_6$-alkylene-C(O)R$^{20a}$, or —S(O)$_2$R—C$_1$-C$_6$-alkylene-N(R$^{21b}$)R$^a$. The reaction is carried out under standard amide coupling conditions known to one of ordinary skill in the art. In particular, the reaction is carried out in the presence of a coupling agent such as HATU, a base such as DIEA, and in a solvent such as DMF. Where applicable, the N-protecting group is then removed using procedures known to one of ordinary skill in the art, such as treating with acid where PG is Boc.

Proceeding as described for Scheme 4, compounds of the invention where B is phenyl substituted with R$^{3a}$ or B is heteroaryl substituted with R$^3$ where R$^{3a}$ and R$^3$ are
 a) —C(O)NR$^8$R$^{8a}$;
 b) —C(O)N(R$^{10}$)C$_1$-C$_6$-alkylene-N(R$^{10a}$)R$^{10b}$;
 c) —C(O)R$^{12}$ where R$^{12}$ is an N-substituted heterocycloalkyl;
 d) —C(O)N(R$^{14}$)N(R$^{14a}$)(R$^{14b}$);
 e) —C(O)N(R$^{16}$)—C$_1$-C$_6$-alkylene-C(O)OR$^{16a}$; or
 f) —C(O)N(R$^{19}$)—C$_1$-C$_6$-alkylene-C(O)R$^{19a}$; or
can be prepared by exchanging the starting materials as necessary. In particular, the intermediate of formula 11:

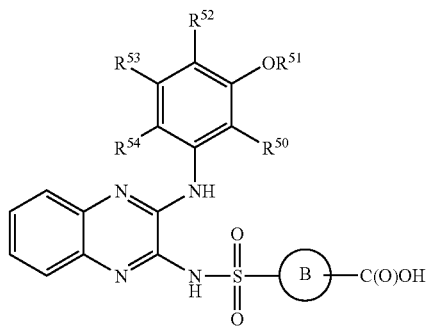

11 is used instead of 8.

Compounds of Formula I where B is phenyl substituted with R$^{3a}$ or B is heteroaryl substituted with R$^3$ where R$^{3a}$ and R$^3$ are —NHC(O)CH$_2$NR$^{7a}$R$^{7b}$ where R$^{7a}$ and R$^{7b}$ are as defined in the Summary of the Invention can be prepared according to Scheme 5.

Scheme 5

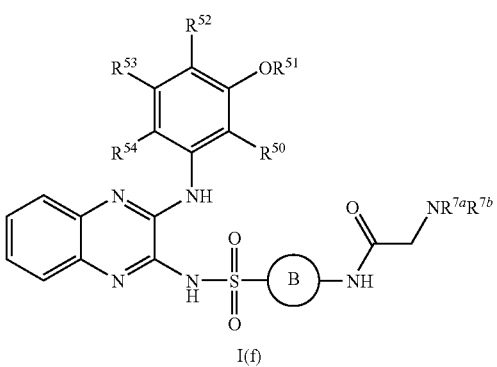

12

NHR$^{7a}$R$^{7b}$ →

I(f)

LG is a leaving group such as bromo or chloro. 12 is reacted with NH(R$^{7b}$)R$^{7a}$ in the presence of a base, such as DIEA, in a solvent such as ACN.

Compounds of Formula I can be prepared according to Scheme 6.

Scheme 6

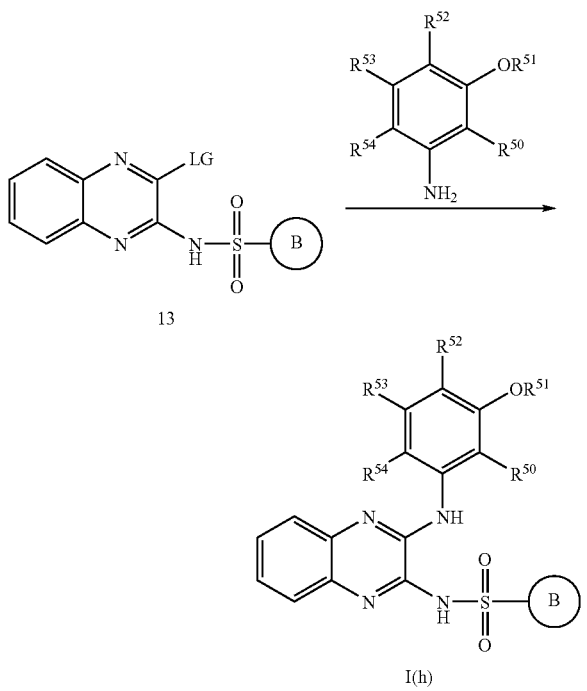

13

I(h)

LG in Scheme 6 is a leaving group such as chloro. The reaction can be carried out by irradiating in a solvent such as DMA. Alternatively, the reaction can be carried out in the presence of acetic acid in a solvent such as DMA and by heating.

Example 8

6-chloro-N-(3-(3,5-dimethoxyphenylamino)quinoxalin-2-yl)pyridine-3-sulfonamide

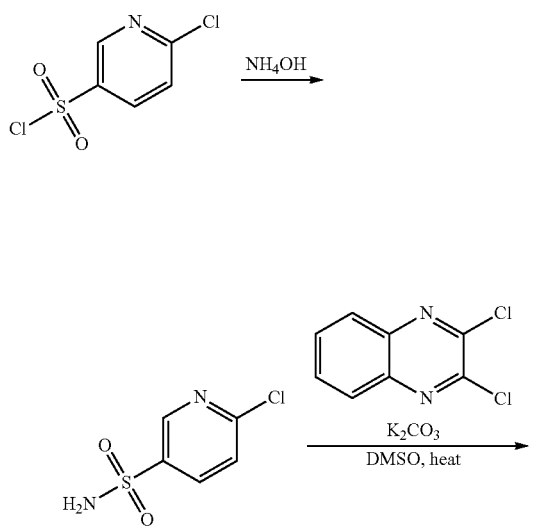

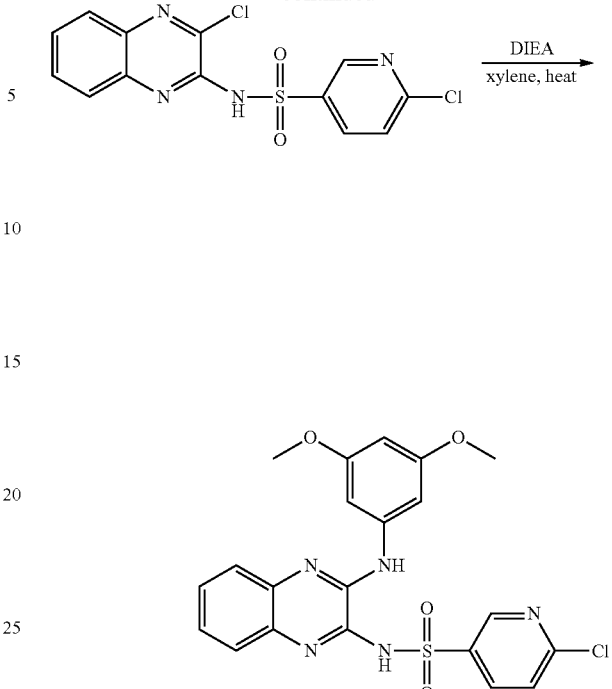

6-chloropyridine-3-sulfonamide. 6-chloropyridine-3-sulfonyl chloride (4.1 g, 19.3 mmol) was stirred in ammonium hydroxide (30 mL) at room temperature for 2 hr. The reaction mixture was diluted with EtOAc (150 mL) and any insoluble material filtered. The filtrate was transferred to a separatory funnel and the phases were separated. The aqueous phase was further extracted with EtOAc (1×15 mL). The combined EtOAc extractions were washed with $H_2O$ (1×50 mL) and saturated NaCl (1×50 mL), dried over $Na_2SO_4$, and concentrated in vacuo to give 6-chloropyridine-3-sulfonamide (2.58 g, 69%). MS (EI) m/z for $C_5H_5Cl_2N_2O_2S$: 190.9 (MH$^+$).

6-chloro-N-(3-chloroquinoxalin-2-yl)pyridine-3-sulfonamide. 2,3-dichloroquinoxaline (1.09 g, 5.48 mmol), 6-chloropyridine-3-sulfonamide (1.05 g, 5.45 mmol), $K_2CO_3$ (753 mg, 5.45 mmol) and dry DMSO (30 mL) were combined and heated to 150° C. with vigorous stirring for 3-4 hr. The reaction mixture was allowed to cool to room temperature, then poured into 1% AcOH in ice water (300 mL) with vigorous stirring. The resulting solids were filtered, washed with $H_2O$ and dried under high vacuum to give 6-chloro-N-(3-chloroquinoxalin-2-yl)pyridine-3-sulfonamide (1.87 g, 96%). MS (EI) m/z for $C_{13}H_8Cl_2N_4O_2S$: 354.99 (MH$^+$).

6-chloro-N-(3-(3,5-dimethoxyphenylamino)quinoxalin-2-yl)pyridine-3-sulfonamide. 6-Chloro-N-(3-chloroquinoxalin-2-yl)pyridine-3-sulfonamide (775 mg, 2.2 mmol), 3,5-dimethoxyaniline (355 mg, 2.3 mmol) and toluene (12 mL) were combined and heated to 125° C. with stirring overnight. The reaction was allowed to cool to room temperature and diluted with $Et_2O$ with vigorous stirring. The resulting solids were filtered, washed with $Et_2O$ and dried to give 6-chloro-N-(3-(3,5-dimethoxy-phenylamino)quinoxalin-2-yl)pyridine-3-sulfonamide (920 mg, 89%). $^1$H NMR (400 MHz, DMSO-d$_6$) δ 12.20 (br s, 1H), 9.12 (d, 1H), 9.01 (br s, 1H), 8.53 (dd, 1H), 7.91 (br d, 1H), 7.77 (d, 1H), 7.60 (dd, 1H), 7.40 (m, 4H), 6.26 (m, 1H), 3.78 (s, 6H). MS (EI) m/z for $C_{21}H_{18}ClN_5O_4S$: 472.0 (MH$^+$).

Example 9

N-(3-(3,5-dimethoxyphenylamino)quinoxalin-2-yl)-6-(2-(dimethylamino)-ethylamino)pyridine-3-sulfonamide

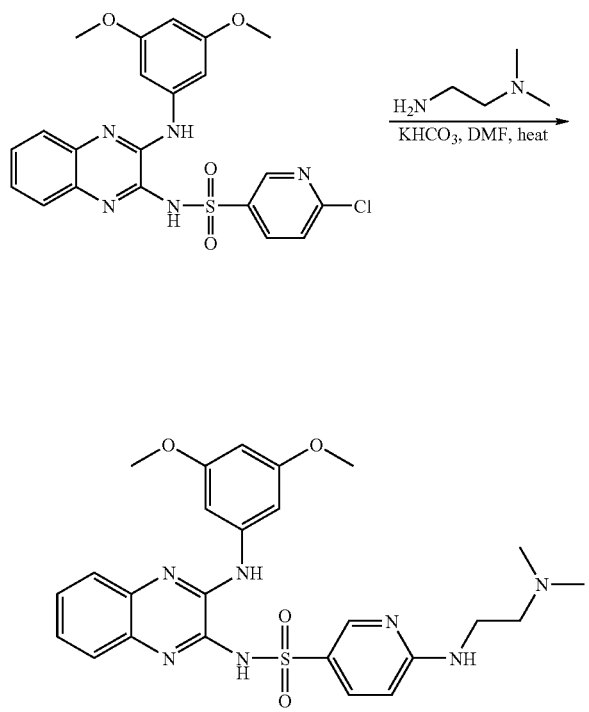

6-chloro-N-(3-(3,5-dimethoxyphenylamino)quinoxalin-2-yl)-pyridine-3-sulfonamide (100 mg, 0.21 mmol), prepared using procedures similar to those used in Example 8, KHCO$_3$ (40 mg, 0.40 mmol), N$^1$,N$^1$-dimethylethane-1,2-diamine (225 μL, 2.0 mmol) and dry DMF (1.0 mL) were combined and heated to 130° C. with stirring overnight. The reaction mixture was concentrated in vacuo and purified by preparative HPLC to give N-(3-(3,5-dimethoxy-phenylamino)-quinoxalin-2-yl)-6-(2-(dimethylamino)ethylamino)pyridine-3-sulfonamide (21.0 mg, 19%). $^1$H NMR (400 MHz, DMSO-d$_6$) δ 8.76 (br s, 1H), 8.63 (d, 1H), 8.07 (dd, 1H), 7.40 (m, 1H), 7.34 (m, 1H), 7.28 (d, 2H), 7.14 (m, 4H), 6.47 (d, 1H), 6.12 (m, 1H), 3.75 (s, 6H), 3.35 (m, 2H), 3.14 (m, 2H), 2.74 (s, 6H). MS (EI) m/z for C$_{25}$H$_{29}$N$_7$O$_4$S: 524.1 (MH$^+$).

Example 10

N-(3-(3,5-dimethoxyphenylamino)quinoxalin-2-yl)-6-(dimethylamino)pyridine-3-sulfonamide was prepared using procedures similar to those used in Example 9. $^1$H NMR (400 MHz, DMSO-d$_6$) δ 12.00 (br s, 1H), 8.92 (br s, 1H), 8.74 (d, 1H), 8.10 (dd, 1H), 7.38 (br s, 1H), 7.54 (m, 1H), 7.33 (m, 4H), 6.70 (d, 1H), 6.22 (s, 1H), 3.77 (s, 6H), 3.08 (s, 6H). MS (EI) m/z for C$_{23}$H$_{24}$N$_6$O$_4$S: 481.1 (MH$^+$).

Example 11

N-(3-(3,5-dimethoxyphenylamino)quinoxalin-2-yl)-6-(2-(dimethylamino)-ethoxy)pyridine-3-sulfonamide

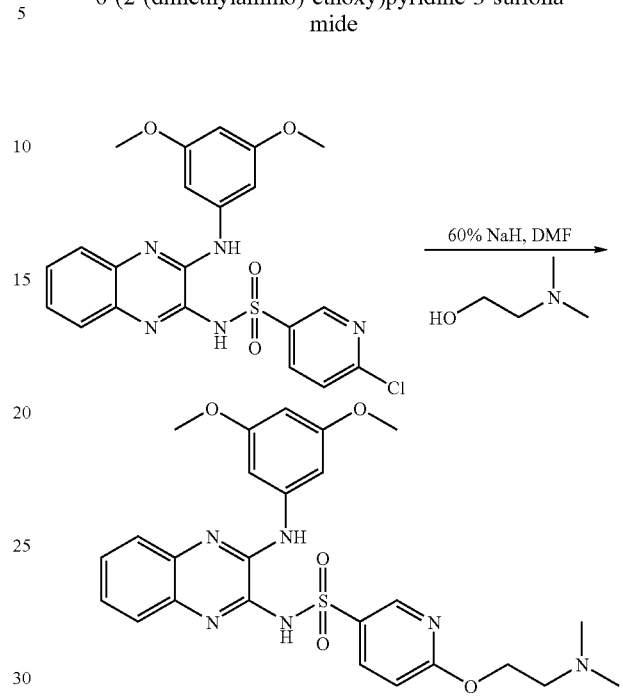

N-(3-(3,5-dimethoxyphenylamino)quinoxalin-2-yl)pyridine-3-sulfonamide (100 mg, 0.21 mmol), prepared using procedures similar to those described above in Example 1, 2-(dimethylamino)ethanol (50 μL, 0.50 mmol) and dry DMF were combined and 60% NaH in oil (80 mg, 2.0 mmol) was added. The mixture was stirred at room temperature overnight. The reaction mixture was concentrated in vacuo and purified by preparative HPLC to give N-(3-(3,5-dimethoxyphenylamino)quinoxalin-2-yl)-6-(2-(dimethylamino)ethoxy)pyridine-3-sulfonamide (23 mg, 21%). $^1$H NMR (400 MHz, DMSO-d$_6$) δ 8.78 (d, 1H), 8.73 (s, 1H), 8.38 (dd, 1H), 7.40 (dd, 1H), 7.31 (m, 3H), 7.14 (m, 2H), 6.85 (d, 1H), 6.12 (m, 1H), 4.56 (m, 2H), 3.76 (s, 6H), 3.43 (m, 2H), 2.77 (s, 6H). MS (EI) m/z for C$_{25}$H$_{28}$N$_6$O$_5$S: 525.1 (MH$^+$).

Example 12

N-(3-(3,5-dimethoxyphenylamino)quinoxalin-2-yl)-6-oxo-1,6-dihydropyridine-3-sulfonamide

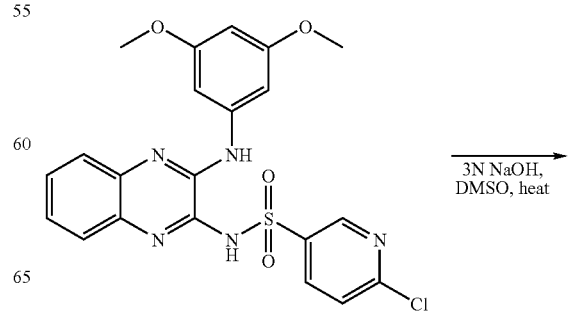

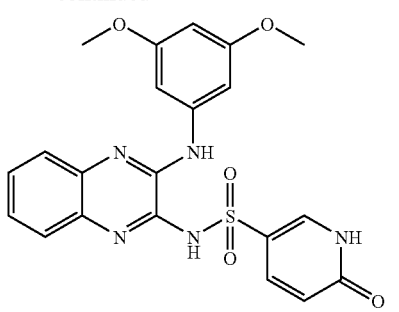

N-(3-(3,5-dimethoxyphenylamino)quinoxalin-2-yl)pyridine-3-sulfonamide (220 mg, 0.47 mmol), prepared using procedures similar to those described above in Example 8, DMSO (5 mL), and 3N NaOH (5 mL) are combined and heated to 100° C. overnight with stirring. Upon cooling to room temperature, the reaction mixture was diluted with H$_2$O and the pH was adjusted to 7.0 with 1N HCl. The resulting solid was filtered, washed with H$_2$O, and air-dried. The solid was then sonicated in EtOAc, filtered, washed with EtOAc, and dried under high vacuum to give N-(3-(3,5-dimethoxyphenylamino)quinoxalin-2-yl)-6-oxo-1,6-dihydropyridine-3-sulfonamide (190 mg, 90%). $^1$H NMR (400 MHz, DMSO-d$_6$) δ 12.23 (br s, 1H), 12.10 (br s, 1H), 8.97 (s, 1H), 8.23 (s, 1H), 7.95 (m, 2H), 7.59 (m, 1H), 7.37 (m, 4H), 6.43 (d, 1H), 6.25 (s, 1H), 3.77 (s, 6H). MS (EI) m/z for C$_{21}$H$_{19}$N$_5$O$_5$S: 454.0 (MH$^+$).

Example 13

N-(3-(2-chloro-5-methoxy-phenylamino)quinoxalin-2-yl)-6-oxo-1,6-dihydropyridine-3-sulfonamide The title compound was prepared according to the above Example 12. $^1$H NMR (400 MHz, DMSO-d$_6$) δ 12.22 (br s, 1H), 12.10 (br s, 1H), 9.16 (s, 1H), 8.60 (s, 1H), 8.14 (d, 1H), 7.94 (m, 1H), 7.85 (dd, 1H), 7.62 (m, 1H), 7.40 (m, 3H) 6.69 (dd, 1H), 6.43 (d, 1H), 3.81 (s, 3H). MS (EI) m/z for C$_{20}$H$_{16}$ClN$_5$O$_4$S: 456.0 (MH$^-$).

Example 14

3-amino-N-(3-(3,5-dimethoxyphenylamino)quinoxalin-2-yl)benzenesulfonamide

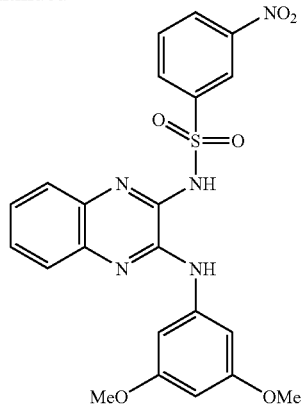

N-(3-(3,5-dimethoxyphenylamino)quinoxalin-2-yl)-3-nitrobenzenesulfonamide. A flask was charged with N-(3-chloroquinoxalin-2-yl)-3-nitrobenzenesulfonamide (5 g, 13.7 mmol), prepared using procedures similar to those in Example 1, 3,5-dimethoxyaniline (4.2 g, 27.4 mmol), and 80 mL of xylene. The reaction mixture was stirred under an N$_2$ atmosphere at 150° C. for 3 hours, after which time, solvent was removed on a rotary evaporator, and 10 mL of Dichloromethane and 50 mL of methanol were added. The slurry was heated to reflux and filtered while hot, resulting in 4.6 g (69.7%) of N-(3-(3,5-dimethoxyphenylamino)quinoxalin-2-yl)-3-nitrobenzenesulfonamide MS (EI) m/z for C$_{22}$H$_{19}$N$_5$O$_6$S: 482.2 (MH$^+$).

Example 15

3-amino-N-(3-(3,5-dimethoxyphenylamino)quinoxalin-2-yl)benzenesulfonamide

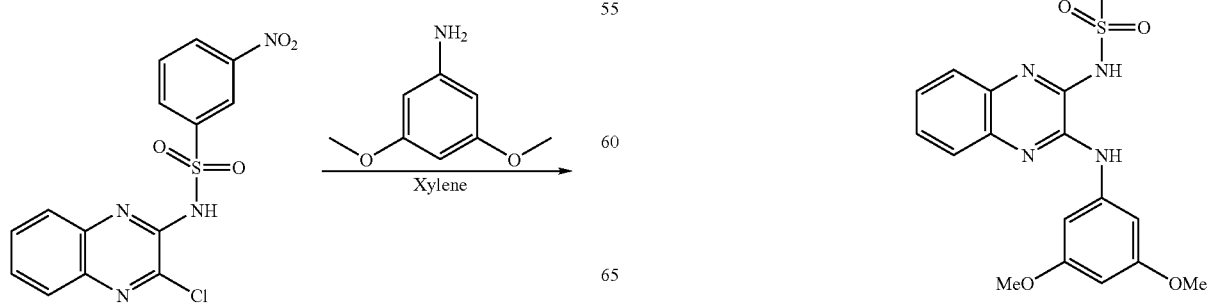

A flask was charged with N-(3-(3,5-dimethoxyphenylamino)quinoxalin-2-yl)-3-nitro-benzenesulfonamide (3.4 g, 7.06 mmol), prepared using procedures similar to those in Example 14, tin chloride solvate (6.4 g, 28.2 mmol), and 30 mL of DMA. A few drops of water were added and the reaction mixture was stirred at 80° C. for 3 hours, after which time, solvent was removed on a rotary evaporator, and 50 mL of water and 10 mL of Methanol were added. The slurry was filtered, and the filtrate was washed with MeOH, water, and diethyl ether (20 mL of each), resulting in 3.25 g 3-amino-N-(3-(3,5-dimethoxy-phenylamino)quinoxalin-2-yl)benzenesulfonamide. $^1$H NMR (400 MHz, DMSO) δ 12.2 (br s, 1H), 8.85 (s, 1H), 7.90 (br s, 1H), 7.50-7.60 (m, 1H), 7.3-7.4 (m, 4H), 7.2 (m, 3H), 6.74 (m, 1H), 6.24 (m, 1H), 5.56 (br s, 2H), 3.76 (s, 6H). MS (EI) m/z for $C_{22}H_{21}N_5O_4S$: 452.0 (MH$^+$).

The following compounds were made using procedures similar to those used in Example 15.

Example 16

Proceeding as above, 3-amino-N-(3-(2,5-dimethoxy-phenylamino)quinoxalin-2-yl)benzenesulfonamide was prepared. $^1$H NMR (400 MHz, DMSO) δ 12.4 (br s, 1H), 9.20 (s, 1H), 8.56 (d, 1H), 7.95 (d, 1H), 7.62 (m, 1H), 7.38 (m, 2H), 7.24 (q, 2H), 7.14 (d, 1H), 6.98 (d, 1H), 6.8 (m, 1H), 6.60 (m, 1H), 5.6 (br s, 2H), 3.78 (d, 6H). MS (EI) m/z for $C_{22}H_{21}N_5O_4S$: 452.3 (MH$^+$).

Example 17

Proceeding as above, 3-amino-N-(3-(2-chloro-5-hydroxyphenylamino)quinoxalin-2-yl)benzenesulfonamide was prepared. MS (EI) m/z for $C_{20}H_{16}ClN_5O_3S$ $1.0 \times C_2H_1O_2F_3$: 442.2, 444.2 (MH$^+$).

Example 18

Proceeding as above, 3-amino-N-(3-(6-methoxyquinolin-8-ylamino)quinoxalin-2-yl)benzenesulfonamide was prepared. MS (EI) m/z for $C_{24}H_{20}N_6O_3S$: 473.0 (MH$^+$).

Example 19

3-amino-N-(3-(3-fluoro-5-methoxy-phenylamino)quinoxalin-2-yl)benzenesulfonamide

MS (EI) m/z for $C_{21}H_{18}FN_5O_3S$: 439.99 (MH$^+$).

Example 20

3-amino-N-(3-(2-chloro-5-methoxy-phenylamino)quinoxalin-2-yl)benzenesulfonamide

MS (EI) m/z for $C_{21}H_{18}ClN_5O_3S$: 457.02 (MH$^+$).

Example 21

3-amino-N-(3-(5-methoxy-2-methyl-phenylamino)quinoxalin-2-yl)benzenesulfonamide

MS (EI) m/z for $C_{22}H_{21}N_5O_3S$: 436.32 (MH$^+$).

Example 22a and Example 22b 3-amino-N-(3-(3-methoxy-5-nitro-phenylamino)quinoxalin-2-yl)benzenesulfonamide and 3-amino-N-(3-(3-amino-5-methoxy-phenylamino)quinoxalin-2-yl)benzenesulfonamide

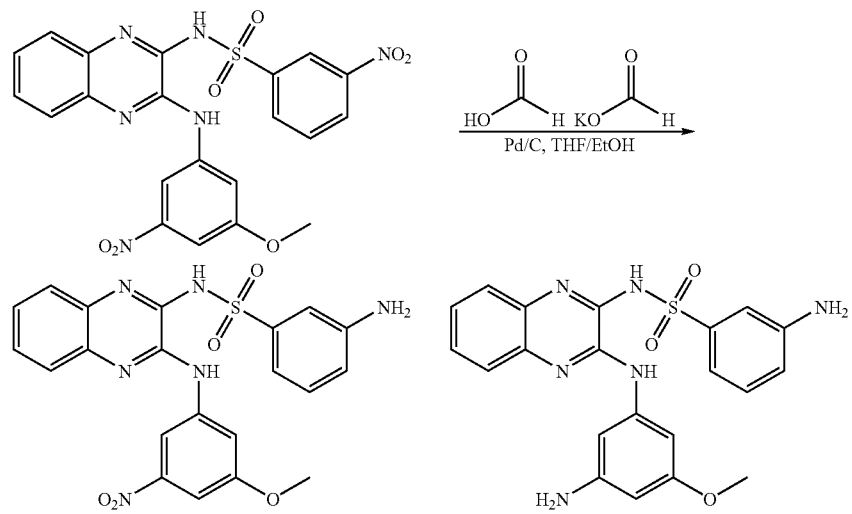

To a mixture of N-(3-{[3-(methyloxy)-5-nitrophenyl]amino}quinoxalin-2-yl)-3-nitrobenzenesulfonamide (400 mg), THF (2 mL) and EtOH (2 mL) was added formic acid (938 μL), potassium formate (203 mg). After the mixture was flushed with N$_2$, 10% wt Pd/C (50 mg) was added. The resulting mixture was heated at 60° C. with stirring. LC/MS analysis indicated that the reaction mixture contained the complete reduced di-amino compound as the major product and the partially reduced mono-amino compound as a minor product. A portion of the crude mixture was purified by HPLC to give the two products. Product A: 3-amino-N-(3-(3-methoxy-5-nitro-phenylamino)quinoxalin-2-yl)benzenesulfonamide. $^1$H NMR (400 MHz, DMSO) δ 12.2 (br s, 1H), 9.51 (s, 1H), 8.77 (s, 1H), 8.21 (s, 1H), 7.92 (s, 1H), 7.48 (m, 1H), 7.43-7.38 (m, 3H), 7.24-7.16 (m, 3H), 6.75 (d, 1H), 5.57 (br s, 2H), 3.90 (s, 3H). MS (EI) for $C_{21}H_{18}N_6O_5S$: 467.00 (MH+). Product B: 3-amino-N-(3-(3-amino-5-methoxy-phenylamino)quinoxalin-2-yl)benzenesulfonamide. $^1$H NMR (400 MHz, DMSO) δ 12.0 (br. s, 1H), 8.53 (s, 1H), 7.84 (s, 1H), 7.56 (d, 1H), 7.37-7.30 (m, 2H), 7.21-7.17 (m, 3H), 6.87 (s, 1H), 6.81 (s, 1H), 6.74 (br s, 2H), 5.91 (s, 1H), 5.56 (br s, 3H), 3.69 (s, 3H). MS (EI) for $C_{21}H_{20}N_6O_3S$: 437.2 (MH+).

Example 23a and Example 23b

N-(3-(3,5-dimethoxy-phenylamino)quinoxalin-2-yl)-3-(hydroxyamino)-benzenesulfonamide and 3-amino-N-(3-{[3,5-(dimethoxy)phenyl]amino}quinoxalin-2-yl)benzenesulfonamide

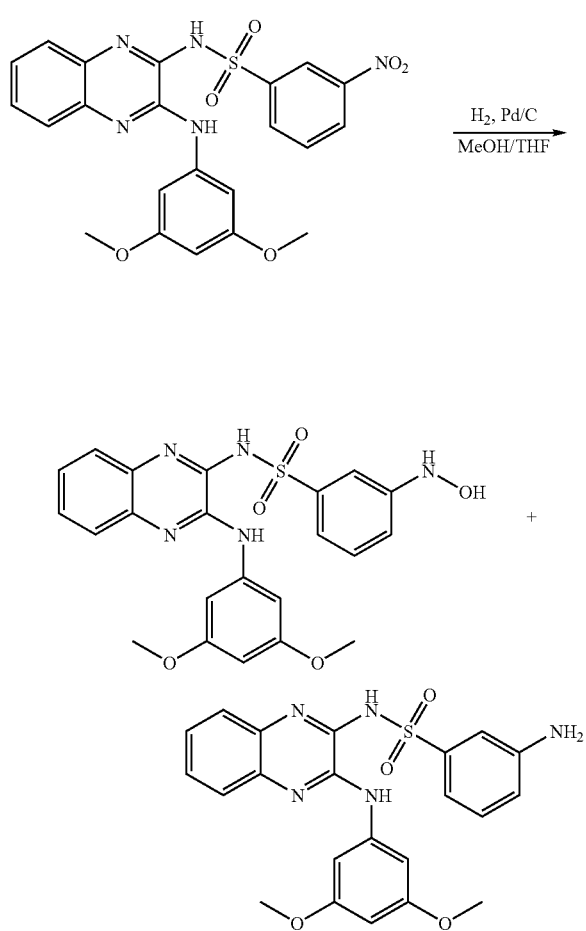

To a solution N-(3-(3,5-dimethoxyphenylamino)quinoxalin-2-yl)-3-nitrobenzenesulfonamide (1.3 g) in 20 mL of THF and 10 mL of MeOH was added 10% wt Pd/C (100 mg). The mixture was stirred under a $H_2$ balloon overnight. A portion of the reaction mixture was taken out and filtered, then purified by HPLC to afford two products. Product A: N-(3-{[3,5-bis(methyloxy)phenyl]amino}quinoxalin-2-yl)-3-(hydroxyamino)benzenesulfonamide. MS (EI) for $C_{22}H_{21}N_5O_5S$: 468.1 (MH+). Product B: 3-amino-N-(3-(3,5-dimethoxy-phenylamino)quinoxalin-2-yl)benzenesulfonamide. $^1$H NMR (400 MHz, DMSO) δ 12.2 (br s, 1H), 8.85 (s, 1H), 7.90 (br s, 1H), 7.50-7.60 (m, 1H), 7.3-7.4 (m, 4H), 7.2 (m, 3H), 6.74 (m, 1H), 6.24 (m, 1H), 5.56 (br s, 2H), 3.76 (s, 6H). MS (EI) for $C_{22}H_{21}N_5O_4S$: 452.0 (MH+).

Example 24

(S)-2-amino-N-(3-(N-(3-(3,5-dimethoxyphenylamino)quinoxalin-2-yl)sulfamoyl)phenyl)propanamide hydrochloride

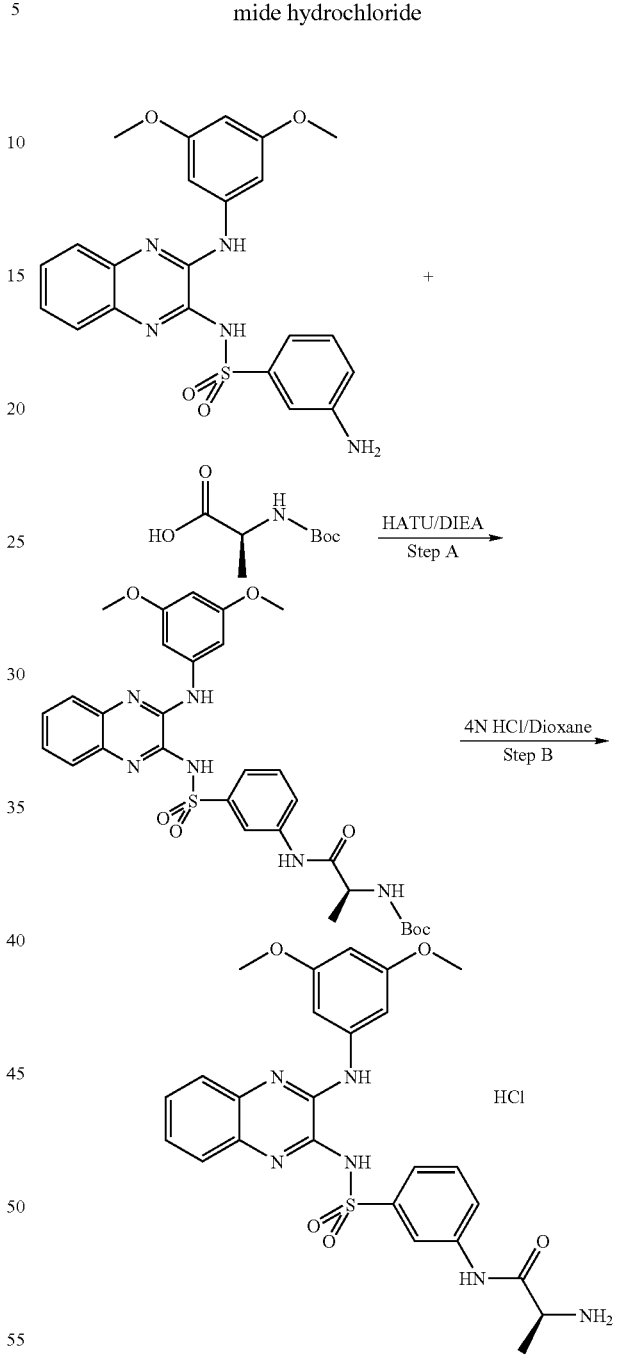

(S)-tert-butyl 1-(3-(N-(3-(3,5-dimethoxyphenylamino)quinoxalin-2-yl)sulfamoyl)phenylamino)-1-oxopropan-2-ylcarbamate. 3-amino-N-(3-(3,5-dimethoxy-phenylamino)quinoxalin-2-yl)benzenesulfonamide (1.1 mmol, 500 mg), prepared using procedures similar to those described above in Example 15, (L)-Boc-Ala-OH (1.5 mmol, 284 mg), dichloromethane (15 mL), DMF (10 mL), DIEA (2 mmol, 330 L), and HATU (2 mmol, 760 mg) stirred at room temperature over night. The crude mixture was column purified using 1/1 ethyl acetate/hexanes on silica to gave 160 mg.

(S)-2-amino-N-(3-(N-(3-(3,5-dim, ethoxyphenylamino) quinoxalin-2-yl)sulfamoyl)phenyl)propanamide hydrochloride. 4 N HCl is dioxane (10 mL) was added to a solution of (S)-tert-butyl 1-(3-(N-(3-(3,5-dimethoxyphenylamino)quinoxalin-2-yl)sulfamoyl)phenylamino)-1-oxopropan-2-ylcarbamate (160 mg) and DCM (15 mL). The mixture was stirred at room temperature for 3 hours. The solvent decanted and ether added to the solid, ether decanted to gave 80 mg product as HCl salt. $^1$H NMR (400 MHz, CD$_3$OD) δ 8.50-8.49 (t, 1H), 7.89-7.87 (m, 1H), 7.74-7.72 (m, 1H), 7.61-7.5 (m, 3H), 7.40-7.36 (m, 2H), 7.21-7.20 (d, 2H), 6.23-6.21 (t, 1H), 4.09-4.03 (q, 1H), 3.78 (s, 6H), 1.60-1.58 (d, 3H); MS (EI) m/z for C$_{25}$H$_{26}$N$_6$O$_5$S.HCl: 523.1 (MH$^+$).

The following compounds were prepared as the free amine and/or HCl salt using procedures similar to those in Example 24. Where the deprotection step is not necessary, Step B in the above scheme was not preformed.

Example 25

N-(2-chloro-5-(N-(3-(2-chloro-5-methoxy-phenylamino)quinoxalin-2-yl)sulfamoyl)phenyl)-2-(methylamino)acetamide The title compound was prepared according to the Examples above. $^1$H NMR (400 MHz, DMSO-d$_6$) δ 10.50 (s, 1H), 9.14 (s, 1H), 9.03 (m, 2H), 8.63 (d, 1H), 8.44 (d, 1H), 7.98 (m, 1H), 7.91 (dd, 1H), 7.80 (d, 1H), 7.67 (m, 1H), 7.44 (m, 3H), 6.71 (dd, 1H), 4.06 (m, 2H), 3.83 (s, 3H), 2.64 (t, 3H). MS (EI) m/z for C$_{24}$H$_{22}$Cl$_2$N$_6$O$_4$S: 561.0 (MH$^+$).

Example 26

(S)-2-amino-N-(3-(N-(3-(2-chloro-5-methoxy-phenylamino)quinoxalin-2-yl)sulfamoyl)phenyl)propanamide hydrochloride $^1$H NMR (400 MHz, CD$_3$OD) δ 8.72-8.71 (d, 1H), 8.48-8.46 (t, 1H), 7.86-7.84 (m, 1H), 7.80-7.78 (m, 1H), 7.63-7.59 (m, 2H), 7.58-7.55 (t, 1H), 7.41-7.38 (m, 2H), 7.24-7.22 (d, 1H), 6.60-6.58 (dd, 1H), 4.10-4.04 (q, 1H), 3.83 (s, 3H), 1.61-1.60 (d, 3H); MS (EI) m/z for C$_{24}$H$_{23}$ClN$_6$O$_4$S.HCl: 527.2 (MH$^+$).

Example 27

(S)-2-amino-N-(3-(N-(3-(2-chloro-5-methoxyphenylamino)quinoxalin-2-yl)sulfamoyl)phenyl)butanamide hydrochloride $^1$H NMR (400 MHz, CD$_3$OD) δ 8.74-8.73 (d, 1H), 8.80-8.47 (t, 1H), 7.87-7.85 (m, 1H), 7.80-7.78 (m, 1H), 7.67-7.61 (m, 2H), 7.59-7.55 (t, 1H), 7.42-7.39 (m, 2H), 7.26-7.24 (d, 1H), 6.62-6.59 (dd, 1H), 3.96-3.93 (t, 1H), 3.84 (s, 3H), 2.02-1.94 (m, 2H, 1.09-1.06 (t, 3H); MS (EI) m/z for C$_{25}$H$_{25}$ClN$_6$O$_4$S.HCl: 541.3 (MH$^+$).

Example 28

(S)—N-(3-(N-(3-(2-chloro-5-methoxyphenylamino)quinoxalin-2-yl)sulfamoyl)phenyl)pyrrolidine-2-carboxamide hydrochloride $^1$H NMR (400 MHz, CD$_3$OD) δ 8.78-8.77 (d, 1H), 8.47-8.46 (t, 1H), 7.87-7.85 (m, 1H), 7.80-7.75 (m, 1H), 7.69-7.65 (m, 2H), 7.59-7.55 (t, 1H), 7.45-7.41 (m, 2H), 7.31-7.28 (d, 1H), 6.65-6.63 (dd, 1H), 4.42-4.38 (m, 1H), 3.86 (s, 3H), 3.48-3.42 (m, 2H), 2.55-2.49 (m, 1H), 2.18-2.08 (m, 3H); MS (EI) m/z for C$_{26}$H$_{25}$ClN$_6$O$_4$S.HCl: 553.3 (MH$^+$).

Example 29

(S)—N-(3-(N-(3-(3,5-dimethoxy-phenylamino)quinoxalin-2-yl)sulfamoyl)phenyl)pyrrolidine-2-carboxamide hydrochloride $^1$H NMR (400 MHz, CD$_3$OD) δ 10.62 (br s, 1H), 8.50-8.49 (t, 1H), 7.90-7.87 (m, 1H), 7.76-7.73 (m, 1H), 7.63-7.58 (m, 3H), 7.43-7.35 (m, 2H), 7.14 (s, 2H), 6.27-6.26 (t, 1H), 4.43-4.38 (m, 1H), 3.78 (s, 6H), 3.48-3.41 (m, 1H), 3.40-3.36 (m, 1H), 2.54-2.48 (m, 1H), 2.19-2.05 (m, 3H); MS (EI) m/z for C$_{27}$H$_{28}$N$_6$O$_5$S.HCl: 549.3 (MH$^+$).

Example 30

(R)-2-amino-N-(3-(N-(3-(3,5-dimethoxy-phenylamino)quinoxalin-2-yl)sulfamoyl)phenyl)-3-hydroxypropanamide hydrochloride $^1$H NMR (400 MHz, CD$_3$OD) δ 8.49-8.48 (t, 1H), 7.89-7.87 (m, 1H), 7.75-7.72 (m, 1H), 7.65-7.62 (m, 2H), 7.62-7.55 (t, 1H), 7.44-7.38 (m, 2H), 7.23-7.22 (d, 2H), 6.27-6.26 (t, 1H), 4.07-4.05 (m, 1H), 3.99-3.93 (m, 2H), 3.80 (s, 6H); MS (EI) m/z for C$_{25}$H$_{26}$N$_6$O$_6$S.HCl: 539.1 (MH$^+$).

Example 31

N-(3-(N-(3-(2-chloro-5-methoxy-phenylamino)quinoxalin-2-yl)sulfamoyl)phenyl)piperidine-3-carboxamide hydrochloride $^1$H NMR (400 MHz, CD$_3$OD) δ 8.79-8.78 (d, 1H), 8.45 (m, 1H), 7.83-7.81 (d, 1H), 7.76-7.74 (m, 1H), 7.636 (m, 2H), 7.54-7.50 (t, 1H), 7.41 (m, 2H), 7.30-7.28 (d, 1H), 6.65-6.62 (dd, 1H), 3.86 (s, 3H), 3.40-3.32 (m, 2H), 3.20-3.13 (m, 3H), 2.93 (m, 1H), 2.15-2.11 (m, 1H), 1.98-1.93 (m, 2H), 1.83 (m, 1H); MS (EI) m/z for C$_{27}$H$_{27}$ClN$_6$O$_4$S.HCl: 567.3 (MH$^+$).

Example 32

(S)-2-amino-N-(3-(N-(3-(3,5-dimethoxyphenylamino)quinoxalin-2-yl)sulfamoyl)phenyl)butanamide hydrochloride MS (EI) m/z for C$_{26}$H$_{28}$N$_6$O$_5$S.HCl: 537.1 (MH$^+$).

Example 33

(R)—N-(3-(N-(3-(3,5-dimethoxy-phenylamino)quinoxalin-2-yl)sulfamoyl)phenyl)pyrrolidine-2-carboxamide hydrochloride MS (EI) m/z for C$_{27}$H$_{28}$N$_6$O$_5$S.HCl: 549.1 (MH$^+$).

Example 34

(R)—N-(3-(N-(3-(2-chloro-5-methoxy-phenylamino)quinoxalin-2-yl)sulfamoyl)phenyl)pyrrolidine-2-carboxamide hydrochloride MS (EI) m/z for C$_{26}$H$_{25}$ClN$_6$O$_4$S.HCl: 553 (MH$^+$).

Example 35

(R)-2-amino-N-(3-(N-(3-(3,5-dimethoxyphenylamino)quinoxalin-2-yl)sulfamoyl)phenyl)propanamide $^1$H NMR (400 MHz, DMSO-$d_6$) δ 10.2 (br s, 1H), 8.82 (s, 1H), 8.27 (m, 1H), 7.75 (m, 2H), 7.33 (m, 5H), 7.13 (m, 2H), 6.14 (t, 1H), 3.77 (s, 6H), 1.39 (d, 3H); MS (EI) m/z for $C_{25}H_{26}N_6O_5S$: 523 (MH$^+$).

Example 36

N-(3-(N-(3-(2-chloro-5-methoxy-phenylamino)quinoxalin-2-yl)sulfamoyl)phenyl)-2-(methylamino)acetamide $^1$H NMR (400 MHz, DMSO-$d_6$) δ 10.6 (s, 1H), 9.48 (s, 1H), 8.95 (br s, 1H), 8.75 (br s, 1H), 8.19 (br s, 1H), 7.77 (dd, 1H), 7.69 (dd, 1H), 7.41 (m, 4H), 7.17 (m, 2H), 6.60 (dd, 1H), 3.91 (s, 2H), 3.82 (s, 6H), 2.62 (s, 3H); MS (EI) m/z for $C_{24}H_{23}ClN_6O_4S$: 527 (MH$^+$).

Example 37

(R)-2-amino-N-(3-(N-(3-(2-chloro-5-methoxy-phenylamino)quinoxalin-2-yl)sulfamoyl)phenyl)propanamide $^1$H NMR (400 MHz, DMSO-$d_6$) δ 10.5 (s, 1H), 9.47 (s, 1H), 8.95 (d, 1H), 8.22 (d, 2H), 8.14 (br s, 2H), 7.76 (m, 2H), 7.40 (m, 4H), 7.17 (m, 2H), 6.60 (m, 1H), 3.97 (q, 1H), 3.96 (s, 3H), 1.45 (d, 3H); MS (EI) m/z for $C_{24}H_{23}ClN_6O_4S$: 527 (MH$^+$).

Example 38

2-amino-N-(3-(N-(3-(2-chloro-5-methoxy-phenylamino)quinoxalin-2-yl)sulfamoyl)phenyl)-2-methylpropanamide $^1$H NMR (400 MHz, DMSO-$d_6$) δ 10.1 (s, 1H), 9.46 (s, 1H), 8.95 (d, 1H), 8.50 (br s, 1H), 8.27 (m, 1H), 7.81 (m, 2H), 7.47 (m, 1H), 7.37 (m, 3H), 7.17 (m, 2H), 6.61 (dd, 1H), 3.83 (s, 3H), 1.60 (s, 6H); MS (EI) m/z for $C_{25}H_{25}ClN_6O_4S$: 541 (MH$^+$).

Example 39

2-amino-N-(3-(N-(3-(3,5-dimethoxy-phenylamino)quinoxalin-2-yl)sulfamoyl)phenyl)-2-methylpropanamide $^1$H NMR (400 MHz, DMSO-$d_6$) δ 10.33 (s, 1H), 8.89 (s, 1H), 8.32 (br s, 4H), 7.92 (m, 3H), 7.59 (m, 2H), 7.37 (m, 4H), 6.24 (s, 1H), 3.76 (s, 6H), 1.61 (s, 6H); MS (EI) m/z for $C_{26}H_{28}N_6O_5S$: 537 (MH$^+$).

Example 40

N-(3-(N-(3-(3,5-dimethoxy-phenylamino)quinoxalin-2-yl)sulfamoyl)-4-methylphenyl)-2-(dimethylamino)acetamide $^1$H NMR (400 MHz, DMSO-$d_6$) δ 10.58 (s, 1H), 9.80 (br s, 1H), 8.85 (s, 1H), 8.25 (s, 1H), 7.67 (dd, 1H), 7.30 (m, 7H), 6.16 (m, 1H), 4.02 (br s, 2H), 3.77 (s, 6H), 2.81 (s, 6H), 2.54 (s, 3H); MS (EI) m/z for $C_{27}H_{30}N_6O_5S$: 551 (MH$^+$).

Example 41

N-(3-(N-(3-(2-chloro-5-methoxy-phenylamino)quinoxalin-2-yl)sulfamoyl)phenyl)-2-((2-(dimethylamino)ethyl)(methyl)amino)acetamide $^1$H NMR (400 MHz, DMSO-$d_6$) δ 10.0 (s, 1H), 9.48 (s, 1H), 8.96 (d, 1H), 8.16 (m, 1H), 7.76 (m, 2H), 7.39 (m, 4H), 7.17 (m, 2H), 6.61 (dd, 1H), 3.82 (s, 3H), 3.40 (br s, 2H), 2.94 (br s, 2H), 2.71 (br t, 2H), 2.60 (s, 6H), 2.33 (s, 3H); MS (EI) m/z for $C_{28}H_{32}ClN_7O_4S$: 598 (MH$^+$).

Example 42

2-amino-N-(3-(N-(3-(2-chloro-5-methoxy-phenylamino)quinoxalin-2-yl)sulfamoyl)phenyl)acetamide $^1$H NMR (400 MHz, DMSO-$d_6$) δ 10.5 (s, 1H), 9.48 (s, 1H), 8.94 (s, 1H), 8.15 (s, 1H), 8.06 (br s, 3H), 7.74 (m, 2H), 7.39 (m, 4H), 7.18 (m, 2H), 6.61 (dd, 1H), 3.83 (s, 3H), 3.77 (s, 2H); MS (EI) m/z for $C_{23}H_{21}ClN_6O_4S$: 513 (MH$^+$).

Example 43

N-(3-(N-(3-(2-acetyl-5-methoxy-phenylamino)quinoxalin-2-yl)sulfamoyl)phenyl)-2-(dimethylamino)acetamide $^1$H NMR (400 MHz, DMSO-$d_6$) δ 12.4 (s, 1H), 10.5 (s, 1H), 9.27 (s, 1H), 8.25 (s, 1H), 8.01 (d, 1H), 7.82 (d, 1H), 7.71 (d, 1H), 7.42 (m, 3H), 7.21 (m, 2H), 6.63 (dd, 1H), 3.91 (m, 5H), 2.75 (s, 6H), 2.61 (s, 3H); MS (EI) m/z for $C_{27}H_{28}N_6O_5S$: 549 (MH$^+$).

Example 44

N-(3-(N-(3-(2-chloro-5-methoxy-phenylamino)quinoxalin-2-yl)sulfamoyl)phenyl)formamide $^1$H NMR (400 MHz, DMSO-$d_6$) δ 12.6 (s, 1H), 10.5 (s, 1H), 9.16 (s, 1H), 8.53 (br s, 1H), 8.35 (m, 2H), 8.02 (s, 1H), 7.56 (m, 7H), 6.70 (dd, 1H), 3.83 (s, 3H); MS (EI) m/z for $C_{22}H_{18}ClN_5O_4S$: 484 (MH$^+$).

Example 45

2-amino-N-(5-(N-(3-(3,5-dimethoxy-phenylamino)quinoxalin-2-yl)sulfamoyl)-2-methylphenyl)acetamide $^1$H NMR (400 MHz, DMSO-$d_6$) δ 12.4 (s, 1H), 10.1 (br s, 1H), 8.82 (s, 1H), 8.20 (m, 3H), 7.82 (m, 1H), 7.30 (m, 6H), 6.20 (s, 1H), 3.85 (s, 2H), 3.77 (s, 6H), 2.26 (s, 3H); MS (EI) m/z for $C_{25}H_{26}N_6O_5S$: 523 (MH$^+$).

Example 46

N-(3-(N-(3-(2-chloro-5-methoxy-phenylamino)quinoxalin-2-yl)sulfamoyl)phenyl)-2-methyl-2-(methylamino)propanamide $^1$H NMR (400 MHz, DMSO-$d_6$) δ 10.09 (s, 1H), 9.46 (s, 1H), 8.95 (m, 3H), 8.28 (s, 1H), 7.81 (m, 2H), 7.41 (m, 4H), 7.17 (m, 2H), 6.60 (dd, 1H), 3.82 (s, 3H), 2.53 (s, 3H), 1.60 (s, 6H); MS (EI) m/z for $C_{26}H_{27}ClN_6O_4S$: 555 (MH$^+$).

Example 47

(S)—N-(3-(N-(3-(2-chloro-5-methoxy-phenylamino)quinoxalin-2-yl)sulfamoyl)phenyl)-2-(methylamino)propanamide $^1$H NMR (400 MHz, DMSO-$d_6$) δ 10.61 (s, 1H), 9.47 (s, 1H), 8.95 (s, 1H), 8.82 (br s, 2H), 8.27 (m, 1H), 7.74 (m, 2H), 7.42 (m, 4H), 7.17 (m, 2H), 6.60 (dd, 1H), 3.90 (m, 1H), 3.82 (s, 3H), 2.59 (s, 3H), 1.49 (d, 3H); MS (EI) m/z for $C_{25}H_{25}ClN_6O_4S$: 541 (MH$^+$).

Example 48

3-amino-N-(5-(N-(3-(2-chloro-5-methoxyphenylamino)quinoxalin-2-yl)sulfamoyl)-2-methylphenyl)propanamide $^1$H NMR (400 MHz, DMSO-$d_6$) δ 12.25 (s, 1H), 9.77 (s, 1H), 8.82 (s, 1H), 7.84 (m, 5H), 7.50 (d, 1H), 7.37 (m, 5H), 6.22 (m, 1H), 3.74 (s, 6H), 3.08 (m, 2H), 2.77 (m, 2H), 2.27 (s, 3H); MS (EI) m/z for $C_{26}H_{28}N_6O_5S$: 537 (MH$^+$).

Example 49

1-amino-N-(3-(N-(3-(2-chloro-5-methoxy-phenylamino)quinoxalin-2-yl)sulfamoyl)phenyl)cyclopropanecarboxamide $^1$H NMR (400 MHz, DMSO-$d_6$) δ 9.54 (br s, 1H), 9.42 (s, 1H), 8.91 (s, 1H), 8.21 (s, 1H), 8.20 (br s, 2H), 7.81 (m, 2H), 7.48 (m, 4H), 7.22 (m, 2H), 6.61 (dd, 1H), 3.82 (s, 3H), 1.63 (m, 2H), 1.26 (m, 2H); MS (EI) m/z for $C_{25}H_{23}ClN_6O_4S$: 539 (MH$^+$).

Example 50

(S)-2-amino-N-(3-(N-(3-(2-chloro-5-methoxy-phenylamino)quinoxalin-2-yl)sulfamoyl)phenyl)-6-(dimethylamino)hexanamide $^1$H NMR (400 MHz, DMSO-$d_6$) δ 9.47 (br s, 1H), 8.95 (d, 1H), 8.26 (m, 1H), 7.73 (m, 2H), 7.30 (m, 4H), 7.26 (m, 4H), 7.16 (m, 2H), 6.59 (dd, 1H), 3.82 (s, 3H), 3.34 (m, 1H), 2.20 (m, 2H), 2.09 (s, 6H), 1.50 (m, 6H); MS (EI) m/z for $C_{29}H_{34}ClN_7O_4S$: 610 (MH$^+$).

Example 51

1-amino-N-(3-(N-(3-(2-chloro-5-methoxy-phenylamino)quinoxalin-2-yl)sulfamoyl)phenyl)cyclopentanecarboxamide $^1$H NMR (400 MHz, DMSO-$d_6$) δ 10.12 (br s, 1H), 9.46 (s, 1H), 8.95 (d, 1H), 8.26 (m, 1H), 8.16 (m, 3H), 7.84 (m, 2H), 7.35 (m, 6H), 6.60 (dd, 1H), 3.82 (s, 3H), 2.34 (m, 2H), 1.91 (m, 6H); MS (EI) m/z for $C_{27}H_{27}ClN_6O_4S$: 567 (MH$^+$).

Example 52

N-(5-(N-(3-(2-chloro-5-methoxyphenylamino)quinoxalin-2-yl)sulfamoyl)-2-methylphenyl)-2-(dimethylamino)acetamide $^1$H NMR (400 MHz, DMSO-$d_6$) δ 12.0 (br s, 1H), 9.98 (s, 1H), 9.43 (s, 1H), 8.91 (m, 1H), 8.08 (s, 1H), 7.84 (dd, 1H), 7.32 (m, 6H), 6.61 (dd, 1H), 4.07 (s, 2H), 3.82 (s, 3H), 2.82 (s, 6H), 2.21 (s, 3H); MS (EI) m/z for $C_{26}H_{27}ClN_6O_4S$: 555 (MH$^+$).

Example 53

1-amino-N-(3-(N-(3-(3,5-dimethoxy-phenylamino)quinoxalin-2-yl)sulfamoyl)phenyl)cyclobutanecarboxamide $^1$H NMR (400 MHz, DMSO-$d_6$) δ 10.34 (br s, 1H), 8.81 (s, 1H), 8.49 (br s, 3H), 8.34 (s, 1H), 7.83 (m, 2H), 7.43 (m, 3H), 7.31 (m, 2H), 7.16 (m, 2H), 6.16 (s, 1H), 3.77 (s, 6H), 2.83 (m, 2H), 2.25 (m, 3H), 2.05 (m, 1H); MS (EI) m/z for $C_{27}H_{28}N_6O_5S$: 549 (MH$^+$).

Example 54

N-(3-(3,5-dimethoxyphenylamino)quinoxalin-2-yl)-3-(3-(2-(dimethylamino)ethyl)ureido)benzenesulfonamide $^1$H NMR (400 MHz, DMSO-$d_6$) δ 8.91 (br s, 1H), 8.81 (s, 1H), 8.08 (s, 1H), 7.60 (s, 1H), 7.38 (m, 9H), 6.28 (m, 1H), 6.15 (s, 1H), 3.78 (s, 6H), 3.40 (m, 2H), 3.08 (m, 2H), 2.74 (s, 6H); MS (EI) m/z for $C_{27}H_{31}N_7O_5S$: 566 (MH$^+$).

Example 55

1-amino-N-(3-(N-(3-(3,5-dimethoxy-phenylamino)quinoxalin-2-yl)sulfamoyl)phenyl)cyclopentanecarboxamide $^1$H NMR (400 MHz, DMSO-$d_6$) δ 12.40 (br s, 1H), 10.58 (s, 1H), 8.46 (m, 4H), 7.80 (m, 3H), 7.59 (m, 2H), 7.34 (m, 4H), 6.25 (m, 1H), 3.76 (s, 6H), 2.35 (m, 2H), 1.90 (m, 8H); MS (EI) m/z for $C_{28}H_{30}N_6O_5S$: 563 (MH$^+$).

Example 56

1-amino-N-(3-(N-(3-(3,5-dimethoxy-phenylamino)quinoxalin-2-yl)sulfamoyl)phenyl)cyclopropanecarboxamide $^1$H NMR (400 MHz, DMSO-$d_6$) δ 9.54 (br s, 1H), 8.84 (s, 1H), 8.29 (s, 1H), 7.75 (m, 2H), 7.39 (m, 6H), 7.17 (m, 2H), 6.16 (m, 1H), 3.78 (s, 6H), 1.52 (m, 2H), 1.17 (m, 2H); MS (EI) m/z for $C_{26}H_{26}N_6O_5S$: 535 (MH$^+$).

Example 57

2-(dimethylamino)ethyl 3-(N-(3-(3,5-dimethoxyphenylamino)quinoxalin-2-yl)sulfamoyl)phenylcarbamate $^1$H NMR (400 MHz, DMSO-$d_6$) δ 9.78 (br s, 1H), 8.79 (s, 1H), 8.19 (s, 1H), 7.66 (d, 1H), 7.31 (m, 9H), 6.14 (m, 1H), 4.17 (t, 2H), 3.78 (s, 6H), 2.54 (t, 2H), 2.21 (s, 6H); MS (EI) m/z for $C_{27}H_{30}N_6O_6S$: 567 (MH$^+$).

Example 58

4-amino-N-(3-(N-(3-(3,5-dimethoxy-phenylamino)quinoxalin-2-yl)sulfamoyl)phenyl)tetrahydro-2H-pyran-4-carboxamide $^1$H NMR (400 MHz, DMSO-$d_6$) δ 12.2 (br s, 1H), 10.6 (s, 1H), 8.74 (m, 5H), 7.93 (m, 2H), 7.47 (m, 6H), 6.24 (m, 1H), 3.77 (m, 10H), 2.45 (m, 2H), 1.81 (m, 2H); MS (EI) m/z for $C_{28}H_{30}N_6O_6S$: 579 (MH$^+$).

Example 59

N-(3-(2-chloro-5-methoxy-phenylamino)quinoxalin-2-yl)-N-3-(2-(dimethylamino)ethyl)benzene-1,3-disulfonamide $^1$H NMR (400 MHz, DMSO-d$_6$) δ 9.35 (m, 2H), 8.92 (m, 1H), 8.64 (s, 1H), 8.30 (m, 1H), 8.11 (s, 1H), 7.86 (m, 1H), 7.68 (m, 1H), 7.49 (s, 1H), 7.42 (m, 2H), 7.21 (m, 2H), 6.61 (m, 1H), 3.82 (s, 3H), 3.05 (m, 4H), 2.74 (s, 6H); MS (EI) m/z for $C_{25}H_{27}ClN_6O_5S_2$: 591 (MH$^+$).

Example 60

N-(3-(2-chloro-5-methoxy-phenylamino)quinoxalin-2-yl)-N3-(3-(dimethylamino)propyl)benzene-1,3-disulfonamide $^1$H NMR (400 MHz, DMSO-d$_6$) δ 9.38 (m, 2H), 8.90 (m, 1H), 8.60 (s, 1H), 8.32 (m, 1H), 8.12 (s, 1H), 7.88 (m, 1H), 7.72 (m, 1H), 7.59 (s, 1H), 7.40 (m, 2H), 7.20 (m, 2H), 6.67 (m, 1H), 3.82 (s, 3H), 2.97 (m, 2H), 2.78 (m, 2H), 2.71 (s, 6H), 1.70 (m, 2H); MS (EI) m/z for $C_{26}H_{29}ClN_6O_5S_2$: 605 (MH$^+$).

Example 61

N-(3-(N-(3-(2-chloro-5-methoxy-phenylamino)quinoxalin-2-yl)sulfamoyl)-4-methylphenyl)-2-(methylamino)acetamide MS (EI) m/z for $C_{25}H_{25}ClN_6O_4S$: 541.0 (MH$^+$).

Example 62

(S)-2-amino-N-(3-(N-(3-(2-chloro-5-methoxy-phenylamino)quinoxalin-2-yl)sulfamoyl)-4-methylphenyl)propanamide MS (EI) m/z for $C_{25}H_{25}ClN_6O_4S$: 541.2 (MH$^+$).

Example 63

(R)-2-amino-N-(3-(N-(3-(2-chloro-5-methoxy-phenylamino)quinoxalin-2-yl)sulfamoyl)-4-methylphenyl)propanamide MS (EI) m/z for $C_{25}H_{25}ClN_6O_4S$: 541.0 (MH$^+$).

Example 64

(S)—N-(3-(N-(3-(3,5-dimethoxy-phenylamino)quinoxalin-2-yl)sulfamoyl)phenyl)-2-(methylamino)propanamide MS (EI) m/z for $C_{26}H_{28}N_6O_5S$: 537.1 (MH$^+$).

Example 65

(R)—N-(3-(N-(3-(2-chloro-5-methoxy-phenylamino)quinoxalin-2-yl)sulfamoyl)phenyl)-2-(methylamino)propanamide MS (EI) m/z for $C_{25}H_{25}ClN_6O_4S$: 541.1 (MH$^+$).

Example 66

(R)—N-(3-(N-(3-(3,5-dimethoxy-phenylamino)quinoxalin-2-yl)sulfamoyl)phenyl)-2-(methylamino)propanamide MS (EI) m/z for $C_{26}H_{28}N_6O_5S$: 537.3 (MH$^+$).

Example 67

N-(3-(N-(3-(3,5-dimethoxy-phenylamino)quinoxalin-2-yl)sulfamoyl)phenyl)piperidine-2-carboxamide MS (EI) m/z for $C_{28}H_{30}N_6O_5S$: 563.1 (MH$^+$).

Example 68

N-(3-(N-(3-(3,5-dimethoxy-phenylamino)quinoxalin-2-yl)sulfamoyl)phenyl)-2-(2-(dimethylamino)ethylamino)acetamide MS (EI) m/z for $C_{28}H_{33}N_7O_5S$: 580.1 (MH$^+$).

Example 69

N-(3-(N-(3-(3,5-dimethoxy-phenylamino)quinoxalin-2-yl)sulfamoyl)phenyl)-2-(4-(methylamino)piperidin-1-yl)acetamide MS (EI) m/z for $C_{30}H_{35}N_7O_6S$: 606.1 (MH$^+$).

Example 70

N-(3-(N-(3-(3,5-dimethoxy-phenylamino)quinoxalin-2-yl)sulfamoyl)phenyl)-2-(4-(dimethylamino)piperidin-1-yl)acetamide MS (EI) m/z for $C_{31}H_{37}N_7O_5S$: 620.1 (MH$^+$).

Example 71

N-(3-(N-(3-(3,5-dimethoxyphenylamino)quinoxalin-2-yl)sulfamoyl)phenyl)-2-(dimethylamino)acetamide $^1$H NMR (400 MHz, DMSO) δ 12.4 (br s, 1H), 10.9 (s, 1H), 9.8 (s, 1H), 8.9 (s, 1H), 8.3 (br s, 1H), 7.9 (d, 2H), 7.8 (d, 1H), 7.6 (t, 2H), 7.4 (q, 2H), 7.3 (s, 1H), 6.25 (s, 1H), 4.15 (s, 2H), 3.8 (s, 6H), 2.9 (s, 6H). MS (EI) m/z for $C_{26}H_{28}N_6O_5S$ 2.0× $C_2H_1O_2F_3$: 537.1 (MH$^+$).

Example 72

N-(3-(N-(3-(2-chloro-5-methoxy-phenylamino)quinoxalin-2-yl)sulfamoyl)phenyl)-2-(ethylamino)acetamide $^1$H NMR (400 MHz, DMSO) δ 10.8 (s, 1H), 9.20 (s, 1H), 8.84 (br s, 2H), 8.64 (br s, 1H), 8.30 (s, 1H), 7.9-8.0 (br s, 1H), 7.80 (t, 2H), 7.55-7.68 (m, 2H), 7.4 (d, 3H), 6.70 (m, 1H), 3.97 (br s, 2H), 3.83 (s, 3H), 3.04 (br s, 2H), 1.3 (t, 3H). MS (EI) m/z for $C_{25}H_{25}ClN_6O_4S$ 2.0×$C_2H_1O_2F_3$: 541.3, 543.2 (MH$^+$).

Example 73

2-(azetidin-1-yl)-N-(3-(N-(3-(2-chloro-5-methoxyphenylamino)quinoxalin-2-yl)sulfamoyl)phenyl)acetamide $^1$H NMR (400 MHz, DMSO) δ 10.8 (s, 1H), 10.2 (s, 1H), 9.2 (s, 1H), 8.7 (s, 1H), 8.3 (s, 1H), 7.9-8.0 (br s, 1H), 7.80 (d, 1H), 7.72 (d, 1H), 7.65 (br s, 1H), 7.56 (t, 1H), 7.40 (d, 3H), 6.70 (m, 1H), 4.28 (s, 2H), 4.15 (m, 4H), 3.82 (s, 3H), 2.32 (br s, 1H). MS (EI) m/z for $C_{26}H_{25}ClN_6O_4S$ 2.0×$C_2H_1O_2F_3$: 553.3, 555.2 (MH$^+$).

Example 74

N-(3-(N-(3-(2-bromo-5-methoxy-phenylamino)quinoxalin-2-yl)sulfamoyl)phenyl)-2-(methylamino)acetamide. The title compound was prepared according to the Examples above. $^1$H NMR (400 MHz, DMSO) δ 10.6 (s, 1H), 9.5 (s, 1H), 8.95 (d, 1H), 8.18 (t, 1H), 7.78 (m, 1H), 7.70 (m, 1H), 7.54 (d, 1H), 7.46 (m, 1H), 7.38 (t, 1H), 7.32 (d, 1H), 7.12-7.22 (m, 2H), 6.56 (m, 1H), 3.90 (s, 2H), 3.82 (s, 3H), 2.62 (s, 3H). MS (EI) m/z for $C_{24}H_{23}BrN_6O_4S$: 572.77, 570.90 (MH$^+$).

Example 75

2-(dimethylamino)-N-(3-(N-(3-(6-methoxy-quinolin-8-ylamino)quinoxalin-2-yl)sulfamoyl)phenyl)acetamide. The title compound was prepared according to the Examples above. $^1$H NMR (400 MHz, DMSO) δ 10.9 (s, 1H), 10.6 (s, 1H), 9.13 (s, 1H), 8.80 (d, 1H), 8.26-8.30 (m, 2H), 7.85 (d, 1H), 7.70 (d, 1H), 7.60 (q, 1H), 7.54 (m, 1H), 7.44 (t, 2H), 7.20 (t, 2H), 6.80 (d, 1H), 4.00 (s, 2H), 3.94 (s, 3H), 2.78 (s, 6H). MS (EI) m/z for $C_{28}H_{27}N_7O_4S$: 558.3 (MH$^+$).

Example 76

N-(3-(N-(3-(2-bromo-5-methoxy-phenylamino)quinoxalin-2-yl)sulfamoyl)phenyl)-2-(dimethylamino)acetamide $^1$H NMR (400 MHz, DMSO) δ 10.6 (s, 1H), 9.4 (s, 1H), 8.9 (s, 1H), 8.25 (s, 1H), 7.78 (d, 1H), 7.70 (d, 1H), 7.54 (d, 1H), 7.48 (d, 1H), 7.40 (t, 2H), 6.56 (d, 1H), 4.02 (s, 2H), 3.82 (s, 3H), 2.80 (s, 6H). MS (EI) m/z for $C_{25}H_{25}BrN_6O_4S$: 586.79, 584.91 (MH$^+$).

Example 77

N-(3-(N-(3-(2-chloro-5-methoxy-phenylamino)quinoxalin-2-yl)sulfamoyl)phenyl)-2-(2-fluoroethylamino)acetamide $^1$H NMR (400 MHz, DMSO) δ 10.6 (s, 1H), 9.4 (s, 1H), 8.9 (d, 1H), 8.20 (s, 1H), 7.78 (d, 1H), 7.70 (d, 1H), 7.48 (m, 1H), 7.36-7.44 (m, 3H), 7.20 (q, 3H), 6.6 (m, 1H), 4.78 (t, 1H), 4.66 (t, 1H), 3.94 (s, 2H), 3.82 (s, 3H), 3.4 (t, 1H), 3.3 (t, 1H). MS (EI) m/z for $C_{25}H_{24}ClFN_6O_4S$: 559.2, 561.2 (MH$^+$).

Example 78

N-(3-(N-(3-(3,5-dimethoxy-phenylamino)quinoxalin-2-yl)sulfamoyl)phenyl)formamide $^1$H NMR (400 MHz, DMSO) δ 12.4 (br s, 1H), 10.5 (s, 1H), 8.90 (s, 1H), 8.3 (s, 1H), 7.9 (br s, 1H), 7.85 (d, 1H), 7.75 (d, 1H), 7.5-7.6 (m, 2H), 7.3-7.4 (m, 4H), 6.2 (s, 1H), 3.8 (s, 3H). MS (EI) m/z for $C_{23}H_{21}N_5O_5S$: 480.1 (MH$^+$).

Example 79

N-(3-(N-(3-(2-chloro-5-methoxy-phenylamino)quinoxalin-2-yl)sulfamoyl)phenyl)-2-(3-(dimethylamino)azetidin-1-yl)acetamide $^1$H NMR (400 MHz, DMSO) δ 10.2 (br s, 1H), 9.5 (s, 1H), 8.95 (d, 1H), 8.2 (s, 1H), 7.75 (d, 1H), 7.65 (d, 1H), 7.45 (d, 1H), 7.40 (d, 1H), 7.30-7.35 (t, 1H), 7.1-7.2 (q, 2H), 6.60 (m, 1H), 3.82 (s, 3H). MS (EI) m/z for $C_{28}H_{30}ClN_7O_4S$: 480.1 (MH$^+$).

Example 80

N-(3-(N-(3-(3,5-dimethoxy-phenylamino)quinoxalin-2-yl)sulfamoyl)phenyl)-2-(pyrrolidin-1-yl)acetamide MS (EI) m/z for $C_{28}H_{30}N_6O_5S$: 563.18 (MH$^+$).

Example 81

N-(3-(N-(3-(2-chloro-5-methoxyphenylamino)quinoxalin-2-yl)sulfamoyl)phenyl)-2-(ethyl(methyl)amino)acetamide $^1$H NMR (400 MHz, DMSO) δ 12.0 (s, 1H), 10.6 (s, 1H), 9.65 (s, 1H), 9.5 (s, 1H), 8.95 (s, 1H), 8.25 (s, 1H), 7.8 (d, 1H), 7.70 (d, 1H), 7.45-7.50 (d, 1H), 7.3-7.4 (m, 3H), 7.2 (t, 2H), 6.60 (d, 1H), 4.02 (br s, 2H), 3.82 (s, 3H), 3.14 (br s, 2H), 2.80 (s, 3H) 1.2 (t, 3H). MS (EI) m/z for $C_{26}H_{27}ClN_6O_4S$: 555.2, 557.3 (MH$^+$).

Example 82

N-(3-(N-(3-(2-chloro-5-methoxy-phenylamino)quinoxalin-2-yl)sulfamoyl)phenyl)-2-(3-(piperidin-1-yl)azetidin-1-yl)acetamide MS (EI) m/z for $C_{31}H_{34}ClN_7O_4S$ 2.0×$C_2H_1O_2F_3$: 636.3, 638.3 (MH$^+$).

Example 83

N-(3-(N-(3-(3-fluoro-5-methoxy-phenylamino)quinoxalin-2-yl)sulfamoyl)phenyl)-2-(methylamino)acetamide MS (EI) m/z for $C_{24}H_{23}FN_6O_4S$: 511.04 (MH$^+$)).

Example 84

N-(3-(N-(3-(3,5-dimethoxy-phenylamino)quinoxalin-2-yl)sulfamoyl)phenyl)-1-methylpiperidine-4-carboxamide MS (EI) m/z for $C_{29}H_{32}N_6O_5S$ 1.0×$C_2H_4O_2$: 577.2 (MH$^+$).

Example 85

N-(3-(N-(3-(3-methoxyphenylamino)quinoxalin-2-yl)sulfamoyl)phenyl)-2-(methylamino)acetamide $^1$H NMR (400 MHz, DMSO) δ 10.6 (s, 1H), 8.82 (s, 1H), 8.22 (t, 1H), 7.86 (t, 1H), 7.76 (m, 1H), 7.66 (m, 1H), 7.46 (m, 1H), 7.41 (m, 1H), 7.38 (t, 1H), 7.28 (m 1H), 7.24 (t, 1H), 7.12 (m, 2H), 6.56 (d, 1H), 3.88 (s, 2H), 3.80 (s, 3H), 2.60 (s, 3H). MS (EI) m/z for $C_{24}H_{24}N_6O_4S$: 492.99 (MH$^+$).

Example 86

N-(3-(N-(3-(2-chloro-5-methoxy-phenylamino)quinoxalin-2-yl)sulfamoyl)phenyl)-2-(2,2,2-trifluoroethylamino)acetamide $^1$H NMR (400 MHz, DMSO) δ 10.4 (s, 1H), 9.2 (s, 1H), 8.65 (s, 1H), 8.4 (s, 1H), 8.00 (m, 1H), 7.80 (d, 1H), 7.75 (d, 1H), 7.65 (q, 1H), 7.55 (t, 1H), 7.40-7.5 (m, 3H), 6.7 (m, 1H), 3.82 (s, 3H), 3.62 (br s, 2H), 3.55 (br d, 2H). MS (EI) m/z for $C_{25}H_{22}C_1F_3N_6O_4S$ 1.0×$C_2H_1O_2F_3$: 595.0, 597.0 (MH$^+$).

Example 87

N-(3-(N-(3-(3,5-dimethoxy-phenylamino)quinoxalin-2-yl)sulfamoyl)phenyl)-3-(piperidin-1-yl)propanamide
MS (EI) m/z for $C_{30}H_{34}N_6O_5S$: 591.2 (MH$^+$).

Example 88

N-(3-(N-(3-(3,5-dimethoxy-phenylamino)quinoxalin-2-yl)sulfamoyl)phenyl)-4-(dimethylamino)butanamide MS (EI) m/z for $C_{28}H_{32}N_6O_5S$ 1.0×$C_2H_4O_2$: 565.2 (MH$^+$).

Example 89

2-(dimethylamino)-N-(3-(N-(3-(3-fluoro-5-methoxy-phenylamino)quinoxalin-2-yl)sulfamoyl)phenyl)acetamide. 1l NMR (400 MHz, DMSO) δ 10.9 (s, 1H), 9.8 (br s, 1H), 9.1 (s, 1H), 8.34 (s, 1H), 7.90 (d, 1H), 7.76 (d, 1H), 7.52-7.68 (m, 4H), 7.40 (m, 2H), 6.54 (m, 1H), 4.16 (s, 2H), 3.82 (s, 3H), 2.86 (s, 6H). MS (EI) m/z for $C_{25}H_{25}FN_6O_4S$: 525.05 (MH$^+$).

Example 90

N-(3-(N-(3-(3,5-dimethoxy-phenylamino)quinoxalin-2-yl)sulfamoyl)phenyl)-2-(piperidin-1-yl)acetamide
MS (EI) m/z for $C_{29}H_{32}N_6O_5S$: 577.37 (MH$^+$).

Example 91

2-(dimethylamino)-N-(3-(N-(3-(3-methoxy-phenylamino)quinoxalin-2-yl)sulfamoyl)phenyl)acetamide
$^1$H NMR (400 MHz, DMSO) δ 10.5 (s, 1H), 8.8 (s, 1H), 8.25 (s, 1H), 7.83 (t, 1H), 7.76 (d, 1H), 7.64 (d, 1H), 7.3-7.48 (m, 4H), 7.22 (t, 1H), 7.12 (t, 2H), 6.56 (m, 1H), 3.96 (s, 2H), 3.78 (s, 3H), 2.76 (s, 6H). MS (EI) m/z for $C_{25}H_{26}N_6O_4S$: 507.1 (MH$^+$).

Example 92

N-(3-(N-(3-(2-chloro-5-hydroxy-phenylamino)quinoxalin-2-yl)sulfamoyl)phenyl)-2-(dimethylamino)acetamide
$^1$H NMR (400 MHz, DMSO) δ 10.8 (s, 1H), 9.9 (s, 1H), 9.8 (s, 1H), 9.1 (s, 1H), 8.55 (s, 1H), 8.34 (s, 1H), 7.9-8.0 (br s, 1H), 7.82 (d, 1H), 7.76 (d, 1H), 7.52-7.66 (m, 2H), 7.42 (t, 1H), 7.26 (d, 1H), 6.50 (m, 1H), 4.16 (s, 2H), 2.86 (s, 6H). MS (EI) m/z for $C_{24}H_{23}ClN_6O_4S$: 527.1, 529.0 (MH$^+$).

Example 93

N-(3-(N-(3-(3,5-dimethoxy-phenylamino)quinoxalin-2-yl)sulfamoyl)phenyl)-2-morpholinoacetamide
MS (EI) m/z for $C_{28}H_{30}N_6O_6S$: 579.1 (MH$^+$).

Example 94

N-(3-(N-(3-(3,5-dimethoxy-phenylamino)quinoxalin-2-yl)sulfamoyl)phenyl)acetamide
MS (EI) m/z for $C_{24}H_{23}N_5O_5S$: 494.0 (MH$^+$).

Example 97

2-amino-N-(3-(N-(3-(2-chloro-5-methoxy-phenylamino)quinoxalin-2-yl)sulfamoyl)-4-methylphenyl)-2-methylpropanamide
MS (EI) m/z for $C_{26}H_{27}ClN_6O_4S$: 556.12 (MH$^+$).

Example 98

N-(3-(N-(3-(2-chloro-5-methoxy-phenylamino)quinoxalin-2-yl)sulfamoyl)phenyl)-2-(dimethylamino)acetamide
MS (EI) m/z for $C_{25}H_{25}ClN_6O_4S$: 542.05 (MH$^+$).

Example 99

2-amino-N-(3-(N-(3-(3,5-dimethoxy-phenylamino)quinoxalin-2-yl)sulfamoyl)phenyl)acetamide
MS (EI) m/z for $C_{24}H_{24}N_6O_5S$: 509.59 (MH$^+$).

Example 100

3-(N-(3-(2-chloro-5-methoxy-phenylamino)quinoxalin-2-yl)sulfamoyl)benzoic acid

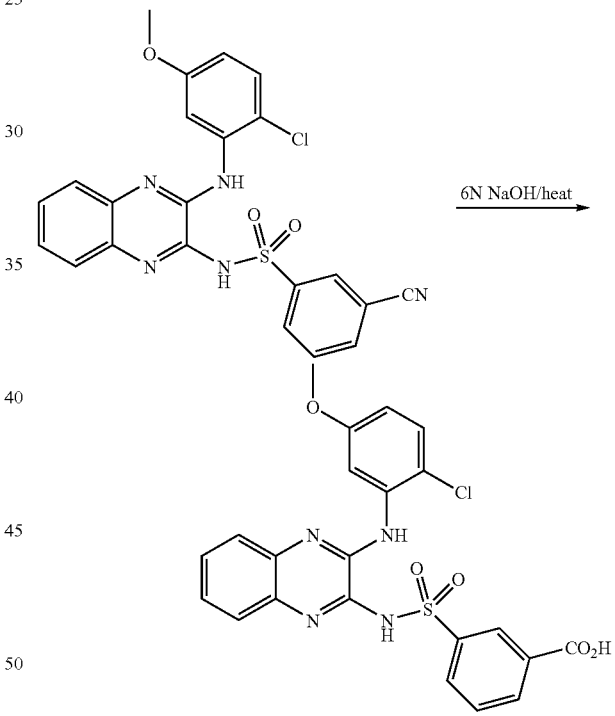

To a solution of N-(3-{[2-chloro-5-(methoxy)-phenyl]amino}quinoxalin-2-yl)-3-cyanobenzenesulfonamide (6.02 g, 12.95 mmol), prepared using procedures similar to those in Example 115 or Example 423, in methanol (20 mL) and 1,4-dioxane (20 mL) was added 6.0 N aqueous sodium hydroxide (40 mL) at room temperature. The solution was stirred at 90° C. for 3.5 h. The reaction was cooled to room temperature and neutralized slowly by adding 2.0 N hydrochloric acid until the pH of the solution became in the 2-3 range at 0° C. The solution was diluted with ethyl acetate (300 mL). The organic layer was washed with saturated aqueous sodium chloride (50 mL) and dried over magnesium sulfate. Filtration and concentration at reduced pressure afforded 3-{[(3-{[2-chloro-5-(methoxy)-phenyl]amino}quinoxalin- 2-yl)amino]sulfonyl}benzoic acid (5.921 g, 94%). MS (EI) m/z for $C_{22}H_{17}ClN_4O_5S$: 485.0 (MH$^+$).

The following compounds were prepared using procedures similar to those used in Example 100.

Example 101

Proceeding as above, 3-(N-(3-(3,5-dimethoxyphenylamino)quinoxalin-2-yl)sulfamoyl)benzoic acid was prepared. MS (EI) m/z for $C_{23}H_{20}N_4O_6S$: 481.0 (MH$^+$).

Example 102

3-(N-(3-(2-chloro-5-methoxyphenylamino)quinoxalin-2-yl)sulfamoyl)-N-(2-methyl-1-(piperidin-1-yl)propan-2-yl)benzamide MS (EI) m/z for $C_3H_{35}ClN_6O_4S$: 623.06 (MH$^+$).

Example 103

3-(N-(3-(2-chloro-5-methoxy-phenylamino)quinoxalin-2-yl)sulfamoyl)-N-(2-methyl-1-oxo-1-(piperidin-1-yl)propan-2-yl)benzamide MS (EI) m/z for $C_{31}H_{33}ClN_6O_5S$: 637.65 (MH$^+$).

Example 104

3-{[(3-{[2-chloro-5-(methoxy)phenyl]amino}quinoxalin-2-yl)amino]sulfonyl}-N-[2-(dimethylamino)ethyl]benzamide

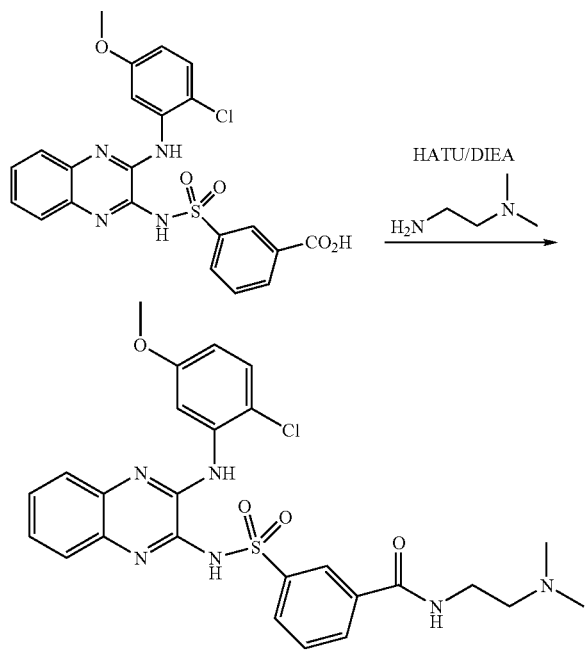

To a solution of 3-{[(3-{[2-chloro-5-(methoxy)phenyl]amino}quinoxalin-2-yl)amino]sulfonyl}benzoic acid (0.20 g, 0.42 mmol), prepared using procedures similar to Example 100, in dimethylformamide (4 mL) were added 2-(7-aza-1H-benzotriazole-1-yl)-1,1,3,3-tetramethyluronium hexafluorophosphate (HATU, 0.32 g, 0.83 mmol) and N-ethyldiisopropylamine (DIEA, 0.13 g, 1.04 mmol) at room temperature. The reaction was stirred for 15 min before N,N-dimethylethane-1,2-diamine (73 mg, 0.83 mmol) was added. The reaction mixture was allowed to stir overnight. The reaction was diluted with ethyl acetate (200 mL) and washed with water (50 mL), saturated aqueous sodium bicarbonate (40 mL), 1.0 N aqueous hydrochloric acid (30 mL), and saturated aqueous sodium chloride (25 mL). The organic layer was dried over magnesium sulfate, filtered and concentrated at reduced pressure to afford 3-{[(3-{[2-chloro-5-(methoxy)phenyl]amino}quinoxalin-2-yl)amino]sulfonyl}-N-[2-(dimethylamino)ethyl]benzamide (0.20 g, 87%) as yellow solid. MS (EI) m/z for $C_{26}H_{27}ClN_6O_4S$: 555.1 (MH$^+$).

The following compounds were prepared using procedures similar to those in Example 104.

Example 105

5-(N-(3-(2-chloro-5-methoxy-phenylamino)quinoxalin-2-yl)sulfamoyl)-N-(2-(dimethylamino)ethyl)-2-methoxybenzamide $^1$H NMR (400 MHz, DMSO-d$_6$) δ 9.45 (s, 1H), 8.95 (d, 1H), 8.57 (d, 1H), 8.28 (t, 1H), 8.14 (dd, 1H), 7.46 (dd, 1H), 7.39 (m, 2H), 7.17 (m, 4H), 6.60 (dd, 1H), 3.89 (s, 3H), 3.82 (s, 3H), 3.38 (m, 2H), 2.43 (m, 2H), 2.21 (s, 6H). MS (EI) m/z for $C_{27}H_{29}ClN_6O_5S$: 585.3 (MH$^+$).

Example 106

5-(N-(3-(2-chloro-5-methoxy-phenylamino)quinoxalin-2-yl)sulfamoyl)-N-(2-(dimethylamino)ethyl)-2-fluorobenzamide $^1$H NMR (400 MHz, DMSO-d$_6$) δ 9.40 (br s, 1H), 9.16 (s, 1H), 8.73 (m, 1H), 8.67 (d, 1H), 8.36 (dd, 1H), 8.26 (m, 1H), 7.94 (br s, 1H), 7.66 (m, 1H), 7.59 (t, 1H), 7.43 (m, 3H), 6.71 (dd, 1H), 3.83 (s, 3H), 3.62 (m, 2H), 3.27 (m, 2H), 2.85 (d, 6H). MS (EI) m/z for $C_{26}H_{26}ClFN_6O_4S$: 573.1 (MH$^+$).

Example 107

3-(N-(3-(3,5-dimethoxyphenylamino)quinoxalin-2-yl)sulfamoyl)-N-(2-(dimethylamino)ethyl)benzamide MS (EI) m/z for $C_{27}H_{30}N_6O_5S$: 551.1 (MH$^+$).

Example 108

3-(N-(3-(2-chloro-5-methoxy-phenylamino)quinoxalin-2-yl)sulfamoyl)-N-(2-(dimethylamino)ethyl)-N-methylbenzamide MS (EI) m/z for $C_{27}H_{29}ClN_6O_4S$: 569.1 (MH$^+$).

Example 109

3-(N-(3-(3,5-dimethoxyphenylamino)quinoxalin-2-yl)sulfamoyl)-N-(2-(dimethylamino)ethyl)-N-methylbenzamide MS (EI) m/z for $C_{28}H_{32}N_6O_5S$: 565.1 (MH$^+$).

Example 110

3-(N-(3-(2-chloro-5-methoxy-phenylamino)quinoxalin-2-yl)sulfamoyl)benzamide

MS (EI) m/z for $C_{22}H_{18}ClN_5O_4S$: 484.0 (MH$^+$).

Example 111

3-(N-(3-(2-chloro-5-methoxy-phenylamino)quinoxalin-2-yl)sulfamoyl)-N-(2-morpholinoethyl)benzamide MS (EI) m/z for $C_{28}H_{29}ClN_6O_5S$: 597.0 (MH$^+$).

Example 112

3-(N-(3-(2-chloro-5-methoxy-phenylamino)quinoxalin-2-yl)sulfamoyl)-N-methylbenzamide. MS (EI) m/z for $C_{23}H_{20}ClN_5O_4S$: 498.0 (MH$^+$).

Example 113

3-(N-(3-(2-chloro-5-methoxy-phenylamino)quinoxalin-2-yl)sulfamoyl)-N-morpholinobenzamide. MS (EI) m/z for $C_{26}H_{25}ClN_6O_5S$: 569.0 (MH$^+$).

Example 114

N-(3-{[2-chloro-5-(methoxy)phenyl]amino}quinoxalin-2-yl)-3-{5-[(dimethylamino)methyl]-1,3,4-oxadiazol-2-yl}benzenesulfonamide

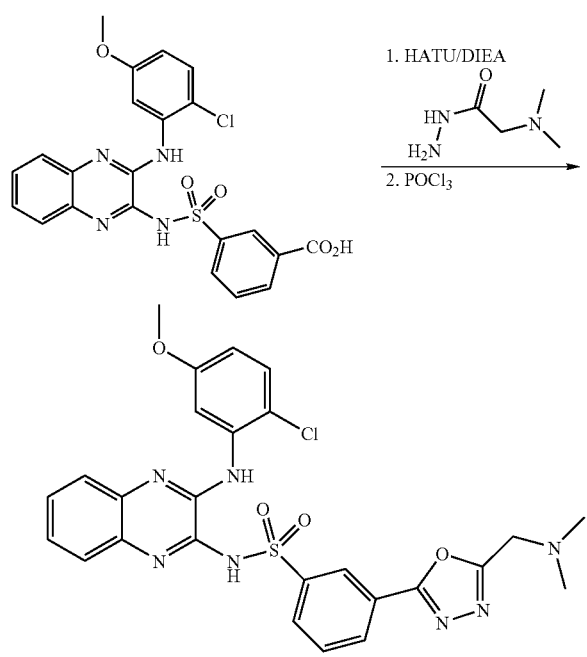

To a solution of 3-{[(3-{[2-chloro-5-(methoxy)phenyl]amino}quinoxalin-2-yl)amino]sulfonyl}benzoic acid (0.25 g, 0.52 mmol), prepared as described above in Example 100, in dimethylformamide (2.6 mL) were added 2-(7-aza-1H-benzotriazole-1-yl)-1,1,3,3-tetramethyluronium hexafluorophosphate (HATU, 0.25 g, 0.67 mmol) and N-ethyldiisopropylamine (DIEA, 0.11 g, 0.88 mmol) at room temperature. The reaction was stirred for 15 min before 2-(dimethylamino)acetohydrazide (78 mg, 0.67 mmol) was added. The reaction mixture was allowed to stir overnight. The reaction was diluted with ethyl acetate (200 mL) and washed with water (30 mL), saturated aqueous sodium bicarbonate (30 mL), 1.0 N aqueous hydrochloric acid (20 mL), and saturated aqueous sodium chloride (25 mL). The organic layer was dried over magnesium sulfate, filtered and concentrated at reduced pressure to afford 180 mg of a coupled intermediate which was then heated in phosphorus oxychloride (5 mL) at 100° C. for 4 h. The reaction was cooled to room temperature and treated with ice water (50 mL) and extracted with dichloromethane (3×50 mL). The organic layer was dried over magnesium sulfate, filtered and concentrated at reduced pressure to afford a crude product which was subjected to reverse phase HPLC to afford N-(3-{[2-chloro-5-(methoxy)-phenyl]amino}quinoxalin-2-yl)-3-{5-[(dimethylamino)methyl]-1,3,4-oxadiazol-2-yl}-benzenesulfonamide (16 mg, 5%) as yellow solid. MS (EI) m/z for $C_{26}H_{24}ClN_7O_4S$: 566.0 (MH$^+$).

Example 115

N-(3-(3-methoxy-5-nitro-phenylamino)-quinoxalin-2-yl)-3-nitrobenzenesulfonamide

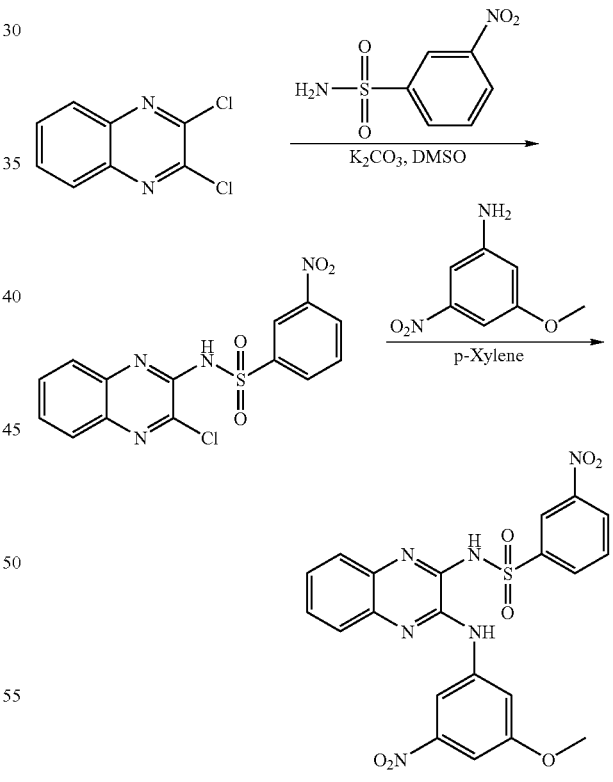

N-(3-chloroquinoxalin-2-yl)-3-nitrobenzenesulfonamide. 2,3-Dichloroquinoxaline (26.1 g, 131.1 mmol), m-Nitrobenzene sulfonamide (26.5 g, 131.1 mmol) and potassium carbonate (18.1 g, 131.1) were dissolved in anhydrous DMSO (500 mL). The reaction was heated to 150° C. for 2 h. The reaction mixture was poured into water (400 mL), followed by addition of 2M HCl (60 mL). The product was extracted with EtOAc (3×500 mL). The organic layers were combined and washed water (2×500 mL) and brine (2×500 mL). The product was then dried with sodium sulfate to give N-(3-chloroquinoxalin-2-yl)-3-nitrobenzenesulfonamide. MS (EI) m/z for $C_{14}H_9ClN_4O_4S$: 364.94, 366.97 (MH$^+$)

N-(3-(3-methoxy-5-nitrophenylamino)quinoxalin-2-yl)-3-nitro-benzenesulfonamide. N-(3-chloroquinoxalin-2-yl)-3-nitrobenzenesulfonamide (700 mg, 1.92 mmol), 3-methoxy-5-nitroaniline (645 mg, 3.84 mmol) and p-xylene (7 mL) were combined and heated to 140° C., then stirred for 16 hours at 130° C. The reaction was allowed to cool, placed in a sep. funnel, diluted with DCM, and washed with 2M HCl and brine and concentrated in vacuo. The resulting solid was washed with Et$_2$O to give N-(3-(3-methoxy-5-nitro-phenylamino)quinoxalin-2-yl)-3-nitrobenzenesulfonamide (400 mg, 42%). MS (EI) m/z for $C_{21}H_{16}N_6O_7S$: 496.94 (MH$^+$).

The following compounds were prepared using procedures similar to those in Example 115.

Example 116

N-(3-(2-chloro-5-methoxyphenylamino)quinoxalin-2-yl)-3-cyanobenzenesulfonamide

MS (EI) m/z for $C_{22}H_{16}ClN_5O_3S$: 465.9 (MH$^+$).

Example 117

3-cyano-N-(3-(3,5-dimethoxy-phenylamino)quinoxalin-2-yl)benzenesulfonamide

MS (EI) m/z for $C_{23}H_{19}N_5O_4S$: 462.3 (MH$^+$).

Example 118

N-(3-(2,5-dimethoxy-phenylamino)quinoxalin-2-yl)-3-fluorobenzenesulfonamide

MS (EI) m/z for $C_{22}H_{19}FN_4O_4S$: 456.0 (MH$^+$).

Example 119

3-bromo-N-(3-(3,5-dimethoxy-phenylamino)quinoxalin-2-yl)benzenesulfonamide

MS (EI) m/z for $C_{22}H_{19}BrN_4O_4S$: 516.9 (MH$^+$).

Example 120

3-bromo-N-(3-(2,5-dimethoxy-phenylamino)quinoxalin-2-yl)benzenesulfonamide

MS (EI) m/z for $C_{22}H_{19}BrN_4O_4S$: 516.9 (MH$^+$).

Example 121

N-(3-(3-methoxyphenylamino)quinoxalin-2-yl)benzenesulfonamide

MS (EI) m/z for $C_{21}H_{18}N_4O_3S$: 407.0 (MH$^+$).

Example 122

N-(3-(4-fluoro-3-methoxyphenylamino)quinoxalin-2-yl)benzenesulfonamide

MS (EI) m/z for $C_{21}H_{17}FN_4O_3S$: 425.0 (MH$^+$).

Example 123

N-(3-(2,5-dimethoxy-phenylamino)quinoxalin-2-yl)-4-methoxybenzenesulfonamide

MS (EI) m/z for $C_{23}H_{22}N_4O_5S$: 467.0 (MH$^+$).

Example 124

N-(3-(3,5-dimethoxy-phenylamino)quinoxalin-2-yl)-4-methoxybenzenesulfonamide

MS (EI) m/z for $C_{23}H_{22}N_4O_5S$: 467.0 (MH$^+$).

Example 125

N-(3-(4-chloro-3-methoxy-phenylamino)quinoxalin-2-yl)benzenesulfonamide

MS (EI) m/z for $C_{21}H_{17}ClN_4O_3S$: 440.9 (MH$^+$).

Example 126

N-(3-(3,5-dimethoxy-phenylamino)quinoxalin-2-yl) thiophene-2-sulfonamide

MS (EI) m/z for $C_{20}H_8N_4O_4S_2$: 443.0 (MH$^+$).

Example 127

N-(3-(6-methoxyquinolin-8-ylamino)quinoxalin-2-yl)-3-nitrobenzenesulfonamide

MS (EI) m/z for $C_{24}H_{18}N_6O_5S$: 502.95 (MH$^+$).

Example 128

3-nitro-N-(3-(pyridin-O-ylamino)quinoxalin-2-yl) benzenesulfonamide. MS (EI) m/z for $C_{19}H_{14}N_6O_4S$: 423.2 (MH$^+$).

Example 129

N-(3-(2-chloropyridin-4-ylamino)quinoxalin-2-yl)-3-nitrobenzenesulfonamide

MS (EI) m/z for $C_{19}H_{13}ClN_6O_4S$: 456.93, 458.90 (MH$^+$).

Example 130

N-(3-(4,6-dimethoxypyrimidin-2-ylamino)quinoxalin-2-yl)-3-nitrobenzenesulfonamide MS (EI) m/z for $C_{20}H_{17}N_7O_6S$: 484.03 (MH$^+$).

Example 131

N-(3-(4-hydroxy-6-methoxypyrimidin-2-ylamino) quinoxalin-2-yl)-3-nitrobenzenesulfonamide MS (EI) m/z for $C_{19}H_{15}N_7O_6S$: 469.97 (MH$^+$).

Example 132

N-(3-(3,5-dimethoxy-phenylamino)quinoxalin-2-yl)-2-fluorobenzenesulfonamide

MS (EI) m/z for $C_{22}H_{19}FN_4O_4S$: 455.3 (MH$^+$).

Example 133

N-(3-(2-bromo-5-methoxy-phenylamino)quinoxalin-2-yl)-3-nitrobenzenesulfonamide

MS (EI) m/z for $C_{21}H_{16}BrN_5O_5S$: 531.82, 532.84 (MH$^+$).

Example 134

N-(3-(3,5-dimethoxy-phenylamino)quinoxalin-2-yl)-4-methylbenzenesulfonamide

MS (EI) m/z for $C_{23}H_{22}N_4O_4S$: 451.0 (MH$^+$).

Example 136

N-(3-(2,5-dimethoxy-phenylamino)quinoxalin-2-yl)-4-methylbenzenesulfonamide

MS (EI) m/z for $C_{23}H_{22}N_4O_4S$: 451.0 (MH$^+$).

Example 137

N-(3-(3-fluoro-5-methoxy-phenylamino)quinoxalin-2-yl)-3-nitrobenzenesulfonamide

MS (EI) m/z for $C_{21}H_{16}FN_5O_5S$: 470.0 (MH$^+$).

Example 138

4-bromo-N-(3-(3,5-dimethoxy-phenylamino)quinoxalin-2-yl)benzenesulfonamide

MS (EI) m/z for $C_{22}H_{19}BrN_4O_4S$: 516.9, 514.9 (MH$^+$).

Example 139

N-(3-(3-methoxyphenylamino)quinoxalin-2-yl)-3-nitro-benzenesulfonamide. MS (EI) m/z for $C_{21}H_{17}N_5O_5S$: 451.93 (MH$^+$).

Example 140

N-(3-(2-chloro-5-hydroxy-phenylamino)quinoxalin-2-yl)-3-nitrobenzenesulfonamide

MS (EI) m/z for $C_{20}H_{14}ClN_5O_5S$: 472.15, 474.13 (MH$^+$).

Example 141

3-acetyl-N-(3-(2-chloro-5-methoxy-phenylamino)quinoxalin-2-yl)benzenesulfonamide MS (EI) m/z for $C_{23}H_{19}ClN_4O_4S$: 483.08 (MH$^+$).

Example 142

N-(3-(3,5-dimethoxy-phenylamino)quinoxalin-2-yl)benzenesulfonamide. MS (EI) m/z for $C_{22}H_{20}N_4O_4S$: 437.49 (MH$^+$).

Example 143

N-(3-(5-methoxy-2-methyl-phenylamino)quinoxalin-2-yl)benzenesulfonamide

MS (EI) m/z for $C_{22}H_{20}N_4O_3S$: 421.46 (MH$^+$).

Example 144

N-(3-(2-chloro-5-methoxy-phenylamino)quinoxalin-2-yl)benzenesulfonamide

MS (EI) m/z for $C_{21}H_{17}ClN_4O_3S$: 440.59 (MH$^+$).

Example 145

N-(3-(2,5-dimethoxy-phenylamino)quinoxalin-2-yl)benzenesulfonamide

MS (EI) m/z for $C_{21}H_{20}N_4O_4S$: 437.53 (MH$^+$).

Example 146

4-chloro-N-(3-(3,5-dimethoxy-phenylamino)quinoxalin-2-yl)benzenesulfonamide

MS (EI) m/z for $C_{22}H_{19}ClN_4O_4S$: 470.54 (MH$^+$).

Example 147

N-(3-(5-methoxy-2-methyl-phenylamino)quinoxalin-2-yl)-3-nitrobenzenesulfonamide

MS (EI) m/z for $C_{22}H_{19}N_5O_5S$: 466.32 (MH$^+$).

Example 148

N-(3-(2-chloro-5-methoxy-phenylamino)quinoxalin-2-yl)-3-nitrobenzenesulfonamide

MS (EI) m/z for $C_{21}H_{16}ClN_5O_5S$: 485.86 (MH$^+$).

Example 149

N-(3-(4-chloro-2,5-dimethoxy-phenylamino)quinoxalin-2-yl)benzenesulfonamide

MS (EI) m/z for $C_{22}H_{19}ClN_4O_4S$: 470.99 (MH$^+$).

Example 150

N-(3-{[3,5-bis(methoxy)phenyl]amino}quinoxalin-2-yl)-3-(2H-tetrazol-5-yl)benzenesulfonamide

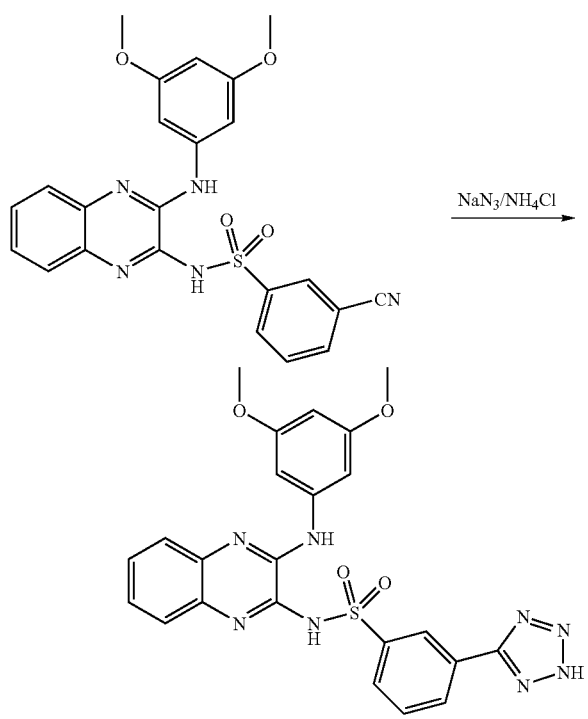

To a stirred solution of 3-cyano-N-(3-(3,5-dimethoxyphenylamino)quinoxalin-2-yl)benzenesulfonamide (0.20 g, 0.44 mmol), prepared using procedures similar to those described in Example 115, in dimethylformamide (1.2 mL) at 50° C. were added sodium azide (0.11 g, 1.76 mmol) and ammonium chloride (94 mg, 1.76 mmol). The crude mixture was heated at 100° C. overnight. The reaction was cooled to room temperature treated with ice water (20 mL) followed by concentrated hydrochloric acid (10 mL). The solid obtained was filtered under reduced pressure and washed with hexane (20 mL), diethyl ether (20 mL), and ethyl acetate (5 mL) to afford N-(3-{[3,5-bis(methoxy)phenyl]amino}) quinoxalin-2-yl)-3-(2H-tetrazol-5-yl)benzenesulfonamide (55 mg, 25%) as light yellow solid. MS (EI) m/z for $C_{23}H_{20}N_8O_4S$: 505.0 (MH$^+$).

Example 151

N-(3-(2,6-dichloropyridin-4-ylamino)quinoxalin-2-yl)-3-nitrobenzenesulfonamide

A mixture of N-(3-chloroquinoxalin-2-yl)-3-nitrobenzenesulfonamide (1 g), 2,6-dichloropyridin-4-amine (760 mg) and p-xylene (10 mL) was heated at 135° C. with stirring overnight. Upon cooling to room temperature, the mixture was dissolved in dichloromethane, washed with 2 N HCl (2×) and brine, concentrated in vacuo to give a crude product of N-{3-[(2,6-dichloropyridin-4-yl)amino]quinoxalin-2-yl}-3-nitrobenzenesulfonamide. A small portion of this crude product was purified by HPLC to give N-{3-[(2,6-dichloropyridin-4-yl)amino]quinoxalin-2-yl}-3-nitrobenzenesulfonamide. $^1$H NMR (400 MHz, DMSO) δ 9.71 (s, 1H), 8.90 (s, 1H), 8.50 (d, 2H), 8.8.41 (d, 1H), 8.30 (s, 2H), 7.88-7.78 (m, 27.65 (d, 1H), 7.47-7.37 (m, 2H); MS (EI) m/z for $C_{19}H_{12}Cl_2N_6O_4S$: 491.1, 493.1 (MH$^+$).

Example 152

N-(3-(2-chloro-6-methoxypyridin-4-ylamino)quinoxalin-2-yl)-3-nitrobenzenesulfonamide To a crude product of N-{3-[(2,6-dichloropyridin-4-yl)amino]quinoxalin-2-yl}-3-nitrobenzenesulfonamide (1.24 g) prepared using procedures similar to those for Example 151, was added anhydrous DMSO (10 mL), followed by sodium methoxide (273 mg). The resulting mixture was heated at 100° C. for 3 days. The mixture was diluted with EtOAc and water, and the pH was adjusted to about 4 by adding acetic acid. The product was extracted with EtOAc (3×). The combined extracts were washed with brine to give the crude product. A portion of the crude product was purified by prep HPLC to give N-(3-{[2-chloro-6-(methyloxy)pyridin-4-yl]amino}quinoxalin-2-yl)-3-nitrobenzenesulfonamide. $^1$H NMR (400 MHz, DMSO) δ 9.44 (s, 1H), 8.90 (s, 1H), 8.50 (d, 1H), 8.42 (d, 1H), 7.88-7.84 (m, 2H), 7.77 (s, 1H), 7.74 (s, 1H), 7.64 (d, 1H), 7.45-7.38 (m, 2H), 3.82 (s, 3H); MS (EI) m/z for $C_{20}H_{15}ClN_6O_5S$: 496.94 (MH$^+$).

Example 153

2-(dimethylamino)-N-(3-(N-(3-(3-(2-(dimethylamino)acetamido)-5-methoxy-phenylamino)quinoxalin-2-yl)sulfamoyl)phenyl)acetamide

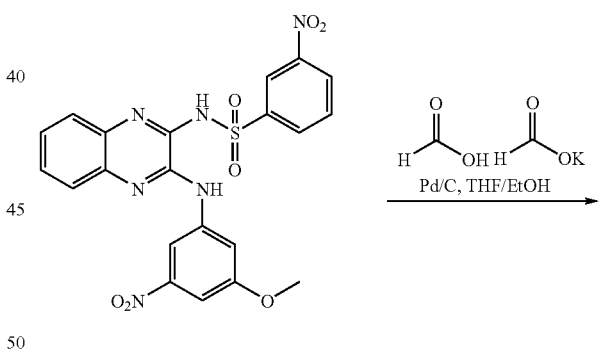

481
-continued

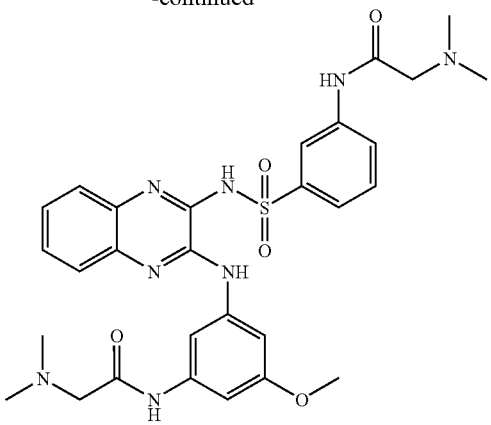

3-amino-N-(3-(3-amino-5-methoxyphenylamino)quinoxalin-2-yl)benzenesulfonamide. N-(3-(3-Methoxy-5-nitrophenylamino)quinoxalin-2-yl)-3-nitrobenzenesulfonamide (400 mg, 0.81 mmol), prepared as described above in Example 115, was dissolved in 1:1 THF:EtOH (4 mL), to which was added formic acid (938 μl, 2.42 mmol) and potassium formate (203 mg, 2.42 mmol). The system was flushed with nitrogen, and then 10% wt Pd/C (50 mg) was added. The reaction was then heated to 60° C. Once the reaction was determined complete by LC-MS, it was allowed to cool, and DMF was added for solubility. The solution was then filtered through a nylon frit to remove the catalyst. The filtrate was diluted water and the pH adjusted to 7 and extracted with DCM (2×) and EtOAc (2×). All organic layers were combined and evaporated to dryness to give 3-amino-N-(3-(3-amino-5-methoxyphenylamino)quinoxalin-2-yl)benzenesulfonamide (330 mg, 93%). MS (EI) m/z for $C_{21}H_{20}N_6O_3S$: 437.06 (MH$^+$)

2-(dimethylamino)-N-(3-(N-(3-(3-(2-(dimethylamino)-acetamido)-5-methoxyphenylamino)quinoxalin-2-yl)-sulfamoyl)phenyl)acetamide. 3-Amino-N-(3-(3-amino-5-methoxyphenylamino)quinoxalin-2-yl)benzenesulfonamide (330 mg, 0.76 mmol), DMF (4 mL), N,N,-Dimethylglycine (312 mg, 3.02 mmol), HATU (1.15 g, 3.02 mmol), and 1.29 (mL) (7.56 mmol) DIEA (1.29 mL, 7.56 mmol) were combined and heated to 90° C., followed by heating at 50° C. for over 16 hours. The reaction was allowed to cool, placed into a sep. funnel diluted with water and aqueous LiCl and extracted with EtOAc. The final compound was then purified by prep. HPLC to give 2-(dimethylamino)-N-(3-(N-(3-(3-(2-(dimethylamino)acetamido)-5-methoxy-phenylamino)-quinoxalin-2-yl)sulfamoyl)phenyl)acetamide. $^1$H NMR (400 MHz, CD$_3$OD) δ 8.45 (t, 1H), 7.93 (t, 1H), 7.85-7.88 (m, 1H), 7.70-7.74 (m, 1H), 7.65-7.68 (m, 1H), 7.58-7.62 (m, 1H), 7.58 (t, 1H), 7.34-7.42 (m, 3H), 7.0 (t, 1H), 4.05 (d, 2H), 3.8 (s, 3H), 2.9-3.0 (d, 12H). MS (EI) m/z for $C_{29}H_{34}N_8O_5S$: 607.2 (MH$^+$).

The following title compounds were prepared using procedures similar to those in Example 153.

482

Example 154

N-(3-(2,5-dimethoxyphenylamino)-7-methylquinoxalin-2-yl)benzenesulfonamide

MS (EI) m/z for $C_{23}H_{22}N_4O_4S$: 451.0 (MH$^+$).

Example 155a and Example 155b

N-(3-(3,5-dimethoxy-phenylamino)quinoxalin-2-yl)-3-(methylamino)benzenesulfonamide and N-(3-(3,5-dimethoxy-phenylamino)quinoxalin-2-yl)-3-(dimethylamino)benzenesulfonamide

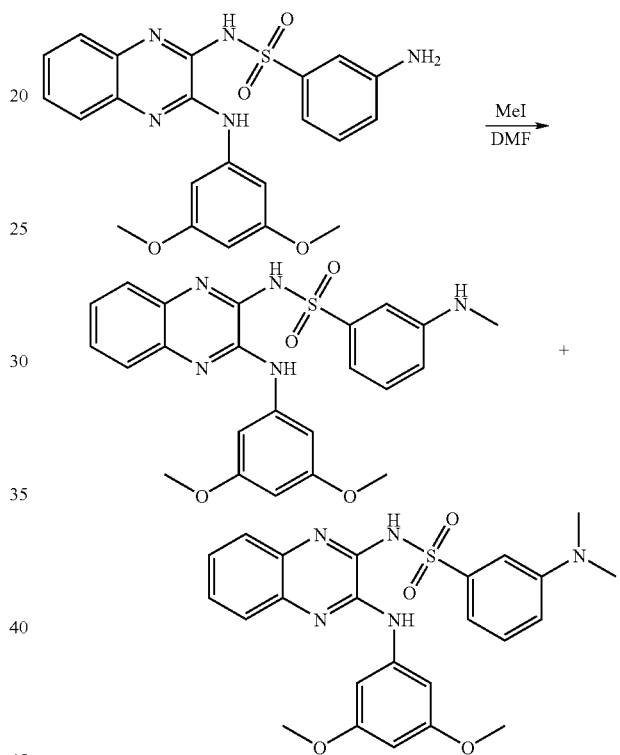

To a solution of 3-amino-N-(3-(3,5-dimethoxy-phenylamino)quinoxalin-2-yl)benzenesulfonamide (414 mg) in DMF (4.5 mL) was added iodomethane (114 mL). The reaction mixture was heated at 35-50° C. until the formation of both mono-methylated and di-methylated products was detected by LC/MS. The mixture was diluted with EtOAc, washed with water, 10% LiCl (2×) and brine. After removal of solvent in vacuo, the crude mixture was purified by flash silica column chromatography eluting with 15% EtOAc in hexanes, affording the mono-methylated and di-methylated products. Product A: N-(3-(3,5-dimethoxyphenylamino)quinoxalin-2-yl)-3-(methylamino)-benzenesulfonamide (35 mg). $^1$H NMR (400 MHz, DMSO) δ 12.2 (s, 1H), 8.93 (s, 1H), 7.85 (d, 1H), 7.58 (d, 1H), 7.40-7.20 (m, 7H), 6.76 (m, 1H), 6.24 (m, 1H), 6.16 (br s, 1H), 3.77 (s, 6H), 2.71 (s, 3H). MS (EI) for $C_{23}H_{23}N_5O_4S$: 466.05 (MH$^+$). Product B: N-(3-(3,5-dimethoxyphenylamino)quinoxalin-2-yl)-3-(dimethylamino)benzenesulfonamide (33 mg). $^1$H NMR (400 MHz, DMSO) δ 1220 (s, 1H), 8.98 (s, 1H), 7.98 (d, 1H), 7.56 (d, 1H), 7.42-7.32 (m, 7H), 6.74 (m, 1H), 6.24 (m, 1H), 3.77 (s, 6H), 2.97 (s, 6H). MS (EI) for $C_{24}H_{25}N_5O_4S$: 480.04 (MH$^+$).

Example 156

N-(3-{[(2-{[3,5-bis(methoxy)phenyl]amino}pyrido[2,3-b]pyrazin-3-yl)amino]sulfonyl}phenyl)-N-2-[2-(dimethylamino)ethyl]-N-2-methylglycinamide

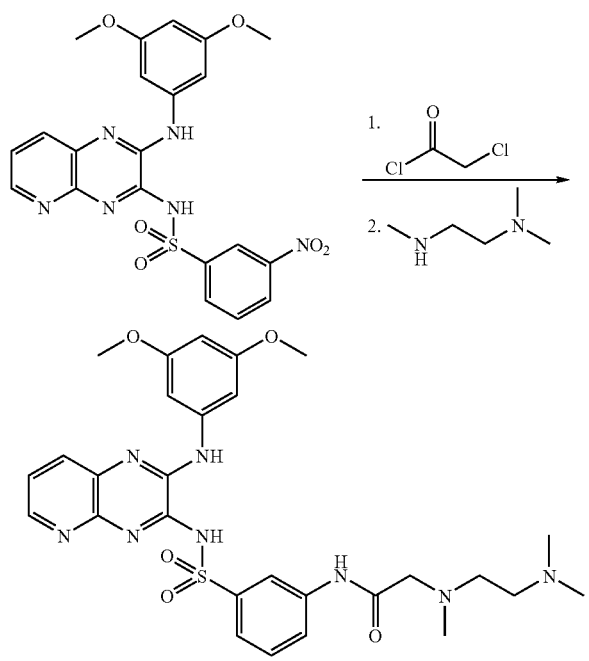

To a THF suspension (1.3 mL) of 3-amino-N-(3-{[3,5-(dimethoxy)-phenyl]amino}-quinoxalin-2-yl)benzenesulfonamide (126 mg, 0.28 mmol), prepared using procedures similar to those described for Example 15, was added 0.143 mL of 2M aqueous $Na_2CO_3$. To this yellow suspension is added dropwise 33 µL (0.42 mmol) of chloroacetyl chloride. The reaction mixture turns clear after a few minutes and is allowed to stir at 23° C. for 1 h. To the reaction is added a DMSO (1 mL) solution containing 180 L (1.4 mmol) of N,N',N' trimethylethylenediamine. The reaction is then warmed to 60° C. and stirred for 18 h. The product is isolated by preparative RP-HPLC($NH_4OAc$/ACN) gradient, the appropriate fractions were pooled and lyophilize to give a solid yellow as the acetic acid salt: 59 mg (51%). $^1$H-NMR (400 MHz, $CDCL_3$): δ 10.1 (br s, 1H), 8.37 (br s, 2H), 8.18 (d, 1H), 7.97 (d, 1H), 7.60 (br d, 1H), 7.27 (s, 2H), 7.20 (br s, 3H), 6.15 (s, 1H), 3.82 (m, 2H), 3.65 (s, 6H), 3.20 (br m, 2H), 2.82 (br s, 8H), 2.42 (s, 3H), 2.02 (s, 3H). MS (EI) m/z for $C_{28}H_{34}N_8O_5S$: 595.84 (MH$^+$).

The following title compounds were prepared using similar procedures to those in Example 156.

Example 157

N-(3-(N-(3-(3,5-dimethoxy-phenylamino)quinoxalin-2-yl)sulfamoyl)phenyl)-2-((3-(dimethylamino)propyl)(methyl)amino)acetamide MS (EI) m/z for $C_{30}H_{37}N_7O_5S$: 608.1 (MH$^+$).

Example 158

2-(1,4'-bipiperidin-1'-yl)-N-(3-(N-(3-(3,5-dimethoxy-phenylamino)quinoxalin-2-yl)sulfamoyl)phenyl)acetamide MS (EI) m/z for $C_{34}H_{41}N_7O_5S$: 660.1 (MH$^+$).

Example 159 tert-butyl 2-(3-(N-(3-(3,5-dimethoxy-phenylamino)quinoxalin-2-yl)sulfamoyl)phenylcarbamoyl)piperidine-1-carboxylate. MS (EI) m/z for $C_{33}H_{38}N_6O_7S$: 663.1 (MH$^+$).

Example 160

3-(N-(3-(2-chloro-5-methoxy-phenylamino)quinoxalin-2-yl)sulfamoyl)-N-(1-(dimethylamino)propan-2-yl)benzamide MS (EI) m/z for $C_{27}H_{29}ClN_6O_4S$: 569.0 (MH$^+$).

Example 161

N-(3-(3,5-dimethoxy-phenylamino)quinoxalin-2-yl)-3-ureidobenzenesulfonamide

MS (EI) m/z for $C_{23}H_{22}N_6O_5S$: 495.40 (MH$^+$).

Example 162

2-(dimethylamino)-N-(3-(N-(3-(5-methoxy-2-methylphenylamino)quinoxalin-2-yl)sulfamoyl)phenyl)acetamide MS (EI) m/z for $C_{26}H_{28}N_6O_4S$: 521.69 (MH$^+$).

Example 163

N-(3-(N-(3-(3,5-dimethoxy-phenylamino)quinoxalin-2-yl)sulfamoyl)phenyl)-2-(4-methylpiperazin-1-yl)acetamide MS (EI) m/z for $C_{29}H_{33}N_7O_5S$: 592.61 (MH$^+$).

Example 164

2-acetamido-N-(3-(N-(3-(3,5-dimethoxyphenylamino)quinoxalin-2-yl)sulfamoyl)phenyl)acetamide MS (EI) m/z for $C_{26}H_{26}N_6O_6S$: 550.59 (MH$^+$).

Example 165 tert-butyl 2-(3-(N-(3-(3,5-dimethoxy-phenylamino)quinoxalin-2-yl)sulfamoyl)phenylamino)-2-oxoethylcarbamate. MS (EI) m/z for $C_{29}H_{32}N_6O_7S$: 609.32 (MH$^+$).

Example 166

N-(2-(3,5-dimethoxy-phenylamino)pyrido[2,3-b]pyrazin-3-yl)-3-nitrobenzenesulfonamide

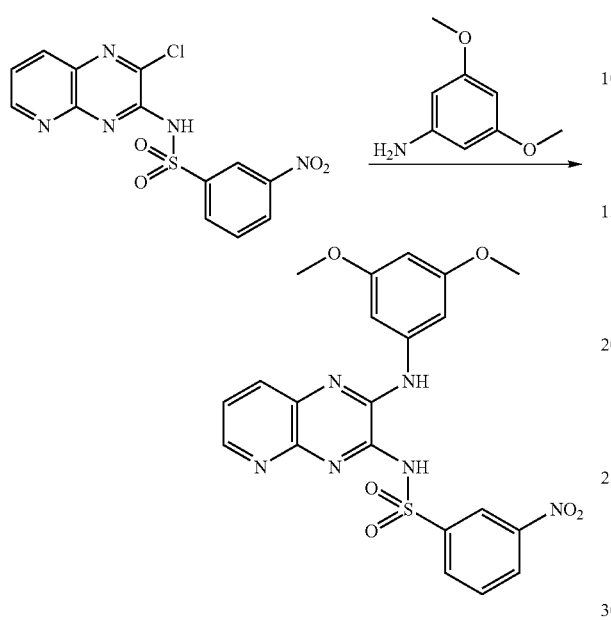

To a xylene suspension (15 mL) of N-(2-chloropyrido[2,3-b]pyrazin-3-yl)-3-nitrobenzenesulfonamide (1 g, 2.7 mmol) (prepared using procedures similar to those in Asier, et al *J. Org Chem* 2005, 70(7), 2878 and Leeson, et al *J. Med. Chem.* 1991, 34, 1243) was added 420 mg (2.7 mmol) of 3,5 dimethoxyaniline. After refluxing the reaction for 1 h, the reaction is cooled, the precipitate is collected by filtration and dried under vacuum to give 830 mg of the product as a ~6:1 mixture of isomers with the major being N-(2-(3,5-dimethoxy-phenylamino)pyrido[2,3-b]pyrazin-3-yl)-3-nitrobenzenesulfonamide which was assigned by known chemical reactivity. Analytical HPLC, ret. time=3.3 min (14%), 3.05 min (86%), (conditions: Phenomenex Gemini C18 50×4.6 column, gradient 5% to 95% MeCN/H$_2$O, in the presence of 0.1% TFA, 5 min run at 3.5 ml/min flow rate, λ=254 nm). $^1$H-NMR (400 MHz, DMSO-d$_6$): major isomer δ9.14 (br s, 1H), 8.69 (dd, 1H), 8.60 (dd, 1H), 8.33 (dt, 2H), 7.77 (t, 1H), 7.49 (dd, 1H), 7.37 d, 2H), 7.05 (s, 1H), 6.26 (t, 1H), 3.77 (s, 6H); MS (EI) m/z for C$_{21}$H$_{18}$N$_6$O$_6$S: 483.08 (MH$^+$).

Example 167

3-amino-N-(2-(3,5-dimethoxy-phenylamino)pyrido[2,3-b]pyrazin-3-yl)benzenesulfonamide To a 1:1 THF/EtOH suspension (1 mL) of N-(3-(3,5-dimethoxyphenylamino)-pyrido[3,2-b]pyrazin-2-yl)-3-nitrobenzenesulfonamide (190 mg, 0.21 mmol) (prepared using procedures similar to those in Examples 166) was added 47 L (1.26 mmol) of formic acid plus 99 mg (1.17 mmol) of potassium formate and 50 mg of 10% palladium on charcoal. After refluxing the reaction for 1 h, hot filtration through celite (washing with a small portion of DMF), dilution with 30 mL of water, the pH was adjusted to 5.5 with 5% NaHCO$_3$, the product is isolated as a precipitate 140 mg (80%) of white powder. Analytical HPLC, ret. time=2.6 min (90%), 3.05 min (10%), 100% pure (conditions: YMC C18 5×4.6 column, gradient 10% to 90% MeCN/H$_2$O, in the presence of 0.1% TFA, 9 min run at 1 ml/min flow rate, λ=254 nm). $^1$H-NMR (400 MHz, CDCL$_3$): δ 8.48 (br s, 1H), 8.34 (dd, 1H), 7.92 (dd, 1H), 7.41 (dd, 1H), 7.15 (m, 3H), 7.13 (d, 2H), 6.86 (dd, 1H), 6.28 (t, 1H), 3.83 (s, 6H); MS (EI) m/z for C$_{21}$H$_{20}$N$_6$O$_4$S: 453.03 (MH$^+$).

Example 168

3-amino-N-(3-{[3,5-bis(methoxy)phenyl]amino}pyrido[2,3-b]pyrazin-2-yl)benzenesulfonamide

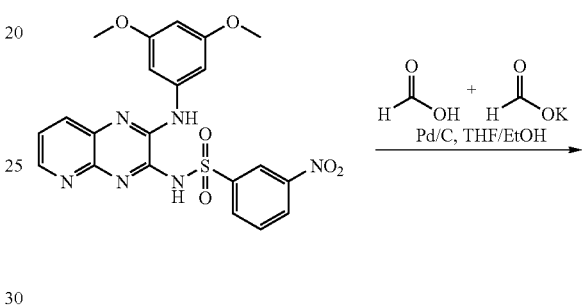

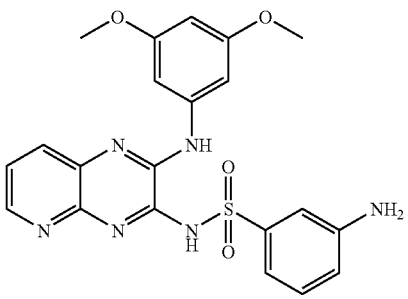

To a 1:1 THF/EtOH suspension (1 mL) of 3-nitro-N-(3-{[3,5-bis(methoxy)-phenyl]amino}pyrido[2,3-b]pyrazin-2-yl)benzenesulfonamide (100 mg, 0.21 mmol) (prepared using procedures similar to those used in Example 166) was added 46 L (0.63 mmol) of formic acid plus 100 mg (0.63 mmol) of potassium formate and 100 mg of 10% palladium on charcoal. After refluxing the reaction for 1 h, hot filtration through celite, and concentration, the product is isolated by preparative RP-HPLC(NH$_4$OAc/ACN) gradient. The appropriate fractions were pooled and lyophilize to give solid yellow product: 3.2 mg (4%). $^1$H-NMR (400 MHz, CDCl$_3$): δ8.62 (d, 1H), 8.52 (s, 1H), 7.62 (d, 1H), 7.3 (m, 4H), 7.18 (d, 2H), 6.88 (d, 1H), 6.27 (t, 1H), 3.96 (br s, 2H), 3.83 (s, 6H). MS (EI) m/z for C$_{21}$H$_{20}$N$_6$O$_4$S: 453.22 (MH$^+$).

Example 169

N-(3-{[2-chloro-5-(methoxy)phenyl]amino}quinoxalin-2-yl)-3-(1-{[2-(dimethylamino)-ethyl]amino}ethyl)benzenesulfonamide trifluoracetic acid salt

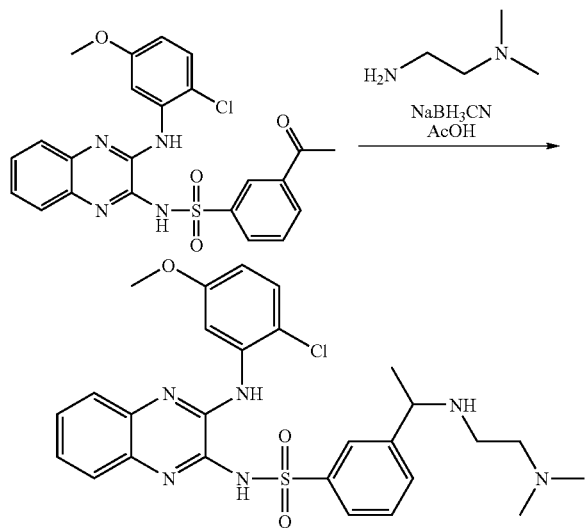

To a dichloroethane solution (0.6 mL) of 3-acetyl-N-(3-{[2-chloro-5-(methoxy)-phenyl]amino}quinoxalin-2-yl)benzenesulfonamide (150 mg, 0.31 mmol), prepared using procedures similar to those in Example 115, and 51 μL (0.37 mmol) of N,N-dimethylethylenediamine was added 19 μL of acetic acid followed by 132 mg (0.62 mmol) of sodium cyanoborohydride. The reaction mixture was refluxed for 18 h under a nitrogen atmosphere. After concentration (in vacuo), the product is isolated by preparative RP-HPLC (0.1% TFA/ACN) gradient, followed by lyophilization of appropriate fractions to give solid yellow solid: 189 mg (90%). ¹H-NMR (400 MHz, d₃-MeOD): δ 8.74 (s, 1H), 8.18 (s, 1H), 8.12 (d, 1H), 7.71 (m, 3H), 7.48 (m, 4H), 7.28 (d, 1H), 6.63 (d, 1H), 4.38 (q, 1H), 3.80 (s, 3H), 3.30 (m, 3H), 3.12 (m, 1H), 2.84 (s, 3H), 1.60 (d, 3H). MS (EI) m/z for $C_{27}H_{31}ClN_6O_3S$: 555.56 (MH⁺).

Example 170

N,N-{[(3-{[(3-{[2-chloro-5-(methoxy)phenyl]amino}quinoxalin-2-yl)amino]sulfonyl}-4-methylphenyl)amino](dimethylamino)methylidene}-N-methylmethanaminium

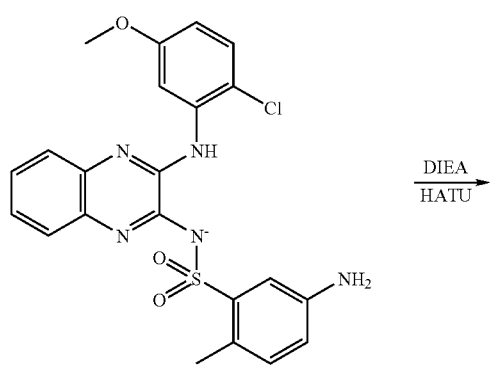

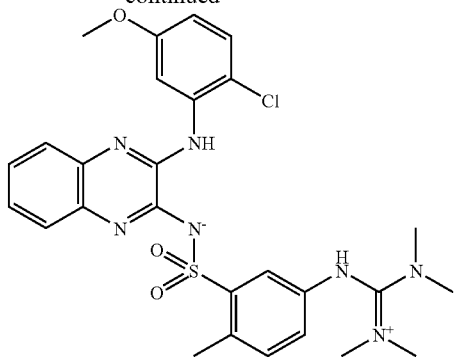

To a dimethylformamide solution (1 mL) of 3-amino-N-(3-{[2-chloro-5-(methoxy)-phenyl]amino}quinoxalin-2-yl) 2-methylbenzenesulfonamide (200 mg, 0.40 mmol), prepared using procedures similar to those described in Example 115, is added 312 μL (1.8 mmol) of DIEA and 122 mg (0.6 mmol) of HATU. After stirring for 18 h at 60° C., the product was precipitated from a 1:1 mixture of hexane/ethyl acetate, filtered and dried to afford 60 mg (26%). ¹H NMR (400 MHz, DMSO-d₆): δ 9.26 (b rs, 1H), 8.96 (br s, 1H), 7.80 (s, 1H), 7.51 (br s, 1H), 7.45 (d, 1H), 7.18 (brm, 4H), 6.91 (br s, 1H), 6.60 (br d, 1H), 3.82 (s, 3H), 3.36 (s, 3H), 2.85 (s, 6H), 2.58 (s, 3H). MS (EI) m/z for $C_{27}H_{31}ClN_7O_3S^+$: 569.32 (MH⁺).

Example 171

2-Bromo-N-(3-(N-(3-(3,5-dimethoxyphenylamino)quinoxalin-2-yl)sulfamoyl)phenyl)acetamide

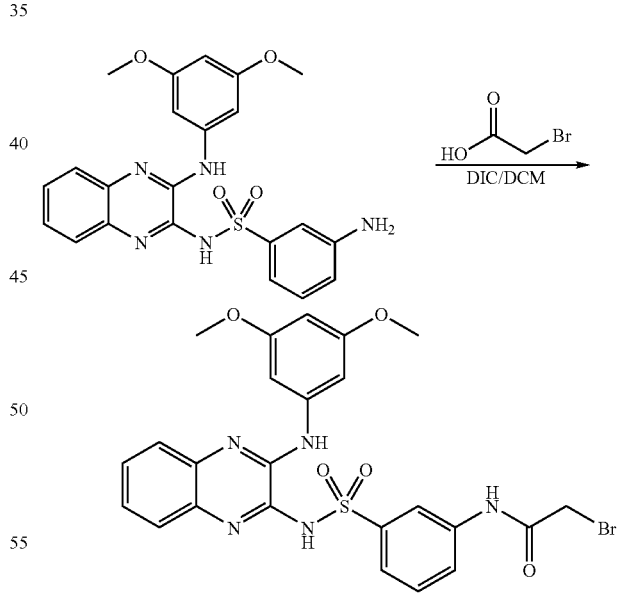

In a 50 mL round-bottom flask was added 2-bromoacetic acid (1.87 g, 13.5 mmol), N,N-diisopropylcarbodiimide (860 mg, 6.8 mmol) and 10 mL DCM. To this mixture was added 3-amino-N-(3-(3,5-dimethoxyphenylamino)quinoxalin-2-yl)benzenesulfonamide (2.03 g, 4.5 mmol), prepared using procedures similar to those in Example 168. The reaction was stirred overnight at room temperature. Complete consumption of the starting aniline was confirmed by LCMS. The solvent was evaporated off to yield the crude product (2-bromo-N-(3-(N-(3-(3,5-dimethoxyphenylamino)quinoxalin-2-yl)sulfamoyl)phenyl)acetamide). This was used directly in the next step without further purification.

General Alkylation Procedure 1

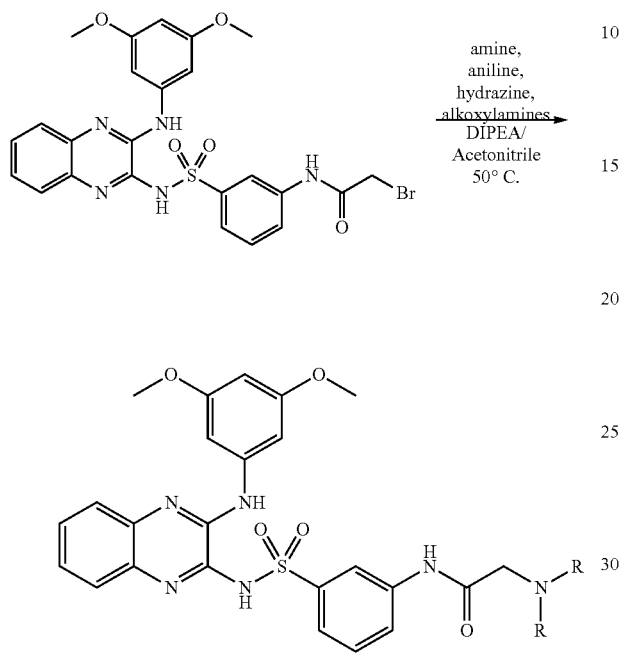

Into a 2-dram vial was placed 2-bromo-N-(3-(N-(3-(3,5-dimethoxy-phenylamino)quinoxalin-2-yl)sulfamoyl)phenyl)acetamide (86 mg, 0.15 mmol), prepared using procedures similar to those in Example 171, along with 2 mL of acetonitrile. Eight equivalents (1.2 mmol) of the desired amine, aniline, hydrazine or alkoxyamine were added followed by the addition of Hunig's Base (41 µL, 0.25 mmol). The reaction then was stirred at 50° C. for one hour (overnight for aniline reagents). Preparative reverse-phase HPLC was used to isolate the desired product directly from the crude reaction mixture. A Waters Fractionlynx preparative reverse-phase HPLC—equipped with a Waters SunFire Prep C18, OCD 5 µM, 30×70 mm column and running a 5-100% gradient with a binary solvent system of 25 mM ammonium acetate in water/acetonitrile—was used to carry out the purification.

The following title compounds were prepared according to General Library Alkylation Procedure 1.

Example 172

N-(3-(N-(3-(3,5-dimethoxy-phenylamino)quinoxalin-2-yl)sulfamoyl)phenyl)-2-(methylamino)acetamide $^1$H-NMR (400 MHz, $d_6$-DMSO): 8.81 (s, 1H), 8.23 (t, 1H), 7.75 (d, 1H), 7.66 (d, 1H), 7.41-7.38 (m, 1H), 7.35 (m, 1H), 7.32 (d, 2H), 7.29-7.27 (m, 1H), 7.14-7.11 (m, 2H), 6.14 (t, 1H), 3.80 (s, 1H), 3.78 (s, 6H), 2.58 (s, 3H), 1.91 (s, 2H); MS (EI) m/z $C_{25}H_{26}N_6O_5S$: 523.6 (MH$^+$).

Example 173

2-(cyclopropylmethylamino)-N-(3-(N-(3-(3,5-dimethoxyphenylamino)quinoxalin-2-yl)sulfamoyl)phenyl)acetamide $^1$H-NMR (400 MHz, $d_6$-DMSO): 10.58 (s, 1H), 8.81 (s, 1H), 8.20 (t, 1H), 7.76 (d, 1H), 7.67 (d, 1H), 7.42-7.36 (m, 2H), 7.32 (d, 2H), 7.27 (s, 1H), 7.14-7.12 (m, 2H), 6.15 (t, 1H), 3.93 (s, 2H), 3.78 (s, 6H), 2.89 (s, 1H), 2.88 (s, 1H), 1.05-1.00 (m, 1H), 0.59 (d, 1H), 0.57 (d, 1H), 0.35 (d, 1H), 0.34 (d, 1H); MS (EI) m/z $C_{28}H_{30}N_6O_5S$: 563.6 (MH$^+$).

Example 174

N-(3-(N-(3-(3,5-dimethoxy-phenylamino)quinoxalin-2-yl)sulfamoyl)phenyl)-2-(2-hydroxy-propylamino)acetamide $^1$H-NMR (400 MHz, $d_6$-DMSO): 10.49 ppm (s, 1H), 8.81 ppm (s, 1H), 8.23 ppm (t, 1H), 8.13 ppm (s, 1H), 7.76 ppm (d, 1H), 7.765-7.763 (dd, 1H), 7.41-7.37 ppm (m, 2H), 7.33-7.32 ppm (d, 1H), 7.30-7.28 ppm (m, 1H), 7.16-7.09 ppm (m, 2H), 6.55 ppm (s, 1H), 6.14 ppm (t, 1H), 5.49 ppm (d, 2H), 5.25 ppm (s, 1H), 3.85 ppm (s, 1H), 3.78 ppm (s, 6H) 3.67-3.59 ppm (m, 1H), 3.00-2.89 ppm (dd, 1H), 2.79-2.76 ppm (m, 1H), 1.10 ppm (d, 1H), 1.01-0.99 ppm (d, 1H); MS (EI) m/z $C_{27}H_{30}N_6O_6S$: 566.6 (MH$^+$).

Example 175

N-(3-(N-(3-(3,5-dimethoxy-phenylamino)quinoxalin-2-yl)sulfamoyl)phenyl)-2-(3-fluorobenzylamino)acetamide $^1$H-NMR (400 MHz, $d_6$-DMSO): 10.42 ppm (s, 1H), 8.82 ppm (s, 1H), 8.23 ppm (s, 1H), 8.14 ppm (s, 1H), 7.75 ppm (d, 1H), 7.65 ppm (d, 1H), 7.49-7.32 ppm (m, 6H), 7.25-7.20 ppm (m, 1H), 7.14-7.12 ppm (m, 2H), 6.55 ppm (s, 1H), 6.15 ppm (t, 1H), 4.14 ppm (s, 2H), 3.78 ppm (s, 6H), 3.74 ppm (s, 2H); MS (EI) m/z $C_{31}H_{29}FN_6O_5S$: 616.7 (MH$^+$).

Example 176

2-(benzylamino)-N-(3-(N-(3-(3,5-dimethoxy-phenylamino)quinoxalin-2-yl)sulfamoyl)phenyl)acetamide MS (EI) m/z $C_{31}H_{30}N_6O_5S$: 599 (MH$^+$).

Example 177

2-(diethylamino)-N-(3-(N-(3-(3,5-dimethoxy-phenylamino)quinoxalin-2-yl)sulfamoyl)phenyl)acetamide MS (EI) m/z $C_{28}H_{32}N_6O_5S$: 565 (MH$^+$).

Example 178

2-(4-(3,4-dichlorophenyl)piperazin-1-yl)-N-(3-(N-(3-(3,5-dimethoxyphenylamino)quinoxalin-2-yl)sulfamoyl)phenyl)acetamide MS (EI) m/z $C_{34}H_{33}Cl_2N_7O_5S$: 722 (MH$^+$).

Example 179

N-(3-(N-(3-(3,5-dimethoxy-phenylamino)quinoxalin-2-yl)sulfamoyl)phenyl)-2-(2,2-dimethylhydrazinyl)acetamide MS (EI) m/z $C_{26}H_{29}N_7O_5S$: 552 (MH$^+$).

Example 180

N-(3-(N-(3-(3,5-dimethoxy-phenylamino)quinoxalin-2-yl)sulfamoyl)phenyl)-2-(p-tolylamino)acetamide MS (EI) m/z $C_{31}H_{30}N_6O_5S$: 599 (MH$^+$).

Example 181

2-(benzyloxyamino)-N-(3-(N-(3-(3,5-dimethoxyphenylamino)quinoxalin-2-yl)sulfamoyl)phenyl)acetamide MS (EI) m/z $C_{31}H_{30}N_6O_6S$: 615 (MH$^+$).

Example 182

2-(2-chlorophenylamino)-N-(3-(N-(3-(3,5-dimethoxyphenylamino)quinoxalin-2-yl)sulfamoyl)phenyl)acetamide MS (EI) m/z $C_{30}H_{27}ClN_6O_5S$: 619 (MH$^+$).

Example 183

N-(3-(N-(3-(3,5-dimethoxyphenylamino)quinoxalin-2-yl)sulfamoyl)phenyl)-2-(isopropylamino)acetamide MS (EI) m/z $C_{27}H_{30}N_6O_5S$: 551 (MH$^+$).

Example 184

2-(4-cyclopentylpiperazin-1-yl)-N-(3-(N-(3-(3,5-dimethoxyphenylamino)quinoxalin-2-yl)sulfamoyl)phenyl)acetamide MS (EI) m/z $C_{33}H_{39}N_7O_5S$: 646 (MH$^+$).

Example 185

N-(3-(N-(3-(3,5-dimethoxy-phenylamino)quinoxalin-2-yl)sulfamoyl)phenyl)-2-(4-propylpiperidin-1-yl)acetamide MS (EI) m/z $C_{32}H_{38}N_6O_5S$: 619 (MH$^+$).

Example 186

N-(3-(N-(3-(3,5-dimethoxy-phenylamino)quinoxalin-2-yl)sulfamoyl)phenyl)-2-(isobutoxyamino)acetamide MS (EI) m/z $C_{28}H_{32}N_6O_6S$: 581

Example 187

2-(3-tert-butylphenylamino)-N-(3-(N-(3-(3,5-dimethoxyphenylamino)quinoxalin-2-yl)sulfamoyl)phenyl)acetamide MS (EI) m/z $C_{34}H_{36}N_6O_5S$: 641 (MH$^+$).

Example 188

N-(3-(N-(3-(3,5-dimethoxy-phenylamino)quinoxalin-2-yl)sulfamoyl)phenyl)-2-(2-phenylpropan-2-ylamino)acetamide MS (EI) m/z $C_{33}H_{34}N_6O_5S$: 627 (MH$^+$).

Example 189

N-(3-(N-(3-(3,5-dimethoxy-phenylamino)quinoxalin-2-yl)sulfamoyl)phenyl)-2-(3-fluoro-4-hydroxyphenylamino)acetamide MS (EI) m/z $C_{30}H_{27}FN_6O_6S$: 619 (MH$^+$).

Example 190

N-(3-(N-(3-(3,5-dimethoxy-phenylamino)quinoxalin-2-yl)sulfamoyl)phenyl)-2-(2-(methylthio)benzylamino)acetamide MS (EI) m/z $C_{32}H_{32}N_6O_5 _2$: 645 (MH$^+$).

Example 191

N-(3-(N-(3-(3,5-dimethoxy-phenylamino)quinoxalin-2-yl)sulfamoyl)phenyl)-2-(5-fluoro-2-methylbenzylamino)acetamide MS (EI) m/z $C_{32}H_{31}FN_6O_5S$: 631 (MH$^+$).

Example 192

N-(3-(N-(3-(3,5-dimethoxy-phenylamino)quinoxalin-2-yl)sulfamoyl)phenyl)-2-(2-phenylpyrrolidin-1-yl)acetamide MS (EI) m/z $C_{34}H_{34}N_6O_5S$: 639 (MH$^+$).

Example 193

2-(2-benzylpyrrolidin-1-yl)-N-(3-(N-(3-(3,5-dimethoxy-phenylamino)quinoxalin-2-yl)sulfamoyl)phenyl)acetamide MS (EI) m/z $C_{35}H_{36}N_6O_5S$: 653 (MH$^+$).

Example 194

N-(3-(N-(3-(3,5-dimethoxy-phenylamino)quinoxalin-2-yl)sulfamoyl)phenyl)-2-(2-phenylmorpholino)acetamide MS (EI) m/z $C_{34}H_{34}N_6O_5S$: 655 (MH$^+$).

Example 195

N-(3-(N-(3-(3,5-dimethoxy-phenylamino)quinoxalin-2-yl)sulfamoyl)phenyl)-2-(2-(pyridin-4-yl)piperidin-1-yl)acetamide MS (EI) m/z $C_{34}H_{35}N_7O_5S$: 654 (MH$^+$).

Example 196

N-(3-(N-(3-(3,5-dimethoxy-phenylamino)quinoxalin-2-yl)sulfamoyl)phenyl)-2-(o-tolylamino)acetamide MS (EI) m/z $C_{31}H_{30}N_6O_5S$: 599 (MH$^+$).

Example 197

N-(3-(N-(3-(3,5-dimethoxy-phenylamino)quinoxalin-2-yl)sulfamoyl)phenyl)-2-(2,4-dimethylbenzylamino)acetamide MS (EI) m/z $C_{33}H_{34}N_6O_5S$: 627 (MH$^+$).

Example 198

N-(3-(N-(3-(3,5-dimethoxy-phenylamino)quinoxalin-2-yl)sulfamoyl)phenyl)-2-(methyl(pyridin-3-ylmethyl)amino)acetamide MS (EI) m/z $C_{31}H_{31}N_7O_5S$: 614 (MH$^+$).

Example 199

2-(3-chloro-4-methylbenzylamino)-N-(3-(N-(3-(3,5-dimethoxyphenylamino)quinoxalin-2-yl)sulfamoyl)phenyl)acetamide MS (EI) m/z $C_{32}H_{31}ClN_6O_5S$: 647 (MH$^+$).

Example 200

N-(3-(N-(3-(3,5-dimethoxy-phenylamino)quinoxalin-2-yl)sulfamoyl)phenyl)-2-((2-(dimethylamino)-ethyl)(methyl)amino)acetamide MS (EI) m/z $C_{29}H_{35}N_7O_5S$: 594 (MH$^+$).

Example 201

2-(4-acetylpiperazin-1-yl)-N-(3-(N-(3-(3,5-dimethoxyphenylamino)quinoxalin-2-yl)sulfamoyl)phenyl)acetamide MS (EI) m/z $C_{30}H_{33}N_7O_6S$: 620 (MH$^+$).

Example 202

N-(3-(N-(3-(3,5-dimethoxyphenylamino)quinoxalin-2-yl)sulfamoyl)phenyl)-2-(methyl(1-methylpyrrolidin-3-yl)amino)acetamide MS (EI) m/z $C_{30}H_{35}N_7O_5S$: 606 (MH$^+$).

Example 203

N-(3-(N-(3-(3,5-dimethoxyphenylamino)quinoxalin-2-yl)sulfamoyl)phenyl)-2-(4-methyl-1,4-diazepan-1-yl)acetamide MS (EI) m/z $C_{30}H_{35}N_7O_5S$: 606 (MH$^+$).

Example 204

2-(4-allylpiperazin-1-yl)-N-(3-(N-(3-(3,5-dimethoxyphenylamino)quinoxalin-2-yl)sulfamoyl)phenyl)acetamide MS (EI) m/z $C_{31}H_{35}N_7O_5S$: 618 (MH$^+$).

Example 205

N-(3-(N-(3-(3,5-dimethoxyphenylamino)quinoxalin-2-yl)sulfamoyl)phenyl)-2-(4-isopropylpiperazin-1-yl)acetamide MS (EI) m/z $C_{31}H_{37}N_7O_5S$: 620 (MH$^+$).

Example 206

N-(3-(N-(3-(3,5-dimethoxy-phenylamino)quinoxalin-2-yl)sulfamoyl)phenyl)-2-(3-(dimethylamino)pyrrolidin-1-yl)acetamide MS (EI) m/z $C_{30}H_{35}N_7O_5S$: 606 (MH$^+$).

Example 207

N-(3-(N-(3-(3,5-dimethoxy-phenylamino)quinoxalin-2-yl)sulfamoyl)phenyl)-2-(3-(dimethylamino)azetidin-1-yl)acetamide MS (EI) m/z $C_{29}H_{33}N_7O_5S$: 592 (MH$^+$).

Example 298

N-(3-(N-(3-(3,5-dimethoxy-phenylamino)quinoxalin-2-yl)sulfamoyl)phenyl)-2-(4-oxopiperidin-1-yl)acetamide MS (EI) m/z $C_{29}H_{30}N_6O_6S$: 591 (MH$^+$).

Example 209

N-(3-(N-(3-(3,5-dimethoxy-phenylamino)quinoxalin-2-yl)sulfamoyl)phenyl)-2-((2-methoxyethyl)(methyl)amino)acetamide MS (EI) m/z $C_{28}H_{32}N_6O_6S$: 581 (MH$^+$).

Example 210

N-(3-(N-(3-(3,5-dimethoxy-phenylamino)quinoxalin-2-yl)sulfamoyl)phenyl)-2-(4-methylbenzyloxyamino)acetamide MS (EI) m/z $C_{32}H_{32}N_6O_6S$: 629 (MH$^+$).

Example 211

N-(3-(N-(3-(3,5-dimethoxy-phenylamino)quinoxalin-2-yl)sulfamoyl)phenyl)-2-(2-methoxybenzyloxyamino)acetamide MS (EI) m/z $C_{32}H_{32}N_6O_7S$: 645 (MH$^+$).

Example 212

N-(3-(N-(3-(3,5-dimethoxy-phenylamino)quinoxalin-2-yl)sulfamoyl)phenyl)-2-(propylamino)acetamide MS (EI) m/z $C_{27}H_{30}N_6O_5S$: 551 (MH$^+$).

Example 213

N-(3-(N-(3-(3,5-dimethoxy-phenylamino)quinoxalin-2-yl)sulfamoyl)phenyl)-2-(ethyl(methyl)amino)acetamide MS (EI) m/z $C_{27}H_{30}N_6O_5S$: 551 (H).

Example 214

2-(allyl(methyl)amino)-N-(3-(N-(3-(3,5-dimethoxyphenylamino)quinoxalin-2-yl)sulfamoyl)phenyl)acetamide MS (EI) m/z $C_{28}H_{30}N_6O_5S$: 563 (MH$^+$).

Example 215

2-(tert-butylamino)-N-(3-(N-(3-(3,5-dimethoxy-phenylamino)quinoxalin-2-yl)sulfamoyl)phenyl)acetamide MS (EI) m/z $C_{28}H_{32}N_6O_5S$: 565 (MH$^+$).

Example 216

N-(3-(N-(3-(3,5-dimethoxy-phenylamino)quinoxalin-2-yl)sulfamoyl)phenyl)-2-(isobutylamino)acetamide MS (EI) m/z $C_{28}H_{132}N_6O_5S$: 565 (MH$^+$).

Example 217

2-(butylamino)-N-(3-(N-(3-(3,5-dimethoxy-phenylamino)quinoxalin-2-yl)sulfamoyl)phenyl)acetamide MS (EI) m/z $C_{28}H_{32}N_6O_5S$: 565 (MH$^+$).

Example 218

N-(3-(N-(3-(3,5-dimethoxy-phenylamino)quinoxalin-2-yl)sulfamoyl)phenyl)-2-(isopropyl(methyl)amino)acetamide MS (EI) m/z $C_{28}H_{32}N_6O_5S$: 565 (MH$^+$).

Example 219

N-(3-(N-(3-(3,5-dimethoxy-phenylamino)quinoxalin-2-yl)sulfamoyl)phenyl)-2-(4-formylpiperazin-1-yl)acetamide MS (EI) m/z $C_{29}H_{31}N_7O_6S$: 606 (MH$^+$).

Example 220

N-(3-(N-(3-(3,5-dimethoxy-phenylamino)quinoxalin-2-yl)sulfamoyl)phenyl)-2-(4-ethylpiperazin-1-yl)acetamide MS (EI) m/z $C_{30}H_{35}N_7O_5S$: 606 (MH$^+$).

Example 221

N-(3-(N-(3-(3,5-dimethoxy-phenylamino)quinoxalin-2-yl)sulfamoyl)phenyl)-2-(4-formyl-1,4-diazepan-1-yl)acetamide MS (EI) m/z $C_{30}H_{33}N_7O_6S$: 620 (MH$^+$).

Example 222

N-(3-(N-(3-(3,5-dimethoxy-phenylamino)quinoxalin-2-yl)sulfamoyl)phenyl)-2-(ethyl(2-hydroxyethyl)amino)acetamide MS (EI) m/z $C_{28}H_{32}N_6O_6S$: 581 (MH$^+$).

Example 223

(S)—N-(3-(N-(3-(3,5-dimethoxy-phenylamino)quinoxalin-2-yl)sulfamoyl)phenyl)-2-(3-hydroxypyrrolidin-1-yl)acetamide MS (EI) m/z $C_{28}H_{30}N_6O_6S$: 579 (MH$^+$).

Example 224

N-(3-(N-(3-(3,5-dimethoxy-phenylamino)quinoxalin-2-yl)sulfamoyl)phenyl)-2-(2,6-dimethylmorpholino)acetamide MS (EI) m/z $C_{30}H_{34}N_6O_6S$: 607 (MH$^+$).

Example 225

N-(3-(N-(3-(3,5-dimethoxy-phenylamino)quinoxalin-2-yl)sulfamoyl)phenyl)-2-(2-methylbenzylamino)acetamide MS (EI) m/z $C_{32}H_{132}N_6O_5S$: 613 (MH$^+$).

Example 226

N-(3-(N-(3-(3,5-dimethoxy-phenylamino)quinoxalin-2-yl)sulfamoyl)phenyl)-2-(2-methoxy-ethylamino)acetamide MS (EI) m/z $C_{27}H_{30}N_6O_6S$: 567 (MH$^+$).

Example 227

N-(3-(N-(3-(3,5-dimethoxyphenylamino)quinoxalin-2-yl)sulfamoyl)phenyl)-2-(thiazolidin-3-yl)acetamide MS (EI) m/z $C_{27}H_{28}N_6O_5S_2$: 581 (MH$^+$).

Example 228

N-(3-(N-(3-(3,5-dimethoxy-phenylamino)quinoxalin-2-yl)sulfamoyl)phenyl)-2-(3-(hydroxymethyl)piperidin-1-yl)acetamide MS (EI) m/z $C_{30}H_{34}N_6O_6S$: 607 (MH$^+$).

Example 229

N-(3-(N-(3-(3,5-dimethoxy-phenylamino)quinoxalin-2-yl)sulfamoyl)phenyl)-2-(2-phenylpropylamino)acetamide MS (EI) m/z $C_{33}H_{34}N_6O_5S$: 627 (MH$^+$).

Example 230

N-(3-(N-(3-(3,5-dimethoxy-phenylamino)quinoxalin-2-yl)sulfamoyl)phenyl)-2-(isobutyl(methyl)amino)acetamide MS (EI) m/z $C_{29}H_{34}N_6O_5S$: 579 (MH$^+$).

Example 231

N-(3-(N-(3-(3,5-dimethoxy-phenylamino)quinoxalin-2-yl)sulfamoyl)phenyl)-2-(phenylamino)acetamide MS (EI) m/z $C_{30}H_{28}N_6O_5S$: 585 (MH$^+$).

Example 232

N-(3-(N-(3-(3,5-dimethoxy-phenylamino)quinoxalin-2-yl)sulfamoyl)phenyl)-2-(2-propylphenylamino)acetamide MS (EI) m/z $C_{33}H_{34}N_6O_5S$: 627 (MH$^+$).

Example 233

N-(3-(N-(3-(3,5-dimethoxy-phenylamino)quinoxalin-2-yl)sulfamoyl)phenyl)-2-(2-isopropylphenylamino)acetamide MS (EI) m/z $C_{33}H_{34}N_6O_5S$: 627 (MH$^+$).

Example 234

N-(3-(N-(3-(3,5-dimethoxy-phenylamino)quinoxalin-2-yl)sulfamoyl)phenyl)-2-(2-fluoro-4-methylphenylamino)acetamide MS (EI) m/z $C_{31}H_{29}FN_6O_5S$: 617 (MH$^+$).

Example 235

2-(4-chlorophenylamino)-N-(3-(N-(3-(3,5-dimethoxy-phenylamino)quinoxalin-2-yl)sulfamoyl)phenyl)acetamide MS (EI) m/z $C_{30}H_{27}ClN_6O_5S$: 619 (MH$^+$).

Example 236

N-(3-(N-(3-(3,5-dimethoxy-phenylamino)quinoxalin-2-yl)sulfamoyl)phenyl)-2-(2-methoxyphenylamino)acetamide MS (EI) m/z $C_{31}H_{30}N_6O_6S$: 615 (MH$^+$).

Example 237

2-(3-chlorophenylamino)-N-(3-(N-(3-(3,5-dimethoxy-phenylamino)quinoxalin-2-yl)sulfamoyl)phenyl)acetamide MS (EI) m/z $C_{30}H_{27}ClN_6O_5S$: 619 (MH$^+$).

Example 238

N-(3-(N-(3-(3,5-dimethoxy-phenylamino)quinoxalin-2-yl)sulfamoyl)phenyl)-2-(2,3-dimethylphenylamino)acetamide MS (EI) m/z $C_{32}H_{32}N_6O_5S$: 613 (MH$^+$).

Example 239

N-(3-(N-(3-(3,5-dimethoxy-phenylamino)quinoxalin-2-yl)sulfamoyl)phenyl)-2-(2-fluorophenylamino)acetamide MS (EI) m/z $C_{30}H_{27}FN_6O_5S$: 603 (MH$^+$).

Example 240

N-(3-(N-(3-(3,5-dimethoxy-phenylamino)quinoxalin-2-yl)sulfamoyl)phenyl)-2-(3-fluorophenylamino)acetamide MS (EI) m/z $C_{30}H_{27}FN_6O_5S$: 603 (MH$^+$).

Example 241

N-(3-(N-(3-(3,5-dimethoxy-phenylamino)quinoxalin-2-yl)sulfamoyl)phenyl)-2-(thiophen-2-ylmethylamino)acetamide MS (EI) m/z $C_{29}H_{28}N_6O_5S_2$: 605 (MH$^+$).

Example 242

2-(cyclohexyl(ethyl)amino)-N-(3-(N-(3-(3,5-dimethoxyphenylamino)quinoxalin-2-yl)sulfamoyl)phenyl)acetamide MS (EI) m/z $C_{32}H_{38}N_6O_5S$: 619 (MH$^+$).

Example 243

2-((cyclopropylmethyl)(propyl)amino)-N-(3-(N-(3-(3,5-dimethoxyphenylamino)quinoxalin-2-yl)sulfamoyl)phenyl)acetamide MS (EI) m/z $C_{31}H_{36}N_6O_5S$: 605 (MH$^+$).

Example 244

2-(allyl(cyclopentyl)amino)-N-(3-(N-(3-(3,5-dimethoxyphenylamino)quinoxalin-2-yl)sulfamoyl)phenyl)acetamide MS (EI) m/z $C_{32}H_{36}N_6O_5S$: 617 (MH$^+$).

Example 245

N-(3-(N-(3-(3,5-dimethoxy-phenylamino)quinoxalin-2-yl)sulfamoyl)phenyl)-2-(ethyl(isopropyl)amino)acetamide MS (EI) m/z $C_{29}H_{34}N_6O_5S$: 579 (MH$^+$).

Example 246

N-(3-(N-(3-(3,5-dimethoxy-phenylamino)quinoxalin-2-yl)sulfamoyl)phenyl)-2-(ethyl(phenyl)amino)acetamide MS (EI) m/z $C_{32}H_{32}N_6O_5S$: 613 (MH$^+$).

Example 247

N-(3-(N-(3-(3,5-dimethoxy-phenylamino)quinoxalin-2-yl)sulfamoyl)phenyl)-2-(2-methylpyrrolidin-1-yl)acetamide MS (EI) m/z $C_{29}H_{132}N_6O_5S$: 577 (MH$^+$).

Example 248

N-(3-(N-(3-(3,5-dimethoxy-phenylamino)quinoxalin-2-yl)sulfamoyl)phenyl)-2-(2-methylpiperidin-1-yl)acetamide MS (EI) m/z $C_{30}H_{34}N_6O_5S$: 591 (MH$^+$).

Example 249

N-(3-(N-(3-(3,5-dimethoxy-phenylamino)quinoxalin-2-yl)sulfamoyl)phenyl)-2-(pyridin-2-ylmethylamino)acetamide MS (EI) m/z $C_{30}H_{29}N_7O_5S$: 600 (MH$^+$).

Example 250

2-(benzyl(methyl)amino)-N-(3-(N-(3-(3,5-dimethoxy-phenylamino)quinoxalin-2-yl)sulfamoyl)phenyl)acetamide MS (EI) m/z $C_{32}H_{32}N_6O_5S$: 613 (MH$^+$).

Example 251

N-(3-(N-(3-(3,5-dimethoxy-phenylamino)quinoxalin-2-yl)sulfamoyl)phenyl)-2-(1-phenylethylamino)acetamide MS (EI) m/z $C_{32}H_{32}N_6O_5S$: 613 (MH$^+$).

Example 252

N-(3-(N-(3-(3,5-dimethoxy-phenylamino)quinoxalin-2-yl)sulfamoyl)phenyl)-2-(3-methylpiperidin-1-yl)acetamide MS (EI) m/z $C_{30}H_{34}N_6O_5S$: 591 (MH$^+$).

Example 253

N-(3-(N-(3-(3,5-dimethoxy-phenylamino)quinoxalin-2-yl)sulfamoyl)phenyl)-2-(4-methylpiperidin-1-yl)acetamide MS (EI) m/z $C_{30}H_{34}N_6O_5S$: 591 (MH$^+$).

Example 254

2-(3,4-dihydroisoquinolin-2(1H)-yl)-N-(3-(N-(3-(3,5-dimethoxyphenylamino)quinoxalin-2-yl)sulfamoyl)phenyl)acetamide MS (EI) m/z $C_{33}H_{32}N_6O_5S$: 625 (MH$^+$).

Example 255

N-(3-(N-(3-(3,5-dimethoxy-phenylamino)quinoxalin-2-yl)sulfamoyl)phenyl)-2-(2,6-dimethylpiperidin-1-yl)acetamide MS (EI) m/z $C_{31}H_{36}N_6O_5S$: 605 (MH$^+$).

Example 256

N-(3-(N-(3-(3,5-dimethoxy-phenylamino)quinoxalin-2-yl)sulfamoyl)phenyl)-2-(3-hydroxybenzylamino)acetamide MS (EI) m/z $C_{31}H_{30}N_6O_6S$: 615 (MH$^+$).

General Library Acylation Procedure 1

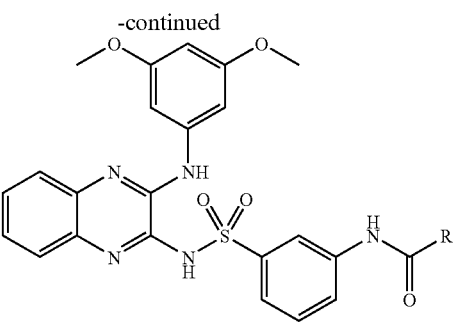

Into a 2-dram vial were added 3-amino-N-(3-(3,5-dimethoxy-phenylamino)quinoxalin-2-yl)benzenesulfonamide (54 mg, 0.12 mmol), prepared using procedures similar to those described in Example 15, DMA (2 mL) and the desired carboxylic acid (0.17 mmol). DIEA (70 μL, 0.4 mmol) followed by HATU (53 mg, 0.14 mmol) were added to the vial and the reaction mixture stirred at 50° C. overnight. Preparative reverse-phase HPLC was used to isolate the desired product directly from the crude reaction mixture. A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification.

The following title compounds were prepared according to General Library Acylation Procedure 1.

Example 257

N-(3-(N-(3-(2-chloro-5-methoxy-phenylamino)quinoxalin-2-yl)sulfamoyl)phenyl)morpholine-4-carboxamide MS (EI) m/z for $C_{26}H_{25}CN_6O_5S$: 567 (MH$^+$).

Example 258

N-(3-(N-(3-(3,5-dimethoxy-phenylamino)quinoxalin-2-yl)sulfamoyl)phenyl)-2-(dimethylamino)acetamide MS (EI) m/z for $C_{26}H_{28}N_6O_5S$: 535.1 (MH$^+$).

Example 259

N-(3-(N-(3-(3,5-dimethoxy-phenylamino)quinoxalin-2-yl)sulfamoyl)phenyl)propionamide $^1$H-NMR (400 MHz, d$_6$-DMSO): 12.37 (s, 1H), 10.20 (s, 1H), 8.88 (s, 1H), 8.37 (s, 1H), 7.93 (s, 1H), 7.77 (t, 2H), 7.59 (t, 1H), 7.51 (t, 1H), 7.41-7.34 (m, 4H), 6.24 (t, 1H), 3.76 (s, 6H), 2.36-2.31 (dd, 2H), 1.10 (s, 1H), 1.08 (s, 1H), 1.06 (s, 1H); MS (EI) m/z $C_{25}H_{25}N_5O_5S$: 508.6 (MH$^+$).

Example 260

N-(3-(N-(3-(3,5-dimethoxy-phenylamino)quinoxalin-2-yl)sulfamoyl)phenyl)pyridazine-4-carboxamide $^1$H-NMR (400 MHz, d$_6$-DMSO): 11.01 (s, 1H), 9.66 (dd, 1H), 9.52 (dd, 1H), 8.90 (s, 1H), 8.55 (s, 1H), 8.13 (dd, 1H), 7.99 (d, 1H), 7.93 (d, 1H), 7.65-7.58 (m, 2H), 7.42-7.35 (m, 4H), 6.24 (t, 1H), 3.75 (s, 6H); MS (EI) m/z $C_{27}H_{23}N_7O_5S$: 558.6 (MH$^+$).

Example 261

N-(3-(N-(3-(3,5-dimethoxy-phenylamino)quinoxalin-2-yl)sulfamoyl)phenyl)-2-methylnicotinamide $^1$H-NMR (400 MHz, d$_6$-DMSO): 10.78 ppm (s, 1H), 8.90 ppm (s, 1H), 8.58-8.57 ppm (dd, 2H), 7.90-7.86 (m, 4H), 7.60-7.56 ppm (m, 2H), 7.42-7.34 (m, 5H), 6.23 ppm (t, 1H), 3.74 ppm (s, 6H), 2.57 ppm (s, 3H); MS (EI) m/z $C_{29}H_{26}N_5O_5S$: 570.6 (MH$^+$).

Example 262

N-(3-(N-(3-(3,5-dimethoxy-phenylamino)quinoxalin-2-yl)sulfamoyl)phenyl)-2-(o-tolyloxy)acetamide $^1$H-NMR (400 MHz, d$_6$-DMSO): 12.37 ppm (s, 1H), 10.41 ppm (s, 1H), 8.90 ppm (s, 1H), 8.41 ppm (s, 1H), 7.93 ppm (s, 1H), 7.90-7.8 (m, 2H), 7.59-7.53 ppm (m, 2H), 7.42-7.33 ppm (m, 4H), 7.17-7.12 ppm (m, 2H), 6.89-6.85 ppm (m, 2H), 6.24 ppm (t, 1H), 4.74 ppm (s, 2H), 3.76 ppm (s, 6H), 2.33 ppm (s, 2H); MS (EI) m/z $C_{31}H_{29}N_5O_6S$: 599.7 (MH$^+$).

Example 263

N-(3-(N-(3-(3,5-dimethoxy-phenylamino)quinoxalin-2-yl)sulfamoyl)phenyl)-3-methoxy-4-methylbenzamide MS (EI) m/z $C_{31}H_{29}N_5O_6S$: 600 (MH$^+$).

Example 264

N-(3-(N-(3-(3,5-dimethoxy-phenylamino)quinoxalin-2-yl)sulfamoyl)phenyl)-3-methoxy-4-methylbenzamide MS (EI) m/z $C_{28}H_{24}N_6O_5S$: 557 (MH$^+$).

Example 265

N-(3-(N-(3-(3,5-dimethoxy-phenylamino)quinoxalin-2-yl)sulfamoyl)phenyl)thiazole-4-carboxamide MS (EI) m/z $C_{26}H_{22}N_6O_5S_2$: 563 (MH$^+$).

Example 266

2-bromo-N-(3-(N-(3-(3,5-dimethoxy-phenylamino)quinoxalin-2-yl)sulfamoyl)phenyl)thiophene-3-carboxamide MS (EI) m/z $C_{27}H_{22}BrN_5O_5S_2$ 640 (MH$^+$).

Example 267

N-(3-(N-(3-(3,5-dimethoxy-phenylamino)quinoxalin-2-yl)sulfamoyl)phenyl)pivalamide MS (EI) m/z $C_{27}H_{29}N_5O_5S$: 536 (MH$^+$).

Example 268

N-(3-(N-(3-(3,5-dimethoxy-phenylamino)quinoxalin-2-yl)sulfamoyl)phenyl)pent-4-enamide MS (EI) m/z $C_{27}H_{27}N_5O_5S$: 534 (MH$^+$).

Example 269

N-(3-(N-(3-(3,5-dimethoxy-phenylamino)quinoxalin-2-yl)sulfamoyl)phenyl)benzamide MS (EI) m/z $C_{29}H_{25}N_5O_5S$: 556 (MH$^+$).

Example 270

N-(3-(N-(3-(3,5-dimethoxy-phenylamino)quinoxalin-2-yl)sulfamoyl)phenyl)butyramide MS (EI) m/z $C_{26}H_{27}N_5O_5S$: 522 (MH$^+$).

Example 271

N-(3-(N-(3-(3,5-dimethoxy-phenylamino)quinoxalin-2-yl)sulfamoyl)phenyl)-2-methoxyacetamide MS (EI) m/z $C_{25}H_{25}N_5O_6S$: 524 (MH$^+$).

Example 272

N-(3-(N-(3-(3,5-dimethoxy-phenylamino)quinoxalin-2-yl)sulfamoyl)phenyl)cyclobutanecarboxamide MS (EI) m/z $C_{27}H_{27}N_5O_5S$: 534 (MH$^+$).

Example 273

N-(3-(N-(3-(3,5-dimethoxy-phenylamino)quinoxalin-2-yl)sulfamoyl)phenyl)-2-methylcyclopropanecarboxamide MS (EI) m/z $C_{27}H_{27}N_5O_5S$: 534 (MH$^+$).

Example 274

N-(3-(N-(3-(3,5-dimethoxy-phenylamino)quinoxalin-2-yl)sulfamoyl)phenyl)-1-methylcyclopropanecarboxamide MS (EI) m/z $C_{27}H_{27}N_5O_5S$: 534 (MH$^+$).

Example 275

N-(3-(N-(3-(3,5-dimethoxy-phenylamino)quinoxalin-2-yl)sulfamoyl)phenyl)-3-methylbutanamide MS (EI) m/z $C_{27}H_{29}N_5O_5S$: 536 (MH$^+$).

Example 276

N-(3-(N-(3-(3,5-dimethoxy-phenylamino)quinoxalin-2-yl)sulfamoyl)phenyl)-2-ethoxyacetamide MS (EI) m/z $C_{26}H_{27}N_5O_6S$: 538 (MH$^+$).

Example 277

N-(3-(N-(3-(3,5-dimethoxy-phenylamino)quinoxalin-2-yl)sulfamoyl)phenyl)-3-methoxypropanamide MS (EI) m/z $C_{26}H_{27}N_5O_6S$: 538 (MH$^+$).

Example 278

N-(3-(N-(3-(3,5-dimethoxy-phenylamino)quinoxalin-2-yl)sulfamoyl)phenyl)-2-hydroxyacetamide MS (EI) m/z $C_{24}H_{23}N_5O_6S$: 510 (MH$^+$).

Example 279

N-(3-(N-(3-(3,5-dimethoxy-phenylamino)quinoxalin-2-yl)sulfamoyl)phenyl)isobutyramide MS (EI) m/z $C_{26}H_{127}N_5O_5S$: 522 (MH$^+$).

Example 280

N-(3-(N-(3-(3,5-dimethoxy-phenylamino)quinoxalin-2-yl)sulfamoyl)phenyl)-1-hydroxycyclopropanecarboxamide MS (EI) m/z $C_{26}H_{25}N_5O_6S$: 536 (MH$^+$).

Example 281

N-(3-(N-(3-(3,5-dimethoxy-phenylamino)quinoxalin-2-yl)sulfamoyl)phenyl)furan-3-carboxamide MS (EI) m/z $C_{27}H_{23}N_5O_6S$: 546 (MH$^+$).

Example 282

N-(3-(N-(3-(3,5-dimethoxy-phenylamino)quinoxalin-2-yl)sulfamoyl)phenyl)tetrahydrofuran-3-carboxamide MS (EI) m/z $C_{27}H_{27}N_5O_6S$: 550 (MH$^+$).

Example 283

N-(3-(N-(3-(3,5-dimethoxy-phenylamino)quinoxalin-2-yl)sulfamoyl)phenyl)tetrahydrofuran-2-carboxamide MS (EI) m/z $C_{27}H_{27}N_5O_6S$: 550 (MH$^+$).

Example 284

N-(3-(N-(3-(3,5-dimethoxy-phenylamino)quinoxalin-2-yl)sulfamoyl)phenyl)furan-2-carboxamide MS (EI) m/z $C_{27}H_{23}N_5O_6S$: 546 (MH$^+$).

Example 285

N-(3-(N-(3-(3,5-dimethoxy-phenylamino)quinoxalin-2-yl)sulfamoyl)phenyl)isonicotinamide MS (EI) m/z $C_{28}H_{124}N_6O_5S$: 557 (MH$^+$).

Example 286

N-(3-(N-(3-(3,5-dimethoxy-phenylamino)quinoxalin-2-yl)sulfamoyl)phenyl)-1H-pyrrole-2-carboxamide MS (EI) m/z $C_{27}H_{24}N_6O_5S$: 545 (MH$^+$).

Example 287

N-(3-(N-(3-(3,5-dimethoxy-phenylamino)quinoxalin-2-yl)sulfamoyl)phenyl)pyrazine-2-carboxamide MS (EI) m/z $C_{27}H_{23}N_7O_5S$: 558 (MH$^+$).

Example 288

N-(3-(N-(3-(3,5-dimethoxy-phenylamino)quinoxalin-2-yl)sulfamoyl)phenyl)-1-methyl-1H-pyrrole-2-carboxamide MS (EI) m/z $C_{28}H_{26}N_6O_5S$: 559 (MH$^+$).

Example 289

N-(3-(N-(3-(3,5-dimethoxy-phenylamino)quinoxalin-2-yl)sulfamoyl)phenyl)-5-methylisoxazole-3-carboxamide MS (EI) m/z $C_{27}H_{24}N_6O_6S$: 561 (MH$^+$).

Example 290

N-(3-(N-(3-(3,5-dimethoxy-phenylamino)quinoxalin-2-yl)sulfamoyl)phenyl)thiophene-2-carboxamide MS (EI) m/z $C_{27}H_{23}N_5O_5S_2$: 562 (MH$^+$).

Example 291

(S)—N-(3-(N-(3-(3,5-dimethoxy-phenylamino)quinoxalin-2-yl)sulfamoyl)phenyl)-1-methylpyrrolidine-2-carboxamide MS (EI) m/z $C_{28}H_{30}N_6O_5S$: 563 (MH$^+$).

Example 292

N-(3-(N-(3-(3,5-dimethoxy-phenylamino)quinoxalin-2-yl)sulfamoyl)phenyl)-2-methylbenzamide MS (EI) m/z $C_{30}H_{27}N_5O_5S$: 570 (MH$^+$).

Example 293

N-(3-(N-(3-(3,5-dimethoxy-phenylamino)quinoxalin-2-yl)sulfamoyl)phenyl)-2-phenylacetamide MS (EI) m/z $C_{30}H_{27}N_5O_5S$: 570 (MH$^+$).

Example 294

N-(3-(N-(3-(3,5-dimethoxy-phenylamino)quinoxalin-2-yl)sulfamoyl)phenyl)-3-methylpicolinamide MS (EI) m/z $C_{29}H_{26}N_6O_5S$, 571 (MH$^+$).

Example 295

N-(3-(N-(3-(3,5-dimethoxy-phenylamino)quinoxalin-2-yl)sulfamoyl)phenyl)-2-(pyridin-3-yl)acetamide MS (EI) m/z $C_{29}H_{26}N_6O_5S$: 571 (MH$^+$).

Example 296

N-(3-(N-(3-(3,5-dimethoxy-phenylamino)quinoxalin-2-yl)sulfamoyl)phenyl)-6-hydroxypicolinamide MS (EI) m/z $C_{28}H_{24}N_6O_6S$: 573 (MH$^+$).

Example 297

N-(3-(N-(3-(3,5-dimethoxy-phenylamino)quinoxalin-2-yl)sulfamoyl)phenyl)-2-fluorobenzamide MS (EI) m/z $C_{29}H_{24}FN_5O_5S$: 574 (MH$^+$).

Example 298

N-(3-(N-(3-(3,5-dimethoxy-phenylamino)quinoxalin-2-yl)sulfamoyl)phenyl)-4-fluorobenzamide MS (EI) m/z $C_{29}H_4FN_5O_5S$: 574 (MH$^+$).

Example 299

N-(3-(N-(3-(3,5-dimethoxy-phenylamino)quinoxalin-2-yl)sulfamoyl)phenyl)-3-fluorobenzamide MS (EI) m/z $C_{29}H_{24}FN_5O_5S$: 574 (MH$^+$).

Example 300

2-cyclohexyl-N-(3-(N-(3-(3,5-dimethoxy-phenylamino)quinoxalin-2-yl)sulfamoyl)phenyl)acetamide MS (EI) m/z $C_{30}H_{133}N_5O_5S$: 576 (MH$^+$).

Example 301

N-(3-(N-(3-(3,5-dimethoxy-phenylamino)quinoxalin-2-yl)sulfamoyl)phenyl)-2-(2-oxocyclopentyl)acetamide MS (EI) m/z $C_{29}H_{29}N_5O_6S$: 576 (MH$^+$).

Example 302

4-cyclopropyl-N-(3-(N-(3-(3,5-dimethoxy-phenylamino)quinoxalin-2-yl)sulfamoyl)phenyl)-4-oxobutanamide MS (EI) m/z $C_{29}H_{29}N_5O_6S$: 576 (MH$^+$).

Example 303

N-(3-(N-(3-(3,5-dimethoxy-phenylamino)quinoxalin-2-yl)sulfamoyl)phenyl)-3-oxocyclohexanecarboxamide MS (EI) m/z $C_{29}H_{129}N_5O_6S$: 576 (MH$^+$).

Example 304

N-(3-(N-(3-(3,5-dimethoxy-phenylamino)quinoxalin-2-yl)sulfamoyl)phenyl)-3-(pyridin-3-yl)propanamide MS (EI) m/z $C_{30}H_{28}N_6O_5S$: 585 (MH$^+$).

Example 305

N-(3-(N-(3-(3,5-dimethoxy-phenylamino)quinoxalin-2-yl)sulfamoyl)phenyl)-2-methoxybenzamide MS (EI) m/z $C_{30}H_{27}N_5O_6S$: 586 (MH$^+$).

Example 306

N-(3-(N-(3-(3,5-dimethoxy-phenylamino)quinoxalin-2-yl)sulfamoyl)phenyl)-3-methoxybenzamide MS (EI) m/z $C_{30}H_{27}N_5O_6S$: 586 (MH$^+$).

Example 307

N-(3-(N-(3-(3,5-dimethoxy-phenylamino)quinoxalin-2-yl)sulfamoyl)phenyl)-2-phenoxyacetamide MS (EI) m/z $C_{30}H_{27}N_5O_6S$: 586 (MH$^+$).

Example 308

N-(3-(N-(3-(3,5-dimethoxy-phenylamino)quinoxalin-2-yl)sulfamoyl)phenyl)-4-methoxybenzamide MS (EI) m/z $C_{30}H_{27}N_5O_6S$: 586 (MH$^+$).

Example 309

N-(3-(N-(3-(3,5-dimethoxy-phenylamino)quinoxalin-2-yl)sulfamoyl)phenyl)-2-(4-fluorophenyl)acetamide MS (EI) m/z $C_{30}H_{26}FN_5O_5S$: 588 (MH$^+$).

Example 310

N-(3-(N-(3-(3,5-dimethoxy-phenylamino)quinoxalin-2-yl)sulfamoyl)phenyl)-2-(2-fluorophenyl)acetamide MS (EI) m/z $C_{30}H_{26}FN_5O_5S$: 588 (MH$^+$).

Example 311

N-(3-(N-(3-(3,5-dimethoxy-phenylamino)quinoxalin-2-yl)sulfamoyl)phenyl)-2-(3-fluorophenyl)acetamide MS (EI) m/z $C_{30}H_{26}FN_5O_5S$: 588 (MH$^+$).

Example 312

2-chloro-3-(N-(3-(3,5-dimethoxy-phenylamino)quinoxalin-2-yl)sulfamoyl)phenyl)benzamide MS (EI) m/z $C_{29}H_{24}ClN_5O_5S$: 590 (MH$^+$).

Example 313

4-chloro-N-(3-(N-(3-(3,5-dimethoxy-phenylamino)quinoxalin-2-yl)sulfamoyl)phenyl)benzamide MS (EI) m/z $C_{29}H_{24}ClN_5O_5S$: 590 (MH$^+$).

Example 314

3-chloro-N-(3-(N-(3-(3,5-dimethoxy-phenylamino)quinoxalin-2-yl)sulfamoyl)phenyl)benzamide MS (EI) m/z $C_{29}H_{24}ClN_5O_5S$: 590 (MH$^+$).

Example 315

(1R,2R) NY (3-(N-(3-(3,5-dimethoxy-phenylamino)quinoxalin-2-yl)sulfamoyl)phenyl)-2-phenylcyclopropanecarboxamide. MS (EI) m/z $C_{32}H_{29}N_5O_5S$: 596 (MH$^+$).

Example 316

N-(3-(N-(3-(3,5-dimethoxy-phenylamino)quinoxalin-2-yl)sulfamoyl)phenyl)-1-phenylcyclopropanecarboxamide MS (EI) m/z $C_{32}H_{29}N_5O_5S$: 596 (MH$^+$).

Example 317

N-(3-(N-(3-(3,5-dimethoxy-phenylamino)quinoxalin-2-yl)sulfamoyl)phenyl)-2-(1H-imidazol-4-yl)acetamide MS (EI) m/z $C_{27}H_{25}N_7O_5S$: 560 (MH$^+$).

Example 318

N-(3-(N-(3-(3,5-dimethoxy-phenylamino)quinoxalin-2-yl)sulfamoyl)phenyl)-4-methoxy-2-methylbenzamide MS (EI) m/z $C_{31}H_{29}N_5O_6S$: 600 (MH$^+$).

Example 319

N-(3-(N-(3-(3,5-dimethoxy-phenylamino)quinoxalin-2-yl)sulfamoyl)phenyl)-2-(4-fluorophenoxy)acetamide MS (EI) m/z $C_{30}H_{26}FN_5O_6S$: 604 (MH$^+$).

Example 320

N-(3-(N-(3-(3,5-dimethoxy-phenylamino)quinoxalin-2-yl)sulfamoyl)phenyl)-5-fluoro-2-methoxybenzamide MS (EI) m/z $C_{30}H_{26}FN_5O_6S$: 604 (MH$^+$).

Example 321

2-(4-chlorophenyl)-N-(3-(N-(3-(3,5-dimethoxy-phenylamino)quinoxalin-2-yl)sulfamoyl)phenyl)acetamide MS (EI) m/z $C_{30}H_{26}ClN_5O_5S$: 604 (MH$^+$).

Example 322

2-(2-chlorophenyl)-N-(3-(N-(3-(3,5-dimethoxy-phenylamino)quinoxalin-2-yl)sulfamoyl)phenyl)acetamide MS (EI) m/z $C_{30}H_{26}ClN_5O_5S$: 604 (MH$^+$).

Example 323

2-(3-chlorophenyl)-N-(3-(N-(3-(3,5-dimethoxy-phenylamino)quinoxalin-2-yl)sulfamoyl)phenyl)acetamide MS (EI) m/z $C_{30}H_{26}ClN_5O_5S$: 604 (MH$^+$).

Example 324

1-acetyl-N-(3-(N-(3-(3,5-dimethoxy-phenylamino)quinoxalin-2-yl)sulfamoyl)phenyl)piperidine-4-carboxamide MS (EI) m/z $C_{30}H_{32}N_6O_6S$: 605 (MH$^+$).

Example 325

N-(3-(N-(3-(3,5-dimethoxy-phenylamino)quinoxalin-2-yl)sulfamoyl)phenyl)-2-(pyridin-4-yl)acetamide MS (EI) m/z $C_{29}H_{26}N_6O_5S$: 571 (MH$^+$).

Example 326

N-(3-(N-(3-(3,5-dimethoxy-phenylamino)quinoxalin-2-yl)sulfamoyl)phenyl)-2-(pyridin-2-yl)acetamide MS (EI) m/z $C_{29}H_{26}N_6O_5S$: 571 (MH$^+$).

Example 327

2,4-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 328

3,4-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 329

2,5-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 330

3,5-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 331

2,3-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 332

N-(3-(N-(3-(3,5-dimethoxy-phenylamino)quinoxalin-2-yl)sulfamoyl)phenyl)pentanamide MS (EI) m/z $C_{27}H_{29}N_5O_5S$: 536 (MH$^+$).

Example 333

N-(3-(N-(3-(3,5-dimethoxy-phenylamino)quinoxalin-2-yl)sulfamoyl)phenyl)-2-methylbutanamide MS (EI) m/z $C_{27}H_{29}N_5O_5S$: 536 (MH$^+$).

Example 334

N-(3-(N-(3-(3,5-dimethoxy-phenylamino)quinoxalin-2-yl)sulfamoyl)phenyl)-1H-imidazole-2-carboxamide MS (EI) m/z $C_{26}H_3N_7O_5S$: 546 (MH$^+$).

Example 335

N-(3-(N-(3-(3,5-dimethoxy-phenylamino)quinoxalin-2-yl)sulfamoyl)phenyl)-1H-imidazole-4-carboxamide MS (EI) m/z $C_{26}H_{23}N_7O_5S$: 546 (MH$^+$).

Example 336

N-(3-(N-(3-(3,5-dimethoxy-phenylamino)quinoxalin-2-yl)sulfamoyl)phenyl)isoxazole-5-carboxamide MS (EI) m/z $C_{26}H_{22}N_6O_6S$: 547 (MH$^+$).

Example 337

N-(3-(N-(3-(3,5-dimethoxy-phenylamino)quinoxalin-2-yl)sulfamoyl)phenyl)-3,3-dimethylbutanamide MS (EI) m/z $C_{28}H_{31}N_5O_5S$: 550 (MH$^+$).

Example 338

N-(3-(N-(3-(3,5-dimethoxy-phenylamino)quinoxalin-2-yl)sulfamoyl)phenyl)-2-methylpentanamide MS (EI) m/z $C_{28}H_{31}N_5O_5S$: 550 (MH$^+$).

Example 339

N-(3-(N-(3-(3,5-dimethoxy-phenylamino)quinoxalin-2-yl)sulfamoyl)phenyl)-2,2-dimethylbutanamide MS (EI) m/z $C_{28}H_{31}N_5O_5S$: 550 (MH$^+$).

Example 340

N-(3-(N-(3-(3,5-dimethoxy-phenylamino)quinoxalin-2-yl)sulfamoyl)phenyl)-4-methylpentanamide MS (EI) m/z $C_{28}H_{31}N_5O_5S$: 550 (MH$^+$).

Example 341

N-(3-(N-(3-(3,5-dimethoxy-phenylamino)quinoxalin-2-yl)sulfamoyl)phenyl)pyrimidine-5-carboxamide MS (EI) m/z $C_{27}H_{23}N_7O_5S$: 558 (MH$^+$).

Example 342

N-(3-(N-(3-(3,5-dimethoxy-phenylamino)quinoxalin-2-yl)sulfamoyl)phenyl)-3-methylfuran-2-carboxamide MS (EI) m/z $C_{28}H_{25}N_5O_6S$: 560 (MH$^+$).

Example 343

N-(3-(N-(3-(3,5-dimethoxy-phenylamino)quinoxalin-2-yl)sulfamoyl)phenyl)thiophene-3-carboxamide MS (EI) m/z $C_{27}H_{23}N_5O_5S_2$: 562 (MH$^+$).

Example 344

N-(3-(N-(3-(3,5-dimethoxy-phenylamino)quinoxalin-2-yl)sulfamoyl)phenyl)-3-oxocyclopentanecarboxamide MS (EI) m/z $C_{28}H_{27}N_5O_6S$: 562 (MH$^+$).

Example 345

N-(3-(N-(3-(3,5-dimethoxy-phenylamino)quinoxalin-2-yl)sulfamoyl)phenyl)-2-(2-methoxyethoxy)acetamide MS (EI) m/z $C_{27}H_{29}N_5O_7S$: 568 (MH$^+$).

Example 346

N-(3-(N-(3-(3,5-dimethoxy-phenylamino)quinoxalin-2-yl)sulfamoyl)phenyl)-4-methylbenzamide MS (EI) m/z $C_{30}H_{27}N_5O_5S$: 570 (MH$^+$).

Example 347

N-(3-(N-(3-(3,5-dimethoxy-phenylamino)quinoxalin-2-yl)sulfamoyl)phenyl)-2-(3-methylisoxazol-4-yl)acetamide MS (EI) m/z $C_{28}H_{26}N_6O_6S$: 575 (MH$^+$).

Example 348

3-cyclopentyl-N-(3-(N-(3-(3,5-dimethoxy-phenylamino)quinoxalin-2-yl)sulfamoyl)phenyl)propanamide MS (EI) m/z $C_{30}H_{33}N_5O_5S$: 576 (MH$^+$).

Example 349

N-(3-(N-(3-(3,5-dimethoxy-phenylamino)quinoxalin-2-yl)sulfamoyl)phenyl)-2-o-tolylacetamide MS (EI) m/z $C_{31}H_{29}N_5O_5S$: 584 (MH$^+$).

Example 350

N-(3-(N-(3-(3,5-dimethoxy-phenylamino)quinoxalin-2-yl)sulfamoyl)phenyl)-2-methoxynicotinamide MS (EI) m/z $C_{29}H_{26}N_6O_6S$: 587 (MH$^+$).

Example 351

N-(3-(N-(3-(3,5-dimethoxy-phenylamino)quinoxalin-2-yl)sulfamoyl)phenyl)-4-fluoro-3-methylbenzamide MS (EI) m/z $C_{30}H_{26}FN_5O_5S$: 588 (MH$^+$).

Example 352

N-(3-(N-(3-(3,5-dimethoxy-phenylamino)quinoxalin-2-yl)sulfamoyl)phenyl)-3-fluoro-2-methylbenzamide MS (EI) m/z $C_{30}H_{26}FN_5O_5S$: 588 (MH$^+$).

Example 353

N-(3-(N-(3-(3,5-dimethoxy-phenylamino)quinoxalin-2-yl)sulfamoyl)phenyl)-3-fluoro-4-methylbenzamide MS (EI) m/z $C_{30}H_{26}FN_5O_5S$: 588 (MH$^+$).

Example 354

N-(3-(N-(3-(3,5-dimethoxy-phenylamino)quinoxalin-2-yl)sulfamoyl)phenyl)-2-fluoro-5-methylbenzamide MS (EI) m/z $C_{30}H_{26}FN_5O_5S$: 588 (MH$^+$).

Example 355

N-(3-(N-(3-(3,5-dimethoxy-phenylamino)quinoxalin-2-yl)sulfamoyl)phenyl)-5-fluoro-2-methylbenzamide MS (EI) m/z $C_{30}H_{26}FN_5O_5S$: 588 (MH$^+$).

Example 356

6-chloro-N-(3-(N-(3-(3,5-dimethoxy-phenylamino)quinoxalin-2-yl)sulfamoyl)phenyl)nicotinamide MS (EI) m/z $C_{28}H_{23}ClN_6O_5S$: 591 (MH$^+$).

Example 357

2-chloro-N-(3-(N-(3-(3,5-dimethoxy-phenylamino)quinoxalin-2-yl)sulfamoyl)phenyl)nicotinamide MS (EI) m/z $C_{28}H_{23}ClN_6O_5S$: 591 (MH$^+$).

Example 358

2-chloro-N-(3-(N-(3-(3,5-dimethoxy-phenylamino)quinoxalin-2-yl)sulfamoyl)phenyl)isonicotinamide MS (EI) m/z $C_{28}H_{23}ClN_6O_5S$: 591 (MH$^+$).

Example 359

N-(3-(N-(3-(3,5-dimethoxy-phenylamino)quinoxalin-2-yl)sulfamoyl)phenyl)-4-(dimethylamino)benzamide MS (EI) m/z $O_{31}H_{30}N_6O_5S$: 599 (MH$^+$).

Example 360

N-(3-(N-(3-(3,5-dimethoxy-phenylamino)quinoxalin-2-yl)sulfamoyl)phenyl)-3-(dimethylamino)benzamide MS (EI) m/z $C_{31}H_{30}N_6O_5S$: 599 (MH$^+$).

Example 361

N-(3-(N-(3-(3,5-dimethoxy-phenylamino)quinoxalin-2-yl)sulfamoyl)phenyl)benzo[d][1,3]dioxole-5-carboxamide MS (EI) m/z $C_{30}H_{25}N_5O_7S$: 600 (MH$^+$).

Example 362

N-(3-(N-(3-(3,5-dimethoxy-phenylamino)quinoxalin-2-yl)sulfamoyl)phenyl)-2-(m-tolyloxy)acetamide MS (EI) m/z $C_{31}H_{29}N_5O_6S$: 600 (MH$^+$).

Example 363

N-(3-(N-(3-(3,5-dimethoxy-phenylamino)quinoxalin-2-yl)sulfamoyl)phenyl)-2-(4-methoxyphenyl)acetamide MS (EI) m/z $C_{31}H_{29}N_5O_6S$: 600 (MH$^+$).

Example 364

N-(3-(N-(3-(3,5-dimethoxy-phenylamino)quinoxalin-2-yl)sulfamoyl)phenyl)-2-(2-methoxyphenyl)acetamide MS (EI) m/z $C_{31}H_{29}N_5O_6S$: 600 (MH$^+$).

Example 365

N-(3-(N-(3-(3,5-dimethoxy-phenylamino)quinoxalin-2-yl)sulfamoyl)phenyl)-2-(3-methoxyphenyl)acetamide MS (EI) m/z $C_{31}H_{29}N_5O_6S$: 600 (MH$^+$).

Example 366

N-(3-(N-(3-(3,5-dimethoxy-phenylamino)quinoxalin-2-yl)sulfamoyl)phenyl)-2-methoxy-4-methylbenzamide MS (EI) m/z $C_{31}H_{29}N_5O_6S$: 600 (MH$^+$).

Example 367

N-(3-(N-(3-(3,5-dimethoxy-phenylamino)quinoxalin-2-yl)sulfamoyl)phenyl)-3-fluoro-4-methoxybenzamide MS (EI) m/z $C_{30}H_{26}FN_5O_6S$: 604 (MH$^+$).

Example 368

N-(3-(N-(3-(3,5-dimethoxy-phenylamino)quinoxalin-2-yl)sulfamoyl)phenyl)-2-fluoro-6-methoxybenzamide MS (EI) m/z $C_{30}H_{26}FN_5O_6S$: 604 (MH$^+$).

Example 369

N-(3-(N-(3-(3,5-dimethoxy-phenylamino)quinoxalin-2-yl)sulfamoyl)phenyl)-3-(4-methoxyphenyl)propanamide MS (EI) m/z $C_{32}H_{31}N_5O_6S$: 614 (MH$^+$).

Example 370

N-(3-(N-(3-(3,5-dimethoxy-phenylamino)quinoxalin-2-yl)sulfamoyl)phenyl)-3-(2-methoxyphenyl)propanamide MS (EI) m/z $C_{32}H_{31}N_5O_6S$: 614 (MH$^+$).

Example 371

N-(3-(N-(3-(3,5-dimethoxy-phenylamino)quinoxalin-2-yl)sulfamoyl)phenyl)-3-(3-methoxyphenyl)propanamide MS (EI) m/z $C_{32}H_{31}N_5O_6S$: 614 (MH$^+$).

Example 372

N-(3-(N-(3-(3,5-dimethoxy-phenylamino)quinoxalin-2-yl)sulfamoyl)phenyl)azetidine-3-carboxamide

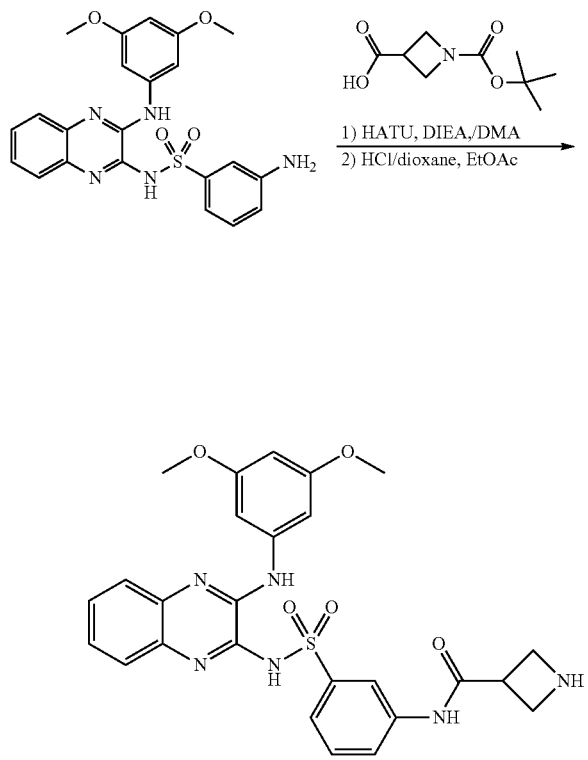

Into a 20 mL vial was added 3-amino-N-(3-(3,5-dimethoxy-phenylamino)quinoxalin-2-yl)benzenesulfonamide (0.24 mmol, 1 equiv), prepared using procedures similar to those described in Example 15, DMA (5 mL) and 1-(tert-butoxycarbonyl)azetidine-3-carboxylic acid (0.336 mmol, 1.4 equiv). Hunig's Base (0.792 mmol, 3.3 equiv) and HATU (0.288 mmol, 1.2 equiv) were added to the vial and the reaction mixture was then stirred at room temperature, overnight. Completion of the reaction was indicated by LCMS. The solvent was removed by rotary evaporation. The crude mixture was carried forward without further purification. The residue was suspended in 5 mL ethyl acetate and chilled in an ice bath. A solution of 4 N HCl in dioxane (3 mL, 5 equiv) was added with stirring. The reaction mixture was then stirred at room temperature overnight. The solid materials were collected by filtration, washed with ethylacetate then purified further by preparative reverse-phase HPLC (ammonium acetate/ACN). A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification. N-(3-(N-(3-(3,5-dimethoxy-phenylamino)quinoxalin-2-yl)sulfamoyl)phenyl)azetidine-3-carboxamide was obtained (26 mg, 20%). $^1$H-NMR (400 MHz, d$_6$-DMSO): 10.26 (s, 1H), 8.81 (s, 1H), 8.25 (t, 1H), 8.14 (s, 1H), 7.74 (d, 1H), 7.69 (d, 1H), 7.41-7.39 (m, 1H), 7.36 (d, 1H), 7.32 (d, 2H), 7.30-7.28 (dd, 1H), 7.14-7.11 (m, 2H), 6.14 (t, 1H), 4.09 (d, 4H), 3.78 (s, 6H); MS (EI) m/z C$_{26}$H$_{26}$N$_6$O$_5$S: 535.6 (MH$^+$).

Example 373

N-(3-(4-fluorophenylamino)quinoxalin-2-yl)benzenesulfonamide

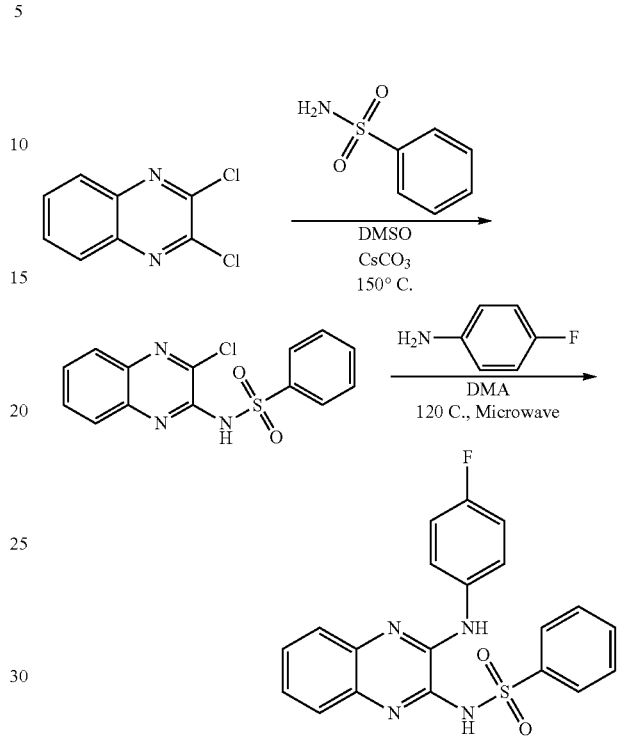

A flask was charged with 2,3-dichloroquinoxaline (3.5 g, 18 mmol), 85 mL of dimethylsulfoxide, benzene sulfonamide (2.8 g, 18 mmol), and cesium carbonate (5.8 g, 18 mmol). The reaction mixture was stirred under an N$_2$ atmosphere for 15 h at 150° C., after which time, it was transferred to a separatory funnel and 100 mL of water were added. Concentrated HCl was then added in order to acidify the reaction mixture to pH<2. The aqueous layer was subsequently washed three times with 90 mL ethyl acetate. The ethyl acetate layers were then washed two times with 150 mL water, three times with 100 mL brine and then dried over sodium sulfate. The ethyl acetate was removed on a rotary-evaporator. A slurry was formed by adding ethyl acetate and dichloromethane to the dried crude product, filtration yielded N-(3-chloroquinoxalin-2-yl)-benzenesulfonamide which was used without further purification. MS (EI) m/z C$_{14}$H$_{10}$ClN$_3$O$_2$S: 319.9 (MH$^+$).

A CEM microwave reaction vessel was charged with N-(3-chloroquinoxalin-2-yl)benzenesulfonamide (52 mg, 0.16 mmol), prepared using procedures similar to those described in the above step, 4-fluoroaniline (36 mg, 0.32 mmol), and 0.8 mL of dimethylacetamide. The vessel was sealed and the reaction mixture was heated under microwave radiation for 25 m at 120° C. in a CEM Discover microwave instrument. Methanol (1 mL) was added to the reaction mixture and after 20 minutes the product precipitated out of the solution. Filtration yielded N-(3-(4-fluorophenylamino)quinoxalin-2-yl) benzenesulfonamide (39 mg, 62%). $^1$H-NMR (400 MHz, d$_6$-DMSO): δ 12.30 (s, 1H), 9.11 (s, 1H), 8.16-8.10 (d, 2H), 8.02-7.90 (m, 3H), 7.68-7.58 (m, 3H), 7.55-7.51 (m, 1H), 7.41-7.32 (m, 2H), 7.25-7.16 (m, 2H); MS (EI) m/z C$_{20}$H$_{15}$FN$_4$O$_2$S: 395.0 (MH$^+$).

Example 374

N-(3-(N-(3-chloroquinoxalin-2-yl)sulfamoyl)phenyl)-2-(dimethylamino)acetamide

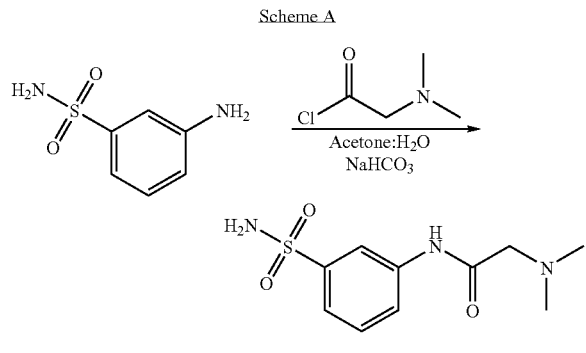

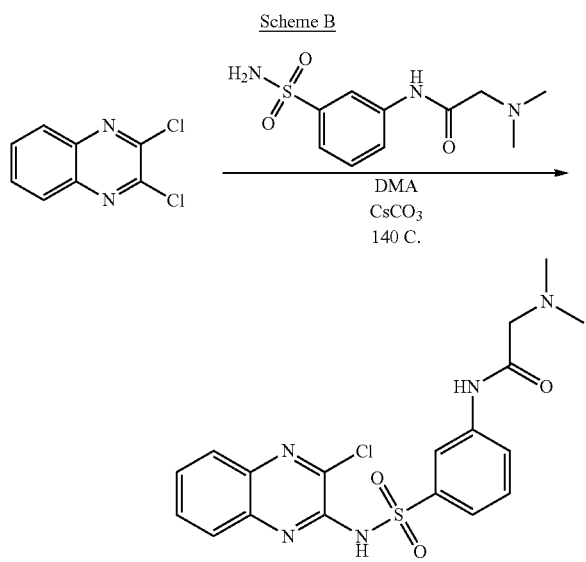

Scheme A

A flask was charged with 3-aminobenzene sulfonamide (3.3 g, 19 mmol), and 20 mL of 1:1 acetone:H$_2$O. The solution was stirred at room temperature until the aminobenzene sulfonamide had dissolved. The flask was then cooled in an ice bath and dimethylamino-acetyl chloride HCl (4.6 g, 29 mmol) was added. To the resulting slurry sodium bicarbonate (4.8 g, 57 mmol) was added over a 15 m period. After 30 min the reaction was removed from the ice bath and allowed to stir at room temperature for 15 h. The reaction mixture was then filtered and washed with methanol and acetonitrile. The filtrate was dried on a rotary evaporator to yield 2-(dimethylamino)-N-(3-sulfamoyl-phenyl)acetamide, which was submitted to the next step without further purification. MS (EI) m/z C$_{10}$H$_{15}$N$_3$O$_3$S: 258.0 (MH$^+$).

Scheme B

A flask was charged with dichloroquinozaline (1.0 g, 5.8 mmol), 10 mL of dimethylacetamide, 2-(dimethylamino)-N-(3-sulfamoylphenyl)acetamide (0.70 g, 2.7 mmol), and cesium carbonate (1.8 g, 5.5 mmol). The reaction mixture was stirred for 3 h at 140° C. and then filtered. The solvent was evaporated from the filtrate on a rotary-evaporator to yield (N-(3-(N-(3-chloroquinoxalin-2-yl)sulfamoyl)phenyl)-2-(dimethylamino)acetamide) which was submitted to the next step without further purification. MS (EI) m/z C$_{18}$H$_{18}$ClN$_5$O$_3$S: 420.0 (MH$^+$).

General Amination Procedure 1a

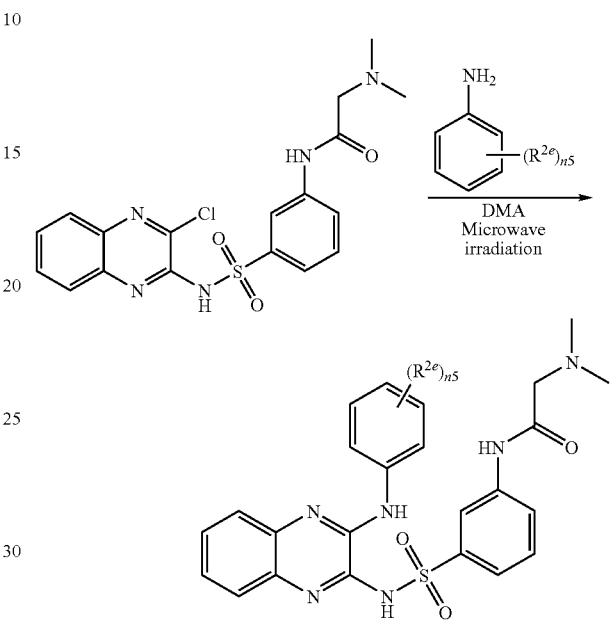

A CEM microwave reaction vessel was charged with N-(3-(N-(3-chloroquinoxalin-2-yl)sulfamoyl)phenyl)-2-(dimethylamino)acetamide (30 mg, 0.071 mmol), prepared using procedures similar to those described in Example 374, the desired aniline (16 mg, 0.14 mmol, 2 eq), and 0.5 mL of dimethylacetamide. The vessel was sealed and the reaction mixture was heated under microwave radiation for 70 min at 140° C. in a CEM Discover microwave instrument. The solvent was then removed by rotary-evaporation. Purification of the final product was accomplished by preparatory reverse-phase HPLC with the eluents 25 mM aqueous NH$_4$OAc/ACN to the desired product.

The following compounds were prepared according to the above General Amination Procedure 1a.

Example 375

2-(dimethylamino)-N-(3-(N-(3-(3-fluorophenylamino)quinoxalin-2-yl)sulfamoyl)phenyl)acetamide $^1$H-NMR (400 MHz, CDCl$_3$): 9.40 ppm (s, 1H), 8.43 ppm (s, 1H), 8.22 ppm (s, 1H), 8.07-8.02 ppm (d, 1H), 7.97-7.93 ppm (d, 1H), 7.76-7.71 (m, 2H), 7.53-7.48 ppm (t, 1H), 7.45-7.36 ppm (m, 4H), 7.35-7.28 ppm (m, 2H), 6.84-6.77 ppm (t, 1H), 3.10 ppm (s, 2H), 2.38 ppm (s, 6H); MS (EI) m/z C$_{24}$H$_{23}$FN$_6$O$_3$S: 495 (MH$^+$).

Example 376

2-(dimethylamino)-N-(3-(N-(3-(4-fluorophenylamino)quinoxalin-2-yl)sulfamoyl)phenyl)acetamide MS (EI) m/z C$_{24}$H$_{23}$FN$_6$O$_3$S: 495 (MH$^+$).

Example 377

N-(3-(N-(3-(4-chloro-phenylamino)quinoxalin-2-yl)sulfamoyl)phenyl)-2-(dimethylamino)acetamide MS (EI) m/z $C_{24}H_{23}ClN_6O_3S$: 511 (MH$^+$).

General Amination Procedure 1b

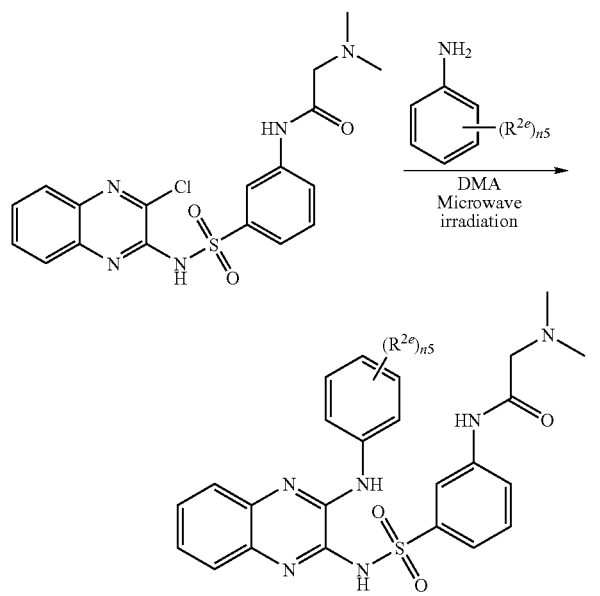

A CEM microwave reaction vessel was charged with N-(3-(N-(3-chloroquinoxalin-2-yl)sulfamoyl)phenyl)-2-(dimethylamino)acetamide (62 mg, 0.147 mmol), prepared using procedures similar to those in Example 374, the desired aniline (0.567 mmol, 4 eq), and 1.0 mL of toluene. The vessel was sealed and the reaction mixture was heated under microwave radiation for 60 min at 180° C. in a CEM Discover microwave instrument. The solvent was removed on a rotary-evaporator. Purification of the final product was done by preparatory HPLC with NH$_4$OAc/ACN as eluent to yield the desired product.

The following compounds were prepared according to the above General Amination Procedure 1b.

Example 378

N-(3-(N-(3-(3-chloro-phenylamino)quinoxalin-2-yl)sulfamoyl)phenyl)-2-(dimethylamino)acetamide
MS (EI) m/z $C_{24}H_{23}ClN_6O_3S$: 511 (MH$^+$).

Example 379

2-(dimethylamino)-N-(3-(N-(3-(4-fluoro-3-methoxyphenylamino)quinoxalin-2-yl)sulfamoyl)phenyl)acetamide. 2-(dimethylamino)-N-(3-(N-(3-(4-fluoro-3-methoxyphenylamino)quinoxalin-2-yl)sulfamoyl)phenyl). $^1$H-NMR (400 MHz, CDCl$_3$): δ 9.47 (s, 1H), 8.36 (s, 1H), 8.29 (s, 1H), 7.91-7.87 (d, 1H), 7.80-7.73 (m, 2H), 7.66-7.63 (d, 1H), 7.53-7.47 (t, 1H), 7.43-7.30 (m, 4H), 7.10-7.04 (t, 1H), 6.55-5.95 (br s, 1H), 3.96 (s, 3H), 3.12 (s, 2H), 2.39 (s, 6H), 2.08 (s, 3H(AcOH); MS (EI) m/z $C_{25}H_{25}FN_6O_4S$: 525 (MH$^+$).

Example 380

N-(3-(3,5-dimethoxy-phenylamino)quinoxalin-2-yl)-4-isopropoxybenzenesulfonamide

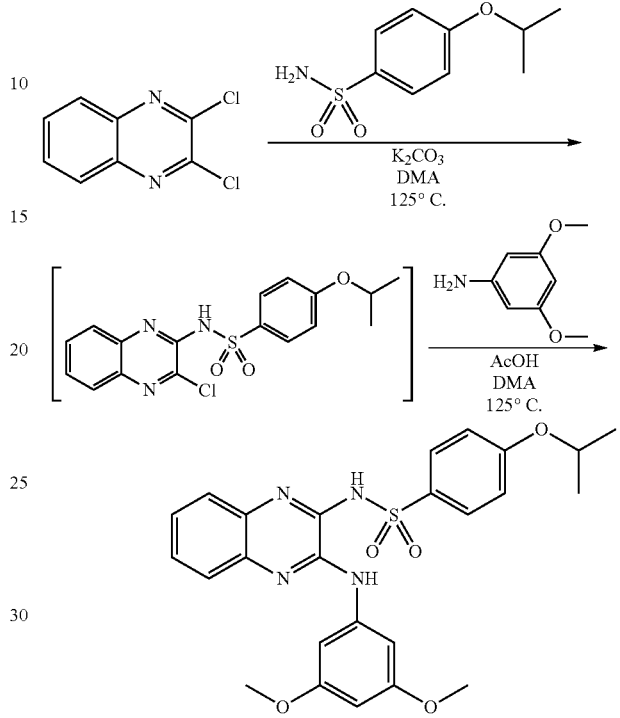

N-(3-(3,5-dimethoxy-phenylamino)quinoxalin-2-yl)-4-isopropoxy-benzenesulfonamide. A solution of 2,3-dichloroquinoxaline (2.0 mL, 0.38 M) was combined with K$_2$CO$_3$ (105 mg, 0.76 mmol) in a glass vial. A solution of 4-isopropoxybenzene sulfonamide (1.75 mL, 0.43 M) was added and the solution was stirred overnight at 125° C. After cooling, acetic acid (45 mL, 0.79 mmol) and 3,5-dimethoxyaniline (230 mg, 1.5 mmol) were added. The reaction mixture was stirred again at 125° C. overnight. Upon cooling, the reaction mixture was diluted with 8 mL of methanol and then 8 mL of water. The precipitate was collected by filtration and recrystallized from N,N-dimethylacetamide/water to give N-(3-(3,5-dimethoxy-phenylamino)quinoxalin-2-yl)-4-isopropoxy-benzenesulfonamide (45 mg, 12%). $^1$H-NMR (400 MHz, d$_6$-DMSO): 12.16 (bs, 1H), 8.93 (s, 1H), 8.03 (d, 2H), 7.92 (bs, 1H), 7.56 (d, 1H), 7.36 (m, 4H), 7.07 (d, 2H), 6.24 (s, 1H), 4.72 (m, 1H), 3.76 (s, 6H), 1.27 (d, 6H); MS (EI) m/z $C_{25}H_{26}N_4O_5S$: 495 (MH$^+$).

Examples 381-411 were synthesized proceeding as above in Example 423. In the cases where the product did not precipitate, the mixture was purified by reverse phase HPLC.

Example 381

3-chloro-N-(3-(3,5-dimethoxy-phenylamino)quinoxalin-2-yl)-4-methylbenzenesulfonamide $^1$H-NMR (400 MHz, d$_6$-DMSO): 12.31 (bs, 1H), 8.96 (s, 1H), 8.18 (s, 1H), 7.98 (d, 1H), 7.92 (bs, 1H), 7.58 (d, 2H), 7.43-7.33 (m, 4H), 6.24 (t, 1H), 3.76 (s, 6H), 2.39 (s, 3H); MS (EI) m/z $C_{23}H_{21}ClN_4O_4S$: 485 (MH$^+$).

Example 382

N-(3-(3,5-dimethoxy-phenylamino)quinoxalin-2-yl)naphthalene-1-sulfonamide
MS (EI) m/z $C_{26}H_{22}N_4O_4S$: 487 (MH$^+$).

Example 383

N-(3-(3,5-dimethoxy-phenylamino)quinoxalin-2-yl)-4-fluorobenzenesulfonamide
MS (EI) m/z $C_{22}H_{19}FN_4O_4S$: 455 (MH$^+$).

Example 384

N-(3-(3,5-dimethoxy-phenylamino)quinoxalin-2-yl)-3-fluorobenzenesulfonamide
MS (EI) m/z $C_{22}H_{19}FN_4O_4S$: 455 (MH$^+$).

Example 385

N-(3-(3,5-dimethoxy-phenylamino)quinoxalin-2-yl)-3-(trifluoromethyl)benzenesulfonamide
MS (EI) m/z $C_{23}H_{19}F_3N_4O_4S$: 505 (MH$^+$).

Example 386

N-(3-(3,5-dimethoxy-phenylamino)quinoxalin-2-yl)-4-(trifluoromethyl)benzenesulfonamide
MS (EI) m/z $C_{23}H_{19}F_3N_4O_4S$: 505 (MH$^+$).

Example 387

N-(3-(3,5-dimethoxy-phenylamino)quinoxalin-2-yl)-4-(trifluoromethoxy)benzenesulfonamide
MS (EI) m/z $C_{23}H_{19}F_3N_4O_5S$: 521 (MH$^+$).

Example 388

N-(4-(N-(3-(3,5-dimethoxy-phenylamino)quinoxalin-2-yl)sulfamoyl)phenyl)acetamide
MS (EI) m/z $C_{24}H_{23}N_5O_5S$: 494 (MH$^+$).

Example 389

N-(3-(3,5-dimethoxy-phenylamino)quinoxalin-2-yl)-4-fluoro-2-methylbenzenesulfonamide
MS (EI) m/z $C_{23}H_{21}FN_4O_4S$: 469 (MH$^+$).

Example 390

N-(3-(3,5-dimethoxy-phenylamino)quinoxalin-2-yl)-2-methylbenzenesulfonamide
MS (EI) m/z $C_{23}H_{22}N_4O_4S$: 451 (MH$^+$).

Example 391

2-chloro-N-(3-(3,5-dimethoxy-phenylamino)quinoxalin-2-yl)benzenesulfonamide
MS (EI) m/z $C_{22}H_{19}ClN_4O_4S$: 471 (MH$^+$).

Example 392

N-(3-(3,5-dimethoxy-phenylamino)quinoxalin-2-yl)-3,5-difluorobenzenesulfonamide
MS (EI) m/z $C_{22}H_{18}F_2N_4O_4S$: 473 (MH$^+$).

Example 393

3,5-dichloro-N-(3-(3,5-dimethoxy-phenylamino)quinoxalin-2-yl)benzenesulfonamide
MS (EI) m/z $C_{22}H_{18}C_2N_4O_4S$: 505 (MH$^+$).

Example 394

N-(3-(3,5-dimethoxy-phenylamino)quinoxalin-2-yl)-3-fluoro-4-methylbenzenesulfonamide
MS (EI) m/z $C_{23}H_{21}FN_4O_4S$: 469 (MH$^+$).

Example 395

N-(3-(3,5-dimethoxy-phenylamino)quinoxalin-2-yl)-2-(trifluoromethyl)benzenesulfonamide
MS (EI) m/z $C_{23}H_{19}F_3N_4O_4S$: 505 (MH$^+$).

Example 396

4-cyano-N-(3-(3,5-dimethoxy-phenylamino)quinoxalin-2-yl)benzenesulfonamide
MS (EI) m/z $C_{23}H_{19}N_5O_4S$: 462 (MH$^+$).

Example 397

N-(3-(3,5-dimethoxy-phenylamino)quinoxalin-2-yl)-1-phenylmethanesulfonamide
MS (EI) m/z $C_{23}H_{22}N_4O_4S$: 451 (MH$^+$).

Example 398

4,5-dichloro-N-(3-(3,5-dimethoxy-phenylamino)quinoxalin-2-yl)thiophene-2-sulfonamide
MS (EI) m/z $C_{20}H_{16}Cl_2N_4O_4S_2$: 511 (MH$^+$).

Example 399

1-(3-chlorophenyl)-N-(3-(3,5-dimethoxy-phenylamino)quinoxalin-2-yl)methanesulfonamide
MS (EI) m/z $C_{23}H_{21}ClN_4O_4S$: 485 (MH$^+$).

Example 400

N-(3-(3,5-dimethoxy-phenylamino)quinoxalin-2-yl)-2,5-dimethylthiophene-3-sulfonamide
MS (EI) m/z $C_{22}H_{22}N_4O_4S_2$: 471 (MH$^+$).

Example 401

N-(3-(3,5-dimethoxy-phenylamino)quinoxalin-2-yl)-3,5-bis(trifluoromethyl)benzenesulfonamide
MS (EI) m/z $C_{24}H_{18}F_6N_4O_4S$: 573 (MH$^+$).

Example 402

N-(3-(3,5-dimethoxy-phenylamino)quinoxalin-2-yl)-4-fluoro-3-(trifluoromethyl)benzenesulfonamide
MS (EI) m/z $C_{23}H_{18}F_4N_4O_4S$: 523 (MH$^+$).

Example 403

5-chloro-N-(3-(3,5-dimethoxy-phenylamino)quinoxalin-2-yl)-1,3-dimethyl-1H-pyrazole-4-sulfonamide
MS (EI) m/z $C_{21}H_{21}ClN_6O_4S$: 489 (MH$^+$).

Example 404

5-chloro-N-(3-(3,5-dimethoxy-phenylamino)quinoxalin-2-yl)-2-methoxybenzenesulfonamide
MS (EI) m/z $C_{23}H_{21}ClN_4O_5S$: 501 (MH$^+$).

Example 405

5-bromo-N-(3-(3,5-dimethoxy-phenylamino)quinoxalin-2-yl)-2-methoxybenzenesulfonamide
MS (EI) m/z $C_{23}H_{21}BrN_4O_5S$: 545 (MH$^+$).

Example 406

2,5-dichloro-N-(3-(3,5-dimethoxy-phenylamino)quinoxalin-2-yl)thiophene-3-sulfonamide
MS (EI) m/z $C_{20}H_{16}Cl_2N_4O_4S_2$: 511 (MH$^+$).

Example 407

N-(3-(3,5-dimethoxy-phenylamino)quinoxalin-2-yl)-3,5-dimethylisoxazole-4-sulfonamide
MS (EI) m/z $C_{21}H_{21}N_5O_5S$: 456 (MH$^+$).

Example 408

N-(3-(3,5-dimethoxy-phenylamino)quinoxalin-2-yl)-2,5-dimethoxybenzenesulfonamide
MS (EI) m/z $C_{24}H_{24}N_4O_6S$: 497 (MH$^+$).

Example 409

3-chloro-N-(3-(3,5-dimethoxy-phenylamino)quinoxalin-2-yl)-4-fluorobenzenesulfonamide
MS (EI) m/z $C_{22}H_{18}ClFN_4O_4S$: 489 (MH$^+$).

Example 410

4-(difluoromethoxy)-N-(3-(3,5-dimethoxy-phenylamino)quinoxalin-2-yl)benzenesulfonamide MS (EI) m/z $C_{23}H_{20}F_2N_4O_5S$: 503 (MH$^+$).

Example 411

N-(3-(3,5-dimethoxy-phenylamino)quinoxalin-2-yl)-3-(methylsulfonyl)benzenesulfonamide MS (EI) m/z $C_{23}H_{22}N_4O_6S_2$: 515 (MH$^+$).

General Acylation Procedure 2

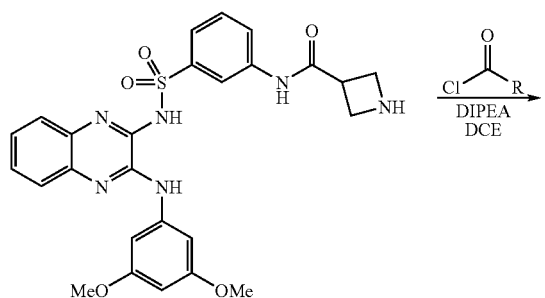

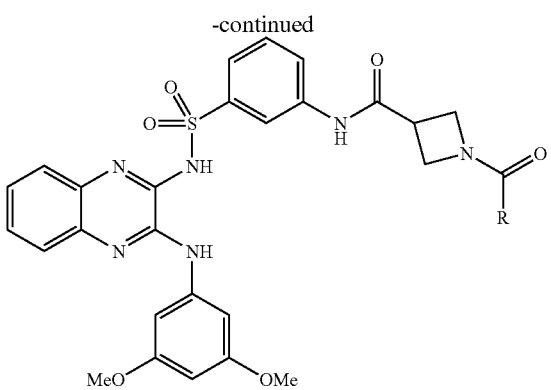

N-(3-(N-(3-(3,5-dimethoxy-phenylamino)quinoxalin-2-yl)-sulfamoyl)phenyl)azetidine-3-carboxamide (125 mg, 0.23 mmol), prepared using procedures similar to those described in Example 372, was dissolved into 5 mL DCE in a mL round-bottom flask. DIEA (1.17 mmol, 5.0 equiv.) was then added with stirring followed by acid chloride (0.47 mmol, 2.0 equiv.). The reaction was then stirred at room temperature for 1 hour or until complete as indicated by LCMS. The solvent was subsequently removed under reduced pressure on a rotary evaporator. The crude material was then redissolved in methanol. Purification of the final product was accomplished by preparatory reverse-phase HPLC with the eluents 25 mM aqueous NH$_4$OAc/CAN. A Waters Fractionlynx preparative reverse-phase HPLC; equipped with a Waters SunFire Prep C18, OCD 5 µM, 30×70 mm column and running a 5-100% gradient with a binary solvent system of 25 mM ammonium acetate in water/acetonitrile; was used to carry out the purification.

The following compounds were prepared according to General Acylation Procedure 2.

Example 412

N-(3-(N-(3-(3,5-dimethoxy-phenylamino)quinoxalin-2-yl)sulfamoyl)phenyl)-1-propionylazetidine-3-carboxamide $^1$H-NMR (400 MHz, d$_6$-DMSO): 12.40 (s, 1H), 10.45 (s, 1H), 8.88 (s, 1H), 8.40 (s, 1H), 7.93 (s, 1H), 7.82 (d, 1H), 7.77 (d, 1H), 7.60-7.45 (m, 2H), 7.41-7.30 (m, 4H), 6.24 (s, 1H), 4.26 (t, 1H), 4.22-4.17 (m, 1H), 3.99 (t, 1H), 3.95-3.89 (m, 1H), 3.76 (s, 6H), 3.59-3.45 (m, 1H), 2.05 (dd, 2H), 0.95 (t, 3H); MS (EI) m/z $C_{29}H_{30}N_6O_6S$: 591 (MH$^+$).

Example 413

1-acetyl-N-(3-{[(3-{[3,5-bis(methoxy)-phenyl]amino}quinoxalin-2-yl)amino]sulfonyl}phenyl)azetidine-3-carboxamide MS (EI) m/z $C_{28}H_{28}N_6O_6S$: 577 (MH$^+$).

Example 414

1-(cyclopropanecarbonyl)-N-(3-(N-(3-(3,5-dimethoxy-phenylamino)quinoxalin-2-yl)sulfamoyl)phenyl)azetidine-3-carboxamide MS (EI) m/z $C_{30}H_{30}N_6O_6S$: 603 (MH+).

General Reductive Amination Procedure 1

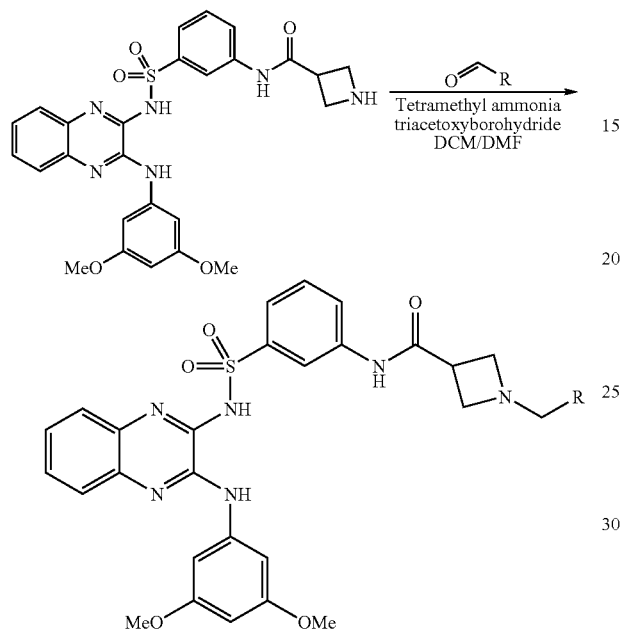

To a solution of N-(3-(N-(3-(3,5-dimethoxy-phenylamino)quinoxalin-2-yl)sulfamoyl)phenyl)azetidine-3-carboxamide (110 mg, 0.19 mmol), prepared using procedures similar to those described in Example 372, in 3 mL of DCE and 200 µL of DMF, aldehyde (0.77 mmol, 4.0 eq.) was added slowly followed by tetramethylammonium triacetoxyborohydride (1.16 mmol, 6.0 eq). The reaction was stirred at room temperature overnight. LC/MS indicated the reaction was completed. The solvent was subsequently removed under reduced pressure on a rotary evaporator. The crude material was then redissolved in methanol. Purification of the final product was accomplished by preparatory reverse-phase HPLC with the eluents 25 mM aqueous NH4OAc/CAN. A Waters Fractionlynx preparative reverse-phase HPLC; equipped with a Waters SunFire Prep C18, OCD 5 µM, 30×70 mm column and running a 5-100% gradient with a binary solvent system of 25 mM ammonium acetate in water/acetonitrile; was used to carry out the purification.

The following title compounds were prepared according to General Reductive Amination Procedure 1.

Example 415

N-(3-(N-(3-(3,5-dimethoxy-phenylamino)quinoxalin-2-yl)sulfamoyl)phenyl)-1-ethylazetidine-3-carboxamide $^1$H-NMR (400 MHz, d$_6$-DMSO): 10.29 (s, 1H), 8.82 (s, 1H), 8.25 (t, 1H), 7.75-7.68 (m, 2H), 7.43-7.38 (m, 1H), 7.375-7.340 (m, 1H), 7.338-7.310 (d, 2H), 7.305-7.262 (m, 1H), 7.15-7.08 (m, 2H), 6.56 (s, 1H), 6.15 (t, 1H), 4.15-4.08 (m, 2H), 4.06-3.95 (m, 2H), 3.78 (s, 6H), 3.65-3.56 (m, 1H), 3.12-3.04 (m, 2H), 1.03 (t, 3H); MS (EI) m/z $C_{28}H_{30}N_6O_5S$: 563 (MH+).

Example 416

1-(cyclopropylmethyl)-N-(3-(N-(3-(3,5-dimethoxy-phenylamino)quinoxalin-2-yl)sulfamoyl)phenyl)azetidine-3-carboxamide MS (EI) m/z $C_{30}H_{32}N_6O_5S$: 589 (MH+).

Example 417

1-benzyl-N-(3-(N-(3-(3,5-dimethoxy-phenylamino)quinoxalin-2-yl)sulfamoyl)phenyl)azetidine-3-carboxamide MS (EI) m/z $C_{33}H_{32}N_6O_5S$: 625 (MH+).

Example 418

N-(3-(N-(3-(3,5-dimethoxy-phenylamino)quinoxalin-2-yl)sulfamoyl)phenyl)-1-(furan-2-ylmethyl)azetidine-3-carboxamide MS (EI) m/z $C_{31}H_{30}N_6O_6S$: 615 (MH+).

Example 419

1-((1H-imidazol-5-yl)methyl)-N-(3-(N-(3-(3,5-dimethoxy-phenylamino)quinoxalin-2-yl)sulfamoyl)phenyl)azetidine-3-carboxamide MS (EI) m/z $C_{30}H_{30}N_5O_5S$: 615 (MH+).

General Amide Formation Procedure 1a

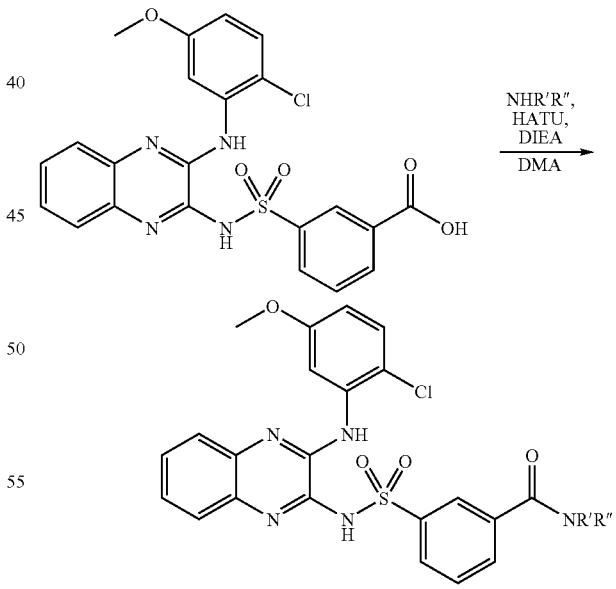

Into a small 1 dram vial was added 3-(N-(3-(2-chloro-5-methoxy-phenylamino)-quinoxalin-2-yl)sulfamoyl)benzoic acid (61 mg, 0.13 mmol, 1.1 equiv), prepared using procedures described for Example 100. The acid was dissolved in DMA (1 mL) and DIEA (42 µL, 0.24 mmol, 2 equiv) was added then added to the solution. The amine reagent (1 mL of 0.12 M solution in DMA) was added to solution with stirring followed by HATU (64 mg, 0.17 mMol, 1.4 equiv). The reaction was stirred overnight at room temperature. Upon completion as indicated by LCMS analysis, 2 mL of methanol was added to the solution. Preparative reverse-phase HPLC was used to isolate the desired product. A Waters Fractionlynx preparative reverse-phase HPLC—equipped with a Waters SunFire Prep C18, OCD 5 μM, 30×70 mm column and running a 5-100% gradient with a binary solvent system of 25 mM ammonium acetate in water/acetonitrile—was used to carry out the purification.

The following compounds were prepared according to General Amide Formation Procedure 1.

Example 420

3-(N-(3-(2-chloro-5-methoxy-phenylamino)quinoxalin-2-yl)sulfamoyl)-N-(3-(dimethylamino)propyl)benzamide. 3-(N-(3-(2-chloro-5-methoxyphenylamino)quinoxalin-2-yl)sulfamoyl)-N-(3-(dimethylamino)propyl)benzamide: $^1$H NMR (400 MHz, $d_6$-DMSO): 9.44 (s, 1H), 8.94 (s, 1H), 8.79 (t, 1H), 8.54 (s, 1H), 8.24 (d, 1H), 7.87 (d, 1H), 7.48 (m, 3H), 7.33 (d, 1H), 7.18 (m, 2H), 6.60 (dd, 1H), 3.82 (1H), 3.04 (m, 3H), 2.51 (m, 5H), 1.91 (s, 1H), 1.86 (m, 3H); MS (EI) m/z for $C_{27}H_{29}ClN_6O_4S$: 569 (MH$^+$).

Example 421

3-(N-(3-(2-chloro-5-methoxy-phenylamino)quinoxalin-2-yl)sulfamoyl)-N-(1-methylazetidin-3-yl)benzamide. 3-(N-(3-(2-chloro-5-methoxyphenylamino)quinoxalin-2-yl)sulfamoyl)-N-(1-methylazetidin-3-yl)benzamide: $^1$H NMR (400 MHz, $d_6$-DMSO): 9.43 (s, 1H), 9.23 (d, 1H), 8.94 (d, 1H), 8.58 (s, 1H), 8.29 (d, 1H), 7.89 (d, 1H), 7.56 (t, 1H), 7.47 (d, 1H), 7.44 (d, 1H), 7.33 (d, 1H), 7.18 (m, 2H), 6.60 (dd, 1H), 4.81 (m, 1H), 4.33 (m, 2H), 4.19 (m, 2H), 3.82 (s, 1H), 2.51 (s, 3H); MS (EI) m/z for $C_{26}H_{25}ClN_6O_4S$: 553 (MH$^+$).

Example 422

3-(N-(3-(2-chloro-5-methoxy-phenylamino)quinoxalin-2-yl)sulfamoyl)-N-(pyridin-4-ylmethyl)benzamide
MS (EI) m/z $C_{28}H_{23}ClN_6O_4S$: 575 (MH$^+$).

Example 423

3-(N-(3-(2-chloro-5-methoxy-phenylamino)quinoxalin-2-yl)sulfamoyl) N-(3-(dimethylamino)propyl)benzamide
MS (EI) m/z $C_{28}H_{26}ClN_7O_4S$: 592 (MH$^+$).

Example 424

N-(3-(2-chloro-5-methoxy-phenylamino)quinoxalin-2-yl)-3-(2,2-dimethylhydrazinecarbonyl)benzenesulfonamide
MS (EI) m/z $C_{24}H_{23}ClN_6O_4S$: 527 (MH$^+$).

Example 425

3-(N-(3-(2-chloro-5-methoxy-phenylamino)quinoxalin-2-yl)sulfamoyl) N-(2-methoxyethyl)benzamide
MS (EI) m/z $C_{25}H_{24}ClN_5O_5S$: 542 (MH$^+$).

Example 426

N-(3-(2-chloro-5-methoxy-phenylamino)quinoxalin-2-yl)-3-(4-methylpiperazine-1-carbonyl)benzenesulfonamide
MS (EI) m/z $C_{27}H_{27}ClN_6O_4S$: 567 (MH$^+$).

Example 427

3-(N-(3-(2-chloro-5-methoxy-phenylamino)quinoxalin-2-yl)sulfamoyl)-N-(2-(pyrrolidin-1-yl)ethyl)benzamide
MS (EI) m/z $C_{28}H_{29}ClN_6O_4S$: 581 (MH$^+$).

Example 428

3-(N-(3-(2-chloro-5-methoxy-phenylamino)quinoxalin-2-yl)sulfamoyl)-N-(2-(pyridin-4-yl)ethyl)benzamide
MS (EI) m/z $C_{29}H_{25}ClN_6O_4S$: 589 (MH$^+$).

Example 429

N-(2-(1H-imidazol-1-yl)ethyl)-3-(N-(3-(2-chloro-5-methoxyphenylamino)quinoxalin-2-yl)sulfamoyl)benzamide
MS (EI) m/z $C_{27}H_{24}ClN_7O_4S$: 578 (MH$^+$).

Example 430

3-(N-(3-(2-chloro-5-methoxy-phenylamino)quinoxalin-2-yl)sulfamoyl)-N-(piperidin-1-yl)benzamide
MS (EI) m/z $C_{27}H_{27}ClN_6O_4S$: 567 (MH$^+$).

Example 431

3-(N-(3-(2-chloro-5-methoxy-phenylamino)quinoxalin-2-yl)sulfamoyl)-N-(2-hydroxyethyl)benzamide
MS (EI) m/z $C_{24}H_{22}ClN_5O_5S$: 528 (MH$^+$).

Example 432

3-(N-(3-(2-chloro-5-methoxy-phenylamino)quinoxalin-2-yl)sulfamoyl)-N-(3-ethoxypropyl)benzamide MS (EI) m/z $C_{27}H_{28}ClN_5O_5S$: 570 (MH$^+$).

Example 433

3-(N-(3-(2-chloro-5-methoxy-phenylamino)quinoxalin-2-yl)sulfamoyl)-N-(3-(pyrrolidin-1-yl)propyl)benzamide
MS (EI) m/z $C_{29}H_{31}ClN_6O_4S$: 595 (MH$^+$).

Example 434

3-(N-(3-(2-chloro-5-methoxy-phenylamino)quinoxalin-2-yl)sulfamoyl)-N-(3-(diethylamino)propyl)benzamide
MS (EI) m/z $C_{29}H_{33}ClN_6O_4S$: 597 (MH$^+$).

Example 435

3-(N-(3-(2-chloro-5-methoxy-phenylamino)quinoxalin-2-yl)sulfamoyl)-N-(3-(2-oxopyrrolidin-1-yl)propyl)benzamide
MS (EI) m/z $C_{29}H_{29}ClN_6O_5S$: 609 (MH$^+$).

Example 436

3-(N-(3-(2-chloro-5-methoxy-phenylamino)quinoxalin-2-yl)sulfamoyl)-N-(pyridin-2-ylmethyl)benzamide
MS (EI) m/z $C_{28}H_{23}ClN_6O_4S$: 575 (MH$^+$).

Example 437

3-(N-(3-(2-chloro-5-methoxy-phenylamino)quinoxalin-2-yl)sulfamoyl)-N-(2-cyanoethyl)-N-methylbenzamide
MS (EI) m/z $C_{26}H_{23}ClN_6O_4S$: 551 (MH$^+$).

Example 438

3-(N-(3-(2-chloro-5-methoxyphenylamino)quinoxalin-2-yl)sulfamoyl)-N-(2-cyanoethyl)-N-ethylbenzamide
MS (EI) m/z $C_{27}H_{25}ClN_6O_4S$: 565 (MH$^+$).

Example 439

3-(N-(3-(2-chloro-5-methoxy-phenylamino)quinoxalin-2-yl)sulfamoyl)-N-(2-(ethylthio)ethyl)benzamide MS (EI) m/z $C_{26}H_{26}ClN_5O_4S_2$: 572 (MH$^+$).

Example 440

3-(N-(3-(2-chloro-5-methoxy-phenylamino)quinoxalin-2-yl)sulfamoyl)-N-(3-propoxypropyl)benzamide
MS (EI) m/z $C_{28}H_{30}ClN_5O_5S$: 584 (MH$^+$).

Example 441

3-(N-(3-(2-chloro-5-methoxy-phenylamino)quinoxalin-2-yl)sulfamoyl)-N-(5-(diethylamino)pentan-2-yl)benzamide MS (EI) m/z $C_{31}H_{37}ClN_6O_4S$: 625 (MH$^+$).

Example 442

3-(N-(3-(2-chloro-5-methoxy-phenylamino)quinoxalin-2-yl)sulfamoyl)-N-(3-methoxypropyl)benzamide MS (EI) m/z $C_{26}H_{26}ClN_5O_5S$: 556 (MH$^+$).

Example 443

3-(N-(3-(2-chloro-5-methoxy-phenylamino)quinoxalin-2-yl)sulfamoyl)-N-(3-morpholinopropyl)benzamide MS (EI) m/z $C_{29}H_{31}ClN_6O_5S$: 611 (MH$^+$).

Example 444

3-(N-(3-(2-chloro-5-methoxy-phenylamino)quinoxalin-2-yl)sulfamoyl)-N-(pyridin-3-ylmethyl)benzamide MS (EI) m/z $C_{28}H_{23}ClN_6O_4S$: 575 (MH$^+$).

Example 445

3-(N-(3-(2-chloro-5-methoxyphenylamino)quinoxalin-2-yl)sulfamoyl)-N-(2-cyanoethyl)benzamide MS (EI) m/z $C_{25}H_{21}ClN_6O_4S$: 537 (MH$^+$).

Example 446

3-(N-(3-(2-chloro-5-methoxy-phenylamino)quinoxalin-2-yl)sulfamoyl)-N-(1-methoxypropan-2-yl)benzamide MS (EI) m/z $C_{26}H_{26}ClN_5O_5S$: 556 (MH$^+$).

Example 447

3-(N-(3-(2-chloro-5-methoxy-phenylamino)quinoxalin-2-yl)sulfamoyl)-N-(2-(methylthio)ethyl)benzamide MS (EI) m/z $C_{25}H_{24}ClN_5O_4S_2$: 558 (MH$^+$).

Example 448

3-(N-(3-(2-chloro-5-methoxy-phenylamino)quinoxalin-2-yl)sulfamoyl)-N-(3-(dimethylamino)propyl)-N-methylbenzamide MS (EI) m/z $C_{28}H_{31}ClN_6O_4S$: 583 (MH$^+$).

Example 449

3-(N-(3-(2-chloro-5-methoxy-phenylamino)quinoxalin-2-yl)sulfamoyl)-N-(3-isopropoxypropyl)benzamide MS (EI) m/z $C_{28}H_{30}ClN_5O_5S$: 584 (MH$^+$).

Example 450

3-(N-(3-(2-chloro-5-methoxy-phenylamino)quinoxalin-2-yl)sulfamoyl)-N-(2-(dimethylamino)ethyl)-N-ethylbenzamide MS (EI) m/z $C_{28}H_{31}ClN_6O_4S$: 583 (MH$^+$).

Example 451

N-(3-butoxypropyl)-3-(N-(3-(2-chloro-5-methoxy-phenylamino)quinoxalin-2-yl)sulfamoyl)benzamide MS (EI) m/z $C_{29}H_{32}ClN_5O_5S$: 598 (MH$^+$).

Example 452

3-(N-(3-(2-chloro-5-methoxy-phenylamino)quinoxalin-2-yl)sulfamoyl)-N-(2-(diethylamino)ethyl)benzamide MS (EI) m/z $C_{28}H_{31}ClN_6O_4S$: 583 (MH$^+$).

Example 453 methyl 3-(3-(N-(3-(2-chloro-5-methoxy-phenylamino)quinoxalin-2-yl)sulfamoyl)benzamido)propanoate. MS (EI) m/z $C_{26}H_{24}ClN_5O_6S$: 570 (MH$^+$).

Example 454

3-(N-(3-(2-chloro-5-methoxy-phenylamino)quinoxalin-2-yl)sulfamoyl)-N-methyl-N-propylbenzamide. MS (EI) m/z $C_{26}H_{26}ClN_5O_4S$: 540 (MH$^+$).

Example 455 ethyl 3-(3-(N-(3-(2-chloro-5-methoxy-phenylamino)quinoxalin-2-yl)sulfamoyl)benzamido)propanoate. MS (EI) m/z $C_{27}H_{26}ClN_5O_6S$: 584 (MH$^+$).

Example 456

3-(N-(3-(2-chloro-5-methoxy-phenylamino)quinoxalin-2-yl)sulfamoyl)-N-(2-(piperidin-1-yl)ethyl)benzamide MS (EI) m/z $C_{29}H_{31}ClN_6O_4S$: 595 (MH$^+$).

Example 457

3-(N-(3-(2-chloro-5-methoxy-phenylamino)quinoxalin-2-yl)sulfamoyl)-N-((1-ethylpyrrolidin-2-yl)methyl)benzamide MS (EI) m/z $C_{29}H_{31}ClN_6O_4S$: 595 (MH$^+$).

Example 458

N-(2-(bis(2-hydroxyethyl)amino)ethyl)-3-(N-(3-(2-chloro-5-methoxyphenylamino)quinoxalin-2-yl)sulfamoyl)benzamide MS (EI) m/z $C_{28}H_{31}ClN_6O_6S$: 615 (MH$^+$).

Example 459

N-(3-(2-chloro-5-methoxy-phenylamino)quinoxalin-2-yl)-3-(3-(diethylamino)pyrrolidine-1-carbonyl)benzenesulfonamide MS (EI) m/z $C_{30}H_{33}ClN_6O_4S$: 609 (MH$^+$).

Example 460

3-(N-(3-(2-chloro-5-methoxy-phenylamino)quinoxalin-2-yl)sulfamoyl)-N-methyl-N-(1-methylpyrrolidin-3-yl)benzamide MS (EI) m/z $C_{28}H_{29}ClN_6O_4S$: 581 (MH$^+$).

Example 461

N-(3-(2-chloro-5-methoxy-phenylamino)quinoxalin-2-yl)-3-(3-(dimethylamino)pyrrolidine-1-carbonyl)benzenesulfonamide MS (EI) m/z $C_{28}H_{29}ClN_6O_4S$: 581 (MH$^+$).

Example 462

3-(N-(3-(2-chloro-5-methoxy-phenylamino)quinoxalin-2-yl)sulfamoyl)-N-(2-methyl-1-morpholinopropan-2-yl)benzamide MS (EI) m/z $C_{30}H_{33}ClN_6O_5S$: 625 (MH$^+$).

Example 463

3-(N-(3-(2-chloro-5-methoxy-phenylamino)quinoxalin-2 yl)sulfamoyl)-N-(1H-pyrrol-1-yl)benzamide MS (EI) m/z $C_{26}H_{21}ClN_6O_4S$: 549 (MH$^+$).

Example 464

3-(N-(3-(2-chloro-5-methoxy-phenylamino)quinoxalin-2-yl)sulfamoyl)-N-(3-oxopyrazolidin-4-yl)benzamide MS (EI) m/z $C_{25}H_{22}ClN_7O_5S$: 568 (MH$^+$).

Example 465

N-(3-(2-chloro-5-methoxy-phenylamino)quinoxalin-2-yl)-3-(2-((dimethylamino)methyl)piperidine-1-carbonyl)benzenesulfonamide MS (EI) m/z $C_{30}H_{33}ClN_6O_4S$: 609 (MH$^+$).

Example 466

N-(3-(2-chloro-5-methoxy-phenylamino)quinoxalin-2-yl)-3-(2-(piperidin-1-ylmethyl)piperidine-1-carbonyl)benzenesulfonamide MS (EI) m/z $C_{33}H_{37}ClN_6O_4S$: 649 (MH$^+$).

Example 467

3-(N-(3-(2-chloro-5-methoxy-phenylamino)quinoxalin-2-yl)sulfamoyl)-N-(1-ethylpiperidin-3-yl)benzamide MS (EI) m/z $C_{29}H_{31}ClN_6O_4S$: 595 (MH$^+$).

General Amide Formation Procedure 1b

The procedure outlined in General Amide Formation Procedure 1a was used to incorporate a number of amines that contained a second amine group protected as the tert-butylcarbamate (i.e. where R', within NHR'R", contained a Boc-protected amine group). The deprotection was carried out after HPLC purification of the Boc-protected precursor.

Into a small 1 dram vial was added 3-(N-(3-(2-chloro-5-methoxy-phenylamino)quinoxalin-2-yl)sulfamoyl)benzoic acid (61 mg, 0.13 mmol, 1.1 equiv). The acid was dissolved in 1 mL of DMA and DIEA (42 µL, 0.24 mmol, 2 equiv) was added then added to the solution. The mono-Boc-protected diamine reagent (1 mL of 0.12 M solution in DMA, 1 equiv) was added to solution with stirring followed by HATU (64 mg, 0.17 mmol, 1.4 equiv). The reaction was stirred overnight at room temperature. Upon completion as indicated by LCMS analysis, 2 mL of methanol was added to the solution. Preparative reverse-phase HPLC was used to isolate the desired product directly from this crude reaction solution. A Waters Fractionlynx preparative reverse-phase HPLC; equipped with a Waters SunFire Prep C18, OCD 5 µM, 30×70 mm column and running a 5-100% gradient with a binary solvent system of 25 mM ammonium acetate in water/acetonitrile; was used to carry out the purification. The product fractions were combined and concentrated to dryness under reduced pressure by rotary evaporation. A solution of 4 N HCl in dioxane (2 mL) was added. The solution was then stirred at room temperature until no starting material was detected. The deprotected product precipitated out of solution as an HCL salt and was collected by filtration, washed with ether and dried under vacuum.

The following compounds were prepared according to the above General Amide Formation Procedure 1b.

Example 468

3-(N-(3-(2-chloro-5-methoxy-phenylamino)quinoxalin-2-yl)sulfamoyl)-N-(piperidin-3-yl)benzamide. 3-(N-(3-(2-chloro-5-methoxyphenylamino)quinoxalin-2-yl)sulfamoyl)-N-(piperidin-3-yl)benzamide: $^1$H NMR (400 MHz, $d_6$-DMSO): 12.82 (s, 1H), 9.12 (s, 1H), 9.04 (s, 1H), 8.85 (d, 1H), 8.65 (s, 1H), 8.55 (s, 1H), 8.18 (m, 1H), 7.98 (s, 1H), 7.69 (m, 2H), 7.43 (m, 2H), 6.69 (dd, 1H), 4.21 (s, 1H), 3.83 (s, 3H), 3.69 (m, 1H), 3.48 (m, 1H), 3.18 (s, 1H), 2.84 (q, 2H), 1.91 (s, 2H); MS (EI) m/z for $C_{27}H_{27}ClN_6O_4S$: 567 (MH$^+$).

Example 469

3-(N-(3-(2-chloro-5-methoxy-phenylamino)quinoxalin-2-yl)sulfamoyl)-N-(piperidin-2-ylmethyl)benzamide. 3-(N-(3-(2-chloro-5-methoxyphenylamino)quinoxalin-2-yl)sulfamoyl)-N-(piperidin-2-ylmethyl)benzamide: NMR (400 MHz, $d_6$-DMSO): 12.78 (s, 1H), 9.16 (s, 1H), 9.09 (s, 1H), 8.79 (s, 1H), 8.59 (d, 2H), 8.22 (t, 2H), 7.99 (s, 1H), 7.74 (t, 1H), 7.66 (s, 1H), 7.42 (m, 2H), 6.69 (dd, 1H), 3.82 (s, 3H), 3.69 (dd, 1H), 3.57 (m, 1H), 3.50 (m, 3H), 3.22 (s, 2H), 2.82 (d, 1H), 1.68 (m, 5H); MS (EI) m/z for $C_{28}H_{29}ClN_6O_4S$: 581 (MH$^+$).

Example 470

3-(3-aminopyrrolidine-1-carbonyl)-N-(3-(2-chloro-5-methoxy-phenylamino)quinoxalin-2-yl)benzenesulfonamide MS (EI) m/z $C_{26}H_{25}ClN_6O_4S$: 553 (MH$^+$).

Example 471

3-(3-aminoazetidine-1-carbonyl)-N-(3-(2-chloro-5-methoxy-phenylamino)quinoxalin-2-yl)benzenesulfonamide MS (EI) m/z $C_{25}H_{23}CN_6O_4S$: 539 (MH$^+$).

Example 472

3-(3-aminopiperidine-1-carbonyl)-N-(3-(2-chloro-5-methoxy-phenylamino)quinoxalin-2-yl)benzenesulfonamide MS (EI) m/z $C_{27}H_{27}ClN_6O_4S$: 567 (MH$^+$).

Example 473

3-(N-(3-(2-chloro-5-methoxy-phenylamino)quinoxalin-2-yl)sulfamoyl)-N-(pyrrolidin-3-yl)benzamide MS (EI) m/z $C_{26}H_{25}ClN_6O_4S$: 553 (MH$^+$).

Example 474

N-(3-(2-chloro-5-methoxy-phenylamino)quinoxalin-2-yl)-3-(3-(methylamino)pyrrolidine-1-carbonyl)benzenesulfonamide MS (EI) m/z $C_{27}H_{27}ClN_6O_4S$: 567 (MH$^+$).

Example 475

N-(2-aminoethyl)-3-(N-(3-(2-chloro-5-methoxy-phenylamino)quinoxalin-2-yl)sulfamoyl)benzamide MS (EI) m/z $C_{24}H_{23}ClN_6O_4S$: 527 (MH$^+$).

Example 476

3-(4-amino-3-oxopyrazolidine-1-carbonyl)-N-(3-(2-chloro-5-methoxyphenylamino)quinoxalin-2-yl)benzenesulfonamide MS (EI) m/z $C_{25}H_{22}ClN_7O_5S$: 568 (MH$^+$).

Example 477

3-(N-(3-(2-chloro-5-methoxyphenylamino)quinoxalin-2-yl)sulfamoyl)-N-((1-methylpiperidin-2-yl)methyl)benzamide 3-(N-(3-(2-chloro-5-methoxyphenylamino)quinoxalin-2-yl)sulfamoyl)-N-(piperidin-2-ylmethyl)benzamide (299 mg, 0.51 mmol, 1 equiv), prepared using procedures similar to those described for Example 514, was dissolved in 2.3 mL of DMA. Formic acid (388 µL, 10.28 mmol, 20 equiv) was added to solution with stirring followed by the addition of formaldehyde (508 µL of 37% aq. solution). The reaction was then stirred at room temperature overnight. Analysis of an aliquot of the reaction mixture by LCMS indicated the complete consumption of starting material. The reaction was diluted with methanol (2 mL). Preparative reverse-phase HPLC was used to isolate the desired product directly from the crude reaction mixture. A Waters Fractionlynx preparative reverse-phase HPLC; equipped with a Waters SunFire Prep C18, OCD 5 µM, 30×70 mm column and running a 5-100% gradient with a binary solvent system of 25 mM ammonium acetate in water/acetonitrile; was used to carry out the purification. $^1$H NMR (400 MHz, $d_6$-DMSO): 9.44 (s, 1H), 8.94 (s, 1H), 8.79 (t, 1H), 8.57 (s, 1H), 8.27 (d, 1H), 7.90 (d, 1H) 7.54 (t, 1H), 7.46 (d, 1H), 7.39 (d, 1H), 7.33 (d, 1H), 7.18 (m, 2H), 6.60 (dd, 1H), 3.82 (s, 3H), 3.59 (m, 2H), 3.00 (s, 1H), 2.90 (s, 3H), 1.62 (m, 7H); MS (EI) m/z for $C_{29}H_{31}ClN_6O_4S$: 595 (MH$^+$).

Example 478

3-(N-(3-(2-chloro-5-methoxyphenylamino)quinoxalin-2-yl)sulfamoyl)-N-(1-methylpiperidin-3-yl)benzamide The title compound was prepared using similar procedures to those used in Example 522

$^1$H NMR (400 MHz, $d_6$-DMSO): 9.43 (s, 1H), 8.93 (s, 1H), 8.59 (s, 1H), 8.24 (d, 1H), 7.87 (d, 1H), 7.47 (m, 2H), 7.40 (d, 1H), 7.33 (d, 1H), 7.19 (m, 2H), 6.60 (dd, 1H), 4.21 (s, 1H), 3.82 (s, 1H), 2.76 (s, 1H), 2.50 (m, 7H), 1.91 (m, 2H), 1.63 (m, 2H); MS (EI) m/z for $C_{28}H_{29}ClN_6O_4S$: 581 (MH$^+$).

BIOLOGICAL EXAMPLES

Biological Example 1

PI3Kalpha Luciferase-Coupled Chemiluminescence Assay Protocol

PI3K activity is measured as the percent of ATP consumed following the kinase reaction using luciferase-luciferin-coupled chemiluminescence. Reactions were conducted in 384-well white, medium binding microtiter plates (Greiner). Kinase reactions were initiated by combining test compounds, ATP, substrate (PIP2), and kinase in a 20 μL volume in a buffer solution. The standard PI3Kalpha assay buffer is composed 50 mM Tris, pH 7.5, 1 mM EGTA, 10 mM $MgCl_2$, 1 mM DTT and 0.03% CHAPS. The standard assay concentrations for enzyme, ATP, and substrate are 0.5-1.1 nM, 1 μM, and 7.5 μM, respectively. The reaction mixture was incubated at ambient temperature for approximately 2 h. Following the kinase reaction, a 10 μL aliquot of luciferase-luciferin mix (Promega Kinase-Glo) was added and the chemiluminescence signal measured using a Victor2 plate reader (Perkin Elmer). Total ATP consumption was limited to 40-60% and IC50 values of control compounds correlate well with literature references.

Certain compounds of the invention demonstrated the ability to bind to PI3K when tested in this assay. The following embodiments are directed to the compounds themselves as well as their use in a method of treating. For example, in one embodiment of the invention, the PI3K inhibitor is selected from the compounds in Table 1 having a PI3K-binding affinity of about 8 μM or less. In another embodiment, the PI3K inhibitor is selected from the compounds in Table 1 having a PI3K-binding affinity of about 4 μM or less. In another embodiment, the PI3K inhibitor is selected from the compounds in Table 1 having a PI3K-binding affinity of about 3 M or less. In another embodiment, the PI3K inhibitor is selected from the compounds in Table 1 having a PI3K-binding affinity of about 2 μM or less. In another embodiment, the PI3K inhibitor is selected from the compounds in Table 1 having a PI3K-binding affinity of about 1.5 μM or less. In another embodiment, the PI3K inhibitor is selected from the compounds in Table 1 having a PI3K-binding affinity of about 1 μM or less. In another embodiment, the PI3K inhibitor is selected from the compounds in Table 1 having a PI3K-binding affinity of about 0.750 μM or less. In another embodiment, the PI3K inhibitor is selected from the compounds in Table 1 having a PI3K-binding affinity of about 0.5 μM or less. In another embodiment, the PI3K inhibitor is selected from the compounds in Table 1 having a PI3K-binding affinity of about 0.3 μM or less. In another embodiment, the PI3K inhibitor is selected from the compounds in Table 1 having a PI3K-binding affinity of about 0.2 μM or less. In another embodiment, the PI3K inhibitor is selected from the compounds in Table 1 having a PI3K-binding affinity of about 0.1 μM or less. In another embodiment, the PI3K inhibitor is selected from the compounds in Table 1 having a PI3K-binding affinity of about 0.075 μM or less. In another embodiment, the PI3K inhibitor is selected from the compounds in Table 1 having a PI3K-binding affinity of about 0.050 μM or less.

Biological Example 2

Phospho AKT Assay

PC3 cells were seeded on 6-well plates at 150,000 cells/well. Cells were cultured for 3 days, then treated with compounds in serum-free medium for 3 hr. EGF (100 ng/ml) was added for the last 10 min. Cells were lysed in TENN buffer. Phospho T308 Akt and total Akt were quantified by ELISA performed according to the Biosource assay protocol. The readings of phospho Akt were normalized to total Akt readings.

Biological Example 3

Phospho S6 Assay

PC3 cells were seeded on 96-well plates at 8,000 cells/well. For each experiment, cells were seeded and treated in duplicated plates: one plate for phospho 86 CellELISA, and one plate for total S6 CellELISA. Cells were cultured on the plates for 3 days, then treated with compounds in serum-free medium for 3 hr in triplicate. Cells were fixed with 4% formaldehyde, quenched with 0.6% H2O2, blocked with 5% BSA, incubated with either phospho S6 antibody or total S6 antibody overnight, incubated with goat-anti-rabbit-IgG-HRP for 1 hr, and developed in chemiluminescent substrate.

Biological Example 4

$PIP_3$ Assay

MCF-7 cells grown in 10-cm dishes were starved for 3 hours in DMEM, and then treated with compounds for 20 minutes. In the last 2 minutes of the incubation with the compounds, EGF (100 ng/ml) was added to stimulate the production of PIP3. The medium was aspirated and the cells were scraped with 10% trichloroacetic acid. The lipids were extracted from the pellet after the cell lysates were centrifuged. PIP3 in the cellular lipid extraction was quantified with the AlphaScreen [Registered™ of PerkinElmer] assay in which Grp1-PH is used as the PIP3 specific probe. The amount of cellular PIP3 was calculated from the standard curve of $diC_8$ PI (3,4,5) P3.

Biological Example 5-10

In Vivo Models

Female and male athymic nude mice (NCr) 5-8 weeks of age and weighing approximately 20 g were used in the following model. Prior to initiation of a study, the animals were allowed to acclimate for a minimum of 48 h. During these studies, animals were provided food and water ad libitum and housed in a room conditioned at 70-75° F. and 60% relative humidity. A 12 h light and 12 h dark cycle was maintained with automatic timers. All animals were examined daily for compound-induced or tumor-related deaths.

PC-3 human prostate adenocarcinoma cells were cultured in vitro in DMEM (Mediatech) supplemented with 20% Fetal Bovine Serum (Hyclone), Penicillin-Streptomycin and non-essential amino acids at 37° C. in a humidified 5% $CO_2$ atmosphere. On day 0, cells were harvested by trypsinization and $3 \times 10^6$ cells (passage 13, 99% viability) in 0.1 mL of ice-cold Hank's balanced salt solution were implanted subcutaneously into the hindflank of 5-8 week old male nude mice. A transponder was implanted in each mouse for identification, and animals were monitored daily for clinical symptoms and survival. Body weights were recorded daily.

U-87 MG human glioblastoma cells were cultured in vitro in DMEM (Mediatech) supplemented with 10% Fetal Bovine Serum (Hyclone), Penicillin-Streptomycin and non-essential amino acids at 37° C. in a humidified 5% $CO_2$ atmosphere. On day 0, cells were harvested by trypsinization and $2\times10^6$ cells (passage 5, 96% viability) in 0.1 mL of ice-cold Hank's balanced salt solution were implanted intradermally into the hindflank of 5-8 week old female nude mice. A transponder was implanted in each mouse for identification, and animals were monitored daily for clinical symptoms and survival. Body weights were recorded daily.

A549 human lung carcinoma cells were cultured in vitro in DMEM (Mediatech) supplemented with 10% Fetal Bovine Serum (Hyclone), Penicillin-Streptomycin and non-essential amino acids at 37° C. in a humidified 5% $CO_2$ atmosphere. On day 0, cells were harvested by trypsinization and $10\times10^6$ cells (passage 12, 99% viability) in 0.1 mL of ice-cold Hank's balanced salt solution were implanted intradermally into the hindflank of 5-8 week old female nude mice. A transponder was implanted in each mouse for identification, and animals were monitored daily for clinical symptoms and survival. Body weights were recorded daily.

A2058 human melanoma cells were cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization and $3\times10^6$ cells (passage 3, 95% viability) in 0.1 ml ice-cold Hank's balanced salt solution were implanted intradermally in the hind-flank of 5-8 week old female athymic nude mice. A transponder was implanted in each mouse for identification, and animals were monitored daily for clinical symptoms and survival. Body weights were recorded daily.

WM-266-4 human melanoma cells were cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization and $3\times10^6$ cells (passage 5, 99% viability) in 0.1 ml ice-cold Hank's balanced salt solution were implanted intradermally in the hind-flank of 5-8 week old female athymic nude mice. A transponder was implanted in each mouse for identification, and animals were monitored daily for clinical symptoms and survival. Body weights were recorded daily.

For subcutaneous or intradermal tumors, the mean tumor weight of each animal in the respective control and treatment groups was determined twice weekly during the study. Tumor weight (TW) was determined by measuring perpendicular diameters with a caliper, using the following formula:

$$\text{tumor weight (mg)} = [\text{tumor volume} = \text{length (mm)} \times \text{width}^2(\text{mm}^2)]/2$$

These data were recorded and plotted on a tumor weight vs. days post-implantation line graph and presented graphically as an indication of tumor growth rates. Percent inhibition of tumor growth (TGI) is determined with the following formula:

$$\left(1 - \left(\frac{(X_f - X_0)}{(Y_f - X_0)}\right)\right) * 100$$

where $X_0$=average TW of all tumors on group day
$X_f$=TW of treated group on Day f
$Y_f$=TW of vehicle control group on Day f If tumors regress below their starting sizes, then the percent tumor regression is determined with the following formula:

$$\left(\frac{(X_0 - X_f)}{X_0}\right) * 100$$

Tumor size is calculated individually for each tumor to obtain a mean±SEM value for each experimental group. Statistical significance is determined using the 2-tailed Student's t-test (significance defined as P<0.05).

Pharmaceutical Composition Examples

The following are representative pharmaceutical formulations containing a compound of Formula I.

Tablet Formulation

The following ingredients are mixed intimately and pressed into single scored tablets.

| Ingredient | Quantity per tablet, mg |
|---|---|
| compound of this invention | 400 |
| Cornstarch | 50 |
| croscarmellose sodium | 25 |
| Lactose | 120 |
| magnesium stearate | 5 |

Capsule Formulation

The following ingredients are mixed intimately and loaded into a hard-shell gelatin capsule.

| Ingredient | Quantity per tablet, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |

-continued

| Ingredient | Amount |
| --- | --- |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| distilled water | q.s. to 100 mL |

Injectable Formulation

The following ingredients are mixed to form an injectable formulation.

| Ingredient | Amount |
| --- | --- |
| compound of this invention | 1.2 g |
| sodium acetate buffer solution | 0.4 M 2.0 mL |
| HCl (1 N) or NaOH (1 M) | q.s. to suitable pH |
| water (distilled, sterile) | q.s. to 20 mL |

All of the above ingredients, except water, are combined and heated to 60-70.degree. C. with stirring. A sufficient quantity of water at 60.degree. C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
| --- | --- |
| compound of this invention | 500 |
| Witepsol ® H-15 | balance |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:

1. A Compound according to Formula I(a):

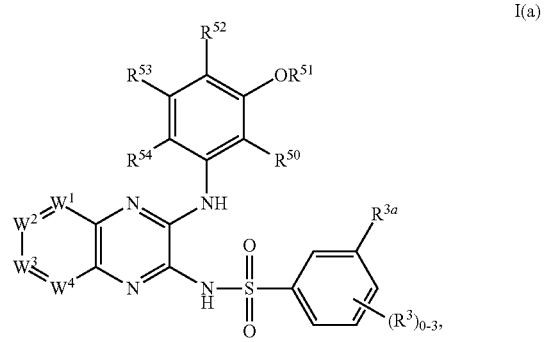

I(a)

or a single stereoisomer or mixture of stereoisomers thereof and optionally as a pharmaceutically acceptable salt thereof, wherein:

$W^1$, $W^2$, $W^3$, and $W^4$ are —C(H)—;

$R^{50}$ is hydrogen;

$R^{51}$ is methyl;

$R^{52}$ is hydrogen;

$R^{53}$ is hydrogen or alkoxy; and $R^{54}$ is hydrogen, alkyl, alkoxy, or halo; or $R^{53}$ and $R^{54}$ together with the carbons to which they are attached form a 6-membered heteroaryl; and $R^3$ is halo or methyl; and $R^{3a}$ is —N($R^7$)C(O)—$C_1$-$C_6$-alkylene-N($R^{7a}$)($R^{7b}$) where $R^7$ is hydrogen and $R^{7a}$ and $R^{7b}$ are independently hydrogen, alkyl, aminoalkyl, alkylaminoalkyl, or dialkylaminoalkyl.

2. The Compound of claim 1 where $R^{51}$ is methyl; and $R^{50}$, $R^{52}$, and $R^{53}$ are hydrogen and $R^{54}$ is halo or alkoxy or $R^{50}$, $R^{52}$, and $R^{54}$ are hydrogen and $R^{53}$ is alkoxy; or a single stereoisomer or mixture of stereoisomers thereof and optionally as a pharmaceutically acceptable salt thereof.

3. The Compound of claim 1, wherein $R^{3a}$ is —NHC(O)CH$_2$NH(CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, or —NHC(O)CH(CH$_3$)NH(CH$_3$), or a single stereoisomer or mixture of stereoisomers thereof and optionally as a pharmaceutically acceptable salt thereof.

4. A Compound of claim 1 which is:

| Structure | Name |
|---|---|
| 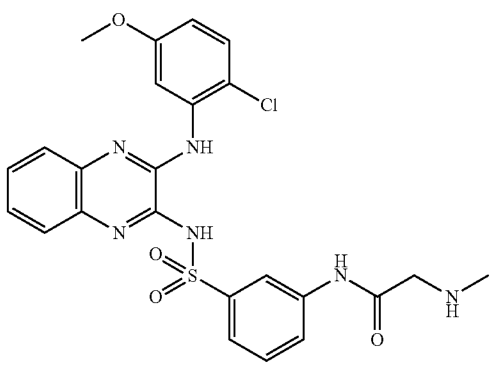 | N-(3-{[(3-{[2-chloro-5-(methoxy)phenyl]amino}quinoxalin-2-yl)amino]sulfonyl}-phenyl)-N-2-methylglycinamide |
| 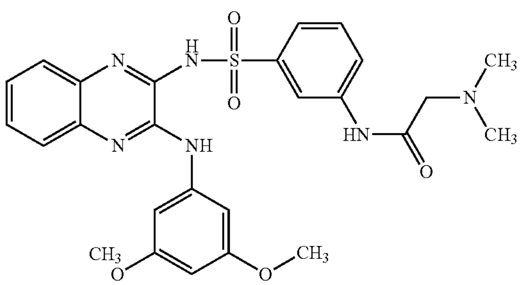 | N-(3-{[(3-{[3,5-bis(methoxy)phenyl]amino}quinoxalin-2-yl)amino]sulfonyl}phenyl)-N-2-,N-2-dimethylglycinamide |
| 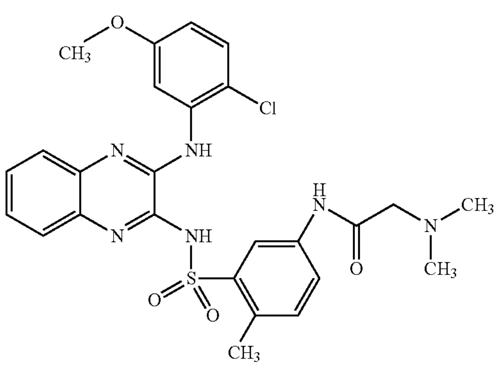 | N-(3-{[(3-{[2-chloro-5-(methoxy)phenyl]amino}quinoxalin-2-yl)amino]sulfonyl}-4-methylphenyl)-N-2-,N-2-dimethylglycinamide |
| 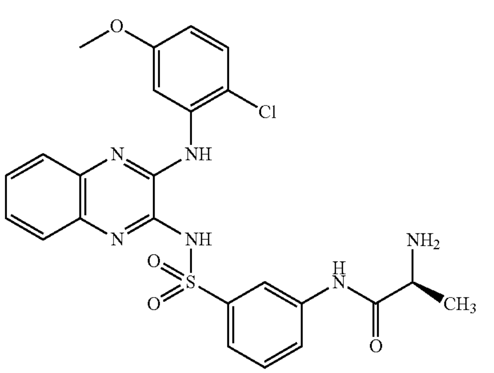 | N-(3-{[(3-{[2-chloro-5-(methoxy)phenyl]amino}quinoxalin-2-yl)amino]sulfonyl}phenyl)-L-alaninamide |

| Structure | Name |
|---|---|
| 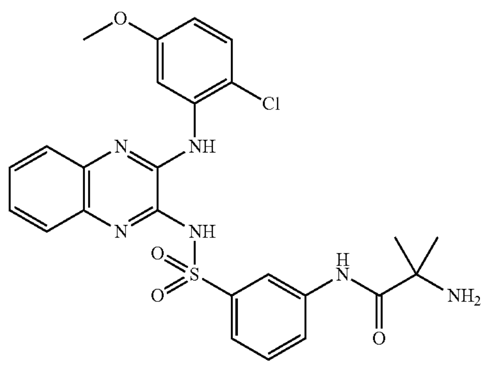 | N-(3-{[(3-{[2-chloro-5-(methoxy)phenyl]amino}quinoxalin-2-yl)amino]sulfonyl}phenyl)-2-methylalaninamide |
| 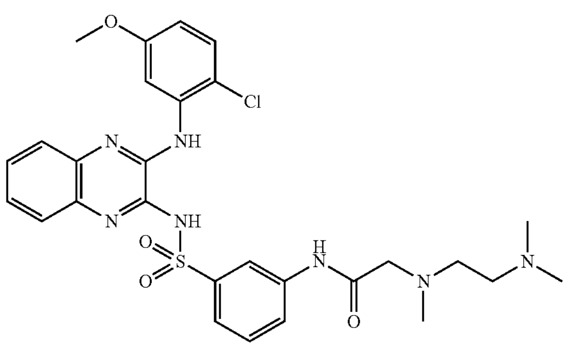 | N-(3-{[(3-{[2-chloro-5-(methoxy)phenyl]amino}quinoxalin-2-yl)amino]sulfonyl}phenyl)-N-2-[2-dimethylamino)ethyl]-N-2-methylglycinamide |
| 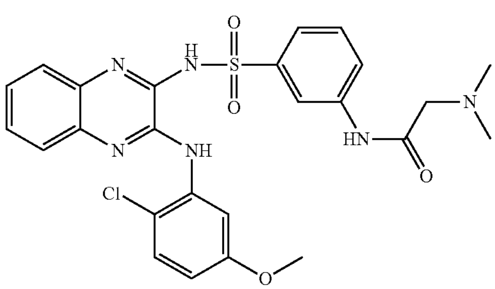 | N-(3-{[(3-{[2-chloro-5-(methoxy)phenyl]amino}quinoxalin-2-yl)amino]sulfonyl}phenyl)-N-2-,N-2-dimethylglycinamide |
| 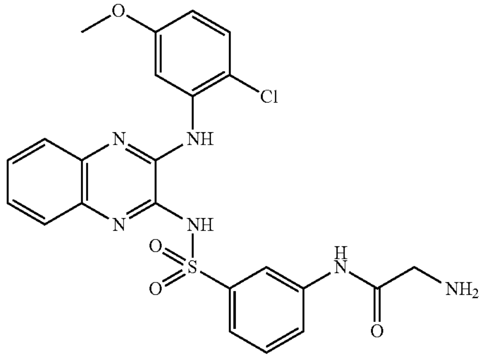 | N-(3-{[(3-{[2-chloro-5-(methoxy)phenyl]amino}quinoxalin-2-yl)amino]sulfonyl}phenyl)glycinamide |

-continued

| Structure | Name |
|---|---|
| 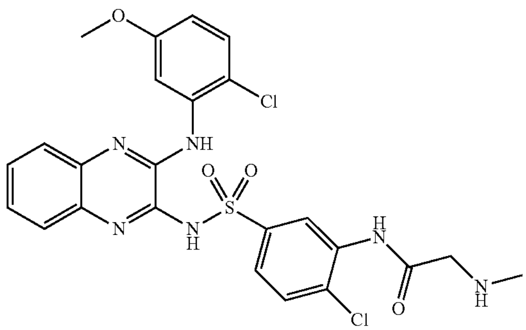 | N-(2-chloro-5-{[(3-{[2-chloro-5-(methoxy)phenyl]amino}quinoxalin-2-yl)amino]sulfonyl}phenyl)-N-2-methylglycinamide |
| 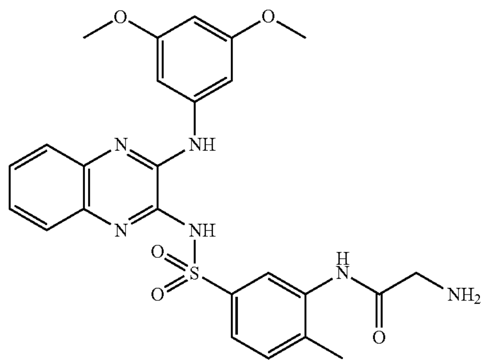 | N-(5-{[3-{[3,5-bus(methoxy)phenyl]amino}quinoxalin-2-yl)amino]sulfonyl}-2-mehtylphenyl)glycinamide |
| 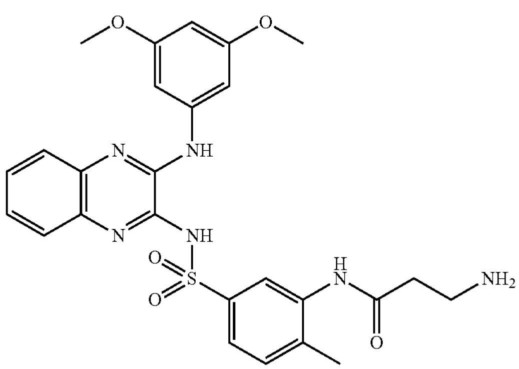 | N-(5-{[(3-{[3,5-bis(methoxy)phenyl]amino}quinoxalin-2-yl)amino]sulfonyl}-2-methylphenyl)-beta-alaninamide |
| | N-(5-{[(3-{[2-chloro-5-(methoxy)phenyl]amino}quinoxalin-2-yl)amino]sulfonyl}-2-methylphenyl)-N-2-,N-2-dimethylglycinamide | or a pharmaceutically acceptable salt thereof.

5. A compound of claim 3 which is

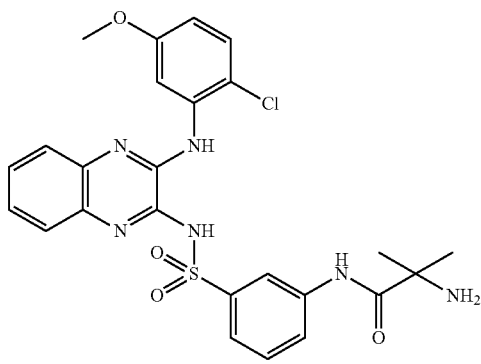

or a pharmaceutically acceptable salt thereof.

6. A pharmaceutical composition comprising a compound of claim 1 or a pharmaceutically acceptable salt thereof, and a pharmaceutically acceptable carrier, excipient, or diluent.

7. A pharmaceutical composition comprising a compound of claim 5 or a pharmaceutically acceptable salt thereof, and a pharmaceutically acceptable carrier, excipient, or diluent.

* * * * *